(12) United States Patent
Klein et al.

(10) Patent No.: US 12,331,134 B2
(45) Date of Patent: Jun. 17, 2025

(54) TRISPECIFIC ANTIBODIES SPECIFIC FOR HER2 AND A BLOOD BRAIN BARRIER RECEPTOR AND METHODS OF USE

(71) Applicant: Hoffmann-La Roche Inc., Little Falls, NJ (US)

(72) Inventors: Christian Klein, Bonstetten (CH); Julia Krueger, Munich (DE); Ekkehard Moessner, Kreuzlingen (CH); Jens Niewoehner, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 266 days.

(21) Appl. No.: 17/837,633

(22) Filed: Jun. 10, 2022

(65) Prior Publication Data

US 2023/0212312 A1    Jul. 6, 2023

Related U.S. Application Data

(63) Continuation of application No. 15/845,970, filed on Dec. 18, 2017, now abandoned, which is a continuation of application No. PCT/EP2016/064124, filed on Jun. 20, 2016.

(30) Foreign Application Priority Data

Jun. 24, 2015   (EP) .................................... 15173640

(51) Int. Cl.
    *C07K 16/32*   (2006.01)
    *C07K 16/18*   (2006.01)
    *C07K 16/28*   (2006.01)
    *A61K 39/00*   (2006.01)

(52) U.S. Cl.
    CPC .............. *C07K 16/32* (2013.01); *C07K 16/18* (2013.01); *C07K 16/2881* (2013.01); *A61K 2039/505* (2013.01); *A61K 2039/507* (2013.01); *C07K 2317/24* (2013.01); *C07K 2317/31* (2013.01); *C07K 2317/33* (2013.01); *C07K 2317/34* (2013.01); *C07K 2317/41* (2013.01); *C07K 2317/51* (2013.01); *C07K 2317/515* (2013.01); *C07K 2317/60* (2013.01); *C07K 2317/622* (2013.01); *C07K 2317/73* (2013.01); *C07K 2317/732* (2013.01); *C07K 2317/734* (2013.01); *C07K 2317/92* (2013.01); *C07K 2317/94* (2013.01)

(58) Field of Classification Search
    CPC .................. C07K 2317/31; C07K 2317/60
    USPC .................................................... 424/136.1
    See application file for complete search history.

(56) References Cited

U.S. PATENT DOCUMENTS

| | | |
|---|---|---|
| 4,816,567 A | 3/1989 | Cabilly et al. |
| 4,933,294 A | 6/1990 | Waterfield et al. |
| 5,202,238 A | 4/1993 | Fell et al. |
| 5,204,244 A | 4/1993 | Fell et al. |
| 5,208,020 A | 5/1993 | Chari et al. |
| 5,401,638 A | 3/1995 | Carney et al. |
| 5,416,064 A | 5/1995 | Chari et al. |
| 5,500,362 A | 3/1996 | Robinson et al. |
| 5,565,332 A | 10/1996 | Hoogenboom et al. |
| 5,571,894 A | 11/1996 | Wels et al. |
| 5,587,458 A | 12/1996 | King et al. |
| 5,635,483 A | 6/1997 | Pettit et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,821,337 A | 10/1998 | Carter et al. |
| 5,869,046 A | 2/1999 | Presta et al. |
| 5,877,296 A | 3/1999 | Hamann et al. |
| 5,959,177 A | 9/1999 | Hein et al. |
| 5,969,108 A | 10/1999 | McCafferty et al. |
| 6,040,498 A | 3/2000 | Stomp et al. |
| 6,171,586 B1 | 1/2001 | Lam et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,602,684 B1 | 8/2003 | Umana et al. |
| 6,630,579 B2 | 10/2003 | Chari et al. |
| 6,737,056 B1 | 5/2004 | Presta et al. |
| 6,982,321 B2 | 1/2006 | Winter et al. |
| 7,087,409 B2 | 8/2006 | Barbas et al. |
| 7,125,978 B1 | 10/2006 | Vezina et al. |

(Continued)

FOREIGN PATENT DOCUMENTS

| CA | 2859755 A1 | * | 6/2013 |
|---|---|---|---|
| CA | 2859755 C | * | 4/2021 |

(Continued)

OTHER PUBLICATIONS

Lee et al Cancer Res 68: (21):8661-6. Nov. 1, 2008.*

(Continued)

*Primary Examiner* — Lynn A Bristol

(74) *Attorney, Agent, or Firm* — Yan Qi

(57) ABSTRACT

The present invention relates to trispecific antibodies binding to HER2 and a blood-brain barrier receptor (BBB-R), methods for their production, pharmaceutical compositions containing said antibodies, and uses thereof.

19 Claims, 59 Drawing Sheets

Specification includes a Sequence Listing.

(56) References Cited

U.S. PATENT DOCUMENTS

| | | |
|---|---|---|
| 7,332,581 B2 | 2/2008 | Presta et al. |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 7,695,936 B2 | 4/2010 | Carter et al. |
| 7,862,817 B2 | 1/2011 | Adams et al. |
| 2002/0164328 A1 | 11/2002 | Shinkawa et al. |
| 2003/0115614 A1 | 6/2003 | Kanda et al. |
| 2003/0157108 A1 | 8/2003 | Presta et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132066 A1 | 7/2004 | Balint et al. |
| 2004/0132140 A1 | 7/2004 | Satoh et al. |
| 2005/0123546 A1 | 6/2005 | Umana et al. |
| 2005/0260186 A1 | 11/2005 | Bookbinder et al. |
| 2006/0104968 A1 | 5/2006 | Bookbinder et al. |

FOREIGN PATENT DOCUMENTS

| | | | |
|---|---|---|---|
| CA | 2796181 C | * | 1/2023 |
| EP | 0404097 B1 | | 9/1996 |
| EP | 0425235 B1 | | 9/1996 |
| JP | 2001-523971 A | | 11/2001 |
| JP | 2014-517823 | | 7/2014 |
| WO | 91/05264 A1 | | 4/1991 |
| WO | 92/22764 A1 | | 12/1992 |
| WO | 93/01161 A1 | | 1/1993 |
| WO | 93/10819 A1 | | 6/1993 |
| WO | 94/11026 A2 | | 5/1994 |
| WO | 94/11026 A3 | | 5/1994 |
| WO | 97/30087 A1 | | 8/1997 |
| WO | 98/45479 A1 | | 10/1998 |
| WO | 98/50431 A2 | | 11/1998 |
| WO | 98/50431 A3 | | 11/1998 |
| WO | 98/58964 A1 | | 12/1998 |
| WO | 99/22764 A1 | | 5/1999 |
| WO | 00/61739 A1 | | 10/2000 |
| WO | 01/29246 A1 | | 4/2001 |
| WO | 02/031140 A1 | | 4/2002 |
| WO | 03/011878 A2 | | 2/2003 |
| WO | 03/011878 A3 | | 2/2003 |
| WO | 03/084570 A1 | | 10/2003 |
| WO | 03/085107 A1 | | 10/2003 |
| WO | 03/085119 A1 | | 10/2003 |
| WO | 2004/056312 A2 | | 7/2004 |
| WO | 2004/065540 A2 | | 8/2004 |
| WO | 2005/035586 A1 | | 4/2005 |
| WO | 2005/035778 A1 | | 4/2005 |
| WO | 2005/053742 A1 | | 6/2005 |
| WO | 2005/100402 A1 | | 10/2005 |
| WO | 2006/029879 A2 | | 3/2006 |
| WO | 2006/029879 A3 | | 4/2006 |
| WO | 2006/044908 A2 | | 4/2006 |
| WO | 2008/077546 A1 | | 7/2008 |
| WO | 2009/080251 A1 | | 7/2009 |
| WO | 2009/080252 A1 | | 7/2009 |
| WO | 2009/080253 A1 | | 7/2009 |
| WO | 2009/080254 A1 | | 7/2009 |
| WO | 2009/089004 A1 | | 7/2009 |
| WO | 2010/136172 A1 | | 12/2010 |
| WO | 2010/145792 A1 | | 12/2010 |
| WO | 2012/091718 A1 | | 7/2012 |
| WO | 2012/130831 A1 | | 10/2012 |
| WO | 2012/143523 A1 | | 10/2012 |
| WO | 2013/026831 A1 | | 2/2013 |
| WO | 2013/055874 A2 | | 4/2013 |
| WO | 2013177062 A3 | * | 11/2013 |
| WO | 2014/033074 A1 | | 3/2014 |
| WO | 2014/144600 A2 | | 9/2014 |
| WO | 2014189973 A3 | * | 11/2014 |
| WO | 2015/031673 A2 | | 3/2015 |
| WO | 2015/052230 A1 | | 4/2015 |
| WO | 2015/077891 A1 | | 6/2015 |
| WO | 2015/091738 A1 | | 6/2015 |

OTHER PUBLICATIONS

Marquez-Ortiz et al (Clin Cancer Res 27(22):6209-21, Nov. 15, 2021).*
Bogen et al (Front Immunol. 2021; 12: 669496; Published online May 10, 2021).*
Almagro, J., et al., "Humanization of antibodies" Front Biosci 13:1619-1633 (Jan. 1, 2008).
Ausubel et al. Current Protocols in Molecular BiologyGreene and Wiley Interscience, New York, ( 1987).
Bange et al., "Molecular Targets for Breast Cancer Therapy and Prevention" Nat Med 7(5):737-744 ( 2001).
Bella, S.R., et al., "HER2 amplification through CISH—chromogenic hybridization in situ—on breast cancer Her 2 2+ by immunohistochemistry—ICH" J Clin Oncol 26(15 Suppl 22147-22147) (May 1, 2008).
Boado, R., et al., "Engineering and expression of a chimeric transferrin receptor monoclonal antibody for blood-brain barrier delivery in the mouse" Biotechnol Bioeng 102(4):1251-1258 (Mar. 1, 2009).
Brack et al., "A bispecific HER2-targeting FynomAb with superior antitumor activity and novel mode of action." Mol Cancer Ther 13(8):2030-2039 ( 2014).
Brodeur et al. Monoclonal Antibody Production Techniques and Applications New York:Marcel Dekker, Inc.,: 51-63 ( 1987).
Brueggemann, M., et al., "Comparison of the effector functions of human immunoglobulins using a matched set of chimeric antibodies" J. Exp. Med. 166(5):1351-1361 (Nov. 1, 1987).
Carter, P., et al., "'Knobs-into-holes' provides a rational design strategy for engineering antibody CH3 domains for heavy chain heterodimerization" Immunotechnology 2(1):73 (Jan. 1996).
Carter, P., et al., "Bispecific human IgG by design" J Immunol Methods 248(1-2):7-15 (Feb. 1, 2001).
Chari et al., "Immunoconjugates containing novel maytansinoids: Promising anticancer drugs" Cancer Res 52:127-131 ( 1992).
Chen et al., "Selection and analysis of an optimized anti-VEGF antibody: Crystal structure of an affinity-matured Fab in complex with antigen" J Mol Biol 293:865-881 ( 1999).
Cho, H.S., et al., "Structure of the extracellular region of HER2 alone and in complex with the Herceptin Fab" Nature 421(6924):756-760 (Feb. 13, 2003).
Chothia, C., et al., "Canonical structures for the hypervariable regions of immunoglobulins" J Mol Biol 196(4):901-917 (Aug. 20, 1987).
Chowdhury, P., "Engineering hot spots for affinity enhancement of antibodies" Methods Mol Biol 207:179-196 ( 2003).
Clackson, T., et al., "Making antibody fragments using phage display libraries" Nature 352(6336):624-628 (Aug. 15, 1991).
Clynes, R., et al., "Fc receptors are required in passive and active immunity to melanoma" PNAS USA 95(2):652-656 (Jan. 1, 1998).
Cragg et al., "Antibody specificity controls in vivo effector mechanisms of anti-CD20 reagents" Blood 103(7):2738-2743 ( 2004).
Cragg et al., "Complement-mediated lysis by anti-CD20 mAb correlates with segregation into lipid rafts" Blood 101(3):1045-1052 ( 2003).
Cunningham, B., et al., "High-resolution epitope mapping of hGH-receptor interactions by alanine-scanning mutagenesis" Science 244(4908):1081-1085 (Jun. 2, 1989).
Dall'Acqua, W., et al., "Antibody humanization by framework shuffling" Methods 36(1):43-60 (Jan. 17, 2005).
Dubowchik, G., et al., "Doxorubicin Immunoconjugates Containing Bivalent, Lysosmally-Cleavable Dipeptide Linkages" Bioorg Med Chem Lett 12(11):1529-1532 (Jun. 3, 2002).
Edelman, G. M., et al., "The Covalent Structure of an Entire γ G Immunoglobulin Molecule" PNAS USA 63(1):78-85 (May 1, 1969).
Felgenhauer et al., "Protein size and cerebrospinal fluid composition" Klin. Wschr 52:1158-1164 ( 1974).

(56) References Cited

OTHER PUBLICATIONS

Flatman, S., et al., "Process analytics for purification of monoclonal antibodies" J Chromatogr B 848(1):79-87 (Mar. 15, 2007).
Franklin, M., et al., "Insights into ErbB Signaling from the Structure of the ErbB2-pertuzumab Complex." Cancer Cell 5(4):317-328 (Apr. 1, 2004).
Fuentes, G., et al., "Synergy between trastuzumab and pertuzumab for human epidermal growth factor 2 (Her2) from colocalization: an in silico based mechanism" Breast Cancer Res 13(3 Suppl R54): 1-9 (May 22, 2011).
Garett et al., "The Crystal Structure of a Truncated ErbB2 Ectodomain Reveals an Active Conformation, Poised to Interact with Other ErbB Receptors" Molecular Cell, 11:495-505 (Feb. 2003).
Gazzano-Sntoro, H., et al., "A non-radioactive complement-dependent cytotoxicity assay for anti-CD20 monoclonal antibody" J Immunol Methods 202(2):163-171 (Mar. 28, 1997).
Gerngross, T., "Advances in the Production of Human Therapeutic Proteins in Yeasts and Filamentous Fungi" Nat Biotechnol 22(11):1409-1414 (Nov. 22, 2004).
Graham F., et al., "Characteristics of a human cell line transformed by DNA from human adenovirus type 5" J Gen Virol 36(1):59-72 (Jul. 1, 1977).
Harlow et al. Cold Spring Harbor, NY:Cold Spring Harbor Laboratory,:65 pages ( 1988).
Haun, R., et al., "Rapid, Reliable Ligation-Independent Cloning of PCR Products Using Modified Plasmid Vectors" Biotechniques 13(4):515-518 (Oct. 1, 1992).
Heeley, R. et al., "Mutations Flanking the Polyglutamine Repeat in the Modulatory Domain of Rat Glucocorticoid Receptor Lead to an Increase in Affinity for Hormone" Endocr Res 28(3):217-229 (Aug. 1, 2002).
Hellstrom, I et al., "Strong antitumor activities of IgG3 antibodies to a human melanoma-associated ganglioside" PNAS USA 82(5):1499-1502 (Mar. 1, 1985)
Hellstrom, I., et al., "Antitumor effects of L6, an IgG2a antibody that reacts with most human carcinomas" PNAS US 83(18):7059-7063 (Sep. 1, 1986).
Hinman, L., et al., "Preparation and characterization of monoclonal antibody conjugates of the calicheamicins: A novel and potent family of antitumor antibiotics" Cancer Res 53(14):3336-3342 (Jul. 15, 1993).
Hollinger, P., et al., "'Diabodies': Small bivalent and bispecific antibody fragments" PNAS. USA 90(14):6444-6448 (Jul. 15, 1993).
Hoogenboom, H., et al., "Overview of antibody phage-display technology and its applications" Methods Mol Biol 178:1-37 (Jan. 1, 2002).
Huston et al., "Protein Engineering of Single-Chain Fv Analogs and Fusion Proteins" Method Enzymol 203:46-88 ( 1991).
Idusogie, E.E., et al., "Engineered antibodies with increased activity to recruit complement" J Immunol 166(4):2571-2575 (Feb. 15, 2001).
Inoue, Satoshi, et al., "Polymalic Acid-Based Nanobiopolymer Provides Efficient Systemic Breast Cancer Treatment by Inhibiting both HER2/neu Receptor Synthesis and Activity" Cancer Res. 71(4):1454-1464 (Feb. 15, 2011).
"International Preliminary Report on Patentability—PCT/EP2016/064124":pp. 1-11 (Dec. 26, 2017).
"International Search Report—PCT/EP2016/064124 mailed Nov. 21, 2016":pp. 1-10 (Nov. 21, 2016).
Jeffrey, S., et al., "Dipeptide-based highly potent doxorubicin antibody conjugates" Bioorg Med Chem Lett 16(2):358-362 (Jan. 15, 2006).
Jones et al., "Replacing the complementarity-determining regions in a human antibody with those from a mouse" Nature 321(6069):522-525 (May 29, 1986).
Kabat et al. Sequences of Proteins of Immunological Interest (Table of Contents, Introduction and Constant Region Sequences sections), 5th edition, Bethesda, MD:NIH, vol. 1:647-723 ( 1991).

Kanda, Y., et al., "Comparison of cell lines for stable production of fucose-negative antibodies with enhanced ADCC" Biotechnol Bioeng 94(4):680-688 (Jul. 5, 2006).
Kashmiri, S., et al., "SDR grafting—a new approach to antibody humanization" Methods 36:25-34 (Jan. 1, 2005).
Kindt et al. Kuby Immunol Sixth edition, New York:W. H. Freeman and Company,:91 ( 2007).
King et al., "Monoclonal antibody conjugates of doxorubicin prepared with branched peptide linkers: Inhibition of aggregation by methoxytriethyleneglycol chains" J Med Chem 45:4336-4343 ( 2002).
Kleven, M., et al., "Transferrin Receptors TfR1 and TfR2 Bind Transferrin through Differing Mechanisms" ACS Biochemistry 57(9):1552-1559 (Feb. 1, 2018).
Klimka, A., et al., "Human anti-CD30 recombinant antibodies by guided phage antibody selection using cell panning" BR J Cancer 83(2):252-260 (Mar. 1, 2000).
Konishi, E., et al., "Utilization of Complement-Dependent Cytotoxicity to Measure Low Levels of Antibodies: Application to Nonstructural Protein 1 in a Model of Japanese Encephalitis Virus" Clinical and Vaccine Immunology 15(1):88-94 ( 2008).
Kratz, F., et al., "Prodrugs of anthracyclines in cancer chemotherapy" Curr Med Chem 13(5):477-523 (Mar. 1, 2006).
Larzar et al. et al., "Engineered antibody Fc variants with enhanced effector function" PNAS 103(11):4005-4010 (Mar. 14, 2006).
Li et al., "Progress in Research of Bifunctional Antibody Drugs" China Medical Biotechnology 9(4):292 (2014).
Li, B. et al., "Bispecific Antibody to ErbB2 Overcomes Trastuzumab Resistance trough Comprehensive Blockade of ErbB2 Heterodimerization" Cancer Research 73(21):6471-6483 (2013).
Li, H., et al., "Optimization of humanized IgGs in glycoengineered Pichia pastoris" Nat Biotechnol 24(2):210-215 (Feb. 1, 2006).
Li, M., et al., "Harnessing homologous recombination in vitro to generate recombinant DNA via SLIC" Nat Methods 4(3):251-256 (Mar. 1, 2007).
Liljeblad, M., et al., "Analysis of agalacto-IgG in rheumatoid arthritis using surface plasmon resonance" Glycoconjugate J 17:323-329 (Jul. 14, 2000).
Lode, H.N., et al., "Targeted therapy with a novel enediyne antibiotic calicheamicin V11 effectively suppresses growth and dissemination of liver metastases in a syngeneic model of murine neuroblastoma" Cancer Res 58(14):2925-2928 (Jul. 15, 1998).
Loisel et al., "Antitumour effects of single or combined monoclonal antibodies directed against membrane antigens expressed by human B cells leukaemia" Molecular Cancer 10:42-54 ( 2011).
Lonberg, N., et al., "Fully human antibodies from transgenic mouse and phage display platforms" Curr Opin Immunol 20(4):450-459 (Aug. 1, 2008).
Lonberg, N.,, "Human antibodies from transgenic animals" Nat Biotechnol 23(9):1117-1125 (Sep. 7, 2005).
Maniatis, T. et al. Molecular Cloning: A Laboratory Manual "Chapter 12: Vectors That Express Cloned DNA in *Escherichia coli*" (with Table of Contents), New York, NY:Coldwater Spring Labatory,:403-433 ( 1982).
Mather, J. et al., "Culture of testicular cells in hormone-supplemented serum-free medium" Ann NY Acad Sci 383:44-68 ( 1982).
Mather, J., "Establishment and Characterization of Two Distinct Mouse Testicular Epithelial Cell Lines" Biol Reprod 23:243-252 ( 1980).
McCafferty, J., et al., "Phage Antibodies: Filamentous Phage Displaying Antibody Variable Domains" Nature 348(6301):552-554 (Dec. 6, 1990).
Meissner, P. et al., "Transient gene expression: recombinant protein production with suspension-adapted HEK293-EBNA cells" Biotechnol Bioeng 75(2):197-203 (Oct. 20, 2001).
Merchant et al., "An Efficient Route to Human Bispecific IgG" Nat Biotechnol. 16:677-681 (Jul. 1998).
Morris, G., et al. Methods in Molec Biol "Epitope Mapping Protocols" Totowa, NJ:Humana Press, vol. 66 ( 1996).
Morrison and OI, "Genetically Engineered Antibody Molecules" Adv Immunol 44:65-92 ( 1989).

(56) References Cited

OTHER PUBLICATIONS

Morrison et al., "Chimeric Human Antibody Molecules: Mouse Antigen-Binding Domains with Human Constant Region Domains" Proc. Natl. Acad. Science USA 81:6851-6855 ( 1984).
Moura, R., et al., "Blood-brain barrier receptors and transporters: an insight on their function and how to exploit them through nanotechnology" Expert Opin Drug Deliv 16(3):271-285 (Mar. 1, 2019).
Nagy, A., et al., "Stability of cytotoxic luteinizing hormone-releasing hormone conjugate (AN-152) containing doxorubicin 14-O-hemiglutarate in mouse and human serum in vitro: Implications for the design of preclinical studies" PNAS USA 97(2):829-834 (Jan. 18, 2000).
Okazaki et al., "Fucose depletion from human IgGI oligosaccharide enhances binding enthalpy and association rate between IgG1 and FγcγRIIIa" J Molec Biol 336:1239-1249 (2004).
Osbourn, J., et al., "From rodent reagents to human therapeutics using antibody guided selection" Methods 36:61-68 (May 1, 2005).
Padlan, E. et al., "A possible procedure for reducing the immunogenicity of antibody variable domains while preserving their ligand-binding properties" Mol Immunol 28(4-5):489-498 (Apr. 30, 1991).
Padlan, E., "Anatomy of the Antibody Molecule" Mol Immunol 31(3):169-217 ( 1994).
Pardridge, W.M., et al., "Selective Transport of an Anti-transferrin Receptor Antibody through the Blood-Brain Barrier in Vivo" J Pharmacol Exp Ther 259(1):66-70 (Oct. 1, 1991).
Plowman et al., "Ligand-specific activation of HER4/p180erbB4, a fourth member of the epidermal growth factor receptor family" Proc. Natl. Acad. Sci. USA 90:1746-1750 ( 1993).
Portolano, S., et al., "Lack of promiscuity in autoantigen-specific H and L chain combinations as revealed by human H and L chain 'Roulette'" J Immunol 150(3):880-887 (Feb. 1, 1993).
Queen, C., et al., "A humanized antibody that binds to the interleukin 2 receptor" PNAS USA 86(24):10029-10033 (Dec. 1, 1989).
Raso et al., "Binary toxins for targeting cancer cells" Immunotechnology 2(4):312 ( 1996).
Remington, J., et al. Remington's Pharmaceutical Sciences (Table of Contents, total in 4 pages), OSOL , eds., 16th edition, Easton, PA:Mack Publishing Company, ( 1980).
Ridgway, J., et al., "Knobs-into-holes engineering of antibody CH3 domains for heavy chain heterodimerization" Protein Eng 9(7):617-621 (Jul. 1, 1996).
Riechmann, L., et al., "Reshaping human antibodies for therapy" Nature 332:323-327 (Mar. 24, 1988).
Ripka, J., et al., "Two chinese hamster ovary glycosylation mutants affected in the conversion of GDP-mannose to GDP-fucose" Arch Biochem Biophys 249(2):533-545 (Sep. 1, 1986).

Sambrook et al. Molecular Cloning: A Laboratory Manual (Table of Contents only, in 32 pages), 2nd edition, Cold Spring Harbor, NY:Cold Spring Harbor Laboratory Press, ( 1989).
Schneider, C., et al., "Primary structure of human transferrin receptor deduced from the mRNA sequence" Nature 311(5987):675-678 (Oct. 18, 1984).
Sias et al., "ELISA for quantitation of the extracellular domain of p185$^{HER2}$ in biological fluids." J Immunol Methods 132(1):73-80 ( 1990).
Silacci, M., et al., "Design, construction, and characterization of a large synthetic human antibody phage display library" Proteomics 5(9):2340-2350 (Jun. 1, 2005).
Stubenrauch, K., et al., "Impact of molecular processing in the hinge region of therapeutic IgG4 antibodies on disposition profiles in cynomolgus monkeys" Drug Metab Dispos 38(1):84-91 (Jan. 1, 2010).
Tanner, Minna, et al., "A Practical Alternative for Fluorescence in Situ Hybridization to Detect HER-2/neu Oncogene Amplification in Archival Breast Cancer Samples" Am J Pathol 157(5):1467-1472 (Nov. 1, 2000).
Torgov, M., et al., "Generation of an intensely potent anthracycline by a monoclonal antibody-(beta)-galactosidase conjugate" Bioconjugate Chem 16(3):717-721 (May 31, 2005).
Urlaub, G., et al., "Isolation of chinese hamster cell mutants deficient in dihydrofolate reductase activity" PNAS US 77(7):4216-4220 (Jul. 1, 1980).
Van Dijk, M., et al., "Human antibodies as next generation therapeutics" Curr Opin Chem Biol 5(4):368-374 (Aug. 1, 2001).
Verhoeyen, M., et al., "Reshaping human antibodies: Grafting an antilysozyme activity" Science 239(4847):1534-1536 (Mar. 25, 1988).
Vitetta et al., "Redesigning Nature's Poisons to Create Anti-Tumor Reagents" Science 238(4830):1098-1104 (Nov. 20, 1987).
Weksler et al., "Blood-brain barrier-specific properties of a human adult brain endothelial cell line" FASEB J. 19(13):1872-4. ( 2005).
Wright, A., et al., "Effect of glycosylation on antibody function: Implications for genetic engineering" Trends Biotechnol 15(1):26-32 (Jan. 1, 1997).
Yamane-Ohnuki, N., et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yazaki and Wu et al., "Expression of recombinant antibodies in mammalian cell lines" Methods Molec Biol 248:255-268 ( 2004).
Zhao, Xiaoxian et al., "Targeting C-type lectin-like molecule-1 for antibody-mediated immunotherapy in acute myeloid leukemia" Hematologica 95(1):71-78 (Jun. 22, 2009).

\* cited by examiner

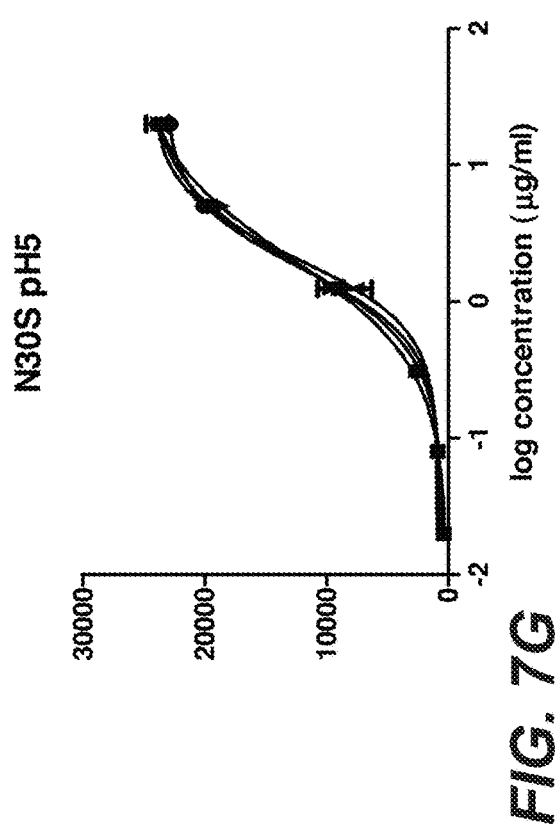
FIG. 7E GA602 pH7.5
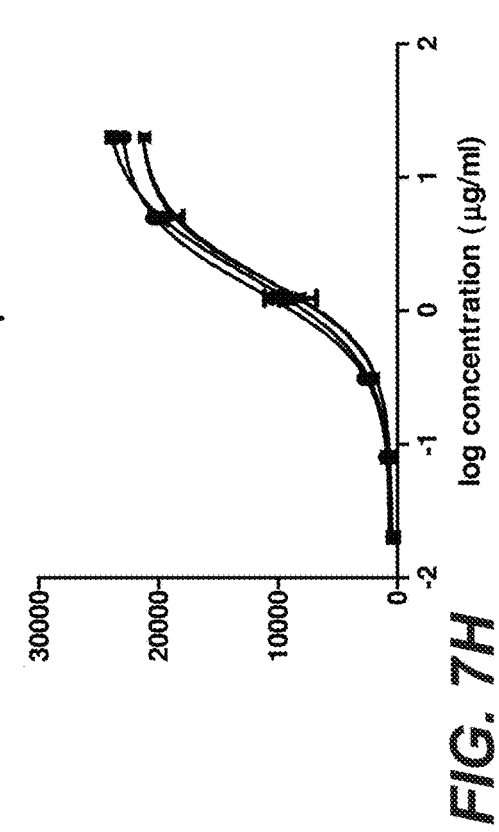
FIG. 7G N30S pH5
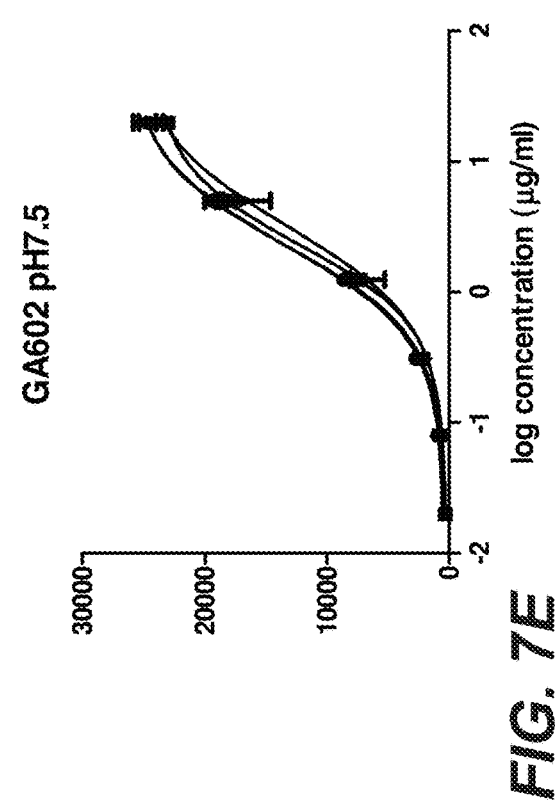
FIG. 7F N30T pH7.5
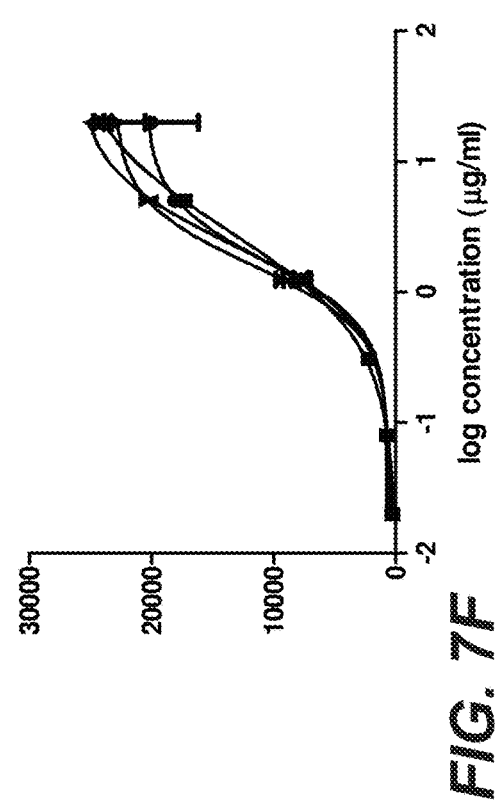
FIG. 7H WT pH5

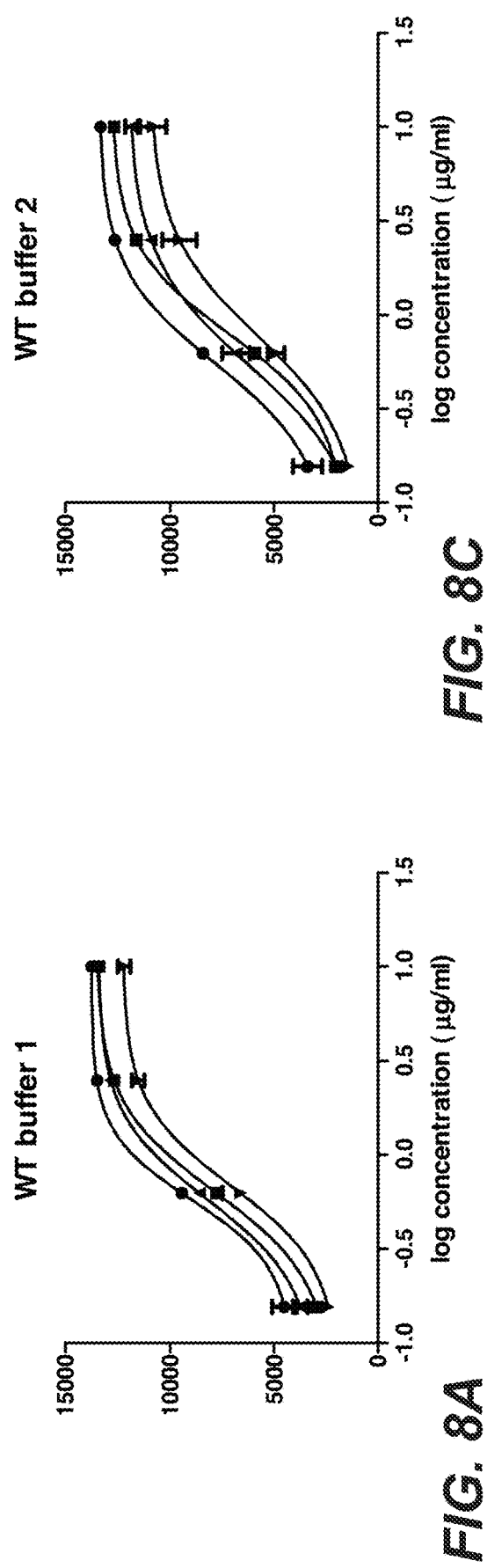
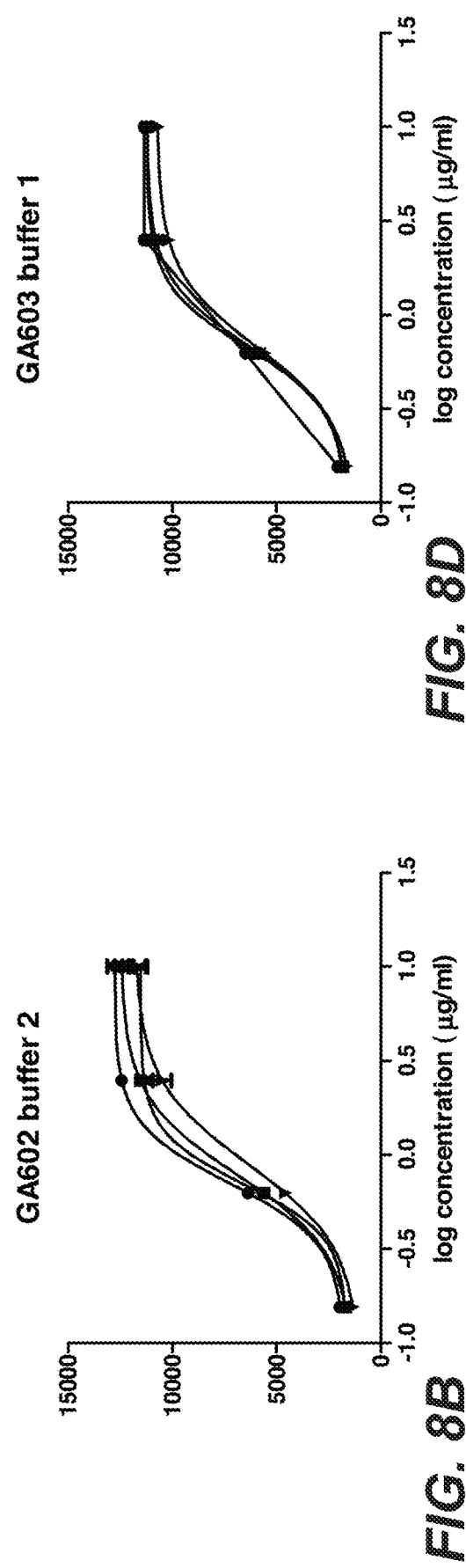
FIG. 8A
FIG. 8B
FIG. 8C
FIG. 8D

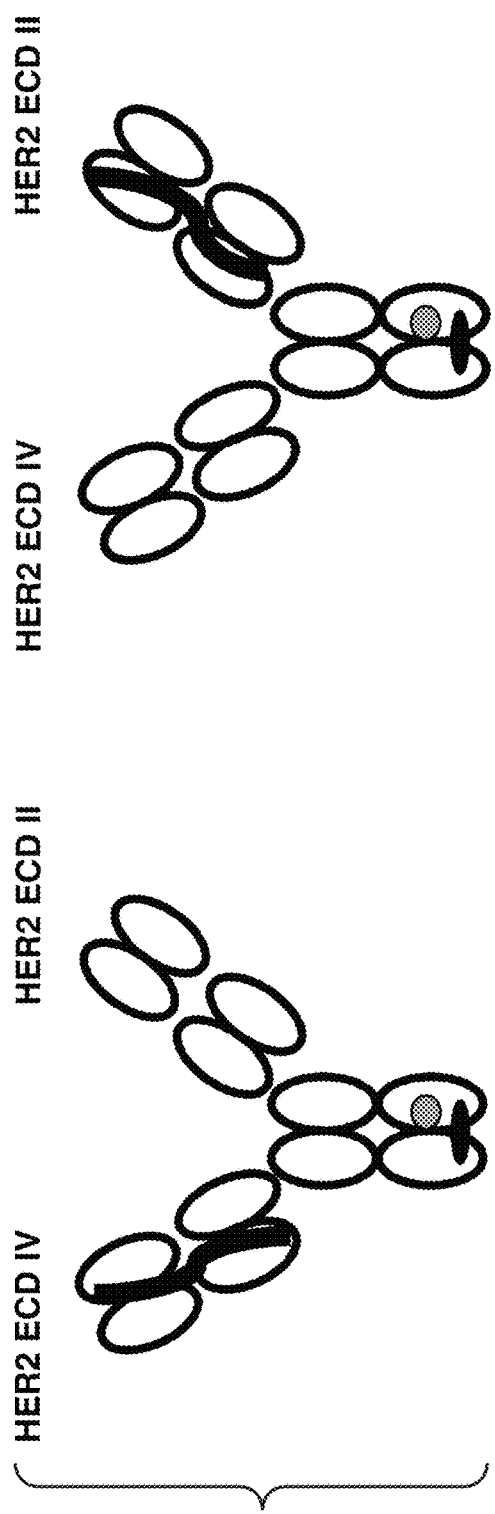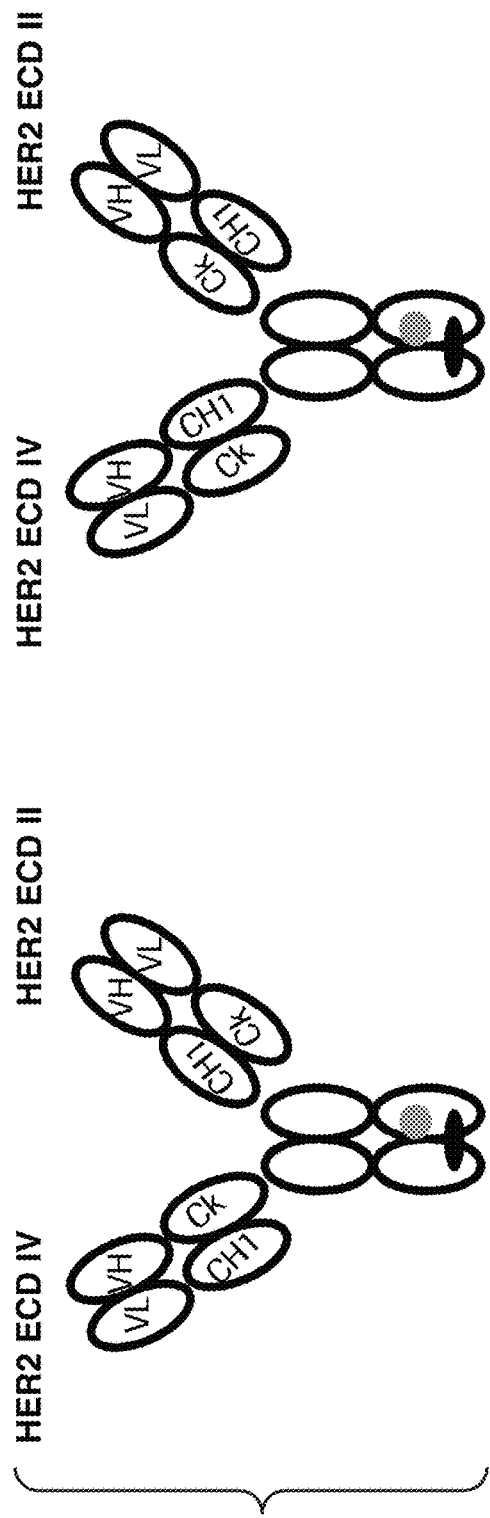
FIG. 10A
FIG. 10B

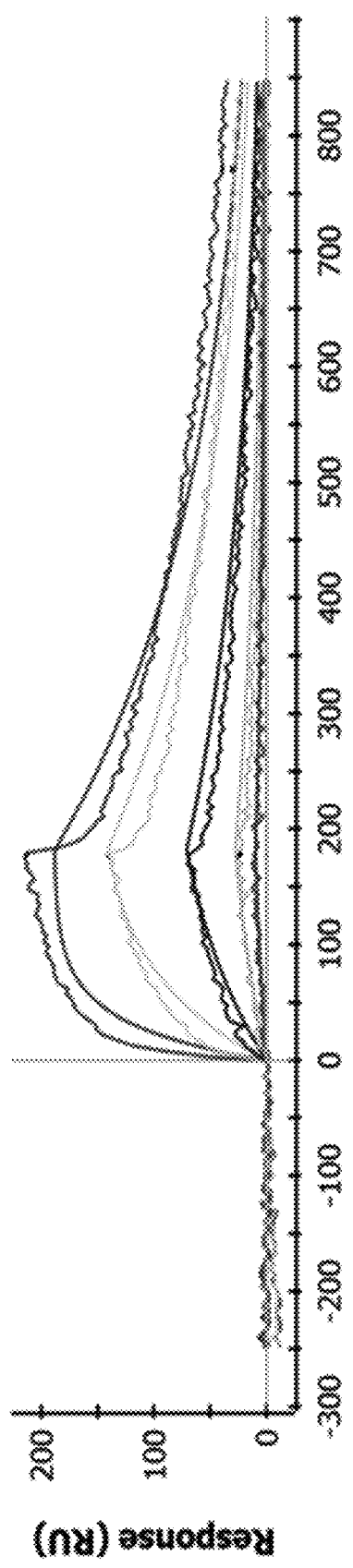
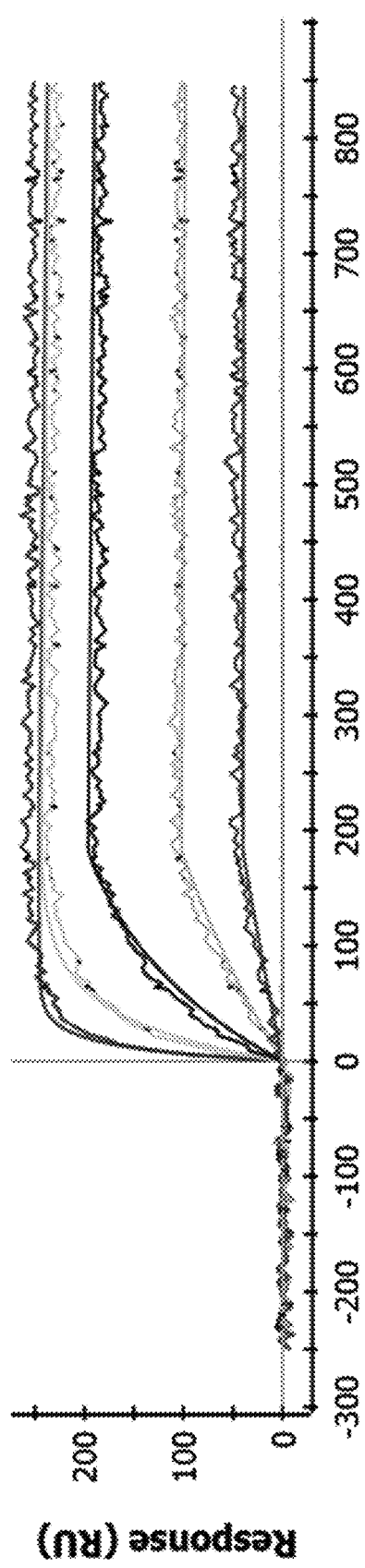
FIG. 20A
FIG. 20B

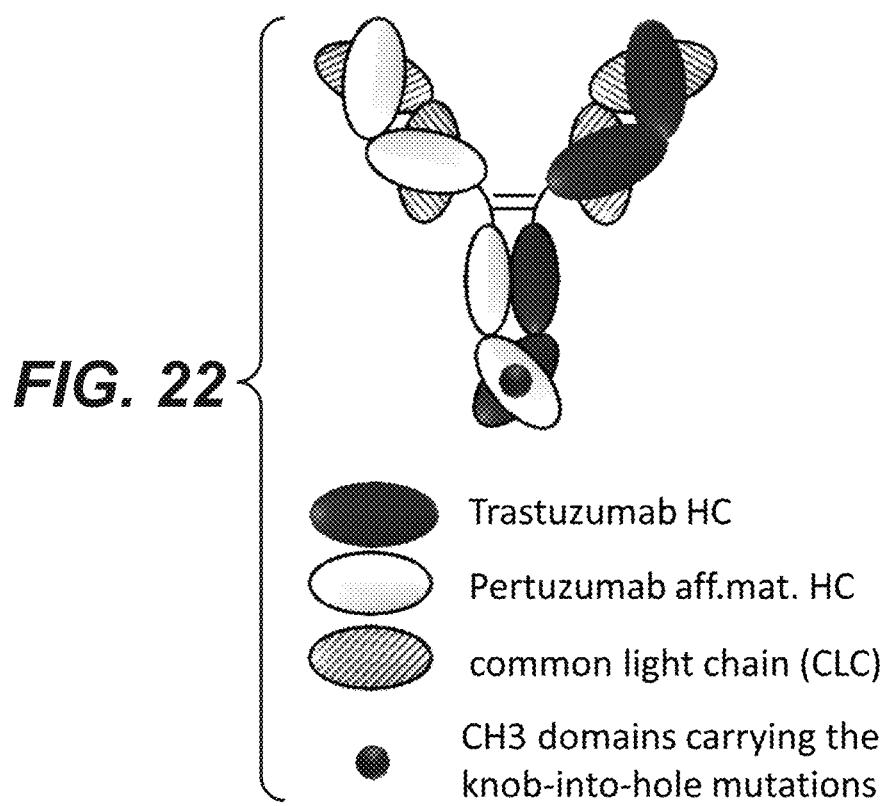

TRISPECIFIC ANTIBODIES SPECIFIC FOR HER2 AND A BLOOD BRAIN BARRIER RECEPTOR AND METHODS OF USE

CROSS REFERENCE TO RELATED APPLICATIONS

This application is a Continuation application of application Ser. No. 15/845,970, filed Dec. 18, 2017, which is a Continuation application of International Application PCT/EP2016/064124, which was filed Jun. 20, 2016, which claims benefit of priority to EP Application No. 15173640.2 filed Jun. 24, 2015, each of which is incorporated herein by reference in its entirety.

SEQUENCE LISTING

This application contains a Sequence Listing which has been submitted electronically in ASCII format and is hereby incorporated by reference in its entirety. Said ASCII copy, created on Jun. 9, 2022, is named P32940-US-2_SeqListing.txt and is 337,340 bytes in size.

FIELD OF THE INVENTION

The present invention relates to trispecific antibodies binding to HER2 and a blood-brain barrier receptor (BBB-R), methods for their production, pharmaceutical compositions containing said antibodies, and uses thereof.

BACKGROUND

Antibodies specific for tumor-associated antigens are a valuable approach in cancer therapy because they mediate selective destruction of tumor cells, while leaving healthy cells and tissues undamaged. Treatment of cancers affecting the central nervous system (CNS) with large molecules such as antibodies remains challenging as brain penetration is severely limited by the largely impermeable blood-brain barrier (BBB). Past studies have shown that a very small percentage (approximately 0.1%) of an IgG circulating in the bloodstream crosses through the BBB into the CNS (Felgenhauer, Klin. Wschr. 52: 1158-1164 (1974)), where the CNS concentration of the antibody may be insufficient to permit a robust effect. Among the many strategies to overcome this obstacle is to utilize transcytosis trafficking pathways of endogenous receptors expressed at the brain capillary endothelium. Recombinant proteins such as monoclonal antibodies have been designed against these receptors to enable receptor-mediated delivery of large molecules to the brain. However, strategies to maximize brain uptake while minimizing reverse transcytosis back to the blood, and the extent of accumulation after therapeutic dosing, remain unexplored. Furthermore, whether antibodies that cross the BBB are pharmacodynamically functional is unknown.

Members of the ErbB family of receptor tyrosine kinases are important mediators of cell growth, differentiation and survival. The receptor family includes four distinct members, including epidermal growth factor receptor (EGFR or ErbB1), HER2 (ErbB2 or p185"e"), HER3 (ErbB3) and HER4 (ErbB4 or tyro2). HER2 is a transmembrane surface-bound receptor tyrosine kinase and is normally involved in the signal transduction pathways leading to cell growth and differentiation. HER2 is a promising target for treatment of breast cancer as it was found to be overexpressed in about one-quarter of breast cancer patients (Bange et al, 2001, Nature Medicine 7:548).

The murine monoclonal antibody 4D5 is targeting HER2 specifically in HER2 overexpressing cancer cells, while having no effect on cells expressing physiological levels of HER2. The humanized (4D5) monoclonal antibody (hu4D5) is commercially known as the drug HERCEPTIN® (trastuzumab, rhuMAb HER2, U.S. Pat. No. 5,821,337), which gained FDA marketing approval in late 1998.

HERCEPTIN® (Trastuzumab) was the first monoclonal antibody developed for the treatment of HER2-positive breast cancer and has increased survival times for patients so that they are now the same as for patients with HER2-negative breast cancer. Before HERCEPTIN® (Trastuzumab) treatment, shorter survival outcomes were expected for patients diagnosed with HER2-positive breast cancer, compared to patients with HER2-negative disease. In the CLEOPATRA study, PERJETA® (pertuzumab) in combination with HERCEPTIN® (Trastuzumab) and chemotherapy has shown the extension of survival times for patients with this aggressive disease even further than HERCEPTIN® (Trastuzumab).

Pertuzumab (PERJETA®, rhuMab 2C4, U.S. Pat. No. 7,862,817) is a humanized monoclonal antibody, which is designed specifically to prevent the HER2 receptor from pairing (dimerising) with other HER receptors (EGFR/HER1, HER3 and HER4) on the surface of cells, a process that is believed to play a role in tumor growth and survival. The combination of PERJETA® (pertuzumab), HERCEPTIN® (Trastuzumab) and chemotherapy is thought to provide a more comprehensive blockade of HER signaling pathways. PERJETA® (pertuzumab) is approved in combination with HERCEPTIN® (trastuzumab) and docetaxel in adult patients with HER2-positive metastatic or locally recurrent unresectable breast cancer and gained FDA approval for neoadjuvant breast cancer treatment in September 2013. Pertuzumab binds to domain II of HER2, essential for dimerization, while Ttrastuzumab binds to extracellular domain IV of HER2.

Li et al (Cancer Research. 2013) describe bispecific, bivalent antibodies to ErbB2 that overcome trastuzumab resistance. The bispecific, bivalent antibodies described therein are based on the native Trastuzumab and Pertuzumab sequences.

Central nervous system (CNS) metastases are observed in up to half of patients with HER2-positive metastatic breast cancer (MBC), with incidence likely to continue to rise due to longer survival through improved systemic treatments. Drugs that specifically block HER2 to stop the growth of cancer cells are called HER2-targeted therapies. Examples of these drugs include HERCEPTIN® (Trastuzumab), TYKERB (lapatinib), PERJETA® (pertuzumab), and KADCYLA® (ado-trastuzumab emtansine), commonly referred to as T-DM1. Some of these drugs may be used together with chemotherapy. Unfortunately, these drugs are not usually able to reach the brain as easily as they can reach the rest of the body, with lapatinib being a possible exception. Therefore, when cancer spreads to the brain it is usually treated with surgery and/or radiation therapy. While radiotherapy-based approaches can be effective, there are potential short- and long-term toxicities, and patients frequently progress. CNS response to existing systemic therapies has been generally poor, and there is a high unmet need with no approved treatment for CNS metastases in HER2-positive MBC.

Surprisingly the inventors of the present application found that optimizing the native Trastuzumab and Pertuzumab sequences and combining these optimized variants with a third binder targeting a blood brain barrier receptor (BBBR)

results in a functional molecule with improved properties compared to the combination of the monospecific antibodies rhuMab 2C4 and hu 4D5. Hence the new trispecific format combines the superior characteristics of the bispecific HER2 antibodies known in the art with the advantages of a classical monospecific HER2 antibody and specific CNS targeting: The novel trispecific antibodies of the present invention are monovalent for the two different HER2 epitopes, resulting in the same avidity effect as the bivalent parental antibodies and specifically target the CNS via a BBBR binding moiety. In contrast, tetravalent antibodies may differ in their avidity for HER2 on cells. The avidity effect of the novel trispecific HER2 antibodies may result in a superior safety window on cell types with low HER2 expression such as in normal tissues or cardiac tissues where inhibition of HER2 and/or ADCC may not be desired.

In one aspect of the invention a trispecific antibody binding to HER2 and a blood-brain barrier receptor (BBB-R) is provided, comprising an IgG molecule wherein one of the Fab fragments is replaced by a crossover Fab fragment. Crossover Fab fragments are Fab fragments wherein either the variable regions or the constant regions of the heavy and light chain are exchanged. Bispecific antibody formats comprising crossover Fab fragments have been described, for example, in WO2009080252, WO2009080253, WO2009080251, WO2009080254, WO2010/136172, WO2010/145792 and WO2013/026831. The native Trastuzumab sequences have been optimized in their CDRs to improve the stability of the antibody CDRs against spontaneous chemical modification, the resulting sequences framework-grafted to avoid mispairing, resulting in highly potent trispecific antibodies that specifically bind to HER2; finally they can be produced with high yield and only low percentage of side products comparable to the conventional parental Her2 antibodies. Chain misparing of light chains resulting from the fact that both pertuzumab and trastuzumab are based on a comparable framework region has been overcome by grafting the CDRs on a completely novel antibody framework.

In another aspect of the invention trispecific antibodies binding to HER2 and a blood-brain barrier receptor (BBB-R) are provided wherein the two binding moieties for HER2 comprise identical light chains based on a consensus of the parental trastuzumab and pertuzumab light chains and the corresponding pertuzumab heavy chain has been remodeled. The use of this so-called 'common light chain' principle, i.e. combining two binders that share one light chain but still have separate specificities, prevents light chain mispairing and in this particular case retains the epitope specificity of the parental antibodies. As a consequence, there are less side products during production, facilitating the homogenous preparation of the trispecific antigen binding molecules at high yields. Surprisingly the inventors of the present invention found that the bispecific HER2 antibodies in the monovalent common light chain format have an increased affinity to the pertuzumab epitope, and show superior inhibitory effects on cell proliferation and induction of cell dependent cytotoxicity (CDC) as compared to the combination of the parental antibodies. Complement dependent cytotoxicity (CDC) is very important for the optimal therapeutic monoclonal antibodies (mAb) function and is totally conserved even after a chemotherapy treatment. However, this activity is generated by some antibodies but not all of them.

SUMMARY

The present invention relates to a trispecific antibody specifically binding to HER2 and a blood-brain barrier receptor (BBB-R), comprising a first monovalent antigen binding site specific for extracellular domain II of HER2 and a second monovalent antigen binding site specific for extracellular domain IV of HER2, and a third monovalent antigen binding site specific for a BBB-R. In one aspect the BBB-R of the third antigen binding site is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In one aspect the third antigen binding site is specific for the transferrin receptor. In one aspect the third antigen binding site specifically binds to an epitope in the transferrin receptor comprised within the amino acid sequence of SEQ ID NO: 202, 203 and/or 204.

In one aspect the trispecific antibody specifically binding to HER2 and a blood-brain barrier receptor (BBB-R), comprises a first Fab molecule capable of specific binding to extracellular domain II of HER2 and a second Fab molecule capable of specific binding to extracellular domain IV of HER2, wherein the sequence of the variable light chain of the first Fab molecule is identical to the sequence of the variable light chain of the second Fab molecule. In one aspect the trispecific antibody specifically binding to HER2 and a blood-brain barrier receptor (BBB-R) comprises (a) a first heavy chain comprising a heavy chain CDR1 comprising an amino acid sequence selected from the group consisting of SEQ ID NO: 55, SEQ ID NO: 58 and SEQ ID NO: 14; a heavy chain CDR 2 comprising an amino acid sequence selected from the group consisting of SEQ ID NO: 77; SEQ ID NO: 15 and SEQ ID NO: 60 and a heavy chain CDR 3 comprising an amino acid sequence selected from the group consisting of SEQ ID NO: 56 or SEQ ID NO: 59 and SEQ ID NO: 16, and (b) a second heavy chain comprising a heavy chain CDR1 comprising the amino acid sequence of SEQ ID NO: 20, a heavy chain CDR2 comprising the amino acid sequence of SEQ ID NO: 29 and a heavy chain CDR3 comprising an amino acid sequence selected from the group consisting of SEQ ID NO: 30 and SEQ ID NO: 79; and (c) a first and a second light chain, wherein the variable light chains of the first and second light chain comprise the CDRs comprising the amino acid sequence of SEQ ID NO: 89, SEQ ID NO: 90 and SEQ ID NO: 19. In one aspect the trispecific antibody specifically binding to HER2 and a blood-brain barrier receptor (BBB-R) comprises two variable light chains comprising an amino acid sequence of SEQ ID NO: 54, a first heavy chain comprising a variable heavy chain comprising an amino acid sequence selected from the group consisting of SEQ ID NO: 64, SEQ ID NO: 70 and SEQ ID NO: 68, and a second heavy chain comprising a variable heavy chain comprising an amino acid sequence selected from the group consisting of SEQ ID NO: 92 and SEQ ID NO: 117. In one aspect the trispecific antibody specifically binding to HER2 and a blood-brain barrier receptor (BBB-R) comprises a first Fab molecule capable of specific binding to extracellular domain II of HER2 and a second Fab molecule capable of specific binding to extracellular domain IV of HER2, wherein either the variable regions or the constant regions of the heavy and light chain of at least one Fab fragment are exchanged. In one aspect the trispecific antibody specifically binding to HER2 and a blood-brain barrier receptor (BBB-R) comprises a first Fab molecule comprising a heavy chain CDR1 comprising the amino acid sequence of SEQ ID NO: 14, a heavy chain CDR2 comprising the amino acid sequence of SEQ ID NO: 15 and a heavy chain CDR3 comprising the amino acid sequence of SEQ ID NO: 16; and a light chain CDR1 comprising the amino acid sequence of SEQ ID NO: 11; a light chain CDR2 comprising the amino acid sequence of SEQ ID NO: 12 and a light chain CDR3 comprising the amino acid sequence of SEQ ID NO: 13, and a second Fab molecule comprising a heavy chain CDR1 comprising the amino acid sequence of SEQ ID NO: 20; a heavy chain CDR2 comprising the amino acid sequence of SEQ ID NO: 108; a heavy chain CDR3 comprising the amino acid sequence of SEQ ID NO: 79; and a light chain CDR1 comprising the amino acid sequence of SEQ ID NO: 107, a light chain CDR2 comprising the amino acid sequence of SEQ ID NO: 18 and a light chain CDR3 comprising the amino acid sequence of SEQ ID NO: 19. In one aspect the trispecific antibody specifically binding to HER2 and a blood-brain barrier receptor (BBB-R) comprises a first Fab molecule comprising a heavy chain CDR1 comprising the amino acid sequence of SEQ ID NO: 14, a heavy chain CDR2 comprising the amino acid sequence of SEQ ID NO: 15 and a heavy chain CDR3 comprising the amino acid sequence of SEQ ID NO: 16; and a light chain CDR1 comprising the amino acid sequence of SEQ ID NO: 11; a light chain CDR2 comprising the amino acid sequence of SEQ ID NO: 12 and a light chain CDR3 comprising the amino acid sequence of SEQ ID NO: 13, and a second Fab molecule comprising a heavy chain CDR1 comprising the amino acid sequence of SEQ ID NO: 20, a heavy chain CDR2 comprising the amino acid sequence of SEQ ID NO: 29, and a heavy chain CDR3 comprising an amino acid sequence selected from the group consisting of SEQ ID NO: 79, SEQ ID NO: 78, SEQ ID NO: 80, SEQ ID NO: 87, SEQ ID NO: 88; and a light chain CDR1 comprising an amino acid sequence selected from the group consisting of SEQ ID NO: 104, SEQ ID NO: 103 and SEQ ID NO: 158; a light chain CDR2 comprising the amino acid sequence of SEQ ID NO: 18 and a light chain CDR3 comprising the amino acid sequence of SEQ ID NO: 19. In one aspect the trispecific antibody specifically binding to HER2 and a blood-brain barrier receptor (BBB-R) comprises a first Fab molecule comprising a variable heavy chain comprising an amino acid sequence of SEQ ID NO: 22 and a variable light chain comprising an amino acid sequence of SEQ ID NO: 24 and wherein a second Fab molecule comprising an amino acid sequence of SEQ ID NO: 105 and a light chain variable region comprising an amino acid sequence of SEQ ID NO: 106. In one aspect the trispecific antibody specifically binding to HER2 and a blood-brain barrier receptor (BBB-R) comprises a third antigen binding site specific for a BBB-R selected from a scFv or a scFab. In one aspect the scFv or scFab is connected to the N-terminus of an IgG molecule comprising the first and second antigen binding site. In one aspect the scFv or scFab is connected to the C-terminus of the first or second subunit of the Fc domain. In one aspect the trispecific antibody specifically binding to HER2 and a blood-brain barrier receptor (BBB-R) comprises a third antigen binding site comprising a 1. a heavy chain CDR1 comprising the amino acid sequence of SEQ ID NO: 186, a heavy chain CDR2 comprising the amino acid sequence of SEQ ID NO: 187 and a heavy chain CDR3 comprising the amino acid sequence selected from the group of SEQ ID NO: 188, SEQ ID NO: 206 or SEQ ID NO: 174; and a light chain CDR1 comprising the amino acid sequence of SEQ ID NO: 189, a light chain CDR2 comprising the amino acid sequence of SEQ ID NO: 190 and a light chain CDR3 comprising the amino acid sequence of SEQ ID NO:191. In one aspect the trispecific antibody specifically binding to HER2 and a blood-brain barrier receptor (BBB-R) comprises a third antigen binding site comprising a heavy chain CDR1 comprising the amino acid sequence of SEQ ID NO: 172, a heavy chain CDR2 comprising the amino acid sequence of SEQ ID NO: 173 and a heavy chain CDR3 comprising the amino acid sequence of SEQ ID NO: 174; and a light chain CDR1 comprising the amino acid sequence of SEQ ID NO: 175, a light chain CDR2 comprising the amino acid sequence of SEQ ID NO: 176 and a light chain CDR3 comprising the amino acid sequence of SEQ ID NO:177.

In one aspect the trispecific antibody specifically binding to HER2 and a blood-brain barrier receptor (BBB-R) comprises a third antigen binding site comprising a variable heavy chain comprising an amino acid sequence of SEQ ID NO: 178 and a variable light chain comprising an amino acid sequence of SEQ ID NO: 179 or a humanized version thereof. In one aspect the trispecific antibody specifically binding to HER2 and a blood-brain barrier receptor (BBB-R) comprises a third antigen binding site comprising 1. a variable heavy chain comprising an amino acid sequence of SEQ ID NO: 192 or SEQ ID NO: 205 and a variable light chain comprising an amino acid sequence of SEQ ID NO: 193.

In one aspect the trispecific antibody specifically binding to HER2 and a blood-brain barrier receptor (BBB-R) comprises a third antigen binding site comprising a heavy chain CDR1 of SEQ ID NO: 180, a heavy chain CDR2 of SEQ ID NO: 181 and a heavy chain CDR3 of SEQ ID NO: 182; and a light chain CDR1 of SEQ ID NO: 183, a light chain CDR2 of SEQ ID NO: 184 and a light chain CDR3 of SEQ ID NO: 185. In one aspect the trispecific antibody specifically binding to HER2 and a blood-brain barrier receptor (BBB-R) comprises a third antigen binding site comprising a variable heavy chain comprising an amino acid sequence of SEQ ID NO: 166 and a variable light chain comprising an amino acid sequence of SEQ ID NO: 167 or a humanized version thereof. In one aspect the trispecific antibody specifically binding to HER2 and a blood-brain barrier receptor (BBB-R) comprises a third antigen binding site comprising a variable heavy chain comprising an amino acid sequence of SEQ ID NO: 194, SEQ ID NO: 195, SEQ ID NO: 196, SEQ ID NO: 197, SEQ ID NO: 198, SEQ ID NO: 199, or SEQ ID NO: 200, and a variable light chain comprising an amino acid sequence selected from the group of SEQ ID NO: 201, SEQ ID NO: 207, SEQ ID NO: 208, or SEQ ID NO:209.

In one aspect the trispecific antibody specifically binding to HER2 and a blood-brain barrier receptor (BBB-R) comprises a third antigen binding site comprising sequence alterations in the CDRs resulting in a reduced affinity.

In a second object the present invention relates to a pharmaceutical composition comprising a trispecific antibody of the present invention.

In a third object the present invention relates to a trispecific antibody of the present invention for the treatment of cancer. In another embodiment, use of the trispecific antibody as a medicament is provided. Preferably said use is for the treatment of cancer. In one aspect said cancer is a HER2-positive cancer with brain metastases.

In further objects the present invention relates to a nucleic acid sequence comprising a sequence encoding a heavy chain of a trispecific antibody of the present invention, a nucleic acid sequence comprising a sequence encoding a light chain of a trispecific antibody of the present invention, an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

BRIEF DESCRIPTION OF THE FIGURES

(FIG. 1B): The single chain Fv (scFv) is fused N-terminally to the light chain in the order VL-VH (TvAB13, SEQ ID NOs 125 and 126). (FIG. 1C) The single chain Fv (scFv) is fused C-terminally to the light chain in the order VL-VH (TvAB16: SEQ ID NOs 127 and 128, TvAB20: SEQ ID NOs 131 and 132). (FIG. 1D): The single chain Fv (scFv) is fused C-terminally to the heavy chain in the order VL-VH (TvAB17: SEQ ID NOs 129 and 130).

(FIG. 2A): Size-exclusion purification of TvAb12 (SEQ ID NOs 123 and 124) on a 26/60 SUPERDEX™ 200 column. (FIG. 2B): SDS-Page analysis of main peak fraction originating from size-exclusion chromatography (NR=non-reducing, R=reducing conditions).

(FIG. 3A): Size-exclusion purification of TvAb16 (SEQ ID NOs 127 and 128) on a 26/60 SUPERDEX™ 200 column. (FIG. 3B): SDS-Page analysis of main peak fraction originating from size-exclusion chromatography (NR=non-reducing, R=reducing conditions).

(FIG. 4A): Size-exclusion purification of TvAb20 (SEQ ID NOs 131 and 132) on a 26/60 SUPERDEX™ 200 column. Main product peak marked with "1". (FIG. 4B) SDS-Page analysis of main peak fraction originating from size-exclusion chromatography (NR=non-reducing, R=reducing conditions).

(FIG. 6A): pH5.0. (FIG. 6B): pH6.0, (FIG. 6C): pH7.4.

FIGS. 7A-7L: Binding of Trastuzumab and Trastuzumab stabilization variants after stress to KPL-4 cells. Trastuzumab and 3 different stabilized Trastuzumab variants were incubated for one, two and three month in buffer with different pH values at 40° C. The stressed antibodies were tested compared to the antibody at time point zero for binding to KPL-4 cells by flow cytometry. "602": D98E mutation in heavy chain and T31V mutation in light chain, "N30T": D98E mutation in heavy chain and N30T mutation in light chain, "N30S": D98E mutation in heavy chain and N30S mutation in light chain.

FIGS. 10A-10B: Schematic drawing of Trastuzumab and Pertuzumab bispecific antibodies in a 1+1 format. (FIG. 10A): single chain Fab (scFab) based molecules (FIG. 10B): cross-over Fab (xFab) based molecules.

(FIG. 11A): SDS-PAGE showing the purified antibody molecule under reduced and non-reduced conditions. (FIG. 11B): HP-SEC analysis of purified CrossMab-XPer.

FIGS. 20A-20B: SPR analysis of the Pertuzumab and Trastuzumab HCs in combination with the newly identified common light chain Pertuzumab (Tras.L3)(QM), SEQ ID No: 54. Shown is the binding of both antibodies to Her2 at different concentrations. Smooth lines represent a global fit of the data to a 1:1 interaction model.

FIG. 22: Schematic drawing of the bi-specific HER2 antibodies with a common light chain.

(FIG. 23A) (FIG. 23B): comprising D1der (SEQ ID NO: 64), (FIG. 23C)(FIG. 23D): comprising G2 (SEQ ID NO: 70), (FIG. 23E)(FIG. 23F): comprising E1 (SEQ ID NO: 68).

(FIG. 27A)(FIG. 27B), Antibody dependent killing of KPL-4 cells with PBMCs (E:T 25:1) or was determined by measuring LDH release after 4 h. (FIG. 27C)(FIG. 27D) Antibody dependent killing of MDA-MB 231 cells with PBMCs (E:T 5:1) was determined by measuring LDH release after 24 h. "Herceptarg CLC D1-der": SEQ ID NOs 64, 54, 92, "Herceptarg CLC G2/2": SEQ ID NOs 70, 54, 92, "Herceptarg CLC E1/1": SEQ ID NOs 68, 54, 92; "GA 604": SEQ ID NOs 109, 110, 111, 112.

DETAILED DESCRIPTION OF EMBODIMENTS OF THE INVENTION

I. Definitions

Throughout the disclosure, the terms "ErbB2", "ErbB2 receptor", "c-Erb-B2", and "HER2" are used interchangeably, and, unless otherwise indicated, refer to a native sequence ErbB2 human polypeptide, or a functional derivative thereof. "ber2", "erbB2" and "c-erb-B2" refer to the corresponding human gene.

Figure 1A:
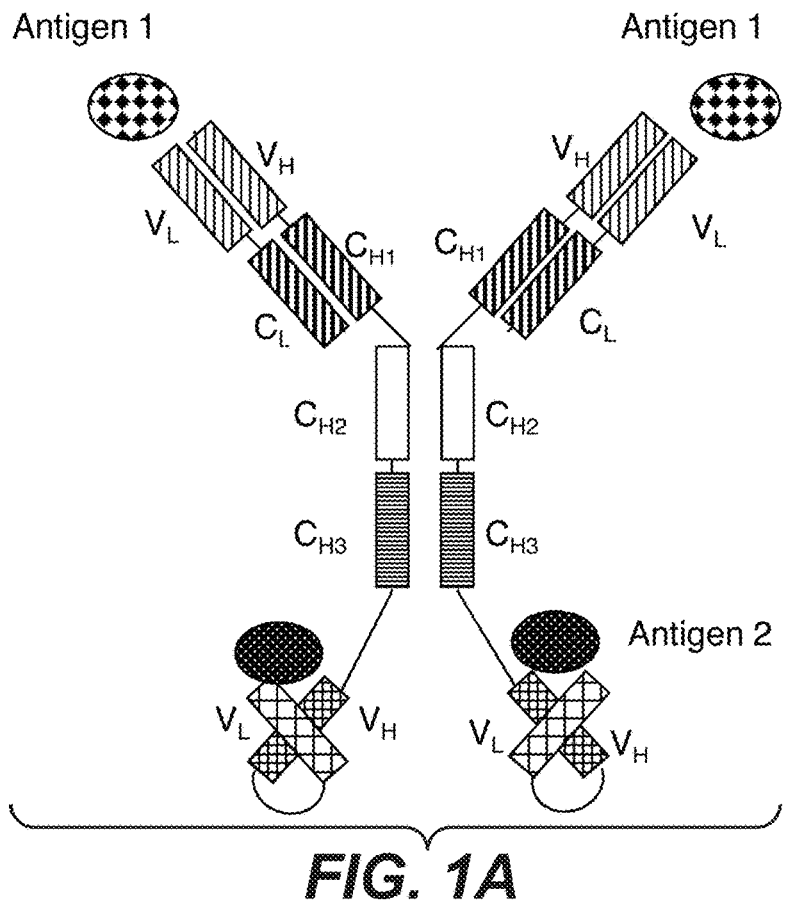
FIGS. 1A-1D: Schematic drawing of Trastuzumab and Pertuzumab bispecific antibodies in a 2+2 IgG-scFv format. The antibodies are bivalent for each antigen binding site and are able to bind two different paratopes in the ErbB2/HER2 receptor (antigen1=trastuzumab specificity, i.e. extracellular domain IV of HER2; antigen2=pertuzumab specificity extracellular domain II of HER2) (FIG. 1A): The single chain Fv (scFv) is fused C-terminally to the heavy chain in the order VH-VL (TvAB12, SEQ ID NOs 123 and 124).
Figure 1B:
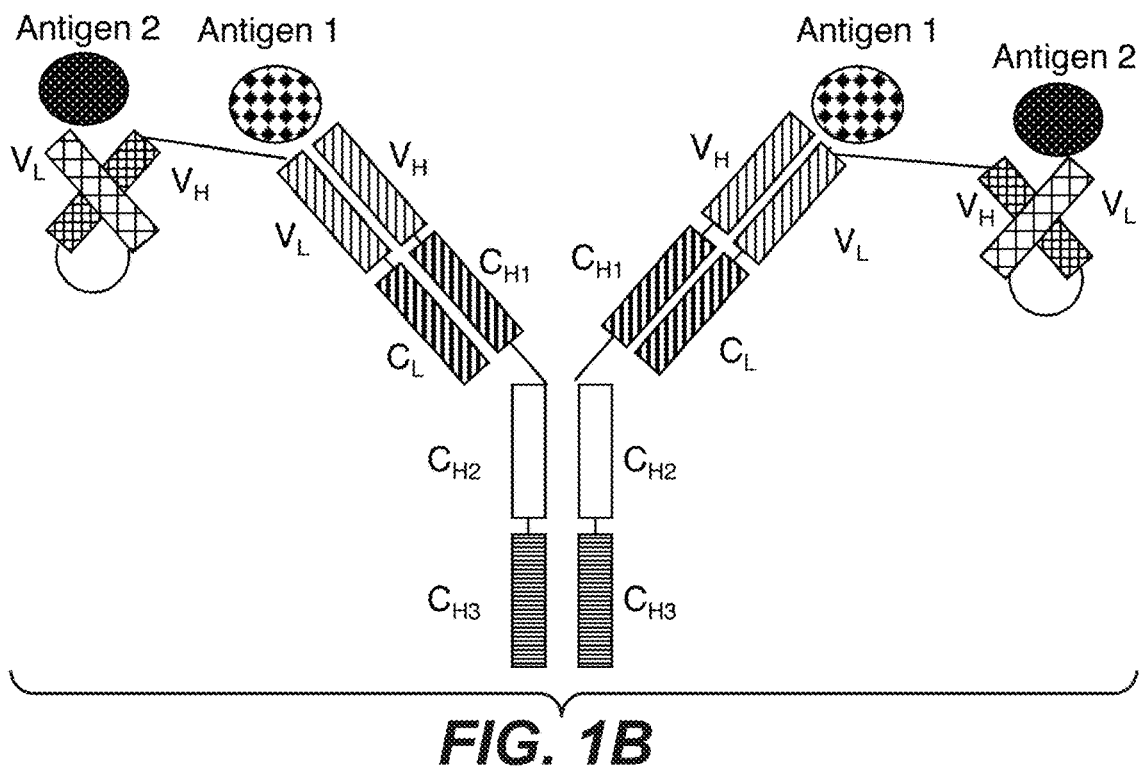
Figure 1C:
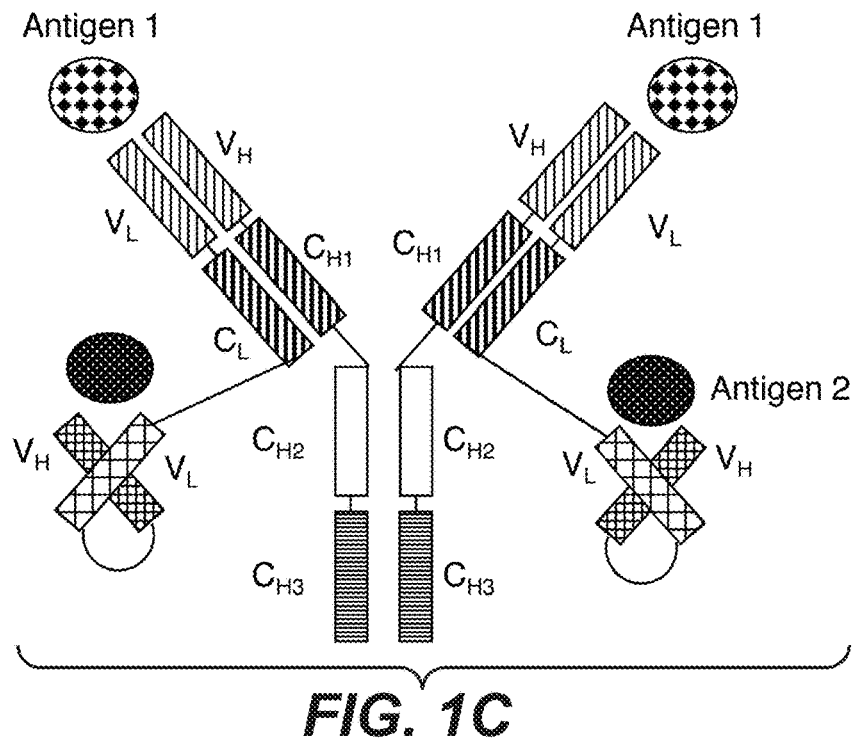
Figure 1D:
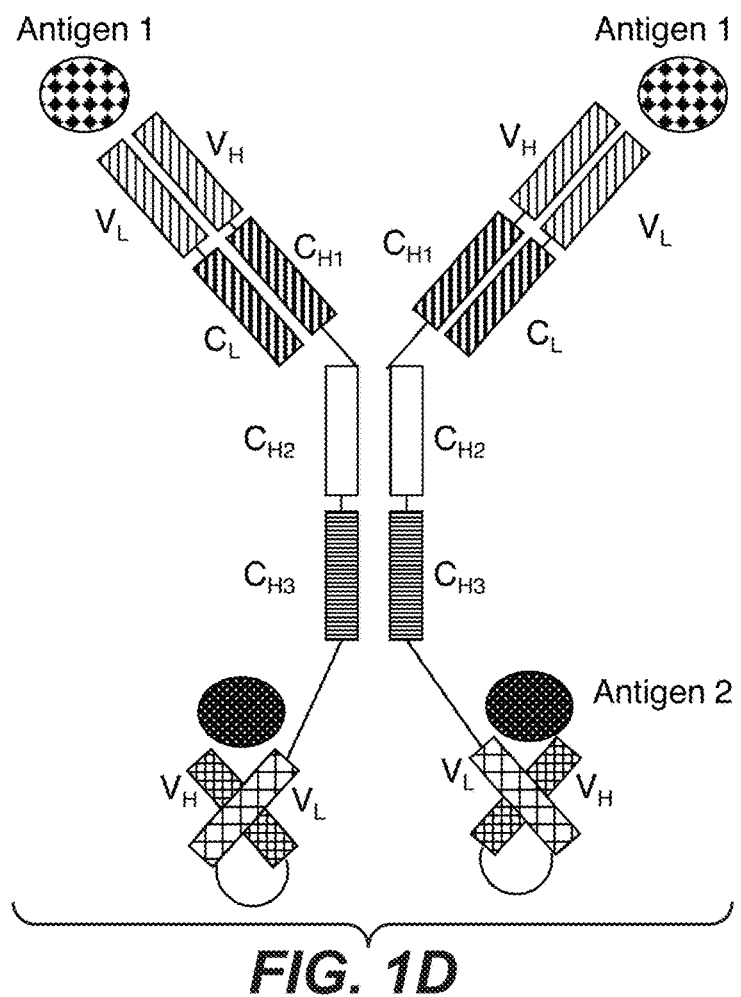
Figure 2A:
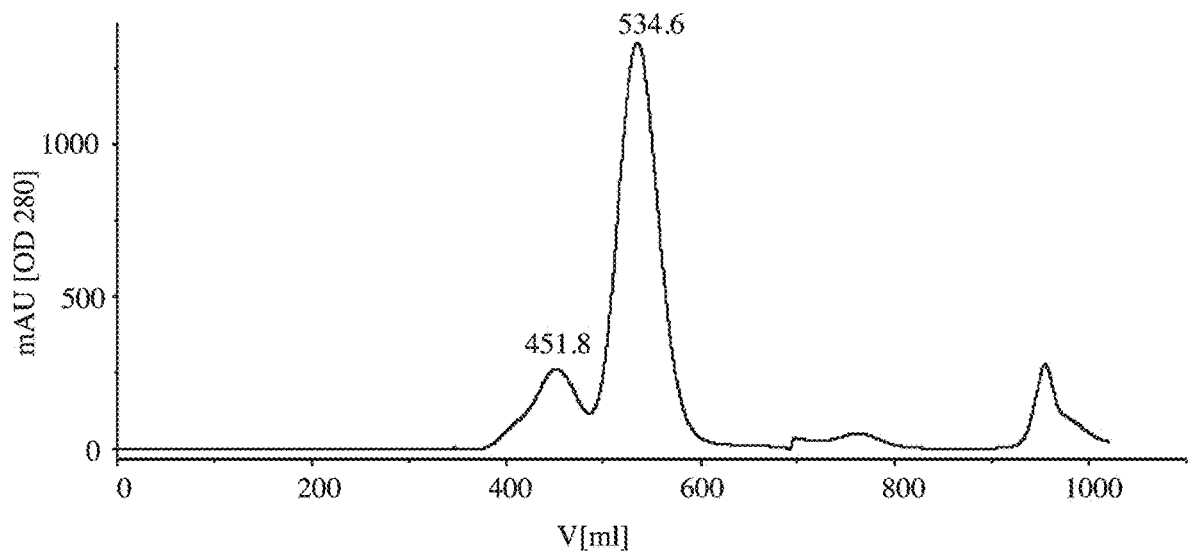
FIGS. 2A-2B: Purification of Trastuzumab and Pertuzumab bispecific antibodies in a 2+2 IgG-scFv format.
Figure 2B:
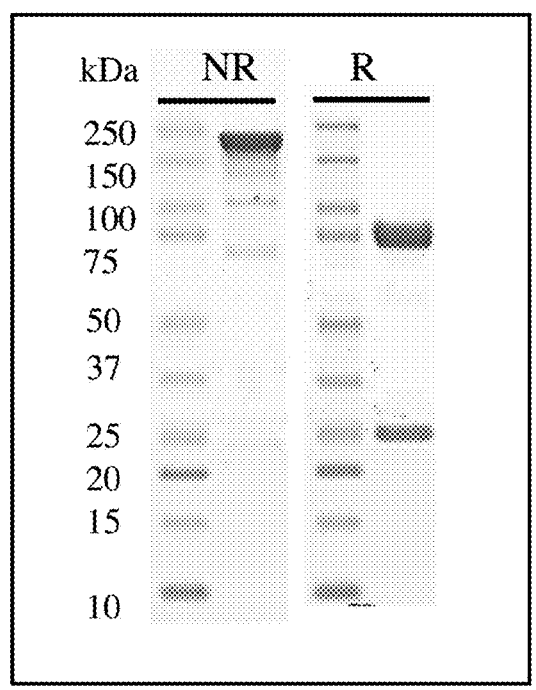
Figure 3A:
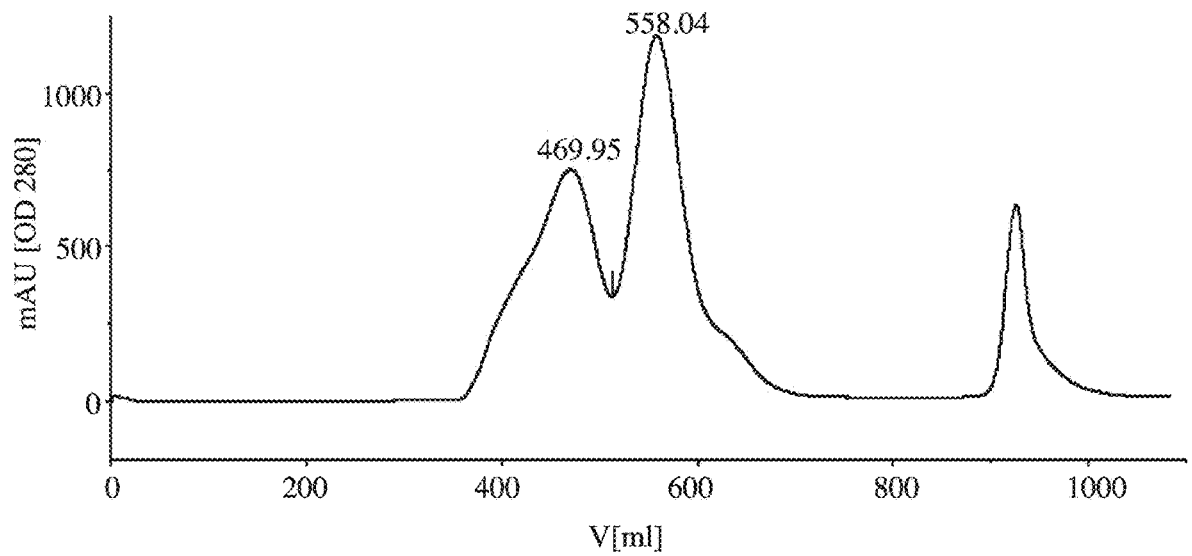
FIGS. 3A-3B: Purification of Trastuzumab and Pertuzumab bispecific antibodies in a 2+2 IgG-scFv format.
Figure 3B:
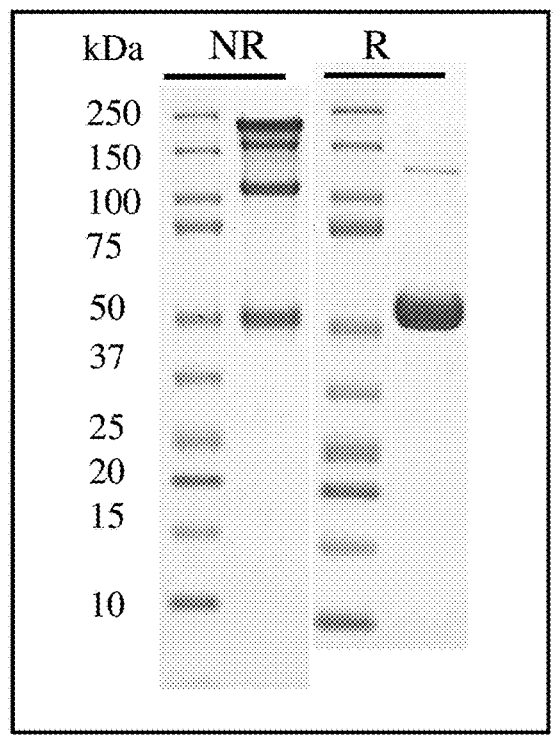
Figure 4A:
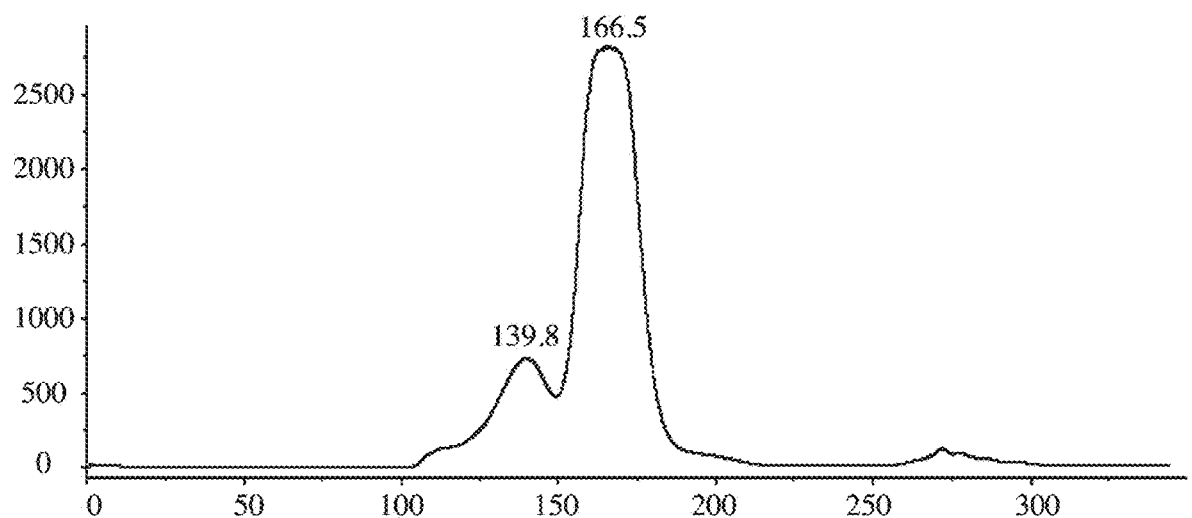
FIGS. 4A-4B: Purification of Trastuzumab and Pertuzumab bispecific antibodies in a 2+2 IgG-scFv format.
Figure 4B:
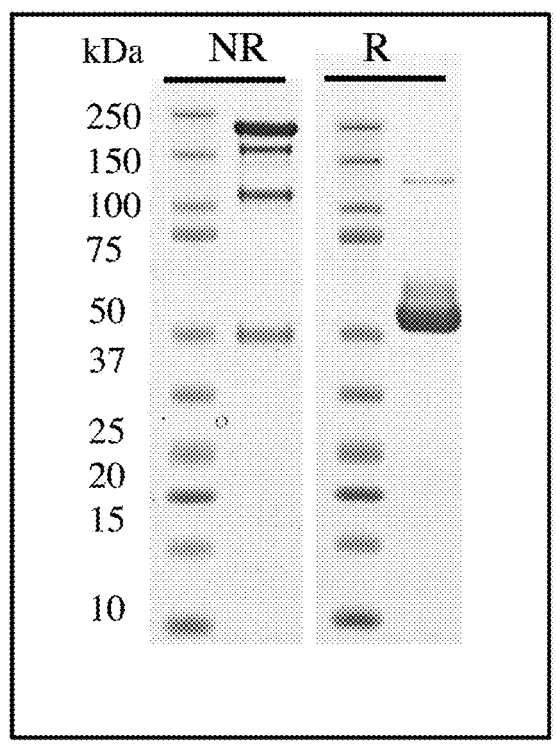
Figure 5A:
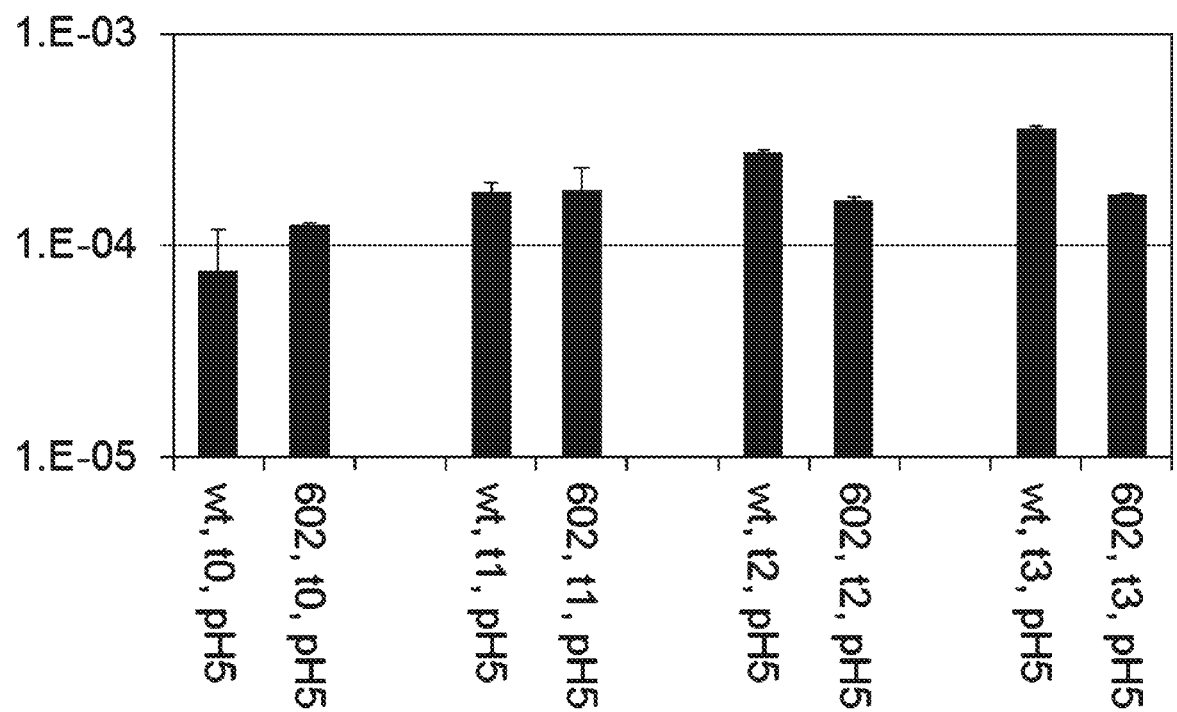
FIGS. 5A-5B: Of-rates of Trastuzumab variants as determined by SPR method (PROTEON™ instrument) after incubating the samples for 1, 2, or 3 months at 40° in buffer 40 mM Histidin, 150 mM NaCl, pH5.0. The off rates of the variant does not change over the investigated time period. "602": D98E mutation in heavy chain and T31V mutation in light chain.
Figure 5B:
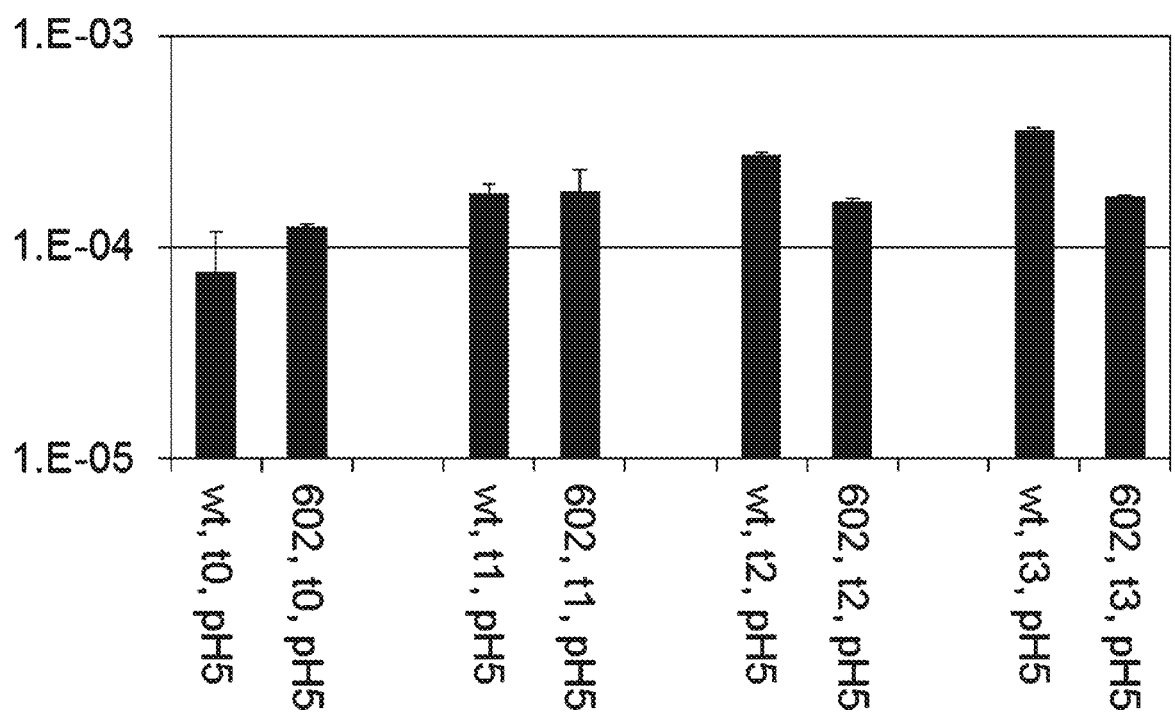
Figure 6A:
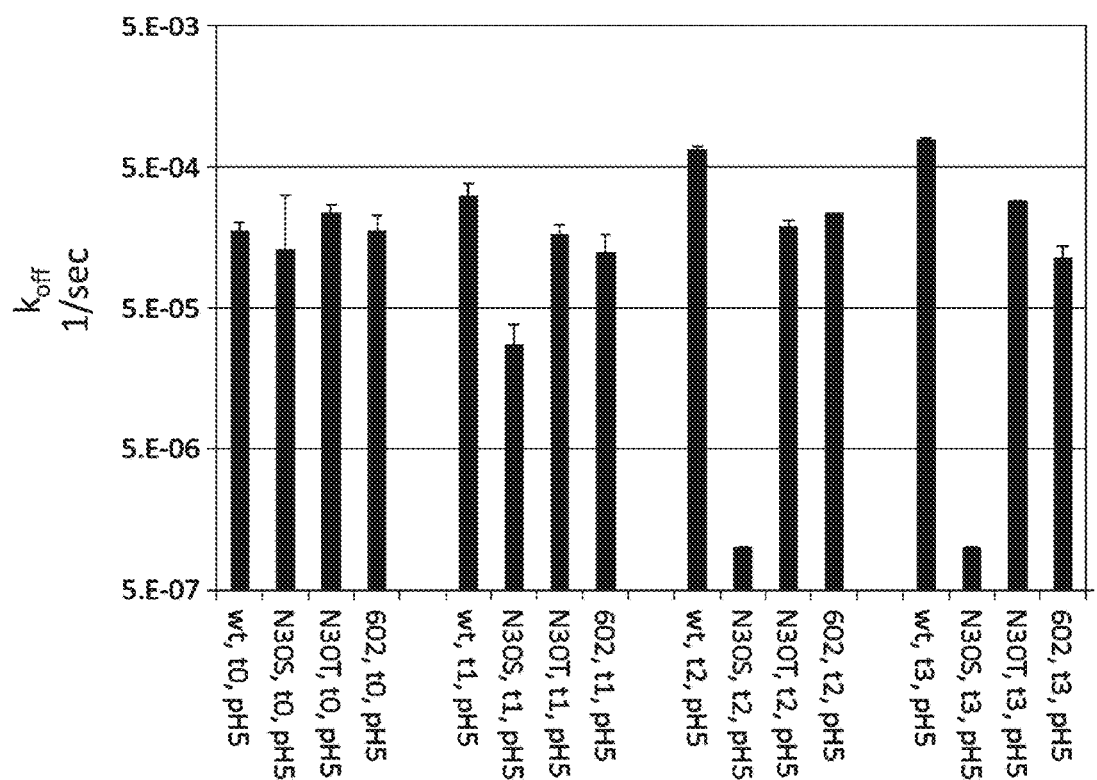
FIGS. 6A-6C: Off-rates of Trastuzumab variants as determined by SPR method (PROTEON™ instrument) after incubating the samples for 1, 2, or 3 months at 40° C. in 40 mM Histidin, 150 mM NaCl, at different pH. The off rates of the N30S variant were very slow, and therefore contain a high degree of uncertainty. "602": D98E mutation in heavy chain and T31V mutation in light chain, "N30T": D98E mutation in heavy chain and N30T mutation in light chain, "N30S": D98E mutation in heavy chain and N30S mutation in light chain.
Figure 6B:
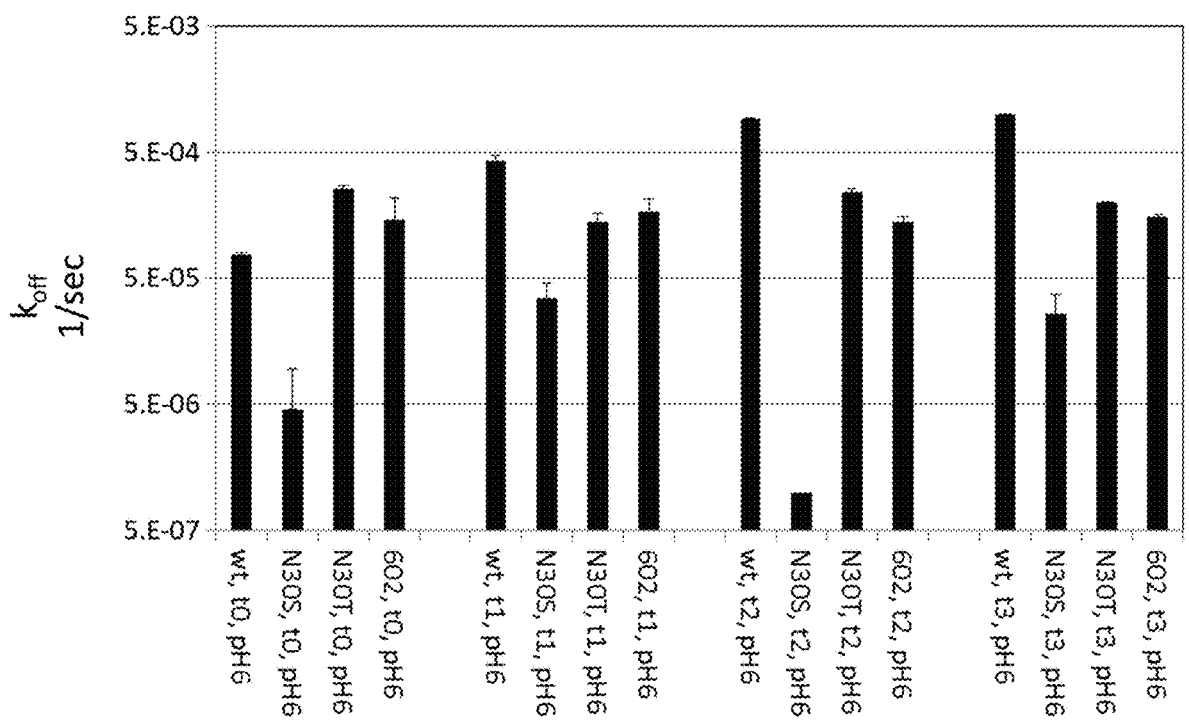
Figure 6C:
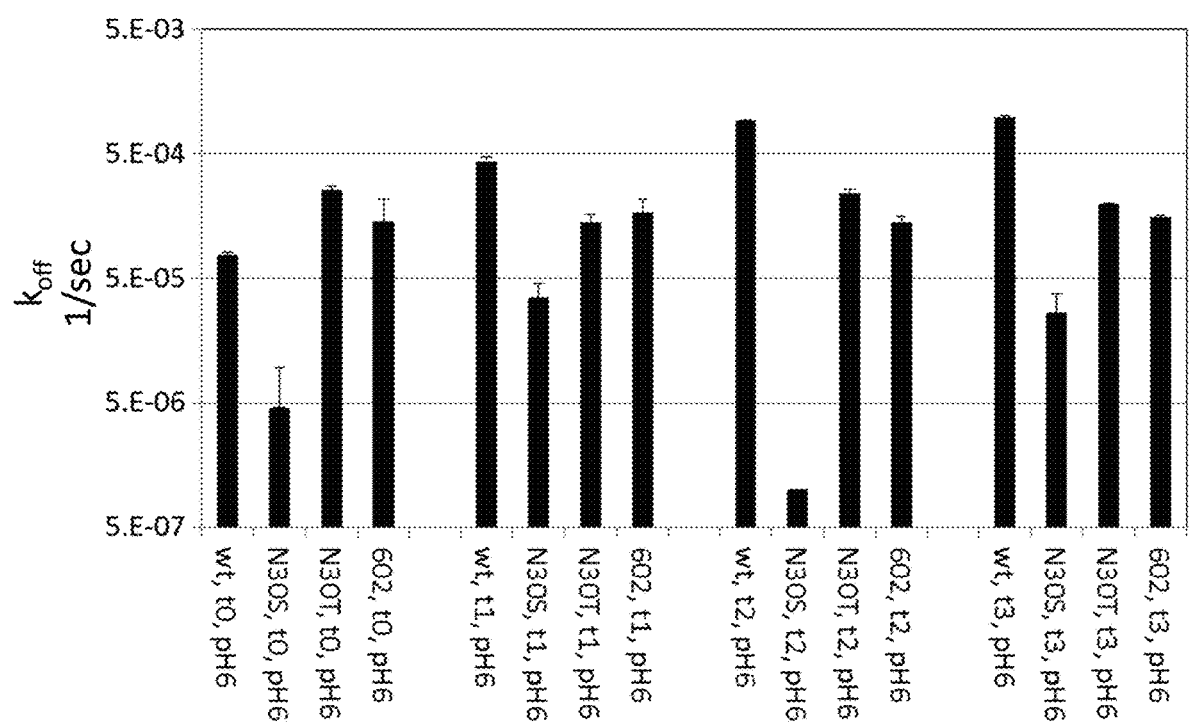
Figure 7A:
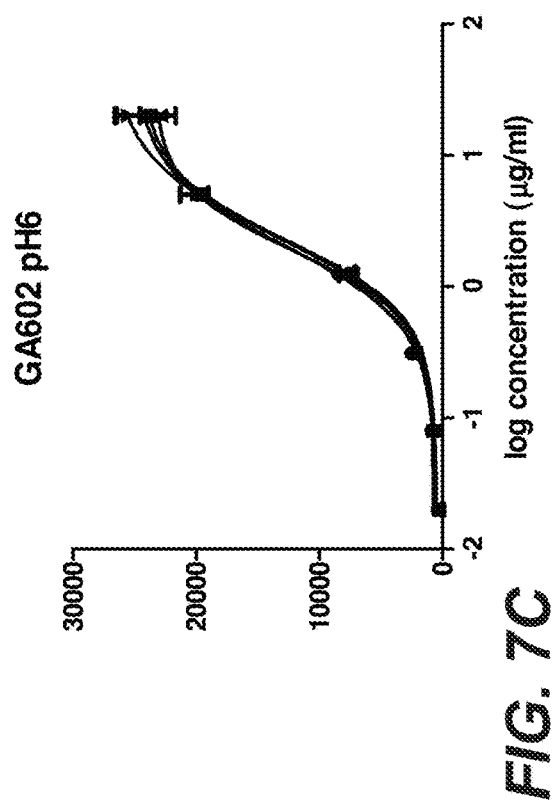
Figure 7C:
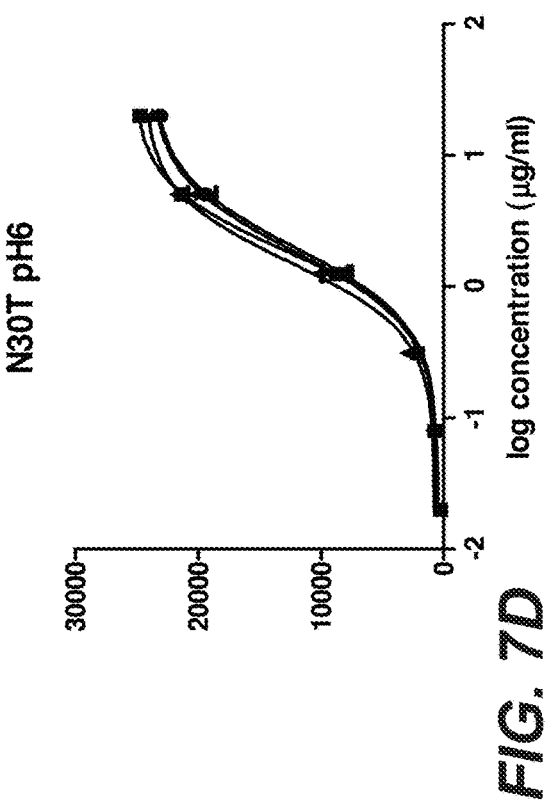
Figure 7B:
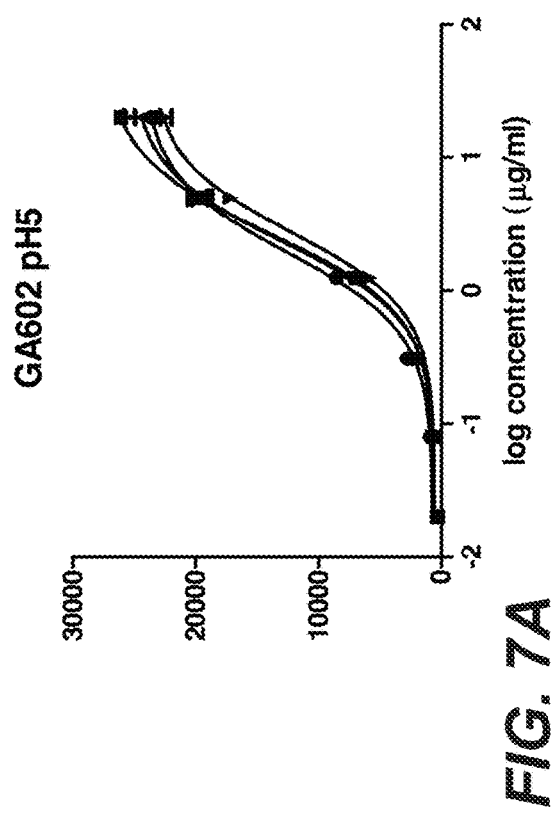
Figure 7D:
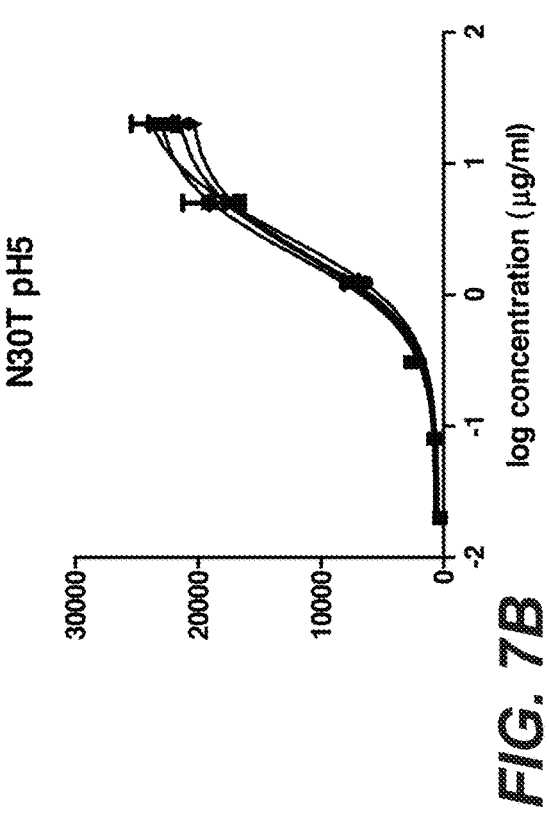
Figure 7I:
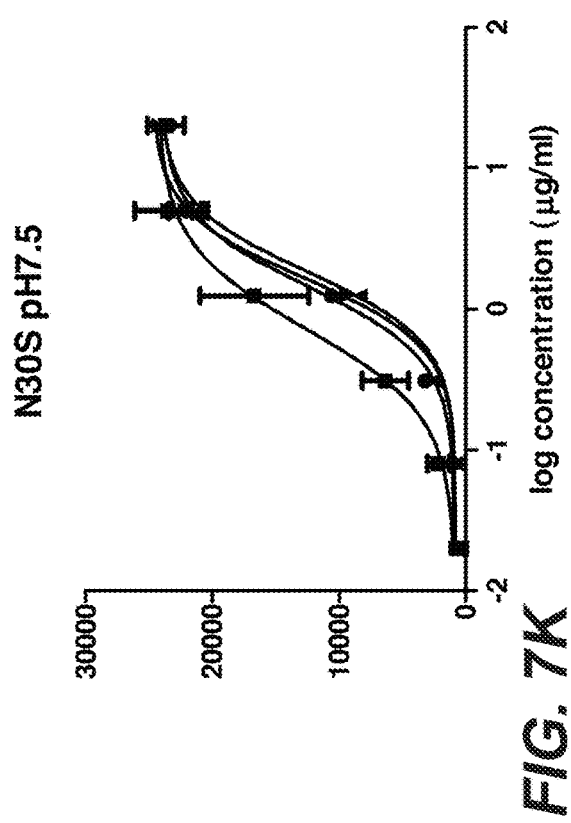
Figure 7K:
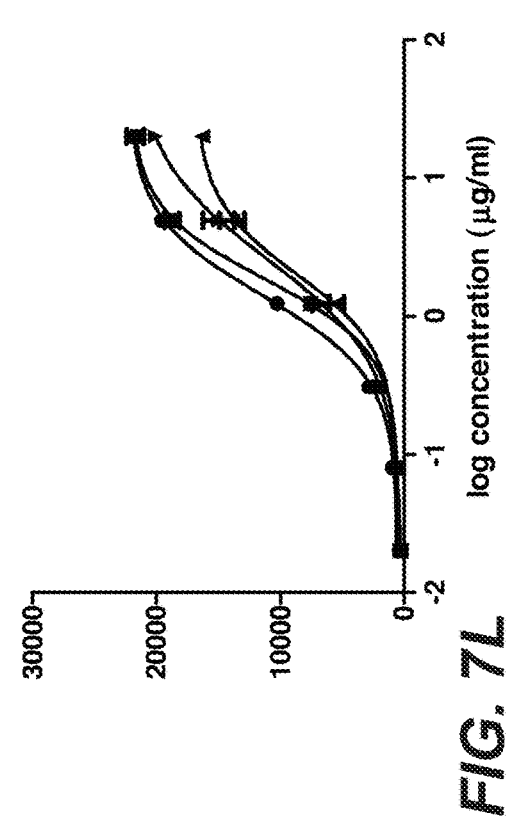
Figure 7J:
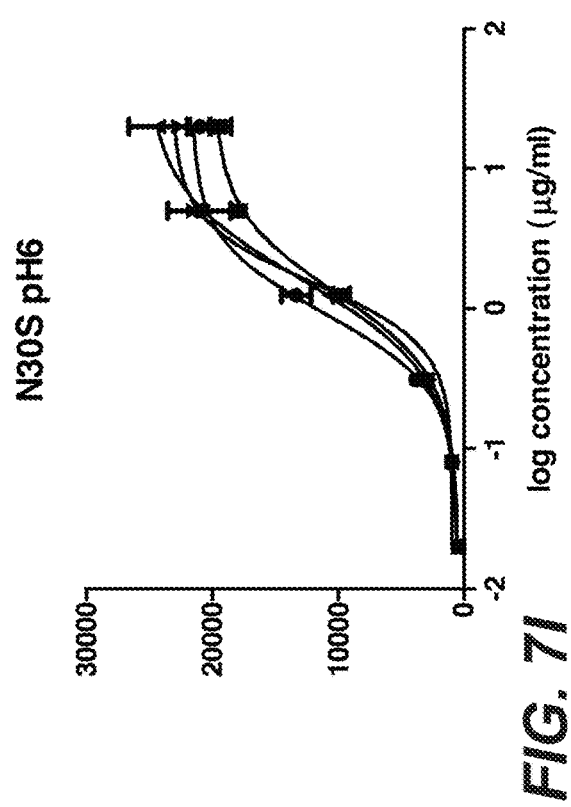
Figure 7L:
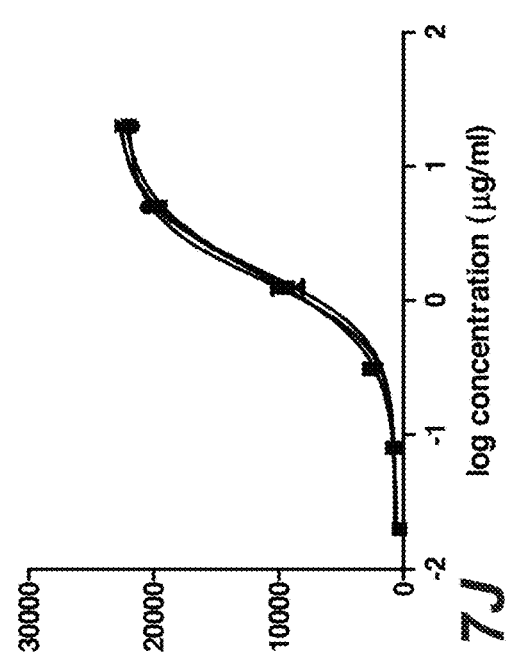
Figure 8E:
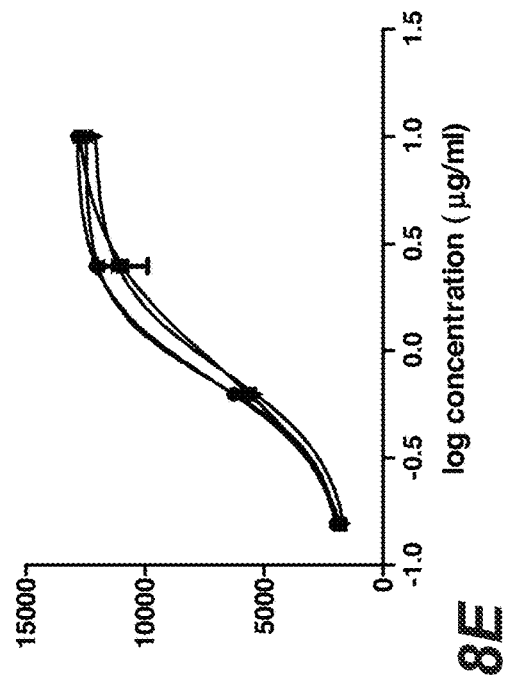
FIGS. 8A-SF: Binding of Trastuzumab and Trastuzumab stabilization variants after stress to KPL4 cells. Trastuzumab and the 2 stabilization variants GA602 (D98E mutation in heavy chain and T31V mutation in light chain) and GA603 (D98E mutation in heavy chain and T31V mutation in light chain and FcRN mutation T307Q und N434A) were incubated for one, two and three month in buffer 1 (40 mM Histidin 150 mM NaCl, pH5.0) or buffer 2 (2.40 mM Histidin 150 mM NaCl, pH6.0) at 40° C. The stressed antibodies were tested compared to the antibody at time point zero for binding to KPL-4 cells by flow cytometry.
Figure 8F:
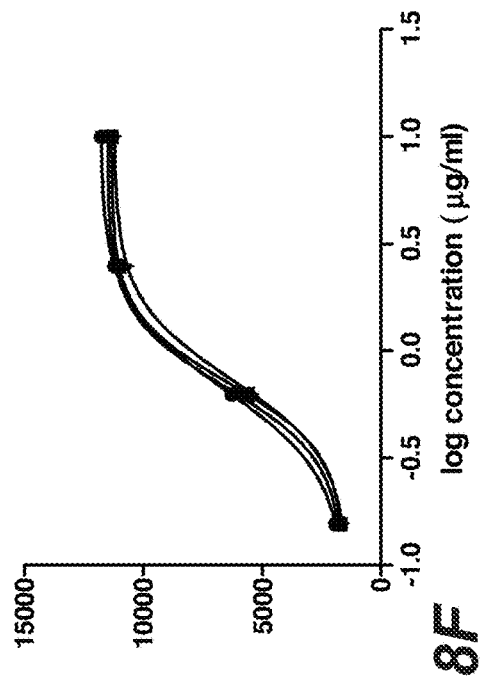
Figure 9A:
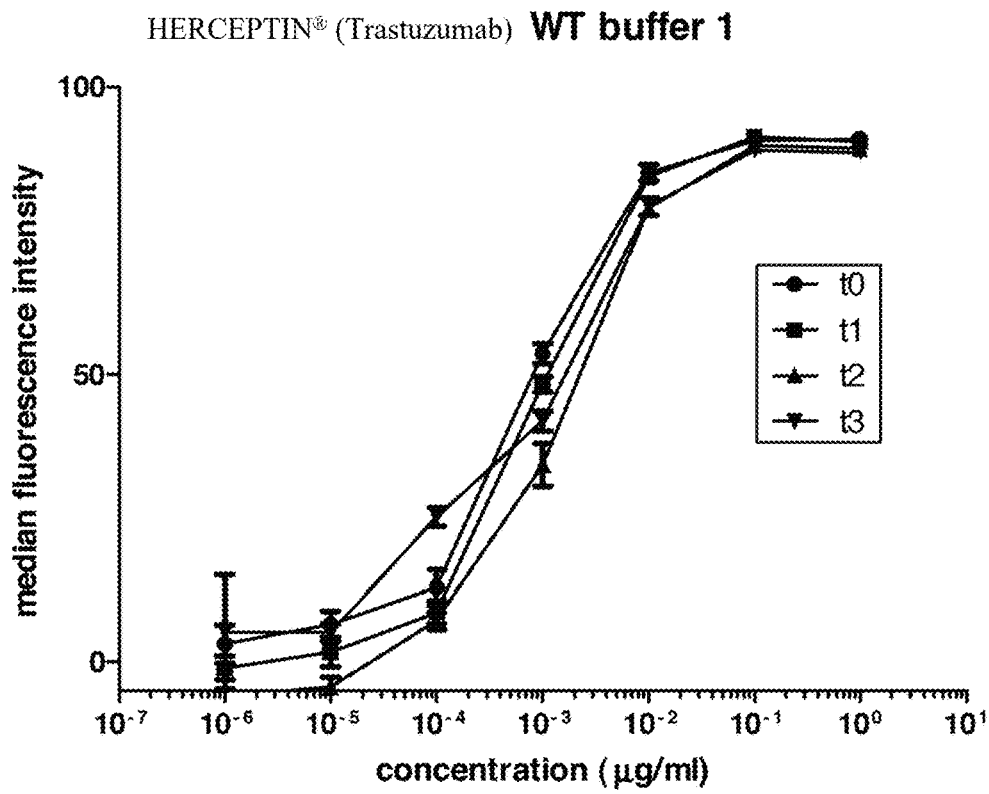
FIGS. 9A-9F: ADCC induction with Trastuzumab, GA602 and GA603 after stress on KPL-4 cells. Trastuzumab and the 2 stabilization variants GA602 (D98E mutation in heavy chain and T31V mutation in light chain) and GA603 (D98E mutation in heavy chain and T31V mutation in light chain and FcRN mutation T307Q und N434A) were incubated for one, two and three month in buffer 1 (40 mM Histidin 150 mM NaCl, pH 5.0) or buffer 2 (2. 40 mM Histidin 150 mM NaCl, pH6.0) at 40° C. The stressed antibodies were tested compared to the antibody at time point zero for ADCC induction after 4 h on KPL-4 cells.
Figure 9B:
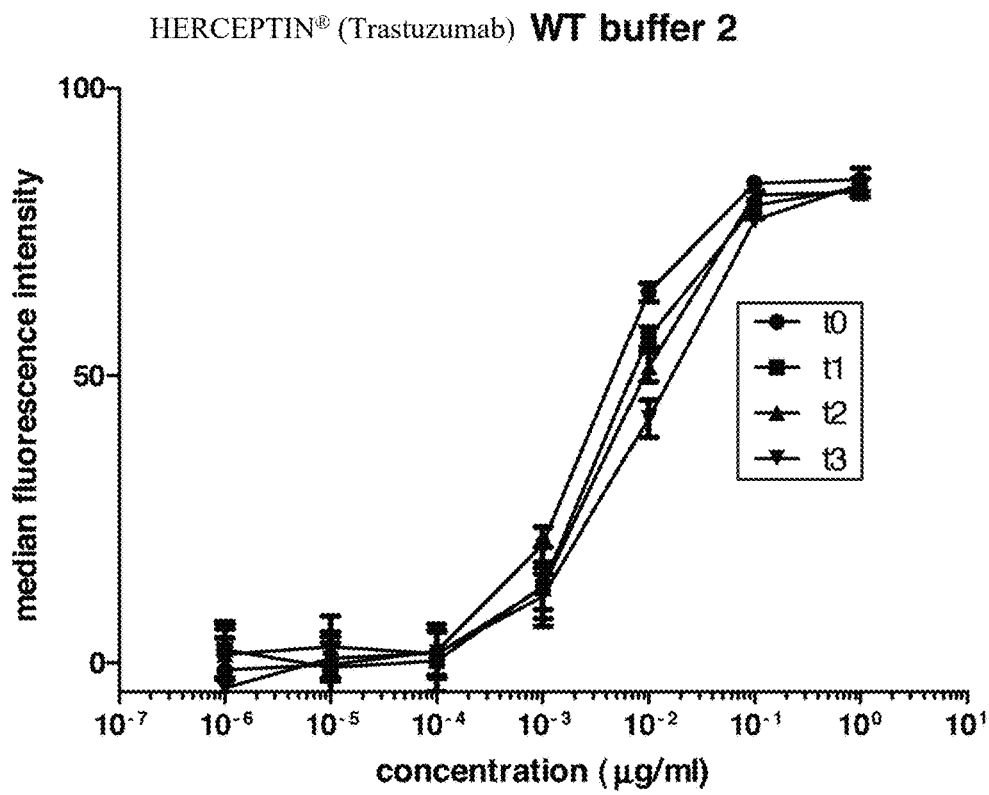
Figure 9C:
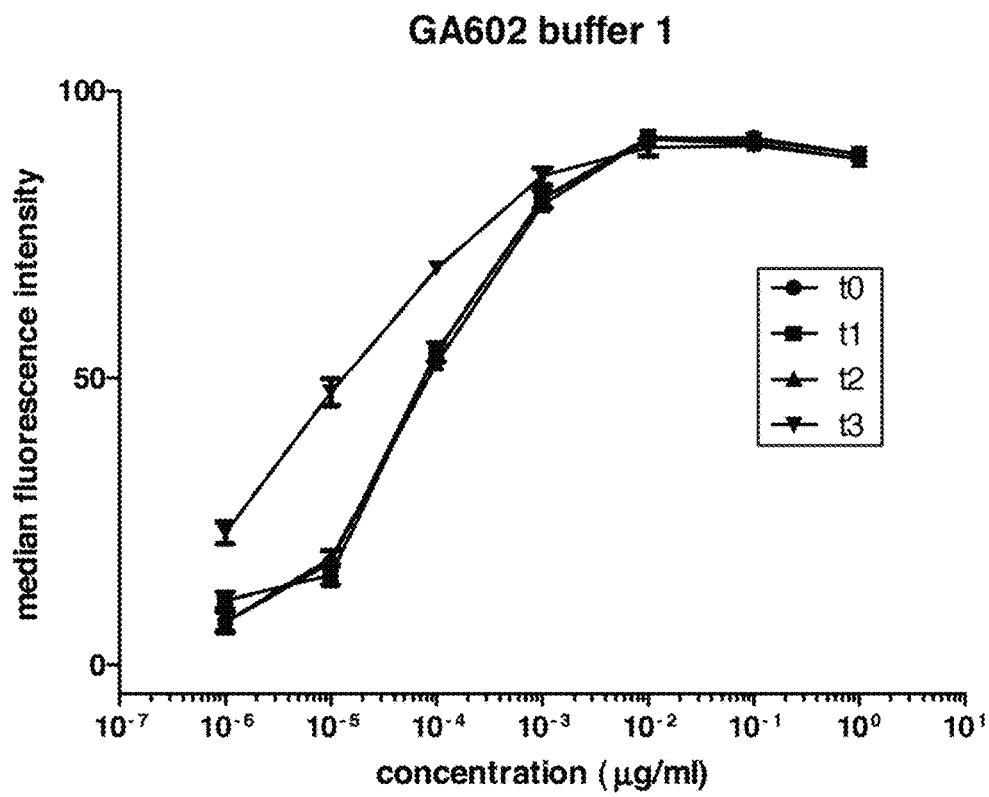
Figure 9D:
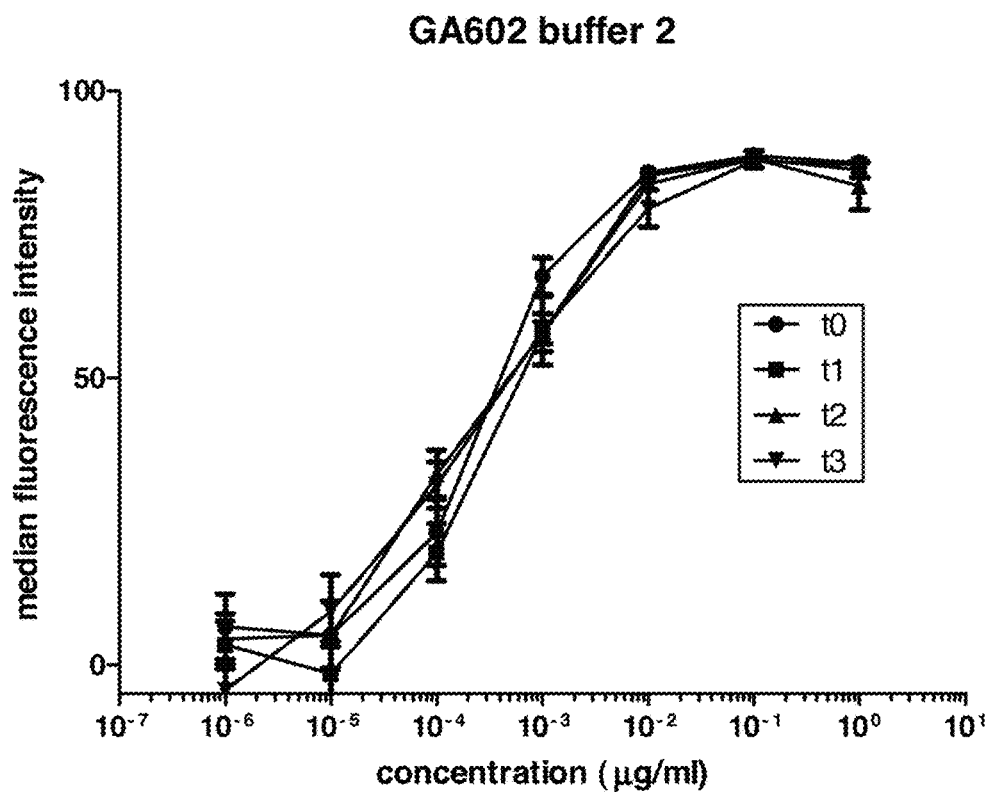
Figure 9E:
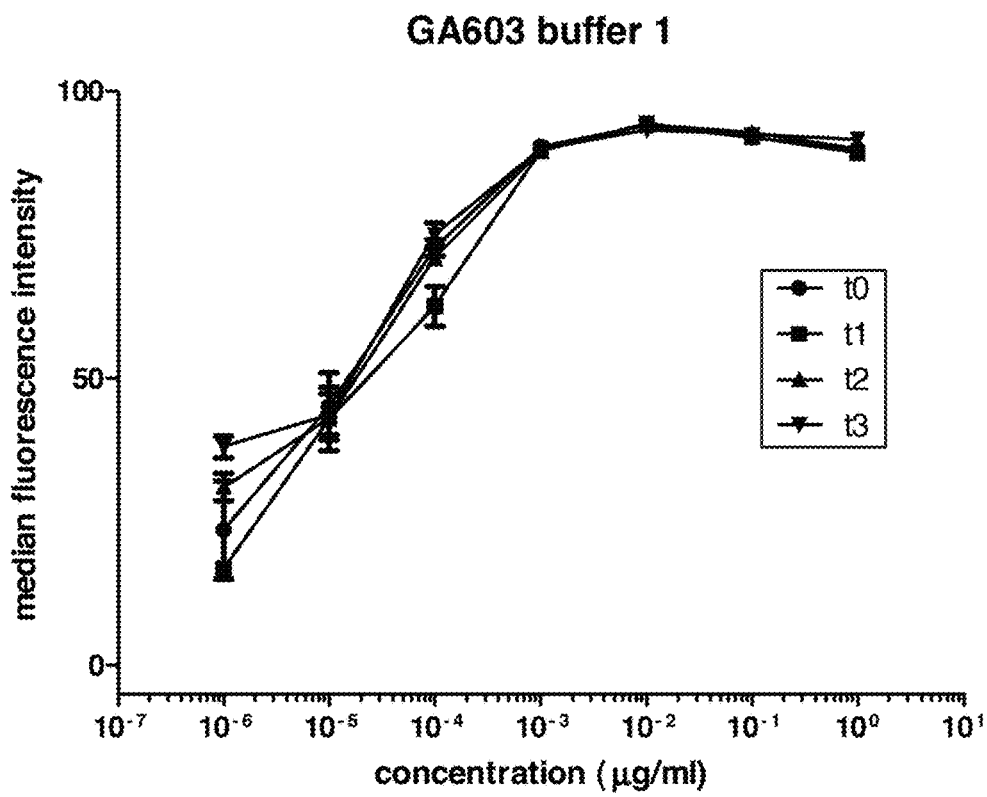
Figure 9F:
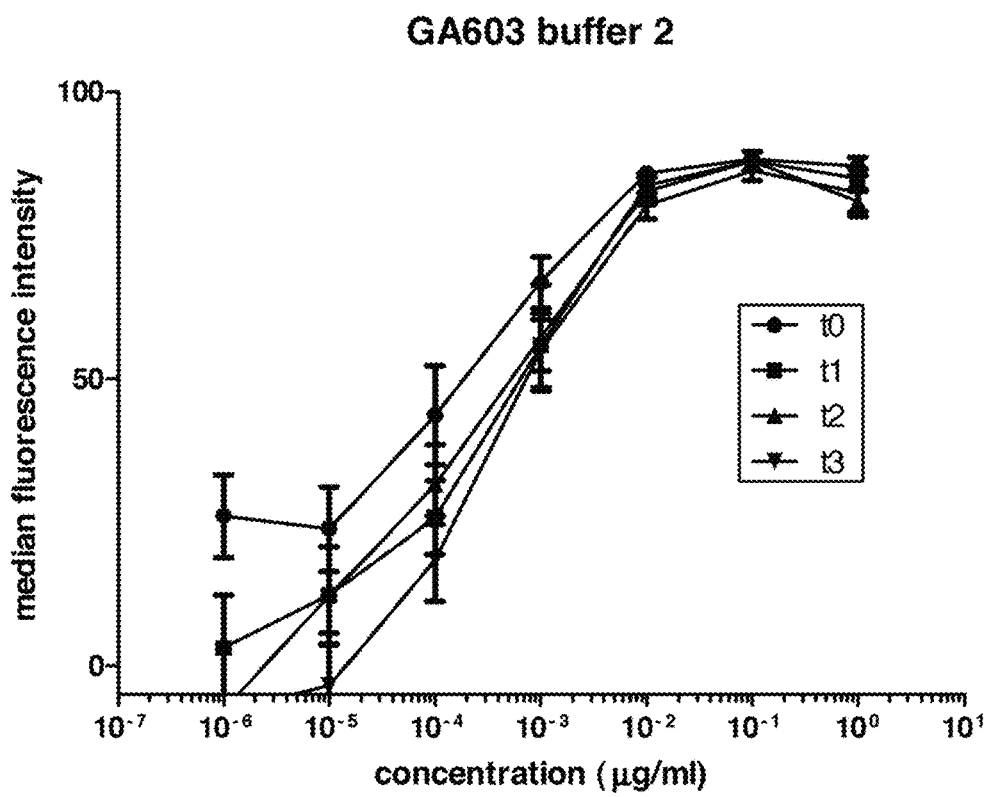

Herein, "HER2 extracellular domain" or "HER2 ECD" refers to a domain of HER2 that is outside of a cell, either anchored to a cell membrane, or in circulation, including fragments thereof. The amino acid sequence of HER2 is shown in FIG. 1 of WO2013055874. In one embodiment, the extracellular domain of HER2 may comprise four domains: "Domain I" (amino acid residues from about 1-195; SEQ ID NO: 1 of WO2013055874), "Domain T" (amino acid residues from about 196-319; SEQ ID NO:2 of WO2013055874), "Domain III" (amino acid residues from about 320-488: SEQ ID NO:3 of WO2013055874), and "Domain IV" (amino acid residues from about 489-630; SEQ ID NO:4 of WO2013055874) (residue numbering without signal peptide). See Garrett et al. Mol. Cell. 11: 495-505 (2003), Cho et al. Nature All: 756-760 (2003), Franklin et al. Cancer Cell 5:317-328 (2004), and Plowman et al. Proc. Natl. Acad. Sci. 90:1746-1750 (1993), as well as FIG. 6 in WO2013055874.

"Antigen binding site specific for extracellular domain II of HER2" refers to the epitope of Pertuzumab (which is also known as recombinant humanized monoclonal antibody 2C4 (rhuMAb 2C4)), also depicted as "epitope 2C4". The "epitope 2C4" is the region in the extracellular domain of HER2 to which the murine antibody 2C4 and Pertuzumab bind (see e.g. WO2013055874). In order to screen for antibodies which bind essentially to the 2C4 epitope, a routine cross-blocking assay such as that described in Antibodies, A Laboratory Manual, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds essentially to the 2C4 epitope of HER2. Epitope 2C4 comprises residues from Domain II (SEQ ID NO: 2 of WO2013055874) in the extracellular domain of HER2. 2C4 and Pertuzumab binds to the extracellular domain of HER2 at the junction of domains I, II and III (SEQ ID NOs: 1, 2, and 3 of WO2013055874, respectively). Franklin et al. Cancer Cell 5:317-328 (2004).

"Antigen binding site specific for extracellular domain IV of HER2" refers to the epitope of Trastuzumab, also depicted as "epitope 4D5". The "epitope 4D5" is the region in the extracellular domain of HER2 to which the antibody 4D5 (ATCC™ CRL 10463) and Trastuzumab bind. This epitope is close to the transmembrane domain of HER2, and within Domain IV of HER2 (SEQ ID NO: 4 of WO2013055874). To screen for antibodies which bind essentially to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds essentially to the 4D5 epitope of HER2 (e.g. any one or more residues in the region from about residue 529 to about residue 625, inclusive of the HER2 ECD, residue numbering including signal peptide).

The "blood-brain barrier" or "BBB" refers to the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The BBB within the brain, the blood-spinal cord barrier within the spinal cord, and the blood-retinal barrier within the retina are contiguous capillary barriers within the CNS, and are herein collectively referred to an the blood-brain barrier or BBB. The BBB also encompasses the blood-CSF barrier (choroid plexus) where the barrier is comprised of ependymal cells rather than capillary endothelial cells.

The term "blood brain barrier receptor" or "BBB-R" refers to an extracellular membrane-linked receptor protein expressed on brain endothelial cells which is capable of transporting molecules across the BBB and can be used to transport exogenous administrated molecules. Examples of BBB-R herein include: transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). In one specific embodiment the BBB-R is a transferrin receptor, preferably a human transferrin receptor and/or a cynomolgous monkey transferrin receptor. The term "transferrin receptor" or "TfR" refers to a transmembrane glycoprotein (with a molecular weight of about 180,000) composed of two disulphide-bonded subunits (each of apparent mo-lecular weight of about 90,000) involved in iron uptake in vertebrates. In one embodiment, the TfR herein is human TfR comprising the amino acid sequence as in Schneider et al. Nature 311: 675-678 (1984). The TfR mediates receptor-mediated transcytosis (RMT)

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "affinity reduced" antibody refers to an antibody with one or more alterations in one or more hypervariable regions (HVRs), compared to a parent antibody which does not possess such alterations, such alterations resulting in a reduction in the affinity of the antibody for antigen. Reduced affinity is advantageous for the exposure of the trispecific antibody specifically binding to HER2 and a blood-brain barrier receptor (BBB-R) in the brain.

The terms "a bispecific HER2 antibody" and "a bispecific antibody that specifically binds to HER2" are used interchangeably and refer to a bispecific antibody that is capable of binding HER2 on both extracellular domains II and IV, respectively, with sufficient affinity such that the antibody is useful as a diagnostic and/or therapeutic agent in targeting cells expressing HER2. In one embodiment, the extent of binding of a bispecific antibody that specifically binds to HER2 on both extracellular domains II and IV to an unrelated, non-HER2 protein is less than about 10% of the binding of the antibody to HER2 as measured, e.g., by a Enzyme-linked immunosorbent assay (ELISA), surface plasmon resonance (SPR) based assays (e.g. BIACORE™) or flow cytometry (FACS). In certain embodiments, a bispecific antibody that specifically binds to HER2 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ to $10^{-13}$ M, e.g., from $10^{-9}$ M to $10^{-13}$ M).

The terms "a trispecific antibody binding to HER2 and a blood-brain barrier receptor (BBB-R)" and "a trispecific antibody that specifically binds to HER2 and BBB-R" are used interchangeably and refer to a trispecific antibody that is capable of binding HER2 on both extracellular domains II and IV and a BBB-R, respectively, with sufficient affinity such that the antibody is useful as a diagnostic and/or therapeutic agent in targeting CNS cells expressing HER2. In one embodiment, the extent of binding of a trispecific antibody that specifically binds to HER2 on both extracellular domains II and IV and a BBB-R to an unrelated, non-HER2 or non BBB-R protein is less than about 10% of the binding of the antibody to HER2 or a BBB-R as measured, e.g., by a Enzyme-linked immunosorbent assay (ELISA), surface plasmon resonance (SPR) based assays (e.g. BIACORE™) or flow cytometry (FACS). In certain embodiments, the antigen binding site specifically binding to a BBB-R of the trispecific antibody has an off-rate of 0.07 to 0.005 l/s for the BBB-R, preferably as determined by SPR.

The term "antibody" herein is used in the broadest sense and encompasses various antibody structures, including but not limited to monoclonal antibodies, polyclonal antibodies, multispecific antibodies (e.g., trispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, cross-Fab fragments; linear antibodies; single-chain antibody molecules (e.g. scFv); and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, "Fab fragment" refers to an antibody fragment comprising a light chain fragment comprising a VL domain and a constant domain of a light chain (CL), and a VH domain and a first constant domain (CHI) of a heavy chain. In one embodiment the trispecific antibodies of the invention comprise at least one Fab fragment, wherein either the variable regions or the constant regions of the heavy and light chain are exchanged. Due to the exchange of either the variable regions or the constant regions, said Fab fragment is also referred to as "cross-Fab fragment" or "xFab fragment" or "crossover Fab fragment". Two different chain compositions of a crossover Fab molecule are possible and comprised in the trispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VL\,VH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CHI domain. In addition, these single chain Fab molecules might be further stabilized by generation of interchain disulfide bonds via insertion of cysteine residues (e.g. position 44 in the variable heavy chain and position 100 in the variable light chain according to Kabat numbering). The term "N-terminus denotes the last amino acid of the N-terminus. The term "C-terminus denotes the last amino acid of the C-terminus.

By "fused" or "connected" is meant that the components (e.g. a Fab molecule and an Fc domain subunit) are linked by peptide bonds, either directly or via one or more peptide linkers.

The term "linker" as used herein refers to a peptide linker and is preferably a peptide with an amino acid sequence with a length of at least 5 amino acids, preferably with a length of 5 to 100, more preferably of 10 to 50 amino acids. In one embodiment said peptide linker is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide linker is $(G_4S)_2$.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CHI, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species, usually prepared by recombinant DNA techniques. Chimeric antibodies comprising a rabbit variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP), cytokine secretion, immune complex-mediated antigen uptake by antigen presenting cells; down regulation of cell surface receptors (e.g. B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering. such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

An "effective amount" of an agent, e.g., a pharmaceutical formulation, refers to an amount effective, at dosages and for periods of time necessary, to achieve the desired therapeutic or prophylactic result.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 ("first subunit") and an IgG CH3 ("second subunit") constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. As also mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of Li, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, MD (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| VH CDR1 | 31-35 | 26-32 | 26-35 |
| VH CDR2 | 50-65 | 52-58 | 50-58 |
| VH CDR3 | 95-102 | 95-102 | 95-102 |
| VL CDR1 | 24-34 | 26-32 | 24-34 |
| VL CDR2 | 50-56 | 50-52 | 50-56 |
| VL CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a trispecific antibody that specifically binds HER2 and a BBB-R" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHI, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (u) and lambda (k), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The terms "cancer" and "cancerous" refer to or describe the physiological condition in mammals that is typically characterized by unregulated cell growth.

A cancer cell with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via in situ hybridization (ISH), including fluorescent in situ hybridization (FISH; see WO98/45479 published October, 1998) and chromogenic in situ hybridization (CISH; see, e.g. Tanner et al., Am. J. Pathol. 157(5): 1467-1472 (2000); Bella et al., J. Clin. Oncol. 26: (May 20 suppl; abstr 22147) (2008)), southern blotting, or polymerase chain reaction (PCR) techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

A "HER2-positive" cancer comprises cancer cells which have higher than normal levels of HER2. Examples of HER2-positive cancer include HER2-positive breast cancer, HER2-positive gastric cancer and HER2-positive ovarian cancer. Optionally, HER2-positive cancer has an immunohistochemistry (IHC) score of 2+ or 3+ and/or an in situ hybridization (ISH) amplification ratio >2.0.

"Metastatic" cancer refers to cancer which has spread from one part of the body (e.g. the breast) to another part of the body. "HER2-positive cancer with brain metastases" refers to HER2-positive cancer which has spread from one part of the body (e.g. the breast) to the central nervous system (CNS). The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, MD (1991) and/or those residues from a "hypervariable loop".

Antibody specificity refers to selective recognition of the antibody for a particular epitope of an antigen. Natural antibodies, for example, are monospecific. The term "monospecific" antibody as used herein denotes an antibody that has one or more binding sites each of which bind to the same epitope of the same antigen.

"Bispecific antibodies" according to the disclosure are antibodies which have two different antigen-binding specificities. Antibodies of the present invention are specific for two different epitopes of HER2, i.e. the extracellular domains II and IV of HER2. The term "bispecific" antibody as used herein denotes an antibody that has at least two binding sites each of which bind to different epitopes of the same antigen.

"Trispecific antibodies" according to the disclosure are antibodies which have three different antigen-binding specificities. Antibodies of the present invention are specific for two different epitopes of HER2, i.e. the extracellular domains II and IV of HER2 and a BBB-R. The term "trispecific" antibody as used herein denotes an antibody that has at least three binding sites each of which bind to different epitopes.

Trispecific antibodies may also be used to localize cytotoxic agents to cells which express HER2 and/or a BBB-R. Trispecific antibodies can be prepared as full length antibodies or antibody fragments.

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The trispecific antibodies according to the invention are at least "trivalent" and may be "multivalent" (e.g. "tetravalent" or "hexavalent").

Antibodies of the present invention have three binding sites and are trispecific. That is, the antibodies may be trispecific even in cases where there are more than three binding sites (i.e. that the antibody is multivalent). Trispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "amino acid" as used within this application denotes the group of naturally occurring carboxy a-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binding" or "specifically binding" refers to the binding of the antibody to an epitope of the antigen in an in-vitro assay, preferably in a surface plasmon resonance assay (SPR, BIACORE™, GE-Healthcare Uppsala, Sweden). The affinity of the binding is defined by the terms ka (rate constant for the association of the antibody from the antibody/antigen complex), kD (dissociation constant), and KD (kD/ka). Binding or specifically binding means a binding affinity (KD) of 10-8 mol/l or less, preferably 10-9 M to 10-13 mol/l.

Binding of the antibody to HER2 or a BBB-R can be investigated by a BIACORE™ assay (GE-Healthcare Uppsala, Sweden). The affinity of the binding is defined by the terms ka (rate constant for the association of the antibody from the antibody/antigen complex), kD (dissociation constant), and KD (kD/ka)

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

II. Compositions and Methods

In one aspect, the invention is based on trispecific antibodies specifically binding to HER2 and a BBB-R. Antibodies of the invention are useful, e.g., for the treatment or diagnosis of cancer, in particular a HER2-positive cancer with brain metastases. In one embodiment the trispecific antibody induces complement-dependent cytotoxicity (CDC) to a higher degree than the combination of Pertuzumab or Trastuzumab. In one such embodiment the complement dependent cytotoxicity of the trispecific antibody is determined by a LDH assay or a complement assay and compared to the complement dependent cytotoxicity of the combination of Pertuzumab and Trastuzumab as determined by the same assay. In one embodiment the complement dependent cytotoxicity is determined in vitro on cancer cells, preferably on breast cancer cells.

A. Exemplary BBB-R Binders Useful in the Trispecific Antibodies Specifically Binding to HER2 and a BBB-R In one aspect of the invention, a trispecific antibody specifically binding to HER2 and a BBB-R is provided, wherein the antibody comprises a first monovalent antigen binding site that specifically binds the extracellular domain II of HER2, a second monovalent antigen binding site that specifically binds the extracellular domain IV of HER2 and a third monovalent antigen binding site specifically binding to a BBB-R.

In one embodiment the BBB-R of the third antigen binding site is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In one preferred embodiment the third antigen binding site is specific for the transferrin receptor, preferably the human transferrin receptor.

In one embodiment, the invention provides a trispecific antibody that specifically binds to extracellular domains II and IV of HER2 and to a BBB-R, comprising an antigen binding site that specifically binds to an epitope in the transferrin receptor comprised within the amino acid sequence of SEQ ID NO: 202, 203 or 204.

In one embodiment, the invention provides a trispecific antibody that specifically binds to extracellular domains II and IV of HER2 and to a BBB-R comprising
a heavy chain comprising
(a) a heavy chain CDR1 comprising the amino acid sequence of SEQ ID NO: 172;
(b) a heavy chain CDR2 comprising the amino acid sequence of SEQ ID NO: 173;
(c) a heavy chain CDR3 comprising the amino acid sequence of SEQ ID NO: 174;
and a light chain comprising
(a) a light chain CDR2 comprising the amino acid sequence of SEQ ID NO: 175;
(b) a light chain CDR2 comprising the amino acid sequence of SEQ ID NO: 176;
(c) a light chain CDR3 comprising the amino acid sequence of SEQ ID NO: 177.

In one embodiment, the invention provides a trispecific antibody that specifically binds to extracellular domains II and IV of HER2 and to a BBB-R comprising a variable light chain comprising an amino acid sequence of SEQ ID NO: 178, a heavy chain comprising a variable heavy chain comprising an amino acid sequence of SEQ ID NO: 179

In one embodiment, the invention provides a trispecific antibody that specifically binds to extracellular domains II and IV of HER2 and to a BBB-R comprising a humanized light chain variable domain derived from the variable light chain comprising an amino acid sequence of SEQ ID NO: 178, a humanized heavy chain variable domain derived from the heavy chain comprising a variable heavy chain comprising an amino acid sequence of SEQ ID NO: 179.

In one embodiment, the invention provides a trispecific antibody that specifically binds to extracellular domains II and IV of HER2 and to a BBB-R comprising
a heavy chain comprising
(a) a heavy chain CDR1 comprising the amino acid sequence of SEQ ID NO: 180;
(b) a heavy chain CDR2 comprising the amino acid sequence of SEQ ID NO: 181;
(c) a heavy chain CDR3 comprising the amino acid sequence of SEQ ID NO: 182;
and a light chain comprising
(a) a light chain CDR1 comprising the amino acid sequence of SEQ ID NO: 183;
(b) a light chain CDR2 comprising the amino acid sequence of SEQ ID NO: 184;
(c) a light chain CDR3 comprising the amino acid sequence of SEQ ID NO: 185.

In one embodiment, the invention provides a trispecific antibody that specifically binds to extracellular domains II and IV of HER2 and to a BBB-R comprising a variable light chain comprising an amino acid sequence of SEQ ID NO: 166, a heavy chain comprising a variable heavy chain comprising an amino acid sequence of SEQ ID NO: 167

In one embodiment, the invention provides a trispecific antibody that specifically binds to extracellular domains II and IV of HER2 and to a BBB-R comprising a humanized light chain variable domain derived from the variable light chain comprising an amino acid sequence of SEQ ID NO: 166, a humanized heavy chain variable domain derived from the heavy chain comprising a variable heavy chain comprising an amino acid sequence of SEQ ID NO: 167.

In one embodiment the monovalent antigen binding site specifically binding to the human Transferrin receptor is further optimized for improved brain exposure. Towards this end, the affinity of the antigen binding site specifically binding to the human Transferrin receptor is reduced by introducing certain mutations into its amino acid sequence.

The equilibrium dissociation constants (KD) are commonly used to describe molecular interactions. It is used as a measure of two molecules' interaction strength (e.g. affinity) with each other. Thus, the KD value is a measure for the strength of a bimolecular interaction. However, the KD value as such does not describe the kinetics of the molecular interaction, i.e. from the KD value it cannot be deduced on the one hand how quickly the two molecules bind to each other (association rate constant or "on rate") and on the other hand how quickly the molecules dissociate (dissociation rate constant or "off-rate"). Characterizing bimolecular interactions only by their KD value neglects the fact that an identical KD value can be made up by extremely different (differing orders of magnitude) on and off-rates as the KD value is the ratio thereof. The on and off-rates are important for characterizing the binding behavior of molecules. The off-rate is especially important because it characterizes the binding duration of e.g. an antibody to its antigen. A long off-rate correlates to a slow dissociation of the formed complex whereas a short off-rate correlates to a quick dissociation.

In order to have a long-lasting (i.e. less frequent dosing requiring) or a tailor-made (e.g. depending on the surrounding conditions) interaction the off-rates have to be determined experimentally. This is even more important as it is next to impossible to predict the off-rate. Additionally the correlation between off-rate and binding affinity is poor as outlined above. For example, due to the fact that the KD value is the ratio of on and off-rate even weak binders can stay bound long to their target whereas tight binders can dissociate rapidly.

Herein are disclosed novel humanized and affinity reduced anti-transferrin receptor binders that have an off-rate for binding to the human transferrin receptor that is within a certain range in order to ensure proper BBB shuttling. It has been found that this range is defined at the one end by the off-rate of the murine anti-transferrin receptor antibody 128.1 (WO93/10819) determined by surface plasmon resonance for the cynomolgus transferrin receptor and at the other end by 5% of that off-rate (i.e. a 20-times slower dissociation). In one embodiment the monovalent antigen binding site specifically binding to the human Transferrin receptor (huTfR) and to the cynomolgus transferrin receptor (cyTfR) has an off-rate determined by surface plasmon resonance for the cynomolgus transferrin receptor between 0.1 1/s and 0.005 1/s.

In one embodiment the off-rate is determined at 500, 250, 125, 62.5, 31.25, 15.625 and 0 nM.

In one embodiment the off-rate is determined using a surface plasmon resonance chip with a biotin surface and a running buffer of 1×PBS supplemented with 250 mM sodium chloride at a flow rate of 10 μL/min. In one embodiment the association is monitored for 180 seconds and the dissociation is monitored for 600 seconds. In one embodiment the off-rate is determined on a BIACORE™ T200. In one embodiment the off-rate is between 0.08 1/s and 0.008 1/s. In one embodiment of all aspects the off-rate is determined at 25° C.

In one embodiment, the invention provides a trispecific antibody that specifically binds to extracellular domains II and IV of HER2 and to a BBB-R comprising a humanized, affinity reduced light chain variable domain derived from the variable light chain comprising an amino acid sequence of SEQ ID NO: 178, a humanized, affinity reduced heavy chain variable domain derived from the heavy chain comprising a variable heavy chain comprising an amino acid sequence of SEQ ID NO: 179.

In one embodiment, the invention provides a trispecific antibody that specifically binds to extracellular domains II and IV of HER2 and to a BBB-R comprising a humanized, affinity reduced light chain variable domain derived from the variable light chain comprising an amino acid sequence of SEQ ID NO: 166, a humanized, affinity reduced heavy chain variable domain derived from the heavy chain comprising a variable heavy chain comprising an amino acid sequence of SEQ ID NO: 167.

In one embodiment, the invention provides a trispecific antibody that specifically binds to extracellular domains II and IV of HER2 and to a BBB-R comprising
a heavy chain comprising
(a) a heavy chain CDR1 comprising the amino acid sequence of SEQ ID NO: 186;
(b) a heavy chain CDR2 comprising the amino acid sequence of SEQ ID NO: 187;
(c) a heavy chain CDR3 comprising the amino acid sequence selected from the group of SEQ ID NO: 188, SEQ ID NO: 206 or SEQ ID NO: 174;
and a light chain comprising
(a) a light chain CDR1 comprising the amino acid sequence of SEQ ID NO: 189;
(b) a light chain CDR2 comprising the amino acid sequence of SEQ ID NO: 190;
(c) a light chain CDR3 of SEQ ID NO: 191.

In one embodiment, the invention provides a trispecific antibody that specifically binds to extracellular domains II and IV of HER2 and to a BBB-R comprising a variable light chain comprising an amino acid sequence of SEQ ID NO: 192, a heavy chain comprising a variable heavy chain comprising an amino acid sequence of SEQ ID NO: 193 or SEQ ID NO: 205.

In one embodiment, the invention provides a trispecific antibody that specifically binds to extracellular domains II and IV of HER2 and to a BBB-R comprising a variable heavy chain comprising an amino acid sequence selected from the group of SEQ ID NO: 194, SEQ ID NO: 195, SEQ ID NO: 196, SEQ ID NO: 197, SEQ ID NO: 198, SEQ ID NO: 199, or SEQ ID NO: 200, and a variable light chain comprising an amino acid sequence selected from the group of SEQ ID NO: 201, SEQ ID NO: 207, SEQ ID NO: 208, or SEQ ID NO:209.

In one embodiment, the BBB-R antigen binding site comprises one single chain Fab (scFab) which is connected to a full length IgG antibody comprising the antigen binding sites specific for extracellular domains II and IV of HER2, wherein the scFab is connected either directly or by a linker to the C-terminal end of the Fc part of one of the heavy chains of the IgG antibody. In another embodiment the scFab is connected to the N-terminus of the IgG antibody, e.g. to the N-terminus of the variable light chain or heavy chain. In one embodiment the scFab is connected to the N-terminus of the IgG antibody with a linker.

In one embodiment, the BBB-R antigen binding site comprises one single chain Fv (scFv) which is connected to a full length IgG antibody comprising the antigen binding sites specific for extracellular domains II and IV of HER2, wherein the scFv is connected either directly or by a linker to the C-terminal end of the Fc part of one of the heavy chains of the IgG antibody. In another embodiment the scFv is connected to the N-terminus of the IgG antibody, e.g. to the N-terminus of the variable light chain or heavy chain. In one embodiment the scFv is connected to the N-terminus of the IgG antibody with a linker.

In one embodiment, the BBB-R antigen binding site comprises one crossover Fab fragment which is connected to a full length IgG antibody comprising the antigen binding sites specific for extracellular domains II and IV of HER2, wherein the crossover Fab fragment is connected either directly or by a linker to the C-terminal end of the Fc part of one of the heavy chains of the IgG antibody. In another embodiment the crossover Fab fragment is connected to the N-terminus of the IgG antibody, e.g. to the N-terminus of the variable light chain or heavy chain. In one embodiment the crossover Fab fragment is connected to the N-terminus of the IgG antibody with a linker. Crossover Fab fragments are Fab fragments wherein either the variable regions or the constant regions of the heavy and light chain are exchanged. Bispecific antibody formats comprising crossover Fab fragments have been described, for example, in WO2009080252, WO2009080253, WO2009080251, WO2009080254, WO2010/136172, WO2010/145792 and WO2013/026831.

In one embodiment, the BBB-R antigen binding site comprises one Fab fragment which is connected to a full length IgG antibody comprising the antigen binding sites specific for extracellular domains II and IV of HER2, wherein the Fab fragment is connected either directly or by a linker to the C-terminal end of the Fc part of one of the heavy chains of the IgG antibody. In another embodiment the Fab fragment is connected to the N-terminus of the IgG antibody, e.g. to the N-terminus of the variable light chain or heavy chain. In one embodiment the Fab fragment is connected to the N-terminus of the IgG antibody with a linker.

The term "linker" denotes a chemical linker or a peptidic linker that covalently connects BBB-R antigen binding site to the full length IgG antibody comprising the antigen binding sites specific for extracellular domains II and IV of HER2.

Single chain peptidic linkers, comprising of from one to twenty amino acid residues joined by peptide bonds, can be used. In certain embodiments, the amino acids are selected from the twenty naturally-occurring amino acids. In certain other embodiments, one or more of the amino acids are selected from glycine, alanine, proline, asparagine, glutamine and lysine. In other embodiments, the linker is a chemical linker. In certain embodiments, the linker is a single chain peptidic linker with an amino acid sequence with a length of at least 25 amino acid residues, in one preferred embodiment with a length of 32 to 50 amino acid residues. In one embodiment the peptidic linker is a (GxS)n linker with G=glycine, S=serine, (x=3, n=8, 9 or 10) or (x=4 and n=6, 7 or 8), in one embodiment with x=4, n=6 or 7, in one preferred embodiment with x=4, n=7. In one embodiment the linker is (G4S)4. In one embodiment the linker is (G4S)6G2.

Conjugation may be performed using a variety of chemical linkers. For example, the BBB-R antigen binding site may be connected to the full length IgG antibody comprising the antigen binding sites specific for extracellular domains II and IV of HER2 using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). The linker may be a "cleavable linker" facilitating release of the full length IgG antibody comprising the antigen binding sites specific for extracellular domains II and IV of HER2 upon delivery to the brain. For example, an acid-labile linker, peptidase-sensitive linker, photolabile linker, dimethyl linker or disulfide-containing linker (Chari et al, Cancer Res. 52 (1992) 127-131; U.S. Pat. No. 5,208,020) may be used.

Covalent conjugation can either be direct or via a linker. In certain embodiments, direct conjugation is by construction of a polypeptide fusion (i.e. by genetic fusion). In certain embodiments, direct conjugation is by formation of a covalent bond between a reactive group on one of the two portions of the BBB-R antigen binding site and a corresponding group or acceptor on the full length IgG antibody comprising the antigen binding sites specific for extracellular domains II and IV of HER2. In certain embodiments, direct conjugation is by modification (i.e. genetic modification) of one of the two molecules to be conjugated to include a reactive group (as non-limiting examples, a sulfhydryl group or a carboxyl group) that forms a covalent attachment to the other molecule to be conjugated under appropriate conditions. Conjugation may also be performed using a variety of linkers. For example, the BBB-R antigen binding site and the full length IgG antibody comprising the antigen binding sites specific for extracellular domains II and IV of HER2 may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptidic linkers, comprised of from one to twenty amino acid residues joined by peptide bonds, may also be used. In certain such embodiments, the amino acid residues are selected from the twenty naturally-occurring amino acids. In certain other such embodiments, one or more of the amino acid residues are selected from glycine, alanine, proline, asparagine, glutamine and lysine. The linker may be a "cleavable linker" facilitating release of the full length IgG antibody comprising the antigen binding sites specific for extracellular domains II and IV of HER2 upon delivery to the brain. For example, an acid-labile linker, peptidase-sensitive linker, photolabile linker, dimethyl linker or disulfide-containing linker (Chari et al, Cancer Res. 52 (1992) 127-131; U.S. Pat. No. 5,208,020) may be used. The above disclosed antigen binding site specifically binding to a BBB-R as outlined in this section are part of trispecific antibodies specifically binding to HER2 and a BBR-R. The antigen binding sites for HER2 as well as the antibody formats of the HER2 binders are described in sections II B and II C below.

B. Exemplary Trispecific Antibodies Specifically Binding to HER2 and a BBB-R with a Common Light Chain In one aspect of the invention, a trispecific antibody specifically binding to HER2 and a BBB-R is provided, wherein the antibody comprises a first monovalent antigen binding site that specifically binds the extracellular domain II of HER2, a second monovalent antigen binding site that specifically binds the extracellular domain IV of HER2 and a third monovalent antigen binding site specifically binding to a BBB-R as outlined in section II A above. The inventors of the present invention surprisingly generated a trispecific antibody wherein both binding moieties (i.e. antigen binding sites) that specifically bind to HER2 share a common light chain that retains the efficacy of the parent monospecific antibodies in terms of inhibition of tumor cell proliferation and has an increased affinity to the extracellular domain II of HER2. The generation of a trispecific molecule with a common light chain that retains the binding properties of both of the parent antibodies is not straight-forward as the common CDRs of the hybrid light chain have to retain the binding specifity for both the extracellular domains II and IV of HER2. The use of this so-called 'common light chain' principle, i.e. combining two binders that share one light chain but still have separate specificities, prevents light chain mispairing and in this particular case retains the epitope specificity of the parental antibodies. As a consequence, there are less side products during production, facilitating the homogenous preparation of HER2 trispecific antigen binding molecules at high yields. The heavy chain of Pertuzumab was further optimized, resulting in a more potent molecule in terms of affinity to the extracellular domain II of HER2. In addition, the Trastuzumab heavy chain has been stabilized by introducing certain mutations into the CDRs. The resulting molecule is superior to the parent Pertuzumab and Trastuzumab monospecific antibodies, plus targets the CNS through its BBB-R binding moiety. The trispecific HER2 antibodies in the monovalent common light chain format have an increased affinity to the pertuzumab epitope, and show superior inhibitory effects on cell proliferation as compared to the combination of the parental antibodies.

In one embodiment a trispecific antibody is provided, comprising a first Fab molecule capable of specific binding to extracellular domain II of HER2 and a second Fab molecule capable of specific binding to extracellular domain IV of HER2, wherein the sequence of the variable light chain of the first Fab molecule is identical to the sequence of the variable light chain of the second Fab molecule (i.e. the first and the second Fab molecule comprise a common light chain); and a third monovalent antigen binding site specifically binding to a BBB-R as outlined in section II A above.

In one embodiment, the invention provides a trispecific antibody that specifically binds to extracellular domains II and IV of HER2 and to a BBB-R comprising
a first heavy chain comprising
(a) a heavy chain CDR1 comprising the amino acid sequence of SEQ ID NO: 55;
(b) a heavy chain CDR2 comprising the amino acid sequence of SEQ ID NO: 77;
(c) a heavy chain CDR3 comprising the amino acid sequence of SEQ ID NO: 56;
and a second heavy chain comprising
(a) a heavy chain CDR1 comprising the amino acid sequence of SEQ ID NO: 20;
(b) a heavy chain CDR2 comprising the amino acid sequence of SEQ ID NO: 29;
(c) a heavy chain CDR3 comprising the amino acid sequence of SEQ ID NO: 30;
and a first and a second light chain comprising
(a) a light chain CDR1 comprising the amino acid sequence of SEQ ID NO: 89;
(b) a light chain CDR2 comprising the amino acid sequence of SEQ ID NO: 90;
(c) a light chain CDR3 comprising the amino acid sequence of SEQ ID NO: 19.

In one embodiment, the invention provides a trispecific antibody that specifically binds to extracellular domains II and IV of HER2 and to a BBB-R comprising
a first heavy chain comprising
(a) a heavy chain CDR1 comprising the amino acid sequence of SEQ ID NO: 14;
(b) a heavy chain CDR2 comprising the amino acid sequence of SEQ ID NO: 60;
(c) a heavy chain CDR3 comprising the amino acid sequence of SEQ ID NO: 16;
and a second heavy chain comprising
(a) a heavy chain CDR1 comprising the amino acid sequence of SEQ ID NO: 20;
(b) a heavy chain CDR2 comprising the amino acid sequence of SEQ ID NO: 29;
(c) a heavy chain CDR3 comprising the amino acid sequence of SEQ ID NO: 30;
and a first and a second light chain comprising
(a) a light chain CDR1 comprising the amino acid sequence of SEQ ID NO: 89;
(b) a light chain CDR2 comprising the amino acid sequence of SEQ ID NO: 90;
(c) a light chain CDR3 comprising the amino acid sequence of SEQ ID NO: 19.

In one embodiment, the invention provides a trispecific antibody that specifically binds to extracellular domains II and IV of HER2 and to a BBB-R comprising
a first heavy chain comprising
(a) a heavy chain CDR1 comprising the amino acid sequence of SEQ ID NO: 58;
(b) a heavy chain CDR2 comprising the amino acid sequence of SEQ ID NO: 15;
(c) a heavy chain CDR3 comprising the amino acid sequence of SEQ ID NO: 59;
and a second heavy chain comprising
(a) a heavy chain CDR1 comprising the amino acid sequence of SEQ ID NO: 20;
(b) a heavy chain CDR2 comprising the amino acid sequence of SEQ ID NO: 29;
(c) a heavy chain CDR3 comprising the amino acid sequence of SEQ ID NO: 30;
and a first and a second light chain comprising
(a) a light chain CDR1 comprising the amino acid sequence of SEQ ID NO: 89;
(b) a light chain CDR2 comprising the amino acid sequence of SEQ ID NO: 90;
(c) a light chain CDR3 comprising the amino acid sequence of SEQ ID NO: 19.

In one embodiment the second heavy chain of any of the embodiments above bears at least one modification in the amino acid sequence that confers higher chemical stability to the CDRs, resulting in retained binding to HER2 under stress conditions. Modifications useful herein are e.g. D98E, D98N, D98T, G99A or G99S. Surprisingly the inventors found that some modifications of the CDRs did not only improve the stability of the molecule but also improved the binding affinity to HER2.

Hence in one embodiment, the invention provides a trispecific antibody that specifically binds to extracellular domains II and IV of HER2 and to a BBB-R comprising
a first heavy chain comprising
(a) a heavy chain CDR1 comprising the amino acid sequence of SEQ ID NO: 55;
(b) a heavy chain CDR2 comprising the amino acid sequence of SEQ ID NO: 77;
(c) a heavy chain CDR3 comprising the amino acid sequence of SEQ ID NO: 56;
and a second heavy chain comprising
(a) a heavy chain CDR1 comprising the amino acid sequence of SEQ ID NO: 20;
(b) a heavy chain CDR2 comprising the amino acid sequence of SEQ ID NO: 29;
(c) a heavy chain CDR3 comprising the amino acid sequence of SEQ ID NO: 79;
and a first and a second light chain comprising
(a) a light chain CDR1 comprising the amino acid sequence of SEQ ID NO: 89;
(b) a light chain CDR2 comprising the amino acid sequence of SEQ ID NO: 90;
(c) a light chain CDR3 comprising the amino acid sequence of SEQ ID NO: 19.

In one embodiment, the invention provides a trispecific antibody that specifically binds to extracellular domains II and IV of HER2 and to a BBB-R comprising
a first heavy chain comprising
(a) a heavy chain CDR1 comprising the amino acid sequence of SEQ ID NO: 14;
(b) a heavy chain CDR2 comprising the amino acid sequence of SEQ ID NO: 60;
(c) a heavy chain CDR3 comprising the amino acid sequence of SEQ ID NO: 16;
and a second heavy chain comprising
(a) a heavy chain CDR1 comprising the amino acid sequence of SEQ ID NO: 20;
(b) a heavy chain CDR2 comprising the amino acid sequence of SEQ ID NO: 29;

(c) a heavy chain CDR3 comprising the amino acid sequence of SEQ ID NO: 79;

and a first and a second light chain comprising (a) a light chain CDR1 comprising the amino acid sequence of SEQ ID NO: 89;

(b) a light chain CDR2 comprising the amino acid sequence of SEQ ID NO: 90;

(c) a light chain CDR3 comprising the amino acid sequence of SEQ ID NO: 19.

In one embodiment, the invention provides a trispecific antibody that specifically binds to extracellular domains II and IV of HER2 and to a BBB-R comprising a first heavy chain comprising (a) a heavy chain CDR1 comprising the amino acid sequence of SEQ ID NO: 58;

(b) a heavy chain CDR2 comprising the amino acid sequence of SEQ ID NO: 15;

(c) a heavy chain CDR3 comprising the amino acid sequence of SEQ ID NO: 59;

and a second heavy chain comprising (a) a heavy chain CDR1 comprising the amino acid sequence of SEQ ID NO: 20;

(b) a heavy chain CDR2 comprising the amino acid sequence of SEQ ID NO: 29;

(c) a heavy chain CDR3 comprising the amino acid sequence of SEQ ID NO: 79;

and a first and a second light chain comprising (a) a light chain CDR1 comprising the amino acid sequence of SEQ ID NO: 89;

(b) a light chain CDR2 comprising the amino acid sequence of SEQ ID NO: 90;

(c) a light chain CDR3 comprising the amino acid sequence of SEQ ID NO: 19.

In one embodiment, the trispecific antibody comprises two variable light chains comprising an amino acid sequence of SEQ ID NO 54 (i.e. a common light chain), a first heavy chain comprising a variable heavy chain comprising an amino acid sequence of SEQ ID NO: 64, and a second heavy chain comprising a variable heavy chain comprising an amino acid sequence of SEQ ID NO 92 and a third monovalent antigen binding site specifically binding to a BBB-R as outlined in section II A above.

In one embodiment, the trispecific antibody comprises two variable light chains comprising an amino acid sequence of SEQ ID NO 54 (i.e. a common light chain), a first heavy chain comprising a variable heavy chain comprising an amino acid sequence of SEQ ID NO: 70, and a second heavy chain comprising a variable heavy chain comprising an amino acid sequence of SEQ ID NO 92 and a third monovalent antigen binding site specifically binding to a BBB-R as outlined in section II A above.

In one embodiment, the trispecific antibody comprises two variable light chains comprising an amino acid sequence of SEQ ID NO 54 (i.e. a common light chain), a first heavy chain comprising a variable heavy chain comprising an amino acid sequence of SEQ ID NO: 68, and a second heavy chain comprising a variable heavy chain comprising an amino acid sequence of SEQ ID NO: 92 and a third monovalent antigen binding site specifically binding to a BBB-R as outlined in section II A above.

In one embodiment the second heavy chain of any of the embodiments above bears at least one modification in the amino acid sequence that confers stability to the CDRs and the binding to the target, e.g. D98E, D98N, D98T, G99A or G99S.

Hence in one embodiment, the trispecific antibody comprises two variable light chains comprising an amino acid sequence of SEQ ID NO: 54 (i.e. a common light chain), a first heavy chain comprising a variable heavy chain comprising an amino acid sequence of SEQ ID NO: 64, and a second heavy chain comprising a variable heavy chain comprising an amino acid sequence of SEQ ID NO: 117 and a third monovalent antigen binding site specifically binding to a BBB-R as outlined in section II A above.

In one embodiment, the trispecific antibody comprises two variable light chains comprising an amino acid sequence of SEQ ID NO:54 (i.e. a common light chain), a first heavy chain comprising a variable heavy chain comprising an amino acid sequence of SEQ ID NO: 70, and a second heavy chain comprising a variable heavy chain comprising an amino acid sequence of SEQ ID NO: 117 and a third monovalent antigen binding site specifically binding to a BBB-R as outlined in section II A above.

In one embodiment, the trispecific antibody comprises two variable light chains comprising an amino acid sequence of SEQ ID NO:54 (i.e. a common light chain), a first heavy chain comprising a variable heavy chain comprising an amino acid sequence of SEQ ID NO: 68, and a second heavy chain comprising a variable heavy chain comprising an amino acid sequence of SEQ ID NO: 117 and a third monovalent antigen binding site specifically binding to a BBB-R as outlined in section II A above.

In one embodiment, the trispecific antibody of the invention comprises a first heavy chain constant region comprising the amino acid sequence of SEQ ID NO: 114.

In one embodiment, the trispecific antibody of the invention comprises a second heavy chain constant region comprising the amino acid sequence of SEQ ID NO: 115.

In another embodiment the trispecific antibody of the invention comprises a first light chain constant region comprising the amino acid sequence of SEQ ID NO: 113.

In another embodiment the trispecific antibody of the invention comprises a second light chain constant region comprising the amino acid sequence of SEQ ID NO: 116.

In one embodiment a trispecific antibody is provided comprising SEQ ID NOs: 165, 163 and 161.

In one embodiment a trispecific antibody is provided comprising SEQ ID NOs: 168, 169 and 161.

In one embodiment the trispecific antibody of any of the above embodiments comprises a Fc domain modification that promotes heterodimerization as outlined in section D below.

C. Exemplary Trispecific Antibodies Specifically Binding to HER2 and a BBB-R Comprising a Crossover Fab Fragment In one embodiment of the invention, a trispecific antibody specifically binding to HER2 and a BBB-R is provided, wherein the antibody comprises a first monovalent antigen binding site that specifically binds to the extracellular domain II of HER2, a second monovalent antigen binding site that specifically binds to the extracellular domain IV of HER2 and a third monovalent antigen binding site specifically binding to a BBB-R as outlined in section II A above. The inventors of the present invention generated a second trispecific antibody format wherein one of the binding moieties (i.e. antigen binding sites) for HER2 is a crossover Fab fragment. In one aspect of the invention a trispecific antibody is provided, comprising an IgG molecule, wherein one of the Fab fragments is replaced by a crossover Fab fragment. Crossover Fab fragments are Fab fragments wherein either the variable regions or the constant regions of the heavy and light chain are exchanged. Bispecific antibody formats comprising crossover Fab fragments have been described, for example, in WO2009080252, WO2009080253, WO2009080251, WO2009080254, WO2010/136172, WO2010/145792 and WO2013/026831. The native Trastuzumab sequence has been optimized by introducing modifications into the CDRs of both the variable heavy chain and the variable light chain to improve stability and affinity, the resulting sequences framework-grafted to avoid mispairing of the light chains in the trispecific molecule, resulting in highly potent trispecific antibodies that target HER2 and a BBB-R that can be produced with high yield and only low percentage of side products. In addition it shows superior inhibition of tumor cell proliferation as compared to the combination of the respective parental antibodies.

In one embodiment, the invention provides a trispecific antibody specifically binding to HER2 and a BBB-R comprising
    a first antigen binding site specific for extracellular domain II of HER2, comprising
      (a) a heavy chain CDR1 comprising the amino acid sequence of SEQ ID NO: 14;
      (b) a heavy chain CDR2 comprising the amino acid sequence of SEQ ID NO: 15;
      (c) a heavy chain CDR3 comprising the amino acid sequence of SEQ ID NO: 16;
      (d) a light chain CDR1 comprising the amino acid sequence of SEQ ID NO: 11;
      (e) a light chain CDR2 comprising the amino acid sequence of SEQ ID NO: 12;
      (f) a light chain CDR3 comprising the amino acid sequence of SEQ ID NO: 13;
    And a second antigen binding site specific for extracellular domain IV of HER2 comprising
      (a) a heavy chain CDR1 comprising the amino acid sequence of SEQ ID NO: 20;
      (b) a heavy chain CDR2 comprising the amino acid sequence of SEQ ID NO: 108;
      (c) a heavy chain CDR3 comprising the amino acid sequence of SEQ ID NO: 79;
      (d) a light chain CDR1 comprising the amino acid sequence of SEQ ID NO: 107;
      (e) a light chain CDR2 comprising the amino acid sequence of SEQ ID NO: 18;
      (f) a light chain CDR3 comprising the amino acid sequence of SEQ ID NO: 19;

In one embodiment, the trispecific antibody comprises a first antigen binding site specific for the extracellular domain II of HER2 comprising a variable heavy chain comprising an amino acid sequence of SEQ ID NO: 22 and a variable light chain comprising an amino acid sequence of SEQ ID NO: 24; and a second antigen binding site specific for the extracellular domain IV of HER2, comprising a heavy chain variable region comprising an amino acid sequence of SEQ ID NO: 105 and a light chain variable region comprising an amino acid sequence of SEQ ID NO: 106, and a third monovalent antigen binding site specifically binding to a BBB-R as outlined in section II A above.

In one embodiment, the invention provides a trispecific antibody that specifically binds to HER2 and a BBB-R comprising
    a first antigen binding site specific for extracellular domain II of HER2 comprising
      (a) a heavy chain CDR1 comprising the amino acid sequence of SEQ ID NO: 14;
      (b) a heavy chain CDR2 comprising the amino acid sequence of SEQ ID NO: 15;
      (c) a heavy chain CDR3 comprising the amino acid sequence of SEQ ID NO: 16;
      (d) a light chain CDR1 comprising the amino acid sequence of SEQ ID NO: 11;
      (e) a light chain CDR2 comprising the amino acid sequence of SEQ ID NO: 12;
      (f) a light chain CDR3 comprising the amino acid sequence of SEQ ID NO: 13.
and a second antigen binding site specific for extracellular domain IV of HER2, comprising
      (a) a heavy chain CDR1 comprising the amino acid sequence of SEQ ID NO: 20;
      (b) a heavy chain CDR2 comprising the amino acid sequence of SEQ ID NO: 29;
      (c) a heavy chain CDR3 comprising the amino acid sequence of SEQ ID NO: 79;
      (d) a light chain CDR1 comprising the amino acid sequence of SEQ ID NO: 104;
      (e) a light chain CDR2 comprising the amino acid sequence of SEQ ID NO: 18;
      (f) a light chain CDR3 comprising the amino acid sequence of SEQ ID NO: 19.

In one embodiment, the trispecific antibody comprises a first antigen binding site specific for the extracellular domain II of HER2 comprising a variable heavy chain comprising an amino acid sequence of SEQ ID NO: 22 and a variable light chain comprising an amino acid sequence of SEQ ID NO: 24; and a second antigen binding site specific for the extracellular domain IV of HER2, comprising a heavy chain variable region comprising an amino acid sequence of SEQ ID NO: 117 and a light chain variable region comprising an amino acid sequence of SEQ ID NO: 118, and a third monovalent antigen binding site specifically binding to a BBB-R as outlined in section II A above.

In one embodiment, the invention provides a trispecific antibody that specifically binds to HER2 and a BBB-R comprising
    a first antigen binding site specific for extracellular domain II of HER2 comprising
      (a) a heavy chain CDR1 comprising the amino acid sequence of SEQ ID NO: 14;
      (b) a heavy chain CDR2 comprising the amino acid sequence of SEQ ID NO: 15;
      (c) a heavy chain CDR3 comprising the amino acid sequence of SEQ ID NO: 16;
      (d) a light chain CDR1 comprising the amino acid sequence of SEQ ID NO: 11;
      (e) a light chain CDR2 comprising the amino acid sequence of SEQ ID NO: 12;
      (f) a light chain CDR3 comprising the amino acid sequence of SEQ ID NO: 13.
and a second antigen binding site specific for extracellular domain IV of HER2, comprising
      (a) a heavy chain CDR1 comprising the amino acid sequence of SEQ ID NO: 20;
      (b) a heavy chain CDR2 comprising the amino acid sequence of SEQ ID NO: 29;
      (c) a heavy chain CDR3 comprising the amino acid sequence selected from the group consisting of SEQ ID NO: 79, SEQ ID NO: 78, SEQ ID NO: 80, SEQ ID NO: 87, SEQ ID NO: 88;
      (d) a light chain CDR1 comprising the amino acid sequence selected from the group consisting of SEQ ID NO: 104, SEQ ID NO: 103 and SEQ ID NO: 158;
      (e) a light chain CDR2 comprising the amino acid sequence of SEQ ID NO: 18;
      (f) a light chain CDR3 comprising the amino acid sequence of SEQ ID NO: 19;

In one embodiment, the trispecific antibody of the invention comprises a first heavy chain constant region comprising the amino acid sequence of SEQ ID NO: 114.

In one embodiment, the trispecific antibody of the invention comprises a first heavy chain constant region comprising the amino acid sequence of SEQ ID NO: 114, wherein the C-terminal Lysine has been removed.

In one embodiment, the trispecific antibody of the invention comprises a second heavy chain constant region comprising the amino acid sequence of SEQ ID NO: 115.

In one embodiment, the trispecific antibody of the invention comprises a second heavy chain constant region comprising the amino acid sequence of SEQ ID NO: 115, wherein the C-terminal Lysine has been removed.

In another embodiment the trispecific antibody of the invention comprises a first light chain constant region comprising the amino acid sequence of SEQ ID NO: 113.

In another embodiment the trispecific antibody of the invention comprises a second light chain constant region comprising the amino acid sequence of SEQ ID NO: 116.

In one embodiment a trispecific antibody is provided comprising SEQ ID NOs: 109, 110, 111 and 112.

In one embodiment a trispecific antibody that specifically binds to HER2 and a BBB-R according to any of the above embodiments comprises
an Fc domain,
one Fab fragment comprising a first antigen binding site specific for the extracellular domain II of HER2,
and one Fab fragment comprising a second antigen binding site specific for the extracellular domain IV of HER2,
wherein either the variable regions or the constant regions of the heavy and light chain of at least one Fab fragment are exchanged and
a third monovalent antigen binding site specifically binding to a BBB-R as outlined in section II A above.

The trispecific antibodies described in this section are monovalent for the extracellular domain II of HER2 and monovalent for the extracellular domain IV of HER2. Due to the exchange of either the variable regions or the constant regions, the Fab fragment above is also referred to as "cross-Fab fragment" or "xFab fragment" or "crossover Fab fragment".

In one embodiment a trispecific antibody that specifically binds to HER2 and a BBB-R according to any of the above embodiments comprises
an Fc domain,
one Fab fragment comprising an antigen binding site specific for the extracellular domain II of HER2, wherein either the variable regions or the constant regions of the heavy and light chain are exchanged.
and one Fab fragment comprising an antigen binding site specific for the extracellular domain IV of HER2, and
a third monovalent antigen binding site specifically binding to a BBB-R as outlined in section II A above.

In one embodiment a trispecific antibody that specifically binds to HER2 and a BBB-R according to any of the above embodiments comprises
an Fc domain,
one Fab fragment comprising an antigen binding site specific for the extracellular domain II of HER2,
and one Fab fragment comprising an antigen binding site specific for the extracellular domain IV of HER2, wherein either the variable regions or the constant regions of the heavy and light chain are exchanged, and
a third monovalent antigen binding site specifically binding to a BBB-R as outlined in section II A above.

In one embodiment a trispecific antibody that specifically binds to HER2 and a BBB-R according to any of the above embodiments comprises
an Fc domain,
one Fab fragment comprising an antigen binding site specific for the extracellular domain II of HER2,
and one Fab fragment comprising an antigen binding site specific for the extracellular domain IV of HER2, wherein the variable regions of the heavy and light chain of the Fab fragment are exchanged;
and a third monovalent antigen binding site specifically binding to a BBB-R as outlined in section II A above.

In one embodiment a trispecific antibody that specifically binds to HER2 and a BBB-R according to any of the above embodiments comprises
an Fc domain,
one Fab fragments comprising an antigen binding site specific for the extracellular domain II of HER2,
and one Fab fragment comprising an antigen binding site specific for the extracellular domain IV of HER2, wherein the constant regions of the heavy and light chain are exchanged, and a third monovalent antigen binding site specifically binding to a BBB-R as outlined in section II A above.

In one embodiment said trispecific antibody that specifically binds to HER2 and a BBB-R according to any of the above embodiments comprises an Fc domain to which two Fab fragments are fused to the N-terminus, wherein either the variable regions or the constant regions of the heavy and light chain of at least one Fab fragment are exchanged and a third monovalent antigen binding site specifically binding to a BBB-R as outlined in section II A above. In one embodiment the two Fab fragments are fused to the N-terminus of the Fc domain through an immunoglobulin hinge region. In one embodiment, the immunoglobulin hinge region is a human IgG1 hinge region. In one embodiment the Fab fragment comprising an antigen binding site specific for the extracellular domain II of HER2, the Fab fragment comprising an antigen binding site specific for the extracellular domain IV of HER2 and the Fc domain are part of an immunoglobulin molecule. In a particular embodiment the immunoglobulin molecule is an IgG class immunoglobulin. In an even more particular embodiment the immunoglobulin is an IgG1 subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin.

In one embodiment a trispecific antibody that specifically binds to HER2 and a BBB-R according to any of the above embodiments comprises an Immunoglobulin G (IgG) molecule with one binding site specific for the extracellular domain II of HER2 and one binding site specific for the extracellular domain IV of HER2, wherein either the variable regions or the constant regions of the heavy and light chain of one arm (Fab fragment) of the IgG molecule are exchanged, and a third monovalent antigen binding site specifically binding to a BBB-R as outlined in section II A above.

In one embodiment a trispecific antibody that specifically binds to HER2 and a BBB-R according to any of the above embodiments comprises an Immunoglobulin G (IgG) molecule with one binding site specific for the extracellular domain II of HER2 and one binding site specific for the extracellular domain IV of HER2, wherein the variable regions of the heavy and light chain of one arm (Fab fragment) of the IgG molecule are exchanged, and a third monovalent antigen binding site specifically binding to a BBB-R as outlined in section II A above. In one embodiment the variable regions of the heavy and light chain of the one arm (Fab fragment) of the IgG molecule which comprises the binding site specific for the extracellular domain IV of HER2 are exchanged.

In one embodiment a trispecific antibody that specifically binds to HER2 and a BBB-R according to any of the above embodiments comprises an Immunoglobulin G (IgG) molecule with one binding site specific for the extracellular domain II of HER2 and one binding site specific for the extracellular domain IV of HER2, wherein the constant regions of the heavy and light chain of one arm (Fab fragment) of the IgG molecule are exchanged, and a third monovalent antigen binding site specifically binding to a BBB-R as outlined in section II A above. In one embodiment the constant regions of the heavy and light chain of the one arm (Fab fragment) of the IgG molecule which comprises the binding site specific for the extracellular domain IV of HER2 are exchanged.

In one embodiment a trispecific antibody that specifically binds to HER2 and a BBB-R according to any of the above embodiments comprises an Immunoglobulin G (IgG) molecule with one binding site specific for the extracellular domain II of HER2 and one binding site specific for the extracellular domain IV of HER2, wherein the complete VH-CH1 and VL-CL domains of one arm (Fab fragment) of the IgG molecule are exchanged; and a third monovalent antigen binding site specifically binding to a BBB-R as outlined in section II A above.

This means that at least one of the Fab fragments is fused to the N-terminus of the Fc domain via the light chain (VLCL). In one embodiment the other Fab fragment is fused to the N-terminus of the Fc domain via the heavy chain (VHCH1). In one embodiment both Fab fragments are fused to the N-terminus of the Fc domain through an immunoglobulin hinge region.

In one embodiment the trispecific antibody of any of the above embodiments comprises a Fc domain modification that promotes heterodimerization as outlined in section D below.

D. Fc Domain Modifications Promoting Heterodimerization

The trispecific antibodies binding to HER2 and a blood-brain barrier receptor (BBB-R) of the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of the antibodies of the invention in recombinant production, it will thus be advantageous to introduce in the Fc domain of the trispecific antibodies of the invention a modification promoting the association of the desired polypeptides.

Accordingly, in particular embodiments the Fc domain of the trispecific antibodies of the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the trispecific antibodies of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)).

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

In one embodiment a trispecific antibodies binding to HER2 and a blood-brain barrier receptor (BBB-R) according to any of the above embodiments comprises an Immunoglobulin G (IgG) molecule comprising a first antigen binding site specific for extracellular domain II of HER2 and a second antigen binding site specific for extracellular domain IV of HER2 and a monovalent third antigen binding site specific for a BBB-R, wherein the Fc part of the first heavy chain comprises a first dimerization module and the Fc part of the second heavy chain comprises a second dimerization module allowing a heterodimerization of the two heavy chains of the IgG molecule.

In a further preferred embodiment, the first dimerization module comprises knobs and the second dimerization module comprises holes according to the knobs into holes strategy (see Carter P.; Ridgway J. B. B.; Presta L. G.: Immunotechnology, Volume 2, Number 1, February 1996, pp. 73-73(1)).

E. Nucleic Acid Sequences, Vectors and Methods of

The invention further provides isolated polynucleotides encoding trispecific antibodies binding to HER2 and a blood-brain barrier receptor (BBB-R) as described herein or a fragment thereof. The polynucleotides encoding trispecific antibodies of the invention may be expressed as a single polynucleotide that encodes the entire trispecific antigen binding molecule or as multiple (e.g., two or more) polynucleotides that are co-expressed. Polypeptides encoded by polynucleotides that are co-expressed may associate through, e.g., disulfide bonds or other means to form a functional trispecific antibody. For example, the light chain portion of a Fab fragment may be encoded by a separate polynucleotide from the portion of the trispecific antibody comprising the heavy chain portion of the Fab fragment, an Fc domain subunit and optionally (part of) another Fab fragment. When co-expressed, the heavy chain polypeptides will associate with the light chain polypeptides to form the Fab fragment. In another example, the portion of the trispecific antibody provided therein comprising one of the two Fc domain subunits and optionally (part of) one or more Fab fragments could be encoded by a separate polynucleotide from the portion of the trispecific antibody provided therein comprising the other of the two Fc domain subunits and optionally (part of) a Fab fragment. When co-expressed, the Fc domain subunits will associate to form the Fc domain.

In one embodiment, the present invention is directed to an isolated polynucleotide encoding a trispecific antibody of the invention or a fragment thereof, wherein the polynucleotide comprises a sequence that encodes a first variable heavy chain sequence as shown in SEQ ID NOs 63, 67 and 69. In one embodiment, the present invention is directed to an isolated polynucleotide encoding a trispecific antibody of the invention or a fragment thereof, wherein the polynucleotide comprises a sequence that encodes a second variable heavy chain sequence as shown in SEQ ID NOs 91 and 133.

In one embodiment, the present invention is directed to an isolated polynucleotide encoding a trispecific antibody of the invention or a fragment thereof, wherein the polynucleotide comprises a sequence that encodes a variable light chain sequence as shown in SEQ ID NO: 53.

In another embodiment, the present invention is directed to an isolated polynucleotide encoding a trispecific antibody or fragment thereof, wherein the polynucleotide comprises a sequence that encodes a polypeptide sequence as shown in SEQ ID NOs 83, 85, 91, 93, 95, 97, 99, 101, 63, 67, 69, 53, 21 and 23.

In another embodiment, the invention is directed to an isolated polynucleotide encoding a trispecific antibody of the invention or a fragment thereof, wherein the polynucleotide comprises a sequence that encodes a first variable heavy chain sequence that is at least about 80%, 85%, 90%, 95%, 96%, 97%, 98%, or 99% identical to an amino acid sequence in SEQ ID NOs 63, 67 and 69.

In another embodiment, the invention is directed to an isolated polynucleotide encoding a trispecific antibody of the invention or a fragment thereof, wherein the polynucleotide comprises a sequence that encodes a second variable heavy chain sequence that is at least about 80%, 85%, 90%, 95%, 96%, 97%, 98%, or 99% identical to an amino acid sequence in SEQ ID NOs 91 and 133.

In another embodiment, the invention is directed to an isolated polynucleotide encoding a trispecific antibody of the invention or a fragment thereof, wherein the polynucleotide comprises a sequence that encodes a variable light chain sequence that is at least about 80%, 85%, 90%, 95%, 96%, 97%, 98%, or 99% identical to an amino acid sequence in SEQ ID NO: 53. In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

In further objects the present invention relates to an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

F. Fc Domain Modifications Reducing Fc Receptor Binding and/or Effector Function In one aspect a trispecific antibodies binding to HER2 and a blood-brain barrier receptor (BBB-R) according to any of the above embodiments comprises an Immunoglobulin G (IgG) molecule wherein the Fc part is modified. The modified Fc part has a reduced binding affinity for the Fcγ receptors compared to a wildtype Fc part.

The Fc domain of the trispecific antibodies of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

In one embodiment according the invention the Fc domain of the trispecific antibodies of the invention is an IgG Fc domain. In a particular embodiment the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat numbering), particularly the amino acid substitution S228P. In a more specific embodiment, the Fc domain is an $IgG_4$ Fc domain comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)). In a further particular embodiment the Fc domain is human.

The Fc domain confers favorable pharmacokinetic properties to the trispecific antibodies of the invention, including a long serum half-life which contributes to good accumulation in the target tissue and a favorable tissue-blood distribution ratio. At the same time it may, however, lead to undesirable targeting of the trispecific antibodies of the invention to cells expressing Fc receptors rather than to the preferred antigen-bearing cells. Accordingly, in particular embodiments the Fc domain of the trispecific antibodies of the invention exhibits reduced binding affinity to an Fc receptor and/or reduced effector function, as compared to a native $IgG_1$ Fc domain. In one such embodiment the Fc domain (or the trispecific antibodies of the invention comprising said Fc domain) exhibits less than 50%, preferably less than 20%, more preferably less than 10% and most preferably less than 5% of the binding affinity to an Fc receptor, as compared to a native IgG$_1$ Fc domain (or a trispecific antibodies of the invention comprising a native IgG$_1$ Fc domain), and/or less than 50%, preferably less than 20%, more preferably less than 10% and most preferably less than 5% of the effector function, as compared to a native IgG$_1$ Fc domain (or a trispecific antibodies of the invention comprising a native IgG$_1$ Fc domain). In one embodiment, the Fc domain (or the trispecific antibodies of the invention comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the Fc receptor is an inhibitory Fc receptor. In a specific embodiment the Fc receptor is an inhibitory human Fcγ receptor, more specifically human FcgRIIB. In one embodiment the effector function is one or more of CDC, ADCC, ADCP, and cytokine secretion. In a particular embodiment the effector function is ADCC. In one embodiment the Fc domain exhibits substantially similar binding affinity to neonatal Fc receptor (FcRn), as compared to a native IgG$_1$ Fc domain. Substantially similar binding to FcRn is achieved when the Fc domain (or the trispecific antibodies of the invention comprising said Fc domain) exhibits greater than about 70%, particularly greater than about 80%, more particularly greater than about 90% of the binding affinity of a native IgG$_i$ Fc domain (or the trispecific antibodies of the invention comprising a native IgG$_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the trispecific antibodies of the invention comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the trispecific antibodies of the invention comprising an engineered Fc domain exhibits less than 20%, particularly less than 10%, more particularly less than 5% of the binding affinity to an Fc receptor as compared to a trispecific antibodies of the invention comprising a non-engineered Fc domain. In a particular embodiment the Fc receptor is an Fcγ receptor. In some embodiments the Fc receptor is a human Fc receptor. In one embodiment the Fc receptor is an inhibitory Fc receptor. In a specific embodiment the Fc receptor is an inhibitory human Fcγ receptor, more specifically human FcgRIIB. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the trispecific antibodies of the invention comprising said Fc domain) exhibits greater than about 70% of the binding affinity of a non-engineered form of the Fc domain (or the trispecific antibodies of the invention comprising said non-engineered form of the Fc domain) to FcRn. The Fc domain, or the trispecific antibodies of the invention of the invention comprising said Fc domain, may exhibit greater than about 80% and even greater than about 90% of such affinity. In certain embodiments the Fc domain of the trispecific antibodies of the invention is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming. In one embodiment the reduced effector function is one or more of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a trispecific antibody of the invention comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position of E233, L234, L235, N297, P331 and P329. In a more specific embodiment the Fc domain comprises an amino acid substitution at a position of L234, L235 and P329. In some embodiments the Fc domain comprises the amino acid substitutions L234A and L235A. In one such embodiment, the Fc domain is an IgG$_1$ Fc domain, particularly a human IgG$_i$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In more particular embodiments the Fc domain comprises the amino acid mutations L234A, L235A and P329G ("P329G LALA"). In one such embodiment, the Fc domain is an IgG$_1$ Fc domain, particularly a human IgG$_1$ Fc domain. The "P329G LALA" combination of amino acid substitutions almost completely abolishes Fcγ receptor binding of a human IgG$_1$ Fc domain, as described in PCT patent application no. PCT/EP2012/055393, incorporated herein by reference in its entirety. PCT/EP2012/055393 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments the Fc domain of the trispecific antibodies of the invention is an IgG$_4$ Fc domain, particularly a human IgG$_4$ Fc domain. In one embodiment the IgG$_4$ Fc domain comprises amino acid substitutions at position S228, specifically the amino acid substitution S228P. To further reduce its binding affinity to an Fc receptor and/or its effector function, in one embodiment the IgG$_4$ Fc domain comprises an amino acid substitution at position L235, specifically the amino acid substitution L235E. In another embodiment, the IgG$_4$ Fc domain comprises an amino acid substitution at position P329, specifically the amino acid substitution P329G. In a particular embodiment, the IgG4 Fc domain comprises amino acid substitutions at positions S228, L235 and P329, specifically amino acid substitutions S228P, L235E and P329G. Such IgG4 Fc domain mutants and their Fcγ receptor binding properties are described in PCT patent application no. PCT/EP2012/055393, incorporated herein by reference in its entirety.

In a particular embodiment the Fc domain exhibiting reduced binding affinity to an Fc receptor and/or reduced effector function, as compared to a native IgG$_i$ Fc domain, is a human IgG$_1$ Fc domain comprising the amino acid substitutions L234A, L235A and optionally P329G, or a human IgG4 Fc domain comprising the amino acid substitutions S228P, L235E and optionally P329G.

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D). In addition to the Fc domains described hereinabove and in PCT patent application no. PCT/EP2012/055393, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIACORE™ instrument (GE Healthcare), and Fc receptors such as may be obtained by recombinant expression. A suitable such binding assay is described herein. Alternatively, binding affinity of Fc domains or cell activating trispecific antigen binding molecules comprising an Fc domain for Fc receptors may be evaluated using cell lines known to express particular Fc receptors, such as human NK cells expressing FcγIIIa receptor.

Effector function of an Fc domain, or trispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the trispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

The following section describes preferred embodiments of the trispecific antibodies of the invention comprising Fc domain modifications reducing Fc receptor binding and/or effector function.

G. Antibody Variants

In certain embodiments, amino acid sequence variants of the trispecific antibodies provided herein are contemplated, in addition to those described above. For example, it may be desirable to improve the binding affinity and/or other biological properties of the trispecific antibody. Amino acid sequence variants of a trispecific antibody may be prepared by introducing appropriate modifications into the nucleotide sequence encoding the trispecific antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

1. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table B under the heading of "conservative substitutions." More substantial changes are provided in Table B under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

2. Glycosylation Variants

In certain embodiments, a trispecific antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the trispecific antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in a trispecific antibody of the invention may be made in order to create antibody variants with certain improved properties.

In one embodiment, trispecific antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about f 3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8. knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Trispecific antibodies variants are further provided with bisected oligosaccharides, e.g., in which a biantennary oligosaccharide attached to the Fc region of the trispecific antibody is bisected by GlcNAc. Such trispecific antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

3. Cysteine Engineered Antibody Variants

In certain embodiments, it may be desirable to create cysteine engineered trispecific antibodies, e.g., "thioMAbs," in which one or more residues of a trispecific antibody are substituted with cysteine residues. In particular embodiments, the substituted residues occur at accessible sites of the trispecific antibody. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

H. Recombinant Methods and Compostions

Trispecific antibodies of the invention may be obtained, for example, by solid-state peptide synthesis (e.g. Merrifield solid phase synthesis) or recombinant production. For recombinant production one or more polynucleotide encoding the trispecific antibodies (or fragments), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a trispecific antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the trispecific antibody (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the trispecific antibody (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the trispecific antibody is desired, DNA encoding a signal sequence may be placed upstream of the nucleic acid encoding a trispecific antibody of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the trispecific antibody may be included within or at the ends of the trispecific antibody (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a trispecific antibody of the invention. As used herein, the term "host cell" refers to any kind of cellular system which can be engineered to generate the trispecific antibodies of the invention or fragments thereof. Host cells suitable for replicating and for supporting expression of trispecific antibodies are well known in the art. Such cells may be transfected or transduced as appropriate with the particular expression vector and large quantities of vector containing cells can be grown for seeding large scale fermenters to obtain sufficient quantities of the trispecific antibody for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CVI line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a trispecific antibody according to the invention is provided, wherein the method comprises culturing a host cell comprising a polynucleotide encoding the trispecific antibody, as provided herein, under conditions suitable for expression of the trispecific antibody, and recovering the trispecific antibody from the host cell (or host cell culture medium).

The components of the trispecific antibody are genetically fused to each other. Trispecific antibodies can be designed such that its components are fused directly to each other or indirectly through a linker sequence. The composition and length of the linker may be determined in accordance with methods well known in the art and may be tested for efficacy. Examples of linker sequences between different components of trispecific antibodies are found in the sequences provided herein. Additional sequences may also be included to incorporate a cleavage site to separate the individual components of the fusion if desired, for example an endopeptidase recognition sequence.

In certain embodiments the Fab fragments forming part of the trispecific antibody comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the trispecific antibodies of the invention. Non-limiting antibodies, antibody fragments, antigen binding domains or variable regions useful in the present invention can be of murine, primate, or human origin. If the trispecific antibody is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, NJ, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the Fab fragments useful in the present invention are engineered to have enhanced binding affinity according to, for example, the methods disclosed in U.S. Pat. Appl. Publ. No. 2004/0132066, the entire contents of which are hereby incorporated by reference. The ability of the trispecific antibody of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE™ T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, NJ). In an exemplary competition assay, immobilized antigen is incubated in a solution comprising a first labeled antibody that binds to the antigen and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, NY).

Trispecific antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the trispecific antibody binds. For example, for affinity chromatography purification of trispecific antibodies of the invention, a matrix with protein A or protein G may be used. Sequential Protein A or G affinity chromatography and size exclusion chromatography can be used to isolate a trispecific antibody essentially as described in the Examples. The purity of the trispecific antibody can be determined by any of a variety of well known analytical methods including gel electrophoresis, high pressure liquid chromatography, and the like.

I. Assays

Trispecific antibodies binding to HER2 and a blood-brain barrier receptor (BBB-R) provided herein may be identified, screened for, or characterized for their physical/chemical properties and/or biological activities by various assays known in the art.

1. Affinity Assays

The affinity of the trispecific antibodies binding to HER2 and a blood-brain barrier receptor (BBB-R) can be determined in accordance with the methods set forth in the Examples by surface plasmon resonance (SPR), using standard instrumentation such as a BIACORE™ instrument (GE Healthcare), and receptors or target proteins such as may be obtained by recombinant expression. Alternatively, binding of trispecific antibody provided therein to HER2 and/or a BBB-R may be evaluated using cell lines expressing the particular receptor or target antigen, for example by flow cytometry (FACS). A specific illustrative and exemplary embodiment for measuring binding affinity is described in the following and in the Examples below.

According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the trispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the trispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, trispecific constructs are captured by an anti human Fab specific antibody (GE Healthcare) that is immobilized on an activated CM5-sensor chip surface as described for the anti Penta-His antibody. The final amount of coupled protein is approximately 12000 RU. The trispecific constructs are captured for 90 s at 300 nM. The target antigens are passed through the flow cells for 180 s at a concentration range from 250 to 1000 nM with a flowrate of 30 µl/min. The dissociation is monitored for 180 s. Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

2. Binding Assays and Other Assays

In one aspect, a trispecific antibody of the invention is tested for its antigen binding activity, e.g., by known methods such as ELISA, Western blot, etc.

In another aspect, competition assays may be used to identify an antibody that competes with a specific anti-HER2 for binding to HER2. In certain embodiments, such a competing antibody binds to the same epitope (e.g., a linear or a conformational epitope) that is bound by a specific anti-HER2 antibody. In another aspect, competition assays may be used to identify an antibody that competes with a specific anti-BBB-R for binding to BBB-R. In certain embodiments, such a competing antibody binds to the same epitope (e.g., a linear or a conformational epitope) that is bound by a specific anti-BBB-R antibody. Detailed exemplary methods for mapping an epitope to which an antibody binds are provided in Morris (1996) "Epitope Mapping Protocols," in Methods in Molecular Biology vol. 66 (Humana Press, Totowa, NJ). Further methods are described in the example section.

3. Activity Assays

In one aspect, assays are provided for identifying trispecific antibodies specific for HER2 and a BBB-R thereof having biological activity. Biological activity may include, e.g., DNA fragmentation, induction of apoptosis and lysis of targeted cells. Antibodies having such biological activity in vivo and/or in vitro are also provided. In one embodiment said activity is induction of complement-dependent cytotoxicity (CDC). In one embodiment said trispecific antibodies induce CDC to a higher degree than pertuzumab or trastuzumab alone. In one embodiment said trispecific antibodies induce CDC to at least an about 10 times higher degree, an about 20 times higher degree or an about 30 times higher degree than pertuzumab or trastuzumab alone. In another embodiment said trispecific antibodies induce CDC to a higher degree than the combination of pertuzumab or trastuzumab. In another embodiment said trispecific antibodies induce CDC to about a 30%, 40%, 50% or 60%, or at least a 30% to 70%, or at least a 40% to 60% higher degree than the combination of pertuzumab or trastuzumab. The complement-dependent cytotoxicity (CDC) assay can be performed with non heat-treated serum or commercially available complement fractions (see e.g. Lazar, G. A. et al. Engineered antibody Fc variants with enhanced effector function. Proc. Natl Acad. Sci. USA 103, 4005-4010 (2006)). Target cell killing can be assessed by several cell viability reagents such as Alamar Blue (Lazar, G. A. et al. Engineered antibody Fc variants with enhanced effector function. Proc. Natl Acad. Sci. USA 103, 4005-4010 (2006), Idusogie, E. E. et al. Engineered antibodies with increased activity to recruit complement. J. Immunol. 166, 2571-2575 (2001)), CELLTITER-GLO® (see e.g. Zhao, X. et al. Targeting C-type lectin-like molecule-1 for antibody-mediated immunotherapy in acute myeloid leukemia. Haematologica 95, 71-78 (2009)), LDH release (see e.g. Konishi, E., Kitai, Y. & Kondo, T. Utilization of complement-dependent cytotoxicity to measure low levels of antibodies: application to nonstructural protein 1 in a model of Japanese encephalitis virus. Clin. Vaccine Immunol. 15, 88-94 (2008) and the examples disclosed herein) or calcein-AM release. In some embodiments said degree of induction of CDC is determined by a LDH release assay or a complement assay measuring binding of complement protein C1q to the antibodies of the invention bound to a cellular antigen. The CDC induction of the trispecific antibody is then compared to the CDC induction of either Pertuzumab or Trastuzumab alone, or the combination of Pertuzumab and Trastuzumab, with all values for CDC induction being assayed in the same assay, with the same cell line and the same respective antibody concentration. If performed in a microtiterplate, the capability of the trispecific antibodies and the controls (either Pertuzumab or Trastuzumab alone, or the combination of Pertuzumab and Trastuzumab) to induce CDC are preferably measured in the same microtiterplate using the same assay. Exemplary assays are disclosed, e.g. in example 18 or 19. In one embodiment said induction of CDC is determined on cancer cells, e.g. breast cancer cells.

In certain embodiments, a trispecific antibody of the invention is tested for such biological activity. Assays for detecting cell lysis (e.g. by measurement of LDH release) or apoptosis (e.g. using the TUNEL assay) are well known in the art. Assays for measuring ADCC or CDC are also described in WO 2004/065540 (see Example 1 therein), the entire content of which is incorporated herein by reference.

J. Pharmaceutical Formulations

Pharmaceutical formulations of a trispecific antibody specific for HER2 and a BBB-R as described herein are prepared by mixing such trispecific antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. The formulations to be used for in vivo administration are generally sterile. Sterility may be readily accomplished, e.g., by filtration through sterile filtration membranes.

K. Therapeutic Methods and Compositions

Any of the trispecific antibodies specific for HER2 and a BBB-R provided herein may be used in therapeutic methods.

In one aspect, a trispecific antibody specific for HER2 and a BBB-R for use as a medicament is provided. In further aspects, a trispecific antibody specific for HER2 and a BBB-R for use in treating cancer is provided. In certain embodiments, a trispecific antibody specific for HER2 and a BBB-R for use in a method of treatment is provided. In certain embodiments, the invention provides a trispecific antibody specific for HER2 and a BBB-R for use in a method of treating an individual having cancer comprising administering to the individual an effective amount of the trispecific antibody specific for HER2 and a BBB-R. In one such embodiment, the method further comprises administering to the individual an effective amount of at least one additional therapeutic agent, e.g., as described below. An "individual" according to any of the above embodiments is preferably a human.

In a further aspect, the invention provides for the use of a trispecific antibody specific for HER2 and a BBB-R in the manufacture or preparation of a medicament In one embodiment, the medicament is for treatment of cancer. In one embodiment said cancer is HER2-positive cancer with brain metastases. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating cancer. In one embodiment, the method comprises administering to an individual having cancer an effective amount of a trispecific antibody specific for HER2 and a BBB-R. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the trispecific antibodies specific for HER2 and a BBB-R provided herein, e.g., for use in any of the above therapeutic methods. In one embodiment, a pharmaceutical formulation comprises any of the trispecific antibodies specific for HER2 and a BBB-R provided herein and a pharmaceutically acceptable carrier. In another embodiment, a pharmaceutical formulation comprises any of the trispecific antibodies specific for HER2 and a BBB-R provided herein and at least one additional therapeutic agent, e.g., as described below.

A trispecific antibody of the invention can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Trispecific antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The trispecific antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a trispecific antibody of the invention will depend on the type of disease to be treated, the type of antibody, the severity and course of the disease, whether the trispecific antibody is administered for preventive or therapeutic purposes, previous therapy, the patient's clinical history and response to the trispecific antibody, and the discretion of the attending physician. The trispecific antibody is suitably administered to the patient at one time or over a series of treatments. Depending on the type and severity of the disease, about 1 µg/kg to 15 mg/kg (e.g. 0.1 mg/kg-10 mg/kg) of the trispecific antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the trispecific antibody would be in the range from about 0.05 mg/kg to about 10 mg/kg. Thus, one or more doses of about 0.5 mg/kg, 2.0 mg/kg, 4.0 mg/kg or 10 mg/kg may be administered to the patient. Such doses may be administered intermittently, e.g. every week or every three weeks (e.g. such that the patient receives from about two to about twenty, or e.g. about six doses of the trispecific antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a trispecific antibody specific for HER2 and a BBB-R of the invention.

L. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a trispecific antibody of the invention. The label or package insert indicates that the composition is used for treating the condition of choice. Moreover, the article of manufacture may comprise (a) a first container with a composition contained therein, wherein the composition comprises a trispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a trispecific antibody specific for HER2 and a BBB-R of the invention.

M. Immunoconjugates

The invention also provides immunoconjugates comprising an trispecific antibody specific for HER2 and a BBB-R herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

III. Examples

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1: Materials and Methods

Unless stated otherwise the following general methods have been applied:

Recombinant DNA Techniques

Standard methods were used to manipulate DNA as described in Sambrook, J. et al., Molecular cloning: A laboratory manual; Cold Spring Harbor Laboratory Press, Cold Spring Harbor, New York, 1989. The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E., A., et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wisconsin) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Example 2: Generation of Trastuzumab and Pertuzumab Bispecific Antibodies in a 2+2 IgG-scFv Format Gene Synthesis Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of the subcloned gene fragments was confirmed by DNA sequencing.

Construction of the Expression Plasmids

The following expression vector was used for the construction of all heavy and light chain encoding expression plasmids. The vector is composed of the following elements:
- a hygromycin resistance gene as a selection marker,
- an origin of replication, oriP, of Epstein-Barr virus (EBV),
- an origin of replication from the vector pUC18 which allows replication of this plasmid in E. coli
- a beta-lactamase gene which confers ampicillin resistance in E. coli,
- the immediate early enhancer and promoter from the human cytomegalovirus (HCMV),
- the human 1-immunoglobulin polyadenylation ("poly A") signal sequence, and The immunoglobulin genes comprising the heavy or light chain were prepared by gene synthesis and cloned into pGA18 (ampR) plasmids as described above. Variable heavy chain constructs were constructed by directional cloning using unique restriction sites. Variable light chain constructs were ordered as gene synthesis comprising VL and CL and constructed by directional cloning using unique restriction sites. The final expression vectors were transformed into E. coli cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Immunoglobulin Variants in HEK293 Cells

Recombinant immunoglobulin variants were expressed by transient transfection of human embryonic kidney 293-F cells using the FreeStyle™ 293 Expression System according to the manufacturer's instruction (Invitrogen, USA). For small scale test expressions 30 ml of $0.5 \times 10^6$ HEK293F cells/ml were seeded one day prior to transfection. The next day, plasmid DNA (1 μg DNA per ml culture volume) was mixed with 1.2 ml OPTI-MEM® I Reduced Serum Medium (Invitrogen, Carlsbad, CA, USA) followed by addition of 40 μl of 293Fectin™ Transfection Reagent (Invitrogen, Carlsbad, CA, USA). The mixture was incubated for 15 min at room temperature and added drop wise to the cells. One day post-transfection each flask was fed with 300 μl L-Glutamine (200 mM, Sigma-Aldrich, Steinheim, Germany) and 600 μl feed7 containing L-asparagine, amino acids, trace elements, ammonium-Fe(III) citrate, ethanolamine, trace elements, D-glucose, FreeStyle medium without RPMI. Three days post-transfection cell concentration, viability and glucose concentration in the medium were determined using an automated cell viability analyzer (Vi-CELL™ XR, Beckman Coulter, Fullerton, CA, USA) and a glucose meter (Accu-CHEK™ Sensor comfort, Roche Diagnostics GmbH, Mannheim, Germany). In addition each flask was fed with 300 μl of L-glutamine, 300 μl non-essential amino acids solution (PAN™ Biotech, Aidenbach, Germany), 300 μl sodium pyruvate (100 mM, Gibco, Invitrogen), 1.2 ml feed7 and ad 5 g/L glucose (D-(+)-Glucose solution 45%, Sigma). Finally, six days post-transfection antibodies were harvested by centrifugation at 3500 rpm in a X3R Multifuge (Heraeus, Buckinghamshire, England) for 15 min at ambient temperature, the supernatant was sterile filtered through a Steriflip filter unit (0.22 mm Millipore Express PLUS PES membrane, Millipore, Bedford, MA) and stored at −20° C. until further use. Large scale transfections up to 5 L were scaled linearly.

Purification of Bispecific and Control Antibodies

Bispecific antibodies were purified from cell culture supernatants by affinity chromatography using Protein A SEPHAROSE™ (GE Healthcare, Sweden) and SUPERDEX™ 200 size exclusion chromatography. Briefly, sterile filtered cell culture supernatants were applied on a HITRAP™ ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M TRIS™ (tris(hydroxymethyl)aminomethane), pH 8.5. Eluted protein fractions were pooled, concentrated with an AMICON™ Ultra centrifugal filter device (MWCO: 30 K, Millipore) to a volume of 3 ml and loaded on a SUPERDEX™ 200 HiLoad 120 ml 16/60 gel filtration column (GE Healthcare, Sweden) equilibrated with 20 mM Histidin, 140 mM NaCl, pH 6.0. Fractions containing purified bispecific and control antibodies with less than 5% high molecular weight aggregates were pooled and stored as 1.0 mg/ml aliquots at −80° C.

Protein Quantification

Proteins were quantified by affinity chromatography using the automated Ultimate 3000 system (Dionex, Idstein, Germany) with a pre-packed Poros® A protein A column (Applied Biosystems, Foster City, CA, USA). All samples were loaded in buffer A (0.2 M $Na_2HPO_4 \cdot [2H_2O]$, pH 7.4) and eluted in buffer B (0.1 M citric acid, 0.2 M NaCl, pH 2.5). In order to determine the protein concentration an extinction coefficient of 1.62 was used for all samples.

Analysis of Purified Proteins

The protein concentration of purified protein samples was determined by measuring the optical density (OD) at 280 nm, using the molar extinction coefficient calculated on the basis of the amino acid sequence. Purity and molecular weight of bispecific and control antibodies were analyzed by SDS-PAGE in the presence and absence of a reducing agent (5 mM 1,4-dithiotreitol) and staining with Coomassie brilliant blue. The NuPAGE® Pre-Cast gel system (Invitrogen, USA) was used according to the manufacturer's instruction (4-20% Tris-Glycine gels). The aggregate content of bispecific and control antibody samples was analyzed by high-performance SEC using a SUPERDEX™ 200 analytical size-exclusion column (GE Healthcare, Sweden) in 200 mM $KH_2PO_4$, 250 mM KCl, pH 7.0 running buffer at 25° C. 25 μg protein were injected on the column at a flow rate of 0.5 ml/min and eluted isocratic over 50 minutes. Integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals).

Analytical HPLC

Antibodies were analyzed using a Agilent HPLC 1100 (Agilent Technologies, Palo Alto, CA, USA) with a TSK-GEL G3000SW gel filtration column (7.5 mm ID×30 cm, TosoHaas Corp., Montgomeryville, PA, USA). 18 µl of the eluted proteins were loaded onto the column in Buffer A (0.05 M $K_2HPO_4/KH_2PO_4$ in 300 mM NaCl, pH 7.5) and separated based on size.

Reducing and Non-Reducing SDS-PAGE

7 µl of the eluted proteins were mixed with 2× sample buffer (NuPAGE® LDS Sample buffer, Invitrogen, Carlsbad, CA, USA) and another 7 µl were mixed with 2× sample buffer containing 10% reducing agent (NuPAGE® Sample Reducing Agent, Invitrogen, Carlsbad, CA, USA). Samples were heated to 70° for 10 min and loaded onto a pre-cast NuPAGE® 4-12% BisTris Gel (Invitrogen, Carlsbad, CA, USA). The gel was run for 45 min at 200V and 125 mA. Afterwards the gel was washed three times with Millipore water and stained with SimplyBlue™ SafeStain (Invitrogen, Carlsbad, CA, USA). The gel was destained overnight in Millipore water. FIGS. 1A-D depict schematically the different variants of Trastuzumab and Pertuzumab bispecific antibodies in a 2+2 IgG-scFv format. All bispecific antibodies are bivalent for each antigen binding site and bind two different paratopes in the ErbB2/HER2 receptor (antigen1=trastuzumab specificity; antigen2=pertuzumab specificity). All bispecific antibodies in a 2+2 IgG-scFv format described herein are non frame-work grafted, non-CDR optimized, not glycoengineered and do not bear any mutation in the Fc part.

FIGS. 2A-B, 3A-B and 4A-B show exemplary size-exclusion purification graphs, SDS-PAGE analysis and analytical HPLC of variants of Trastuzumab and Pertuzumab bispecific antibodies in a 2+2 IgG-scFv format. No data shown for TvAB17, TvAB13 and variants HERCEPTIN® (Trastuzumab)-scFv_A to E; all variants of Trastuzumab and Pertuzumab bispecific antibodies in a 2+2 IgG-scFv format were produced with the same quality.

TABLE 1a

Sequences of Trastuzumab and Pertuzumab bispecific antibodies in a 2 + 2 IgG-scFv format

| SEQ ID NO | Name | Sequence |
|---|---|---|
| | TvAB12_2431_TrastuzumabHCscFvOmnitarg(HC_LC) | |
| 123 | Light chain (kappa) [Trastuzumb, 1016] | diqmtqspsslsasvgdrvtitcrasqdvntavawyqqkpgkapklliysasflysgvpsrfsgs rsgtdftltisslqpedfatyycqqhyttpptfgqgtkveikrtvaapsvfifppsdeqlksgtasvv cllnnfypreakvqwkvdnalqsgnsqesvteqdskdstyslsstltlskadyekhkvyacevt hqglsspvtksfnrgec |
| 124 | Heavy chain [Trastuzumb + scFv Omnitarg, RB40] | evqlvesgggIvqpggslrlscaasgfnikdtyihwvrqapgkglewvariyptngytryadsv kgrftisadtskntaylqmnslraedtavyycsrwggdgfyamdywgqgtivtvssastkgps vfplapssketsggtaalgclvkdyfpepvtvswnsgaltsgvhtfpavlqssglyslssvvtvps sslgtqtyicnvnhkpsntkvdkkvepkscdkthtcppcpapellggpsvflfppkpkdtlmis rtpevtcvvvdvshedpevkfnwyvdgvevhnaktkpreeqynstyrvvsvltvlhqdwlng keykckvsnkalpapiektiskakgqprepqvytlppsreemtknqvsltclvkgfypsdiave wesngqpennykttppvldsdgsfflyskltvdksrwqqgnvfscsvmhealhnhytqksIsl spgkggggsggggsggggsevqlvesgggIvqpggslrIscaasgftftdytmdwvrqapgk clewvadvnpnsggsiynqrfkgrftlsvdrskntlylqmnslraedtavyycarnlgpsfyfdy wgqgtivtvssggggsggggsggggsggggsdiqmtqspsslsasvgdrvtitckasqdvsig vawyqqkpgkapklliysasyrytgvpsrfsgsgsgtdifitisslqpedfatyycqqyyiypytf gcgtkveik |
| | TvAB13 [TvAb13_1330scFvTrastuzumab(LC_HC)OmnitargLC_IntronA_cDNA] | |
| 125 | Light chain [scFv Trastuzumab + Omnitarg, RB34] | diqmtqspsslsasvgdrvtitcrasqdvntavawyqqkpgkapklliysasflysgvpsrfsgs rsgtdftltisslqpedfatyycqqhyttpptfgqgtkveikggggsggggsggggsevqlvesg ggIvqpggslrlscaasgfnikdtyihwvrqapgkglewvariyptngytryadsvkgrftisad tskntaylqmnslraedtavyycsrwggdgfyamdywgqgtivtvssggggsggggsgggg sdiqmtqspsslsasvgdrvtitckasqdvsigvawyqqkpgkapklliysasyrytgvpsrfsg sgsgtdftltisslqpedfatyycqqyyiypytfgqgtkveikrtvaapsvfifppsdeqlksgtas vvcllnnfypreakvqwkvdnalqsgnsqesvteqdskdstyslsstltlskadyekhkvyace vthqglsspvtksfnrgec |
| 126 | Heavy chain (Omnitarg, RB33) | evqlvesgggIvqpggslrIscaasgftftdytmdwvrqapgkglewvadvnpnsggsiynqr fkgrftlsvdrskntlylqmnslraedtavyycarnlgpsfyfdywgqgtivtvssastkgpsvfp lapsskstsggtaalgclvkdyfpepvtvswnsgaltsgvhtfpavlqssglyslssvvtvpssslg tqtyicnvnhkpsntkvdkkvepkscdkthtcppcpapellggpsvflfppkpkdtlmisrtpe vtcvvvdvshedpevkfnwyvdgvevhnaktkpreeqynstyrvvsvltvlhqdwlngkey kckvsnkalpapiektiskakgqprepqvytlppsrdeltknqvsltclvkgfypsdiavewesn gqpennykttppvldsdgsfflyskltvdksrwqqgnvfscsvmhealhnhytqkslslspgk |
| | TvAB16 [TVAb16_2330TrastuzumabLCscFvOmnitarg(LC_HC)] | |
| 127 | Light chain [Trastuzumb + scFvOmnitarg, RB35] | diqmtqspsslsasvgdrvtitcrasqdvntavawyqqkpgkapklliysasflysgvpsrfsgs rsgtdftltisslqpedfatyycqqhyttpptfgqgtkveikrtvaapsvfifppsdeqlksgtasvv cllnnfypreakvqwkvdnalqsgnsqesvteqdskdstyslsstltlskadyekhkvyacevt hqglsspvtksfnrgecggggsggggsggggsdiqmtqspsslsasvgdrvtitckasqdvsig |

TABLE 1a-continued

Sequences of Trastuzumab and Pertuzumab bispecific antibodies in a 2 + 2 IgG-scFv format

| SEQ ID NO | Name | Sequence |
|---|---|---|
|  |  | vawyqqkpgkapklliysasyrytgvpsrfsgsgsgtdifitisslqpedfatyycqqyyiypytf gqgtkveikggggsggggsggggsevqlvesgggglvqpgsslrlscaasgftftdytmdwvrq apgkglewvadvnpnsggsiynqrfkgrftlsvdrskntlylqmnslraedtavyycarnlgps fyfdywgqgtivtvss |
| 128 | Heavy chain [Trastuzumb, 1036] | evqlvesgggglvqpggslrlscaasgfnikdtyihwvrqapgkglewvariyptngytryadsv kgrftisadtskntaylqmnslraedtavyycsrwggdgfyamdywgqgtivtvssastkgps vfplapssksstsggtaalgclvkdyfpepvtvswnsgaltsgvhtfpavlqssglyslssvvtvps sslgtqtyicnvnhkpsntkvdkkvepkscdkthtcppcpapellggpsvflfppkpkdtlmis rtpevtcvvvdvshedpevkfnwyvdgvevhnaktkpreeqynstyrvvsvltvlhqdwlng keykckvsnkalpapiektiskakgqprepqvytlppsrdeltknqvsltclvkgfypsdiave wesngqpennykttppvldsdgsfflysklvtdksrwqqgnvfscsvmhealhnhytqkslsl spgk |
|  | TvAB17 [TvAb17_2431_TrastuzumabHCscFvOmnitarg(LC_HC)] |  |
| 129 | Light chain (kappa) [Trastuzumb, 1016+ | diqmtqspsslsasvgdrvtitcrasqdvntavawyqqkpgkapklliysasflysgvpsrfsgs rsgtdftltisslqpedfatyycqqhyttpptfgqgtkveikrtvaapsvfifppsdeqlksgtasvv cllnnfypreakvqwkvdnalqsgnsqesvteqdskdstyslsstltlskadyekhkvyacevt hqglsspvtksfnrgec |
| 130 | Heavy chain [Trastuzumb + scFvOmnitarg, RB43] | evqlvesgggglvqpggslrlscaasgfnikdtyihwvrqapgkglewvariyptngytryadsv kgrftisadtskntaylqmnslraedtavyycsrwggdgfyamdywgqgtivtvssastkgps vfplapssksstsggtaalgclvkdyfpepvtvswnsgaltsgvhtfpavlqssglyslssvvtvps sslgtqtyicnvnhkpsntkvdkkvepkscdkthtcppcpapellggpsvflfppkpkdtlmis rtpevtcvvvdvshedpevkfnwyvdgvevhnaktkpreeqynstyrvvsvltvlhqdwlng keykckvsnkalpapiektiskakgqprepqvytlppsreemtknqvsltclvkgfypsdiave wesngqpennykttppvldsdgsfflyskltvdksrwqqgnvfscsvmhealhnhytqkslsl spgkggggsggggsggggsdiqmtqspsslsasvgdrvtitckasqdvsigvawyqqkpgka pklliysasyrytgvpsrfsgsgsgtdftltisslqpedfatyycqqyyiypytfgcgtkveikggg gsggggsggggsggggsevqlvesgggglvqpggslrlscaasgftftdytmdwvrqapgkcle wvadvnpnsggsiynqrfkgrftlsvdrskntlylqmnslraedtavyycarnlgpsfyfdywg qgtivtvss |
|  | TvAB20 [TVAB20_4441TrastuzumabLCscFvOmnitarg(LC_HC)] |  |
| 131 | Light chain [Trastuzumb + scFv Omnitarg, RB61] | diqmtqspsslsasvgdrvtitcrasqdvntavawyqqkpgkapklliysasflysgvpsrfsgs rsgtdftltisslqpedfatyycqqhyttpptfgqgtkveikrtvaapsvfifppsdeqlksgtasvv cllnnfypreakvqwkvdnalqsgnsqesvteqdskdstyslsstltlskadyekhkvyacevt hqglsspvtksfnrgecggggsggggsggggsdiqmtqspsslsasvgdrvtitckasq dvsigvawyqqkpgkapklliysasyrytgvpsrfsgsgsgtdifitisslqpedfatyycqqyi yppytfgcgtkveikggggsggggsggggsggggsevqlvesgggglvqpggslrlscaasgftft dytmdwvrqapgkclewvadvnpnsggsiynqrfkgrftlsvdrskntlylqmnslraedtav yycarnlgpsfyfdywgqgtivtvss |
| 132 | Heavy chain [Trastuzumb, 1036] | evqlvesgggglvqpggslrlscaasgfnikdtyihwvrqapgkglewvariyptngytryadsv kgrftisadtskntaylqmnslraedtavyycsrwggdgfyamdywgqgtivtvssastkgps vfplapssksstsggtaalgclvkdyfpepvtvswnsgaltsgvhtfpavlqssglyslssvvtvps sslgtqtyicnvnhkpsntkvdkkvepkscdkthtcppcpapellggpsvflfppkpkdtlmis rtpevtcvvvdvshedpevkfnwyvdgvevhnaktkpreeqynstyrvvsvltvlhqdwlng keykckvsnkalpapiektiskakgqprepqvytlppsrdeltknqvsltclvkgfypsdiave wesngqpennykttppvldsdgsfflyskltvdksrwqqgnvfscsvmhealhnhytqkslsl spgk |
|  | Herceptarg 2 + 2 OmniE |  |
| 145 | Heavy chain with scFv Trastuzumab stabilized with disulphide bonding | evqlvesgggglvqpggslrlscaasgftftdytmdwvrqapgkglewvadvnpnsggsiynqrfkgrftls vdrskntlylqmnslraedtavyycarnlgpsfyfdywgqgtivtvssastkgpsvfplapssksstsggtaaI gclvkdyfpepvtvswnsgaltsgvhtfpavlqssglyslssvvtvpsssigtqtyicnvnhkpsntkvdkkv epkscdkthtcppcpapellggpsvflfppkpkdtlmisrtpevtcvvvdvshedpevkfnwyvdgvevh naktkpreeqynstyrvvsvltvlhqdwlngkeykckvsnkalpapiektiskakgqprepqvytlppsrde ltknqvsltclvkgfypsdiavewesngqpennykttppvldsdgsfflyskltvdksrwqqgnvfscsvmh ealhnhytqkslslspgkggggsggggsevqlvesgggglvqpggslrlscaasgfnikdtyihwvrqapgk glewvariyptngytryadsvkgrftisadtskntaylqmnslraedtavyycsrwggegfyamdywgcg tivtvssggggsggggsggggsdiqmtqspsslsasvgdrvtitcrasqdvnavawyqqkpgkcpkliy sasflysgvpsrfsgsrsgtdftltisslqpedfatyycqqhyttpptfgqgtlweik |
| 146 | Pertuzumab light chain | diqmtqspsslsasvgdrvtitckasqdvsigvawyqqkpgkapklliysasyrytgvpsrfsgsgsgtdftlt isslqpedfatyycqqyyiypytfgqgtkveikrtvaapsvfifppsdeqlksgtasvvcllnnfypreakvqw kvdnalqsgnsqesvteqdskdstyslsstltlskadyekhkvyacevthqglsspvtksfnrgec |

TABLE 1 b

Variants of TvAB12_2431_TrastuzumabHCscFvOmnitarg(HC_LC) with a stabilizing disulphide bond in the scFv part to reduce aggregation levels

| Name of molecule | Disulphide position (VH-VL) |
|---|---|
| Trastuzumab_scFv_WT | WT |
| Trastuzumab_scFv_A | 44-100 |
| Trastuzumab_scFv_B | 45-98 |
| Trastuzumab_scFv_C | 101-46 |
| Trastuzumab_scFv_D | 103-44 |
| Trastuzumab_scFv_E | 105-43 |

Example 3: Proliferation Inhibition Assay with Trastuzumab and Pertuzumab Bispecific Antibodies in a 2+2 IgG-scFv Format Cell Lines MDA-MB 175 VII cells were maintained in DMEM/F12 medium (Gibco) supplemented with 10% fetal calf serum and 2 mL L-glutamine. Propagation of cell lines followed standard cell culture protocols.

The ability of the bispecific antibodies to inhibit proliferation was assessed in the cell line MDA-MB-175 VII. MDA-MB-175 VII were cultured in DMEM/F12 medium (Gibco) supplemented with 10% fetal calf serum, 2 mM L-glutamine. Cells in the logarithmic growth phase were detached, counted and 2×10e4 cells were seeded in 100 µL medium per well of a 96-well cell culture plate. Cells were maintained overnight in the incubator and the following day 100 µL of the respective antibodies diluted in medium were added in form of a dilution series to the cells. After a total incubation time of 6 days cell growth was assessed in an Alamar Blue (Invitrogen) assay. The assay was performed as recommended by the manufacturer.

TABLE 2 shows the potency of selected bispecific antibodies in the proliferation assay.

| Antibody | SEQ ID NO: | EC50 [nM] |
|---|---|---|
| Herceptarg WT | | 1.84 |
| Herceptarg A | | 1.89 |
| Herceptarg B | | 2.66 |
| Herceptarg C | | 2.56 |
| Herceptarg D | | 1.63 |
| Herceptarg E | | 1.75 |
| TvAb12 | 123/124 | 4.90 |
| CrossMab | 119/120/121/122 | 4.75 |
| Pertuzumab | | 2.11 |
| Pertuzumab + HERCEPTIN ® (Trastuzumab) | | 1.70 |
| HERCEPTIN ® (Trastuzumab) | | 2.92 |

Example 4: Herceptarg Stabilisation

The aspartate isomerization site at position 98 of the heavy chain and the asparagine deamidation site at position 30 of the light chain are stability hotspots of trastuzumab. Those two positions affect the stability and integrity of the antigen binding capacity of the antibody. This problem was overcome by introducing the lyophilized formulations using either sodium succinate or histidine buffer. In order to increase stability and storage half-life we intended to replace those known sources of instability by amino acids, or amino acid stretches that should have a higher intrinsic stability. We tested herefore the replacement of Asp98 by Glu in the heavy chain and the replacement of Asn30 by Ser, as well Thr31 by Val in the light chain. Those mutations were abbreviated D98E, N30S, and T31V. T31V does not directly influence the deamidation of N30, but it was assumed that the residue adjacent on the C-terminal side of an Asparagine would influence the stability properties of a polypeptide chain.

The antibody samples were incubated over a period of either 1, 2, or 3 months at 40° C. in one of the three buffers: 40 mM Histidin, 150 mM NaCl, pH5.0, 40 mM Histidin, 150 mM NaCl, pH6.0, or 40 mM Histidin, 150 mM NaCL, pH7.4. The protein concentration during this period was always 1 mg/ml. After the indicated time points, samples were taken and shock frozen in liquid nitrogen, and then kept at −80° C. until further analysis. This analysis was carried out on a PROTEON™ XPR36 instrument (BioRad). Approximately 700 RU of Her2, respectively, were immobilized on 2 channels of a GLM chip using amine coupling (vertical orientation). Trastuzumab variants were measured in duplicates at 6 different analyte concentrations (100, 50, 25, 12.5, 6.25, 0 nM) by injections in horizontal orientation at 100 µl/min. Association rate were recorded for 180s, the dissociation rate for 600s. Regeneration was performed by two pulses of 10 mM glycine pH 1.5 and 50 mM NaOH for 60s at 150 µl/min (horizontal orientation). In total four different Trastuzumab variants were measured. In the first experiment (Tables 3 and 4), only the unmodified Trastuzumab and variant 602 (D98E of heavy chain and T31V of light chain) were tested. In the second experiment the unmodified Trastuzumab, variant 602 (D98E of heavy chain and T31V of light chain) and variants VH:D98E/VL: N30S VH:D98E/VL: N30T were tested (Table 5, 6, 7).

Results:

All variants show the same affinity towards recombinant Her2 antigen as the parental Trastuzumab molecule. After exposure to pH5 or pH6 at 40° C., Trastuzumab lost affinity by a factor ~5, mainly driven by increasing the off-rate and keeping the on-rate unchanged. Variant 602 showed almost undistinguishable affinities before and after pH stress. Variant N30S had a higher affinity from the beginning compared to the parental Trastuzumab, which stayed approximately constant during the stress conditions. The variants D98E (VH) together with either N30S, N30T, or T31V (VL) were used in the further experiments. Results are shown in FIGS. 5A-B and 6A-C and the tables below.

TABLE 3

Kinetic affinity parameters of Trastuzumab variants as determined by SPR method (PROTEON™ instrument) after incubating the samples for 1, 2, or 3 months at 40° in 40 mM Histidin, 150 mM NaCl, pH5.0 buffer. Each measurement was done in duplicate and both experimental values are shown. Tested were the synthesized Trastuzmab (wt) and compared to the D98E T31V variant in the heavy and light chain, respectively (named clone 602).

| pH5 | | t0 ka | t0 kd | t0 KD | t1 ka | t1 kd | t1 KD | t2 ka | t2 kd | t2 KD | t3 ka | t3 kd | t3 KD |
|---|---|---|---|---|---|---|---|---|---|---|---|---|---|
| wt | 1 | 2.4E+05 | 1.1E−04 | 4.3E−10 | 3.3E+05 | 1.6E−04 | 5.0E−10 | 2.9E+05 | 2.6E−04 | 9.2E−10 | 2.8E+05 | 3.4E−04 | 1.2E−09 |
|  | 2 | 2.4E+05 | 4.4E−05 | 1.8E−10 | 2.8E+05 | 1.9E−04 | 7.0E−10 | 2.8E+05 | 2.8E−04 | 9.9E−10 | 2.9E+05 | 3.6E−04 | 1.3E−09 |
| 602 | 1 | 2.6E+05 | 1.2E−04 | 4.6E−10 | 2.7E+05 | 2.2E−04 | 8.0E−10 | 2.9E+05 | 1.7E−04 | 5.8E−10 | 3.0E+05 | 1.7E−04 | 5.8E−10 |
|  | 2 | 2.3E+05 | 1.3E−04 | 5.4E−10 | 2.8E+05 | 1.4E−04 | 5.2E−10 | 2.9E+05 | 1.6E−04 | 5.3E−10 | 3.1E+05 | 1.7E−04 | 5.5E−10 |

TABLE 4

Kinetic affinity parameters of Trastuzumab variants similar to table 3. Here the samples are incubated at 40° in 40 mM Histidin, 150 mM NaCl, pH6.0 for the same time intervals as before.

| pH6 | | t0 ka | t0 kd | t0 KD | t1 ka | t1 kd | t1 KD | t2 ka | t2 kd | t2 KD | t3 ka | t3 kd | t3 KD |
|---|---|---|---|---|---|---|---|---|---|---|---|---|---|
| wt | 1 | 2.8E+05 | 9.5E−05 | 3.4E−10 | 3.0E+05 | 1.5E−04 | 5.1E−10 | 2.5E+05 | 3.1E−04 | 1.2E−09 | 2.3E+05 | 4.0E−04 | 1.7E−09 |
|  | 2 | 2.8E+05 | 8.6E−05 | 3.1E−10 | 2.8E+05 | 2.1E−04 | 7.7E−10 | 2.6E+05 | 3.3E−04 | 1.3E−09 | 2.4E+05 | 4.1E−04 | 1.8E−09 |
| 602 | 1 | 2.9E+05 | 1.4E−04 | 4.8E−10 | 3.0E+05 | 1.6E−04 | 5.2E−10 | 3.0E+05 | 1.6E−04 | 5.3E−10 | 3.0E+05 | 1.8E−04 | 5.9E−10 |
|  | 2 | 2.8E+05 | 1.4E−04 | 5.0E−10 | 2.9E+05 | 1.5E−04 | 5.1E−10 | 2.9E+05 | 1.6E−04 | 5.5E−10 | 2.9E+05 | 1.7E−04 | 5.7E−10 |

TABLE 5

Kinetic affinity parameters of Trastuzumab variants similar to table 3. Here the samples are incubated at 40° in 40 mM Histidin, 150 mM NaCl, pH5.0 for the same time intervals as before. Samples included are the resynthesized Trastuzumab (wt), the D98E T31V variant in the heavy and the light chain, respectively (named clone 602. This was produced in CHO instead HEK). Also the light chain variants N30S, and N30T (both have the D98E heavy chain variant)

| pH5 | | t0 ka | t0 kd | t0 KD | t1 ka | t1 kd | t1 KD |
|---|---|---|---|---|---|---|---|
| 602 | 1 | 2.20E+05 | 1.40E−04 | 6.34E−10 | 2.32E+05 | 9.14E−05 | 3.95E−10 |
| CHO | 2 | 2.32E+05 | 2.13E−04 | 9.21E−10 | 2.10E+05 | 1.54E−04 | 7.35E−10 |
| N30T | 1 | 2.19E+05 | 2.11E−04 | 9.64E−10 | 2.21E+05 | 1.46E−04 | 6.61E−10 |
|  | 2 | 2.18E+05 | 2.61E−04 | 1.20E−09 | 2.05E+05 | 1.85E−04 | 9.02E−10 |
| N30S * | 1 | 2.59E+05 | 2.59E−19 | 1.00E−24 | 2.54E+05 | 1.93E−05 | 7.58E−11 |
|  | 2 | 2.44E+05 | 2.36E−17 | 9.68E−23 | 2.42E+05 | 3.47E−05 | 1.43E−10 |
| wt | 1 | 2.51E+05 | 1.60E−04 | 6.39E−10 | 2.30E+05 | 3.62E−04 | 1.58E−09 |
|  | 2 | 2.29E+05 | 1.93E−04 | 8.43E−10 | 2.13E+05 | 2.66E−04 | 1.25E−09 |

| pH5 | | t2 ka | t2 kd | t2 KD | t3 ka | t3 kd | t3 KD |
|---|---|---|---|---|---|---|---|
| 602 | 1 | 2.32E+05 | 2.36E−04 | 1.02E−09 | 2.01E+05 | 9.67E−05 | 4.81E−10 |
| CHO | 2 | 2.37E+05 | 2.35E−04 | 9.89E−10 | 2.08E+05 | 1.30E−04 | 6.25E−10 |
| N30T | 1 | 2.20E+05 | 1.77E−04 | 8.05E−10 | 2.31E+05 | 2.87E−04 | 1.24E−09 |
|  | 2 | 2.01E+05 | 2.02E−04 | 1.00E−09 | 2.27E+05 | 2.82E−04 | 1.24E−09 |
| N30S * | 1 | 2.49E+05 | 1.16E−16 | 4.64E−22 | 2.54E+05 | 4.11E−18 | 1.62E−23 |
|  | 2 | 2.37E+05 | 3.71E−16 | 1.57E−21 | 2.37E+05 | 6.06E−17 | 2.55E−22 |
| wt | 1 | 2.38E+05 | 6.47E−04 | 2.72E−09 | 2.33E+05 | 7.72E−04 | 3.32E−09 |
|  |  | 2.26E+05 | 6.88E−04 | 3.05E−09 | 2.18E+05 | 7.91E−04 | 3.62E−09 |

* Due to slow dissociation rates, the off-rates and the disassociation constant contain a high degree of uncertainty.

TABLE 6

Kinetic affinity parameters of Trastuzumab variants similar to table 3.
Here the samples are incubated at 40° in 40 mM Histidin, 150 mM NaCl, pH6.0
for the same time intervals as before. Samples included are the resynthesized
Trastuzumab (wt), the D98E T31V variant in the heavy and the light chain,
respectively (named clone 602. This was produced in CHO instead HEK).
Also the light chain variants N30S, and N30T (both have the D98E heavy chain variant)

| pH6 | | t0 | | | t1 | | |
|---|---|---|---|---|---|---|---|
| | | ka | kd | KD | ka | kd | KD |
| 602 | 1 | 2.07E+05 | 9.33E−05 | 4.51E−10 | 2.30E+05 | 1.37E−04 | 5.94E−10 |
| CHO | 2 | 2.16E+05 | 1.97E−04 | 9.12E−10 | 2.16E+05 | 2.02E−04 | 9.32E−10 |
| N30T | 1 | 2.24E+05 | 2.45E−04 | 1.09E−09 | 2.03E+05 | 1.24E−04 | 6.10E−10 |
| | 2 | 2.31E+05 | 2.71E−04 | 1.17E−09 | 1.93E+05 | 1.57E−04 | 8.13E−10 |
| N30S * | 1 | 2.56E+05 | 1.18E−17 | 4.62E−23 | 2.65E+05 | 2.77E−05 | 1.04E−10 |
| | 2 | 2.48E+05 | 8.14E−06 | 3.28E−11 | 2.51E+05 | 4.23E−05 | 1.68E−10 |
| wt | 1 | 2.23E+05 | 7.43E−05 | 3.33E−10 | 2.22E+0 | 54.60E−04 | 2.07E−09 |
| | 2 | 2.23E+05 | 7.98E−05 | 3.59E−10 | 2.21E+05 | 4.03E−04 | 1.82E−09 |

| pH6 | | t2 | | | t3 | | |
|---|---|---|---|---|---|---|---|
| | | ka | kd | KD | ka | kd | KD |
| 602 | 1 | 2.19E+05 | 1.29E−04 | 5.87E−10 | 2.14E+05 | 1.50E−04 | 7.01E−10 |
| CHO | 2 | 2.07E+05 | 1.52E−04 | 7.31E−10 | 2.13E+05 | 1.60E−04 | 7.50E−10 |
| N30T | 1 | 2.11E+05 | 2.27E−04 | 1.08E−09 | 2.08E+05 | 2.01E−04 | 9.67E−10 |
| | 2 | 2.05E+05 | 2.55E−04 | 1.24E−09 | 2.03E+05 | 1.98E−04 | 9.75E−10 |
| N30S * | 1 | 2.38E+05 | 8.97E−19 | 3.77E−24 | 2.36E+05 | 1.84E−05 | 7.80E−11 |
| | 2 | 2.25E+05 | 4.30E−17 | 1.91E−22 | 2.33E+05 | 3.41E−05 | 1.46E−10 |
| wt | 1 | 2.31E+05 | 9.24E−04 | 4.00E−09 | 1.89E+05 | 9.91E−04 | 5.24E−09 |
| | 2 | 2.20E+05 | 9.31E−04 | 4.24E−09 | 1.78E+05 | 9.95E−04 | 5.58E−09 |

* Due to slow dissociation rates, the off-rates and the disassociation constant contain a high degree of uncertainty.

TABLE 7

Kinetic affinity parameters of Trastuzumab variants similar to table 3.
Here the samples are incubated at 40° in 40 mM Histidin, 150 mM NaCl, pH7.4
for the same time intervals as before. Samples included are the resynthesized
Trastuzumab (wt), the D98E T31V variant in the heavy and the light chain,
respectively (named clone 602. This was produced in CHO instead HEK).
Also the light chain variants N30S, and N30T (both have the D98E heavy chain variant)

| pH7.4 | | t0 | | | t1 | | |
|---|---|---|---|---|---|---|---|
| | | ka | kd | KD | ka | kd | KD |
| 602 | 1 | 2.15E+05 | 1.23E−04 | 5.71E−10 | 2.32E+05 | 1.80E−04 | 7.78E−10 |
| CHO | 2 | 2.17E+05 | 2.08E−04 | 9.55E−10 | 2.19E+05 | 2.31E−04 | 1.06E−09 |
| N30T | 1 | 2.46E+05 | 2.19E−04 | 8.87E−10 | 2.15E+05 | 1.86E−04 | 8.65E−10 |
| | 2 | 2.20E+05 | 2.30E−04 | 1.04E−09 | 2.00E+05 | 2.03E−04 | 1.02E−09 |
| N30S | 1 | 2.58E+05 | 1.35E−06 | 5.25E−12 | 2.60E+05 | 2.55E−05 | 9.82E−11 |
| | 2 | 2.36E+05 | 2.24E−05 | 9.46E−11 | 2.49E+05 | 6.31E−18 | 2.53E−23 |
| wt | 1 | 2.25E+05 | 7.49E−05 | 3.33E−10 | 1.99E+05 | 8.80E−04 | 4.43E−09 |
| | 2 | 2.12E+05 | 9.85E−05 | 4.65E−10 | 2.00E+05 | 8.78E−04 | 4.40E−09 |

| pH7.4 | | t2 | | | t3 | | |
|---|---|---|---|---|---|---|---|
| | | ka | kd | KD | ka | kd | KD |
| 602 | 1 | 1.97E+05 | 1.05E−04 | 5.34E−10 | 2.02E+05 | 2.24E−04 | 1.11E−09 |
| CHO | 2 | 1.82E+05 | 1.33E−04 | 7.30E−10 | 2.00E+05 | 2.14E−04 | 1.07E−09 |
| N30T | 1 | 2.12E+05 | 2.64E−04 | 1.25E−09 | 1.94E+05 | 1.41E−04 | 7.26E−10 |
| | 2 | 1.98E+05 | 2.84E−04 | 1.44E−09 | 1.73E+05 | 1.54E−04 | 8.87E−10 |
| N30S | 1 | 2.43E+05 | 7.28E−21 | 2.99E−26 | 2.37E+05 | 6.30E−05 | 2.66E−10 |
| | 2 | 2.27E+05 | 1.24E−05 | 5.46E−11 | 2.21E+05 | 6.55E−05 | 2.97E−10 |
| wt | 1 | 1.64E+05 | 1.35E−03 | 8.27E−09 | 1.55E+05 | 1.79E−03 | 1.15E−08 |
| | 2 | 1.67E+05 | 1.29E−03 | 7.72E−09 | 1.45E+05 | 1.63E−03 | 1.12E−08 |

* Due to slow dissociation rates, the off-rates and the disassociation constant contain a high degree of uncertainty.

Example 5: Binding of Trastuzumab and Trastuzumab Stabilization Variants after Stress to KPL-4 Cells Binding KPL-4 cells were harvested and resuspended in FACS buffer. 0.2 Mio cells were seeded into a 96 well round bottom plate. The plate was centrifuged at 400 g for 3 min to pellet the cells. The supernatant was removed and the cells were resuspended in 40 µl of the diluted antibodies. The plate was incubated for 30 min at 4° C. to allow binding of the antibodies. To remove unbound antibodies the cells were centrifuged again and washed twice with FACS buffer. To detect the antibodies the cells were resuspended in 12 µl diluted secondary goat anti-human Fc specific FITC-labeled secondary antibody (Jackson ImmunoResearch #109-096-098) and incubated again for 30 min at 4° C. Afterwards the cells were washed twice with FACS buffer, resuspended in 200 µl FACS buffer and the fluorescence was measured with BD CantoII.

ADCC

Target cells were harvested, washed, stained with calcein (Invitrogen), resuspended in AIM V® medium (Life Technologies), and plated at a concentration of $3\times10^4$ cells/well. The respective antibody dilutions were added in triplicates to the cells and incubated for 10 min before addition of the effector cells (peripheral blood mononuclear effector cells [PBMCs]). Effector (E) and target (T) cells were then incubated for the indicated time at 37° C. at the indicated E:T ratio (triplicates for all samples). After incubation the cells were washed once with PBS and then lysed with borate buffer. Calcein retention was measured in a Wallac VICTOR3™ 1420 Multilabel Counter. ADCC was calculated using the following formula:

$$\text{Percentage } ADCC = \left(\left[\frac{\text{sample release} - \text{spontaneous release}}{\text{maximal release} - \text{spontaneous release}}\right]\right) \times 100.$$

Spontaneous release, corresponding to target cells incubated with effector cells without antibody, was defined as 0% cytotoxicity, and maximal release (target cells lysed with 1% TRITON™ (t-octylphenoxypolyethoxyethanol) X-100) was defined as 100% cytotoxicity. The average percentage of ADCC and standard deviations of the triplicates of each experiment were calculated. Results are shown in FIGS. 7A-L, 8A-F, and 9A-F.

Example 6: Generation of Herceptarg CrossMab and Framework Grafting on Novel LC06 Based Framework to Achieve Less Mispairing Gene Synthesis Desired gene segments were prepared by Geneart AG (Regensburg, Germany) from synthetic oligonucleotides and PCR products by automated gene synthesis. The gene segments encoding heavy or light chains with C-terminal attachment of scFv antibody fragments, "knobs-into-hole" antibody heavy chains carrying S354C and T366W mutations and "knobs-into-hole" heavy chains carrying Y349C, T366S, L368A and Y407V mutations in the CH3 domain in combination with unmodified VH domains, crossed C kappa domains or scFab antibody fragments as well as unmodified antibody light chains or CHI domain exchanged light chains are flanked by singular restriction endonuclease cleavage sites (BamHI-XbaI, BamHI-XmnI or BamHI-KpnI) and were cloned into pGA18 (ampR) plasmids. The plasmid DNA was purified from transformed bacteria and concentration determined by UV spectroscopy. The DNA sequence of the subcloned gene fragments was confirmed by DNA sequencing. All constructs were designed with a 5'-end DNA sequence coding for a leader peptide (MGWSCIILFL-VATATGVHS (SEQ ID NO: 157)), which targets proteins for secretion in eukaryotic cells.

Construction of the Expression Plasmids

The expression vector that was used for the construction of all "knobs-into-hole" heavy chain as well as antibody light chain encoding expression plasmids comprises the following elements:

a hygromycin resistance gene as a selection marker,
 an origin of replication, oriP, of Epstein-Barr virus (EBV),
 an origin of replication from the vector pUC18 which allows replication of this plasmid in *E. coli*
 a beta-lactamase gene which confers ampicillin resistance in *E. coli*,
 the immediate early enhancer and promoter from the human cytomegalovirus (HCMV),
 the human 1-immunoglobulin polyadenylation ("poly A") signal sequence, and
 unique BamHI and XbaI restriction sites.

The immunoglobulin genes comprising heavy or light chains with C-terminal attachment of scFv antibody fragments, "knobs-into-hole" heavy chains with unmodified VH domains, crossed C kappa domains or scFab fragments as well as unmodified light chains or CHI domain exchanged light chains were prepared by gene synthesis and cloned into pGA18 (ampR) plasmids as described. The pG18 (ampR) plasmids carrying the synthesized DNA segments and the expression vector were digested with BamHI and XbaI, BamHI and XmnI or BamHI and KpnI restriction enzymes (Roche Molecular Biochemicals) and subjected to agarose gel electrophoresis. Purified heavy or light chains with C-terminal attachment of scFv antibody fragments, "knobs-into-hole" heavy and unmodified or domain exchanged light chain encoding DNA segments were then ligated to the isolated expression vector BamHI/XbaI, BamHI/XmnI or BamHI/KpnI fragment resulting in the final expression vectors. The final expression vectors were transformed into *E. coli* cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Bispecific Antibodies in HEK293 Cells

Recombinant bispecific antibodies were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1\times10^6$ viable cells/ml one day before transfection. For transfection, DNA was prepared in 10 ml Dulbecco's PBS (PAA, Austria) using 162.5 µl of 293-FreeFREE™ Transfection Reagent (Merck, USA) and 125 µg of heavy with N-terminal attachment of scFab encoding DNA in a plasmid ratio of 1:1 with "Knobs-into-hole" heavy chain 1 and 2 and light chain plasmid DNA in a 1:1:1 molar ratio in 250 ml final transfection volume. For transfection of Cross Mabs, a plasmid ratio of 1:1:1:1, 1:1:1:2, 1:1:1:4, 1:1:1:8 of "Knobs-into-hole" heavy chain 1: unmodified light chain: C kappa domain exchanged "Knobs-into-hole" heavy chain 2: CHI domain exchanged light chain was prepared. The CH1-VL light chain plasmid ration was used at 1×, 2×, 4× and 8× molar ratios to assess the optimization of chain pairing using a combination of CE-SDS and Q-TOF spectrometry. Antibody containing cell culture supernatants were harvested 7 days after transfection by centrifugation at 14000 g for 30 minutes and filtered through a sterile filter (0.22 µm). Supernatants were stored at −20° C. until purification. The sequences of the resulting antibodies are shown below in table 8.

Preparation of the Glycoengineered Derivatives of Bispecific <Her2GlyMab> Antibodies Glycoengineered derivatives of bispecific <Her2GlyMab> antibodies were produced by co-transfecting HEK293-EBNA cells with the mammalian antibody heavy and light chain expression vectors using a calcium phosphate-transfection approach. Exponentially growing HEK293-EBNA cells were transfected by the calcium phosphate method. For the production of the glycoengineered antibody, the cells were co-transfected with a plasmid for a fusion GnTIII polypeptide expression and a second plasmid for mannosidase II expression, respectively. Plasmid ratios of bispecific antibodies were added as described in the material and methods section above. Cells were grown as adherent monolayer cultures in T flasks using DMEM culture medium supplemented with 10% FCS, and were transfected when they were between 50 and 80% confluent. For the transfection of a T75 flask, 7.5 (to 8) million cells were seeded 24 hours before transfection in ca 14 ml DMEM culture medium supplemented with FCS (at 10% V/V final), (eventually 250 µg/ml neomycin) and cells were placed at 37° C. in an incubator with a 5% CO2 atmosphere overnight. For each T75 flask to be transfected, a solution of DNA, CaCl2) and water was prepared by mixing 47 µg total plasmid vector DNA, 235 µl of a 1M CaCl2) solution, and adding water to a final volume of 469 µl. To this solution, 469 µl of a 50 mM HEPES, 280 mM NaCl, 1.5 mM Na2HPO4 solution at pH 7.05 were added, mixed immediately for 10 sec and left to stand at room temperature for 20 sec. The suspension was diluted with ca. 12 ml of DMEM supplemented with 2% FCS, and added to the 175 in place of the existing medium. The cells were incubated at 37° C., 5% CO2 for about 17 to 20 hours, then medium was replaced with ca. 12 ml DMEM, 10% FCS. The conditioned culture medium was harvested 5 to 7 days post-transfection centrifuged for 5 min at 210-300*g, sterile filtered through a 0.22 µm filter (or alternatively centrifuged for 5 min at 1200 rpm, followed by a second centrifugation for 10 min at 4000 rpm) and kept at 4° C.

Glycoengineered antibodies were purified and formulated as described above for the non-glycoengineered antibodies. The oligosaccharides attached to the Fc region of the antibodies were analysed as described below to determine the amount of fucose.

Framework Grafting

Rationale: Similar framework of trastuzumab and pertuzumab allows mis-pairing of light chains: Both Trastuzumab and Pertuzumab have a $V_H III$ $V_L kI$ framework and therefore the light chain interface affinity to both heavy chains is identical.

In order to avoid mispairing of light chains in the crossMab Herceptarg bispecific antibody, the Trastuzumab framework of "CrossMabXPer Her2GlyMab" was exchanged with the framework of the non-related antibody LC06. Trastuzumab is related to germlines hVH3_66 and hVK1D_39 whereas the antibody LC06 corresponds to germlines hVbase_VH1_1 germline and hVL_3, respectively. Pertuzumab is related to hVH3_23 and hVK1D_13 showing a very similar framework system compared to Trastuzumab.

Both germline acceptor frameworks of LC06 are different from the Trastuzumab framework, especially, the LC06 lambda light chain, compared to the Trastzumab kappa light chain. The antibody Fab crystal structure of Trastuzumab has been superimposed and the compatibility of the framewords have been structrally evaluated. CDRI, II and III of the Trastuzumab light chain were grafted onto the new Lambda framework of LC06. Mutations included were D98E and N30S, the N30S was used in favour of T31V because of the increase in affinity to the Her2 extracellular domain with the N30S modification. It was thought that any reduction of the Kd caused by the CDR grafting could be compensated by the use of the N30S mutation. Some accommodations in the acceptor frameworks were required in order to get the CDRs in their biological active conformation; for example A(LC06 lambda) at the Kabat position 71 of the light chain has been backmutated to F(Trastuzumab kappa). The original VHIII-VLkI (Kappa I family) framework of Pertuzumab was maintained. The resulting bispecific antibody is depicted as "CrossMab-CDRG Her2GlyMab", with sequences as shown in Table 8 below.

TABLE 8

Sequences of Herceptarg CrossMab bispecific antibodies.

| Construct | SEQ ID NO | Sequence |
|---|---|---|
| OAscFab1 Her2GlyMab | | |
| scFab Trastuzumab heavy chain 1 | 133 | diqmtqspsslsasvgdrvtitcrasqdynyavawyqqkpgkapklliysasflysgypsrfsg srsgtdftltisslqpedfatyycqqhyttpptfgqgtkveikrtvaapsvfifppsdeqlksgtas vvcllnnfypreakvqwkvdnalqsgnsqesvteqdskdstyslsstltlskadyekhkvyac evthqglsspvtksfnrgecggggsggggsggggsggggsggggsggggsggevqlvesgg glvqpggslrlscaasgfnikdtyihwyrqapgkglewvariyptngytryadsvkgrftisadt skntaylqmnslraedtavyycsrwggegfyamdywgqgtlytyssastkgpsvfplapssk stsggtaalgclykdyfpepytyswnsgaltsgyhtfpaylqssglyslssyytypssslgtqtyi cnvnhkpsntkvdkkvepkscdkthtcppcpapellggpsvflfppkpkdtlmisrtpevtcv vvdvshedpevkfnwyydgvevhnaktkpreeqynstyryvsyltylhqdwlngkeykck vsnkalpapiektiskakgqprepqvytlppcrdeltknqvslwclvkgfypsdiavewesng qpennykttppyldsdgsfflyskltvdksrwqqgnyfscsvmhealhnhytqksls1spgk |
| Pertuzumab heavy chain 2 | 134 | evqlvesgggglvqpggslrlscaasgftftdytmdwyrqapgkglewvadynpnsggsiyn qrfkgrftlsydrskntlylqmnslraedtavyycarnlgpsfyfdywgqgtlytyssastkgps vfplapsskstsggtaalgclykdyfpepytyswnsgaltsgyhtfpaylqssglyslssyytyp ssslgtqtyicnynhkpsntkvdkkvepkscdkthtcppcpapellggpsvflfppkpkdtlm |

TABLE 8-continued

Sequences of Herceptarg CrossMab bispecific antibodies.

| Construct | SEQ ID NO | Sequence |
|---|---|---|
| | | isrtpevtcvvvdvshedpevkfnwyvdgvevhnaktkpreeqynstyrvvsyltvlhqdwl<br>ngkeykckvsnkalpapiektiskakgqprepqvctlppsrdeltknqvslscavkgfypsdi<br>avewesngqpennykttppvldsdgsfflvskltvdksrwqqgnvfscsvmhealhnhytq<br>kslslspgk |
| Pertuzumab<br>lght chain 1 | 135 | diqmtqspsslsasvgdrvtitckasqdvsigvawyqqkpgkapkllysasyrytgvpsrfsg<br>sgsgtdftltisslqpedfatyycqqyyiypytfgqgtkveikrtvaapsvfifppsdeqlksgtas<br>vvellnnfypreakvqwkvdnalqsgnsqesvteqdskdstyslsstltlskadyekhkvyac<br>evthqglsspvtksfnrgec |

OAscFab2 Her2GlyMab

| Construct | SEQ ID NO | Sequence |
|---|---|---|
| Pertuzumab<br>heavy chain 1 | 136 | evqlvesgggglvqpggslrlscaasgftftdytmdwvrqapgkglewvadvnpnsggsiyn<br>qrfkgrftlsvdrskntlylqmnslraedtavyycarnlgpsfyfdywgqgtivtvssastkgps<br>vfplapssktstsggtaalgclvkdyfpepvtvswnsgaltsgvhtfpavlqssglyslssvvtvp<br>ssslgtqtyicnvnhkpsntkvdkkvepkscdkthtcppcpapellggpsvflfppkpkdtlm<br>isrtpevtcvvvdvshedpevkfnwyvdgvevhnaktkpreeqynstyrvvsyltvlhqdwl<br>ngkeykckvsnkalpapiektiskakgqprepqvctlppsrdeltknqvslscavkgfypsdi<br>avewesngqpennykttppvldsdgsfflvskltvdksrwqqgnvfscsvmhealhnhytq<br>kslslspgk |
| Pertuzumab<br>light chain 1 | 137 | diqmtqspsslsasvgdrvtitckasqdvsigvawyqqkpgkapkllysasyrytgvpsrfsg<br>sgsgtdftltisslqpedfatyycqqyyiypytfgqgtkveikrtvaapsvfifppsdeqlksgtas<br>vvellnnfypreakvqwkvdnalqsgnsqesvteqdskdstyslsstltlskadyekhkvyac<br>evthqglsspvtksfnrgec |
| scFab<br>Trastuzumab<br>heavy chain 2 | 138 | evqlvesgggglvqpggslrlscaasgfnikdtyihwvrqapgkglewvariyptngytryads<br>vkgrftisadtskntaylqmnslraedtavyycsrwggegfyamdywgqgtivtvssastkg<br>psvfplapssktstsggtaalgclvkdyfpepvtvswnsgaltsgvhtfpavlqssglyslssvvt<br>vpssslgtqtyicnvnhkpsntkvdkkvepkscdkthtcppcpapellggpsvflfppkpkdt<br>lmisrtpevtcvvvdvshedpevkfnwyvdgvevhnaktkpreeqynstyrvvsyltvlhq<br>dwlngkeykckvsnkalpapiektiskakgqprepqvytlpperdeltknqvslwclvkgfy<br>psdiavewesngqpennykttppvldsdgsfflyskltvdksrwqqgnvfscsvmhealhn<br>hytqkslslspgkggggsggggsggggsggggsggggsggggsggdiqmtqspsslsasvg<br>drvtitcrasqdvnvavawyqqkpgkapkllyasflysgvpsrfsgsrsgtdifitisslqped<br>fatyycqqhyttpptfgqgtkveikrtvaapsvfifppsdeqlksgtasvvellnnfypreakvq<br>wkvdnalqsgnsqesvteqdskdstyslsstltlskadyekhkvyacevthqglsspvtksfnr<br>gee |

OAscFabPer1 Her2GlyMab

| Construct | SEQ ID NO | Sequence |
|---|---|---|
| scFab<br>Pertuzumab<br>heavy chain 1 | 139 | evqlvesgggglvqpggslrlscaasgftftdytmdwvrqapgkglewvadvnpnsggsiyn<br>qrfkgrftlsvdrskntlylqmnslraedtavyycarnlgpsfyfdywgqgtivtvssastkgps<br>vfplapssktstsggtaalgclvkdyfpepvtvswnsgaltsgvhtfpavlqssglyslssvvtvp<br>ssslgtqtyicnvnhkpsntkvdkkvepkscdkthtcppcpapellggpsvflfppkpkdtlm<br>isrtpevtcvvvdvshedpevkfnwyvdgvevhnaktkpreeqynstyrvvsyltvlhqdwl<br>ngkeykckvsnkalpapiektiskakgqprepqvctlppsrdeltknqvslscavkgfypsdi<br>avewesngqpennykttppvldsdgsfflvskltvdksrwqqgnvfscsvmhealhnhytq<br>kslslspgkggggsggggsggggsggggsggggsggggsggdiqmtqspsslsasvgdrvt<br>itckasqdvsigvawyqqkpgkapkllysasyrytgvpsrfsgsgsgtdifitisslqpedfaty<br>ycqqyyiypytfgqgtkveikrtvaapsvfifppsdeqlksgtasvvellnnfypreakvqwk<br>vdnalqsgnsqesvteqdskdstyslsstltlskadyekhkvyacevthqglsspvtksfnrgec |
| Trastuzumab<br>heavy chain 2 | 140 | evqlvesgggglvqpggslrlscaasgfnikdtyihwvrqapgkglewvariyptngytryads<br>vkgrftisadtskntaylqmnslraedtavyycsrwggegfyamdywgqgtivtvssastkg<br>psvfplapssktstsggtaalgclvkdyfpepvtvswnsgaltsgvhtfpavlqssglyslssvvt<br>vpssslgtqtyicnvnhkpsntkvdkkvepkscdkthtcppcpapellggpsvflfppkpkdt<br>lmisrtpevtcvvvdvshedpevkfnwyvdgvevhnaktkpreeqynstyrvvsvltvlhq<br>dwlngkeykckvsnkalpapiektiskakgqprepqvytlpperdeltknqvslwclvkgfy<br>psdiavewesngqpennykttppvldsdgsfflyskltvdksrwqqgnvfscsvmhealhn<br>hytqkslslspgk |
| Trastuzumab<br>light chain 2 | 141 | diqmtqspsslsasvgdrvtitcrasqdvnvavawyqqkpgkapkllyasflysgvpsrfsg<br>srsgtdftltisslqpedfatyycqqhyttpptfgqgtkveikrtvaapsvfifppsdeqlksgtas<br>vvellnnfypreakvqwkvdnalqsgnsqesvteqdskdstyslsstltlskadyekhkvyac<br>evthqglsspvtksfnrge |

OAscFabPer2 Her2GlyMab

| Construct | SEQ ID NO | Sequence |
|---|---|---|
| Trastuzumab<br>heavy chain 1 | 142 | evqlvesgggglvqpggslrlscaasgfnikdtyihwvrqapgkglewvariyptngytryads<br>vkgrftisadtskntaylqmnslraedtavyycsrwggegfyamdywgqgtivtvssastkg<br>psvfplapssktstsggtaalgclvkdyfpepvtvswnsgaltsgvhtfpavlqssglyslssvvt<br>vpssslgtqtyicnvnhkpsntkvdkkvepkscdkthtcppcpapellggpsvflfppkpkdt<br>lmisrtpevtcvvvdvshedpevkfnwyvdgvevhnaktkpreeqynstyrvvsltvlhq |

TABLE 8-continued

Sequences of Herceptarq CrossMab bispecific antibodies.

| Construct | SEQ ID NO | Sequence |
|---|---|---|
| | | dwlngkeykckvsnkalpapiektiskakgqprepqvytlpperdeltknqvslwclvkgfy psdiavewesngqpennykttppvldsdgsfflyskltvdksrwqqgnvfscsvmhealhn hytqkslslspgk |
| Trastuzumab light chain 1 | 143 | diqmtqspsslsasvgdrvtitcrasqdvnvavawyqqkpgkapllliysasflysgvpsrfsg srsgtdftltisslqpedfatyycqqhyttpptfgqgtkveikrtvaapsvfifppsdeqlksgtas vvcllnnfypreakvqwkvdnalqsgnsqesvteqdskdstyslsstltlskadyekhkvyac evthqglsspvtksfnrgec |
| scFab Pertuzumab heavy chain 2 | 144 | evqlvesggglvqpggslrlscaasgftftdytmdwvrqapgkglewvadvnpnsggsiyn qrfkgrftlsydrskntlylqmnslraedtavyycarnlgpsfyfdywgqgtlytyssastkgps vfplapssktstsggtaalgclvkdyfpepvtvswnsgaltsgvhtfpavlqssglyslssvvtvp ssslgtqtyicnvnhkpsntkvdkkvepkscdkthtcppcpapellggpsvflfppkpkdtlm isrtpevtcvvvdvshedpevkfnwyvdgvevhnaktkpreeqynstyrvvsvltvlhqdwl ngkeykckvsnkalpapiektiskakgqprepqvctlppsrdeltknqvslscavkgfypsdi avewesngqpennykttppvldsdgsfflvskltvdksrwqqgnvfscsvmhealhnhytq kslslspgkggggsggggsggggsggggsggggsggggsdiqmtqspsslsasvgdrvt itckasqdvsigvawyqqkpgkapllliysasyrytgvpsrfsgsgsgtdifitisslqpedfaty ycqqyyiypytfgqgtkveikrtvaapsvfifppsdeqlksgtasvvcllnnfypreakvqwk vdnalqsgnsqesvteqdskdstyslsstltlskadyekhkvyacevthqglsspvtksfnrgec |

Cros sMab-XPer Her2GlyMab

| XPertuzumab heavy chain | 109 | evqlvesggglvqpggslrlscaasgftftdytmdwvrqapgkglewvadvnpnsggsiyn qrfkgrftlsydrskntlylqmnslraedtavyycamlgpsfyfdywgqgtivtvssasvaaps vfifppsdeqlksgtasvvcllnnfypreakvqwkvdnalqsgnsqesvteqdskdstyslsst itlskadyekhkvyacevthqglsspvtksfnrgecdkthtcppcpapellggpsvflfppkpk dtlmisrtpevtcvvvdvshedpevkfnwyvdgvevhnaktkpreeqynstyrvvsvltvlh qdwlngkeykckvsnkalpapiektiskakgqprepqvytlppcrdeltknqvslwclvkgf ypsdiavewesngqpennykttppvldsdgsfflyskltvdksrwqqgnvfscsvmhealh nhytqkslslspgk |
|---|---|---|
| XPertuzumab light chain | 110 | diqmtqspsslsasvgdrvtitckasqdvsigvawyqqkpgkapllliysasyrytgvpsrfsg sgsgtdftltisslqpedfatyycqqyyiypytfgqgtkveikssastkgpsvfplapssksts ggt aalgclvkdyfpepvtvswnsgaltsgvhtfpavlqssglyslssvvtvpssslgtqtyicnvnh kpsntkvdkkvepksc |
| Trastuzumab heavy chain (VH$_{D98E}$ CH1) | 96 | evqlvesggglvqpggslrlscaasgfnikdtyihwvrqapgkglewvariyptngytryads vkgrftisadtskntaylqmnslraedtavyycsrwggegfyamdywgqgtivtvssastkg psvfplapssktsggtaalgclvkdyfpepvtvswnsgaltsgvhtfpavlqssglyslssvvt vpssslgtqtyicnvnhkpsntkvdkkvepkscdkthtcppcpapellggpsvflfppkpkdt lmisrtpevtcvvvdvshedpevkfnwyvdgvevhnaktkpreeqynstyrvvsvltvlhq dwlngkeykckvsnkalpapiektiskakgqprepqvctlppsrdeltknqvslscavkgfyp sdiavewesngqpennykttppvldsdgsfflvskltvdksrwqqgnvfscsvmhealhnh ytqkslslspgk |
| Trastuzumab light chain (VL$_{T31V}$ CL) | 86 | diqmtqspsslsasvgdrvtitcrasqdvnvavawyqqkpgkapllliysasflysgvpsrfsg srsgtdftltisslqpedfatyycqqhyttpptfgqgtkveikrtvaapsvfifppsdeqlksgtas vvcllnnfypreakvqwkvdnalqsgnsqesvteqdskdstyslsstltlskadyekhkvyac evthqglsspvtksfnrgec |

CrossMab-XTra Her2GlyMab

| Pertuzumab heavy chain | 119 | evqlvesggglvqpggslrlscaasgftftdytmdwvrqapgkglewvadvnpnsggsiyn qrfkgrftlsydrskntlylqmnslraedtavyycarnlgpsfyfdywgqgtivtvssasvaaps vfifppsdeqlksgtasvvcllnnfypreakvqwkvdnalqsgnsqesvteqdskdstyslsst itlskadyekhkvyacevthqglsspvtksfnrgecdkthtcppcpapellggpsvflfppkpk dtlmisrtpevtcvvvdvshedpevkfnwyvdgvevhnaktkpreeqynstyrvvsvltvlh qdwlngkeykckvsnkalpapiektiskakgqprepqvctlppsrdeltknqvslscavkgfy psdiavewesngqpennykttppvldsdgsfflvskltvdksrwqqgnvfscsvmhealhn hytqkslslspgk |
|---|---|---|
| Pertuzumab light chain | 120 | diqmtqspsslsasvgdrvtitckasqdvsigvawyqqkpgkapllliysasyrytgvpsrfsg sgsgtdftltisslqpedfatyycqqyyiypytfgqgtkveikrtvaapsvfifppsdeqlksgtas vvcllnnfypreakvqwkvdnalqsgnsqesvteqdskdstyslsstltlskadyekhkvyac evthqglsspvtksfnrgec |
| XTrastuzumab heavy chain | 121 | evqlvesggglvqpggslrlscaasgfnikdtyihwvrqapgkglewvariyptngytryads vkgrftisadtskntaylqmnslraedtavyycsrwggegfyamdywgqgtivtvssastkg psvfplapssktsggtaalgclvkdyfpepvtvswnsgaltsgvhtfpavlqssglyslssvvt vpssslgtqtyicnvnhkpsntkvdkkvepkscdkthtcppcpapellggpsvflfppkpkdt lmisrtpevtcvvvdvshedpevkfnwyvdgvevhnaktkpreeqynstyrvvsvltvlhq dwlngkeykckvsnkalpapiektiskakgqprepqvytlppcrdeltknqvslwclvkgfy psdiavewesngqpennykttppvldsdgsfflyskltvdksrwqqgnvfscsvmhealhn hytqkslslspgk |

TABLE 8-continued

Sequences of Herceptarg CrossMab bispecific antibodies.

| Construct | SEQ ID NO | Sequence |
|---|---|---|
| XTrastuzuma light chain | 122 | diqmtqspsslsasvgdrvtitcrasqdvnvavawyqqkpgkapkllysasflysgvpsrfsg srsgtdftltisslqpedfatyycqqhyttpptfgqgtkveikssastkgpsvfplapssksstsggta algclvkdyfpepvtvswnsgaltsgvhtfpavlqssglyslssvvtvpssslgtqtyicnvnhk psntkvdkkvepksc |

Optimized Trastuzumab sequences: CrossMab-XTra Her2GlyMab and CrossMab-XPer Her2GlyMab

| Construct | SEQ ID NO | Sequence |
|---|---|---|
| Trastuzumab VH (D98E) | 117 | evqlvesgggvlqpggslrlscaasgfnikdtyihwvrqapgkglewvariyptngytryads vkgrftisadtskntaylqmnslraedtavyycsrwggegfyamdywgqgtlvtvss |
| Trastuzumab CH1 | 115 | astkgpsvfplapssksstsggtaalgclvkdyfpepvtvswnsgaltsgvhtfpavlqssglysl ssvvtvpssslgtqtyicnvnhkpsntkvdkkvepkscdkth |
| Trastuzumab VL (T31V) | 118 | diqmtqspsslsasvgdrvtitcrasqdvnvavawyqqkpgkapkllysasflysgvpsrfsg srsgtdftltisslqpedfatyycqqhyttpptfgqgtkveikr |
| Trastuzumab CL | 116 | tvaapsvfifppsdeqlksgtasvvcllnnfypreakvqwkvdnalqsgnsqesvteqdskds tyslsstltlskadyekhkvyacevthqglsspvtksfnrgec |
| Trastuzumab VH CDR1 | 20 | gfnikdtyih |
| Trastuzumab VH CDR2 | 29 | riyptngytryadsvkg |
| Trastuzumab VH CDR3 | 79 | wggegfyamdy |
| Trastuzumab VL CDR1 | 104 | rasqdvnvava |
| Trastuzumab VL CDR2 | 18 | sasflys |
| Trastuzumab VL CDR3 | 19 | qqhyttppt |

CrossMab-CDRG Her2GlyMab

| Construct | SEQ ID NO | Sequence |
|---|---|---|
| XPertuzumab heavy chain (VHCL) | 109 | evqlvesgggvlqpggslrlscaasgftftdytmdwvrqapgkglewvadvnpnsggsiyn qrfkgrftlsvdrskntlylqmnslraedtavyycarnlgpsfyfdywgqgtlvtvssasvaaps vfifppsdeqlksgtasvvcllnnfypreakvqwkvdnalqsgnsqesvteqdskdstyslsst ltlskadyekhkvyacevthqglsspvtksfnrgecdkthtcppcpapellggpsvflfppkpk dtlmisrtpevtcvvvdvshedpevkfnwyvdgvevhnaktkpreeqynstyrvvsyltvlh qdwlngkeykckvsnkalpapiektiskakgqprepqvytlpperdeltknqvslwclvkgf ypsdiavewesngqpennykttppvldsdgsfflyskltvdksrwqqgnvfscsvmhealh nhytqkslsspgk |
| Pertuzumab light chain (VLCH1) | 110 | diqmtqspsslsasvgdrvtitckasqdvsigvawyqqkpgkapkllysasyrytgvpsrfsg sgsgtdftltisslqpedfatyycqqyyiypytfgqgtkveikssastkgpsvfplapsksststggt aalgclvkdyfpepvtvswnsgaltsgvhtfpavlqssglyslssvvtvpssslgtqtyicnvnh kpsntkvdkkvepksc |
| Trastuzumab CDRG heavy chain (VHCH1) | 111 | qvqlvqsgaevkkpgasvkvsckasgfnikdtyihwvrqapgqglewmgriyptngytrya qkfqgrvtmtrdtsistaymelsrlrsddtavyycsrwggegfyamdywgqgtmvtvssast kgpsvfplapssksstsggtaalgclvkdyfpepvtvswnsgaltsgvhtfpavlqssglyslssv vtvpssslgtqtyicnvnhkpsntkvdkkvepkscdkthtcppcpapellggpsvflfppkpk dtlmisrtpevtcvvvdvshedpevkfnwyvdgvevhnaktkpreeqynstyrvvsyltvlh qdwlngkeykckvsnkalpapiektiskakgqprepqvctlppsrdeltknqvslscavkgfy psdiavewesngqpennykttppvldsdgsfflvskltvdksrwqqgnvfscsvmhealhn hytqkslsspgk |
| Trastuzumab CDRG light chain (VLCL) | 112 | diqltqppsysvapgqtaritcgasqdvstavawyqqkpgqapvlvvysasflysgipsrfsgs rsgtdftltisrveagdeadyycqqhyttpptfgtgtkvtlrtvaapsvfifppsdeqlksgtasv vellnnfypreakvqwlcvdnalqsgnsqesvteqdskdstyslsstltlskadyekhkvyace vthqglsspvtksfnrgec |
| Trastuzumab CDRG VH (D98E, CDRG) | 105 | evqlvqsgaevkkpgasvkvsckasgfnikdtyihwvrqapgqglewmgriyptngytrya qkfqgrvtmtrdtsistaymelsrlrsddtavyycsrwggegfyamdywgqgtmvtvss |
| Trastuzumab CH1 | 115 | astkgpsvfplapssksstsggtaalgclvkdyfpepvtvswnsgaltsgvhtfpavlqssglysl ssvvtvpssslgtqtyicnvnhkpsntkvdkkvepkscdkth |

TABLE 8-continued

Sequences of Herceptarg CrossMab bispecific antibodies.

| Construct | SEQ ID NO | Sequence |
|---|---|---|
| Trastuzumab CDRG VL (N30T, CDRG) | 106 | diqltqppsysvapgqtaritcgasqdvstavawyqqkpgqapvlvvysasflysgipsrfsgs rsgtdftltisrveagdeadyycqqhyttpptfgtgtkvtvlr |
| Trastuzumab CL | 116 | tvaapsvfifppsdeqlksgtasvvellnnfypreakvqwkvdnalqsgnsqesvteqdskds tyslsstltlskadyekhkvyacevthqglsspvtksfnrgec |
| Trastuzumab CDRG VH CDR1 | 20 | gfnikdtyih |
| Trastuzumab CDRG VH CDR2 | 108 | riyptngytryaqkfqg |
| Trastuzumab CDRG VH CDR3 | 79 | wggegfyamdy |
| Trastuzumab CDRG VL CDR1 | 107 | gasqdvstava |
| Trastuzumab CDRG VL CDR2 | 18 | sasflys |
| Trastuzumab CDRG VL CDR3 | 19 | qqhyttppt |

Pertuzumab sequences in CrossMab-CDRG Her2GlyMab, CrossMab-XTra Her2GlyMab and CrossMab-XPer Her2GlyMab: see Pertuzumab wt (parent) sequences Table 32

Purification of Bispecific Antibodies

Bispecific antibodies were purified from cell culture supernatants by affinity chromatography using MABSELECT SURE™ SEPHAROSE™ (GE Healthcare, Sweden) and SUPERDEX™ 200 size exclusion (GE Healthcare, Sweden) chromatography. Briefly, sterile filtered cell culture supernatants were captured on a MABSELECT SURE™ resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted protein fractions were pooled, neutralized with 2M TRIS™ (tris(hydroxymethyl)aminomethane), pH 9.0 and further purified by size exclusion chromatography using a SUPERDEX™ 200 26/60 GL (GE Healthcare, Sweden) column equilibrated with 20 mM histidine, 140 mM NaCl, pH 6.0. Size exclusion chromatography fractions were analysed by CE-SDS (Caliper Life Science, USA) and bispecific antibody containing fractions were pooled and stored at −80° C.

Analysis of Purified Proteins

The protein concentration of purified protein samples was determined by measuring the optical density (OD) at 280 nm, using the molar extinction coefficient calculated on the basis of the amino acid sequence. Purity, antibody integrity and molecular weight of bispecific and control antibodies were analyzed by CE-SDS using microfluidic LABCHIP® technology (Caliper Life Science, USA). 5 μl of protein solution was prepared for CE-SDS analysis using the HT Protein Express Reagent Kit according manufacturer's instructions and analysed on LABCHIP® GXII system using a HT Protein Express Chip. Data were analyzed using LABCHIP® GX Software version 3.0.618.0. The aggregate content of bispecific and control antibody samples was analyzed by high-performance SEC using a SUPERDEX™ 200 analytical size-exclusion column (GE Healthcare, Sweden) in 200 mM $KH_2PO_4$, 250 mM KCl, pH 7.0 running buffer at 25° C. 25 μg protein were injected on the column at a flow rate of 0.5 ml/min and eluted isocratic over 50 minutes.

Mass Spectrometry

The integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals). The amount of heavy and light chain mis-pairing was also quantified.

Surface Plasmon Resonance

| Instrument: | BIAacore T100 (GE Healthcare) Software: BIACORE ™ T100 Control, Version 2.02/ 2.03 BIACORE ™ T100 Evaluation, Version 2.02/ 2.03 BIACORE ™ B3000 (Biacore) Software: BIACORE ™ B3000 Control, Version 4.1.2 BIAEvaluation, Version 4.1.1 |
|---|---|

Assayformat Chip: CM5-Chip

Kinetic constants and resulting affinities of <Her2GlyMab>—molecules were measured for both "Trastuzumab"— and "Pertuzumab"—functionalities respectively. These two functionalities were distinguished via pre-complexation of Her2 with either amine coupled parental MAb "Trastuzumab" (FC1/2) or "Pertuzumab"

FC3/4). Complex formation of parental MAb and Her2 commensed after injection of Her2 ECD.

As a consequence of pre-complexed parental MAb "Trastuzumab"/Her2 all "° Trastuzumab"-binding sites are saturated, but all "Pertuzumab"-binding sites are available and vice versa. Finally the binding of the "<Her2GlyMab>"-molecules to be analyzed was measured via injections using increasing concentrations with each cycle. Association and dissociation observed were calculated with a Langmuir 1:1 binding model. To minimize dissociation of Her2 during the measurements, the kinetic constants were measured at T=25° C.

Amine Coupling of Capture Molecules

Standard amine coupling on flow cells 1 to 4 according to the manufacturer's instructions: CM5 Chip, T=25° C., running buffer: HBS-N buffer, activation by mixture of EDC/NHS, aimed at 800 RU; the parental Abs "Trastuzumab" or "Pertuzumab" were diluted in coupling buffer sodium acetate, pH 4.5, c=2-3 µg/mL; finally remaining activated carboxyl groups were blocked by injection of 1 M Ethanolamine.

Chip surface on flow cell 1 and 3 (with either amine coupled parental mAb "Trastuzumab" or "Pertuzumab") were used as reference control surface for correction of possible buffer-effects or non-specific binding.

Kinetic Characterization of <Her2GlyMab> Molecules at 25° C.

Running buffer: PBS

All samples were diluted with running buffer+1 mg/mL BSA.

Capturing of HER2 ECD on flow cells 2 and 4: c=100 nM, flow 5 µl/min, time 120 sec. Analyte samples: A classical concentration series of the <Her2GlyMab>-molecules were analyzed at five concentrations (c=300, 100, 33.33, 11.11 und 3.7 nM.) at a flow rate of 50 µl/min was injected. Singles for each concentration, one as a duplicate; association time: 180 sec., dissociation time: 900 sec.

Final regeneration was performed after each cycle using 10 mM Glycin pH 2.5 for amine coupled Mab "Trastuzumab" and 25 mM NaOH for amine coupled Mab "Pertuzumab", contact time each 60 sec, flow rate 30 µl/min.

Kinetic parameters were calculated by using double referencing (control reference: binding of analyte to Mabs Trastuzumab and Pertuzumab respectively; Flow Cell: 1 respectively 3), concentration "0" used as the blank Calculations were performed with model 'Langmuir binding 1:1, RI (refractive index)=0.

Results: Expression & Purification Bispecific, Bivalent <Her2GlyMab> Antibody Molecules According the procedures described in the materials and methods above, the bispecific, bivalent <Her2GlyMab> antibody molecules OAscFab1, OAscFab2, OAscFabPer1, OAscFabPer2, CrossMab-XPer, CrossMab-XTra and CrossMab-CDRG were expressed and purified. In each molecule the VH and VL of part are based on optimized Trastuzumab sequences with mutations T31V or N30T in the variable light chain and mutation D98E in the heavy chain and the Pertuzumab parent sequence respectively. The schematic structure of the antibodies is shown in FIGS. 10A-B. The sequences are shown in Table 8 above.

Figure 11A:
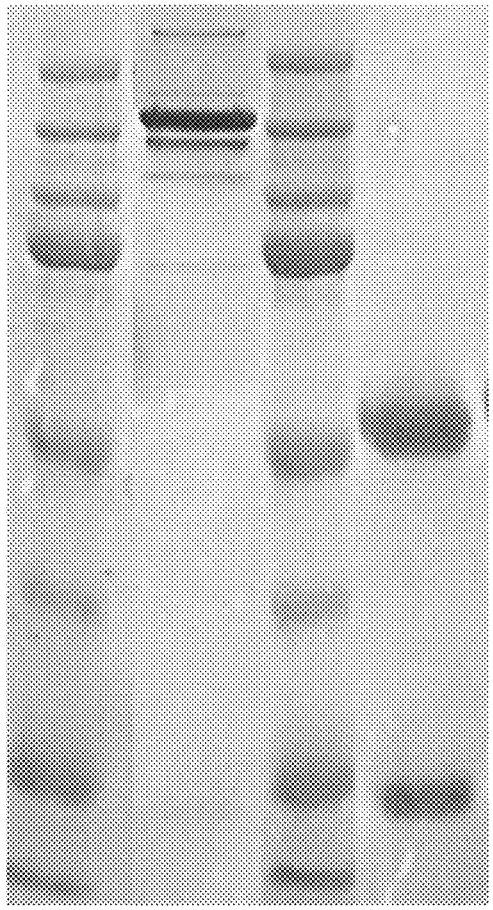
FIGS. 11A-11B: Purification of CrossMab-XPer (SEQ ID NOs 109, 110, 96, 86).
Figure 11B:
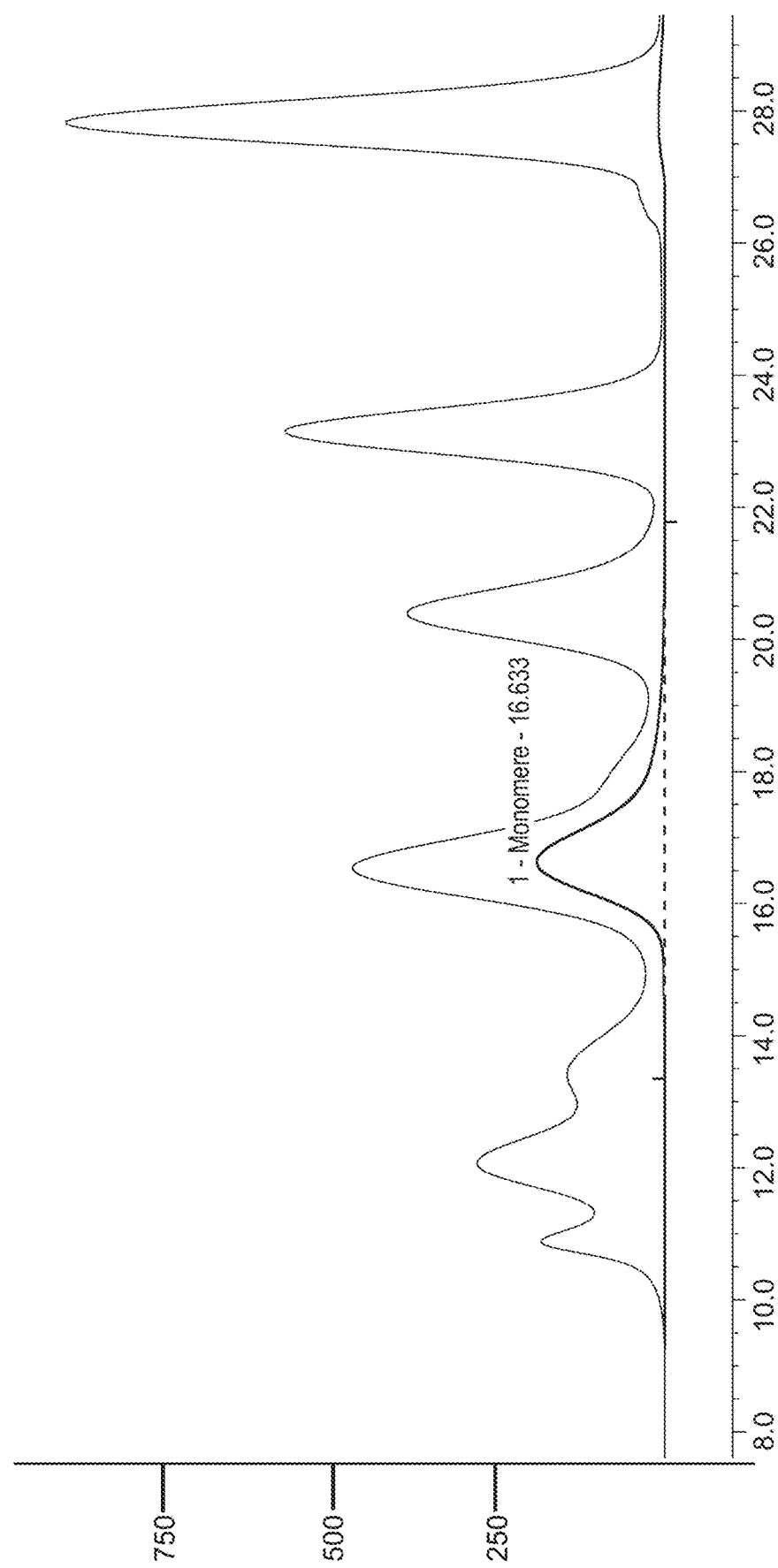

Expression of <Her2GlyMab> antibody molecules OAscFab1 Her2 GlyMab, OAscFab2 Her2 GlyMab, OAscFabPer1 Her2 GlyMab, OAscFabPer2 Her2 GlyMab (all glycoengineered, Knobs-into-holes, with the Trastuzumab scFab bearing D98E and T31V mutations), CrossMab-XPer Her2 GlyMab, CrossMab-XTra Her2 GlyMab (both glycoengineered, Knobs-into-holes, with the Trastuzumab cross-Fab bearing D98E and T31V mutations), and CrossMab-CDRG Her2 GlyMab (glycoengineered, Knobs-into-holes, CDR grafted, with the Trastuzumab cross-Fab bearing D98E and N30S mutations) was confirmed by western blotting and HP-SEC (FIGS. 11A-B). Purification of OAscFab1, OAscFab2, OAscFabPer1, OAscFabPer2, CrossMab-XPer, CrossMab XTra and CrossMab-CDRG led to the yields shown in Table 9. All OAscFab constructs showed less than 90% monomer post purification, the reduced purity of these molecules could not be increased by optimization of the plasmid ratios in expression (data not shown). However, optimization of the plasmid chain ratios in expression proved to increase the monomeric fraction present post purification of the CrossMab antibodies as described below.

TABLE 9

Her2GlyMab Purification - Analysis of the percentage aggregation post protein A and SEC purification using HP-SEC and the respective protein yields calculated by UV spectroscopy A280 of the glycoengineered constructs.

| Name | Purity post protein A (%) | Expression yield post protein A (mg/L) | Purity post SEC (%) | Expression yield post SEC (mg/L) |
|---|---|---|---|---|
| OAscFab1 (SEQ ID NOS 133, 134, 135) | 48.4 | 144 | 90 | 31.6 |
| OAscFab2 (SEQ ID NOS 136, 137, 138) | 41 | 42.9 | 93.6 | 12.6 |
| OAscFabPer1 (SEQ ID NOS 139, 140, 141) | 41.6 | 43.4 | 88.8 | 4.6 |
| OAscFabPer2 (SEQ ID NOS 142, 143, 144) | 38.2 | 34.2 | 86.7 | 6.6 |
| CrossMab-XTra (SEQ ID NOS 119, 120, 121, 122) | 65.1 | 28.4 | 73 | 10.6 |
| CrossMab-XPer (SEQ ID NOS 109, 110, 96, 86) | 76.4 | 30.9 | 85 | 17.9 |
| CrossMab-CDRG (SEQ ID NOS 109, 110, 111, 112) | 73 | 31.5 | 95 | 11.9 |

Example 7: Expression & Purification Bispecific, Bivalent <Her2GlyMab> Antibody Molecules Optimization of the Plasmid Ratios Used in Expression CrossMab-XTra According the procedures described in the materials and methods above, the bispecific, bivalent <Her2GlyMab> antibody molecule CrossMab-XTra, was expressed with molar plasmid ratios of 1:1:1:1, 1:1:1:2, 1:1:1:4 and 1:1:1:8 and purified. Expression of CrossMab-XTra was confirmed by Western blot. After Protein A purification of cell culture supernatants the construct showed at a 1:1:1:1 equimolar plasmid ratio approximately 73% of bispecific antibody with the expected molecular weight of approximately 148 kDa as detected by Q-TOF MS; 11% containing 2× Pertuzumab light chains paired with Pertuzumab and XTrastuzumab heavy chains; 9% intact XTrastuzumab antibodies (both heavy and light chains originating from XTrastuzumab) with the formation of the heavy chain hole-hole association; 4% XTrastuzumab heavy chain hole-hole association combined with Pertuzumab light chains only; and 3% XTrastuzumab heavy chain hole-hole association with 1× XTrastuzumab light chain and 1× Pertuzumab light chain. The 1:1:1:2 plasmid ratio where the molar ratio of the crossed Trastuzumab light chain (XHerLC) was expressed 2-fold, showed approximately 81% of bispecific antibody with the expected molecular weight of approximately 148 kDa as detected by Q-TOF MS; 1% containing 2× Pertuzumab light chains paired with Pertuzumab and XTrastuzumab heavy chains; 16% intact XTrastuzumab antibodies (both heavy and light chains originating from XTrastuzumab) with the formation of the heavy chain hole-hole association; XTrastuzumab heavy chain hole-hole association combined with Pertuzumab light chains only were not detected; and 1% XTrastuzumab heavy chain hole-hole association with 1× XTrastuzumab light chain and 1× Pertuzumab light chain.

The 1:1:1:4 plasmid ratio where the molar ratio of the crossed Trastuzumab light chain was expressed 4-fold, showed approximately 64% of bispecific antibody with the expected molecular weight of approximately 148 kDa as detected by Q-TOF MS; 2× Pertuzumab light chains paired with Pertuzumab and XTrastuzumab heavy chains was not detected, however, 12% 2× XTrastuzumab light chains paired with Pertuzumab and XTrastuzumab heavy chains was detected for the first time at this ratio; 24% intact XTrastuzumab antibodies (both heavy and light chains originating from XTrastuzumab) with the formation of the heavy chain hole-hole association; XTrastuzumab heavy chain hole-hole association combined with Pertuzumab light chains only were not detected; XTrastuzumab heavy chain hole-hole association with 1× XTrastuzuHab light chain and 1× Pertuzumab light chain were not detected.

The 1:1:1:8 plasmid ratio where the molar ratio of the crossed Trastuzumab light chain was expressed 8-fold, showed approximately 45% of bispecific antibody with the expected molecular weight of approximately 148 kDa as detected by Q-TOF MS; 2× Pertuzumab light chains paired with Pertuzumab and XTrastuzumab heavy chains was not detected, however, 28% 2× XTrastuzumab light chains paired with Pertuzumab and XTrastuzumab heavy chains was detected for the first time at this ratio; 27% intact XTrastuzumab antibodies (both heavy and light chains originating from XTrastuzumab) with the formation of the heavy chain hole-hole association; XTrastuzumab heavy chain hole-hole association combined with Pertuzumab light chains only were not detected; XTrastuzumab heavy chain hole-hole association with 1× XTrastuzumab light chain and 1× Pertuzumab light chain were not detected.

TABLE 10

CrossMab-XTra Her2GlyMab - Q-TOF analysis and quantification of the by-product profile of the Her2GlyMab antibody constructs comparing the optimization plasmid titration of the crossed Trastuzumab light chain (XHer LC).

| Detected protein species in MS | CrossMab-XTra Her2GlyMab 1:1:1:1 | CrossMab-XTra Her2GlyMab 1:1:1:2 | CrossMab-XTra Her2GlyMab 1:1:1:4 | CrossMab-XTra Her2GlyMab 1:1:1:8 |
|---|---|---|---|---|
| 1 × XHer HC; 1 × Per HC; 2 × XHer LC | N.D. | N.D. | ~12% | ~28% |
| 2 × XHer HC; 2 × XHer LC | ~9% | ~16% | ~24% | ~27% |
| CrossMab-XTra Her2GlyMab (100%) | ~73% | ~81% | ~64% | ~45% |
| 2 × XHer HC; 1 × XHer LC; 1 × Per HC | ~3% | ~1% | N.D. | N.D. |
| 1 × XHer HC; 1 × Per HC; 2 × Per LC | ~11% | ~1% | N.D. | N.D. |
| 2 × XHer HC; 2 × Per LC | ~4% | N.D. | N.D. | N.D. |

N.D.—Not Detected

CrossMab-XPer

After Protein A purification of cell culture supernatants the construct showed at a 1:1:1:1 equimolar plasmid ratio approximately 85% of bispecific antibody with the expected molecular weight of approximately 148 kDa as detected by Q-TOF MS; 2% containing 2× XPertuzumab light chains paired with XPertuzumab and Trastuzumab heavy chains; 1% intact Trastuzumab antibodies (both heavy and light chains originating from Trastuzumab) with the formation of the heavy chain hole-hole association; 12% 2× Trastuzumab light chains paired with XPertuzumab and Trastuzumab heavy chains. No further species were detected.

The 1:1:1:2 plasmid ratio where the molar ratio of the crossed Pertuzumab light chain (XPerLC) was expressed 2-fold, showed approximately 89% of bispecific antibody with the expected molecular weight of approximately 148 kDa as detected by Q-TOF MS; 7% containing 2× XPertuzumab light chains paired with XPertuzumab and Trastuzumab heavy chains; intact Trastuzumab antibodies (both heavy and light chains originating from Trastuzumab) with the formation of the heavy chain hole-hole association were not detected; 4% 2× Trastuzumab light chains paired with XPertuzumab and Trastuzumab heavy chains.

The 1:1:1:4 plasmid ratio where the molar ratio of the crossed Pertuzumab light chain (XPerLC) was expressed 4-fold, showed approximately 74% of bispecific antibody with the expected molecular weight of approximately 148 kDa as detected by Q-TOF MS; 25% containing 2× XPertuzumab light chains paired with XPertuzumab and Trastuzumab heavy chains; intact Trastuzumab antibodies (both heavy and light chains originating from Trastuzumab) with the formation of the heavy chain hole-hole association were not detected; 1% 2× Trastuzumab light chains paired with XPertuzumab and Trastuzumab heavy chains.

The 1:1:1:8 plasmid ratio where the molar ratio of the crossed Pertuzumab light chain (XPerLC) was expressed 8-fold, showed approximately 52% of bispecific antibody with the expected molecular weight of approximately 148 kDa as detected by Q-TOF MS; 48% containing 2× XPertuzumab light chains paired with XPertuzumab and Trastuzumab heavy chains; intact Trastuzumab antibodies (both heavy and light chains originating from Trastuzumab) with the formation of the heavy chain hole-hole association were not detected; 2× Trastuzumab light chains paired with XPertuzumab and Trastuzumab heavy chains were not detected.

CrossMab-CDRG

Figure 12A:
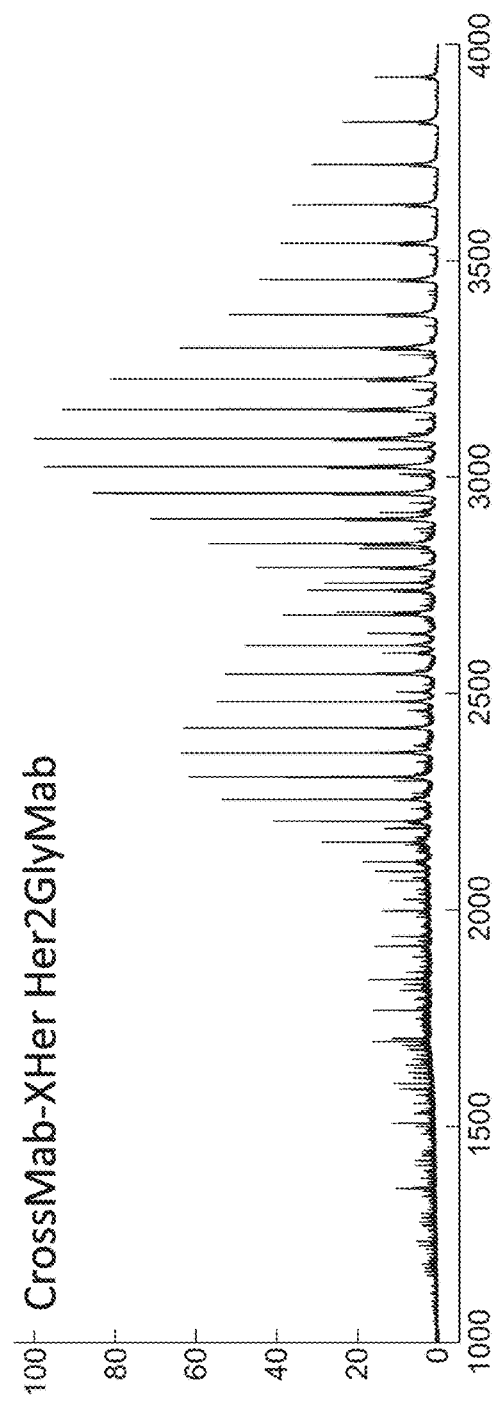
FIGS. 12A-12B: Q-TOF mass spectrometry comparison of the spectra of CrossMab-XTra (top, SEQ ID NOs 119, 120, 121, 122) and CrossMab-CDRG (bottom, SEQ ID NOs 109, 110, 111, 112) estimating the integrity and purity of the antibody molecules.
Figure 12B:
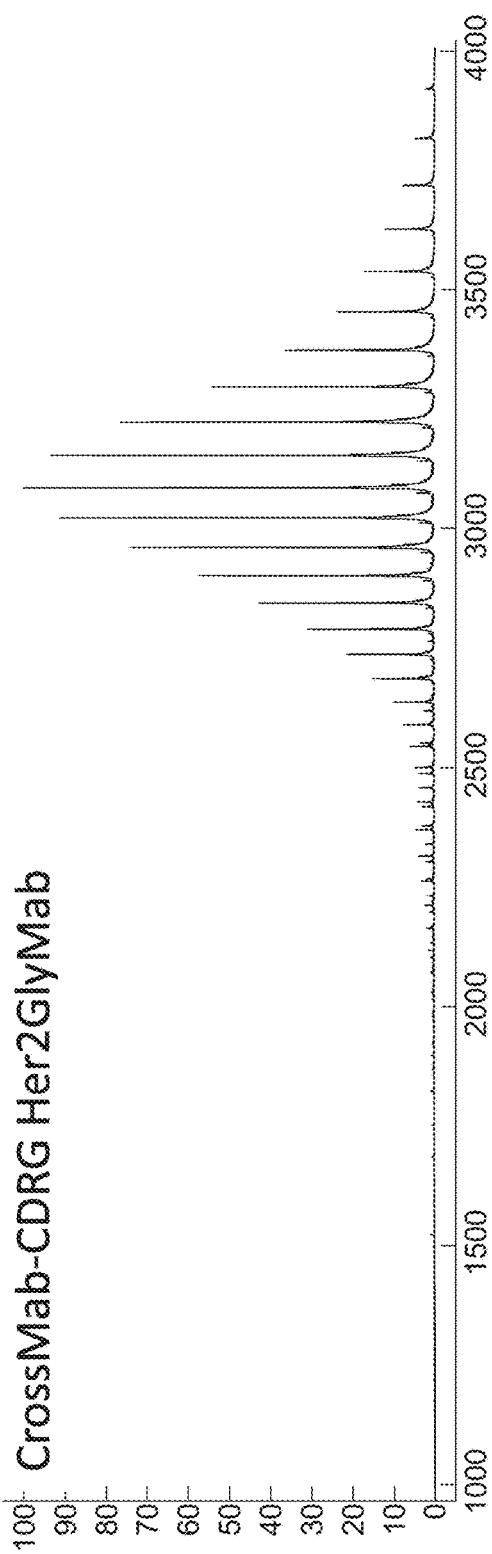

After Protein A purification of cell culture supernatants the construct showed at a 1:1:1:1 equimolar plasmid ratio approximately 95% of bispecific antibody with the expected molecular weight of approximately 148 kDa as detected by Q-TOF MS and 5% containing 2× XPertuzumab light chains paired with XPertuzumab and Trastuzumab (HerCDRG) heavy chains. No further species were detected, therefore, further optimization of the plasmid ratios was not performed. The MS spectra performed on the antibodies CrossMab-XHer and CrossMab-CDRG to compare the byproduct profile can be seen in FIGS. 12A-B.

TABLE 12

CrossMab-CDRG Her2GlyMab - Q-TOF analysis and quantification of the by-product profile of the Her2GlyMab antibody construct detecting the presence of mispaired antibody heavy and light chains.

| Detected protein species in MS | CrossMab-CDRG Her2GlyMab 1:1:1:1 |
|---|---|
| 2 × XPer HC; 2 × XPer LC | N. D. |
| 2 × HerCDRG HC; 2 × HerCDRG LC | N. D. |
| CrossMab-CDRG Her2GlyMab (100%) | ~95% |
| 1 × HerCDRG HC; 1 × XPer HC; 2 × XPer LC | ~5% |

N.D.—Not Detected

Example 8: Simultaneous Binding of Bispecific Antibodies to Both Antigens

The binding of the bispecific antibody was analyzed via BIACORE™ as described above. In separate assay format samples (CrossMabXPer as well as for OAscFab1 and OAscFab2) were proven to be functional for Trastuzumab as well as Pertuzumab specificity. CrossMabXPer showed kinetic constants and resulting affinities in the same order of magnitude as the positive controls. Except for a slightly reduced ka-rate constant for the Trastuzumab mediated binding OAscFab1 and OAscFab2 showed kinetic constants and resulting affinities in the same order of magnitude as the positive controls i.e the parental Mabs.

Partly bivalent binding of the positive controls-depending on the ligand density on the CM5-Chip may cause the variation of the dissociation rate constants in the two experiments depicted in this example.

TABLE 11

CrossMab-XPer Her2GlyMab - Q-TOF analysis and quantification of the by-product profile of the Her2GlyMab antibody constructs comparing the optimization plasmid titration of the crossed Trastuzumab light chain (XPer LC).

| Detected protein species in MS | CrossMab-XPer Her2GlyMab 1:1:1:1 | CrossMab-XPer Her2GlyMab 1:1:1:2 | CrossMab-XPer Her2GlyMab 1:1:1:4 | CrossMab-XPer Her2GlyMab 1:1:1:8 |
|---|---|---|---|---|
| 1 × Her HC; 1 × XPer HC; 2 × XPer LC | ~2% | ~7% | ~25% | ~48% |
| 2 × Her HC; 2 × Her LC | ~1% | n.d. | n.d. | n.d. |
| CrossMab-XPer Her2GlyMab (100%) | ~85% | ~89% | ~74% | ~52% |
| 1 × Her HC; 1 × XPer HC; 2 × Her LC | ~12% | ~4% | ~1% | n.d. |

N.D.—Not Detected.

TABLE 13

SPR analysis of the Her2GlyMab affinities-The association and dissociation rates of the antibodies were measure using a BIACORE ™T100 with a CM5-Chip at 25° C.

| Experiment | T = 25° C. analyzed function | analyte | $k_a$ [$M^{-1} \cdot s^{-1}$] | $k_d$ [$s^{-1}$] | t(1/2) [min] | $K_D$ [M] |
|---|---|---|---|---|---|---|
| UJ2530 | "Trastuzumab" | Trastuzumab | 3.9E+05 | 8.7E−05 | 132.5 | 2.2E−10 |
| UJ2530 | "Trastuzumab" | Pertuzumab | | no binding as expected | | |
| UJ2530 | "Trastuzumab" | CrossMabXPer | 1.0E+05 | 7.6E−05 | 151.9 | 7.4E−10 |
| UJ2530 | "Pertuzumab" | Trastuzumab | | no binding as expected | | |
| UJ2530 | "Pertuzumab" | Pertuzumab | 4.7E+05 | 9.8E−05 | 118.1 | 2.1E−10 |
| UJ2530 | "Pertuzumab" | CrossMabXPer | 2.0E+05 | 1.8E−04 | 66.0 | 8.7E−10 |
| UJ2530_b | "Trastuzumab" | Trastuzumab | 7.0E+05 | 3.0E−05 | 382.9 | 4.3E−11 |
| UJ2530_b | "Trastuzumab" | Pertuzumab | | no binding as expected | | |
| UJ2530_b | "Trastuzumab" | OAscFab1 | 1.6E+04 | 8.7E−05 | 133.5 | 5.4E−09 |
| UJ2530_b | "Trastuzumab" | OAscFab2 | 1.8E+04 | 1.1E−04 | 100.6 | 6.2E−09 |
| UJ2530_b | "Pertuzumab" | Trastuzumab | | no binding as expected | | |
| UJ2530_b | "Pertuzumab" | Pertuzumab | 2.4E+05 | 2.6E−04 | 44.8 | 1.1E−09 |
| UJ2530_b | "Pertuzumab" | OAscFab1 | 1.2E+05 | 2.6E−04 | 44.3 | 2.2E−09 |
| UJ2530_b | "Pertuzumab" | OAscFab2 | 1.7E+05 | 2.6E−04 | 44.8 | 1.5E−09 |

Example 9: In Vitro Evaluation of 1+1 Herceptarg CrossMAb and Glycoengineered Herceptarg Crossmab Proliferation Inhibition Assay AlamarBlue® (Invitrogen) was used for the measurement of the metabolic activity and proliferation of (A) BT474 and (B) N87 cells after a 5 day incubation in presence of HER2 CrossMab (CrossMab-XTra Her2GlyMab, SEQ ID NOs 119, 120, 121, 122), Trastuzumab, Pertuzumab or the combination of Trastuzumab/Pertuzumab. The bioreduction of the dye reduces the amount of the oxidized form (blue) and concomitantly increases the fluorescent intermediate (red).

Target cells were harvested, washed, resuspended in RPMI 1640 (Gibco)+10% FCS+1% GlutaMAX™ (Gibco) and plated at a concentration of 1×10⁴ cells/well. Cells were incubated for 3 hours in the cell incubator before respective antibody dilutions were added. Plates were gently shaken and incubated for 5 days in the cell incubator.

25 µl/well of Alamar Blue were added to the plate and incubated for 7 h in the incubator. Absorbance was monitored at 584 nm and 612 nm in a Wallac VICTOR3™ 1420 Multilabel Counter.

For calculation of the percentage of proliferation inhibition, non-treated controls samples were included in the assay and defined as 100% proliferation. The average percentage of proliferation inhibition of the triplicates of each experiment was calculated.

Figure 13A:
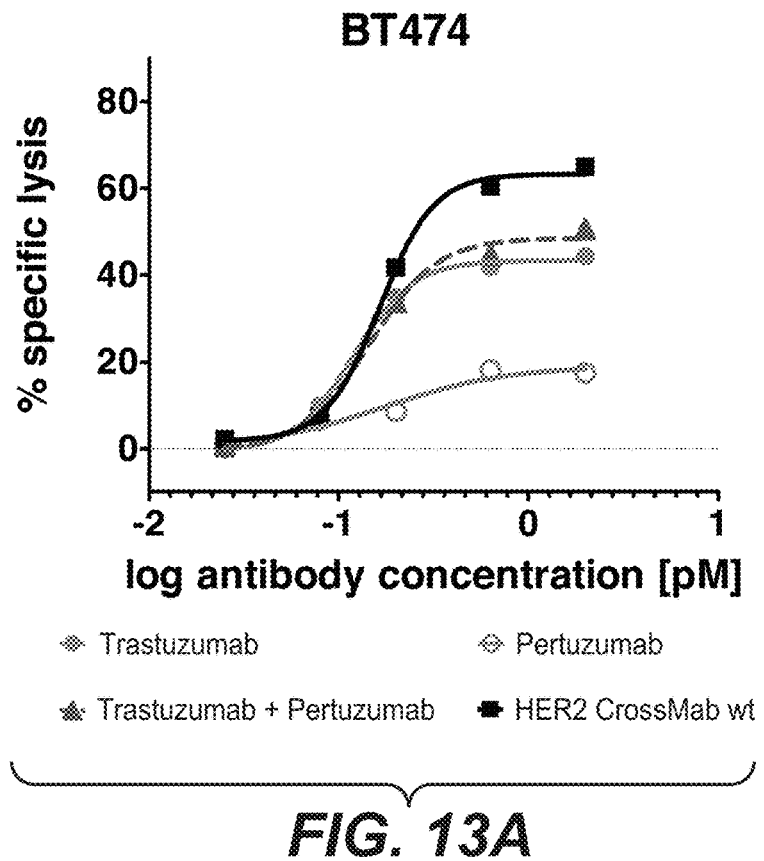
FIGS. 13A-13B: Proliferation inhibition by non-glycoengineered HER2 CrossMab (SEQ ID NOs 119, 120, 121, 122) after 5 days of incubation as measured in an AlamarBlue® assay. (A) BT474 cells (B) N87 cells.
Figure 13B:
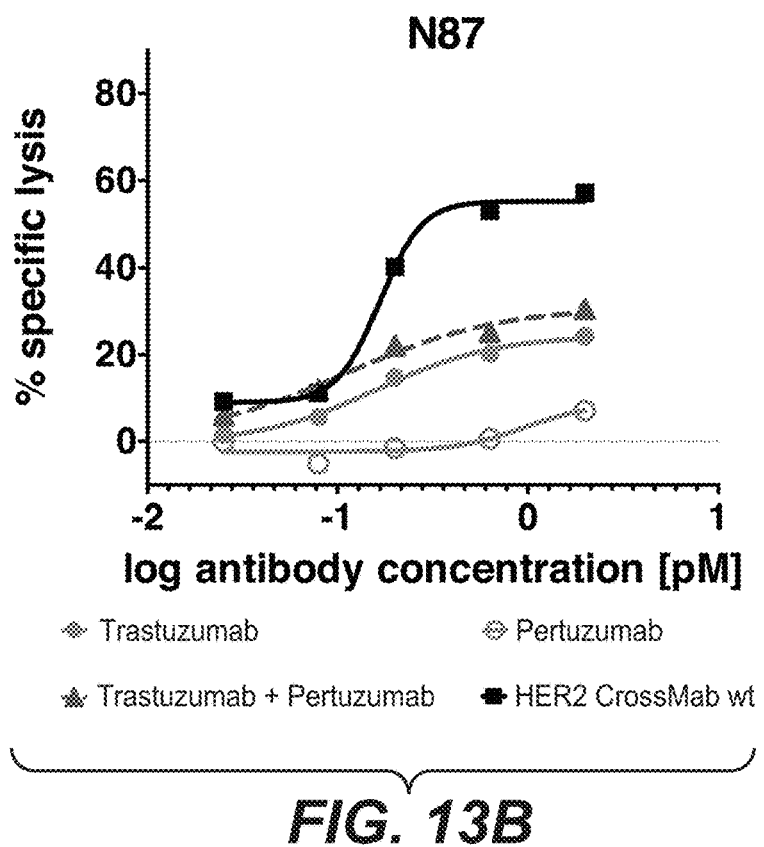

Results are shown in FIGS. 13A-B.

ADCC Assay

ADCC mediated by HER2 CrossMab (CrossMab-XTra Her2GlyMab, SEQ ID NOs 119, 120, 121, 122), Trastuzumab, Pertuzumab or the combo of Trastuzumab/Pertuzumab was assessed on KPL-4 (A), T47D (B) and Calu-3 (C) cells.

Target cells were harvested, washed, resuspended in AIM V® medium (Life Technologies), and plated at a concentration of 3×10⁴ cells/well. The respective antibody dilutions were added in triplicates to the cells and incubated for 10 min before addition of the effector cells (peripheral blood mononuclear effector cells [PBMCs]). Effector (E) and target (T) cells were then incubated for 4 h at 37° C. at an E:T ratio of 25:1 (triplicates for all samples). Lactate dehydrogenase (LDH) release was measured using the LDH Cytotoxicity Detection Kit (Roche Applied Science). ADCC was calculated using the following formula:

$$\text{Percentage } ADCC = \left(\left[\frac{\text{sample release} - \text{spontaneous release}}{\text{maximal release} - \text{spontaneous release}}\right]\right) \times 100.$$

Figure 14A:
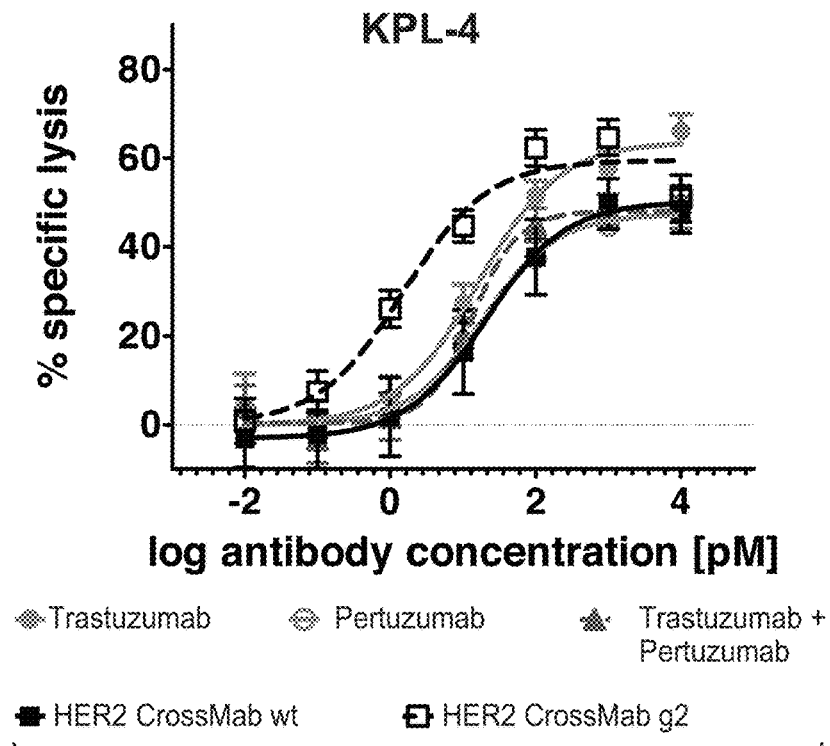
FIGS. 14A-14C: ADCC induced by different HER2 specific antibodies using (FIG. 14A) KPL-4, (FIG. 14B) T47D and (FIG. 14C) Calu-3 as target cells (E:T=25:1, effectors human PBMCs, incubation time 4 h). "HER2 crossmab wt": SEQ ID NOs 119, 120, 121, 122, non glycoengineered; "HER2 crossmab g2": SEQ ID NOs 119, 120, 121, 122, glycoengineered.
Figure 14B:
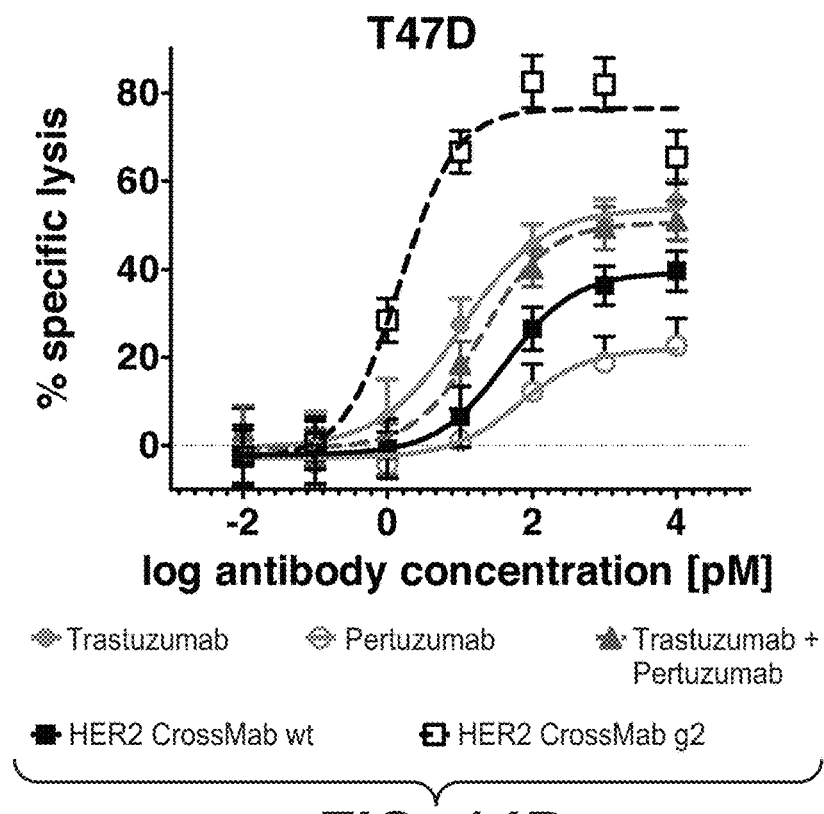
Figure 14C:
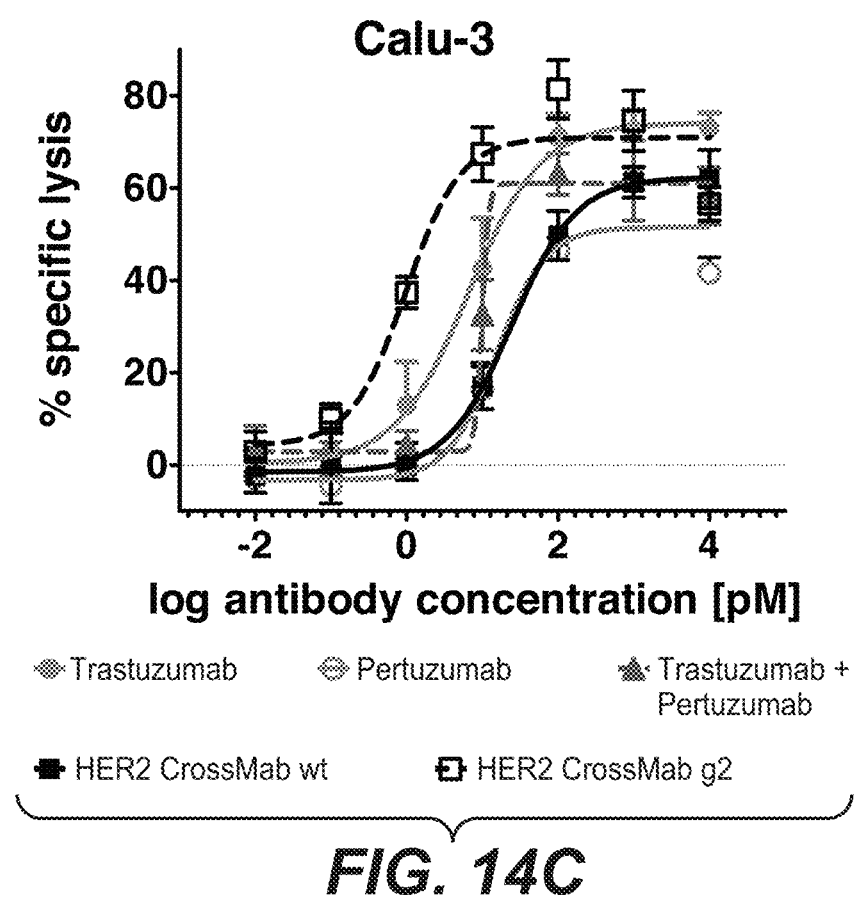
Figure 15A:
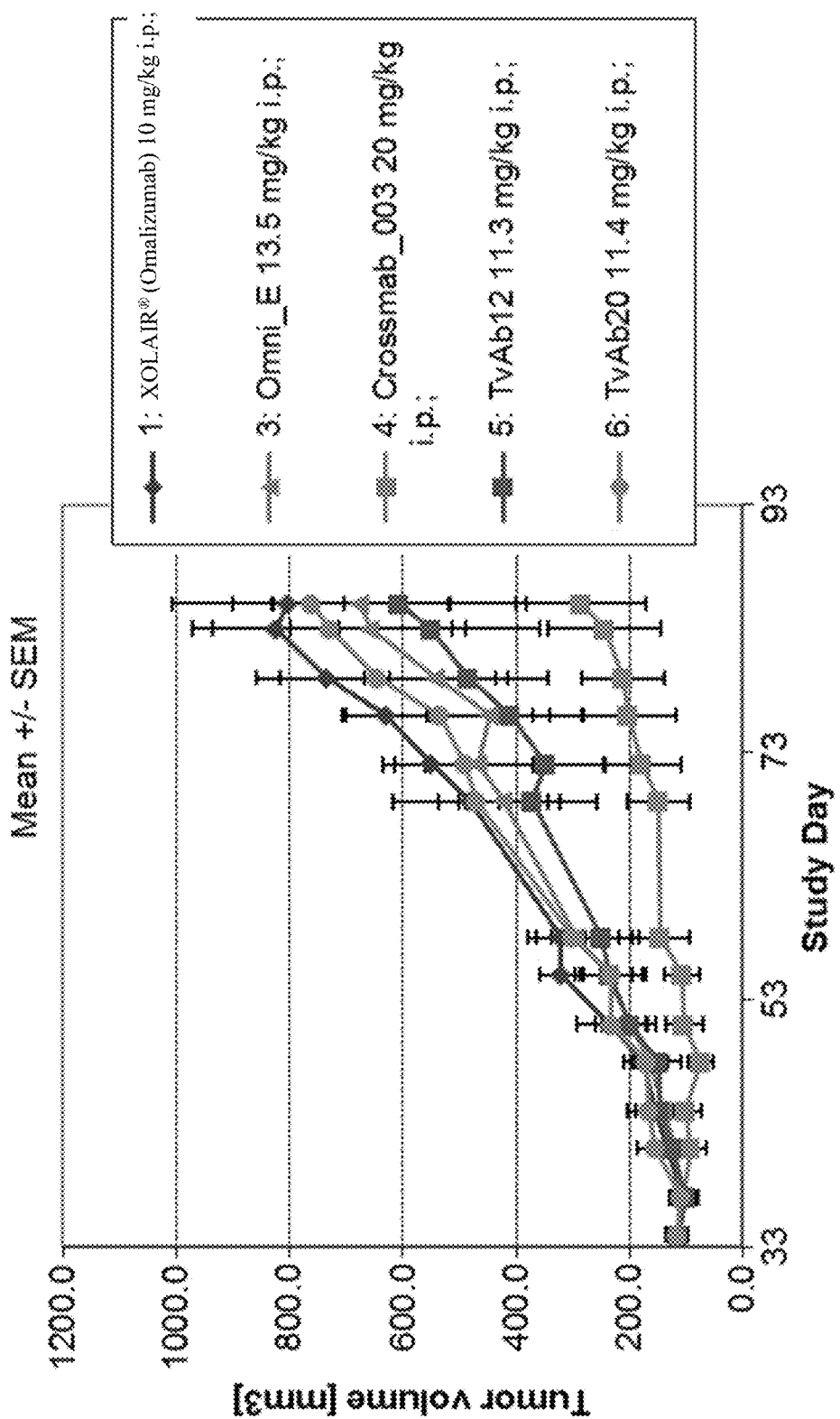
FIGS. 15A-15C: Antitumor activity of different anti-Her2 antibodies in the Calu3 non-small cell lung cancer xenograft (Experiment: BispecHer2_PZ_Calu3 001). SCID beige mice with Calu3 xenograft tumors were treated i.p. once weekly at the indicated dosages for 7 weeks. XOLAIR® (Omalizumab) a humanized IgG1 antibody targeting human IgE was used as a control. Statistical analysis based on medians at endpoint (day 85) reveals that compared to Xolair the bispecific HER2 antibodies suppressed tumor growth by 87.5% (s.); OmniE (SEQ ID NOs 145, 146) by 43.7% (n.s.); Crossmab_003 (SEQ ID NOs 119, 120, 121, 122, non glycoengineered) by 92.1% (s.); TvAb12 (SEQ ID NOs 123 and 124) by 59.8% (n.s.) and TvAb20 (SEQ ID NOs 131 and 132) by 12.6% (n.s.). Tumor growth curves are depicted as mean+/−SEM (n=8 in each group).
Figure 15B:
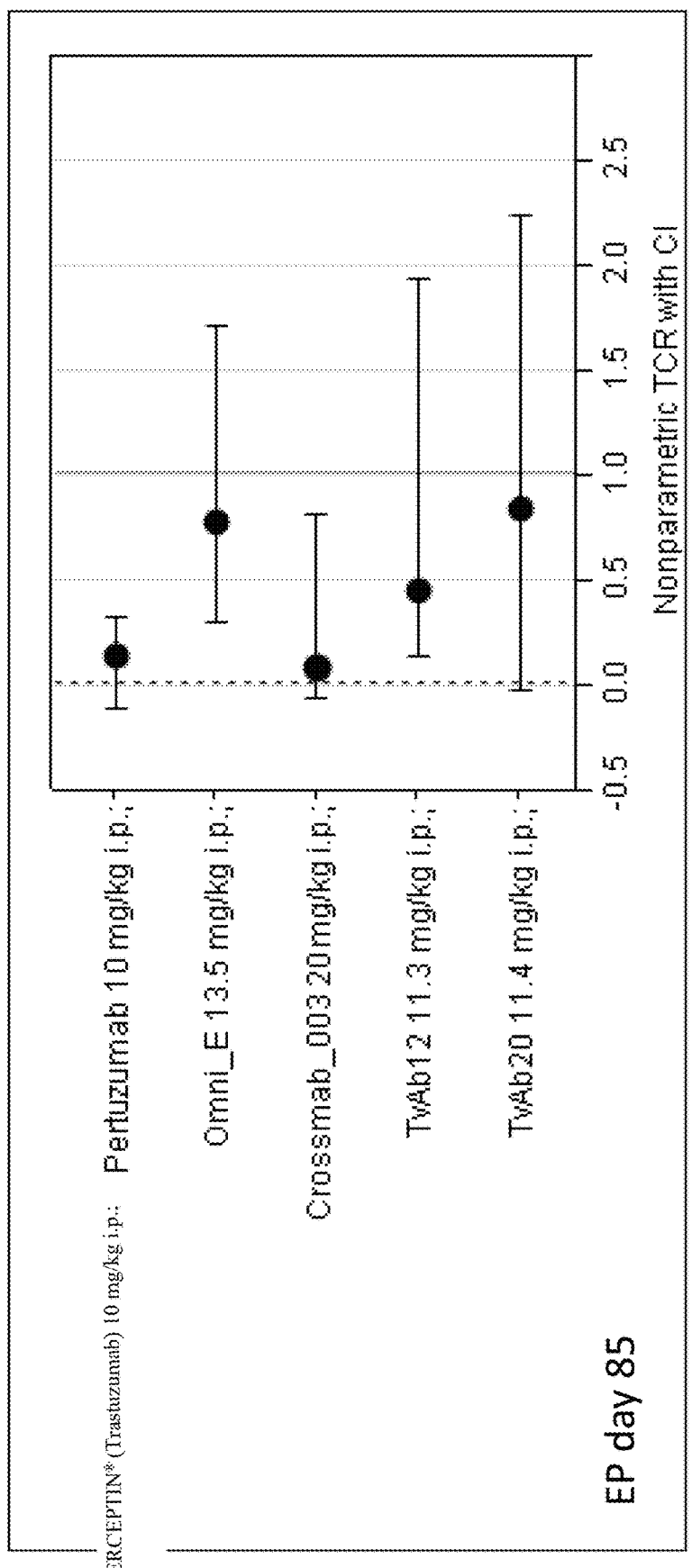
Figure 15C:
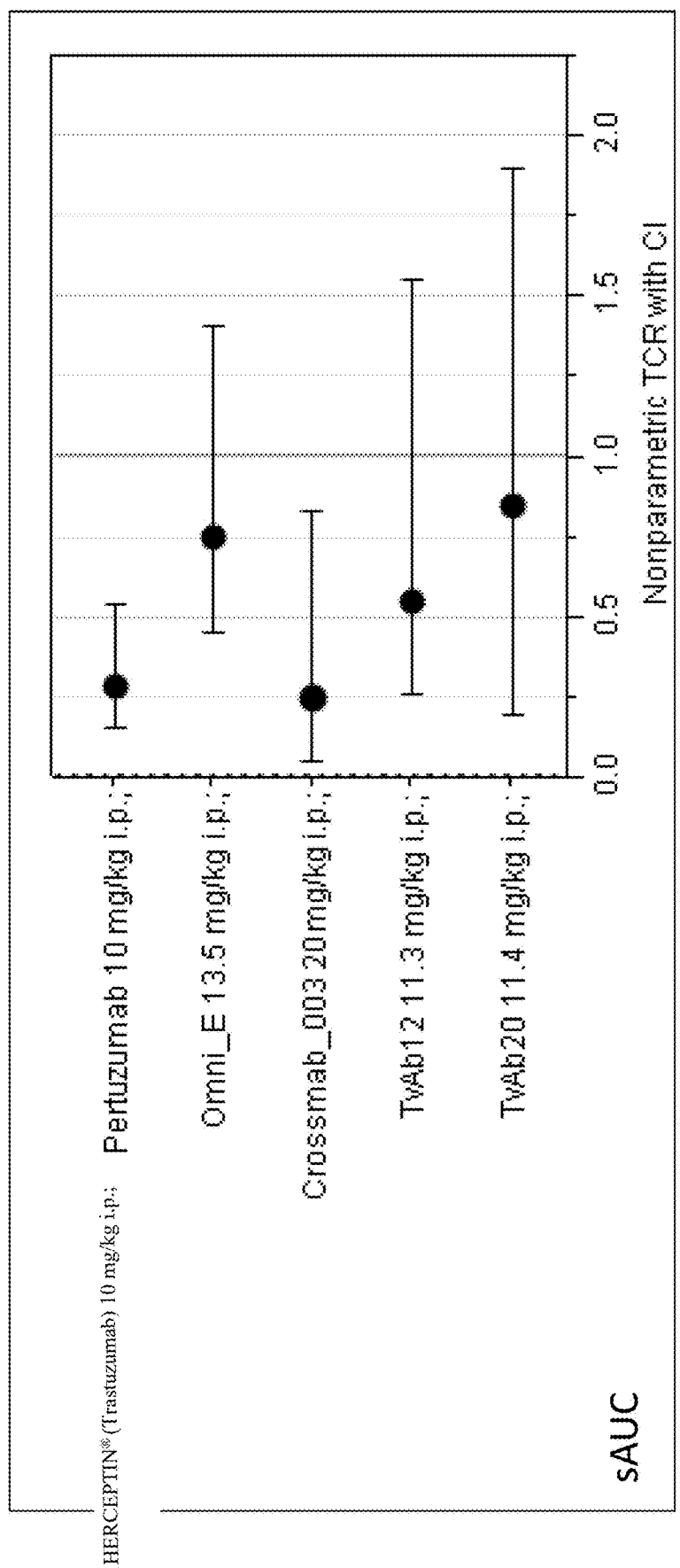
Figure 16A:
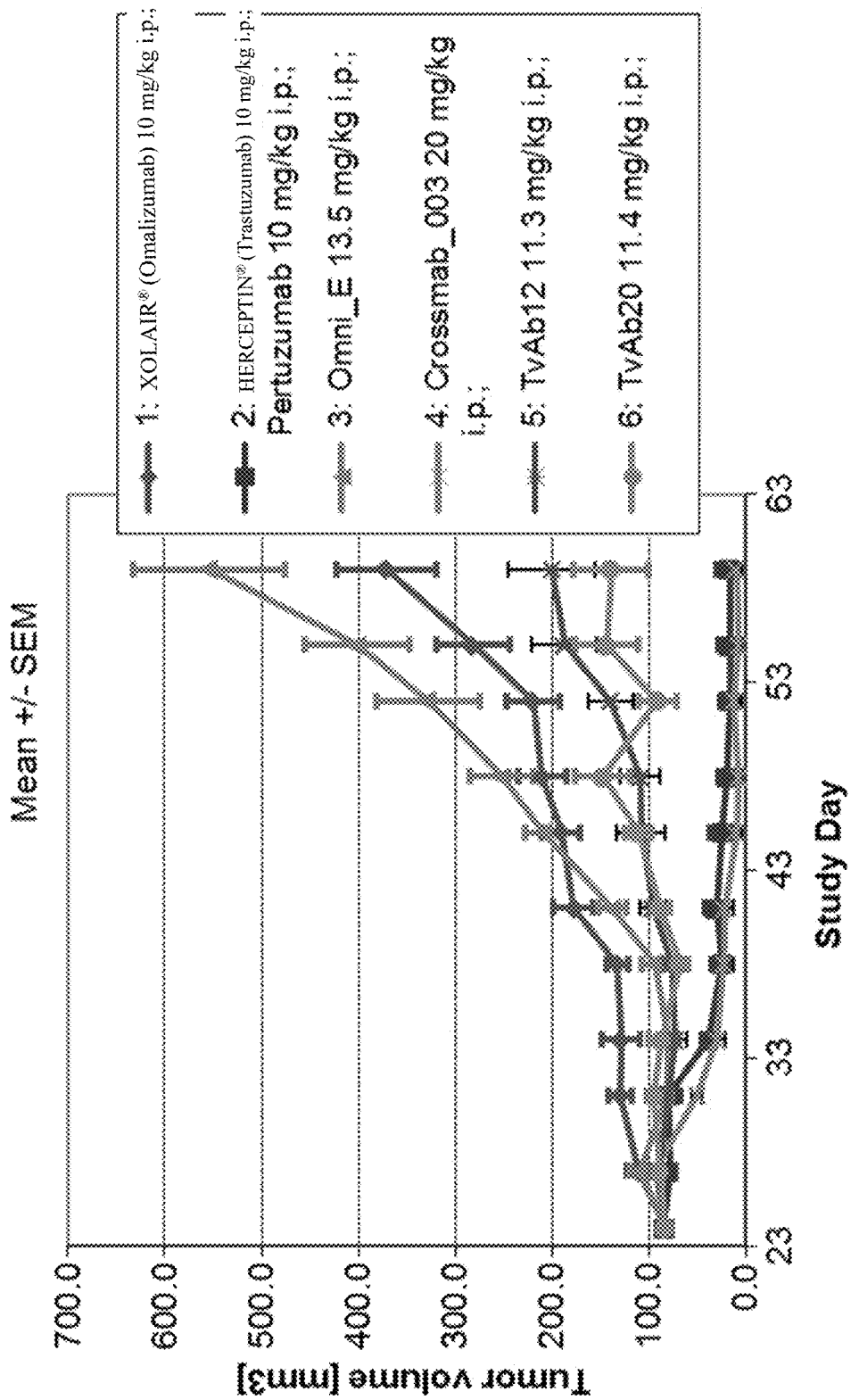
FIGS. 16A-16C: Antitumor activity of different anti-Her2 antibodies in the KPL-4 breast cancer xenograft (Experiment: Bispec.Her2_PZ_KPL-4_002). SCID beige mice with KPL-4 xenograft tumors were treated i.p. once weekly at the indicated dosages for 5 weeks. Xolair a humanized IgG1 antibody targeting human IgE was used as a control. Statistical analysis based on medians at endpoint (day 59) reveals that compared to Xolair the bispecific HER2 antibodies suppressed tumor growth by 120.8% (s.); Crossmab_003 (SEQ ID NOs 119, 120, 121, 122, non glycoengineered) by 120.6% (s.); TvAb12 (SEQ ID NOs 123 and 124) by 70.1% (s.); TvAb20 (SEQ ID NOs 131 and 132) by 83.4% (s.). OmniE (SEQ ID NOs 145, 146) had no significant effect on tumor growth. Tumor growth curves are depicted as mean+/−SEM (n=9 in each group).
Figure 16B:
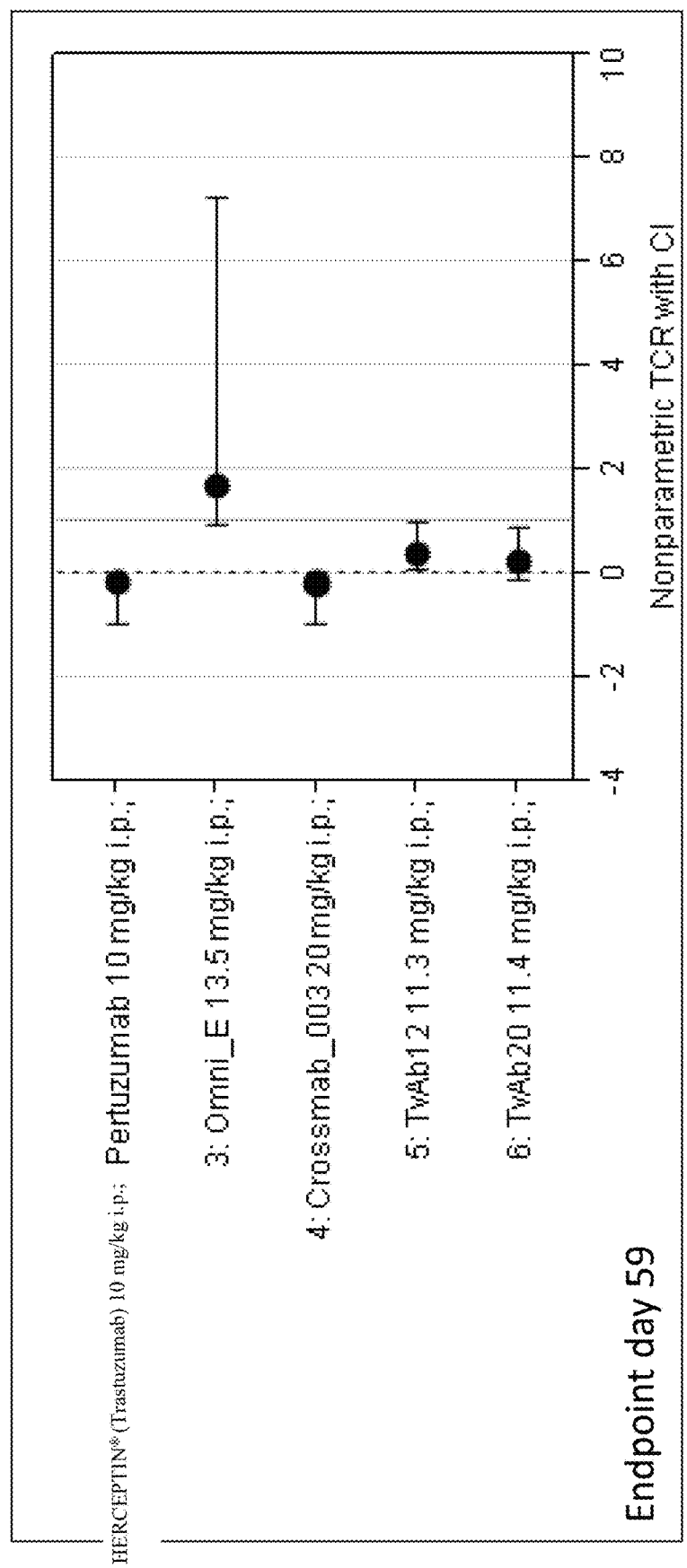
Figure 16C:
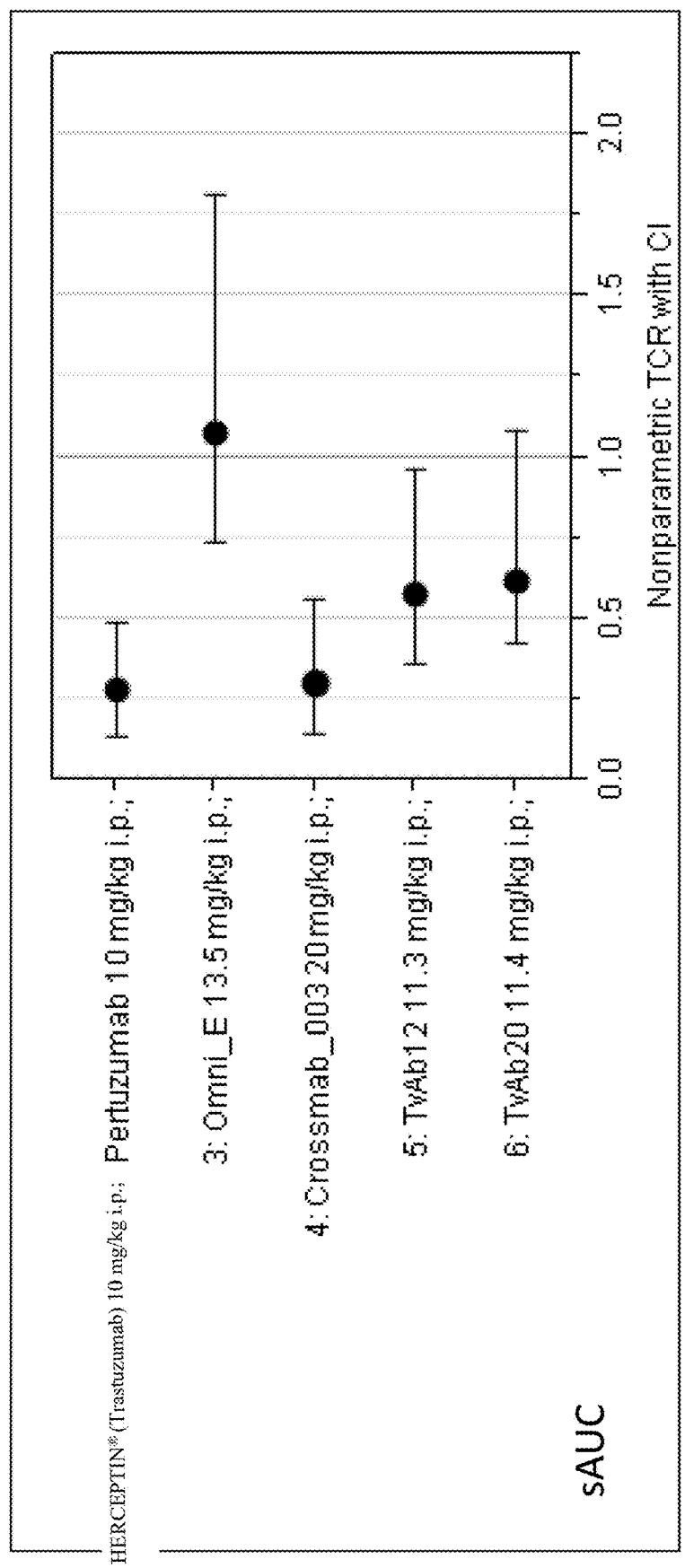
Figure 17A:
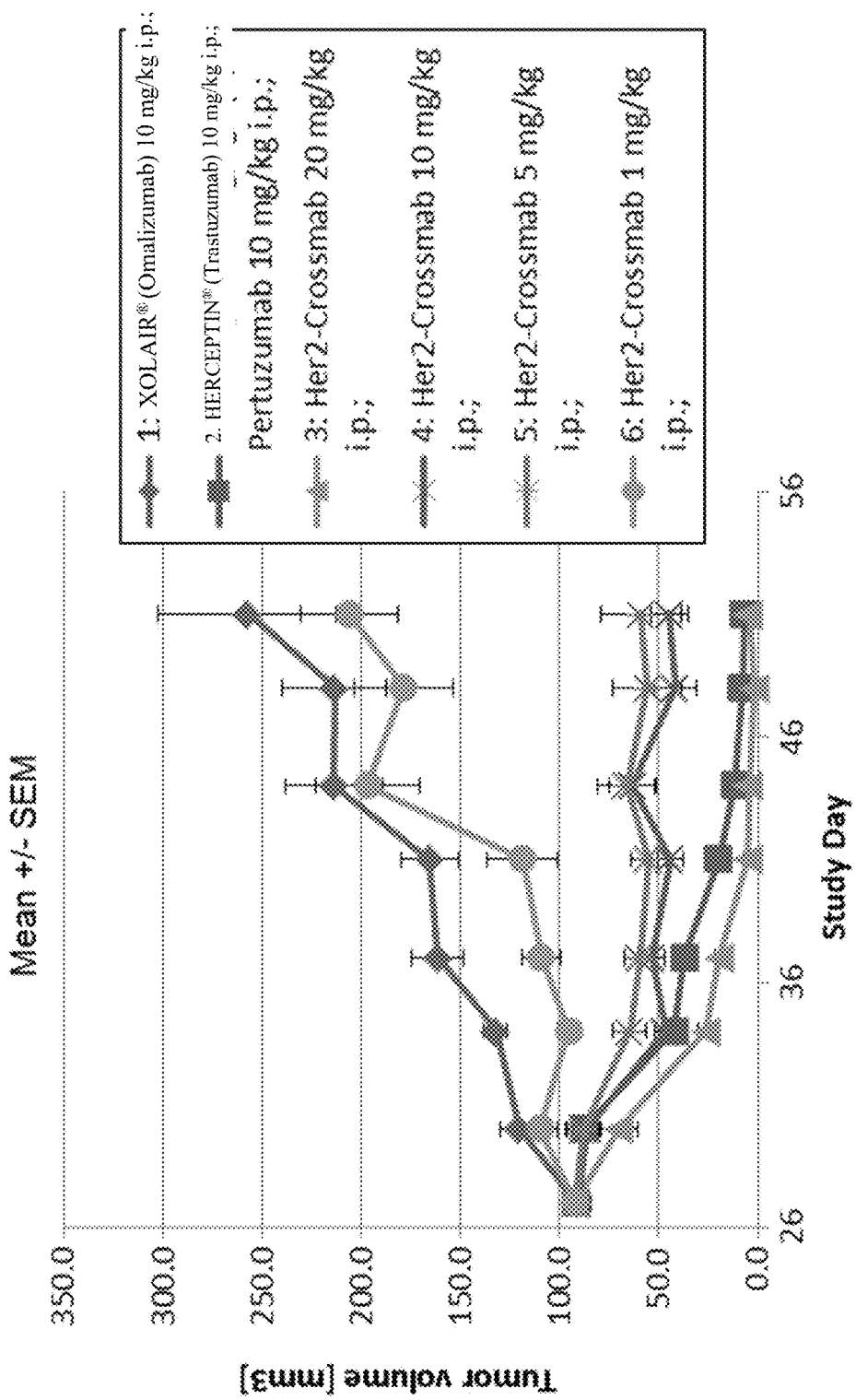
FIGS. 17A-17C: Antitumor activity of anti-Her2_005 crossmab antibody (SEQ ID NOs 119, 120, 121, 122, non glycoengineered) in the KPL-4 breast cancer xenograft (Experiment: Bispec.Her2_PZ_KPL-4_003). SCID beige mice with KPL-4 xenograft tumors were treated i.p. once weekly with escalating dosages of the crossmab ranging from 1 to 20 mg/kg for 5 weeks. Xolair a humanized IgG1 antibody targeting human IgE was used as a control. Statistical analysis based on medians at endpoint (day 70) reveals that compared to Xolair the bispecific HER2 antibodies suppressed tumor growth by 121.8% (s.); The Her2 crossmab_005 suppressed tumor growth at a dosage of 1 mg/kg by 25.1% (n.s.); at 5 mg/kg by 112.3% (s.); at 10 mg/kg by 109.5% (s.) and by 20 mg/kg by 121.8% (s.). Tumor growth curves are depicted as mean+/−SEM (n=10 in each group).
Figure 17B:
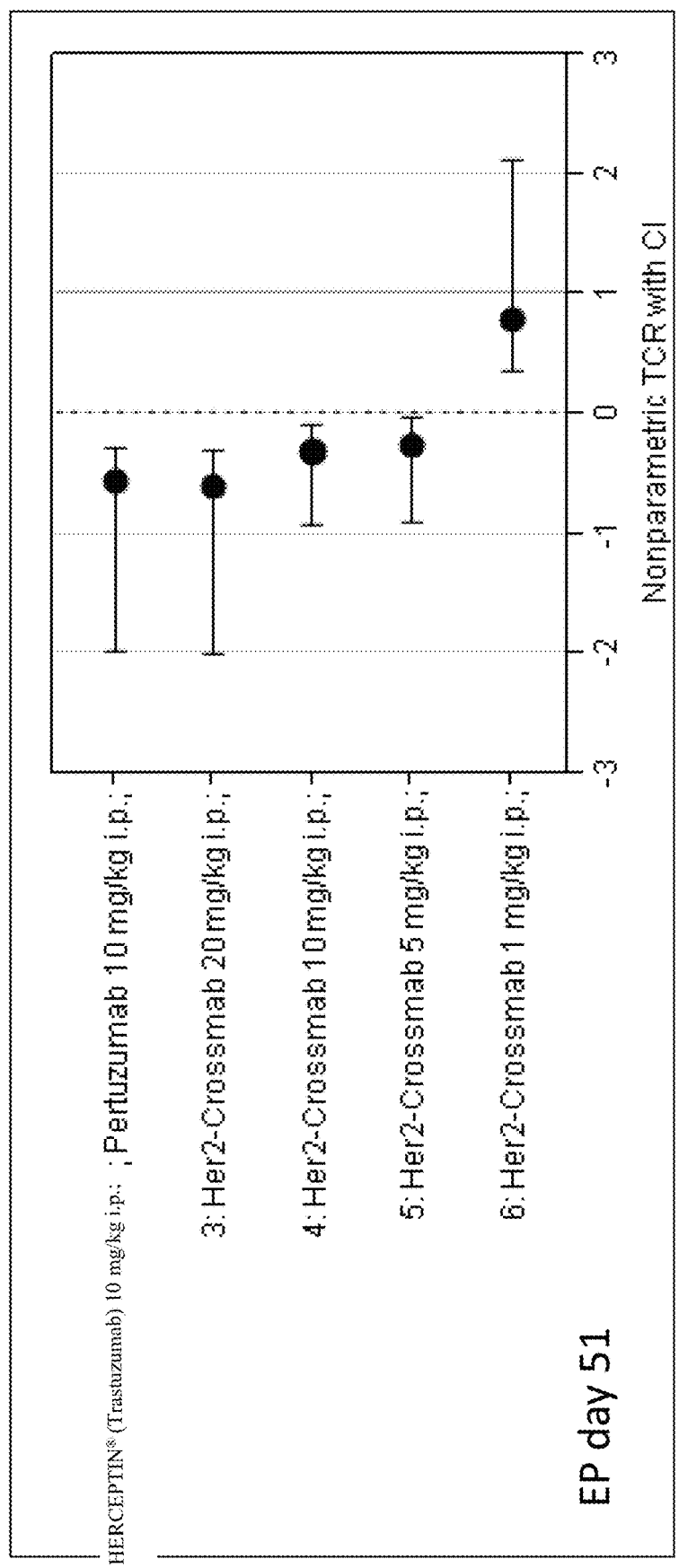
Figure 17C:
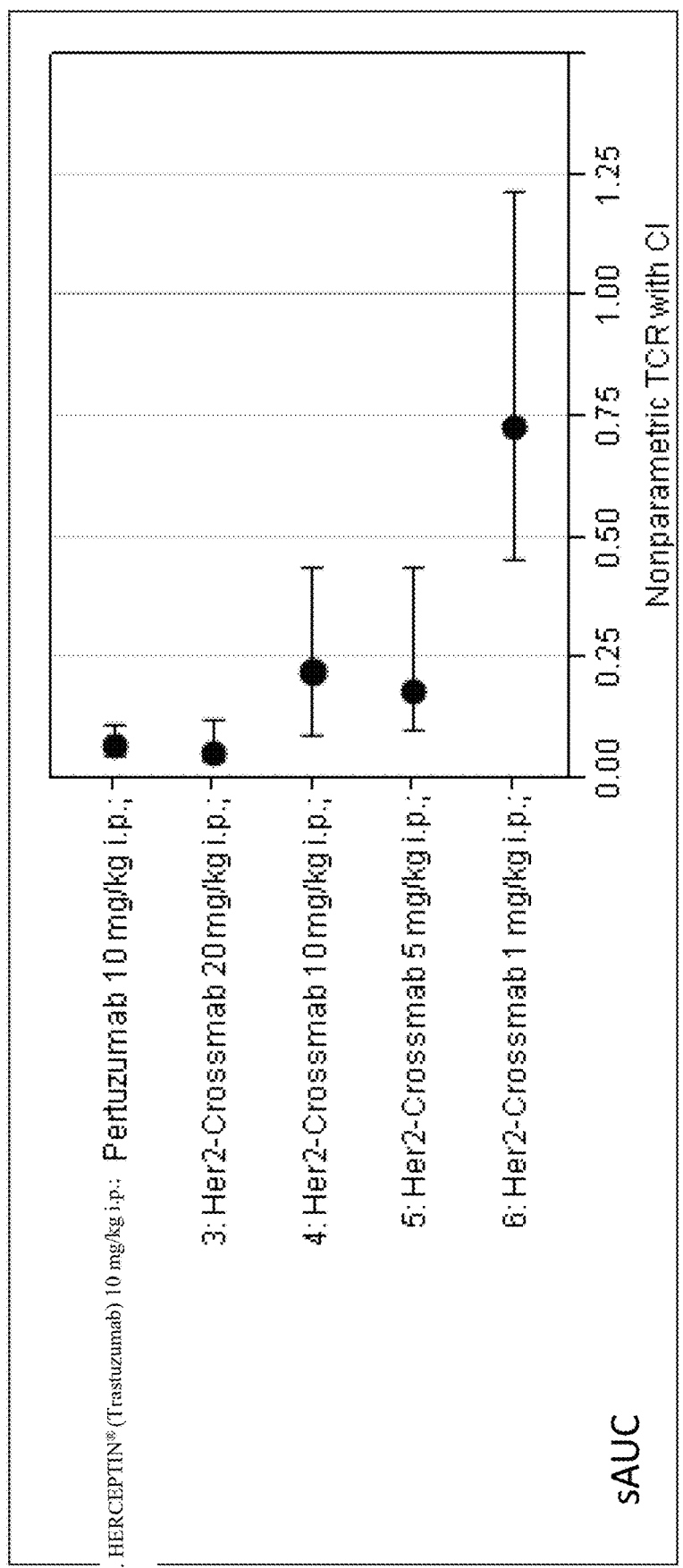
Figure 18A:
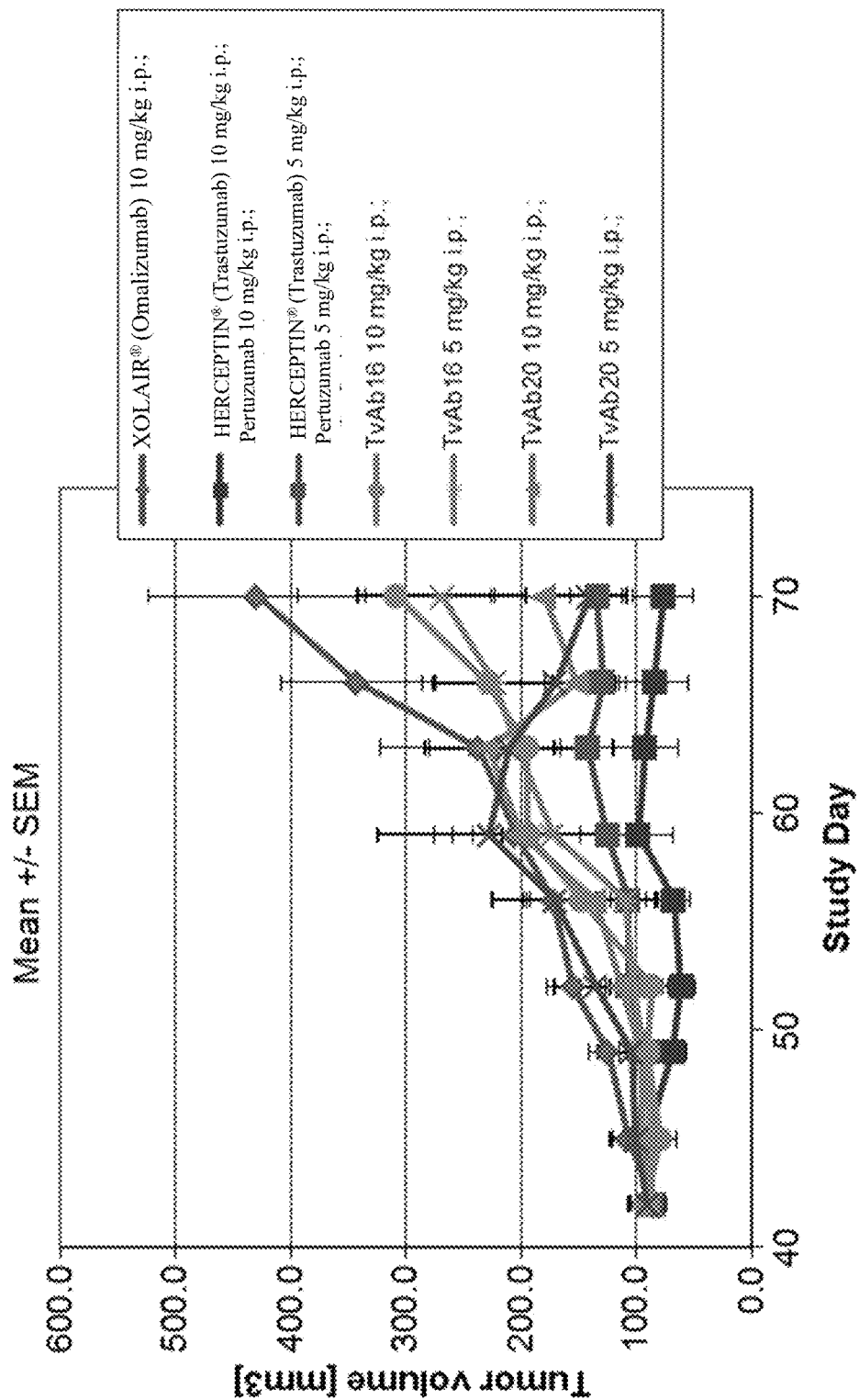
FIGS. 18A-18C: Antitumor activity of different anti-Her2 antibodies in the KPL-4 breast cancer xenograft (Experiment: Bispec.Her2_PZ_KPL-4_009). SCID beige mice with KPL-4 xenograft tumors were treated i.p. once weekly with the different compounds for 4 weeks. Xolair a humanized IgG1 antibody targeting human IgE was used as a control. Statistical analysis based on medians at endpoint (day 70) reveals that compared to Xolair the bispecific HER2 antibodies (each dosed at 5 mg/kg) suppressed tumor growth by 83.2% (s.) and both given at a dosage of 10 mg/kg each by 109.5% (s.). TvAb 16 (SEQ ID NOs 127 and 128) given at two different dosages (5 mg/kg and 10 mg/kg) had no significant anti-tumoral effect. TvAb20 (SEQ ID NOs 131 and 132), at a dosage of 5 mg/kg, suppressed tumor growth by 75.3% (s.) and at a dosage of 10 mg/kg by 59.8% (n.s.). Tumor growth curves are depicted as mean+/−SEM (n=10 in each group).
Figure 18B:
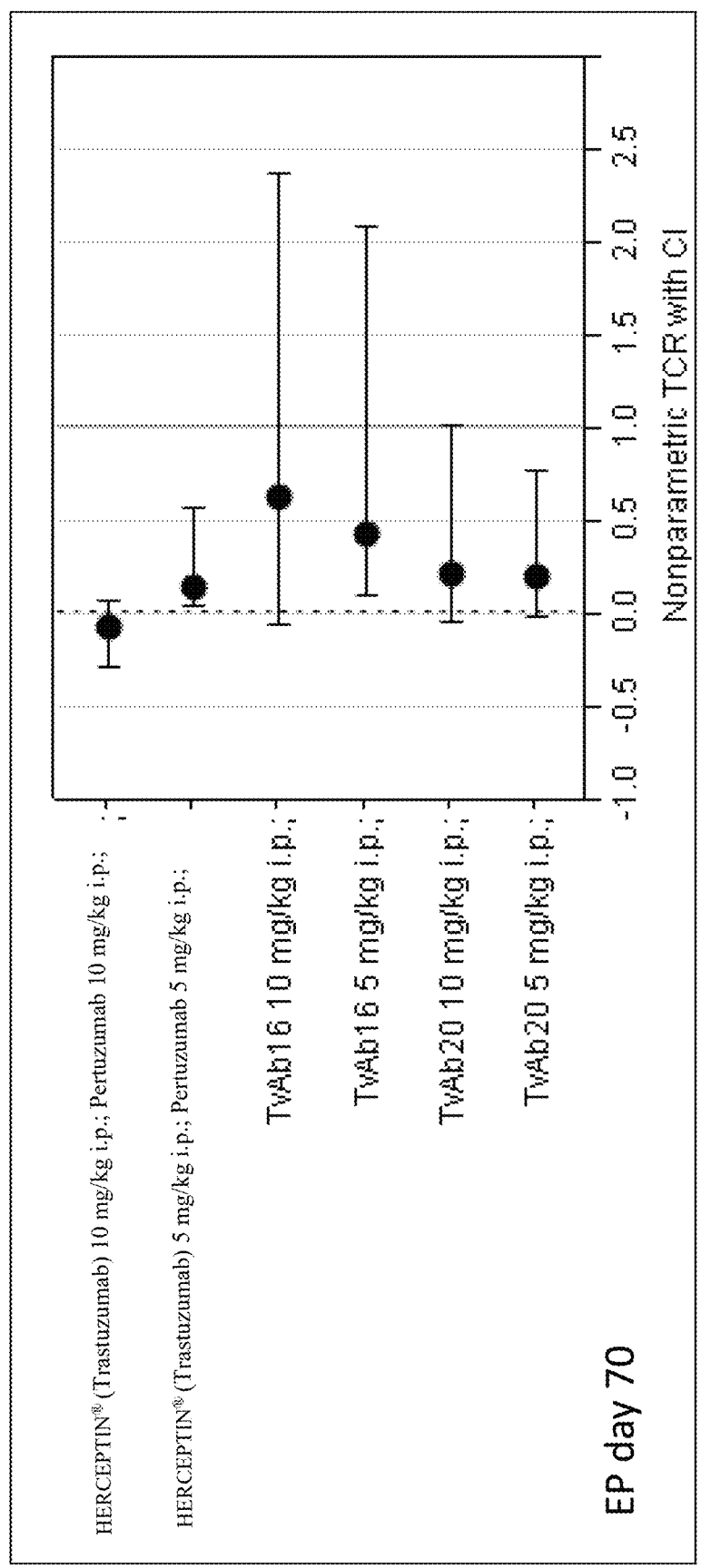
Figure 18C:
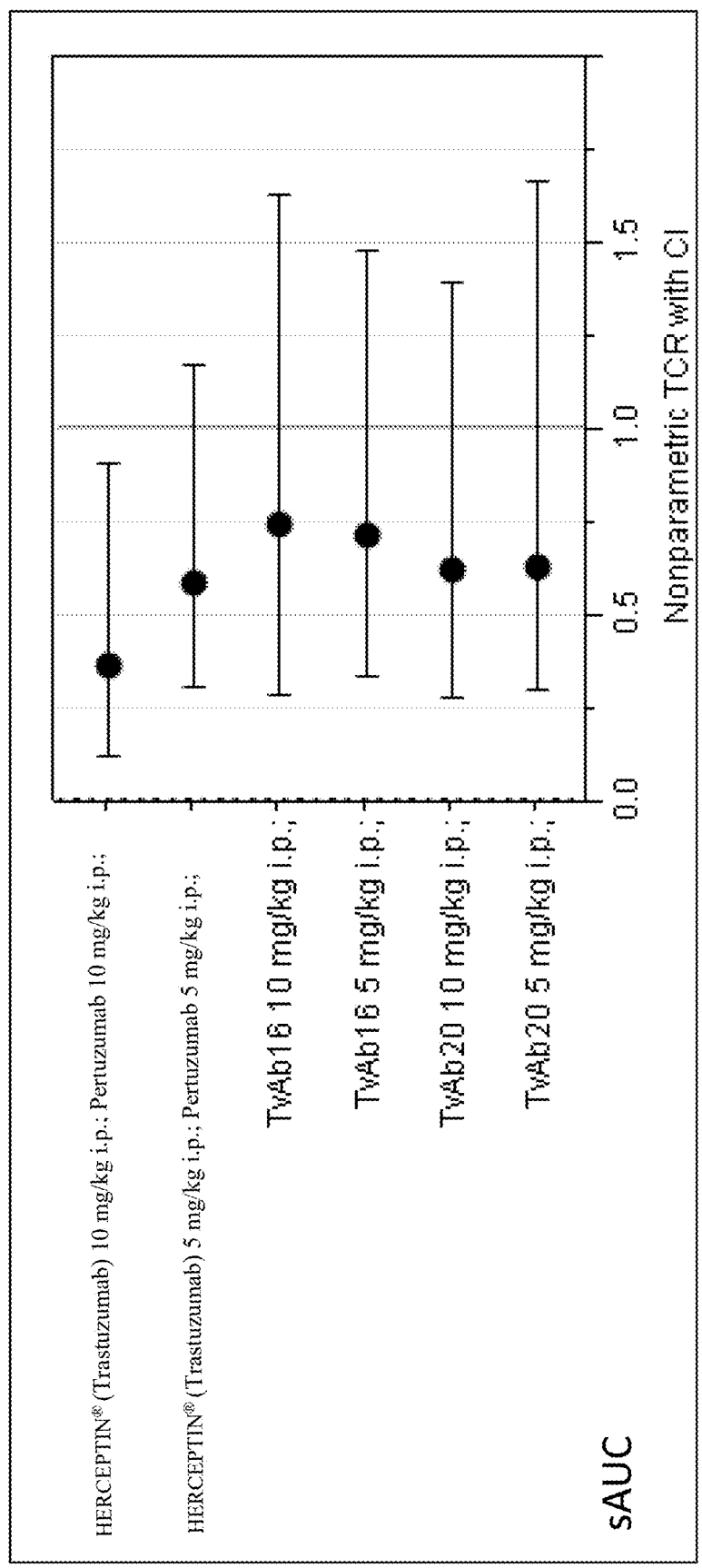
Figure 19A:
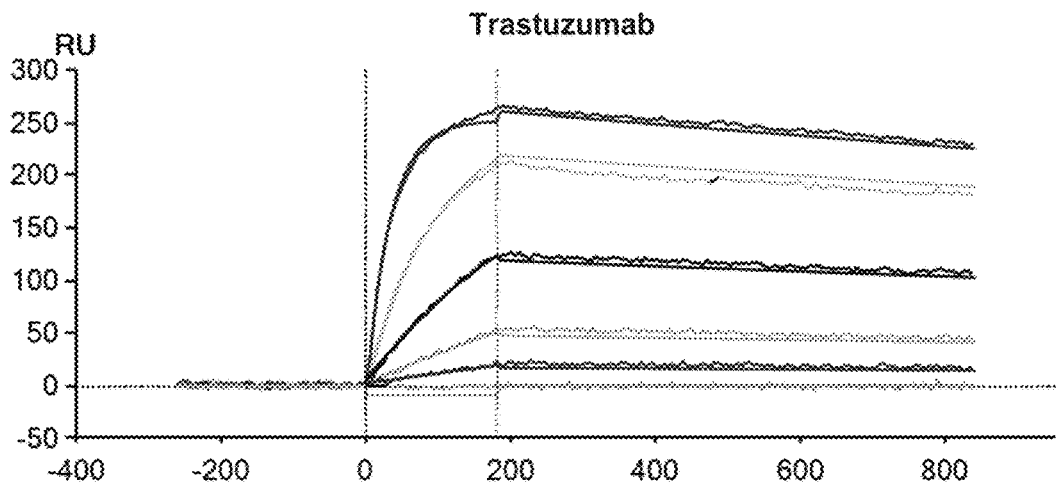
FIGS. 19A-19F: SPR analysis of initial Pertuzumab/Trastuzumab hybrid light chains. SPR-based kinetic analyses of Pertuzumab, Trastuzumab, and sequence combinations with the initial Pertuzumab hybrid LCs harboring amino acid residues of the Trastuzumab LCDR3 region. Smooth lines represent a global fit of the data to a 1:1 interaction model. PertuzumabTrasL3: SEQ ID No: 26, PertuzumabTras Y91H: SEQ ID No: 28.
Figure 19B:
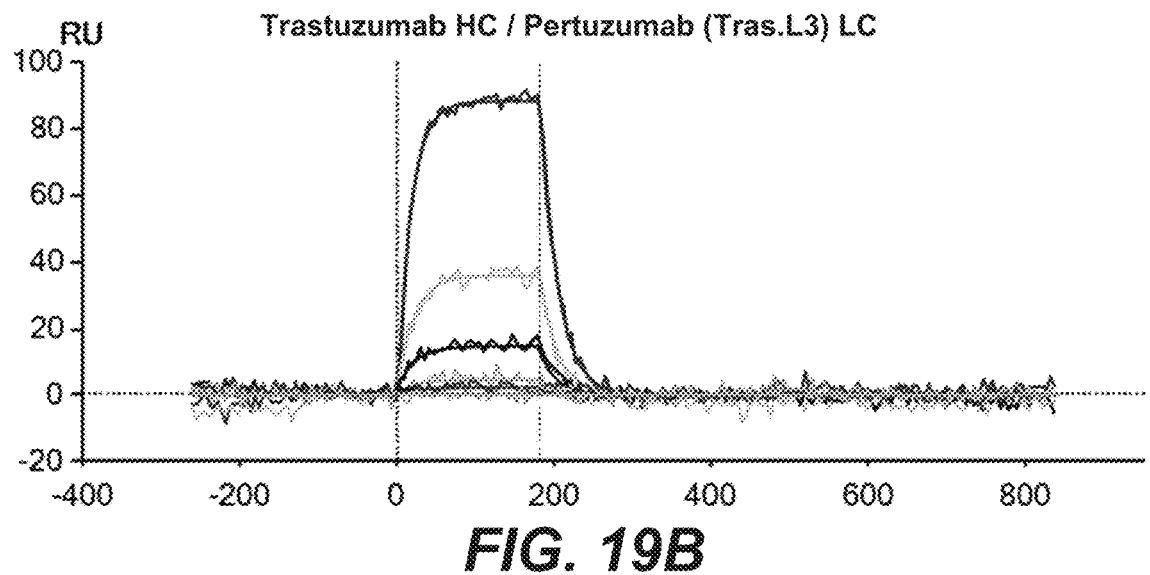
Figure 19C:
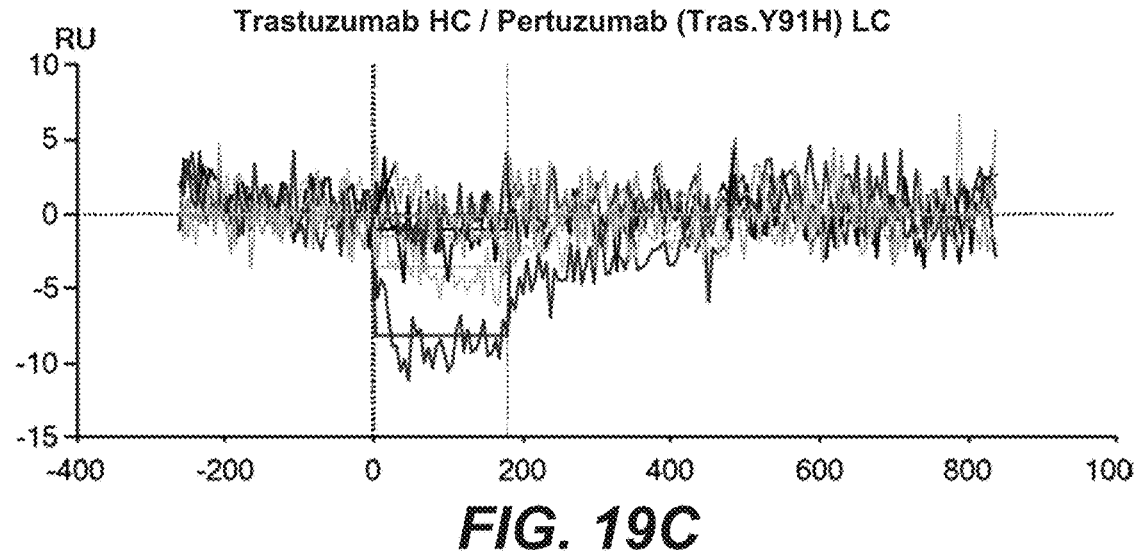
Figure 19D:
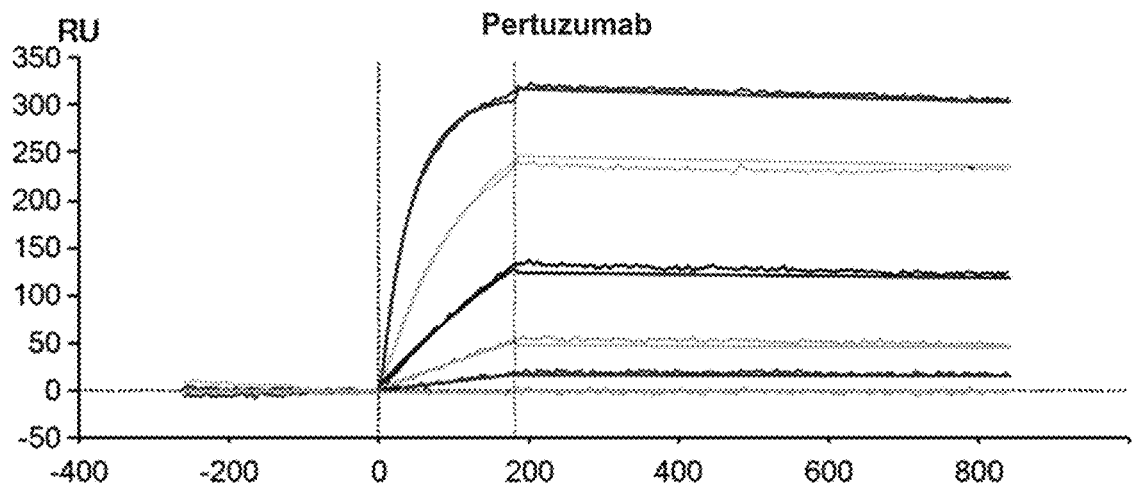
Figure 19E:
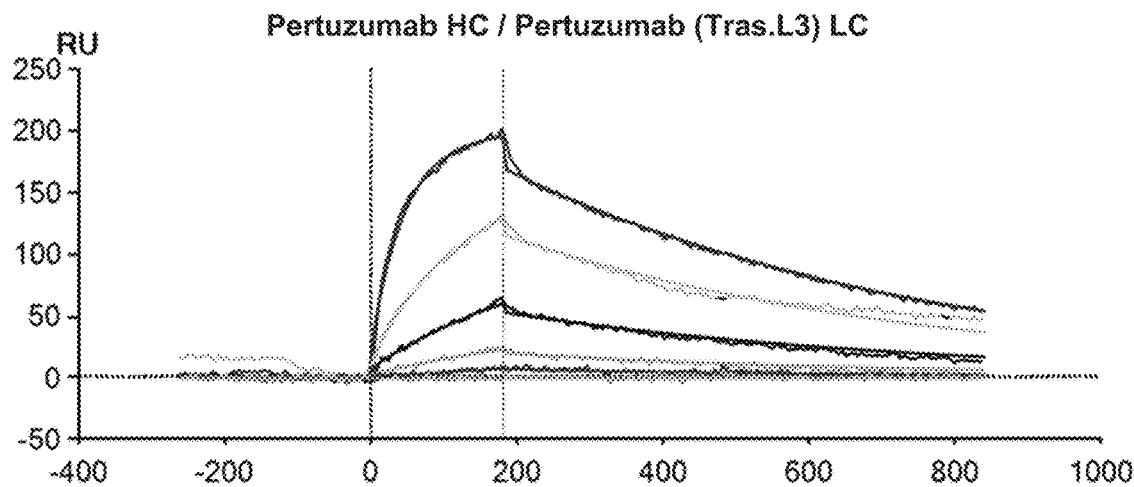
Figure 19F:
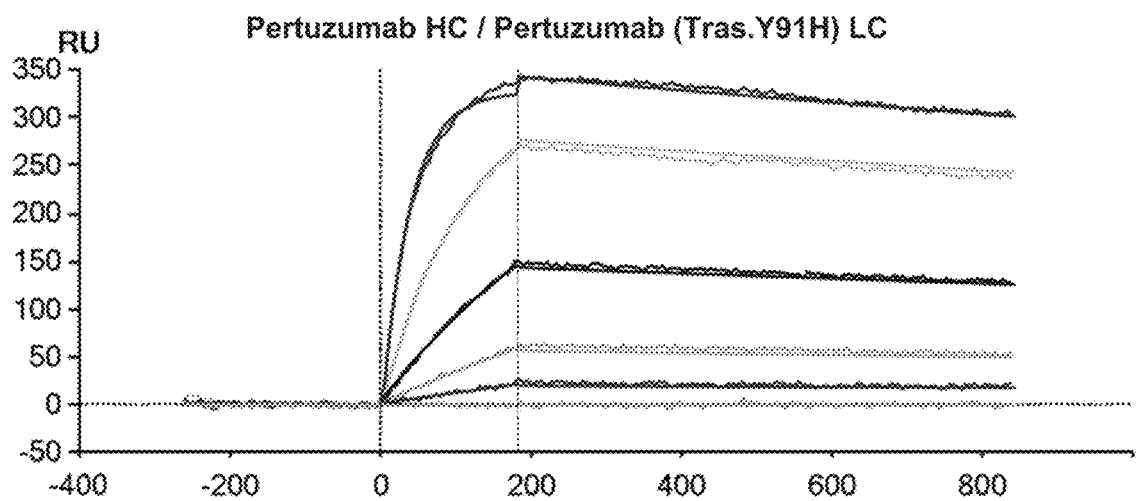
Figure 21A:
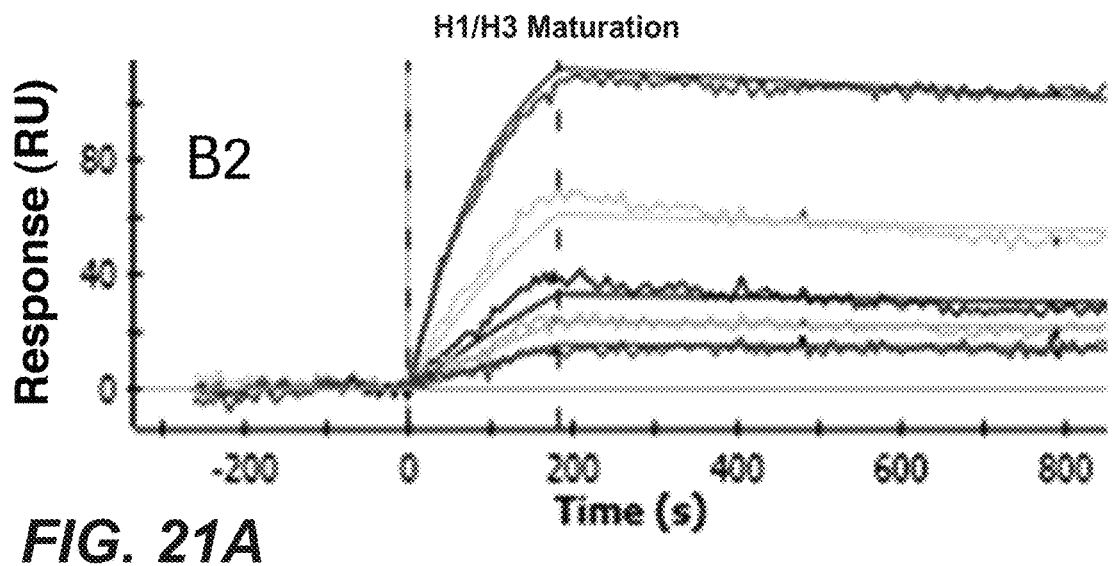
FIGS. 21A-21F: Characterization of the affinity-matured Pertuzumab clones identified by phage display. SPR analysis of the identified affinity-matured clones. Shown is the binding of bacterial Fabs to Her2 at different concentrations. Smooth lines represent a global fit of the data to a 1:1 interaction model. B2: SEQ ID No: 66, D1: SEQ ID No: 62, E1: SEQ ID No: 68, C8: SEQ ID No: 72, G2: SEQ ID No: 70, AL: SEQ ID No: 74.
Figure 21B:
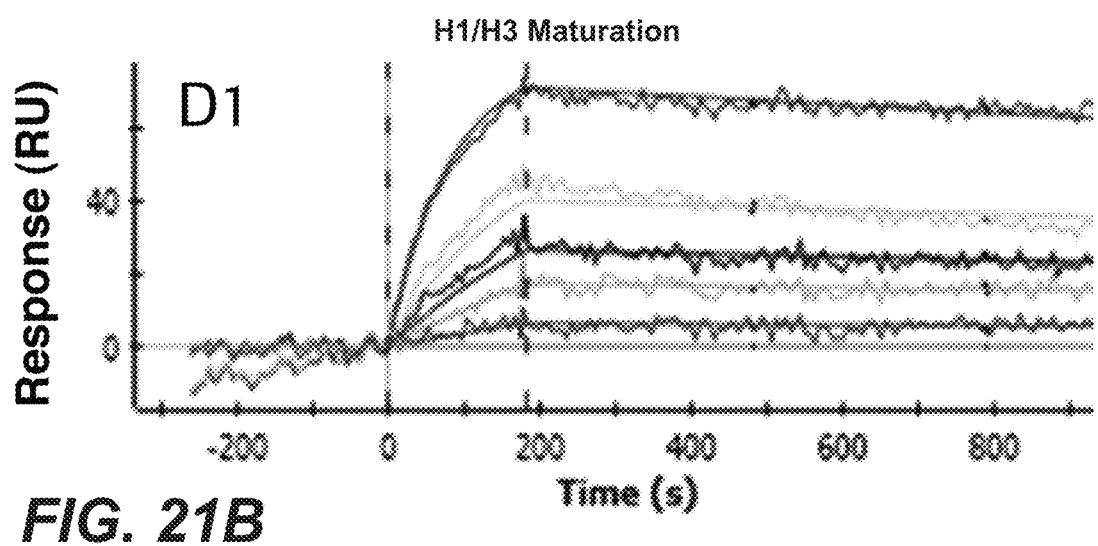
Figure 21C:
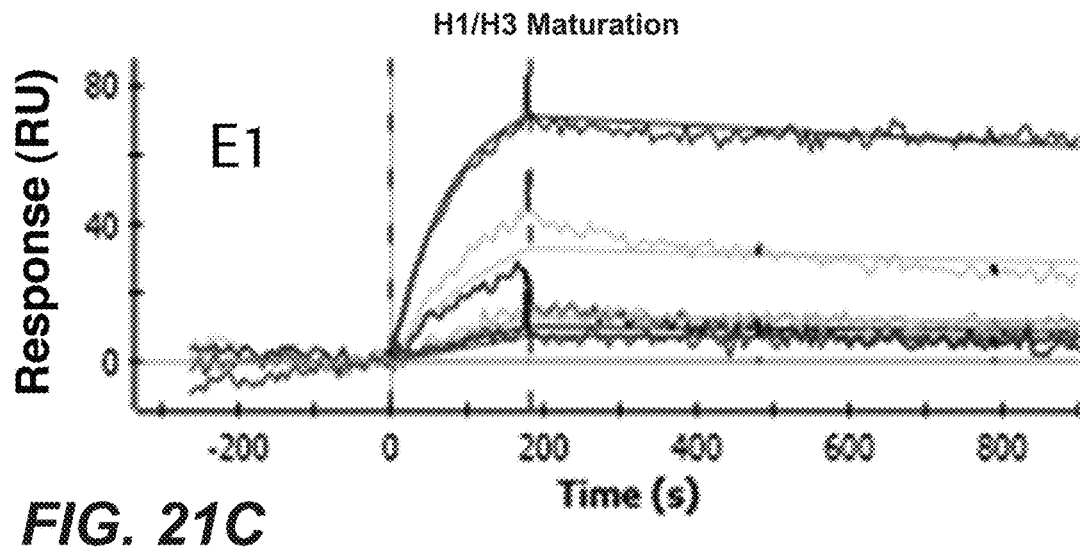
Figure 21D:
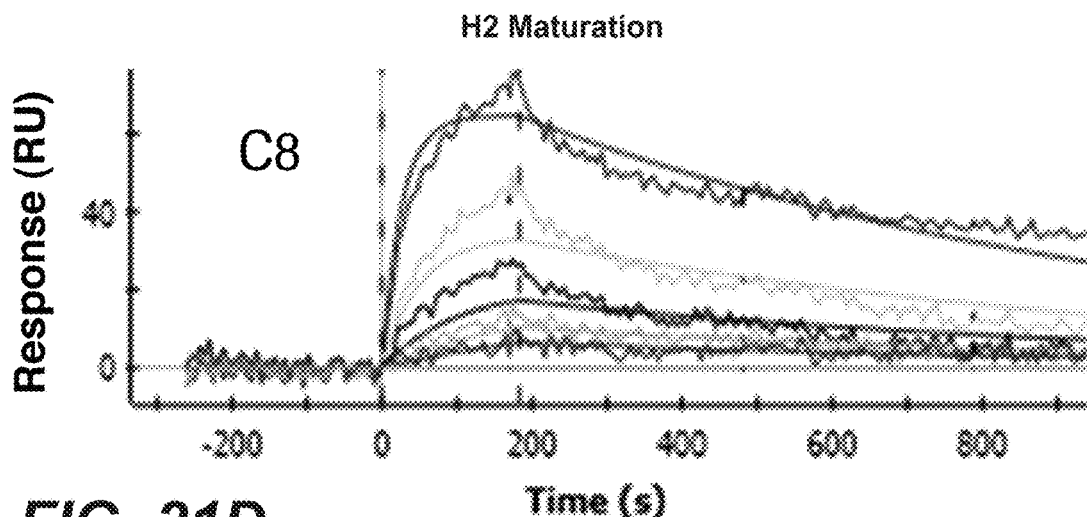
Figure 21E:
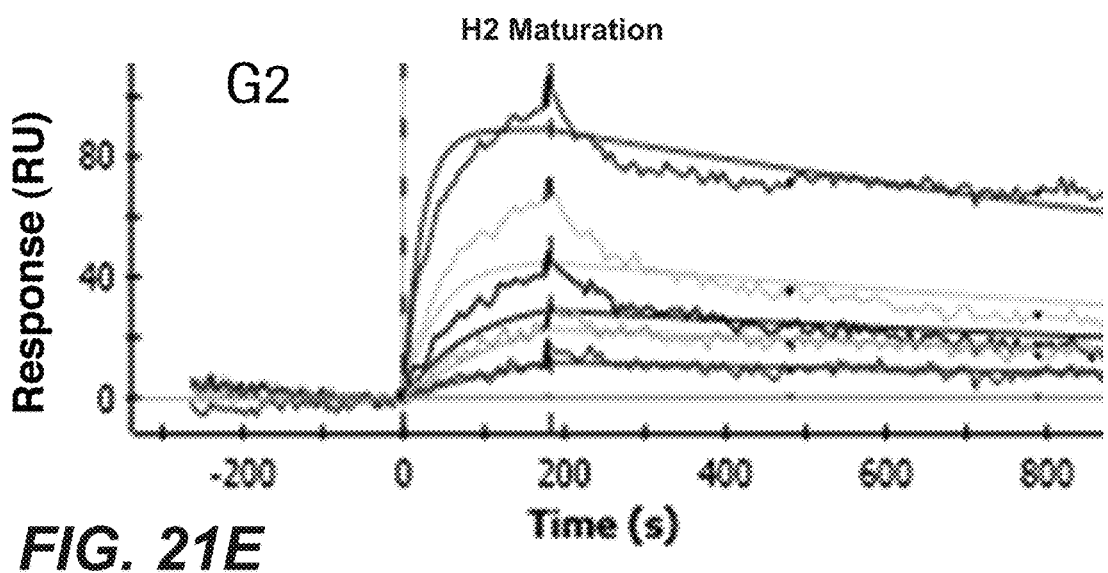
Figure 21F:
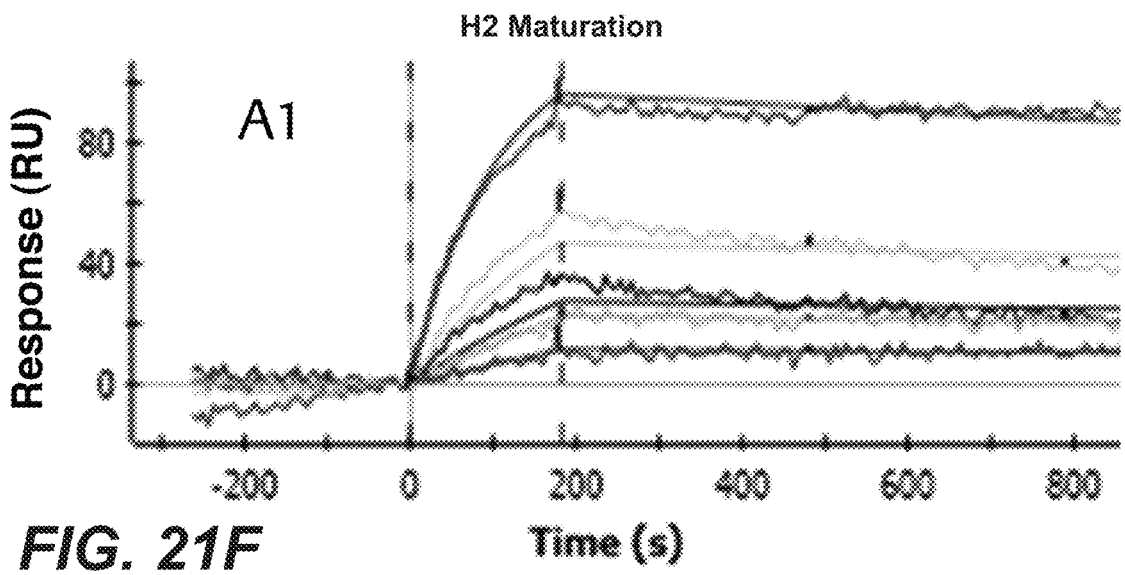
Figure 23A:
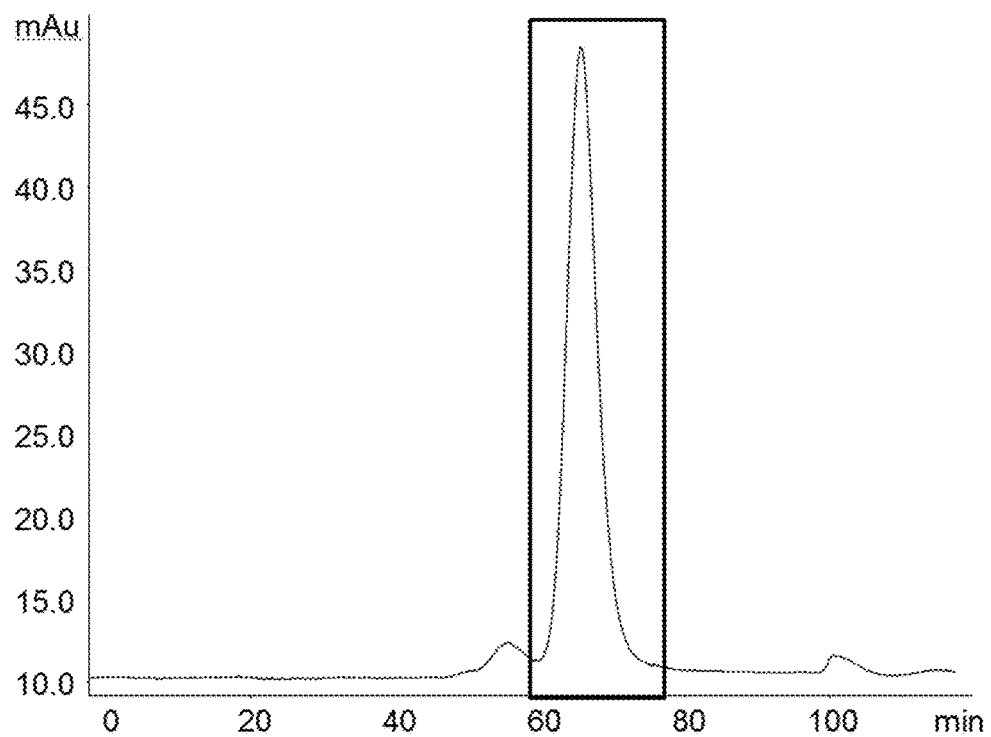
FIGS. 23A-23F: Purification and analytical characterization of the bi-specific HER2 antibodies with a common light chain. The purification method involved an affinity step (protein A) followed by size exclusion chromatography (SUPERDEX™ 200, GE Healthcare). The final product was analyzed and characterized by analytical size exclusion chromatography (SUPERDEX™ 200 column).
Figure 23B:
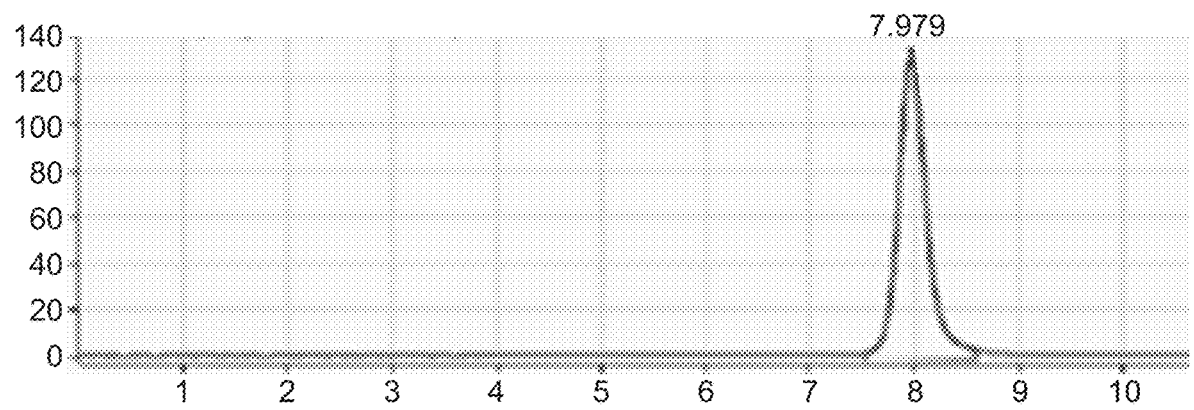
Figure 23C:
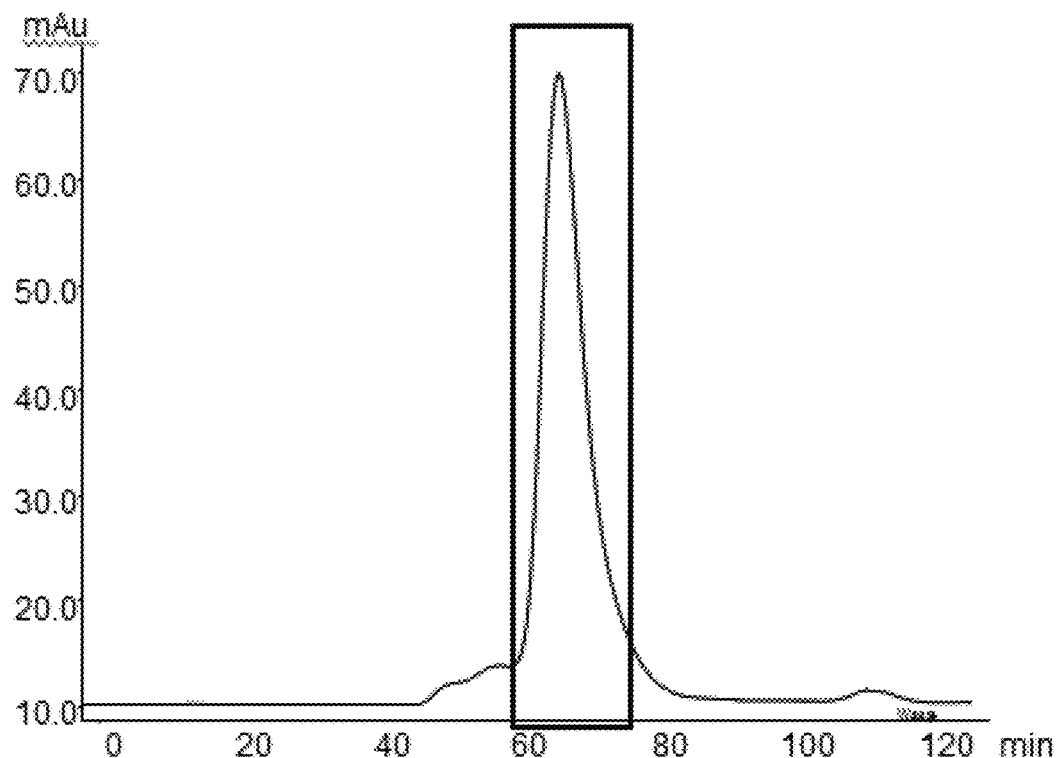
Figure 23D:
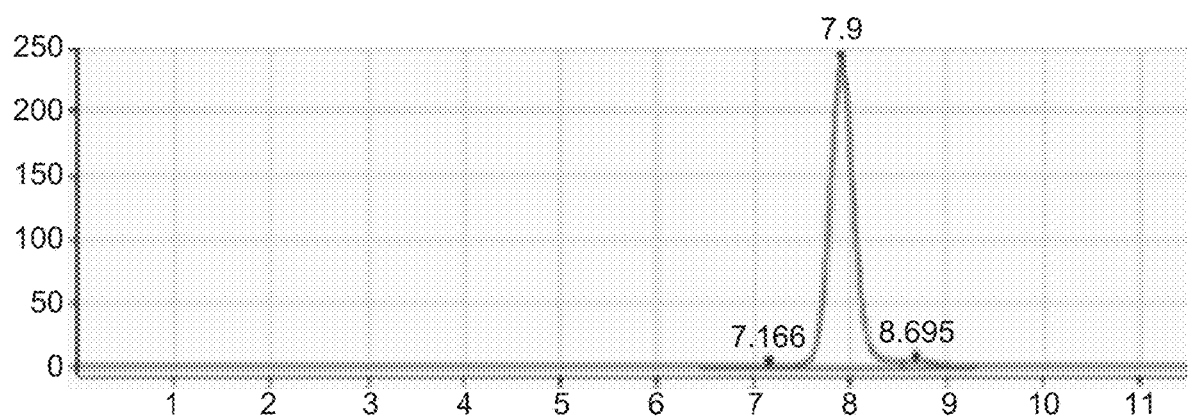
Figure 23E:
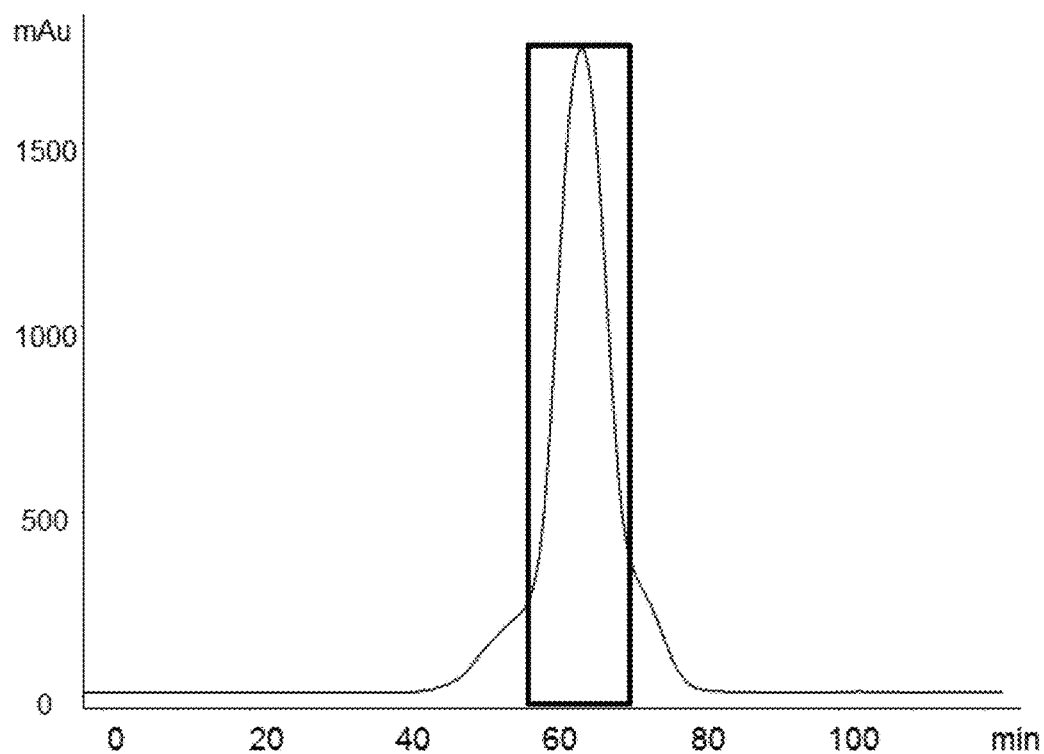
Figure 23F:
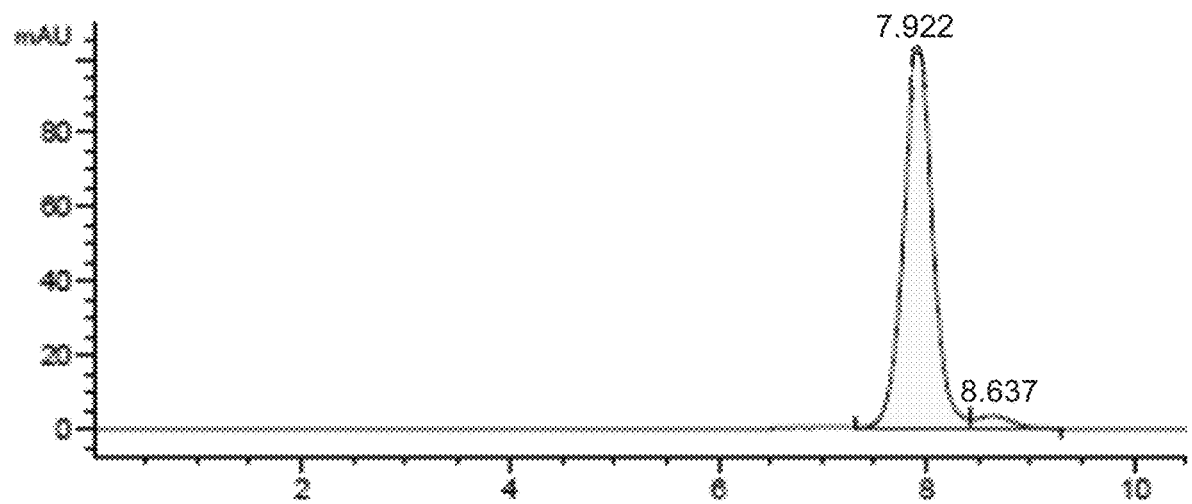
Figure 24A:
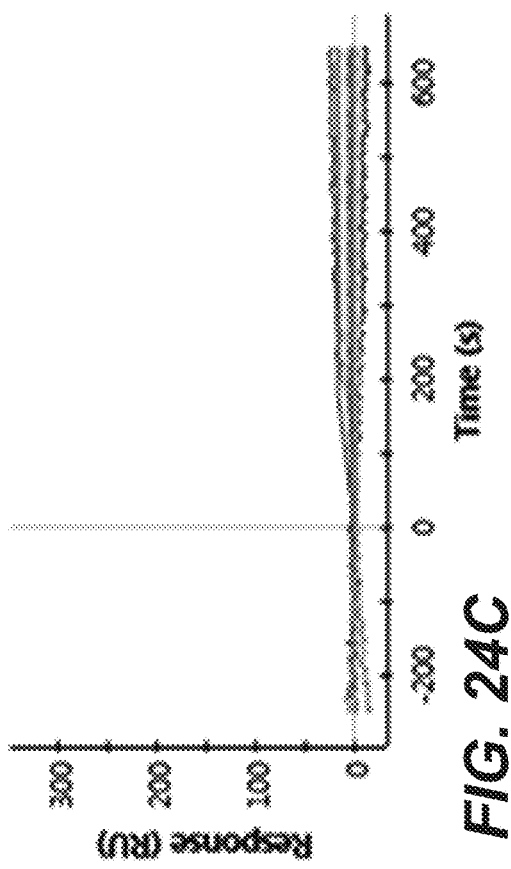
FIGS. 24A-24D: SPR analysis of the Her2 knock-out variants. Shown are the sensograms of Trastuzumab and Pertuzumab binding to both knock-out variants. Smooth lines represent a global fit of the data to a 1:1 interaction model.
Figure 24C:
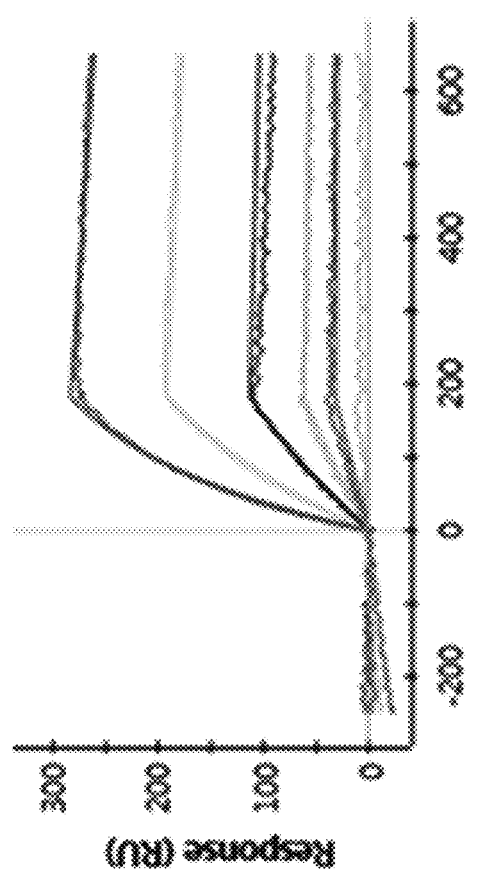
Figure 24B:
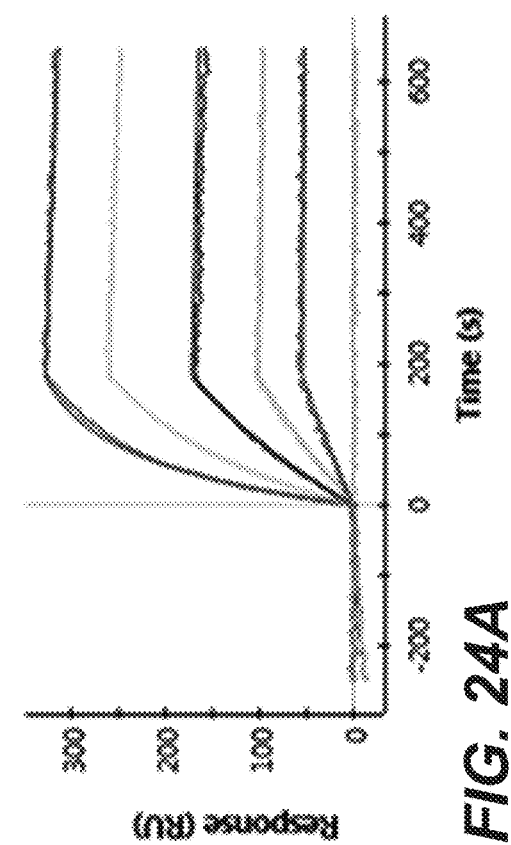
Figure 24D:
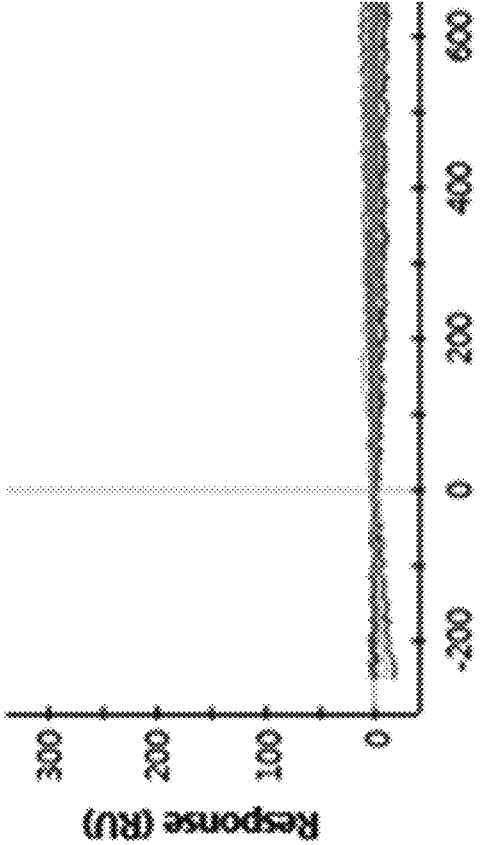

Spontaneous release, corresponding to target cells incubated with effector cells without antibody, was defined as 0% cytotoxicity, with maximal release (target cells lysed with 1% TRITON™ (t-octylphenoxypolyethoxyethanol) X-100) defined as 100% cytotoxicity. The average percentage of ADCC and standard deviations of the triplicates of each experiment were calculated. Results are shown in FIGS. 14A-C.

Example 10: In Vivo Characterization of HER2 CrossMab: Effect of Bispecific Antibodies Targeting HER2 on Tumor Growth in Calu3 Lung Cancer and KPL4 Breast Cancer Xenograft In Vitro Cultured Cells—Calu3

This human lung adenocarcinoma cancer cell line has been established from a human caucasian male with lung cancer. Cells were obtained from Chugai Pharmaceuticals Co., Ltd. and passaged in house for working cell bank. Tumor cells are routinely cultured in RPMI medium (PAN Biotech, Germany) supplemented with 10% fetal bovine serum glutamine (PAN Biotech, Germany) at 37° C. in a water-saturated atmosphere at 5% CO2. Culture passage is performed with trypsin/EDTA 1× (PAN) splitting twice/week. Cell passage P6 is used for in vivo study.

In Vitro Cultured Cells—KPL4

This human breast cancer cell line has been established from the malignant pleural effusion of a breast cancer patient with an inflammatory skin metastasis. Cells have been provided by Professor J. Kurebayashi (Kawasaki Medical School, Kurashiki, Japan). Tumor cells are routinely cultured in DMEM medium (PAN Biotech, Germany) supplemented with 10% fetal bovine serum (PAN Biotech, Germany) and 2 mM L-glutamine (PAN Biotech, Germany) at 37° C. in a water-saturated atmosphere at 5% CO2. Culture passage is performed with trypsin/EDTA 1× (PAN) splitting twice/week. Cell passage P6 is used for in vivo study.

Animals

Female SCID beige (C.B.-17) mice; age 10-12 weeks; body weight 18-20 g (Charles River Germany, Sulzfeld) or female BALB/C nu/nu mice; age 8-10 weeks; body weight >20 g (Bomholtgard, Denmark) are maintained under specific-pathogen-free condition with daily cycles of 12 h light/12 h darkness according to international guidelines (GV-Solas; Felasa; TierschG). After arrival animals are housed in the quarantine part of the animal facility for one week to get accustomed to new environment and for observation. Continuous health monitoring is carried out on regular basis. Diet food (Alltromin) and water (acidified pH 2.5-3) are provided ad libitum. The experimental study was reviewed and approved by local government; registration no. 55.2-1-54-2531.2-3-08 Scid-beige orthotop rodent breast cancer model and 211-2531.2-16/00. 1.2.2 subcutan tumor model.

Tumor Cell Injection

At the day of injection tumor cells are harvested (trypsin-EDTA) from culture flasks (Greiner TriFlask) and transferred into 50 ml culture medium, washed once and resuspended in PBS. After an additional washing step with PBS and filtration (cell strainer; Falcon Ø 100 μm) the final cell titer is adjusted to 1.5×108/ml. Tumor cell suspension is carefully mixed with transfer pipette to avoid cell aggregation. Anesthesia is performed using a Stephens inhalation unit for small animals with preincubation chamber (PLEXIGLAS®), individual mouse nose-mask (silicon) and not flammable or explosive anesthesia compound Isoflurane (Pharmacia-Upjohn, Germany) in a closed circulation system. Two days before injection, coat of the SCID beige mice are shaved. For subcutaneous injection of Calu3 cells, skin of anaesthetized animals is carefully lifted up with an anatomic forceps and 100 μl cell suspension (=5.0×10e6 cells) is injected subcutaneously in the right flank of the animals. Cell suspension is filled into a 1.0 ml tuberculin syringe (Braun, Melsungen) using a wide injection needle (0.45×25 mm). KPL-4 cells (3×10e6 cells) are injected orthotopically in a volume of 20 μl into the right penultimate inguinal mammary fat pad of each anesthetized mouse. For the orthotopic implantation, the cell suspension is injected through the skin under the nipple using a using a Hamilton microliter syringe and a 30G×1/2" needle.

Monitoring

Animals are controlled daily for detection of clinical symptoms of adverse effects. For monitoring throughout the experiment the body weight of the animals is documented two times weekly and the tumor volume is measured by caliper twice weekly. Tumor volume was calculated according to NCI protocol (Tumor weight=1/2ab$^2$, where "a" and "b" are the long and the short diameters of the tumor, respectively). Termination criteria were the critical tumor mass (up to 1.7 g or [[Ø]] diameter >1.5 cm), body weight loss more than 20% from baseline, tumor ulceration or poor general condition of the animals. Study exclusion criteria for the animals are described and approved in the corresponding "Animal Testing Notice".

Treatment of Animals

Mice were randomized for tumor volume, for KPL4 a mean of 80 mm$^3$, for Calu3 a mean of 100 mm$^3$. Mice were treated once weekly with a volume of 10 ml/kg intra peritoneal. For combination treatment Trastuzumab was given first and Pertuzumab was given 24 hrs thereafter. Results are shown in Tables 14 to 17 and FIGS. 15A-C, 16A-C, 17A-C, and 18A-C.

TABLE 14

BispecHer2_Pz_Calu3_001 (FIGS. 15A-C): CrossMAb_003
non-ge: non glycoengineered CrossMab-XTra Her2GlyMab
(SEQ ID NOs 119, 120, 121, 122), negative control: anti-IgE antibody
(Omalizumab), Herceptarg 2 + 2 OmniE: Pertuzumab antibody with
the Trastuzumab scFV added onto the c-terminus of the heavy chains.
The trastuzumab scFv contains a stabilizing disulphide bond between
VH 105-VL 43 (SEQ ID NOs: 145, 146), TvAb12 and TvAb20:
scFv 2 + 2 HER2 bispecific antibodies, see example 2.

| Group | No of animals | Compound | Dose (mg/kg) | Route/Mode of administration | No of treatments | Cumulative dose (mg/kg) |
|---|---|---|---|---|---|---|
| 1 | 8 | negative control | 10 | i.p. once weekly | 7 | 70 |
| 2 | 8 | Trastuzumab + | 10 | i.p. once weekly | 7 | 70 |
|   |   | Pertuzumab | 10 | i.p. once weekly | 7 | 70 |
| 3 | 8 | Herceptarg 2 + 2 OmniE | 13.5 | i.p. once weekly | 7 | 94.5 |
| 4 | 8 | CrossMAb_003 non-ge | 20 | i.p. once weekly | 7 | 140 |
| 5 | 8 | TvAb12 | 11.3 | i.p. once weekly | 7 | 79.1 |
| 6 | 8 | TvAb20 | 11.4 | i.p. once weekly | 7 | 79.8 |

TABLE 15

BispecHER2_PZ_KPL-4_002 (FIGS. 16A-C): CrossMAb_003
non-ge: non glycoengineered CrossMab-XTra Her2GlyMab
(SEQ ID NOs 119, 120, 121, 122), negative control: anti-IgE antibody
(Omalizumab), Herceptarg 2 + 2 OmniE: Pertuzumab antibody with
the Trastuzumab scFV added onto the c-terminal of the heavy chains.
The trastuzumab scFv contains a stabilizing disulphide bond between
VH 105-VL 43 (SEQ ID NOs: 145, 146), TvAb12 and TvAb20:
scFv 2 + 2 HER2 bispecific antibodies, see example 2.

| Group | No of animals | Compound | Dose (mg/kg) | Route/Mode of administration | No of treatments | Cumulative dose (mg/kg) |
|---|---|---|---|---|---|---|
| 1 | 9 | Negative control | 10 | i.p. once weekly | 5 | 50 |
| 2 | 9 | Trastuzumab + | 10 | i.p. once weekly | 5 | 50 |
|   |   | Pertuzumab | 10 | i.p. once weekly |   | 50 |
| 3 | 9 | Herceptarg 2 + 2 OmniE | 13.5 | i.p. once weekly | 5 | 67.5 |
| 4 | 9 | CrossMAb_003 non-ge | 20 | i.p. once weekly | 5 | 100 |
| 5 | 9 | TvAb12 | 11.3 | i.p. once weekly | 5 | 56.5 |
| 6 | 9 | TvAb20 | 11.42 | i.p. once weekly | 5 | 57.1 |

TABLE 16

Bispec.HER2_PZ_KPL-4_003 (FIGS. 17A-C): CrossMAb_005
non glycoengineered CrossMab-XTra Her2GlyMab
(SEQ ID NOs 119, 120, 121, 122), negative control:
anti-IgE antibody (Omalizumab).

| Group | No of animals | Compound | Dose (mg/kg) | Route/Mode of administration | No of treatments | Cumulative dose (mg/kg) |
|---|---|---|---|---|---|---|
| 1 | 10 | Negative control | 10 | i.p. once weekly | 5 | 50 |
| 2 | 10 | Trastuzumab + | 10 | i.p. once weekly | 5 | 50 |
|   |    | Pertuzumab | 10 | i.p. once weekly |   | 50 |
| 3 | 10 | Her2_Crossmab_005 | 20 | i.p. once weekly | 5 | 100 |
| 4 | 10 | Her2_Crossmab_005 | 10 | i.p. once weekly | 5 | 50 |
| 5 | 10 | Her2_Crossmab_005 | 5 | i.p. once weekly | 5 | 25 |
| 6 | 10 | Her2_Crossmab_005 | 1 | i.p. once weekly | 5 | 5 |

TABLE 17

Exploratory_PZ_KPL-4_009 (FIGS. 18A-C): negative control:
anti-IgE antibody (Omalizumab), TvAb16 and TvAb20:
scFv 2 + 2 HER2 bispecific antibodies, see example 2.

| Group | No of animals | Compound | Dose (mg/kg) | Route/Mode of administration | No of treatments | Cumulative dose (mg/kg) |
|---|---|---|---|---|---|---|
| 1 | 10 | Negative control | 10 | i.p. once weekly | 4 | 40 |
| 2 | 10 | Trastuzumab + | 10 | i.p. once weekly | 4 | 40 |
|   |    | Pertuzumab | 10 | i.p. once weekly | 4 | 40 |
| 3 | 10 | Trastuzumab + | 5 | i.p. once weekly | 4 | 20 |
|   |    | Pertuzumab | 5 | i.p. once weekly | 4 | 20 |
| 4 | 10 | TvAb16 | 10 | i.p. once weekly | 4 | 40 |
| 5 | 10 | TvAb16 | 5 | i.p. once weekly | 4 | 20 |
| 6 | 10 | TvAb20 | 10 | i.p. once weekly | 4 | 40 |
| 7 | 10 | TvAb20 | 5 | i.p. once weekly | 4 | 20 |

Example 11: Generation of a Common Light Chain for Trastuzumab and Pertuzumab

Gene Synthesis

Desired gene segments, where required, were either generated by PCR using appropriate templates or were synthesized at Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow subcloning into the respective expression vectors. All constructs were designed with a 5'-end DNA sequence coding for a leader peptide which targets proteins for secretion in eukaryotic cells. SEQ ID NOs: 155, 156, and 157 give exemplary leader peptides.

Cloning of Antigen Expression Vectors

A DNA fragment encoding amino acids 1 to 629 of matured Tyrosine kinase-type cell surface receptor HER2 (Her2, Uniprot: P04626) was cloned in frame into a mammalian recipient vector containing an N-terminal leader sequence. In addition, the construct contains a C-terminal avi-tag allowing specific biotinylation during co-expression with Bir A biotin ligase and a His-tag used for purification by immobilized-metal affinity chromatography (IMAC) (SEQ ID NOs 1 and 2).

The antigen expression is generally driven by an MPSV promoter and transcription is terminated by a synthetic polyA signal sequence located downstream of the CDS. In addition to the expression cassette, each vector contains an EBV oriP sequence for autonomous replication in EBV-EBNA expressing cell lines.

Production and Purification of Antigens and Antibodies

Both antigens and antibodies were transiently transfected into HEK 293 cells, stably expressing the EBV-derived protein EBNA. A simultaneously co-transfected plasmid encoding biotin ligase Bir A allowed avi tag-specific biotinlylation in vivo. The proteins were then purified using a protein A column followed by gel filtration.

Design of Trastuzumab/Pertuzumab Common Light Chains

For the generation of a common light chain (CLC) for Trastuzumab and Pertuzumab, the individual light chains (LC) were analyzed and compared. Sequence analysis revealed that both variable domains originate from the same germline sequence. Given that the Trastuzumab LCDR3 in general and residue H91 in particular interact specifically with the Trastuzumab-specific epitope on Her2, the first attempt to create a Trastuzumab/Pertuzumab CLC was done as follows: Either the complete LCDR3 region or only residue H91 of Trastuzumab substituted the corresponding positions in the Pertuzumab LC. As a result, a hybrid LC construct was created encoding Pertuzumab-derived LCDR1 and 2 but harboring Trastuzumab-derived LCDR3 amino acid residues. The resulting CLCs, named either "Pertuzumab (Tras.L3) LC" (DNA sequence of variable domains listed as SEQ ID NO: 25) or "Pertuzumab (Tras.Y91H) LC" (SEQ ID NO: 27), were co-expressed with either the Trastuzumab or the Pertuzumab HC. The resulting four antibodies (protein sequence of variable domains listed as SEQ ID NOs: 22 and 26, "Pertuzumab HC"×"Pertuzumab (Tras.L3) LC"; SEQ ID NO: 92 and 26, "Trastuzumab HC"×"Pertuzumab (Tras.L3) LC"; SEQ ID NOs: 22 and 28, "Pertuzumab HC"×"Pertuzumab (Trast.Y91H) LC"; SEQ ID NO: 92 and 28, "Trastuzumab HC"×"Pertuzumab (Tras.Y91H) LC") were purified from mammalian-derived cell culture supernatant and binding to Her2 was measured and compared with the respective parental antibodies (SEQ ID NOs: 22 and 24, "Pertuzumab HC"×"Pertuzumab LC"; SEQ ID NO: 92 and 82, "° Trastuzumab HC"×"Trastuzumab LC") by SPR.

Affinity-Determination by SPR Using BioRad's PROTEON™ XPR36 Biosensor

The Affinity ($K_D$) of the new antibody chain combinations was measured by surface plasmon resonance using a PROTEON™ XPR36 instrument (Biorad) at 25° C. In a first step, 6500 RU of anti-human IgG (Sigma 12136, polyclonal goat antibody) recognizing hu IgG (Fc-specific) was immobilized on all 6 channels of a GLM chip by Amine coupling (NaAcetate pH4, 30 µl/min, 300s) (vertical orientation).

Each antibody was diluted with PBST (10 mM phosphate, 150 mM sodium chloride pH 7.4, 25 0.005% TWEEN™ (polysorbate) 20) to 2 µg/ml, and then injected for 60s at 30 µl/minute to achieve immobilization levels of about 400 response units (RU) in vertical orientation. Injection of Her2: For one-shot kinetics measurements, injection direction was changed to horizontal orientation, three-fold dilution series of purified Her2 (varying concentration ranges between 300 and 3.7 nM) were injected simultaneously at 100 µl/min along separate channels 1-5, with association times of 180s, and dissociation times of 600s. Buffer (PBST) was injected along the sixth channel to provide an "in-line" blank for referencing. Regeneration was performed by two pulses of 10 mM glycine pH 1.5 and 50 mM NaOH for 30s at 100p/min (horizontal orientation). Association rate constants ($k_{on}$) and dissociation rate constants ($k_{off}$) were calculated using a simple one-to-one Langmuir binding model in PROTEON™ Manager v3.1 software by simultaneously fitting the association and dissociation sensorgrams. The equilibrium dissociation constant ($K_D$) was calculated as the ratio $k_{off}/k_{on}$.

As expected, both control antibodies Trastuzumab and Pertuzumab recognized Her2 with their known affinities in the low nanomolar or sub-nanomolar range. However, while the affinity of Pertuzumab HC in combination with the newly designed "Pertuzumab (Tras.Y91H) LC" was slightly reduced, the same light chain in combination with Trastuzumab HC did not yield any detectable binding. This indicates that a single Trastuzumab-derived point mutation (Y91H) in the Pertuzumab LC is not sufficient translate binding to Her2 in this chain combination. This is in contrast to the second CLC variant "Pertuzumab LC (Trast. L3)" which resulted in weak binding when combined with Trastuzumab HC, while binding was reduced but clearly visible when co-expressed with the Pertuzumab HC. A summary of the kinetic and thermodynamic measurements is given in FIGS. 19A-F and Table 18. Based on this finding, the CLC "Pertuzumab LC (Trast. L3)" was further modified in order to restore Her2 binding in combination with Trastuzumab HC while affecting the affinity as little as possible when co-expressed with Pertuzumab HC.

TABLE 18

Kinetic and thermodynamic parameters of Trastuzumab, Pertuzumab, and hybrid molecules thereof

| Clone | ka [1/Ms] | kd [1/s] | KD [M] |
|---|---|---|---|
| Trastuzumab | 1.01E+05 | 2.24E−04 | 2.21E−09 |
| Pertuzumab | 8.08E+04 | 6.69E−05 | 1.47E−10 |
| Pertuzumab HC Pertuzumab (Tras.L3) LC | 6.47E+04 | 1.73E−03 | 2.67E−08 |
| Pertuzumab HC Pertuzumab(Tras. Y91H) LC | 8.99E+04 | 1.98E−04 | 2.21E−09 |
| Trastuzumab HC Pertuzumab(Tras.L3) LC | 4.19E+04 | 0.05 | 1.09E−06 |
| Trastuzumab HC Pertuzumab(Tras. Y91H) LC | N/A | N/A | N/A |

Example 12: Affinity-Improvement of the Common Light Chain

Introduction and Characterization of Additional Trastuzumab-Specific LCDR Residues into the Pertuzumab (Tras.L3) LC Based on the results of the previous SPR measurement, binding of the designed CLC "Pertuzumab (Trast. L3) LC" in combination with the Pertuzumab HC led to a reduced but still well detectable binding. In contrast, co-expression of the CLC with Trastuzumab HC resulted in a very weak affinity in the micromolar range and was significantly reduced compared to the parental Trastuzumab antibody.

In order to further evolve the generation of a CLC and improve the binding in combination with the Trastuzumab HC, additional Trastuzumab-specific amino acid of the LCDR1, 2, and 3 as well in framework 3 region that are specific for Trastuzumab were individually introduced into the sequence of the previously designed "Pertuzumab (Trast.L3) LC" (DNA sequence of variable domains listed as SEQ ID NO: 31, 33, 35, 37, 39, 41, 43, 45, 47, 49, and 51). The resulting constructs (protein sequence of variable domains listed as SEQ ID NO: 32, 34, 36, 38, 40, 42, 44, 46, 48, 50, and 52) were co-expressed with the Trastuzumab HC (SEQ ID NO: 92) or the Pertuzumab HC (SEQ ID NO: 22) and purified from mammalian-derived cell culture supernatant. Binding to Her2 was measured and compared with the respective parental antibodies.

Affinity-Determination of the "Pertuzumab (Trast.L3) LC" Variants by SPR

The Affinity ($K_D$) of the new antibody chain combinations was measured by surface plasmon resonance using a PROTEON™ XPR36 instrument (Biorad) and was performed as described before. A summary of the kinetic and thermodynamic measurements is given in table 19.

Interestingly, none of the additional single mutations in the "Pertuzumab (Tras.L3) LC" variants significantly affected the affinity when combined with the Pertuzumab and the affinity was comparable to "Pertuzumab HC"× "Pertuzumab (Tras.L3) LC". However, combination of the "Pertuzumab (Tras.L3) LC" variants with the Trastuzumab HC resulted in significant differences. While back mutations to the Pertuzumab sequence in the LCDR3 region (P94Y and T96Y) (protein sequence of variable domains listed as SEQ ID NOs: 50 and 52) completely abolished binding to Her2, introduction of Pertuzumab-specific mutations (SEQ ID NOs: 32, 34, 36, 38, 40, 42, 44, 46, and 48) yielded an equal or improved affinity compared to the initial combination "Trastuzumab HC"×"Pertuzumab (Tras.L3) LC". In particular, introduction of the mutations 131T, G32A, Y53F, and G66R led to the most significant improvement in binding.

Simultaneous Introduction of Most Significant Trastuzumab-Specific Residues into the "Pertuzumab (Tras.L3) LC"

Based on the binding measurement described above, introduction of the 4 most relevant Trastuzumab-specific mutations into the "Pertuzumab (Tras.L3) LC" was combined. The protein sequences of the variable domains containing either the individual mutations are listed as SEQ ID NOs: 36, 40, 42, and 48) The chain containing the "quadruple mutation" was named "Pertuzumab (Tras.L3) (QM) LC" (SEQ ID NOs: 54).

Affinity-Determination of the "Pertuzumab (Trast.L3)(QM) LC" by SPR

In order to characterize the new "Pertuzumab (Tras.L3) (QM) LC" and to determine the binding affinity when combined with either Pertuzumab HC or Trastuzumab HC, a further SPR experiment was performed. The Affinity ($K_D$) of the new antibody chain combinations was measured using a PROTEON™ XPR36 instrument (Biorad) and was performed as described before. A summary of the kinetic and thermodynamic measurements is given in FIGS. 20A-B and Table 20.

Similar to the individual mutations that were introduced and characterized before, the affinity of the antibody comprising the Pertuzumab HC and the "Pertuzumab (Tras.L3) (QM) LC" did not significantly decrease compared to the initial chain combination "Pertuzumab HC"×"Pertuzumab (Tras.L3) LC". For both chain combinations, the affinity was in the range of 26 to 34 nM. Interestingly, the combination of the "Trastuzumab HC" with the "Pertuzumab (Tras.L3) (QM) LC" leads to a very strong improvement of the affinity to Her2. Furthermore, its affinity of 200 pM is even better than the measured affinity of the parental antibody Trastuzumab (2.2 nM). Given that the combination of "Pertuzumab (Tras.L3) (QM) LC" with Trastuzumab HC fully restores (or even exceeds) binding to Her2 and considering that the combination with the Pertuzumab HC diminishes but not abrogates binding to Her2, it was apparent to use the "Pertuzumab (Tras.L3) (QM) LC" as a CLC for both Her2 specificities and restore binding to the Pertuzumab-specific epitope by affinity-maturation of the Pertuzumab HC.

TABLE 19

Kinetic and thermodynamic parameters of antibodies comprising either a Trastuzumab or Pertuzumab HC in combination of additional CLC hybrid molecules

| | Pertuzumab HC | | | Trastuzumab HC | | |
|---|---|---|---|---|---|---|
| Clone | ka [1/Ms] | kd [1/s] | KD [M] | ka [1/Ms] | kd [1/s] | KD [M] |
| Tras.L3 (K24R) | 4.57E+05 | 2.11E−03 | 4.62E−09 | 3.77E+05 | 2.52E−02 | 6.68E−08 |
| Tras.L3 (S30N) | 5.30E+05 | 1.80E−03 | 3.40E−09 | 3.96E+05 | 2.56E−03 | 6.46E−08 |
| Tras.L3 (I31T) | 4.31E+05 | 1.75E−03 | 4.06E−09 | 4.73E+05 | 3.41E−03 | 7.21E−09 |
| Tras.L3 (I31V) | 4.40E+05 | 1.92E−03 | 4.35E−09 | 4.13E+05 | 1.16E−02 | 2.80E−08 |
| Tras.L3 (G32A) | 5.11E+05 | 1.87E−03 | 3.66E−09 | 6.75E+05 | 2.68E−03 | 3.97E−09 |
| Tras.L3 (Y53F) | 3.16E+05 | 2.54E−03 | 8.03E−09 | 3.81E+05 | 1.71E−02 | 4.49E−08 |
| Tras.L3 (R54L) | 4.64E+05 | 2.26E−03 | 4.87E−09 | 4.16E+05 | 2.97E−02 | 7.15E−08 |

TABLE 19-continued

Kinetic and thermodynamic parameters of antibodies comprising either a Trastuzumab or Pertuzumab HC in combination of additional CLC hybrid molecules

| Clone | Pertuzumab HC | | | Trastuzumab HC | | |
|---|---|---|---|---|---|---|
| | ka [1/Ms] | kd [1/s] | KD [M] | ka [1/Ms] | kd [1/s] | KD [M] |
| Tras.L3 (T56S) | 4.43E+05 | 2.45E−03 | 5.52E−09 | 4.70E+05 | 2.32E+02 | 4.94E−08 |
| Tras.L3 (G66R) | 3.58E+05 | 2.47E−03 | 6.91E−09 | 5.14E+05 | 5.58E−03 | 1.09E−08 |
| Tras.L3 (T94Y) | 8.05E+05 | 6.30E−04 | 7.82E−10 | N/A | N/A | N/A |
| Tras.L3 (P96Y) | 3.44E+05 | 9.70E−04 | 2.82E−09 | N/A | N/A | N/A |
| Tras.L3 | 4.22E+05 | 2.09E−03 | 4.96E−09 | 3.25E+05 | 2.36E−02 | 7.25E−08 |

TABLE 20

Kinetic and thermodynamic parameters of antibodies comprising either a Trastuzumab or Pertuzumab HC and the final CLC

| Clone | ka [1/Ms] | kd [1/s] | KD [M] |
|---|---|---|---|
| Pertuzumab HC Pertuzumab (Tras.L3)(QM) LC | 9.46E+04 | 3.24E−03 | 3.42E−08 |
| Trastuzumab HC Pertuzumab (Tras.L3)(QM) LC | 2.69E+05 | 5.42E−05 | 2.02E−10 |

Example 13: Affinity Maturation of the Pertuzumab Heavy Chain

Generation of Pertuzumab-Based H1/H3 and H2 Affinity Maturation Libraries

Generation of affinity-matured Pertutzumab-derived heavy chains was carried out by phage display using standard protocols (Silacci et al, 2005).

For the generation of Pertuzumab-derived HCs with improved affinity when jointly expressed with "Pertuzumab (Tras.L3) (QM) LC" a maturation library randomized in CDR1 and 3 or in CDR2 was generated. The sequence of the Pertuzumab HC (SEQ ID NO: 22) and of the "Pertuzumab (Tras.L3) (QM) LC" (SEQ ID NO: 54) was cloned into a phagemid and used as a template for the randomization. For the generation of the Pertuzumab HC affinity maturation library randomized in CDR1 and 3, three fragments were assembled by "splicing by overlapping extension" (SOE) PCR and cloned into the phage vector. The following primer combinations were used to generate the library fragments: fragment 1 (LMB3 (SEQ ID NO: 147) and AM_omni_H1_TN-ba (SEQ ID NO: 148), fragment 2 (RJH108 (omni_3'H1_fo) (SEQ ID NO: 149) and RJH109 (omni_5'H3_re) (SEQ ID NO: 150), and fragment 3 (AM_omni_H3_TN_fo (SEQ ID NO: 151) and RJH99 (SEQ ID NO: 152). After assembly of sufficient amounts of full length randomized fragment, it was digested with MunI/NheI alongside with identically treated acceptor phagemid vector. 6 ug of Fab library insert were ligated with 24 ug of phagemid vector. Purified ligations were used for 60 transformations resulting in 6×10 exp9 transformants. Phagemid particles displaying the Pertuzumab affinity maturation library were rescued and purified by PEG/NaCl purification to be used for selections.

The generation of the CDR2-randomized Pertuzumab HC affinity maturation library was done similarly, but only 2 fragments were generated, assembled and cloned into the phagemid using the same restriction enzymes as before. The following primer combinations were used to generate the library fragments: fragment 1 (LMB3 (SEQ ID NO: 147) and RJH10 (omni_5'H2ba) (SEQ ID NO: 153) and fragment 2 (AM_omni_h2_TN_fo (SEQ ID NO: 154) and RJH99 (SEQ ID NO:152). Purified ligations were used for 60 transformations resulting in 4×10 exp9 transformants. Phagemid particles displaying the Pertuzumab affinity maturation library were rescued and purified by PEG/NaCl purification to be used for selections.

TABLE 21 a

Primer combinations for the generation of the CDR1 and 3-randomized Pertuzumab affinity-maturation library
Pertuzumab HC affinity maturation (CDR1 and 3)

| fragment | 5'Primer | 3'Primer |
|---|---|---|
| PCR1 | LMB3 | AM_omni_H1_TN-ba |
| PCR2 | RJH108 (omni_3'H1_fo) | RJH109 (omni_5'H3_re) |
| PCR3 | AM_omni_H3_TN_fo | RJH99 |

TABLE 21 b)

Primer sequences for the generation of the CDR1 and 3-randomized Pertuzumab affinity-maturation library
Pertuzumab HC affinity maturation (CDR1 and 3)

| SEQ ID | Name | Sequence |
|---|---|---|
| 147 | LMB3 | CAGGAAACAGCTATGACCATGATTAC |
| 148 | AM_omni_H1_TN-ba | CCGGTGCCTGACGAACCCAATCCAT 4 3 2 1 AAAGGTAAAACCGCTTGCTGCACAGCTC<br>1 T = 60%, S/G/R/N/D = 20% (4% each), rest = 20% (1.7% each)<br>2 D = 60%, S/N/T/A/R/E/Q/G = 30% (3.8% each), rest = 10% (1.1% each) |

TABLE 21 b)-continued

Primer sequences for the generation of the CDR1 and 3-randomized Pertuzumab affinity-maturation library
Pertuzumab HC affinity maturation (CDR1 and 3)

| SEQ ID | Name | Sequence |
|---|---|---|
| | | 3 Y = 60%, F/S/H/N/D/T = 30% (5.0% each), rest = 10% (0.9%) |
| | | 4 T = 60%, A/G/V/S/P/D/N = 30% (4.3% each), rest = 10% (1.0%) |
| 149 | RJH108 (omni_3' H1_fo) | ATGGATTGGGTTCGTCAGGCACCGGGTAAAGG |
| 150 | RJH109 (omni_5' H3_re) | ATTACGTGCACAATAATACACTGCGGTATCCTC |
| 151 | AM_omni H3_TN_fo | TACCGCAGTGTATTATTGTGCACGT 4a 5 5a 6 7 TTC 8 TTTGATTATTGGGGTCAGGGCACCCTGGTTAC<br>4a N = 60%, G/D/E/Q/V/S/A/P/R/L/T/Y = 40% (3.3% each)<br>5 L = 60%, G/Y/S/A/D/T/R/P/V/N/W/F/I/E = 40% (2.9% each)<br>5a G = 60%, Y/S/A/D/T/R/P/L/V/N/W/F/I/E = 40% (2.9% each)<br>6 P = 60%, G/Y/S/A/D/T/R/L/V/N/W/F/I/E = 40% (2.9% each)<br>7 S = 60%, G/Y/P/A/D/T/R/L/V/N/W/F/I/E = 40% (2.9% each)<br>8 Y = 60%, G/A/P/W/S/D/T/F/R/K/H = 40% (3.6% each) |
| 152 | RJH99 | GGCTGAGACTCCTCAAGAGAAGGATTAG |

TABLE 22 a

Primer combinations for the generation of the CDR2-randomized Pertuzumab affinity-maturation library
Pertuzumab HC affinity maturation (CDR2)

| fragment | 5'Primer | 3'Primer |
|---|---|---|
| PCR1 | LMB3 | RJH110(omni_5'H2_ba) |

TABLE 22 b)

Primer combinations for the generation of the CDR2-randomized Pertuzumab affinity-maturation library
Pertuzumab HC affinity maturation (CDR2)

| SEQ ID | Name | Sequence |
|---|---|---|
| 153 | RJH110 (omni_5' H2_ba) | ATTAACATCTGCAACCCATTCCAGACCTTTAC |
| 154 | AM_omni_ h2_TN_fo | GGTCTGGAATGGGTTGCAGATGTTAAT 9 10 11 12 GGT 13 ATT 14 AC 15 CGTTTTAAAGGTCGTTTTACCCTGAG<br>9 P = 60%, G/A/S/T/D/N/F/Y = 30% (3.8% each), rest = 10% (1.0% each)<br>10 N = 60%, S/D/G/T/R/A = 30% (5.0% each), rest = 10% (0.8%)<br>11 S = 60%, G = 10%, rest = 30% (1.8% each) |

Selection of Affinity Matured Pertuzumab HC-Derived Clones

Selections against the extracellular domain (ECD) of human Her2 were carried out using HEK293-expressed protein. The antigen was enzymatically biotinylated by co-expression of the biotin ligase Bir A via an N-terminal avi-tag. Panning rounds were performed in solution according to the following pattern: 1. binding of ~$10^{12}$ phagemid particles to 10 nM biotinylated Her2 ECD for 0.5 h in a total volume of 1 ml, 2. capture of biotinylated Her2 ECD and specifically bound phage particles by addition of 5.4×$10^7$ streptavidin-coated magnetic beads for 10 min, 3. washing of beads using 5×1 ml PBS/TWEEN™ (polysorbate) 20 and 5×1 ml PBS, 4. elution of phage particles by addition of 1 ml 100 mM TEA for 10 min and neutralization by adding 500 µl M Tris/HCl pH 7.4, 5. re-infection of exponentially growing E. coli TG1 bacteria, and 6.infection with helper-phage VCSM13 and subsequent PEG/NaCl precipitation of phagemid particles to be used in subsequent selection rounds. Selections were carried out over 3 rounds using decreasing (from 20×$10^{-9}$ M to 1×$10^{-9}$M) antigen concentrations. In round 2 and 3, capture of antigen:phage complexes was performed using neutravidin plates instead of streptavidin beads. In addition, neutravidin plates were washed for 3h in 2 1 PBS. Specific binders were identified by ELISA as follows: 100 µl of 30 nM biotinylated Her2 ECD per well were coated on neutravidin plates. Fab-containing bacterial supernatants were added and binding Fabs were detected via their Flag-tags by using an anti-Flag/HRP secondary antibody. ELISA-positive clones were bacterially expressed as soluble Fab fragments in 96-well format and supernatants were subjected to a kinetic screening experiment by SPR-analysis using PROTEON™ XPR36.

Affinity-Determination of Affinity-Matured Pertuzumab HC Variants by SPR

The Affinity ($K_D$) of the new Pertuzumab HC variants was measured by surface plasmon resonance. In a first step, 7000 RU of polyclonal anti-human Fab antibody were immobilized on all 6 channels of a GLM chip by Amine coupling (NaAcetate pH4.5, 30 µl/min, 300s) (vertical orientation).

Each antibody-containing bacterial supernatant was filtered and 3-fold diluted with PBS, and then injected for 180s at 30 µl/minute to achieve immobilization levels of between 100 and 400 response units (RU) in vertical orientation. Injection of Her2: For one-shot kinetics measurements, injection direction was changed to horizontal orientation, two-fold dilution series of purified Her2 (varying concentration ranges between 100 and 6.25 nM) were injected simultaneously at 100 µl/min along separate channels 1-5, with association times of 180s, and dissociation times of 1000s. Buffer (PBST) was injected along the sixth channel to provide an "in-line" blank for referencing. Regeneration was performed by two pulses of 10 mM glycine pH 1.5 and 50 mM NaOH for 30s at 100 µl/min (horizontal orientation). Association rate constants ($k_{on}$) and dissociation rate constants ($k_{off}$) were calculated using a simple one-to-one Langmuir binding model in PROTEON™ Manager v3.1 software by simultaneously fitting the association and dissociation sensorgrams. The equilibrium dissociation constant ($K_D$) was calculated as the ratio $k_{off}/k_{on}$. Clones expressing Fabs with the highest affinity constants were identified and the heavy chains of the corresponding phagemids were sequenced. The thermodynamic measurement of the most affine Pertuzumab HC variants (protein sequence of variable domains listed as SEQ ID NOs: 62, 66, 68, 70, 72, and 74) is summarized in Table 23 and FIGS. 21A-F.

TABLE 23

Affinity of selected affinity matured Pertuzumab clone variants in combination with the common light chain (CLC)

| Pertuzumab heavy chain | affinity (nM) |
| --- | --- |
| Pertuzumab | 34 |
| Aff.mat. clone D1 | 1 |
| Aff.mat. clone B2 | 1 |
| Aff.mat. clone E1 | 0.5 |
| Aff.mat. clone G2 | 1 |
| Aff.mat. clone C8 | 3 |
| Aff.mat. clone A1 | 1 |

Example 14: Characterization of the Trastuzumab/Pertuzumab Bispecific Antibodies Generation of the Trastuzumab/Pertuzumab bi-specific anti-Her antibodies with a CLC In the following step, the affinity-matured Pertuzumab HC as well as the Trastuzumab HC were expressed in combination with the CLC named "Pertuzumab (Tras.L3) (QM) LC" in a bispecific antibody format. For the generation of such bispecific antibodies with a CLC, heterodimerization of the 2 different HCs was achieved by application of the knob-into-hole technology. Variable domains of the Pertuzumab affinity-matured clones E1 and G2 (protein sequence of variable domains listed as SEQ ID NOs: 68 and 70) as well as a clone "D1-derived" (D1-der) sequence (SEQ ID NOs: 64) were cloned into a human IgG1 HC containing the "hole" mutations in domain CH3. A schematic overview of the bispecific antibody with a CLC is shown in FIG. 22.

Affinity-maturation clone "D1-der" combines the CDR1 and 3 mutations of clone D1 (SEQ ID NOs: 62) with additional CDR2 mutations found in other selected clones. The variable domain of the Trastuzumab HC (SEQ ID NO: 92) was cloned into a human IgG1 HC harboring the "knob" mutations in domain CH3. The resulting constructs, called "Herceptarg" constructs, were co-expressed and purified from mammalian-derived cell culture supernatant. A summary of the analytical data for all three bi-specific antibodies is shown clones in FIGS. 23A-F and Table 24.

TABLE 24

Production of HER2 antibody with common light chain

| Antibody | yield/liter (mg/l) | % Monomer |
| --- | --- | --- |
| Herceptarg CLC G2 | 41.3 | 100 |
| Herceptarg CLC E1 | 72.1 | 96 |
| Herceptarg CLC D1-der. | 20.1 | 100 |

Generation of Her2 Knock-Out Antigen Variants

In order to analyze and characterize binding of the Herceptarg bi-specific antibodies to each of both epitopes on Her2, Her2 knock-out variants were designed. In these variants, either of the two specific epitopes was deleted by mutation of the amino acids that interact with the respective antibody chains.

For expression and purification, the respective DNA fragments were fused in frame to an N-terminal leader sequence and a C-terminal human IgG1 Fc coding fragment serving as solubility- and purification tag. An avi-tag at the C-terminal end of the Fc fragment allowed in vivo biotinylation. In order to express the antigen in a monomeric form, these Fc chains contained the "knob" mutations (SEQ ID NOs: 5 and 6, Her2 ECD-Fc(knob); SEQ ID NOs: 7 and 8, Her2 ECD (Pertuzumab KO)-Fc(knob); SEQ ID NOs: 9 and 10, Her2 ECD (Trastuzumab KO)-Fc(knob)) and was co-expressed in combination with an "Fc-hole" counterpart (SEQ ID NOs: 3 and 4).

Affinity-Determination of the Herceptarg Bi-Specific Antibodies by SPR

The Affinity ($K_D$) of the new bi-specific antibodies to each of their epitopes in her2 was measured by SPR using a PROTEON™ XPR36 instrument (Biorad) at 25° C. In a first step, 11000 RU of a polyclonal goat anti-human IgG (Sigma I2136) recognizing human IgG (Fc-specific) was immobilized on all 6 channels of a GLM chip by Amine coupling (NaAcetate pH4, 30 µl/min, 300s) (vertical orientation).

Each antibody was diluted with PBST (10 mM phosphate, 150 mM sodium chloride pH 7.4, 0.005% TWEEN™ (polysorbate) 20) to 2 µg/ml, and then injected for 60s at 30 µl/minute to achieve immobilization levels of about 400 response units (RU) in vertical orientation. Injection of Her2: For one-shot kinetics measurements, injection direction was changed to horizontal orientation, two-fold dilution series of purified monovalent Her2-Fc protein constructs (varying concentration ranges between 100 and 6.25 nM) were injected simultaneously at 100 µl/min along separate channels 1-5, with association times of 180s, and dissociation times of 600s. Buffer (PBST) was injected along the sixth channel to provide an "in-line" blank for referencing. Regeneration was performed by two pulses of 10 mM glycine pH 1.5 and 50 mM NaOH for 30s at 100 µl/min (horizontal orientation). Association rate constants ($k_{on}$) and dissociation rate constants ($k_{off}$) were calculated using a simple one-to-one Langmuir binding model in PROTEON™ Manager v3.1 software by simultaneously fitting the association and dissociation sensorgrams. The equilibrium dissociation constant ($K_D$) was calculated as the ratio $k_{off}/k_{on}$.

All antibodies including Trastuzumab, Pertuzumab as well as three bi-specific Herceptarg constructs comprising the affinity-matured Pertuzumab HCs, the Trastuzumab HC, and the CLC "Pertuzumab (Trast.L3) (QM)" were tested for binding to both Her2 knock-out variants. As expected, both Trastuzumab and Pertuzumab bind to their respective Her2 epitope with the excepted affinity. Binding to their corresponding knock-out variant was abolished (FIGS. 24A-D). These results demonstrate that the use of Her2 knock-out epitope variants allows dissecting the binding of the bispecific antibodies and analyzing the individual affinity of both specificities. Determination of the individual $K_D$ values of each Herceptarg clone variant revealed a constant binding affinity to the Trastuzumab epitope in the expected range of 0.6 to 1.8 nM. In contrast, binding to the Pertuzumab epitope depends on the affinity-matured Pertuzumab HC. Among the three Herceptarg clone variants, clone "D1-der" was found to have the highest affinity (0.16 nM). A summary of the Thermodynamic data is shown in table 25. In summary, this experiment confirms that we were able to generate a bi-specific antibody with a CLC and specific for the epitopes Trastuzumab and Pertuzumab.

Binding Analysis of the Herceptarg Clone Variants to KPL-4 Cells

Figure 25:
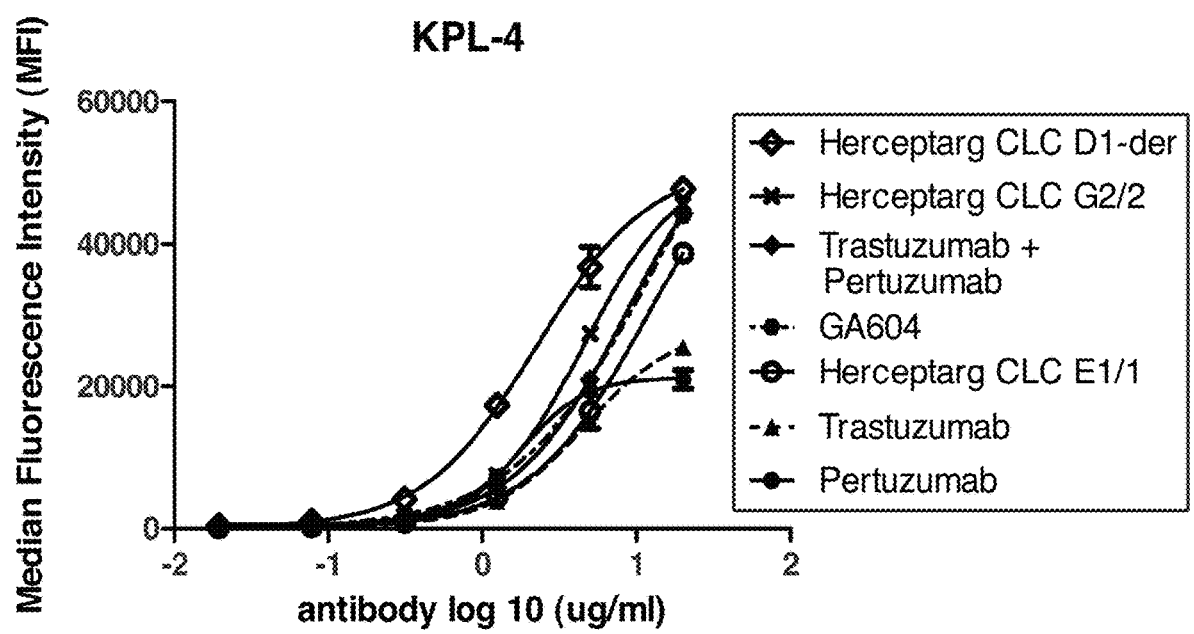
FIG. 25: Binding of bi-specific HER2 antibodies with a common light chain clone variants to KPL-4 cells. KPL-4 cells were stained with increasing concentrations of the indicated antibodies. The antibodies were detected with a FITC labeled anti-human secondary and the fluorescence was determined by flow cytometry. "Herceptarg CLC D1-der": SEQ ID NOs 64, 54, 92, "Herceptarg CLC G2/2": SEQ ID NOs 70, 54, 92, "Herceptarg CLC E1/1": SEQ ID NOs 68, 54, 92; "GA 604": SEQ ID NOs 109, 110, 111, 112.
Figure 26A:
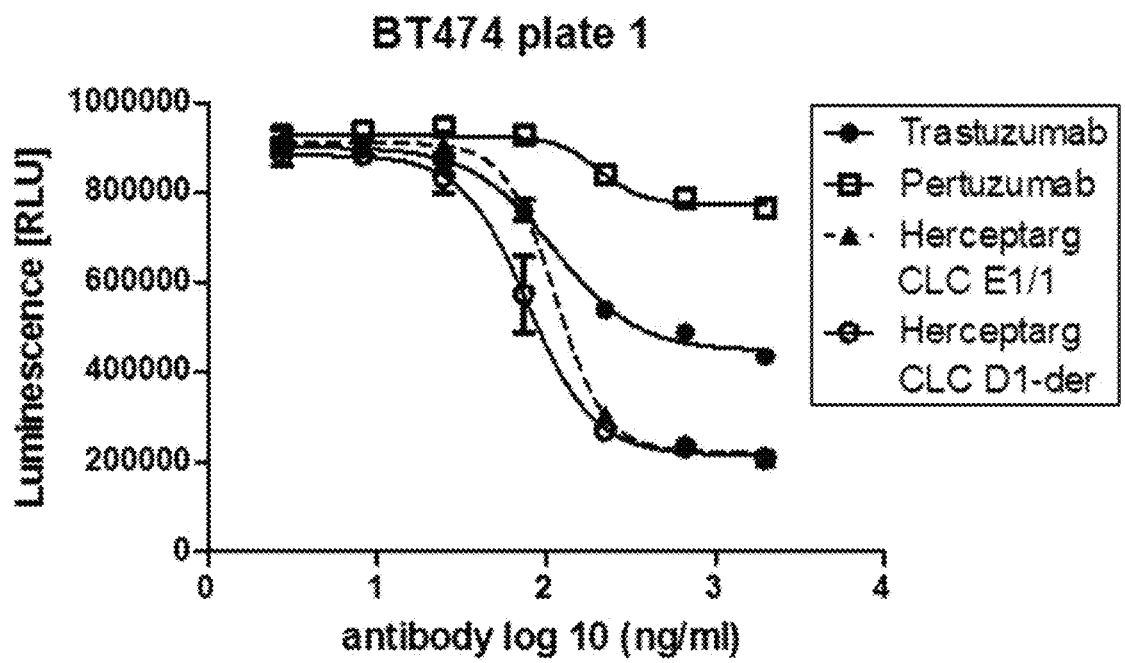
FIGS. 26A-26F: Proliferation inhibition of BT474, N87, and SkBr3 cells with bi-specific HER2 antibodies with common light chain done variants. BT474 (FIG. 26A)(FIG. 26B), N87 (FIG. 26C)(FIG. 26D), and SkBr3 (FIG. 26E) (FIG. 26F) cells were treated with the three different Herceptarg variants. As controls Trastuzumab, Pertuzumab and the combination of both were included. After 5 days, proliferation inhibition was determined with CELLTITER-GLO®. "Herceptarg CLC D1-der": SEQ ID NOs 64, 54, 92, "Herceptarg CLC G2/2": SEQ ID NOs 70, 54, 92, "Herceptarg CLC E1/1": SEQ ID NOs 68, 54, 92; "GA 604": SEQ ID NOs 109, 110, 111, 112.
Figure 26B:
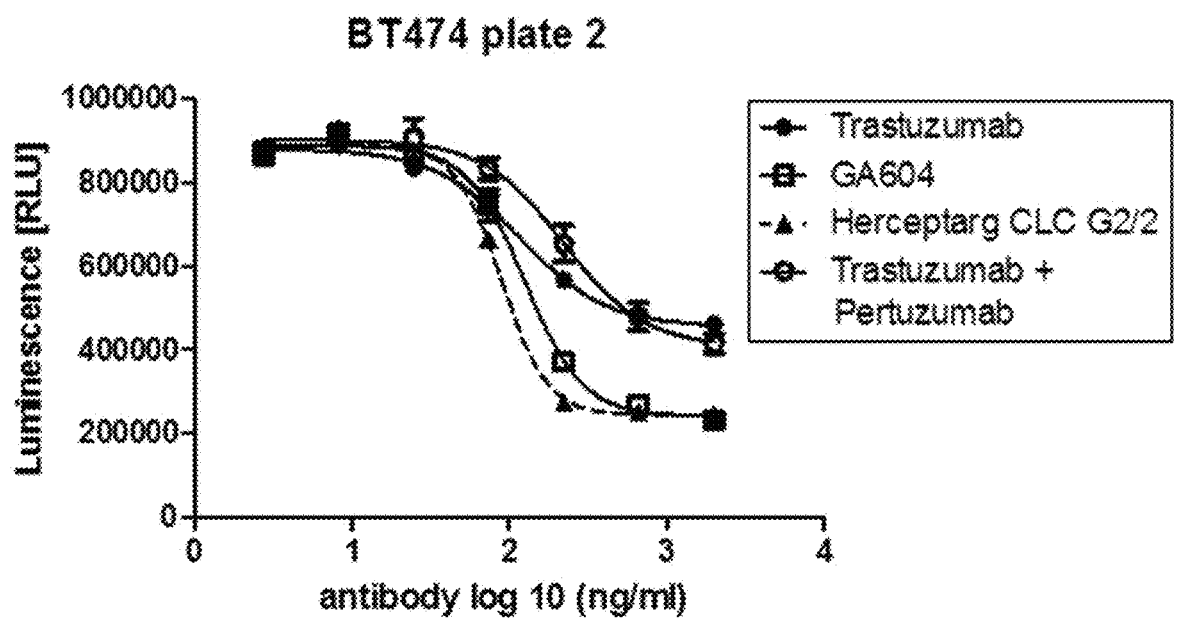
Figure 26C:
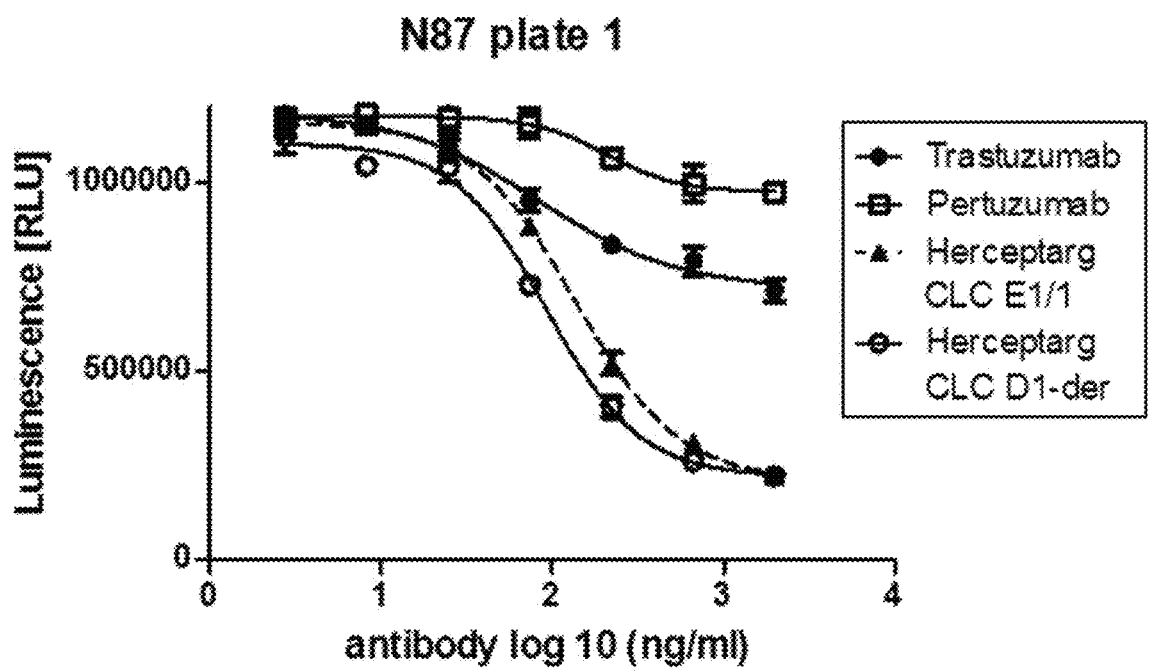
Figure 26D:
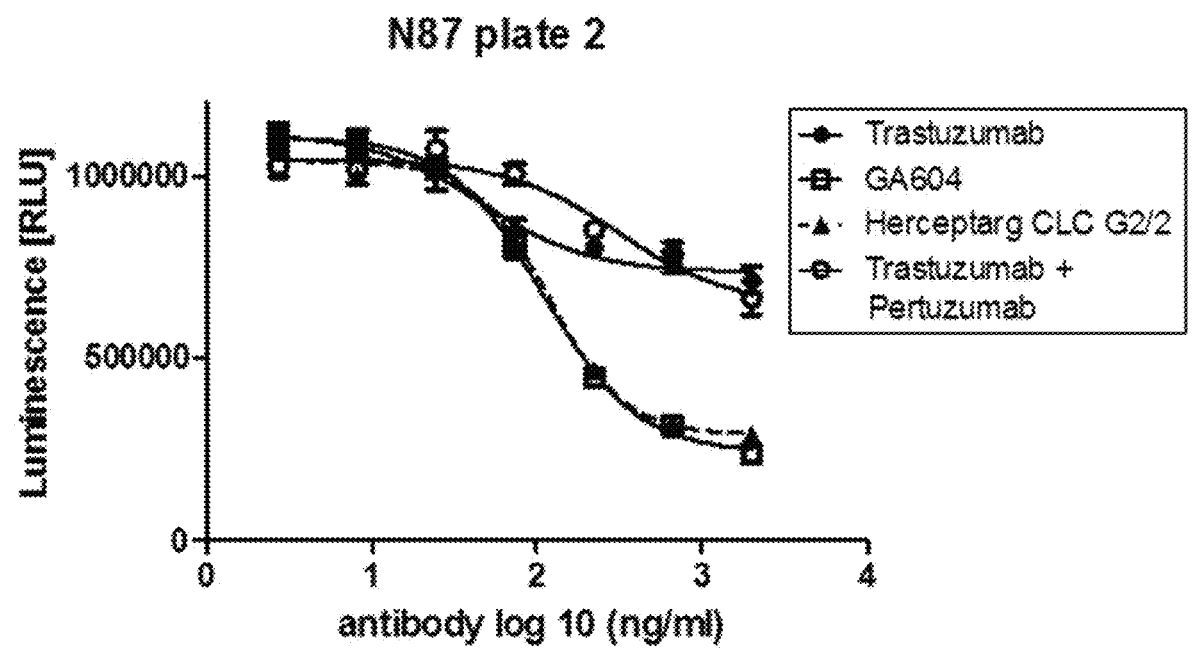
Figure 26E:
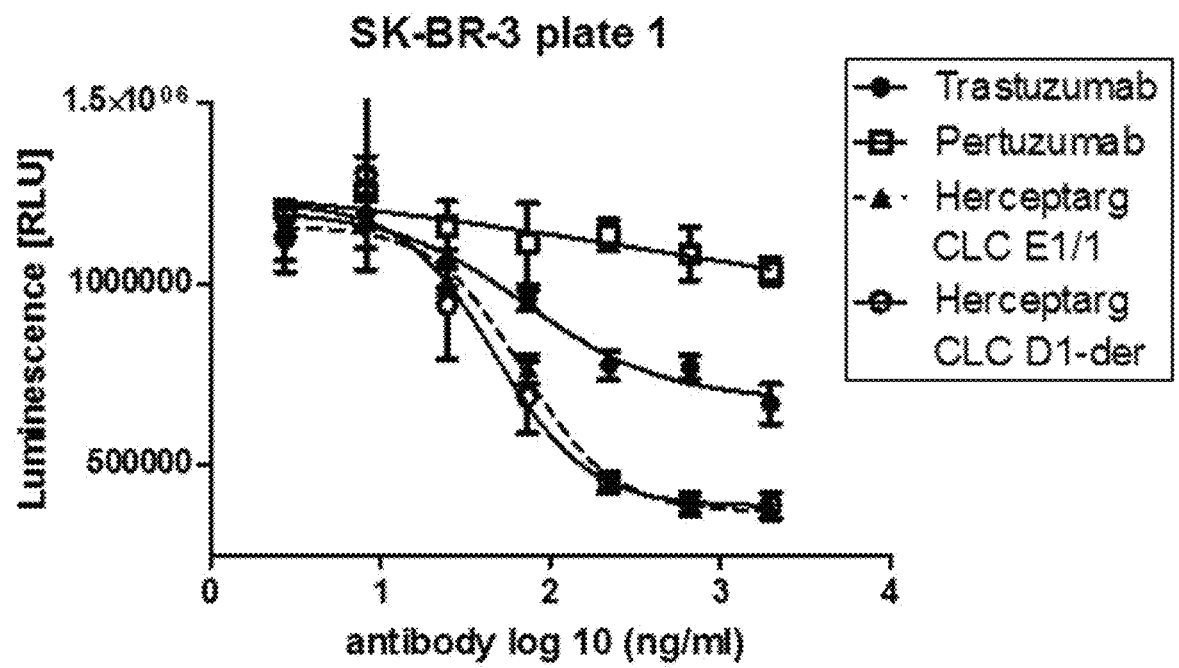
Figure 26F:
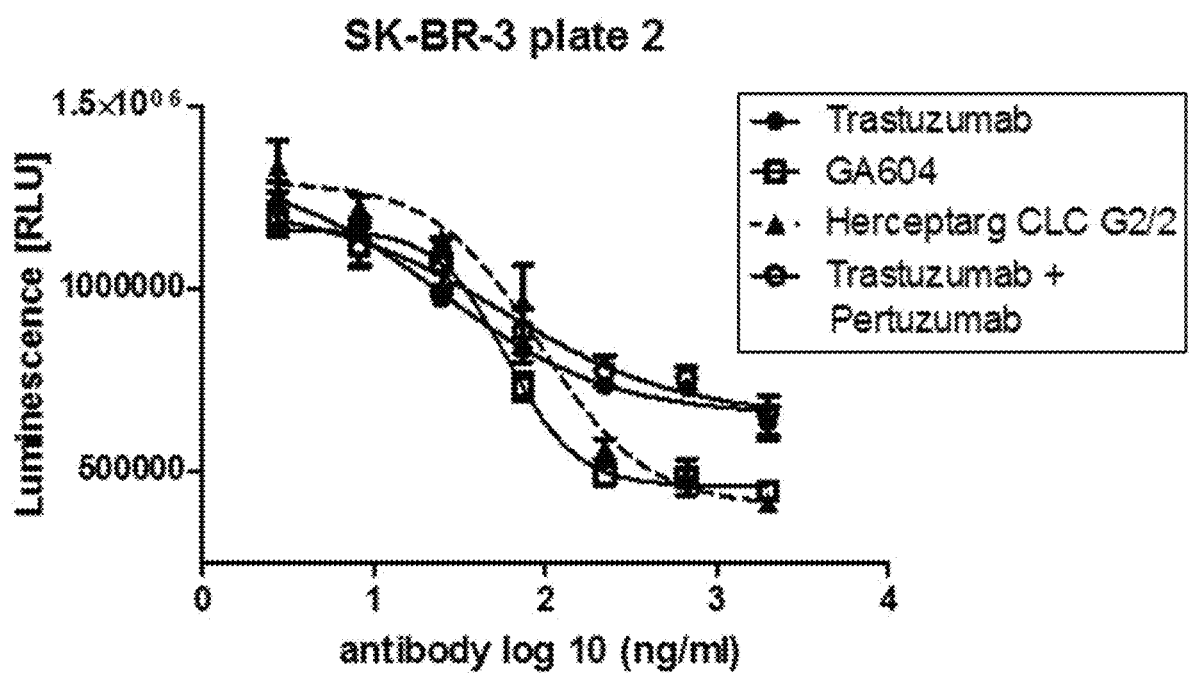
Figure 27A:
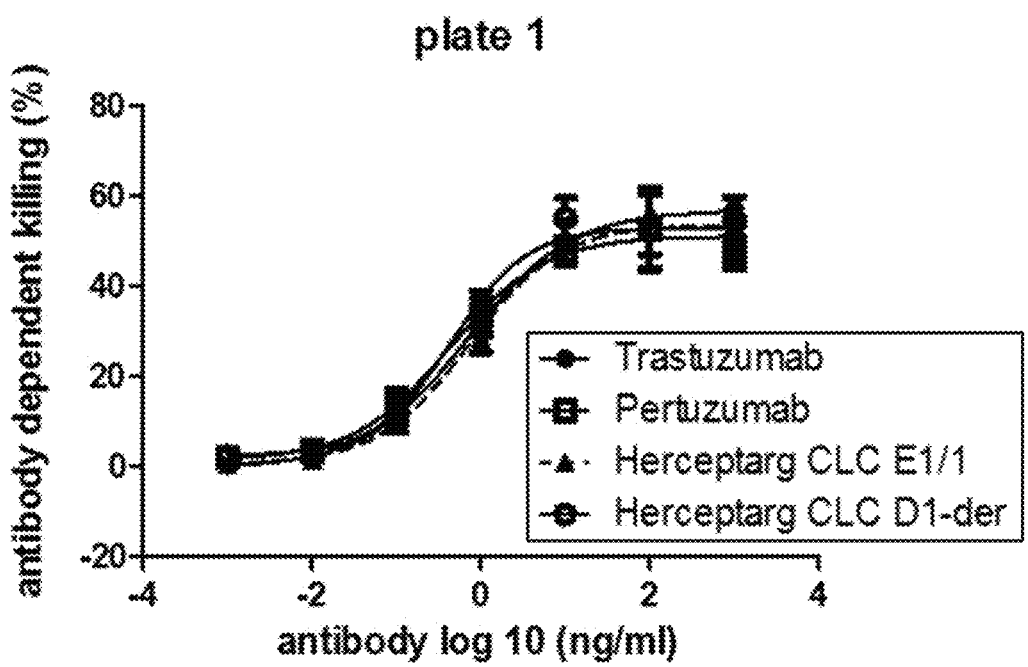
FIGS. 27A-27D: Killing of KPL-4 cells and MDA-MB 231 with bi-specific HER2 antibodies with common light chain variants.
Figure 27B:
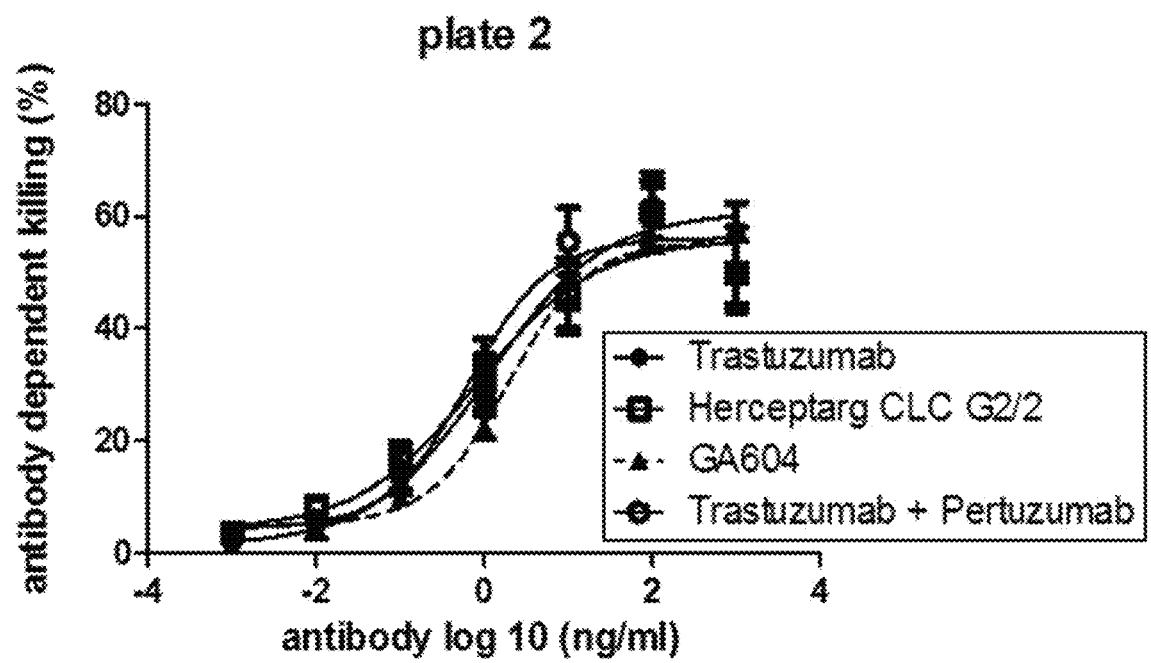
Figure 27C:
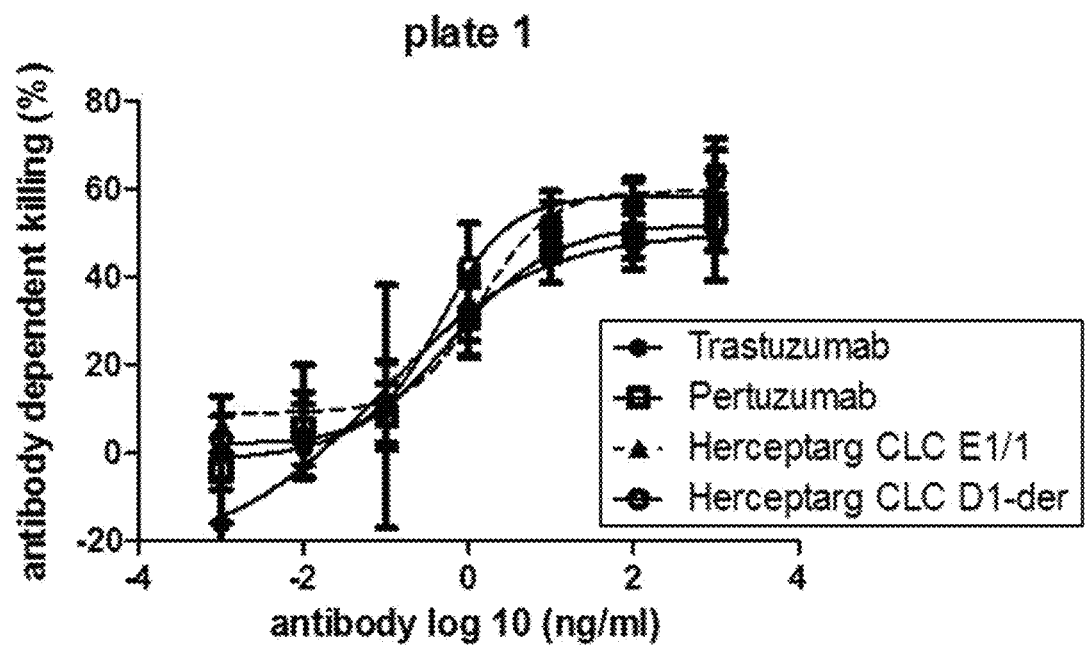
Figure 27D:
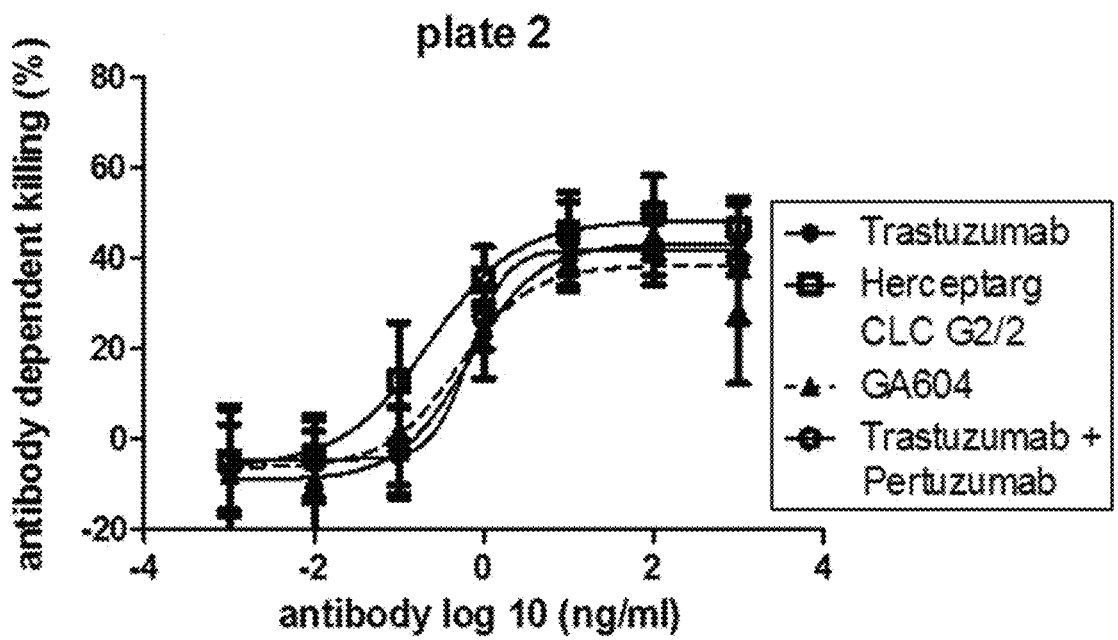

KPL-4 cells were harvested and resuspended in FACS buffer. 0.2 Mio cells were seeded into a 96 well round bottom plate. The plate was centrifuged at 400 g for 3 min to pellet the cells. The supernatant was removed and the cells were resuspended in 40 µl of the diluted antibodies. The plate was incubated for 30 min at 4° C. to allow binding of the antibodies. To remove unbound antibodies the cells were centrifuged again and washed twice with FACS buffer. To detect the antibodies the cells were resuspended in 12 µl diluted secondary goat anti-human Fc specific FITC-labeled secondary antibody (Jackson ImmunoResearch #109-096-098) and incubated again for 30 min at 4° C. Afterwards the cells were washed twice with FACS buffer, resuspended in 200 µl FACS buffer and the fluorescence was measured with BD CantoII. Results are shown in FIG. 25.

TABLE 25

Affinity of selected bi-specific antibodies affinity matured Pertuzumab clone variants in combination with the CLC

| clone | KD (nM) Trastuzumab Epitope | KD (nM) Pertuzumab Epitope |
|---|---|---|
| Trastuzumab | 2.17 | N/A |
| Pertuzumab | N/A | 0.62 |
| Herceptarg E1 | 0.72 | 1.32 |
| Herceptarg G2 | 1.82 | 9.65 |
| Herceptarg D1-derived | 0.6 | 0.16 |
| Herceptarg crossmab | 0.8 | 0.84 |

TABLE 26

Proliferation inhibition of various cell types (IC50 values with confidence interval)

| cell line | Trastuzumab | Pertuzumab | Trastuzumab + Pertuzumab | Herceptarg CLC E1/1 | Herceptarg CLC D1-der | Herceptarg CLC G2/2 | GA604 |
|---|---|---|---|---|---|---|---|
| BT474 | 110.8 (96.7-127.0) | 205.4 (156-270.7) | 222.3 (176.5-280.1) | 114.1 (106-122.7) | 78.38 (69.03- 89) | 89.99 (82.3-98.4) | 125.4 (113.6-138.4) |
| N87 | 83.13 (59.7-115.7) | 205.8 (126.3-335) | 312.9 (156.5-625.6) | 136.5 (126.6-147) | 92.7 (80.7-106.5) | 119.1 (107.6-132) | 109.6 (98.3-122.2) |
| SkBr3 | 73.73 (43.54-124.8) | nd | 55.63 (25.97-119.2) | 69.01 (55.78-85.4) | 47.54 (26.61-84.9) | 92.59 (70.1-122.3) | 59.84 (50.2-71.4) |

Proliferation Inhibition Mediated by the Herceptarg Binding Variants

Target cells were harvested, washed, resuspended in RPMI 1640 (Gibco)+10% FCS+1% GlutaMAX™ (Gibco) and plated at a concentration of $5 \times 10^{i3}$ cells/well. Cells were incubated for 4 hours in the cell incubator before respective antibody dilutions were added. Plates were gently shaked and incubated for 5 days in the cell incubator. The plates were equilibrated to room temperature and 100 µl/well of the freshly prepared CELLTITER-GLO® (Promega) substrate were added to each well. Luminescence was measured in a Wallac VICTOR3™ 1420 Multilabel Counter. Results are shown in Table 26 and FIGS. 26A-F.

Herceptarg Clones-Mediated Antibody-Dependent Cell-Mediated Cytotoxicity (ADCC)

Target cells were harvested, washed, resuspended in AIM V® medium (Life Technologies), and plated at a concentration of $3 \times 10^4$ cells/well. The respective antibody dilutions were added in triplicates to the cells and incubated for 10 min before addition of the effector cells (peripheral blood mononuclear effector cells [PBMCs]). Effector (E) and target (T) cells were then incubated for the indicated time at 37° C. at the indicated E:T ratio (triplicates for all samples). Lactate dehydrogenase (LDH) release was measured using the LDH Cytotoxicity Detection Kit (Roche Applied Science). ADCC was calculated using the following formula:

$$\text{Percentage } ADCC = \left(\left[\frac{\text{sample release} - \text{spontaneous release}}{\text{maximal release} - \text{spontaneous release}}\right]\right) \times 100.$$

Spontaneous release, corresponding to target cells incubated with effector cells without antibody, was defined as 0% cytotoxicity, and maximal release (target cells lysed with 1% TRITON™ (t-octylphenoxypolyethoxyethanol) X-100) was defined as 100% cytotoxicity. The average percentage of ADCC and standard deviations of the triplicates of each experiment were calculated. Results are shown in FIGS. 27A-D.

TABLE 27

Leader Peptides

| SEQ ID | Protein sequence |
|---|---|
| 155 | MDWTWRILFLVAAATGAHS |
| 156 | MDMRVPAQLLGLLLLWFPGARC |
| 157 | MGWSCIILFLVATATGVHS |

Example 15: Proliferation Assay $1\times10^4$ BT-474 cells/well were cultured in RPMI/10% FCS in a 96-well flat bottom plate. After 24 hrs growth medium was removed and titrated amounts of indicated antibodies were added (premixed in culture medium) to a final volume of 100 µl. To determine the number of viable cells in culture, the CELLTITER-GLO® Luminescent Cell Viability Assay was performed by quantifying the present ATP levels as an indicator of metabolically active cells. Thus, after six days of culture, 100 µl CELLTITER-GLO® Reaction Mix (Promega, cat. no. #G7571) was added to the cells, shook for 2 min before 75 µl of the lysate was transferred to a separate 96-well flat bottom titer plate (Costar, cat. no. #3917). After additional mixing, luminescence was assed according to the manufacturer's instructions using a Tecan Infinite Reader.

Figure 28:
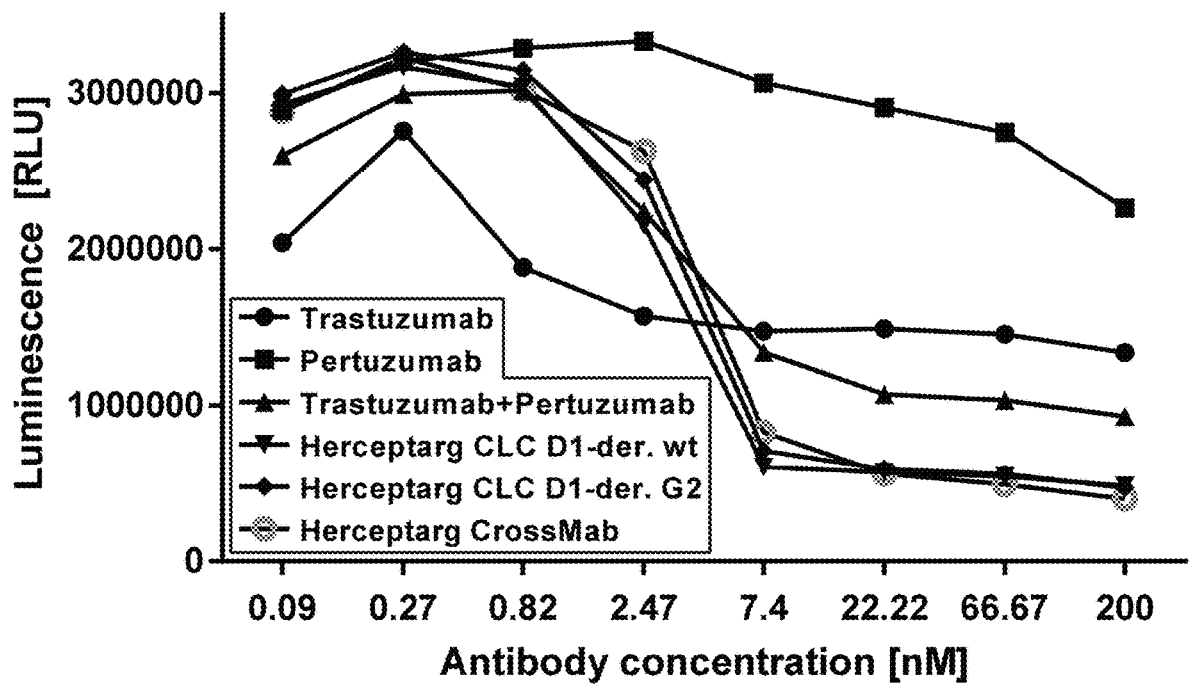
FIG. 28: Proliferation inhibition of BT474 cells with bi-specific HER2 antibodies with common light chain clone variants. BT474 cells were treated with the different Herceptarg variants. As controls Trastuzumab, Pertuzumab and the combination of both were included. After 6 days, proliferation inhibition was determined with CELLTITER-GLO®"Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Results are shown in Table 28 and FIG. 28.

In the proliferation assay it was shown that the bispecific Her2 antibodies inhibited proliferation of BT-474 cells more potently than Pertuzumab or Trastuzumab alone or in combination. The following bispecific Her2 antibodies were tested: Herceptarg CLC D1-der wt": SEQ ID NOs 64, 54, 92, Herceptarg CLC Di-der G2": SEQ ID NOs 64, 54, 92 (glycoengineered variant) "Herceptarg CrossMab": SEQ ID NOs 109, 110, 111, 112.

TABLE 28

IC50 BT474 proliferation assay

| Antibody treatment | IC50 Proliferation [nM] |
|---|---|
| Trastuzumab | n.d. |
| Pertuzumab | n.d. |
| Trastuzumab+ Pertuzumab | 6.20 |
| Herceptarg CLC D1-der. wt | 3.31 |
| Herceptarg CLC D1-der. G2 | 3.93 |
| Herceptarg CrossMab | 4.75 |

Example 16: C1q FACS Binding Assay $3\times10^5$ BT-474 cells were incubated with 10 µg/ml of indicated antibody on ice. The following bispecific Her2 antibodies were tested: Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

After 30 min, 10 µg/ml C1q (Sigma, C1740) was added and additionally incubated for 20 min. After washing, cells were counterstained with commercial PE-labeled anti-C1q antibody (Cedarlane, CL7611PE-SP). After further incubation (30 min, ice), cells were washed twice and analyzed on a FACS Canto II.

Figure 29:
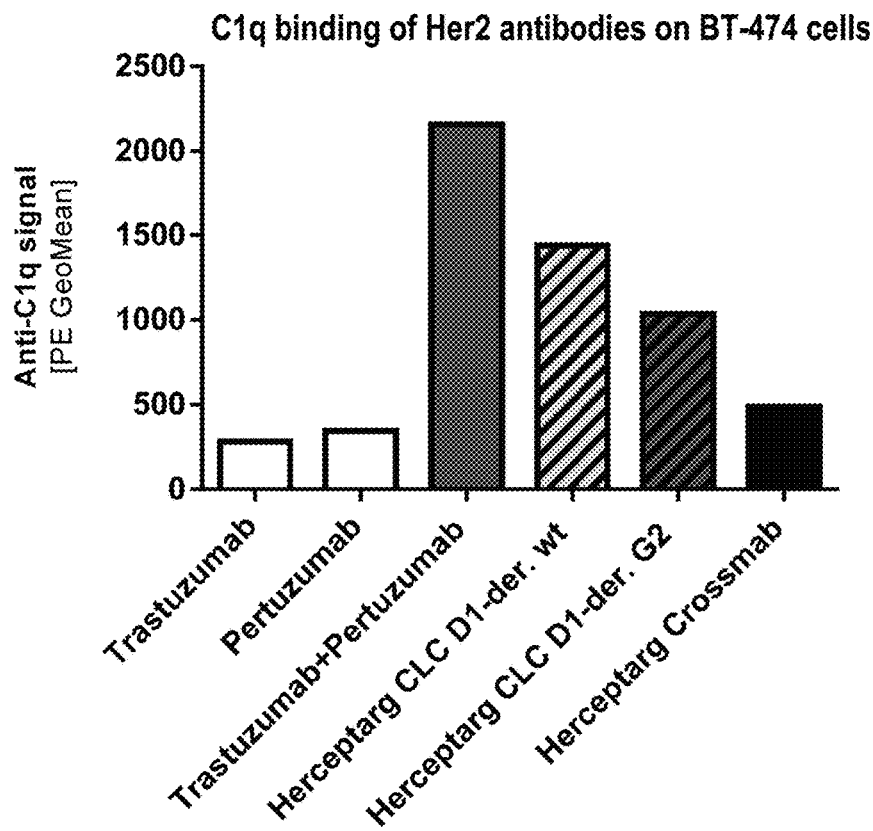
FIG. 29: C1q binding of Her2 antibodies on BT-474 cells. BT474 cells were incubated with the three Herceptarg variants. As controls Trastuzumab, Pertuzumab and the combination of both were included. "Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Results are shown in FIG. 29 and Table 29. This C1q assay illustrates the binding of recombinant complement factor C1q to different Her antibodies on BT-474 cells. It was shown that the highest C1q binding resulted upon treatment with the combination of Trastuzumab and Pertuzumab, followed by the two CLC bispecific Her2 antibodies. Treatment with the Crossmab resulted only in a slightly elevated C1q binding.

TABLE 29

C1q binding assay

| antibody/antibodies | PE-signal (geomean) |
|---|---|
| trastuzumab | 282 |
| pertuzumab | 344 |
| combination of trastuzumab and pertuzumab | 2157 |
| bispecific anti-HER2 antibody, common light chain | 1439 |
| bispecific anti-HER2 antibody, common light chain, glycoengineered | 1036 |
| bispecific anti-HER2 antibody, CrossMab format | 489 |

Example 17: LDH Assay with Baby Rabbit Complement (BRC)

CHO-K1 Nxre19 cells (IL15R transfected CHO-K1) were seeded at 10,000 cells/well on 96-well flat bottom cell culture plates (NUNC, 100 µL/well) and cultivated overnight. IL15-Fc fusion polypeptide was added (25 µL/well in 5-fold end-concentration) and incubated for one hour. Thereafter, one vial of Baby Rabbit complement (Cedarlane, Cat. No. CL3441) was reconstituted with 1 mL of Aqua bidest. The complement solution was diluted with medium and 25 µL added to the wells. After four hours the plates were centrifuged at 200 g and 100 µL/well were transferred to another 96-well flat bottom plate. Thereafter 100 µL of LDH reaction mix (Cytotoxicity Detection Kit, Roche Diagnostic GmbH, Mannheim, Germany) was added. After an incubation time of 20 min. at 37° C. optical density (OD) was measured at 492/690 nm on a Tecan SUNRISE™ reader.

TABLE 30

LDH assay with BRC

| | signal [OD] | |
|---|---|---|
| sample | BRC 1/40 | BRC 1/30 |
| 9000 ng/ml IL15-Fc-fusion with HUC | 11.3 | 12.3 |
| 3000 ng/ml IL15-Fc-fusion with HUC | 12.3 | 17.0 |
| 1000 ng/ml IL15-Fc-fusion with HUC | 10.2 | 13.6 |
| 333.3 ng/ml IL15-Fc-fusion with HUC | 7.8 | 12.2 |
| 111.1 ng/ml IL15-Fc-fusion with HUC | 8.3 | 13.0 |
| 37.04 ng/ml IL15-Fc-fusion with HUC | 14.9 | 19.7 |
| 12.35 ng/ml IL15-Fc-fusion with HUC | 43.2 | 53.0 |

TABLE 30-continued

LDH assay with BRC

| sample | signal [OD] | |
| --- | --- | --- |
| | BRC 1/40 | BRC 1/30 |
| 4.12 ng/ml IL15-Fc-fusion with HUC | 41.5 | 63.8 |
| 0 ng/ml IL 15-Fc-fusion with HUC | 42.4 | 48.4 |

It can be seen that BRC has a low background toxicity and shows dose dependent complement toxicity.

Example 18: CDC (Complement Dependent Cytotoxicity) Activation on BT-474 Cells (LDH Release)

$1 \times 10^4$ cells/well were incubated with 10 µg/ml of the indicated antibodies for 30 min at 37° C. in 150 µl. The following bispecific Her2 antibodies were tested: Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Then 50 µl Baby Rabbit Complement (Cedarlane, cat. no. CL3441, batch no. 6312) was added and incubated for further 2 hrs. Then, the s/n was transferred and mixed with 50 µl LDH Reaction Mix (Roche) and, after a further incubation of 15 min, extinktion (Ex.) at 490/620 nm was analyzed on a Tecan SUNRISE™ Reader. The specific antibody dependent toxicity (mean+/−SD of n=4) on BT-474 cell was calculated as follows: (Ex. sample−Ex. spontaneous lysis/Ex. maximal lysis−spontaneous lysis)×100.

Figure 30:
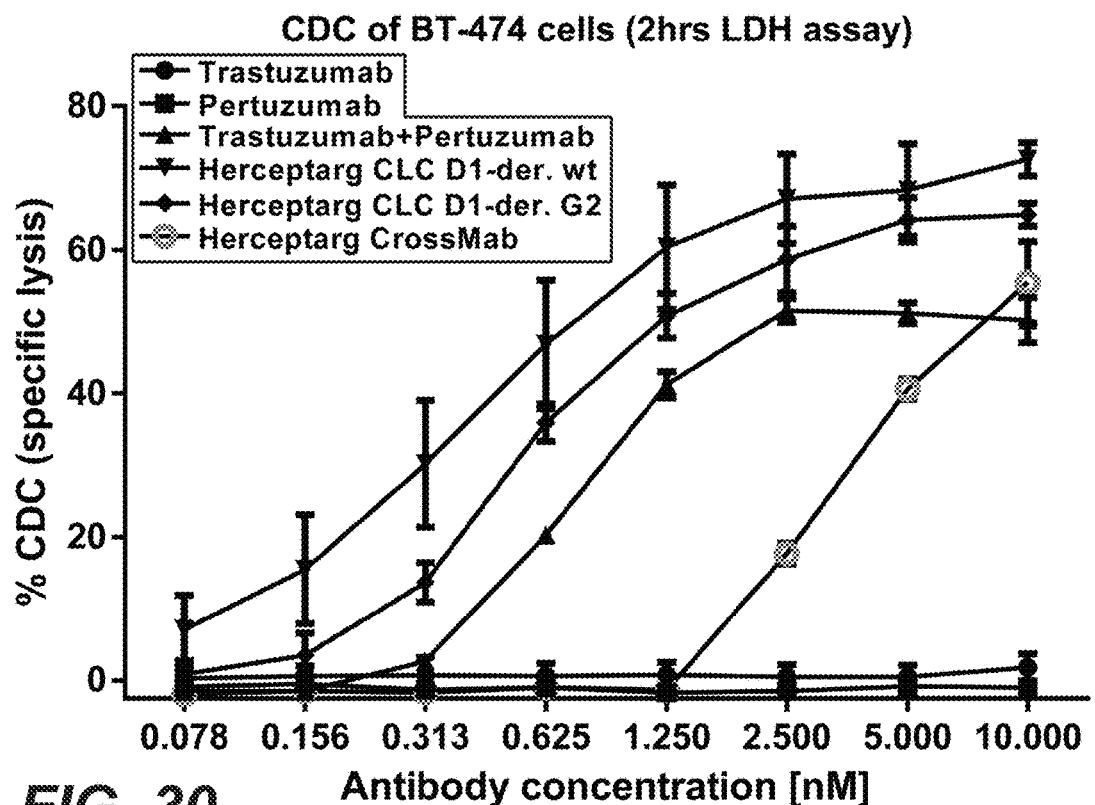
FIG. 30: CDC activation on BT-474 cells (LDH release). BT474 cells were incubated with the three Herceptarg variants. As controls Trastuzumab, Pertuzumab and the combination of both were included. "Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109,110,111, 112.

Results are shown in FIG. 30.

This CDC assay shows the release of LDH as a marker for dying/dead cells upon treatment of different anti-Her2 antibodies (formats, combination) in the presence of baby rabbit complement. Here, the combination of Trastuzumab and Pertuzumab resulted in a significant induction of CDC, whereas the parental antibodies alone did not. Surprisingly, both CLC Herceptarg variants provoked even superior CDC effects, whereas the Herceptarg Crossmab treatment results in a CDC reaction less effective than the combination of the parental antibodies.

Example 19: CDC (Complement Dependent Cytotoxicity)—Mediated Killing of BT-474 Cells (ACEA)

$1 \times 10^4$ BT-474 cells/well were seeded on 96-well E-Plates (ACEA Biosciences Inc.) and grown overnight in an Xcelligence device. Growth medium was removed and cells were washed once with serum-free AIM-V™ medium (Gibco). 50 µl/well AIM-V™ medium and 50 µl antibody in AIM-V™ (3-fold end concentration) were added and incubated for 20 min. 50 µl Baby Rabbit Complement (Cedarlane) was added and CellIndex (CI; as representative for the viability of the cells) was measured every 5 minutes (see curve). The following bispecific Her2 antibodies were tested: Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.

Specific CDC was calculated according following formula, whereas CI is the normalized cell index:

$$\% \ CDC = \frac{CI \ \text{Complement control} - CI \ \text{sample}}{CI \ \text{Component control}} \times 100$$

At two representative time points (1 hr and 2 hrs after starting the reaction, specific lysis (=CDC-induced cell death) was calculated and shown in the diagram (mean+/SEM of n=4).

Figure 31A:
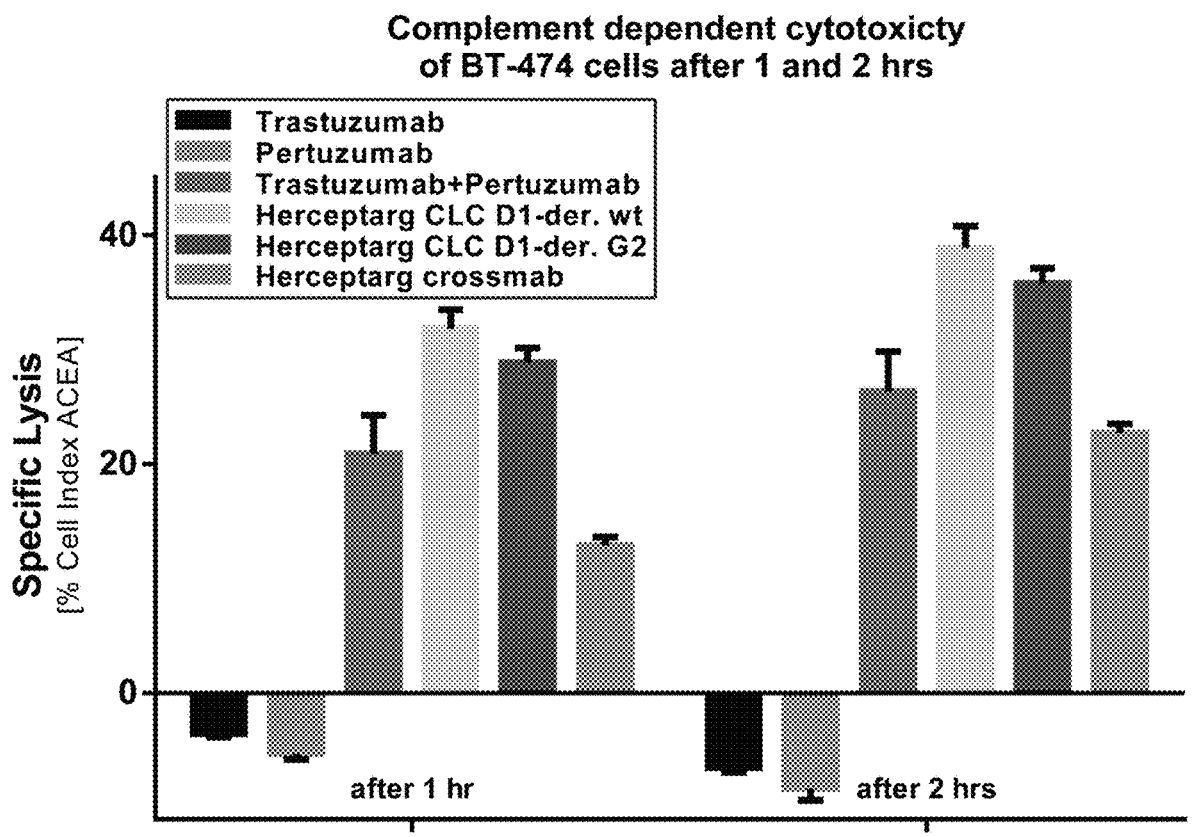
FIGS. 31A-31B: CDC mediated killing of BT-474 cells (ACEA). BT474 cells were incubated with the three Herceptarg variants. As controls Trastuzumab, Pertuzumab and the combination of both were included. "Herceptarg CLC D1-der wt": SEQ ID NOs 64, 54, 92, Herceptarg CLC D1-der G2": SEQ ID NOs 64, 54, 92 (glycoengineered variant) "Herceptarg CrossMab": SEQ ID NOs 109, 110, 111, 112.
Figure 31B:
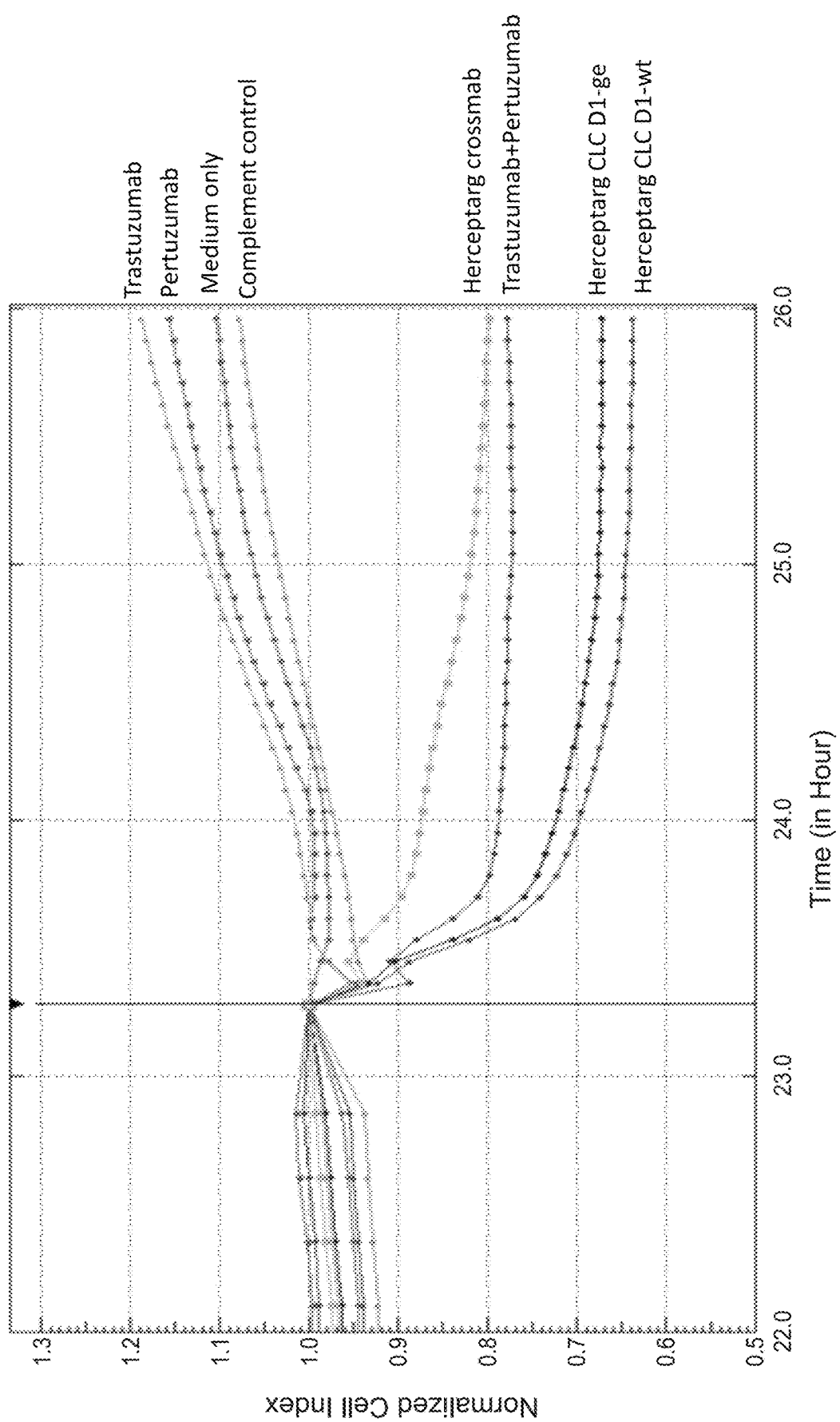

Results are shown in FIGS. 31A-B and Table 31. This CDC assay illustrates a change in the cell index as a marker for dying/dead cells upon treatment with different anti-Her2 antibodies (formats, combination) in the presence of baby rabbit complement: Here, the combination of Trastuzumab and Pertuzumab resulted in a significant induction of CDC, whereas the parental antibodies alone did not. Surprisingly, both CLC Herceptarg variants provoked even superior CDC effects, whereas the Herceptarg Crossmab treatment results in a CDC reaction less effective than the combination of the parental antibodies.

One possible reason for the superiority of Herceptarg CLC D1-der may be the slightly higher affinity to the Trastuzumab epitope as well as the significantly higher affinity to the Pertuzumab epitope (see also Table 25).

TABLE 31

CDC (complement dependent cytotoxicity)-
mediated killing of BT-474 cells (ACEA)

| antibody/antibodies | specific lysis [% cell index ACEA] | |
| --- | --- | --- |
| | 1 hour | 2 hours |
| trastuzumab | −3.5 ± 0.6 | −6.5 ± 0.8 |
| pertuzumab | −5.3 ± 1.0 | −8.3 ± 2.1 |
| combination of trastuzumab and pertuzumab | 20.9 ± 6.7 | 26.3 ± 7.0 |
| bispecific anti-HER2 antibody, common light chain (D1 der) | 31.8 ± 3.4 | 38.9 ± 3.7 |
| bispecific anti-HER2 antibody, common light chain, glycoengineered (D1 der) | 28.8 ± 2.6 | 35.8 ± 2.6 |
| bispecific anti-HER2 antibody, CrossMab format | 12.9 ± 1.4 | 22.7 ± 1.6 |

Example 20: Mouse Xenograft Studies

Cell Line KPL4

This human breast cancer cell line has been established from the malignant pleural effusion of a breast cancer patient with an inflammatory skin metastasis. Cells have been provided by Professor J. Kurebayashi (Kawasaki Medical School, Kurashiki, Japan). Tumor cells were routinely cultured in DMEM medium (PAN Biotech, Germany) supplemented with 10% fetal bovine serum (PAN Biotech, Germany) and 2 mM L-glutamine (PAN Biotech, Germany) at 37° C. in a water-saturated atmosphere at 5% CO2. Culture passage was performed with trypsin/EDTA 1× (PAN) splitting twice/week. Cell passage P6 was used for in vivo study.

Mice

Female SCID beige (C.B.-17) mice; age 10-12 weeks; body weight 18-20 g (Charles River Germany, Sulzfeld); body weight >20 g are maintained under specific-pathogen-free condition with daily cycles of 12 h light/12 h darkness according to international guidelines (GV-Solas; Felasa; TierschG). After arrival animals were housed in the quarantine part of the animal facility for one week to get accustomed to new environment and for observation. Continuous health monitoring was carried out on regular basis. Diet food (Alltromin) and water were provided ad libitum. The experimental study was reviewed and approved by local government.

Tumor Cell Injection

At the day of injection tumor cells were harvested (trypsin-EDTA) from culture flasks (Greiner TriFlask) and transferred into 50 ml culture medium, washed once and resuspended in PBS. After an additional washing step with PBS and filtration (cell strainer; Falcon Ø 100 μm) the final cell titer was adjusted to 1.5×10e8/ml. Tumor cell suspension was carefully mixed with transfer pipette to avoid cell aggregation. Anesthesia was performed using a Stephens inhalation unit for small animals with preincubation chamber (PLEXIGLAS®), individual mouse nose-mask (silicon) and not flammable or explosive anesthesia compound Isoflurane (Pharmacia-Upjohn, Germany) in a closed circulation system. Two days before injection, coat of the SCID beige mice were shaved and KPL-4 cells (3×10e6 cells) were injected orthotopically in a volume of 20 μl (using a Hamilton microliter syringe and a 30G×1/2" needle) into the right penultimate inguinal mammary fat pad of each anesthetized mouse. The cell suspension was injected through the skin under the nipple.

Monitoring

Animals were controlled daily for detection of clinical symptoms of adverse effects. For monitoring throughout the experiment the body weight of the animals was documented two times weekly and the tumor volume was measured by caliper twice weekly. Tumor volume was calculated according to NCI protocol (Tumor weight=1/2ab2, where "a" and "b" are the long and the short diameters of the tumor, respectively). Termination criteria were the critical tumor mass (up to 1.7 g or Ø>1.5 cm), body weight loss more than 20% from baseline, tumor ulceration or poor general condition of the animals. Study exclusion criteria for the animals are described and approved in the corresponding "Tierversuchsanzeige".

Treatment

Mice were randomized for tumor volume of 80 mm$^3$ and subsequently treated once weekly with a volume of 10 ml/kg intra peritoneal. For combination treatment HERCEPTIN® (Trastuzumab) was given first and PERJETA® (pertuzumab) was given 24 hrs thereafter.

Figure 32:
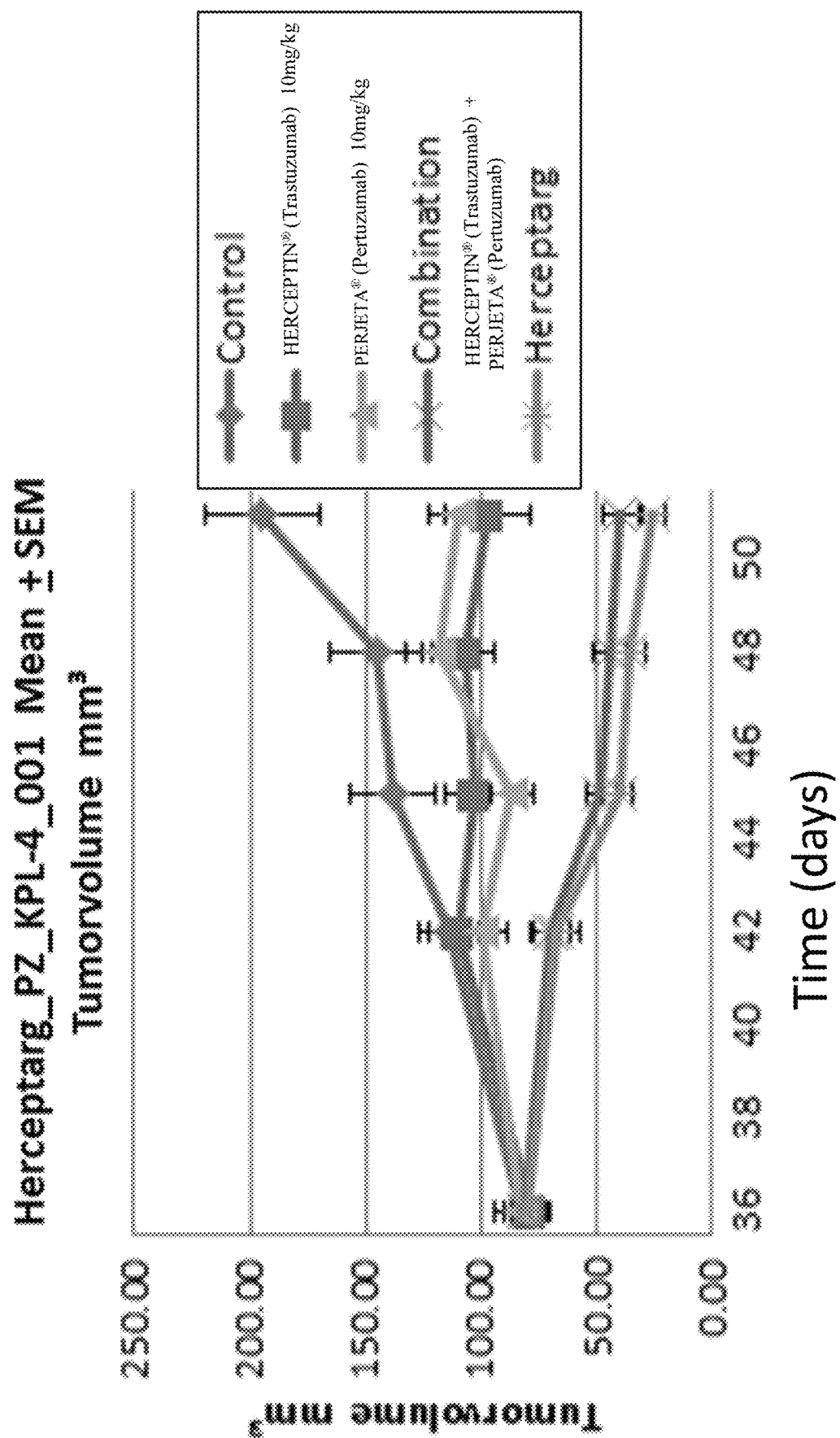
FIG. 32: In vivo activity of bispecific antibodies. Tumor volume in mouse xenograft models after treatment with different Her2 bispecific molecules (10 mg/kg) was compared to treatment with Trastuzumab, Pertuzumab and the combination of both. "Herceptarg": SEQ ID NOs 64, 54, 92. "Control": Xolair, a non Her2 binding antibody.

The following bispecific Her2 antibodies was tested: Herceptarg CLC-D1-der: SEQ ID Nos 64, 54, 92. Results are shown in FIG. 32.

| Group | No of animals | Compound | Dose (mg/kg) | Route/Mode of administration |
|---|---|---|---|---|
| 1 | 9 | Control (Xolair) | 10 | i.p. once weekly |
| 2 | 9 | HERCEPTIN® (Trastuzumab) | 10 | i.p. once weekly |
| 3 | 9 | PERJETA® (pertuzumab) | 10 | i.p. once weekly |
| 4 | 9 | HERCEPTIN® (Trastuzumab) plus PERJETA® (pertuzumab) | 10 plus 10 | i.p. once weekly |
| 5 | 8 | Herceptarg CLC-D1-der | 10 | i.p. once weekly |

TABLE 32

Parent sequences of Pertuzumab and Trastuzumab

| SEQ ID NO | Name | Sequence |
|---|---|---|
| Pertuzumab wt (parent) sequences | | |
| 22 | Pertuzumab wt VH (10289) | EVQLVESGGGLVQPGGSLRLSCAASGFTFTDYTMDWVRQAPGKGLEWVADVNPNSGGSIYNQRFKGRFTLSVDRSKNTLYLQMNSLRAEDTAVYYCARNLGPSFYFDYWGQGTLVTVSS |
| 21 | Pertuzumab wt VH (10289) DNA | GAGGTGCAGCTGGTCGAGTCTGGCGGCGGACTGGTGCAGCCTGGCGGCAGCCTGAGACTGAGCTGCGCCGCCAGCGGCTTCACCTTCACCGACTACACCATGGACTGGGTGCGGCAGGCCCCTGGCAAGGGCCTGGAATGGGTGGCCGACGTGAACCCCAACAGCGGCGGCAGCATCTACAACCAGCGGTTCAAGGGCCGGTTCACCCTGAGCGTGGACAGAAGCAAGAACACCCTGTACCTCCAGATGAACAGCCTGCGGGCCGAGGACACCGCCGTGTACTACTGCGCCCGGAACCTGGGCCCCAGCTTCTACTTCGACTACTGGGGCCAGGGCACCCTGGTGACCGTGAGCAGCGCTAGCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGC |
| 14 | Pertuzumab wt VH CDR1 | GFTFTDYTMD |
| 15 | Pertuzumab wt VH CDR2 | DVNPNSGGSIYNQRFKG |
| 16 | Pertuzumab wt VH CDR3 | NLGPSFYFDY |
| 114 | Pertuzumab wt CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| 24 | Pertuzumab wt VL (10290) | DIQMTQSPSSLSASVGDRVTITCKASQDVSIGVAWYQQKPGKAPKLLIYSASYRYTGVPSRFSGSGSGTDFTLTISSLQPEDFATYYCQQYYIYPYTFGQGTKVEIK |

TABLE 32-continued

Parent sequences of Pertuzumab and Trastuzumab

| SEQ ID NO | Name | Sequence |
|---|---|---|
| 23 | Pertuzumab wt VL (10290) DNA | GACATCCAGATGACCCAGAGCCCCAGCAGCCTGAGCGCCAGCGTGGG CGACAGAGTGACCATCACCTGCAAGGCCAGCCAGGACGTGTCCATCG GCGTGGCCTGGTATCAGCAGAAGCCCGGCAAGGCCCCCAAGCTGCTG ATCTACAGCGCCAGCTACCGGTACACAGGCGTGCCCAGCCGGTTCAG CGGCAGCGGCTCCGGCACCGACTTCACCCTGACCATCAGCAGCCTGC AGCCCGAGGACTTCGCCACCTACTACTGCCAGCAGTACTACATCTAC CCCTACACCTTCGGCCAGGGCACCAAGGTGGAGATCAAG |
| 11 | Pertuzumab wt VL CDR1 | KASQDVSIGVA |
| 12 | Pertuzumab wt VL CDR2 | SASYRYT |
| 13 | Pertuzumab wt VL CDR3 | QQYYIYPYT |
| 113 | Pertuzumab wt CL | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGEC |

Trastuzumab wt (parent) sequences

| SEQ ID NO | Name | Sequence |
|---|---|---|
| 82 | Trastuzumab VL (4245) | DIQMTQSPSSLSASVGDRVTITCRASQDVNTAVAWYQQKPGKAPKLL IYSASFLYSGVPSRFSGSRSGTDFTLTISSLQPEDFATYYCQQHYTT PPTFGQGTKVEIK |
| 81 | Trastuzumab VL (4245) DNA | GACATCCAGATGACCCAGAGCCCCAAGCTCTCTGTCTGCCTCTGTGGG CGACAGAGTGACCATCACCTGCAGAGCCAGCCAGGACGTGAACACAG CCGTGGCCTGGTATCAGCAGAAGCCAGGCAAGGCCCCAAAGCTGCTG ATCTACAGCGCCAGCTTCCTGTACAGCGGCGTGCCAAGCAGATTCAG CGGCAGCAGAAGCGGCACAGACTTCACCCTGACCATCAGCAGCCTGC AGCCAGAGGACTTCGCCACCTACTACTGCCAGCAGCACTACACCACC CCACCAACCTTCGGACAGGGCACCAAGGTGGAGATCAAG |
| 17 | Trastuzumab wt VL CDR1 | RASQDVNTAVA |
| 18 | Trastuzumab wt VL CDR2 | SASFLYS |
| 19 | Trastuzumab wt VL CDR3 | QQHYTTPPT |
| 116 | Trastuzumab wt CL | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGEC |
| 92 | Trastuzumab VH (11345) | EVQLVESGGGLVQPGGSLRLSCAASGFNIKDTYIHWVRQAPGKGLEW VARIYPTNGYTRYADSVKGRFTISADTSKNTAYLQMNSLRAEDTAVY YCSRWGGDGFYAMDYWGQGTLVTVSS |
| 91 | Trastuzumab VH (11345) DNA | GAAGTGCAATTGGTGGAAAGCGGCGGCGGCCTGGTGCAACCGGGCGG CAGCCTGCGTCTGAGCTGCGCGGCCTCCGGATTTAACATAAAGGACA CATACATCCACTGGGTGCGCCAAGCACCTGGGAAGGGTCTCGAGTGG GTGGCTCGGATTTACCCAACAAATGGCTACACCAGGTATGCGGATAG CGTGAAAGGCCGTTTTACCATTTCAGCTGATACTTCGAAGAACACCG CCTATCTGCAAATGAACAGCCTGCGTGCGGAAGATACGGCCGTGTAT TATTGCTCGCGTTGGGGAGGAGACGGGTTCTATGCTATGGATTACTG GGGCCAAGGCACCCTGGTGACGGTTAGCTCA |
| 20 | Trastuzumab wt VH CDR1 | GFNIKDTYIH |
| 29 | Trastuzumab wt VH CDR2 | RIYPTNGYTRYADSVKG |
| 30 | Trastuzumab wt VH CDR3 | WGGDGFYAMDY |
| 115 | Trastuzumab wt CH1 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKV |

TABLE 33

Sequences of antibodies with common light chain

| SEQ ID NO | Name | Sequence |
|---|---|---|
| | | Pertuzumab/ Trastuzumab hybrid light chains |
| 26 | Pertuzumab VL (Trast. L3) (10403) | DIQMTQSPSSLSASVGDRVTITCKASQDVSIGVAWYQQKPGKAPKLL IYSASYRYTGVPSRFSGSGSGTDFTLTISSLQPEDFATYYCQQHYTT PPTFGQGTKVEIK |
| 25 | Pertuzumab VL (Trast. L3) (10403)DNA | GACATCCAGATGACCCAGAGCCCCAGCAGCCTGAGCGCCAGCGTGGG CGACAGAGTGACCATCACATGCAAGGCCAGCCAGGACGTGTCCATCG GCGTGGCCTGGTATCAGCAGAAGCCCGGCAAGGCCCCCAAGCTGCTG ATCTACAGCGCCAGCTACCGGTACACCGGCGTGCCCAGCAGATTCAG CGGCAGCGGCTCCGGCACCGACTTCACCCTGACCATCAGCAGCCTGC AGCCCGAGGACTTCGCCACCTACTACTGCCAGCAGCACTACACCACC CCCCCCACCTTCGGCCAGGGCACCAAGGTGGAAATCAAG |
| 28 | Pertuzumab VL (Trast. H91) (10404) | DIQMTQSPSSLSASVGDRVTITCKASQDVSIGVAWYQQKPGKAPKLL IYSASYRYTGVPSRFSGSGSGTDFTLTISSLQPEDFATYYCQQHYIY PYTFGQGTKVEIK |
| 27 | Pertuzumab VL (Trast. H91) (10404)DNA | GACATCCAGATGACCCAGAGCCCCAGCAGCCTGAGCGCCAGCGTGGG CGACAGAGTGACCATCACCTGCAAGGCCAGCCAGGACGTGTCCATCG GCGTGGCCTGGTATCAGCAGAAGCCCGGCAAGGCCCCCAAGCTGCTG ATCTACAGCGCCAGCTACCGGTACACAGGCGTGCCCAGCCGGTTCAG CGGCAGCGGCTCCGGCACCGACTTCACCCTGACCATCAGCAGCCTGC AGCCCGAGGACTTCGCCACCTACTACTGCCAGCAGCACTACATCTAC CCCTACACCTTCGGCCAGGGCACCAAGGTGGAGATCAAG |
| 32 | Pertuzumab VL (Tras.L3) K24R (10949) | DIQMTQSPSSLSASVGDRVTITCRASQDVSIGVAWYQQKPGKAPKLL IYSASYRYTGVPSRFSGSGSGTDTTLTISSLQPEDFATYYCQQHYTT PPTFGQGTKVEIK |
| 31 | Pertuzumab VL (Tras.L3) K24R (10949)DNA | GACATCCAGATGACCCAGAGCCCCAGCAGCCTGAGCGCCAGCGTGGG CGACAGAGTGACCATCACATGCCGGGCCAGCCAGGACGTGTCCATCG GCGTGGCCTGGTATCAGCAGAAGCCCGGCAAGGCCCCCAAGCTGCTG ATCTACAGCGCCAGCTACCGGTACACCGGCGTGCCCAGCAGATTCAG CGGCAGCGGCTCCGGCACCGACTTCACCCTGACCATCAGCAGCCTGC AGCCCGAGGACTTCGCCACCTACTACTGCCAGCAGCACTACACCACC CCCCCCACCTTCGGCCAGGGCACCAAGGTGGAAATCAAG |
| 34 | Pertuzumab VL (Tras.L3) S30N (10950) | DIQMTQSPSSLSASVGDRVTITCKASQDVNIGVAWYQQKPGKAPKLL IYSASYRYTGVPSRFSGSGSGTDFTLTISSLQPEDFATYYCQQHYTT PPTFGQGTKVEIK |
| 33 | Pertuzumab VL(Tras.L3) S30N (10950)DNA | GACATCCAGATGACCCAGAGCCCCAGCAGCCTGAGCGCCAGCGTGGG CGACAGAGTGACCATCACATGCAAGGCCAGCCAGGACGTGAACATCG GCGTGGCCTGGTATCAGCAGAAGCCCGGCAAGGCCCCCAAGCTGCTG ATCTACAGCGCCAGCTACCGGTACACCGGCGTGCCCAGCAGATTCAG CGGCAGCGGCTCCGGCACCGACTTCACCCTGACCATCAGCAGCCTGC AGCCCGAGGACTTCGCCACCTACTACTGCCAGCAGCACTACACCACC CCCCCCACCTTCGGCCAGGGCACCAAGGTGGAAATCAAG |
| 36 | Pertuzumab VL (Tras.L3) I31T (10951) | DIQMTQSPSSLSASVGDRVTITCKASQDVSTGVAWYQQKPGKAPKLL IYSASYRYTGVPSRFSGSGSGTDFTLTISSTQPEDFATYYCQQHYTT PPTFGQGTKVEIK |
| 35 | Pertuzumab VL (Tras.L3) I31T (10951)DNA | GACATCCAGATGACCCAGAGCCCCAGCAGCCTGAGCGCCAGCGTGGG CGACAGAGTGACCATCACATGCAAGGCCAGCCAGGACGTGTCCACCG GCGTGGCCTGGTATCAGCAGAAGCCCGGCAAGGCCCCCAAGCTGCTG ATCTACAGCGCCAGCTACCGGTACACCGGCGTGCCCAGCAGATTCAG CGGCAGCGGCTCCGGCACCGACTTCACCCTGACCATCAGCAGCCTGC AGCCCGAGGACTTCGCCACCTACTACTGCCAGCAGCACTACACCACC CCCCCCACCTTCGGCCAGGGCACCAAGGTGGAAATCAAG |
| 38 | Pertuzumab VL (Tras.L3) I31V (10952) | DIQMTQSPSSLSASVGDRVTITCKASQDVSVGVAWYQQKPGKAPKLL IYSASYRYTGVPSRFSGSGSGTDFTLTISSLQPEDFATYYCQQHYTT PPTFGQGTKVEIK |

TABLE 33-continued

Sequences of antibodies with common light chain

| SEQ ID NO | Name | Sequence |
|---|---|---|
| 37 | Pertuzumab VL (Tras.L3) I31V (10952)DNA | GACATCCAGATGACCCAGAGCCCCAGCAGCCTGAGCGCCAGCGTGGG<br>CGACAGAGTGACCATCACATGCAAGGCCAGCCAGGACGTGTCCGTCG<br>GCGTGGCCTGGTATCAGCAGAAGCCCGGCAAGGCCCCCAAGCTGCTG<br>ATCTACAGCGCCAGCTACCGGTACACCGGCGTGCCCAGCAGATTCAG<br>CGGCAGCGGCTCCGGCACCGACTTCACCCTGACCATCAGCAGCCTGC<br>AGCCCGAGGACTTCGCCACCTACTACTGCCAGCAGCACTACACCACC<br>CCCCCCACCTTCGGCCAGGGCACCAAGGTGGAAATCAAG |
| 40 | Pertuzumab VL (Tras.L3) G32A (10953) | DIQMTQSPSSLSASVGDRVTITCKASQDVSIAVAWYQQKPGKAPKLL<br>IYSASYRYTGVPSRFSGSGSGTDFTLTISSLQPEDFATYYCQQHYTT<br>PPTFGQGTKVEIK |
| 39 | Pertuzumab VL (Tras.L3) G32A (10953)DNA | GACATCCAGATGACCCAGAGCCCCAGCAGCCTGAGCGCCAGCGTGGG<br>CGACAGAGTGACCATCACATGCAAGGCCAGCCAGGACGTGTCCATCG<br>CCGTGGCCTGGTATCAGCAGAAGCCCGGCAAGGCCCCCAAGCTGCTG<br>ATCTACAGCGCCAGCTACCGGTACACCGGCGTGCCCAGCAGATTCAG<br>CGGCAGCGGCTCCGGCACCGACTTCACCCTGACCATCAGCAGCCTGC<br>AGCCCGAGGACTTCGCCACCTACTACTGCCAGCAGCACTACACCACC<br>CCCCCCACCTTCGGCCAGGGCACCAAGGTGGAAATCAAG |
| 42 | Pertuzumab VL (Tras.L3) Y53F (10954) | DIQMTQSPSSLSASVGDRVTITCKASQDVSIGVAWYQQKPGKAPKLL<br>IYSASFRYTGVPSRFSGSGSGTDFTLTISSLQPEDFATYYCQQHYTT<br>PPTFGQGTKVEIK |
| 41 | Pertuzumab VL(Tras.L3) Y53F (10954) DNA | GACATCCAGATGACCCAGAGCCCCAGCAGCCTGAGCGCCAGCGTGGG<br>CGACAGAGTGACCATCACATGCAAGGCCAGCCAGGACGTGTCCATCG<br>GCGTGGCCTGGTATCAGCAGAAGCCCGGCAAGGCCCCCAAGCTGCTG<br>ATCTACAGCGCCAGCTTCCGGTACACCGGCGTGCCCAGCAGATTCAG<br>CGGCAGCGGCTCCGGCACCGACTTCACCCTGACCATCAGCAGCCTGC<br>AGCCCGAGGACTTCGCCACCTACTACTGCCAGCAGCACTACACCACC<br>CCCCCCACCTTCGGCCAGGGCACCAAGGTGGAAATCAAG |
| 44 | Pertuzumab VL (Tras.L3) R54L (10955) | DIQMTQSPSSLSASVGDRVTITCKASQDVSIGVAWYQQKPGKAPKLL<br>IYSASYLYTGVPSRFSGSGSGTDFTLTISSLQPEDFATYYCQQHYTT<br>PPTFGQGTKVEIK |
| 43 | Pertuzumab (Tras.L3) R54L (10955) DNA | GACATCCAGATGACCCAGAGCCCCAGCAGCCTGAGCGCCAGCGTGGG<br>CGACAGAGTGACCATCACATGCAAGGCCAGCCAGGACGTGTCCATCG<br>GCGTGGCCTGGTATCAGCAGAAGCCCGGCAAGGCCCCCAAGCTGCTG<br>ATCTACAGCGCCAGCTACCTGTACACCGGCGTGCCCAGCAGATTCAG<br>CGGCAGCGGCTCCGGCACCGACTTCACCCTGACCATCAGCAGCCTGC<br>AGCCCGAGGACTTCGCCACCTACTACTGCCAGCAGCACTACACCACC<br>CCCCCCACCTTCGGCCAGGGCACCAAGGTGGAAATCAAG |
| 46 | Pertuzumab (Tras.L3) T56S (10956) | DIQMTQSPSSLSASVGDRVTITCKASQDVSIGVAWYQQKPGKAPKLL<br>IYSASYRYSGVPSRFSGSGSGTDFTLTISSLQPEDFATYYCQQHYTT<br>PPTFGQGTKVEIK |
| 45 | Pertuzumab (Tras.L3) T56S (10956) DNA | GACATCCAGATGACCCAGAGCCCCAGCAGCCTGAGCGCCAGCGTGGG<br>CGACAGAGTGACCATCACATGCAAGGCCAGCCAGGACGTGTCCATCG<br>GCGTGGCCTGGTATCAGCAGAAGCCCGGCAAGGCCCCCAAGCTGCTG<br>ATCTACAGCGCCAGCTACCGGTACAGCGGCGTGCCCAGCAGATTCAG<br>CGGCAGCGGCTCCGGCACCGACTTCACCCTGACCATCAGCAGCCTGC<br>AGCCCGAGGACTTCGCCACCTACTACTGCCAGCAGCACTACACCACC<br>CCCCCCACCTTCGGCCAGGGCACCAAGGTGGAAATCAAG |
| 48 | Pertuzumab (Tras.L3) G66R (10957) | DIQMTQSPSSLSASVGDRVTITCKASQDVSIGVAWYQQKPGKAPKLL<br>IYSASYRYTGVPSRFSGSRSGTDFTLTISSLQPEDFATYYCQQHYTT<br>PPTFGQGTKVEIK |
| 47 | Pertuzumab (Tras.L3) G66R (10957) DNA | GACATCCAGATGACCCAGAGCCCCAGCAGCCTGAGCGCCAGCGTGGG<br>CGACAGAGTGACCATCACATGCAAGGCCAGCCAGGACGTGTCCATCG<br>GCGTGGCCTGGTATCAGCAGAAGCCCGGCAAGGCCCCCAAGCTGCTG<br>ATCTACAGCGCCAGCTACCGGTACACCGGCGTGCCCAGCAGATTCAG |

TABLE 33-continued

Sequences of antibodies with common light chain

| SEQ ID NO | Name | Sequence |
|---|---|---|
| | | CGGCAGCCGCTCCGGCACCGACTTCACCCTGACCATCAGCAGCCTGC<br>AGCCCGAGGACTTCGCCACCTACTACTGCCAGCAGCACTACACCACC<br>CCCCCCACCTTCGGCCAGGGCACCAAGGTGGAAATCAAG |
| 50 | Pertuzumab (Tras.L3) T94Y (10958) | DIQMTQSPSSLSASVGDRVTITCKASQDVSIGVAWYQQKPGKAPKLL<br>IYSASYRYTGVPSRFSGSGSGTDFTLTISSLQPEDFATYYCQQHYTY<br>PPTFGQGTKVEIK |
| 49 | Pertuzumab (Tras.L3) T94Y (10958) DNA | ACATCCAGATGACCCAGAGCCCCAGCAGCCTGAGCGCCAGCGTGGGC<br>GACAGAGTGACCATCACATGCAAGGCCAGCCAGGACGTGTCCATCGG<br>CGTGGCCTGGTATCAGCAGAAGCCCGGCAAGGCCCCCAAGCTGCTGA<br>TCTACAGCGCCAGCTACCGGTACACCGGCGTGCCCAGCAGATTCAGC<br>GGCAGCGGCTCCGGCACCGACTTCACCCTGACCATCAGCAGCCTGCA<br>GCCCGAGGACTTCGCCACCTACTACTGCCAGCAGCACTACACCTACC<br>CCCCCACCTTCGGCCAGGGCACCAAGGTGGAAATCAAG |
| 52 | Pertuzumab (Tras.L3) P96Y (10959) | DIQMTQSPSSLSASVGDRVTITCKASQDVSIGVAWYQQKPGKAPKLL<br>IYSASYRYTGVPSRFSGSGSGTDFTLTISSLQPEDFATYYCQQHYTT<br>PYTFGQGTKVEIK |
| 51 | Pertuzumab (Tras.L3) P96Y (10959) DNA | GACATCCAGATGACCCAGAGCCCCAGCAGCCTGAGCGCCAGCGTGGG<br>CGACAGAGTGACCATCACATGCAAGGCCAGCCAGGACGTGTCCATCG<br>GCGTGGCCTGGTATCAGCAGAAGCCCGGCAAGGCCCCCAAGCTGCTG<br>ATCTACAGCGCCAGCTACCGGTACACCGGCGTGCCCAGCAGATTCAG<br>CGGCAGCGGCTCCGGCACCGACTTCACCCTGACCATCAGCAGCCTGC<br>AGCCCGAGGACTTCGCCACCTACTACTGCCAGCAGCACTACACCACC<br>CCCTACACCTTCGGCCAGGGCACCAAGGTGGAAATCAAG |
| 54 | Pertuzumab (Tras.L3) (QM) (11055) | DIQMTQSPSSLSASVGDRVTITCKASQDVSTAVAWYQQKPGKAPKLL<br>IYSASFRYTGVPSRFSGSRSGTDFTLTISSLQPEDFATYYCQQHYTT<br>PPTFGQGTKVEIK |
| 53 | Pertuzumab (Tras.L3) (QM) (11055) DNA | GACATCCAGATGACCCAGAGCCCCAGCAGCCTGTCTGCCAGCGTGGG<br>CGACAGAGTGACCATCACATGCAAGGCCAGCCAGGACGTGTCCACAG<br>CCGTGGCCTGGTATCAGCAGAAGCCTGGCAAGGCCCCCAAGCTGCTG<br>ATCTACAGCGCCAGCTTCCGGTACACCGGCGTGCCCAGCAGATTCAG<br>CGGCAGCAGATCCGGCACCGACTTCACCCTGACCATCAGCTCCCTGC<br>AGCCCGAGGACTTCGCCACCTACTACTGCCAGCAGCACTACACCACC<br>CCCCCCACATTTGGCCAGGGCACCAAGGTGGAAATCAAG |
| 89 | Pertuzumab (Tras.L3) (QM)-CDR1 | KASQDVSTAVA |
| 90 | Pertuzumab (Tras.L3) (QM)-CDR2 | SASFRYT |
| 19 | Pertuzumab (Tras.L3) (QM)-CDR3 | QQHYTTPPT |

Pertuzumab/Trastuzumab hybrid light chain affinity matured VH clones

| SEQ ID NO | Name | Sequence |
|---|---|---|
| 62 | Pertuzumab aff.mat. clone D1 | EVQLVESGGGLVQPGGSLRLSCAASGFTFNDYTMDWVRQAPGKGLEW<br>VADVNPNSGGSIYNQRFKGRFTLSVDRSKNTLYLQMNSLRAEDTAVY<br>YCARNLGPFFYFDYWGQGTLVTVSS |
| 61 | Pertuzumab aff.mat. clone D1 DNA | GAGGTGCAATTGGTTGAAAGCGGTGGTGGTCTGGTTCAGCCTGGTGG<br>TAGCCTGCGTCTGAGCTGTGCAGCAAGCGGTTTTACCTTTAACGATT<br>ATACCATGGATTGGGTTCGTCAGGCACCGGGTAAAGGTCTGGAATGG<br>GTTGCAGATGTTAATCCGAATAGCGGTGGTAGCATTTATAACCAGCG<br>TTTTAAAGGTCGTTTTACCCTGAGCGTTGATCGTAGCAAAAATACCC<br>TGTATCTGCAAATGAATAGTCTGCGTGCAGAGGATACCGCAGTGTAT<br>TATTGTGCACGTAACCTGGGTCCGTTCTTCTACTTTGATTATTGGGG<br>TCAGGGCACCCTGGTTACCGTTAGCAGC |
| 55 | Pertuzumab aff.mat. clone D1-VH CDR1 | GFTFNDYTMD |

TABLE 33-continued

Sequences of antibodies with common light chain

| SEQ ID NO | Name | Sequence |
|---|---|---|
| 15 | Pertuzumab aff.mat. clone D1-VH CDR2 | DVNPNSGGSIYNQRFKG |
| 56 | Pertuzumab aff.mat. clone D1-VH CDR3 | NLGPFFYFDY |
| 64 | Pertuzumab aff.mat. clone D1-derived | EVQLVESGGGLVQPGGSLRLSCAASGFTFNDYTMDWVRQAPGKGLEWVADVNPNSGGSIVNRRFKGRFTLSVDRSKNTLYLQMNSLRAEDTAVYYCARNLGPFFYFDYWGQGTLVTVSS |
| 63 | Pertuzumab aff.mat. clone D1-derived, DNA | GAGGTGCAATTGGTTGAAAGCGGTGGTGGTCTGGTTCAGCCTGGTGGTAGCCTGCGTCTGAGCTGTGCAGCAAGCGGTTTTACCTTTAACGATTATACCATGGATTGGGTTCGTCAGGCACCGGGTAAAGGTCTGGAATGGGTTGCAGATGTTAATCCGAATAGCGGTGGTAGCATTGTTAACCGTCGTTTTAAAGGTCGTTTTACCCTGAGCGTTGATCGTAGCAAAAATACCCTGTATCTGCAAATGAATAGTCTGCGTGCAGAGGATACCGCAGTGTATTATTGTGCACGTAACCTGGGTCCGTTCTTCTACTTTGATTATTGGGGTCAGGGCACCCTGGTTACCGTTAGCAGC |
| 55 | Pertuzumab aff.mat. clone D1-derived VH CDR1 | GFTFNDYTMD |
| 77 | Pertuzumab aff.mat. clone D1-derived VH CDR2 | DVNPNSGGSIVNRRFKG |
| 56 | Pertuzumab aff.mat. clone D1-derived VH CDR3 | NLGPFFYFDY |
| 66 | Pertuzumab aff.mat. clone B2 | EVQLVESGGGLVQPGGSLRLSCAASGFTFNDYTMDWFRQAPGKGLEWVADVNPNSGGSIYNQRFKGRFTLSVDRSKNTLYLQMNSLRAEDTAVYYCARNLGPNFYFDYWGQGTLVTVSS |
| 65 | Pertuzumab aff.mat. clone B2, DNA | GAGGTGCAATTGGTTGAAAGCGGTGGTGGTCTGGTTCAGCCTGGTGGTAGCCTGCGTCTGAGCTGTGCAGCAAGCGGTTTTACCTTTAACGATTATACCATGGATTGGTTTCGTCAGGCACCGGGTAAAGGTCTGGAATGGGTTGCAGATGTTAATCCGAATAGCGGTGGTAGCATTTATAACCAGCGTTTTAAAGGTCGTTTTACCCTGAGCGTTGATCGTAGCAAAAATACCCTGTATCTGCAAATGAATAGTCTGCGTGCAGAGGATACCGCAGTGTATTATTGTGCACGTAATCTGGGTCCGAACTTCTACTTTGATTATTGGGGTCAGGGCACCCTGGTTACCGTTAGCAGC |
| 55 | Pertuzumab aff.mat. clone B2-VH CDR1 | GFTFNDYTMD |
| 15 | Pertuzumab aff.mat. clone B2-VH CDR2 | DVNPNSGGSIYNQRFKG |
| 57 | Pertuzumab aff.mat. clone B2-VH CDR3 | NLGPNFYFDY |
| 68 | Pertuzumab aff.mat. clone E1 | EVQLVESGGGLVQPGGSLRLSCAASGFTFADYTMDWVRQAPGKGLEWVADVNPNSGGSIYNQRFKGRFTLSVDRSKNTLYLQMNSLRAEDTAVYYCARNLGPWFYFDYWGQGTLVTVSS |

TABLE 33-continued

Sequences of antibodies with common light chain

| SEQ ID NO | Name | Sequence |
|---|---|---|
| 67 | Pertuzumab aff.mat. clone E1, DNA | GAGGTGCAATTGGTTGAAAGCGGTGGTGGTCTGGTTCAGCCTGGTGG TAGCCTGCGTCTGAGCTGTGCAGCAAGCGGTTTTACCTTTGCAGATT ATACCATGGATTGGGTTCGTCAGGCACCGGGTAAAGGTCTGGAATGG GTTGCAGATGTTAATCCGAATAGCGGTGGTAGCATTTATAACCAGCG TTTTAAAGGTCGTTTTACCCTGAGCGTTGATCGTAGCAAAAATACCC TGTATCTGCAAATGAATAGTCTGCGTGCAGAGGATACCGCAGTGTAT TATTGTGCACGTAATCTGGGTCCGTGGTTCTACTTTGATTATTGGGG TCAGGGCACCCTGGTTACCGTTAGCAGC |
| 58 | Pertuzumab aff.mat. clone E1- VH CDR1 | GFTFADYTMD |
| 15 | Pertuzumab aff.mat. clone E1- VH CDR2 | DVNPNSGGSIYNQRFKG |
| 59 | Pertuzumab aff.mat. clone E1- VH CDR3 | NLGPWFYFDY |
| 70 | Pertuzumab aff.mat. clone G2 | EVQLVESGGGLVQPGGSLRLSCAASGFTFTDYTMDWVRQAPGKGLEW VADVNPNSGGYIVNRRFKGRFTLSVDRSKNTLYLQMNSLRAEDTAVY YCARNLGPSFYFDYWGQGTLVTVSS |
| 69 | Pertuzumab aff.mat. clone G2, DNA | GAGGTGCAATTGGTTGAAAGCGGTGGTGGTCTGGTTCAGCCTGGTGG TAGCCTGCGTCTGAGCTGTGCAGCAAGCGGTTTTACCTTTACCGATT ACACAATGGATTGGGTTCGTCAGGCACCGGGTAAAGGTCTGGAATGG GTTGCAGATGTTAATCCGAACTCTGGTGGTTACATTGTTAACCGTCG TTTTAAAGGTCGTTTTACCCTGAGCGTTGATCGTAGCAAAAATACCC TGTATCTGCAAATGAATAGTCTGCGTGCAGAGGATACCGCAGTGTAT TATTGTGCACGTAATCTGGGTCCGAGCTTCTATTTTGATTATTGGGG TCAGGGCACCCTGGTTACCGTTAGCAGC |
| 14 | Pertuzumab aff.mat. clone G2- VH CDR1 | GFTFTDYTMD |
| 60 | Pertuzumab aff.mat. clone G2- VH CDR2 | DVNPNSGGYIVNRRFKG |
| 16 | Pertuzumab aff.mat. clone G2- VH CDR3 | NLGPSFYFDY |
| 72 | Pertuzumab aff.mat. clone C8 | EVQLVESGGGLVQPGGSLRLSCAASGFTFTDYTMDWVRQAPGKGLEW VADVNPNSGGSIMNRRFKGRFTLSVDRSKNTLYLQMNSLRAEDTAVY YCARNLGPSFYFDYWGQGTLVTVSS |
| 71 | Pertuzumab aff.mat. clone C8, DNA | GAGGTGCAATTGGTTGAAAGCGGTGGTGGTCTGGTTCAGCCTGGTGG TAGCCTGCGTCTGAGCTGTGCAGCAAGCGGTTTTACCTTTACCGATT ACACAATGGATTGGGTTCGTCAGGCACCGGGTAAAGGTCTGGAATGG GTTGCAGATGTTAATCCGAACTCTGGTGGTTCTATTATGAACCGTCG TTTTAAAGGTCGTTTTACCCTGAGCGTTGATCGTAGCAAAAATACCC TGTATCTGCAAATGAATAGTCTGCGTGCAGAGGATACCGCAGTGTAT TATTGTGCACGTAATCTGGGTCCGAGCTTCTATTTTGATTATTGGGG TCAGGGCACCCTGGTTACCGTTAGCAGC |
| 14 | Pertuzumab aff.mat. clone C8- VH CDR1 | GFTFTDYTMD |
| 75 | Pertuzumab aff.mat. clone C8- VH CDR2 | DVNPNSGGSIMNRRFKG |

TABLE 33-continued

Sequences of antibodies with common light chain

| SEQ ID NO | Name | Sequence |
|---|---|---|
| 16 | Pertuzumab aff.mat. clone C8-VH CDR3 | NLGPSFYFDY |
| 74 | Pertuzumab aff.mat. clone A1 | EVQLVESGGGLVQPGGSLRLSCAASGFTFTDYTMDWVRQAPGKGLEW VADVNPNSGGSIVNQRFKGRFTLSVDRSKNTLYLQMNSLRAEDTAVY YCARNLGPWFYFDYWGQGTLVTVSS |
| 73 | Pertuzumab aff.mat. clone A1, DNA | GAGGTGCAATTGGTTGAAAGCGGTGGTGGTCTGGTTCAGCCTGGTGG TAGCCTGCGTCTGAGCTGTGCAGCAAGCGGTTTTACCTTTACCGATT ACACAATGGATTGGGTTCGTCAGGCACCGGGTAAAGGTCTGGAATGG GTTGCAGATGTTATCCGAACTCTGGTGGTTCTATTGTTAACCAGCG TTTTAAAGGTCGTTTTACCCTGAGCGTTGATCGTAGCAAAAATACCC TGTATCTGCAAATGAATAGTCTGCGTGCAGAGGATACCGCAGTGTAT TATTGTGCACGTAATCTGGGTCCGTGGTTCTACTTTGATTATTGGGG TCAGGGCACCCTGGTTACCGTTAGCAGC |
| 14 | Pertuzumab aff.mat. clone A1-VH CDR1 | GFTFTDYTMD |
| 76 | Pertuzumab aff.mat. clone A1-VH CDR2 | DVNPNSGGSIVNQRFKG |
| 59 | Pertuzumab aff.mat. clone A1-VH CDR3 | NLGPWFYFDY |

Trastuzumab Stabilization Variants

| SEQ ID NO | Name | Sequence |
|---|---|---|
| 84 | Trastuzumab VL T31A (6641) | DIQMTQSPSSLSASVGDRVTITCRASQDVNAAVAWYQQKPGKAPKLL IYSASFLYSGVPSRFSGSRSGTDFTLTISSLQPEDFATYYCQQHYTT PPTFGQGTKVEIK |
| 83 | Trastuzumab VL T31A (6641) | GATATCCAGATGACCCAGTCTCCATCCTCCCTGTCTGCATCTGTAGG AGACAGAGTCACCATCACTTGCCGGGCAAGTCAGGACGTGAACGCCG CTGTAGCGTGGTACCAGCAGAAACCAGGTAAGGCACCGAAGCTATTA ATTTATAGTGCGAGCTTCCTGTACAGTGGGGTCCCGTCGCGTTTTAG CGGCTCTCGATCCGGCACGGATTTTACCCTGACCATTAGCAGCCTGC AGCCTGAAGACTTTGCGACATATTATTGCCAACAGCACTACACAACT CCTCCCACCTITGGCCAGGGTACGAAAGTTGAAATTAA |
| 103 | Trastuzumab VL T31A (6641)CDR1 | RASQDVNAAVA |
| 18 | Trastuzumab VL T31A (6641)CDR2 | SASFLYS |
| 19 | Trastuzumab VL T31A (6641)CDR3 | QQHYTTPPT |
| 86 | Trastuzumab VL T31V (6642) | DIQMTQSPSSLSASVGDRVTITCRASQDVNVAVAWYQQKPGKAPKLL IYSASFLYSGVPSRFSGSRSGTDFTLTISSLQPEDFATYYCQQHYTT PPTFGQGTKVEIK |
| 85 | Trastuzumab VL T31V (6642)DNA | GATATCCAGATGACCCAGTCTCCATCCTCCCTGTCTGCATCTGTAGG AGACAGAGTCACCATCACTTGCCGGGCAAGTCAGGACGTGAACGTGG CTGTAGCGTGGTACCAGCAGAAACCAGGTAAGGCACCGAAGCTATTA ATTTATAGTGCGAGCTTCCTGTACAGTGGGGTCCCGTCGCGTTTTAG CGGCTCTCGATCCGGCACGGATTTTACCCTGACCATTAGCAGCCTGC AGCCTGAAGACTTTGCGACATATTATTGCCAACAGCACTACACAACT CCTCCCACCTTTGGCCAGGGTACGAAAGTTGAAATTAAAG |

TABLE 33-continued

Sequences of antibodies with common light chain

| SEQ ID NO | Name | Sequence |
|---|---|---|
| 104 | Trastuzumab VL T31V (6642)CDR1 | RASQDVNVAVA |
| 18 | Trastuzumab VL T31V (6642)CDR2 | SASFLYS |
| 19 | Trastuzumab VL T31V (6642)CDR3 | QQHYTTPPT |
| 158 | Trastuzumab VL N30S CDR1 | RASQDVSTAVA |
| 94 | Trastuzumab VH (D98N) (6636) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGNGFYAMDYWGQGTLVTVSS |
| 93 | Trastuzumab VH (D98N) (6636) DNA | GAAGTGCAATTGGTGGAAAGCGGCGGCGGCCTGGTGCAACCGGGCGGCAGCCTGCGTCTGAGCTGCGCGGCCTCCGGATTTAACATAAAGGACACATACATCCACTGGGTGCGCCAAGCACCTGGGAAGGGTCTCGAGTGGGTGGCTCGGATTTACCCAACAAATGGCTACACCAGGTATGCGGATAGCGTGAAAGGCCGTTTTACCATTTCAGCTGATACTTCGAAGAACACCGCCTATCTGCAAATGAACAGCCTGCGTGCGGAAGATACGGCCGTGTATTATTGCTCGCGTTGGGGAGGAAACGGGTTCTATGCTATGGATTACTGGGGCCAAGGCACCCTGGTGACGGTTAGCTCA |
| 20 | Trastuzumab VH (D98N) (6636) CDR1 | GFNIKDTYIH |
| 29 | Trastuzumab VH (D98N) (6636) CDR2 | RIYPTNGYTRYADSVKG |
| 78 | Trastuzumab VH (D98N) (6636) CDR3 | WGGNGFYAMDY |
| 96 | Trastuzumab VH (D98E) (6637) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGEGFYAMDYWGQGTLVTVSS |
| 95 | Trastuzumab VH (D98E) (6637) DNA | GAAGTGCAATTGGTGGAAAGCGGCGGCGGCCTGGTGCAACCGGGCGGCAGCCTGCGTCTGAGCTGCGCGGCCTCCGGATTTAACATAAAGGACACATACATCCACTGGGTGCGCCAAGCACCTGGGAAGGGTCTCGAGTGGGTGGCTCGGATTTACCCAACAAATGGCTACACCAGGTATGCGGATAGCGTGAAAGGCCGTTTTACCATTTCAGCTGATACTTCGAAGAACACCGCCTATCTGCAAATGAACAGCCTGCGTGCGGAAGATACGGCCGTGTATTATTGCTCGCGTTGGGGAGGAGAGGGGTTCTATGCTATGGATTACTGGGGCCAAGGCACCCTGGTGACGGTTAGCTCA |
| 20 | Trastuzumab VH (D98E) (6637) CDR1 | GFNIKDTYIH |
| 29 | Trastuzumab VH (D98E) (6637) CDR2 | RIYPTNGYTRYADSVKG |
| 79 | Trastuzumab VH (D98E) (6637) CDR3 | WGGEGFYAMDY |
| 98 | Trastuzumab VH (D98T) (6638) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGTGFYAMDYWGQGTLVTVSS |
| 97 | Trastuzumab VH (D98T) (6638) DNA | GAAGTGCAATTGGTGGAAAGCGGCGGCGGCCTGGTGCAACCGGGCGGCAGCCTGCGTCTGAGCTGCGCGGCCTCCGGATTTAACATAAAGGACACATACATCCACTGGGTGCGCCAAGCACCTGGGAAGGGTCTCGAGTGGGTGGCTCGGATTTACCCAACAAATGGCTACACCAGGTATGCGGATAG |

TABLE 33-continued

Sequences of antibodies with common light chain

| SEQ ID NO | Name | Sequence |
|---|---|---|
| | | CGTGAAAGGCCGTTTTACCATTTCAGCTGATACTTCGAAGAACACCG<br>CCTATCTGCAAATGAACAGCCTGCGTGCGGAAGATACGGCCGTGTAT<br>TATTGCTCGCGTTGGGGAGGAACCGGGTTCTATGCTATGGATTACTG<br>GGGCCAAGGCACCCTGGTGACGGTTAGCTCA |
| 20 | Trastuzumab VH (D98T) (6638) CDR1 | GFNIKDTYIH |
| 29 | Trastuzumab VH (D98T) (6638) CDR2 | RIYPTNGYTRYADSVKG |
| 80 | Trastuzumab VH (D98T) (6638) CDR3 | WGGTGFYAMDY |
| 100 | Trastuzumab VH (G99A) (6639) | EVQLVESGGGLVQPGGSLRLSCAASGFNIKDTYIHWVRQAPGKGLEW<br>VARIYPTNGYTRYADSVKGRFTISADTSKNTAYLQMNSLRAEDTAVY<br>YCSRWGGD<u>A</u>FYAMDYWGQGTLVTVSS |
| 99 | Trastuzumab VH (G99A) (6639) DNA | GAAGTGCAATTGGTGGAAAGCGGCGGCGGCCTGGTGCAACCGGGCGG<br>CAGCCTGCGTCTGAGCTGCGCGGCCTCCGGATTTAACATAAAGGACA<br>CATACATCCACTGGGTGCGCCAAGCACCTGGGAAGGGTCTCGAGTGG<br>GTGGCTCGGATTTACCCAACAAATGGCTACACCAGGTATGCGGATAG<br>CGTGAAAGGCCGTTTTACCATTTCAGCTGATACTTCGAAGAACACCG<br>CCTATCTGCAAATGAACAGCCTGCGTGCGGAAGATACGGCCGTGTAT<br>TATTGCTCGCGTTGGGGAGGAGACGCCTTCTATGCTATGGATTACTG<br>GGGCCAAGGCACCCTGGTGACGGTTAGCTCA |
| 20 | Trastuzumab VH (G99A) (6639) CDR1 | GFNIKDTYIII |
| 29 | Trastuzumab VH (G99A) (6639) CDR2 | RIYPTNGYTRYADSVKG |
| 87 | Trastuzumab VH (G99A) (6639) CDR3 | WGGDAFYAMDY |
| 102 | Trastuzumab VH (G99S) (6640) | EVQLVESGGGLVQPGGSLRLSCAASGFNIKDTYIHWVRQAPGKGLEW<br>VARIYPTNGYTRYADSVKGRFTISADTSKNTAYLQMNSLRAEDTAVY<br>YCSRWGGD<u>S</u>FYAMDYWGQGTLVTVSS |
| 101 | Trastuzumab VH (G99S) (6640) DNA | GAAGTGCAATTGGTGGAAAGCGGCGGCGGCCTGGTGCAACCGGGCGG<br>CAGCCTGCGTCTGAGCTGCGCGGCCTCCGGATTTAACATAAAGGACA<br>CATACATCCACTGGGTGCGCCAAGCACCTGGGAAGGGTCTCGAGTGG<br>GTGGCTCGGATTTACCCAACAAATGGCTACACCAGGTATGCGGATAG<br>CGTGAAAGGCCGTTTTACCATTTCAGCTGATACTTCGAAGAACACCG<br>CCTATCTGCAAATGAACAGCCTGCGTGCGGAAGATACGGCCGTGTAT<br>TATTGCTCGCGTTGGGGAGGAGACAGCTTCTATGCTATGGATTACTG<br>GGGCCAAGGCACCCTGGTGACGGTTAGCTCA |
| 20 | Trastuzumab VH (G99S) (6640) CDR1 | GFNIKDTYIII |
| 29 | Trastuzumab VH (G99S) (6640) CDR2 | RIYPTNGYTRYADSVKG |
| 88 | Trastuzumab VH (G99S) (6640) CDR3 | WGGDSFYAMDY |

TABLE 34

Antigens

| SEQ ID NO | Name | Sequence |
|---|---|---|
| 2 | Her2 ECD | MGWSCIILFLVATATGVHSTQVCTGTDMKLRLPASPETHLDMLRHLY QGCQVVQGNLELTYLPTNASLSFLQDIQEVQGYVLIAHNQVRQVPLQ RLRIVRGTQLFEDNYALAVLDNGDPLNNTTPVTGASPGGLRELQLRS LTEILKGGVLIQRNPQLCYQDTILWKDIFHKNNQLALTLIDTNRSRA CHPCSPMCKGSRCWGESSEDCQSLTRTVCAGGCARCKGPLPTDCCHE QCAAGCTGPKHSDCLACLHFNHSGICELHCPALVTYNTDTFESMPNP EGRYTFGASCVTACPYNYLSTDVGSCTLVCPLHNQEVTAEDGTQRCE KCSKPCARVCYGLGMEHLREVRAVTSANIQEFAGCKKIFGSLAFLPE SFDGDPASNTAPLQPEQLQVFETLEEITGYLYISAWPDSLPDLSVFQ NLQVIRGRILHNGAYSLTLQGLGISWLGLRSLRELGSGLALIHHNTH LCFVHTVPWDQLFRNPHQALLHTANRPEDECVGEGLACHQLCARGHC WGPGPTQCVNCSQFLRGQECVEECRVLQGLPREYVNARHCLPCHPEC QPQNGSVTCFGLEADQCVACAHYKDPPFCVARCPSGVKPDLSYMPIW KFPDEEGACQPCPINCTHSCVDLDDKGCPAEQRASPLTVDEQLYFQG GSGLNDIFEAQKIEWHEARAHHHHHH |
| 1 | Her2 ECD DNA | ACCCAAGTGTGCACCGGCACAGACATGAAGCTGCGGCTCCCTGCCAG TCCCGAGACCCACCTGGACATGCTCCGCCACCTCTACCAGGGCTGCC AGGTGGTGCAGGGGAAACCTGGAACTCACCTACCTGCCCACCAATGC AGCCTGTCCTTCCTGCAGGATATCCAGGAGGTGCAGGGCTACGTGCT CATCGCTCACAACCAAGTGAGGCAGGTCCCACTGCAGAGGCTGCGGA TTGTGCGAGGCACCCAGCTCTTTGAGGACAACTATGCCCTGGCCGTG CTAGACAATGGAGACCCGCTGAACAATACCACCCCTGTCACAGGGGC CTCCCCAGGAGGCCTGCGGGAGCTGCAGCTTCGAAGCCTCACAGAGA TCTTGAAAGGAGGGGTCTTGATCCAGCGGAACCCCCAGCTCTGCTAC CAGGACACGATTTTGTGGAAGGACATCTTCCACAAGAACAACCAGCT GGCTCTCACACTGATAGACACCAACCGCTCTCGGGCCTGCCACCCCT GTTCTCCGATGTGTAAGGGCTCCCGCTGCTGGGGAGAGAGTTCTGAG GATTGTCAGAGCCTGACGCGCACTGTCTGTGCCGGTGGCTGTGCCCG CTGCAAGGGGCCACTGCCCACTGACTGCTGCCATGAGCAGTGTGCTG CCGGCTGCACGGGCCCCAAGCACTCTGACTGCCTGGCCTGCCTCCAC TTCAACCACAGTGGCATCTGTGAGCTGCACTGCCCAGCCCTGGTCAC CTACAACACAGACACGTTTGAGTCCATGCCCAATCCCGAGGGCCGGT ATACATTCGGCGCCAGCTGTGTGACTGCCTGTCCCTACAACTACCTT TCTACGGACGTGGGATCCTGCACCCTCGTCTGCCCCCTGCACAACCA AGAGGTGACAGCAGAGGATGGAACACAGCGGTGTGAGAAGTGCAGCA AGCCCTGTGCCCGAGTGTGCTATGGTCTGGGCATGGAGCACTTGCGA GAGGTGAGGGCAGTTACCAGTGCCAATATCCAGGAGTTTGCTGGCTG CAAGAAGATCTTTGGGAGCCTGGCATTTCTGCCGGAGAGCTTTGATG GGGACCCAGCCTCCAACACTGCCCCGCTCCAGCCAGAGCAGCTCCAA GTGTTTGAGACTCTGGAAGAGATCACAGGTTACCTATACATCTCAGC ATGGCCGGACAGCCTGCCTGACCTCAGCGTCTTCCAGAACCTGCAAG TAATCCGGGGACGAATTCTGCACAATGGCGCCTACTCGCTGACCCTG CAAGGGCTGGGCATCAGCTGGCTGGGGCTGCGCTCACTGAGGGAACT GGGCAGTGGACTGGCCCTCATCCACCATAACACCCACCTCTGCTTCG TGCACACGGTGCCCTGGGACCAGCTCTTTCGGAACCCGCACCAAGCT CTGCTCCACACTGCCAACCGGCCAGAGGACGAGTGTGTGGGCGAGGG CCTGGCCTGCCACCAGCTGTGCGCCCGAGGGCACTGCTGGGGTCCAG GGCCCACCCAGTGTGTCAACTGCAGCCAGTTCCTTCGGGGCCAGGAG TGCGTGGAGGAATGCCGAGTACTGCAGGGGCTCCCAGGGAGTATGT GAATGCCAGGCACTGTTTGCCGTGCCACCCTGAGTGTCAGCCCCAGA ATGGCTCAGTGACCTGTTTTGGACTGGAGGCTGACCAGTGTGTGGCC TGTGCCCACTATAAGGACCCTCCCTTCTGCGTGGCCCGCTGCCCCAG CGGTGTGAAACCTGACCTCTCCTACATGCCCATCTGGAAGTTTCCAG ATGAGGAGGGCGCATGCCAGCCTTGCCCCATCAACTGCACCCACTCC TGTGTGGACCTGGATGACAAGGGCTGCCCCGCCGAGCAGAGAGCCAG CCCTCTGACGGTCGACGAACAGTTATATTTTCAGGGCGGCTCAGGCC TGAACGACATCTTCGAGGCCCAGAAGATCGAGTGGCACGAGGCTCGA GCTCACCACCATCACCATCAC |
| 4 | Fc (hole) | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVCTLPPSRDELTKN QVSLSCAVKGFYPSDIAVEWESNGQPENNYKTTPPVLDSDGSFFLVS KLTVDKSRWQQGNVFSCSVMHEALHNRFTQKSLSLSPGK |
| 3 | Fc (hole) DNA | GACAAAACTCACACATGCCCACCGTGCCCAGCACCTGAACTCCTGGG GGGACCGTCAGTCTTCCTCTTCCCCCCAAAACCCAAGGACACCCTCA TGATCTCCCGGACCCCTGAGGTCACATGCGTGGTGGTGGACGTGAGC CACGAAGACCCTGAGGTCAAGTTCAACTGGTACGTGGACGGCGTGGA GGTGCATAATGCCAAGACAAAGCCGCGGGAGGAGCAGTACAACAGCA CGTACCGTGTGGTCAGCGTCCTCACCGTCCTGCACCAGGACTGGCTG AATGGCAAGGAGTACAAGTGCAAGGTCTCCAACAAAGCCCTCCCAGC CCCCATCGAGAAAACCATCTCCAAAGCCAAAGGGCAGCCCCGAGAAC |

TABLE 34-continued

Antigens

| SEQ ID NO | Name | Sequence |
|---|---|---|
| | | CACAGGTGTGCACCCTGCCCCCATCCCGGGATGAGCTGACCAAGAAC<br>CAGGTCAGCCTCTCGTGCGCAGTCAAAGGCTTCTATCCCAGCGACAT<br>CGCCGTGGAGTGGGAGAGCAATGGGCAGCCGGAGAACAACTACAAGA<br>CCACGCCTCCCGTGCTGGACTCCGACGGCTCCTTCTTCCTCGTGAGC<br>AAGCTCACCGTGGACAAGAGCAGGTGGCAGCAGGGGAACGTCTTCTC<br>ATGCTCCGTGATGCATGAGGCTCTGCACAACCGCTTCACGCAGAAGA<br>GCCTCTCCCTGTCTCCGGGTAAA |
| 6 | Her2 ECD-<br>Fc (knob) | TQVCTGTDMKLRLPASPETHLDMLRHLYQGCQVVQGNLELTYLPTNA<br>SLSFLQDIQEVQGYVLIAHNQVRQVPLQRLRIVRGTQLFEDNYALAV<br>LDNGDPLNNTTPVTGASPGGLRELQLRSLIEILKGGVLIQRNPQLCY<br>QDTILWKDIFHKNNQLALTLIDTNRSRACHPCSPMCKGSRCWGESSE<br>DCQSLTRTVCAGGCARCKGPLPTDCCHEQCAAGCTGPKHSDCLACLH<br>FNHSGICELHCPALVTYNTDTFESMPNPEGRYTFGASCVTACPYNYL<br>STDVGSCTLVCPLHNQEVTAEDGTQRCEKCSKPCARVCYGLGMEHLR<br>EVRAVTSANIQEFAGCKKIFGSLAFLPESFDGDPASNTAPLQPEQLQ<br>VFETLEEITGYLYISAWPDSLPDLSVFQNLQVIRGRILHNGAYSLTL<br>QGLGISWLGLRSLRELGSGLALIHHNTHLCFVHTVPWDQLFRNPHQA<br>LLHTANRPEDECVGEGLACHQLCARGHCWGPGPTQCVNCSQFLRGQE<br>CVEECRVLQGLPREYVNARHCLPCHPECQPQNGSVTCFGLEADQCVA<br>CAHYKDPPFCVARCPSGVKPDLSYMPIWKFPDEEGACQPCPINCTHS<br>CVDLDDKGCPAEQRASPLTVDGGSPTPPTPGGGSADKTHTCPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPAPIEKTISKAKGQPREPQVYTLPPCRDELTKNQVSLWCLVKGFY<br>PSDIAVEWESNGQPENNYKTTPPVLDSDGSFFLYSKLTVDKSRWQQG<br>NVFSCSVMHEALHNHYTQKSLSLSPGKSGGLNDIFEAQKIEWHE |
| 5 | Her2 ECD-<br>Fc (knob)<br>DNA | ACCCAAGTGTGCACCGGCACAGACATGAAGCTGCGGCTCCCTGCCAG<br>TCCCGAGACCCACCTGGACATGCTCCGCCACCTCTACCAGGGCTGCC<br>AGGTGGTGCAGGGAAACCTGGAACTCACCTACCTGCCCACCAATGCC<br>AGCCTGTCCTTCCTGCAGGATATCCAGGAGGTGCAGGGCTACGTGCT<br>CATCGCTCACAACCAAGTGAGGCAGGTCCCACTGCAGAGGCTGCGGA<br>TTGTGCGAGGCACCCAGCTCTTTGAGGACAACTATGCCCTGGCCGTG<br>CTAGACAATGGAGACCCGCTGAACAATACCACCCCTGTCACAGGGGC<br>CTCCCCAGGAGGCCTGCGGGAGCTGCAGCTTCGAAGCCTCACAGAGA<br>TCTTGAAAGGAGGGGTCTTGATCCAGCGGAACCCCCAGCTCTGCTAC<br>CAGGACACGATTTTGTGGAAGGACATCTTCCACAAGAACAACCAGCT<br>GGCTCTCACACTGATAGACACCAACCGCTCTCGGGCCTGCCACCCCT<br>GTTCTCCGATGTGTAAGGGCTCCCGCTGCTGGGGAGAGAGTTCTGAG<br>GATTGTCAGAGCCTGACGCGCACTGTCTGTGCCGGTGGCTGTGCCCG<br>CTGCAAGGGGCCACTGCCCACTGACTGCTGCCATGAGCAGTGTGCTG<br>CCGGCTGCACGGGCCCCAAGCACTCTGACTGCCTGGCCTGCCTCCAC<br>TTCAACCACAGTGGCATCTGTGAGCTGCACTGCCCAGCCCTGGTCAC<br>CTACAACACAGACACGTTTGAGTCCATGCCCAATCCCGAGGGCCGGT<br>ATACATTCGGCGCCAGCTGTGTGACTGCCTGTCCCTACAACTACCTT<br>TCTACGGACGTGGGATCCTGCACCCTCGTCTGCCCCCTGCACAACCA<br>AGAGGTGACAGCAGAGGATGGAACACAGCGGTGTGAGAAGTGCAGCA<br>AGCCCTGTGCCCGAGTGTGCTATGGTCTGGGCATGGAGCACTTGCGA<br>GAGGTGAGGGCAGTTACCAGTGCCAATATCCAGGAGTTTGCTGGCTG<br>CAAGAAGATCTTTGGGAGCCTGGCATTTCTGCCGGAGAGCTTTGATG<br>GGGACCCAGCCTCCAACACTGCCCCGCTCCAGCCAGAGCAGCTCCAA<br>GTGTTTGAGACTCTGGAAGAGATCACAGGTTACCTATACATCTCAGC<br>ATGGCCGGACAGCCTGCCTGACCTCAGCGTCTTCCAGAACCTGCAAG<br>TAATCCGGGGACGAATTCTGCACAATGGCGCCTACTCGCTGACCCTG<br>CAAGGGCTGGGCATCAGCTGGCTGGGGCTGCGCTCACTGAGGGAACT<br>GGGCAGTGGACTGGCCCTCATCCACCATAACACCCACCTCTGCTTCG<br>TGCACACGGTGCCCTGGGACCAGCTCTTTCGGAACCCGCACCAAGCT<br>CTGCTCCACACTGCCAACCGGCCAGAGGACGAGTGTGTGGGCGAGGG<br>CCTGGCCTGCCACCAGCTGTGCGCCCGAGGGCACTGCTGGGGTCCAG<br>GGCCCACCCAGTGTGTCAACTGCAGCCAGTTCCTTCGGGGCCAGGAG<br>TGCGTGGAGGAATGCCGAGTACTGCAGGGGCTCCCCAGGGAGTATGT<br>GAATGCCAGGCACTGTTTGCCGTGCCACCCTGAGTGTCAGCCCCAGA<br>ATGGCTCAGTGACCTGTTTTGGACTGGAGGCTGACCAGTGTGTGGCC<br>TGTGCCCACTATAAGGACCCTCCCTTCTGCGTGGCCCGCTGCCCCAG<br>CGGTGTGAAACCTGACCTCTCCTACATGCCCATCTGGAAGTTTCCAG<br>ATGAGGAGGGCGCATGCCAGCCTTGCCCCATCAACTGCACCCACTCC<br>TGTGTGGACCTGGATGACAAGGGCTGCCCCGCCGAGCAGAGAGCCAG<br>CCCTCTGACGGTCGACGGTGGTAGTCCGACACCTCCGACACCTGGGG<br>GTGGTTCTGCAGACAAAACTCACACATGCCCACCGTGCCCAGCACCT<br>GAACTCCTGGGGGGACCGTCAGTCTTCCTCTTCCCCCCAAAACCCAA<br>GGACACCCTCATGATCTCCCGGACCCCTGAGGTCACATGCGTGGTGG<br>TGGACGTGAGCCACGAAGACCCTGAGGTCAAGTTCAACTGGTACGTG<br>GACGGCGTGGAGGTGCATAATGCCAAGACAAAGCCGCGGGAGGAGCA |

TABLE 34-continued

Antigens

| SEQ ID NO | Name | Sequence |
|---|---|---|
| | | GTACAACAGCACGTACCGTGTGGTCAGCGTCCTCACCGTCCTGCACC<br>AGGACTGGCTGAATGGCAAGGAGTACAAGTGCAAGGTCTCCAACAAA<br>GCCCTCCCAGCCCCCATCGAGAAAACCATCTCCAAAGCCAAAGGGCA<br>GCCCCGAGAACCACAGGTGTACACCCTGCCCCCATGCCGGGATGAGC<br>TGACCAAGAACCAGGTCAGCCTGTGGTGCCTGGTCAAAGGCTTCTAT<br>CCCAGCGACATCGCCGTGGAGTGGGAGAGCAATGGGCAGCCGGAGAA<br>CAACTACAAGACCACGCCTCCCGTGCTGGACTCCGACGGCTCCTTCT<br>TCCTCTACAGCAAGCTCACCGTGGACAAGAGCAGGTGGCAGCAGGGG<br>AACGTCTTCTCATGCTCCGTGATGCATGAGGCTCTGCACAACCACTA<br>CACGCAGAAGAGCCTCTCCCTGTCTCCGGGTAAATCCGGAGGCCTGA<br>ACGACATCTTCGAGGCCCAGAAGATTGAATGGCACGAG |
| 8 | Her2 ECD (pertuzumab KO)-Fc (knob) | TQVCTGTDMKLRLPASPETHLDMLRHLYQGCQVVQGNLELTYLPTNA<br>SLSFLQDIQEVQGYVLIAHNQVRQVPLQRLRIVRGTQLFEDNYALAV<br>LDNGDPLNNTTPVTGASPGGLRELQLRSLTEILKGGVLIQRNPQLCY<br>QDTILWKDIFHKNNQLALTLIDTNRSRACHPCSPMCKGSRCWGESSE<br>DCQSLTRTVCAGGCARCKGPLPTDCCHEQCAAGCTGPKHSDCLACLH<br>FNHSGICELHCPALVTYNTDTRESMPNPEGRYRFGASCVTACPYNYL<br>STDRGSCTLVCPLANQEVTAEDGTQRCEKCSKPCARVCYGLGMEHLR<br>EVRAVTSANIQEFAGCKKIFGSLAFLPESFDGDPASNTAPLQPEQLQ<br>VFETLEEITGYLYISAWPDSLPDLSVFQNLQVIRGRILHNGAYSLTL<br>QGLGISWLGLRSLRELGSGLALIHHNTHLCFVHTVPWDQLFRNPHQA<br>LLHTANRPEDECVGEGLACHQLCARGHCWGPGPTQCVNCSQFLRGQE<br>CVEECRVLQGLPREYVNARHCLPCHPECQPQNGSVTCFGLEADQCVA<br>CAHYKDPPFCVARCPSGVKPDLSYMPIWKFPDEEGACQPCPINCTHS<br>CVDLDDKGCPAEQRASPLTVDGGSPTPPTPGGGSADKTHTCPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPAPIEKTISKAKGQPREPQVYTLPPCRDELTKNQVSLWCLVKGFY<br>PSDIAVEWESNGQPENNYKTTPPVLDSDGSFFLYSKLTVDKSRWQQG<br>NVFSCSVMHEALHNHYTQKSLSLSPGKSGGLNDIFEAQKIEWHE |
| 7 | Her2 ECD (pertuzumab KO)-Fc (knob) DNA | ACCCAAGTGTGCACCGGCACAGACATGAAGCTGCGGCTCCCTGCCAG<br>TCCCGAGACCCACCTGGACATGCTCCGCCACCTCTACCAGGGCTGCC<br>AGGTGGTGCAGGGAAACCTGGAACTCACCTACCTGCCCACCAATGCC<br>AGCCTGTCCTTCCTGCAGGATATCCAGGAGGTGCAGGGCTACGTGCT<br>CATCGCTCACAACCAAGTGAGGCAGGTCCCACTGCAGAGGCTGCGGA<br>TTGTGCGAGGCACCCAGCTCTTTGAGGACAACTATGCCCTGGCCGTG<br>CTAGACAATGGAGACCCGCTGAACAATACCACCCCTGTCACAGGGGC<br>CTCCCCAGGAGGCCTGCGGGAGCTGCAGCTTCGAAGCCTCACAGAGA<br>TCTTGAAAGGAGGGGTCTTGATCCAGCGGAACCCCCAGCTCTGCTAC<br>CAGGACACGATTTTGTGGAAGGACATCTTCCACAAGAACAACCAGCT<br>GGCTCTCACACTGATAGACACCAACCGCTCTCGGGCCTGCCACCCCT<br>GTTCTCCGATGTGTAAGGGCTCCCGCTGCTGGGGAGAGAGTTCTGAG<br>GATTGTCAGAGCCTGACGCGCACTGTCTGTGCCGGTGGCTGTGCCCG<br>CTGCAAGGGGCCACTGCCCACTGACTGCTGCCATGAGCAGTGTGCTG<br>CCGGCTGCACGGGCCCCAAGCACTCTGACTGCCTGGCCTGCCTCCAC<br>TTCAACCACAGTGGCATCTGTGAGCTGCACTGCCCAGCCCTGGTCAC<br>CTACAACACAGACACGCGGGAGTCCATGCCCAATCCCGAGGGCCGGT<br>ATAGATTCGGCGCCAGCTGTGTGACTGCCTGTCCCTACAACTACCTT<br>TCTACGGACCGGGATCCTGCACCCTCGTCTGCCCCCTGGCCAACCA<br>AGAGGTGACAGCAGAGGATGGAACACAGCGGTGTGAGAAGTGCAGCA<br>AGCCCTGTGCCCGAGTGTGCTATGGTCTGGGCATGGAGCACTTGCGA<br>GAGGTGAGGGCAGTTACCAGTGCCAATATCCAGGAGTTTGCTGGCTG<br>CAAGAAGATCTTTGGGAGCCTGGCATTTCTGCCGGAGAGCTTTGATG<br>GGGACCCAGCCTCCAACACTGCCCCGCTCCAGCCAGAGCAGCTCCAA<br>GTGTTTGAGACTCTGGAAGAGATCACAGGTTACCTATACATCTCAGC<br>ATGGCCGGACAGCCTGCCTGACCTCAGCGTCTTCCAGAACCTGCAAG<br>TAATCCGGGGACGAATTCTGCACAATGGCGCCTACTCGCTGACCCTG<br>CAAGGGCTGGGCATCAGCTGGCTGGGGCTGCGCTCACTGAGGGAACT<br>GGGCAGTGGACTGGCCCTCATCCACCATAACACCCACCTCTGCTTCG<br>TGCACACGGTGCCCTGGGACCAGCTCTTTCGGAACCCGCACCAAGCT<br>CTGCTCCACACTGCCAACCGGCCAGAGGACGAGTGTGTGGGCGAGGG<br>CCTGGCCTGCCACCAGCTGTGCGCCCGAGGGCACTGCTGGGGTCCAG<br>GGCCCACCCAGTGTGTCAACTGCAGCCAGTTCCTTCGGGGCCAGGAG<br>TGCGTGGAGGAATGCCGAGTACTGCAGGGGCTCCCCAGGGAGTATGT<br>GAATGCCAGGCACTGTTTGCCGTGCCACCCTGAGTGTCAGCCCCAGA<br>ATGGCTCAGTGACCTGTTTTGGACTGGAGGCTGACCAGTGTGTGGCC<br>TGTGCCCACTATAAGGACCCTCCCTTCTGCGTGGCCCGCTGCCCCAG<br>CGGTGTGAAACCTGACCTCTCCTACATGCCCATCTGGAAGTTTCCAG<br>ATGAGGAGGGCGCATGCCAGCCTTGCCCCATCAACTGCACCCACTCC<br>TGTGTGGACCTGGATGACAAGGGCTGCCCCGCCGAGCAGAGAGCCAG<br>CCCTCTGACGGTCGACGGTGGTAGTCCGACACCTCCGACACCCGGGG<br>GTGGTTCTGCAGACAAAACTCACACATGCCCACCGTGCCCAGCACCT |

TABLE 34-continued

Antigens

| SEQ ID NO | Name | Sequence |
|---|---|---|
| | | GAACTCCTGGGGGGACCGTCAGTCTTCCTCTTCCCCCCAAAACCCAA<br>GGACACCCTCATGATCTCCCGGACCCCTGAGGTCACATGCGTGGTG<br>TGGACGTGAGCCACGAAGACCCTGAGGTCAAGTTCAACTGGTACGTG<br>GACGGCGTGGAGGTGCATAATGCCAAGACAAAGCCGCGGGAGGAGCA<br>GTACAACAGCACGTACCGTGTGGTCAGCGTCCTCACCGTCCTGCACC<br>AGGACTGGCTGAATGGCAAGGAGTACAAGTGCAAGGTCTCCAACAAA<br>GCCCTCCCAGCCCCCATCGAGAAAACCATCTCCAAAGCCAAAGGGCA<br>GCCCCGAGAACCACAGGTGTACACCCTGCCCCCATGCCGGGATGAGC<br>TGACCAAGAACCAGGTCAGCCTGTGGTGCCTGGTCAAAGGCTTCTAT<br>CCCAGCGACATCGCCGTGGAGTGGGAGAGCAATGGGCAGCCGGAGAA<br>CAACTACAAGACCACGCCTCCCGTGCTGGACTCCGACGGCTCCTTCT<br>TCCTCTACAGCAAGCTCACCGTGGACAAGAGCAGGTGGCAGCAGGGG<br>AACGTCTTCTCATGCTCCGTGATGCATGAGGCTCTGCACAACCACTA<br>CACGCAGAAGAGCCTCTCCCTGTCTCCGGGTAAATCCGGAGGCCTGA<br>ACGACATCTTCGAGGCCCAGAAGATTGAATGGCACGAG |
| 10 | Her2 ECD (trastuzumab KO)-Fc (knob) | TQVCTGTDMKLRLPASPETHLDMLRHLYQGCQVVQGNLELTYLPTNA<br>SLSFLQDIQEVQGYVLIAHNQVRQVPLQRLRIVRGTQLFEDNYALAV<br>LDNGDPLNNTTPVTGASPGGLRELQLRSLTEILKGGVLIQRNPQLCY<br>QDTILWKDIFHKNNQLALTLIDTNRSRACHPCSPMCKGSRCWGESSE<br>DCQSLTRTVCAGGCARCKGPLPTDCCHEQCAAGCTGPKHSDCLACLH<br>FNHSGICELHCPALVTYNTDTFESMPNPEGRYTFGASCVTACPYNYL<br>STDVGSCTLVCPLHNQEVTAEDGTQRCEKCSKPCARVCYGLGMEHLR<br>EVRAVTSANIQEFAGCKKIFGSLAFLPESFDGDPASNTAPLQPEQLQ<br>VFETLEEITGYLYISAWPDSLPDLSVFQNLQVIRGRILHNGAYSLTL<br>QGLGISWLGLRSLRELGSGLALIHHNTHLCFVHTVPWDQLFRNPHQA<br>LLHTANRPEDECVGEGLACHQLCARGHCWGPGPTQCVNCSQFLRGQE<br>CVEECRVLQGLPREYVNARHCLPCHPECQPQNGSVTCFGLEARQCVA<br>CAHYKDRRCVARCPSGVKPDLSYMPIWKFPDEEGACQPCPINCTHSC<br>VDLDDKGCPAEQRASPLTVDGGSPTPPTPGGGSADKTHTCPPCPAPE<br>LLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKA<br>LPAPIEKTISKAKGQPREPQVYTLPPCRDELTKNQVSLWCLVKGFYP<br>SDIAVEWESNGQPENNYKTTPPVLDSDGSFFLYSKLTVDKSRWQQGN<br>VFSCSVMHEALHNHYTQKSLSLSPGKSGGLNDIFEAQKIEWHE |
| 9 | Her2 ECD (trastuzumab KO)-Fc (knob) DNA | ACCCAAGTGTGCACCGGCACAGACATGAAGCTGCGGCTCCCTGCCAG<br>TCCCGAGACCCACCTGGACATGCTCCGCCACCTCTACCAGGGCTGCC<br>AGGTGGTGCAGGGAAACCTGGAACTCACCTACCTGCCCACCAATGCC<br>AGCCTGTCCTTCCTGCAGGATATCCAGGAGGTGCAGGGCTACGTGCT<br>CATCGCTCACAACCAAGTGAGGCAGGTCCCACTGCAGAGGCTGCGGA<br>TTGTGCGAGGCACCCAGCTCTTTGAGGACAACTATGCCCTGGCCGTG<br>CTAGACAATGGAGACCCGCTGAACAATACCACCCCTGTCACAGGGGC<br>CTCCCCAGGAGGCCTGCGGGAGCTGCAGCTTCGAAGCCTCACAGAGA<br>TCTTGAAAGGAGGGGTCTTGATCCAGCGGAACCCCCAGCTCTGCTAC<br>CAGGACACGATTTTGTGGAAGGACATCTTCCACAAGAACAACCAGCT<br>GGCTCTCACACTGATAGACACCAACCGCTCTCGGGCCTGCCACCCCT<br>GTTCTCCGATGTGTAAGGGCTCCCGCTGCTGGGGAGAGAGTTCTGAG<br>GATTGTCAGAGCCTGACGCGCACTGTCTGTGCCGGTGGCTGTGCCCG<br>CTGCAAGGGGCCACTGCCCACTGACTGCTGCCATGAGCAGTGTGCTG<br>CCGGCTGCACGGGCCCCAAGCACTCTGACTGCCTGGCCTGCCTCCAC<br>TTCAACCACAGTGGCATCTGTGAGCTGCACTGCCCAGCCCTGGTCAC<br>CTACAACACAGACACGTTTGAGTCCATGCCCAATCCCGAGGGCCGGT<br>ATACATTCGGCGCCAGCTGTGTGACTGCCTGTCCCTACAACTACCTT<br>TCTACGGACGTGGGATCCTGCACCCTCGTCTGCCCCCTGCACAACCA<br>AGAGGTGACAGCAGAGGATGGAACACAGCGGTGTGAGAAGTGCAGCA<br>AGCCCTGTGCCCGAGTGTGCTATGGTCTGGGCATGGAGCACTTGCGA<br>GAGGTGAGGGCAGTTACCAGTGCCAATATCCAGGAGTTTGCTGGCTG<br>CAAGAAGATCTTTGGGAGCCTGGCATTTCTGCCGGAGAGCTTTGATG<br>GGGACCCAGCCTCCAACACTGCCCCGCTCCAGCCAGAGCAGCTCCAA<br>GTGTTTGAGACTCTGGAAGAGATCACAGGTTACCTATACATCTCAGC<br>ATGGCCGGACAGCCTGCCTGACCTCAGCGTCTTCCAGAACCTGCAAG<br>TAATCCGGGGACGAATTCTGCACAATGGCGCCTACTCGCTGACCCTG<br>CAAGGGCTGGGCATCAGCTGGCTGGGCTGCGCTCACTGAGGGAACT<br>GGGCAGTGGACTGGCCCTCATCCACCATAACACCCACCTCTGCTTCG<br>TGCACACGGTGCCCTGGGACCAGCTCTTTCGGAACCCGCACCAAGCT<br>CTGCTCCACACTGCCAACCGGCCAGAGGACGAGTGTGTGGGCGAGGG<br>CCTGGCCTGCCACCAGCTGTGCGCCCGAGGGCACTGCTGGGGTCCAG<br>GGCCCACCCAGTGTGTCAACTGCAGCCAGTTCCTTCGGGGCCAGGAG<br>TGCGTGGAGGAATGCCGAGTACTGCAGGGGCTCCCCAGGGAGTATGT<br>GAATGCCAGGCACTGTTTGCCGTGCCACCCTGAGTGTCAGCCCCAGA<br>ATGGCTCAGTGACCTGTTTTGGACTGGAGGCTCGGCAGTGTGTGGCC<br>TGTGCCCACTATAAGGACAGACGGTGCGTGGCCCGCTGCCCCAGCGG<br>TGTGAAACCTGACCTCTCCTACATGCCCATCTGGAAGTTTCCAGATG |

TABLE 34-continued

Antigens

| SEQ ID NO | Name | Sequence |
|---|---|---|
| | | AGGAGGGCGCATGCCAGCCTTGCCCCATCAACTGCACCCACTCCTGT<br>GTGGACCTGGATGACAAGGGCTGCCCCGCCGAGCAGAGAGCCAGCCC<br>TCTGACGGTCGACGGTGGTAGTCCGACACCTCCGACACCCGGGGGTG<br>GTTCTGCAGACAAAACTCACACATGCCCACCGTGCCCAGCACCTGAA<br>CTCCTGGGGGGACCGTCAGTCTTCCTCTTCCCCCCAAAACCCAAGGA<br>CACCCTCATGATCTCCCGGACCCCTGAGGTCACATGCGTGGTGGTGG<br>ACGTGAGCCACGAAGACCCTGAGGTCAAGTTCAACTGGTACGTGGAC<br>GGCGTGGAGGTGCATAATGCCAAGACAAAGCCGCGGGAGGAGCAGTA<br>CAACAGCACGTACCGTGTGGTCAGCGTCCTCACCGTCCTGCACCAGG<br>ACTGGCTGAATGGCAAGGAGTACAAGTGCAAGGTCTCCAACAAAGCC<br>CTCCCAGCCCCCATCGAGAAAACCATCTCCAAAGCCAAAGGGCAGCC<br>CCGAGAACCACAGGTGTACACCCTGCCCCCATGCCGGGATGAGCTGA<br>CCAAGAACCAGGTCAGCCTGTGGTGCCTGGTCAAAGGCTTCTATCCC<br>AGCGACATCGCCGTGGAGTGGGAGAGCAATGGGCAGCCGGAGAACAA<br>CTACAAGACCACGCCTCCCGTGCTGGACTCCGACGGCTCCTTCTTCC<br>TCTACAGCAAGCTCACCGTGGACAAGAGCAGGTGGCAGCAGGGGAAC<br>GTCTTCTCATGCTCCGTGATGCATGAGGCTCTGCACAACCACTACAC<br>GCAGAAGAGCCTCTCCCTGTCTCCGGGTAAATCCGGAGGCCTGAACG<br>ACATCTTCGAGGCCCAGAAGATTGAATGGCACGAG |

TABLE 35

Full-length antibody sequences of common light chain
antibody "D1 der"

| SEQ ID NO | Name | Sequence |
|---|---|---|
| 159 | Trastuzumab VHCH1-Fc KNOB | EVQLVESGGGLVQPGGSLRLSCAASGFNIKDTYIHWVRQAPGKGLEW<br>VARIYPTNGYTRYADSVKGRFTISADTSKNTAYLQMNSLRAEDTAVY<br>YCSRWGGDGFYAMDYWGQGTLVTVSSASTKGPSVFPLAPSSKSTSGG<br>TAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAP<br>ELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNK<br>ALPAPIEKTISKAKGQPREPQVYTLPPCRDELTKNQVSLWCLVKGFY<br>PSDIAVEWESNGQPENNYKTTPPVLDSDGSFFLYSKLTVDKSRWQQG<br>NVFSCSVMHEALHNHYTQKSLSLSPGK |
| 160 | Trastuzumab VHCH1- Fc KNOB DNA | GAAGTGCAATTGGTGGAAAGCGGCGGCGGCCTGGTGCAACCGGGCGGCAGCC<br>TGCGTCTGAGCTGCGCGGCCTCCGGATTTAACATAAAGGACACATACATCCA<br>CTGGGTGCGCCAAGCACCTGGGAAGGGTCTCGAGTGGGTGGCTCGGATTTAC<br>CCAACAAATGGCTACACCAGGTATGCGGATAGCGTGAAAGGCCGTTTTACCA<br>TTTCAGCTGATACTTCGAAGAACACCGCCTATCTGCAAATGAACAGCCTGCG<br>TGCGGAAGATACGGCCGTGTATTATTGCTCGCGTTGGGGAGGAGACGGGTTC<br>TATGCTATGGATTACTGGGGCCAAGGCACCCTGGTGACGGTTAGCTCAGCTA<br>GCACCAAGGGCCCATCGGTCTTCCCCCTGGCACCCTCCTCCAAGAGCACCTC<br>TGGGGGCACAGCGGCCCTGGGCTGCCTGGTCAAGGACTACTTCCCCGAACCG<br>GTGACGGTGTCGTGGAACTCAGGCGCCCTGACCAGCGGCGTGCACACCTTCC<br>CGGCTGTCCTACAGTCCTCAGGACTCTACTCCCTCAGCAGCGTGGTGACCGT<br>GCCCTCCAGCAGCTTGGGCACCCAGACCTACATCTGCAACGTGAATCACAAG<br>CCCAGCAACACCAAGGTGGACAAGAAAGTTGAGCCCAAATCTTGTGACAAAA<br>CTCACACATGCCCACCGTGCCCAGCACCTGAACTCCTGGGGGGACCGTCAGT<br>CTTCCTCTTCCCCCCAAAACCCAAGGACACCCTCATGATCTCCCGGACCCCT<br>GAGGTCACATGCGTGGTGGTGGACGTGAGCCACGAAGACCCTGAGGTCAAGT<br>TCAACTGGTACGTGGACGGCGTGGAGGTGCATAATGCCAAGACAAAGCCGCG<br>GGAGGAGCAGTACAACAGCACGTACCGTGTGGTCAGCGTCCTCACCGTCCTG<br>CACCAGGACTGGCTGAATGGCAAGGAGTACAAGTGCAAGGTCTCCAACAAA<br>CCCTCCCAGCCCCCATCGAGAAAACCATCTCCAAAGCCAAAGGGCAGCCCCG<br>AGAACCACAGGTGTACACCCTGCCCCCATGCCGGGATGAGCTGACCAAGAAC<br>CAGGTCAGCCTGTGGTGCCTGGTCAAAGGCTTCTATCCCAGCGACATCGCCG<br>TGGAGTGGGAGAGCAATGGGCAGCCGGAGAACAACTACAAGACCACGCCTCC<br>CGTGCTGGACTCCGACGGCTCCTTCTTCCTCTACAGCAAGCTCACCGTGGAC<br>AAGAGCAGGTGGCAGCAGGGGAACGTCTTCTCATGCTCCGTGATGCATGAGG<br>CTCTGCACAACCACTACACGCAGAAGAGCCTCTCCCTGTCTCCGGGTAAA |

TABLE 35-continued

Full-length antibody sequences of common light chain antibody "D1 der"

| SEQ ID NO | Name | Sequence |
|---|---|---|
| 161 | Common light chain VLCL | DIQMTQSPSSLSASVGDRVTITCKASQDVSTAVAWYQQKPGKAPKLLIYSAS FRYTGVPSRFSGSRSGTDFTLTISSLQPEDFATYYCQQHYTTPPTFGQGTKV EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC |
| 162 | Common light chain VLCL - DNA | GACATCCAGATGACCCAGAGCCCCAGCAGCCTGTCTGCCAGCGTGGGCGACAGAGTG ACCATCACATGCAAGGCCAGCCAGGACGTGTCCACAGCCGTGGCCTGGTATCAGCAG AAGCCTGGCAAGGCCCCCAAGCTGCTGATCTACAGCGCCAGCTTCCGGTACACCGGC GTGCCCAGCAGATTCAGCGGCAGCAGATCCGGCACCGACTTCACCCTGACCATCAGC TCCCTGCAGCCCGAGGACTTCGCCACCTACTACTGCCAGCAGCACTACACCACCCCC CCCACATTTGGCCAGGGCACCAAGGTGGAAATCAAGCGTACGGTGGCTGCACCATCT GTCTTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGATAAC GCCCTCCAATCGGGTAACTCCCAGGAGAGTGTCACAGAGCAGGACAGCAAGGACAGC ACCTACAGCCTCAGCAGCACCCTGACGCTGAGCAAAGCAGACTACGAGAAACACAAA GTCTACGCCTGCGAAGTCACCCATCAGGGCCTGAGCTCGCCCGTCACAAAGAGCTTC AACAGGGGAGAGTGT |
| 163 | Pertuzumab VHCH1 Fc hole | EVQLVESGGGLVQPGGSLRLSCAASGFTFNDYTMDWVRQAPGKGLEWVADVN PNSGGSIVNRRFKGRFTLSVDRSKNTLYLQMNSLRAEDTAVYYCARNLGPFF YFDYWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLH QDWLNGKEYKCKVSNKALPAPIEKTISKAKGQPREPQVCTLPPSRDELTKNQ VSLSCAVKGFYPSDIAVEWESNGQPENNYKTTPPVLDSDGSFFLVSKLTVDK SRWQQGNVFSCSVMHEALHNHYTQKSLSLSPGK |
| 164 | Pertuzumab VHCH1 Fc hole DNA | GAAGTTCAGCTGGTTGAAAGCGGTGGTGGTCTGGTTCAGCCTGGTGGTAGCC TGCGTCTGAGCTGTGCAGCAAGCGGTTTTACCTTTAACGATTATACCATGGA TTGGGTTCGTCAGGCACCGGGTAAAGGTCTGGAATGGGTTGCAGATGTTAAT CCGAATAGCGGTGGTAGCATTGTTAACCGTCGTTTTAAAGGTCGTTTTACCC TGAGCGTTGATCGTAGCAAAAATACCCTGTATCTGCAAATGAATAGTCTGCG TGCAGAGGATACCGCAGTGTATTATTGTGCACGTAACCTGGGTCCGTTCTTC TACTTTGATTATTGGGGTCAGGGCACCCTGGTTACCGTTAGCAGCGCTAGCA CCAAGGGCCCAAGCGTGTTCCCTCTGGCCCCCAGCAGCAAGAGCACAAGCGG CGGAACAGCCGCCTGGGCTGCCTGGTCAAGGACTACTTCCCCGAGCCCGTG ACAGTGTCCTGGAACAGCGGAGCCCTGACCAGCGGCGTGCACACCTTTCCAG CCGTGCTGCAGAGCAGCGGCCTGTACAGCCTGAGCAGCGTGGTCACAGTGCC TAGCAGCAGCCTGGGCACCCAGACCTACATCTGCAACGTGAACCACAAGCCC AGCAACACCAAGGTGGACAAGAAGGTGGAGCCCAAGAGCTGCGACAAGACCC ACACCTGTCCCCCTTGTCCTGCCCCTGAGCTGCTGGGCGGACCCAGCGTGTT CCTGTTCCCCCCAAAGCCCAAGGACACCCTGATGATCAGCCGGACCCCCGAA GTGACCTGCGTGGTGGTGGACGTGTCCCACGAGGACCCTGAAGTGAAGTTCA ATTGGTACGTGGACGGCGTGGAGGTGCACAATGCCAAGACCAAGCCCCGGGA GGAACAGTACAACAGCACCTACCGGGTGGTGTCCGTGCTGACCGTGCTGCAC CAGGACTGGCTGAACGGCAAAGAGTACAAGTGCAAGGTCTCCAACAAGGCCC TGCCTGCCCCCATCGAGAAAACCATCAGCAAGGCCAAGGGCCAGCCCAGAGA ACCCCAGGTGTGCACCCTGCCCCCCAGCAGAGATGAGCTGACCAAGAACCAG GTGTCCCTGAGCTGTGCCGTCAAGGGCTTCTACCCCAGCGATATCGCCGTGG AGTGGGAGAGCAACGGCCAGCCTGAGAACAACTACAAGACCACCCCCCCTGT GCTGGACAGCGACGGCAGCTTCTTCCTGGTGTCCAAACTGACCGTGGACAAG AGCCGGTGGCAGCAGGGCAACGTGTTCAGCTGCAGCGTGATGCACGAGGCCC TGCACAACCACTACACCCAGAAGTCCCTGAGCCTGAGCCCCGGCAAG |

Example 21: Generation of Trivalent HER2 (Extracellular Domain IV)—HER2 (Extracellular Domain II)—Transferrin Specific Antibodies Generation of the Expression Plasmids Desired proteins were expressed by transient transfection of human embryonic kidney cells (HEK 293). For the expression of a desired gene/protein (e.g. antibody-Fab multimeric protein) a transcription unit comprising the following functional elements was used:
The immediate early enhancer and promoter from the human cytomegalovirus (P-CMV) including intron A,
a murine immunoglobulin heavy chain signal sequence (SS),
a gene/protein to be expressed (e.g. full length antibody heavy chain), and
the bovine growth hormone polyadenylation sequence (BGH pA).

Besides the expression unit/cassette including the desired gene to be expressed the basic/standard mammalian expression plasmid contains:
An origin of replication from the vector pUC18 which allows replication of this plasmid in *E. coli*, and
a beta-lactamase gene which confers ampicillin resistance in *E. coli*

Expression plasmids coding for the following antibody+/−scFab proteins were constructed:

1. BBB-0580 Trivalent Herceptarg-scFab(8D3)

Heavy chain knob (HERCEPTIN® (Trastuzumab) (D98E)(IgG1) knob SS-(G4S)4-VL-Ck-(G4S)6-GG-VH-CH1) (Seq. 21832/SEQ ID NO.: 165)

Composition of the knob HERCEPTIN® (Trastuzumab) (D98E)-scFab(8D3) heavy chain fusion protein:

HERCEPTIN® (Trastuzumab) (D89E) human IgG1 heavy chain without C-terminal Lys containing CH3 knob mutation T366W and the S354C mutation for the formation of an additional disulfide bridge
Glycine-Serine-linker
Variable light chain domain (VL) variant of the mouse 8D3 anti-transferrin antibody (Boado et al., 2009)
Human C-kappa light chain
Glycine-Serine-linker
Variable heavy chain domain (VL) variant of the mouse 8D3 anti-transferrin antibody (Boado et al., 2009)
Human IgG1 CHI heavy chain domain
Heavy chain hole (Pertuzumab(aff.mat.)(IgG1) hole SS (Seq. ID NO.: 163) Composition of the hole Pertuzumab (aff.mat.) heavy chain protein:
Pertuzumab(aff.mat.) human IgG1 heavy chain containing the CH3 hole mutations T366S, Y407V and L368A and the Y349C mutation for the formation of an additional disulfide bridge
Light chain (CLC-Herc combo) (clone D1-derSEQ ID NO.: 161)
See example 14

2. BBB-0581 Trivalent Herceptarg(LALA)-scFab(8D3)

Heavy chain knob (HERCEPTIN® (Trastuzumab) (D98E)(IgG1) LALA-PG knob SS-(G4S)4-VL-Ck-(G4S)6-GG-VH-CH1) (Seq. 21834, SEQ ID. NO.: 168) Composition of the knob HERCEPTIN® (Trastuzumab) (D98E)-scFab(8D3) heavy chain fusion protein:

HERCEPTIN® (Trastuzumab) (D89E) human IgG1 heavy chain without C-terminal Lys containing:
CH2 mutations L234A, L235A and P329G to impair Fc gamma receptor-mediated interaction with immune effector cells as well as complement activation
CH3 knob mutation T366W and the S354C mutation for the formation of an additional disulfide bridge
Glycine-Serine-linker
Variable light chain domain (VL) variant of the mouse 8D3 anti-transferrin antibody (Boado et al., 2009), SEQ ID NO.: 178
Human C-kappa light chain
Glycine-Serine-linker
Variable heavy chain domain (VL) variant of the mouse 8D3 anti-transferrin antibody (Boado et al., 2009), SEQ ID NO.: 179
Human IgG1 CHI heavy chain domain
Heavy chain hole (Pertuzumab(aff.mat.)(IgG1) LALA-PG hole SS (Seq. 21836, SEQ ID NO.: 169)
Composition of the hole Pertuzumab(aff.mat.) heavy chain protein:
Pertuzumab(aff.mat.) human IgG1 heavy chain containing:
CH2 mutations L234A, L235A and P329G to impair Fc gamma receptor-mediated interaction with immune effector cells as well as complement activation
CH3 hole mutations T366S, L368A and Y407V and the Y349C mutation for the formation of an additional disulfide bridge
CH3 hole mutations H435R and Y436F to avoid protein purification of heavy chain hole-hole dimers
Light chain (CLC-Herc combo) (clone D1-derSEQ ID NO.: 161)
See example 14

3. BBB-0582 Bivalent Herceptarg(LALA) (Control Molecule without BBB-R Binder)

Heavy chain knob (HERCEPTIN® (Trastuzumab) (D98E)(IgG1) LALA-PG (Seq. 21835, SEQ ID. NO.: 170)

Composition of the knob HERCEPTIN® (Trastuzumab) (D98E) heavy chain protein:

HERCEPTIN® (Trastuzumab) (D89E) human IgG1 heavy chain containing:
CH2 mutations L234A, L235A and P329G to impair Fc gamma receptor-mediated interaction with immune effector cells as well as complement activation
CH3 knob mutation T366W and the S354C mutation for the formation of an additional disulfide bridge
Heavy chain hole (Pertuzumab(aff.mat.)(IgG1) LALA-PG hole SS (Seq. 21836 SEQ ID. NO.: 163)
Composition of the hole Pertuzumab(aff.mat.) heavy chain protein:
Pertuzumab(aff.mat.) human IgG1 heavy chain containing:
CH2 mutations L234A, L235A and P329G to impair Fc gamma receptor-mediated interaction with immune effector cells as well as complement activation
CH3 hole mutations T366S, L368A and Y407V and the Y349C mutation for the formation of an additional disulfide bridge
CH3 hole mutations H435R and Y436F to avoid protein purification of hole-hole dimers
Light chain (CLC-Herc combo) (clone D1-derSEQ ID NO.: 161)
See example 14

4. Herceptarg (Control Molecule without BBB-R Binder)

Heavy chain knob (HERCEPTIN® (Trastuzumab) (D98E)(IgG1) (SEQ ID NO.: 171) Composition of the knob HERCEPTIN® (Trastuzumab) (D98E) heavy chain protein:

HERCEPTIN® (Trastuzumab) (D89E) human IgG1 heavy chain containing CH3 knob mutation T366W and the S354C mutation for the formation of an additional disulfide bridge
Heavy chain hole (Pertuzumab(aff.mat.)(IgG1) hole SS (Seq. 21836 SEQ ID. NO.: 163) Composition of the hole Pertuzumab(aff.mat.) heavy chain protein:
Pertuzumab(aff.mat.) human IgG1 heavy chain containing CH3 hole mutations T366S, L368A and Y407V and the Y349C mutation for the formation of an additional disulfide bridge
Light chain (CLC-Herc combo) (clone D1-derSEQ ID NO.: 161)
See example 14

Sequences are shown in tables 36 and 37.

Ref. Boado R J, Zhang Y, Wang Y, Pardridge W M. Engineering and expression of a chimeric transferrin receptor monoclonal antibody for blood-brain barrier delivery in the mouse. Biotechnol Bioeng. 2009; 102(4):1251-8.

Example 22: Purification of Trivalent HER2 (Extracellular Domain IV)—HER2 (Extracellular Domain II)—Transferrin Specific Antibodies and Control Antibodies without BBB-R Binder The antibody chains were generated by transient transfection of HEK293 cells (human embryonic kidney cell line 293-derived) cultivated in F17 Medium (Invitrogen Corp.). For transfection 293—FreeFREET™ Transfection Reagent (Merck, Millipore) was used. The antibody chains were expressed from three different plasmids, coding for the trivalent Herceptarg-scFab(8D3) knob and hole heavy chains and the Herceptarg light chain or the bivalent Herceptarg knob and hole heavy chains and the Herceptarg light chain, respectively. For transfection the three plasmids were used at plasmid ratios of 2:1:1 (LC: HC knob: HC hole) for trivalent Herceptarg-scFab(8D3), of 1:1:2 (LC: HC knob: HC hole) for trivalent Herceptarg(LALA)-scFab(8D3) and bivalent Herceptarg(LALA) and of 2:1:1(LC: HC knob: HC hole) for bivalent Herceptarg. Transfections were performed as specified in the manufacturer's instructions. Antibody-containing cell culture supernatants were harvested seven days after transfection. Supernatants were stored frozen until purification.

Proteins were purified from filtered cell culture supernatants. Supernatants were applied to a protein A SEPHAROSET™ column (GE Healthcare) and washed with PBS pH 7.4. Elution of antibodies was achieved with 100 mM Citarate buffer at pH 3.0 followed by immediate neutralization of the sample to pH 6.5. Aggregated protein and other byproducts were separated from monomeric antibodies by size exclusion chromatography (SEC; SUPERDEX™ 200; GE Healthcare) in 20 mM histidine, 140 mM NaCl, pH 6.0. Every single fraction was analyzed on analytical SEC (MABPAC™ SEC-1, Thermo Scientific) and on a chip-based capillary electrophoresis system (CE-SDS, LABCHIP® GX, Caliper) for the quantification of incompletely assembled molecules and other byproducts. Monomeric antibody fractions without byproducts were pooled. After concentration using a MILLIPORE AMICON® Ultra (30 molecular weight cut off) centrifugal concentrator the protein was stored at −80° C. Analytical characterization of the end product was done by UV protein determination, CE-SDS, size exclusion chromatography, mass spectrometry and also by endotoxin determination.

Example 23: Binding Analysis of Herceptarg-scFab(8D3) and Control Antibodies to BT474-M1 and BA/F3 Cells HER2+BT474-M1 and TfR+BA/F3 cells were used as target cells for binding analysis of Herceptarg-scFab(8D3) and Herceptarg control molecules. BT474-M1 cells were maintained in RPMI 1640 supplemented with 10% fetal calf serum and 2 mL L-glutamine and BA/F3 cells were maintained in RPMI 1640, 10% FCS, 2 mM L-glutamine and 10 ng/ml rmIL-3.

Propagation of Cell Lines Followed Standard Cell Culture Protocols.

Figure 33:
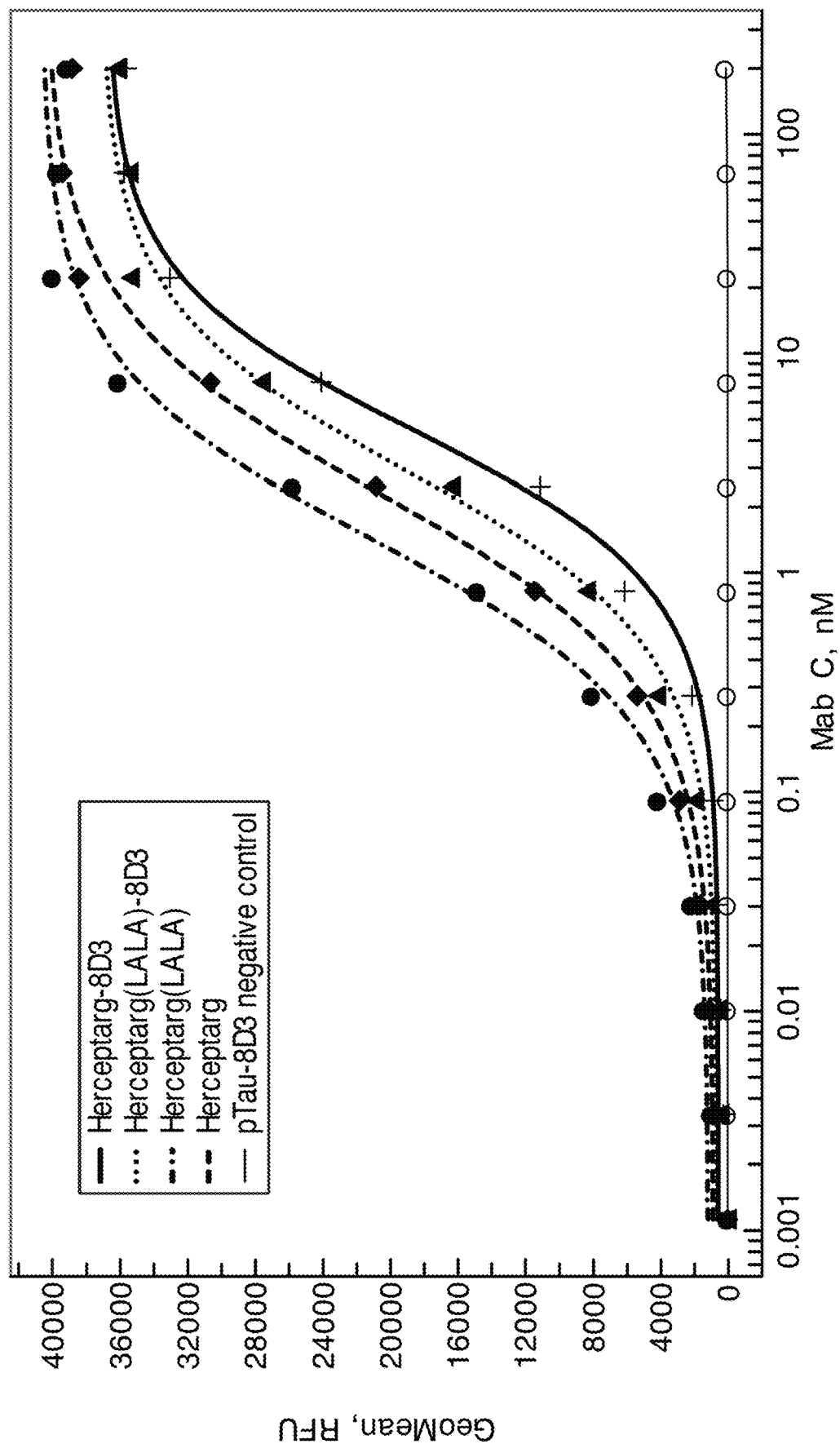
FIG. 33: FACS binding of trispecific antibodies specific for HER2 and transferrin receptor to HER2+BT474-M1 cells. "Herceptarg-8D3" (SEQ ID NOs.: 165, 163, 161) and "Herceptarg (LALA)-8D3" (SEQ ID NOs.: 168, 169, 161) are trispecific, trivalent antibodies specific for extracellular domains II and IV of HER2 and the transferrin receptor. Positive control: "Herceptarg-LALA" (SEQ ID NOs: 170, 169, 161) and "Herceptarg" (SEQ ID NOs.: 171, 163, 161) are bispecific, bivalent antibodies specific for extracellular domains II and IV of HER2. Negative control "pTAU-8D3" is a bispecific antibody specific for the transferrin receptor and pTau (SEQ ID. NOs: 210, 211, 212).
Figure 34:
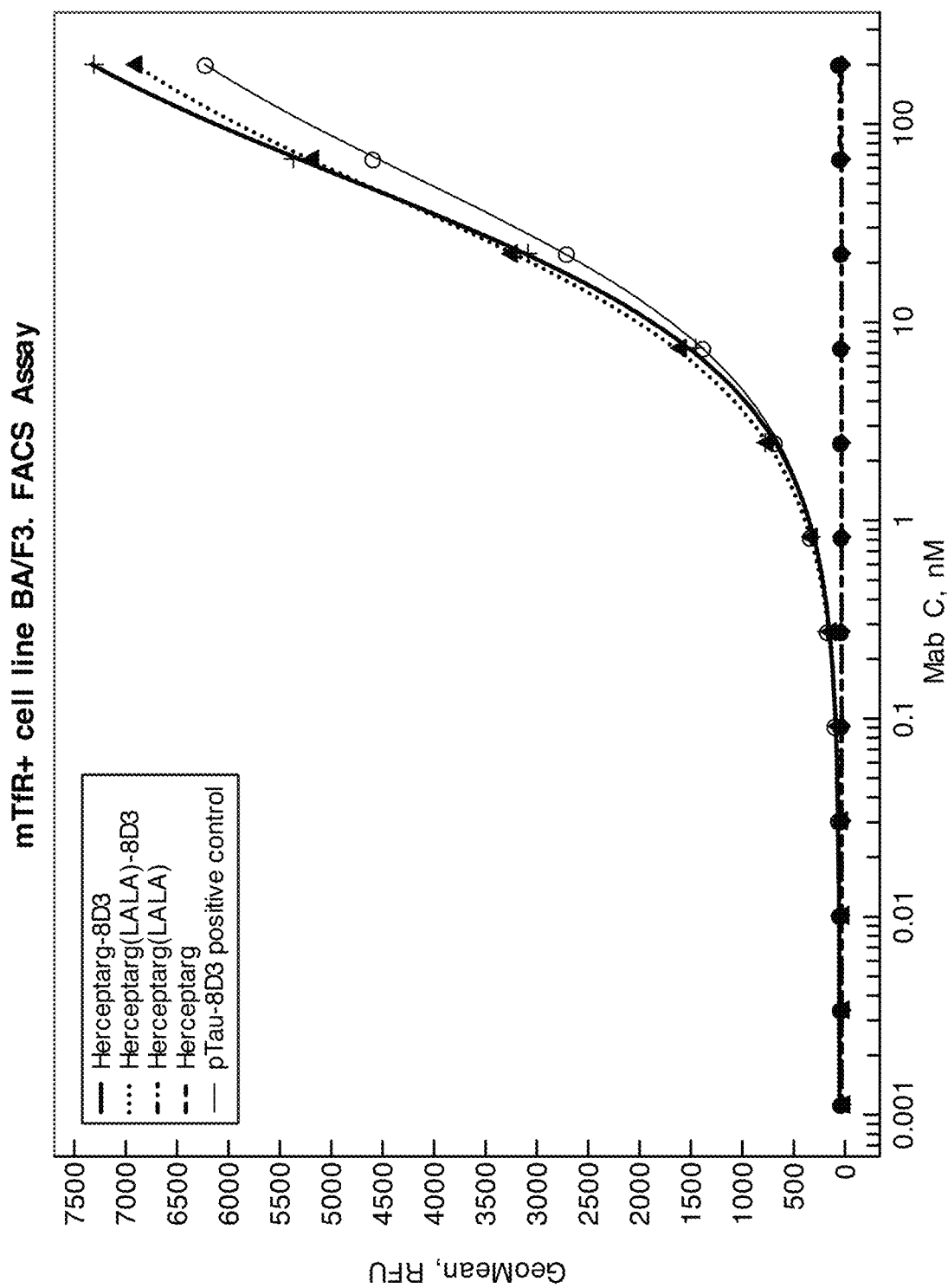
FIG. 34: FACS binding of trispecific antibodies specific for HER2 and transferrin receptor to Transferrin receptor expressing (TfR+) BAF3 cells. "Herceptarg-8D3" (SEQ ID NOs.: 165, 163, 161) and "Herceptarg (LALA)-8D3" (SEQ ID NOs.: 168, 169, 161) are trispecific, trivalent antibodies specific for extracellular domains II and IV of HER2 and the transferrin receptor. Positive control: "Herceptarg-LALA" (SEQ ID NOs: 170, 169, 161) and "Herceptarg" (SEQ ID NOs.: 171, 163, 161) are bispecific, bivalent antibodies specific for extracellular domains II and IV of HER2. Positive control "pTAU-8D3" is a bispecific antibody specific for the transferrin receptor and pTau (SEQ ID. NOs: 210, 211, 212).

BT474-M1 and BA/F3 cells were harvested and resuspended in FACS buffer. 0.2 Mio cells were seeded into a 96 well round bottom plate. The plate was centrifuged at 350 g for 3 min to pellet the cells. The supernatant was removed and the cells were resuspended in 120 µl of the diluted antibodies. The plate was incubated for 1h at 4° C. to allow binding of the antibodies. To remove unbound antibodies the cells were centrifuged again and washed twice with FACS buffer. To detect the antibodies the cells were resuspended in 100 µl diluted goat anti-human Fcγ specific PE-labeled secondary antibody (Jackson ImmunoResearch #109-116-170) and incubated again for 30 min at 4° C. Afterwards the cells were washed twice with FACS buffer, resuspended in 50 µl FACS buffer and the fluorescence was measured with BD Canto II. Results are shown in FIGS. 33 and 34. All Herceptarg antibodies specifically bind to HER2+BT474-M1 cells and the Herceptarg-scFab(8D3) fusion proteins bind to TfR+BA/F3 cells.

Example 24: Proliferation Inhibition Assay with Trivalent HER2 (Extracellular Domain IV)—HER2 (Extracellular Domain II)—Transferrin Specific Antibodies and Control Antibodies without BBB-R Binder on HER2+BT474-M1 Cells The ability of the Herceptarg molecules to inhibit proliferation was assessed in the cell line BT474-M1. Cells in the logarithmic growth phase were detached, counted and $4 \times 10^3$ cells were seeded in 60 µL medium per well of a 96-well cell culture plate. Cells were maintained overnight in the incubator and the following day 60 µL of the respective antibodies diluted in medium were added in form of a dilution series to the cells. After a total incubation time of 5 days cell growth was assessed by CELLTITER-GLO® Luminescent Cell Viability Assay. The assay was performed as recommended by the manufacturer.

Figure 35:
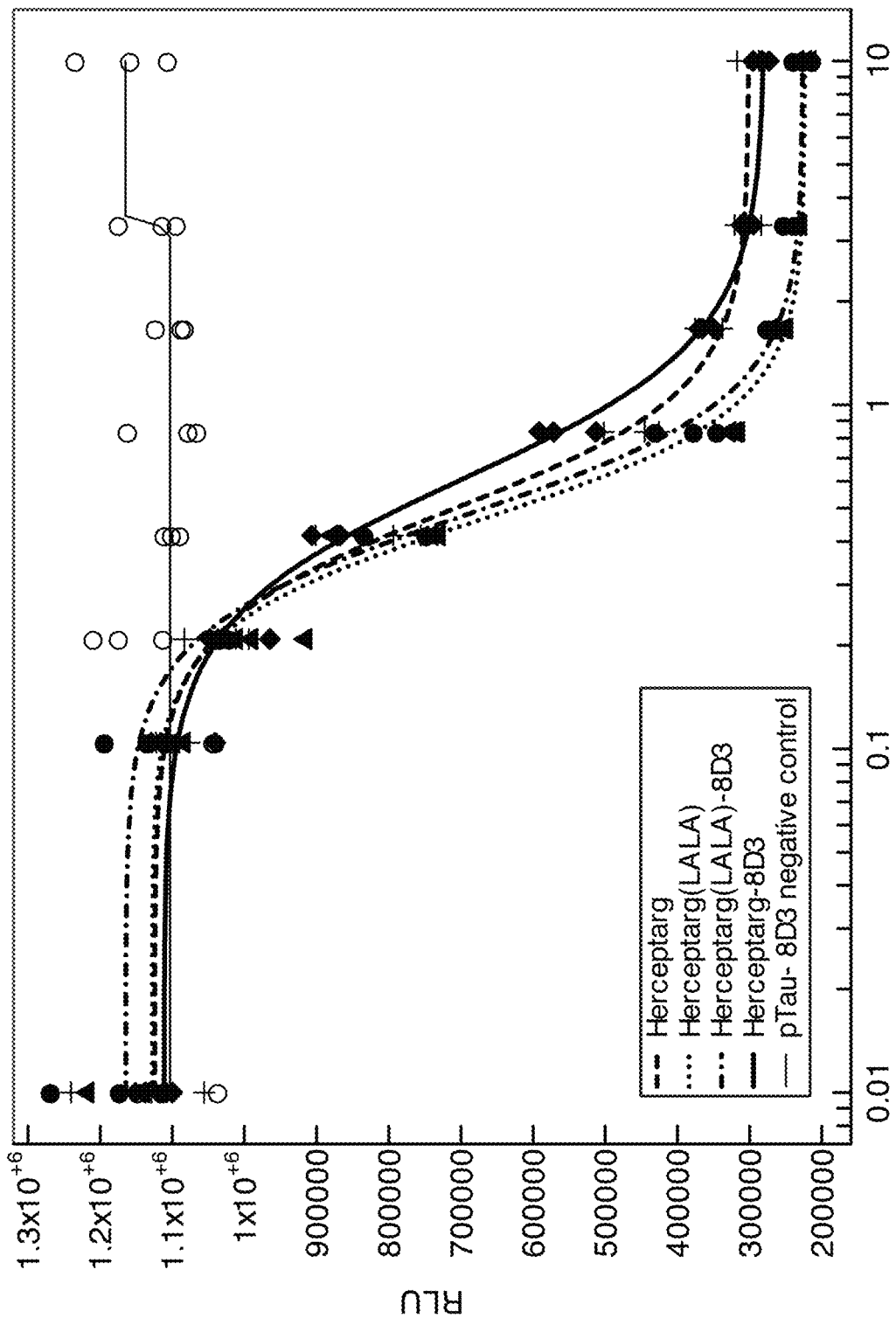
FIG. 35: Proliferation inhibition assay of trispecific antibodies specific for HER2 and transferrin receptor. Herceptarg-8D3" (SEQ ID NOs.: 165, 163, 161) and "Herceptarg (LALA)-8D3" (SEQ ID NOs.: 168, 169, 161) are trispecific, trivalent antibodies specific for extracellular domains II and IV of HER2 and the transferrin receptor. Positive control: "Herceptarg-LALA" (SEQ ID NOs: 170, 169, 161) and "Herceptarg" (SEQ ID NOs.: 171, 163, 161) are bispecific, bivalent antibodies specific for extracellular domains II and IV of HER2. Negative control "pTAU-8D3" is a bispecific antibody specific for the transferrin receptor and pTau (SEQ ID. NOs: 210, 211, 212).

FIG. 35 shows inhibition of BT474-M1 cell proliferation after incubation with Herceptarg+/−scFab(8D3) molecules.

TABLE 36

BBB-R binders

| SEQ ID NO | Description | | Sequence |
|---|---|---|---|
| 172 | 2/99 | CDR-H1 | FSLSSY |
| 173 | 2/99 | CDR-H2 | YIWSGGSTDYASWA |
| 174 | 2/99 | CDR-H3 | RYGTSYPDYGDANGFDP |
| 175 | 2/99 | CDR-L1 | QASQSISSYLS |
| 176 | 2/99 | CDR-L2 | RAS |
| 177 | 2/99 | CDR-L3 | CYSSSNVDN |
| 178 | 2/99 | VH | QSMEESGGRLVTPGTPLTLTCTVSGFSLSSYAMSWVRQAPGKGLEWIGYIWSGGSTDYASWAKGRFTISKTSTTVDLKITSPTTEDTATYFCARRYGTSYPDYGDANGFDPWGPGTLVTVSS |
| 179 | 2/99 | VL | AYDMTQTPASVEVAVGGTVTIKCQASQSISSYLSWYQQKPGQRPKLLIYRASTLASGVSSRFKGSGSGTQFTLTISGVECADAATYYCQQCYSSSNVDNTFGGGTEVVVKR |

TABLE 36-continued

BBB-R binders

| SEQ ID NO | Description | Sequence |
|---|---|---|
| 180 | 4/94 CDR-H1 | GFNIKDT |
| 181 | 4/94 CDR-H2 | RIDPANGDTKCDPKFQ |
| 182 | 4/94 CDR-H3 | YLYPYYFD |
| 183 | 4/94 CDR-L1 | SESVDTY |
| 184 | 4/94 CDR-L2 | GAS |
| 185 | 4/94 CDR-L3 | TYNYPL |
| 166 | 4/94 VH | EVQLQQSGAVLVKPGASVKLSCPASGFNIKDTYIHWVIQRPEQGLEWIGRIDP ANGDTKCDPKFQVKATITADTSSNTAYLQLSSLTSEDTAVYFCVRDYLYPYYF DFWGQGTTLTVSS |
| 167 | 4/94 VL | KIVMTQSPKSMSMSVGERVTLNCRASESVDTYVSWYQQKPEQSPELLIYGAS NRYTGVPDRFTGSGSATDFTLTISSVQAEDLADYYCGQTYNYPLTFGAGTKLE LKR |
| 186 | Humanized 2/99 CDR-H1 | SYAMS |
| 187 | Humanized 2/99 CDR-H2 | YIWSGGSTDY ASWAKS |
| 188 | Humanized 2/99 CDR-H3 | RYGTSYPDYGDASGFDP |
| 206 | Humanized 2/99 CDR-H3 variant | RYGTSYPDYGDAQGFDP |
| 189 | Humanized 2/99 CDR-L1 | RASQSISSYL A |
| 190 | Humanized 2/99 CDR-L2 | RASTLAS |
| 191 | Humanized 2/99 CDR-L3 | QQNYASSNVD NT |
| 192 | Humanized 2/99 VH | QSMQESGPGL VKPSQTLSLT CTVSGFSLSS YAMSWIRQHP GKGLEWIGYIWSGGSTDYASWAKSRVTISK TSTTVSLKLS SVTAADTAVY YCARRYGTSYPDYGDASGFDPWGQGTLVTV SS |
| 205 | Humanized 2/99 VH variant | QSMQESGPGL VKPSQTLSLT CTVSGFSLSS YAMSWIRQHP GKGLEWIGYI WSGGSTDYAS WAKSRVTISK TSTTVSLKLS SVTAADTAVY YCARRYGTSYPDYGDAQGFDPWGQGTLVTVSS |
| 193 | Humanized 2/99 VL | AIQLTQSPSS LSASVGDRVT ITCRASQSIS SYLAWYQQKP GKAPKLLIYR ASTLASGVPS RFSGSGSGTD FTLTISSLQP EDFATYYCQQ NYASSNVDNT FGGGTKVEI |
| 194 | Humanized 2/99 VH variant 1 | QVQLVQSGAE VKKPGASVKV SCKASGFNIK DTYIHWVIQA PGQGLEWMGR IDPANGDTKS DPKFQVRVTI TADTSTSTVY MELSSLRSED TAVYYCVRDY LYPYYFDFWG QGTTVTVSS |
| 195 | Humanized 2/99 VH variant 2 | QVQLVQSGAE VKKPGASVKV SCKASGFNIK DTYIHWVIQA PGQGLEWMGR IDPANGDTKS APKFQVRVTI TADTSTSTVY MELSSLRSED TAVYYCVRDY LYPYYFDFWG QGTTVTVSS |
| 196 | Humanized 2/99 VH variant 3 | QVQLVQSGAE VKKPGASVKV SCKASGFNIK DTYIHWVIQA PGQGLEWMGR IDPANGDTKS DPKFQGRVTI TADTSTSTVY MELSSLRSED TAVYYCVRDY LYPYYFDFWG QGTTVTVSS |
| 197 | Humanized 2/99 VH variant 4 | QVQLVQSGAE VKKPGSSVKV SCKASGFNIK DTYIHWVIQA PGQGLEWMGR IDPANGDTKS DPKFQGRVTI TADESTAY MELSSLRSED TAVYYCVRDY LYPYYFDFWG QGTTVTVSS |

TABLE 36-continued

BBB-R binders

| SEQ ID NO | Description | Sequence |
|---|---|---|
| 198 | Humanized 2/99 VH variant 5 | QVQLVQSGAE VKKPGSSVKV SCKASGFNIK DTYIHWVIQR PGQGLEWMGR IDPANGDTKS DPKFQGRVTI TADESTSTAY MELSSLRSED TAVYYCVRDY LYPYYFDFWG QGTTVTVSS |
| 199 | Humanized 2/99 VH variant 6 | QVQLQESGPG LVKPSETLSL TCTVSGFNIK DTYIHWVIQR PGKGLEWIGR IDPANGDTKS DPSLQSRVTI SADTSKNQAS LKLSSVTAAD TAVYYCVRDY LYPYYFDFWG QGTTVTVSS |
| 200 | Humanized 2/99 VH variant 7 | EVQLVESGGG LVQPGGSLRL SCAASGFNIK DTYIHWVIQA PGKGLEWVGR IDPANGDTKS DPSVQVRATI SADTSKNTAY LQMNSLRAED TAVYYCVRDY LYPYYFDFWG QGTTVTVSS |
| 201 | Humanized 2/99 VL variant 1 | KIQMTQSPSS LSASVGDRVT ITCRASESVD TYVSWYQQKP GKAPKLLIYG ASNRYTGVPS RFSGSGSGTD FTLTISSLQP EDFADYYCGQ TYNYPLTFGQ GTKLEI |
| 207 | Humanized 2/99 VL variant 2 | KIVLTQSPGT LSLSPGERAT LSCRASESVD TYVSWYQQKP GQAPRLLIYG ASNRYTGVPD RFSGSGSGTD FTLTISRLEP EDFADYYCGQ TYNYPLTFGQ GTKLEI |
| 208 | Humanized 2/99 VL variant 3 | EIVLTQSPGT LSLSPGERAT LSCRASESVD TYVSWYQQKP GQAPRLLIYG ASNRYTGVPD RFSGSGSGTD FTLTISRLEP EDFADYYCGQ TYNYPLTFGQ GTKLEI |
| 209 | Humanized 2/99 VL variant 4 | KIVLTQSPGT LSLSPGERAT LSCRASESVD TYVSWYQQKP GQAPRLLIYG ASNRYTGIPD RFSGSGSGTD FTLTISRLEP EDFADYYCGQ TYNYPLTFGQ GTKLEI |

TABLE 37

Trivalent HER2 (extracellular domain IV)- HER2 (extracellular domain II)- Transferrin specific antibodies and control antibodies without BBB-R binder

| SEQ ID NO | Description | Sequence |
|---|---|---|
| | | BBB-0580/Herceptarg-scFab(8D3) |
| 165 | Her-knob-scFab(8D3) Heavy chain 21832 | evqlvesggglvqpggslrlscaasgfnikdtyihwvrqapgkglewvariyptngytry adsvkgrftisadtskntaylqmnslraedtavyycsrwggegfyamdywgqgtlvtvss astkgpsvfplapssksstsggtaalgclvkdyfpepvtvswnsgaltsgvhtfpavlqssgl yslssvvtvpssslgtqtyicnvnhkpsntkvdkkvepkscdkthtcppcpapellggpsv flfppkpkdtlmisrtpevtcvvvdvshedpevkfnwyvdgvevhnaktkpreeqynst yrvvsvltvlhqdwlngkeykckvsnkalpapiektiskakgqprepqvytlppcrdelt knqvslwclvkgfypsdiavewesngqpennykttppvldsdgsfflysklitvdksrwq qgnvfscsvmhealhnhytqkslslspgggsgggsgggsgggsgggsdiqmtqspasls asleeivtitcqasqdignwlawyqqkpgkspqlliygatsladgvpsrfsgsrsgtqfslki srvqvedigiyyclqayntpwtfgggtkveikrtvaapsvfifppsdeqlksgtasvvclln nfypreakvqwkvdnalqsgnsqesvteqdskdstyslsstltlskadyekhkvyacevt hqglsspvtksfnrgecggggsggggsggggsggggsggggsggggsggevqlvesgg glvqpgnsltlscvasgftfsnygmhwirqapkkglewiamiyydsskmnyadtvkgr ftisrdnskntlylemnslrsedtamyycavptshyvvdvwgqgvsvtvssastkgpsvf plapssksstsggtaalgclvkdyfpepvtvswnsgaltsgvhtfpavlqssglyslssvvtv pssslgtqtyicnvnhkpsntkvdkkvepksc |
| 163 | Per-hole Heavy chain 21833 | evqlvesggglvqpggslrlscaasgftfndytmdwvrqapgkglewvadvnpnsgsi vnrrfkgrftlsvdrskntlylqmnslraedtavyycarnlgpffyfdywgqgtlvtvssast kgpsvfplapssksstsggtaalgclvkdyfpepvtvswnsgaltsgvhtfpavlqssglysl ssvvtvpssslgtqtyicnvnhkpsntkvdkkvepkscdkthtcppcpapellgggpsvflf ppkpkdtlmisrtpevtcvvvdvshedpevkfnwyvdgvevhnaktkpreeqynstyr vvsvltvlhqdwlngkeykckvsnkalpapiektiskakgqprepqvctlppsrdeltkn qvslscavkgfypsdiavewesngqpennykttppvldsdgsfflvskltvdksrwqqg nvfscsvmhealhnhytqkslslspgk |

TABLE 37-continued

Trivalent HER2 (extracellular domain IV)- HER2 (extracellular domain II)-
Transferrin specific antibodies and control antibodies without BBB-R binder

| SEQ ID NO | Description | Sequence |
|---|---|---|
| 161 | Her/Per CLC 21831 | diqmtqspsslsasvgdrvtitckasqdvstavawyqqkpgkapklliysasfrytgvpsr fsgsrsgtdftltisslqpedfatyycqqhyttpptfgqgtkveik rtvaapsvfifppsdeqlksgtasvvcllnnfypreakvqwkvdnalqsgnsqesvteqds kdstyslsstltlskadyekhkvyacevthqglsspvtksfnrgec |

BBB-0581/Herceptarg(LALA-PG)-scFab(8D3)

| SEQ ID NO | Description | Sequence |
|---|---|---|
| 168 | Her-knob-LALA-PG-scFab(8D3) Heavy chain 21834 | evqlvesgggvqpggslrlscaasgfnikdtyihwvrqapgkglewvariyptngytry adsvkgrftisadtskntaylqmnslraedtavyycsrwggegfyamdywgqgtlvtvss astkgpsvfplapsskstsggtaalgclvkdyfpepvtvswnsgaltsgvhtfpavlqssgl yslssvvtvpssslgtqtyicnvnhkpsntkvdkkvepkscdkthtcppcpapeaaggps vflfppkpkdtlmisrtpevtcvvvdvshedpevkfnwyvdgvevhnaktkpreeqyn styrvvsvltvlhqdwlngkeykckvsnkalgapiektiskakgqprepqvytlppcrdel tknqvslwclvkgfypsdiavewesngqpennykttppvldsdgsfflysklvtdksrw qqgnvfscsvmhealhnhytqkslslspgggsgggsgggsgggsgggsdiqmtqspasl sasleeivtitcqasqdignwlawyqqkpgkspqlliygatsladgvpsrfsgsrsgtqfslk isrvqvedigiyyclqayntpwtfgggtkveikrtvaapsvfifppsdeqlksgtasvvcll nnfypreakvqwkvdnalqsgnsqesvteqdskdstyslsstltlskadyekhkvyacev thqglsspvtksfnrgecgggsgggsgggsgggsgggsgggsgggsggevqlvesg gglvqpgnsltlscvasgftfsnygmhwirqapkkglewiamiyydsskmnyadtvkg rftisrdnskntlylemnslrsedtamyycavptshyvvdvwgqgvsvtvssastkgpsv fplapsskstsggtaalgclvkdyfpepvtvswnsgaltsgvhtfpavlqssglyslssvvtv pssslgtqtyicnvnhkpsntkvdkkvepksc |
| 169 | Per-hole LALA-PG Heavy chain 21836 | Evqlvesgggvqpggslrlscaasgftfndytmdwvrqapgkglewvadvnpnsggs ivnrrfkgrftlsvdrskntlylqmnslraedtavyycarnlgpffyfdywgqgtlvtvssas tkgpsvfplapsskstsggtaalgclvkdyfpepvtvswnsgaltsgvhtfpavlqssglys lssvvtvpssslgtqtyicnvnhkpsntkvdkkvepkscdkthtcppcpapeaaggpsvf lfppkpkdtlmisrtpevtcvvvdvshedpevkfnwyvdgvevhnaktkpreeqynst yrvvsvltvlhqdwlngkeykckvsnkalgapiektiskakgqprepqvctlppsrdeltk nqvslscavkgfypsdiavewesngqpennykttppvldsdgsfflvskltvdksrwqq gnvfscsvmhealhnrftqkslslspgk |
| 161 | Her/Per CLC 21831 | diqmtqspsslsasvgdrvtitckasqdvstavawyqqkpgkapklliysasfrytgvpsr fsgsrsgtdftltisslqpedfatyycqqhyttpptfgqgtkveik rtvaapsvfifppsdeqlksgtasvvcllnnfypreakvqwkvdnalqsgnsqesvteqds kdstyslsstltlskadyekhkvyacevthqglsspvtksfnrgec |

BBB-0582/Herceptarg-LALA-PG (control molecule without BBB-R binder)

| SEQ ID NO | Description | Sequence |
|---|---|---|
| 170 | Her-knob-LALA-PG Heavy Chain 21835 | evqlvesgggvqpggslrlscaasgfnikdtyihwvrqapgkglewvariyptngytry adsvkgrftisadtskntaylqmnslraedtavyycsrwggegfyamdywgqgtlvtvss astkgpsvfplapsskstsggtaalgclvkdyfpepvtvswnsgaltsgvhtfpavlqssgl yslssvvtvpssslgtqtyicnvnhkpsntkvdkkvepkscdkthtcppcpapeaaggps vflfppkpkdtlmisrtpevtcvvvdvshedpevkfnwyvdgvevhnaktkpreeqyn styrvvsvltvlhqdwlngkeykckvsnkalgapiektiskakgqprepqvytlppcrdel tknqvslwclvkgfypsdiavewesngqpennykttppvldsdgsfflysklvtdksrw qqgnvfscsvmhealhnhytqkslslspgk |
| 169 | Per-hole LALA-PG Heavy chain 21836 | Evqlvesgggvqpggslrlscaasgftfndytmdwvrqapgkglewvadvnpnsggs ivnrrfkgrftlsvdrskntlylqmnslraedtavyycarnlgpffyfdywgqgtlvtvssas tkgpsvfplapsskstsggtaalgclvkdyfpepvtvswnsgaltsgvhtfpavlqssglys lssvvtvpssslgtqtyicnvnhkpsntkvdkkvepkscdkthtcppcpapeaaggpsvf lfppkpkdtlmisrtpevtcvvvdvshedpevkfnwyvdgvevhnaktkpreeqynst yrvvsvltvlhqdwlngkeykckvsnkalgapiektiskakgqprepqvctlppsrdeltk nqvslscavkgfypsdiavewesngqpennykttppvldsdgsfflvskltvdksrwqq gnvfscsvmhealhnrftqkslslspgk |
| 161 | Her/Per CLC 21831 | diqmtqspsslsasvgdrvtitckasqdvstavawyqqkpgkapklliysasfrytgvpsr fsgsrsgtdftltisslqpedfatyycqqhyttpptfgqgtkveik rtvaapsvfifppsdeqlksgtasvvcllnnfypreakvqwkvdnalqsgnsqesvteqds kdstyslsstltlskadyekhkvyacevthqglsspvtksfnrgec |

Herceptarg (control molecule without BBB-R binder)

| SEQ ID NO | Description | Sequence |
|---|---|---|
| 171 | pETR13573 Her-knob heavy chain | evqlvesgggvqpggslrlscaasgfnikdtyihwvrqapgkglewvariyptngytry adsvkgrftisadtskntaylqmnslraedtavyycsrwggegfyamdywgqgtlvtvss astkgpsvfplapsskstsggtaalgclvkdyfpepvtvswnsgaltsgvhtfpavlqssgl yslssvvtvpssslgtqtyicnvnhkpsntkvdkkvepkscdkthtcppcpapellggpsv flfppkpkdtlmisrtpevtcvvvdvshedpevkfnwyvdgvevhnaktkpreeqynst yrvvsvltvlhqdwlngkeykckvsnkalpapiektiskakgqprepqvytlppcrdelt |

TABLE 37-continued

Trivalent HER2 (extracellular domain IV)- HER2 (extracellular domain II)-
Transferrin specific antibodies and control antibodies without BBB-R binder

| SEQ ID NO | Description | Sequence |
|---|---|---|
| | | knqvslwclvkgfypsdiavewesngqpennykttppvldsdgsfflyskltvdksrwq qgnvfscsvmhealhnhytqkslslspgk |
| 163 | Per-hole Heavy chain 21833 | evqlvesggglvqpggslrlscaasgftfndytmdwvrqapgkglewvadvnpnsggsi vnrrfkgrftlsvdrskntlylqmnslraedtavyycarnlgpffyfdywgqgtlvtvssast kgpsvfplapsskstsggtaalgclvkdyfpepvtvswnsgaltsgvhtfpavlqssglysl ssvvtvpssslgtqtyicnvnhkpsntkvdkkvepkscdkthtcppcpapellggpsvflf ppkpkdtlmisrtpevtcvvvdvshedpevkfnwyvdgvevhnaktkpreeqynstyr vvsvltvlhqdwlngkeykckvsnkalpapiektiskakgqprepqvctlppsrdeltkn qvslscavkgfypsdiavewesngqpennykttppvldsdgsfflvskltvdksrwqqg nvfscsvmhealhnhytqkslslspgk |
| 161 | Her/Per CLC 21831 | diqmtqspsslsasvgdrvtitckasqdvstavawyqqkpgkapklliysasfrytgvpsr fsgsrsgtdftltisslqpedfatyycqqhyttpptfgqgtkveik rtvaapsvfifppsdeqlksgtasvvcllnnfypreakvqwkvdnalqsgnsqesvteqds kdstyslsstltlskadyekhkvyacevthqglsspvtksfnrgec |

TABLE 38

Sequence of pTAU-BBB-R control molecule

| SEQ ID NO | Description | Sequence |
|---|---|---|
| 210 | 8936_pTau_Rb Mab86_VL_hu Igkappa | Aqvltqttspvsaavgstvtiscqssqsvrtnklawfqqkpgqppkrliysastldfgvpsrf sasgsgtqftltisdvqcddaatyyclgyfdcsiadcvafgggtevvvkrtvaapsvfifpps deqlksgtasvvcllnnfypreakvqwkvdnalqsgnsqesvteqdskdstyslsstltlsk adyekhkvyacevthqglsspvtksfnrgec |
| 211 | 8975-pTau-Rb86-hugamma1-SS-hole | Qsveesggrlvtpgtpltltctvsgfslssnainwvrqapgkglewigyiaysgntyyasw akgrftiskasttvdlkmtsptaedtgtyfcgksniwgpgtlvtvslastkgpsvfplapssk stsggtaalgclvkdyfpepvtvswnsgaltsgvhtfpavlqssglyslssvvtvpssslgtq tyicnvnhkpsntkvdkkvepkscdkthtcppcpapellggpsvflfppkpkdtlmisrt pevtcvvvdvshedpevkfnwyvdgvevhnaktkpreeqynstyrvvsvltvlhqdwl ngkeykckvsnkalpapiektiskakgqprepqvctlppsrdeltknqvslscavkgfyp sdiavewesngqpennykttppvldsdgsfflvskltvdksrwqqgnvfscsvmhealh nhytqkslslspgk |
| 212 | 8976-pTau-Rb86-hugamma1-SS-knob-mTfR-8D3-scFab | qsveesggrlvtpgtpltltctvsgfslssnainwvrqapgkglewigyiavsgntyyaswa kgrftiskasttvdlkmtsptaedtgtyfcgksniwgpgtivtvslastkgpsvfplapsskst sggtaalgclvkdyfpepvtvswnsgaltsgvhtfpavlqssglyslssvvtvpssslgtqty icnvnhkpsntkvdkkvepkscdkthtcppcpapellggpsvflfppkpkdtlmisrtpe vtcvvvdvshedpevkfnwyvdgvevhnaktkpreeqynstyrvvsvltvlhqdwlng keykckvsnkalpapiektiskakgqprepqvytlppcrdeltknqvslwclvkgfypsd iavewesngqpennykttppvldsdgsfflyskltvdksrwqqgnvfscsvmhealhnh ytqkslslspggggsggggsggggsggggsdiqmtqspaslsasleeivtitcqasqdignw lawyqqkpgkspqlliygatsladgvpsrfsgsrsgtqfslkisrvqvedigiyyclqaynt pwtfgggtkveikrtvaapsvfifppsdeqlksgtasvvcllnnfypreakvqwkvdnal qsgnsqesvteqdskdstyslsstltlskadyekhkvyacevthqglsspvtksfnrgecgg ggsggggsggggsggggsggggsggggsggevqlvesggglvqpgnsltlscvasgftf snygmhwirqapkkglewiamiyydsskmnyadtvkgrftisrdnskntlylemnslr sedtamyycavptshyvvdvwgqgvsvtvssastkgpsvfplapsskstsggtaalgclv kdyfpepvtvswnsgaltsgvhtfpavlqssglyslssvvtvpssslgtqtyicnvnhkpsn tkvdkkvepksc |

Example 25: Characterization of Monovalent Anti TfR Antibodies

Identification of human and cynomolgus TfR-binding antibodies by cell ELISA To screen rabbit B-cell or mouse hybridoma supernatants for antibodies recognizing human and cynomolgus TfR a cell ELISA using stably transfected CHO-Ki cells way employed. Stable transfectants were obtained by transfecting CHO-Ki cells with expression plasmids containing expression cassettes for the human or cynomolgus TfR as well as for neomycin-phosphotransferase. After transfection, cells were diluted in growth medium containing 500 μg/mL G418 (Life Technologies). After appearance of growing clones, cells were detached, stained with MEM-75 (Abcamn) or 13E4 (Life Technologies) and PE-labeled secondary antibodies for human or cynomolgus TfR and highly fluorescent cells sorted as single cells into 96-well-plate wells (FACS Aria). After 7 days of growth, clones were again checked for TfR expression and best expressing clones selected for cell ELISA experiments.

Briefly, 15,000 cells were seeded per well of a 384-well plate and incubated for 18 h at 37° C., 5% CO2. Supernatant was removed using an automated washer (BIOTEK), and 30 µL of antibody-containing supernatant added to each well, followed by 24 µL of growth medium. After 2 hours of incubation, wells were emptied and 30 µL of 0.05% glutaraldehyde in PBS added for 45 mini. at RT. After 3 washes with PBS/0.025% TWEEN™ (polysorbate) 20 (PBST), 30 µL of anti-rabbit-HRP or anti-mouse-HRP (Southern Biotech) diluted 1:5000 in Blocking buffer was added and plates incubated for 1 hour at RT. Wells were washed 6 times with PBST and signal was generated using 30 µL of TMB per well and absorbance measured at 450 nm.

Cloning and Expression of Anti-TfR Antibodies

Recombinant DNA techniques

Standard methods were used to manipulate DNA as described in Sambrook, J. et al., Molecular cloning: A laboratory manual; Cold Spring Harbor Laboratory Press, Cold Spring Harbor, New York, 1989. The molecular biological reagents were used according to the manufacturer's instructions.

Gene and oligonucleotide synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR The respective oligonucleotides were prepared by metabion GmbH (Planegg-Martinsried, Germany).

PCR Amplification of V-Domains

Total RNA was prepared from B-cells lysate (resuspended in RLT buffer—Qiagen—Cat. No 79216) using the NUCLEOSPIN™ 8/96 RNA kit (Macherey & Nagel; 740709.4, 740698) according to manufacturer's protocol. RNA was eluted with 60 µL RNAse free water. 6 µL of RNA was used to generate cDNA by reverse transcriptase reaction using the SUPERSCRIPT™ III First-Strand Synthesis SuperMix (Invitrogen 18080-400) and an oligo-dT-primer according to the manufacturer's instructions. All steps were performed on a Hamilton ML Star System. 4 µL of cDNA were used to amplify the immunoglobulin heavy and light chain variable regions (VH and VL) with the ACCUPRIME™ SuperMix (Invitrogen 12344-040) in a final volume of 50 µL using the primers rbHC.up and rbHC.do for the heavy chain, rbLC.up and rbLC.do for the light chain of Wild Type Rabbit B cells and BcPCR_FHLC_leader.fw and BcPCR_huCkappa.rev for the light chain of transgenic rabbit B-cells (see Table below). All forward primers were specific for the signal peptide (of respectively VH and VL) whereas the reverse primers were specific for the constant regions (of respectively VH and VL). The PCR conditions for the RbVH+RbVL were as follows: Hot start at 94° C. for 5 min.; 35 cycles of 20 sec. at 94° C., 20 sec. at 70° C., 45 sec. at 68° C., and a final extension at 68° C. for 7 min. The PCR conditions for the HuVL were as follows: Hot start at 94° C. for 5 min.; 40 cycles of 20 sec. at 94° C., 20 sec. at 52° C., 45 sec. at 68° C., and a final extension at 68° C. for 7 min.

TABLE 39

| | |
|---|---|
| rbHC.up (SEQ ID NO: 213) | AAGCTTGCCACCATGGAGACTGGGCTGCGCTGGCTTC |
| rbHCf.do (SEQ ID NO: 214) | CCATTGGTGAGGGTGCCCGAG |
| rbLC.up (SEQ ID NO: 215) | AAGCTTGCCACCATGGACAYGAGGGCCCCCACTC |
| rbLC.do (SEQ ID NO: 216) | CAGAGTRCTGCTGAGGTTGTAGGTAC |
| BcPCR_FHLC_leader.fw (SEQ ID NO: 217) | ATGGACATGAGGGTCCCCGC |
| BcPCR_huCkappa.rev (SEQ ID NO: 218) | GATTTCAACTGCTCATCAGATGGC |

8 µL of 50 µL PCR solution were loaded on a 48 E-GEL™ 2% (Invitrogen G8008-02). Positive PCR reactions were cleaned using the NUCLEOSPIN™ Extract II kit (Macherey & Nagel; 740609250) according to manufacturer's protocol and eluted in 50 µL elution buffer. All cleaning steps were performed on a Hamilton ML Starlet System.

Recombinant Expression of Rabbit Monoclonal Bivalent Antibodies

For recombinant expression of rabbit monoclonal bivalent antibodies, PCR-products coding for VH or VL were cloned as cDNA into expression vectors by the overhang cloning method (RS Haun et al., BioTechniques (1992) 13, 515-518; M Z Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Three variants of the basic plasmid were used: one plasmid containing the rabbit IgG constant region designed to accept the VH regions while two additional plasmids containing rabbit or human kappa LC constant region to accept the VL regions.

Linearized expression plasmids coding for the kappa or gamma constant region and VL NH inserts were amplified by PCR using overlapping primers.

Purified PCR products were incubated with T4 DNA-polymerase which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

For antibody expression, the isolated HC and LC plasmids were transiently co-transfected into HEK293 cells and the supernatants were harvested after 1 week.

Generation of Vectors for the Expression of Rabbit Monoclonal Monovalent Antibodies For recombinant expression of selected candidates as monoclonal monovalent antibodies rabbit constant regions of all VH chains were converted into human constant regions enclosing the knob-mutation in the CH3 segment. For VL chains derived from rabbit wild-type B-cells, rabbit C kappa constant regions were converted into human. 4 µL of cDNA of the selected candidates were used to amplify the immunoglobulin heavy and light chain variable regions with the ACCUPRIME™ SuperMix (Invitrogen 12344-040) in a final volume of 50 µL with forward primers specific for the signal peptide and reverse primers specific for the CDR3-J region with (at the 3' end) overlap sequence (20 bp) homologous to the human constant regions (respectively of VH and VL). The PCR conditions for the VH and VL chain amplification were as follows: Hot start at 94° C. for 5 min.; 35 cycles of 20 sec. at 94° C., 20 sec. at 68° C., 45 sec. at 68° C., and a final extension at 68° C. for 7 min.

PCR-products coding for VH or VL were cloned as cDNA into expression vectors by the overhang cloning method (RS Haun et al., BioTechniques (1992) 13, 515-518; M Z Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Two variants of the basic plasmid were used: one plasmid containing the human IgG constant region designed to accept the new amplified VH chain and a second plasmid containing the human kappa LC constant region to accept the VL chain.

Linearized expression plasmids coding for the kappa or gamma constant region and VL NH inserts were amplified by PCR using overlapping primers.

Purified PCR products were incubated with T4 DNA-polymerase which generated single-strand overhangs. The reaction was stopped by dCTP addition. In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

Transient Expression of the Monovalent Anti-TfR Antibodies

The antibodies were generated in vivo in transiently transfected HEK293 cells (human embryonic kidney cell line 293-derived) cultivated in F17 Medium (Invitrogen Corp.). For transfection "293 FREE™" Transfection Reagent (Novagen) was used. Antibodies and antibody-based modified molecules as described above were expressed from individual expression plasmids. Transfections were performed as specified in the manufacturer's instructions. Recombinant protein-containing cell culture supernatants were harvested three to seven days after transfection. Supernatants were stored at reduced temperature (e.g. −80° C.) until purification. General information regarding the recombinant expression of human immunoglobulins in e.g. HEK293 cells is given in: Meissner, P. et al., Biotechnol. Bioeng. 75 (2001) 197-203.

hCMEC/D3 Cell Culture for Transcytosis Assays

Medium and supplements for hCMEC/D3 (Weksler, B. B. et al., FASEB J. 19 (2005), 1872-1874) were obtained from Lonza. hCMEC/D3 cells (passages 26-29) were cultured to confluence on collagen-coated coverslips (microscopy) or flasks in EBM2 medium containing 2.5% FBS, a quarter of the supplied growth factors and fully complemented with supplied hydrocortisone, gentamycin and ascorbic acid.

For all transcytosis assays, high density pore (1×108 pores/cm2) PET membrane filter inserts (0.4 µm, 12 mm diameter) were used in 12-well cell culture plates. Optimum media volumes were calculated to be 400 µL and 1600 µL for apical and basolateral chambers, respectively. Apical chambers of filter inserts were coated with rat tail collagen I (7.5 µg/cm2) followed by fibronectin (5 µg/mL), each incubation lasting for 1 hour at RT. hCMEC/D3 cells were grown to confluent monolayers (approx. 2×105 cells/cm2) for 10-12 days in EMB2 medium.

Transcytosis Assay of Monovalent Transferrin Receptor Specific Antibodies

The entire assay was performed in serum-free EBM2 medium. Filter inserts with cells were incubated apically with monovalent antibodies (concentration: 2.67 µg/mL) for 1 hour at 37° C. following which the entire apical and basolateral media were collected. From these values, paracellular flux was calculated. The monolayers were washed at RT in serum-free medium apically (400 µL) and basolaterally (1600 µL) 3×3-5 min. each. All the washes were collected to monitor efficiency of removal of the unbound antibody. Pre-warmed medium was added to the apical chamber and the filters transferred to a fresh 12 well plate (blocked overnight with PBS containing 1% BSA) containing 1600 µL pre-warmed medium. At this point, cells on filters were lysed in 500 µL RIPA buffer in order to determine specific antibody uptake. The remaining filters were incubated at 37° C. and samples collected at various time points to determine apical and/or basolateral release of antibody. The content of antibody in the samples was quantified using a highly sensitive IgG ELISA. For each time point, data were generated from three filter cell cultures.

Sensitive IgG ELISA after Transcytosis Assay

The entire procedure was performed at RT using an automated washer for the wash steps. A 384-well plate was coated with 30 µL/well of 1 µg/mL anti-human/mouse-IgG, Fc □-specific in PBS for 2 hours followed by 1 hour incubation in blocking buffer PBS containing 1% BSA or 1% CroteinC for human and mouse IgG assays, respectively). Serially diluted samples from the transcytosis assay and standard concentrations of the antibody used in the transcytosis assay were added to the plate and incubated for 2 hours. After four washes, 30 µL/well of 50 ng/mL anti-human/mouse-F(ab)2-Biotin in blocking buffer was added and incubated for a further 2 hours. Following 6 washes, 30 µL/well of 50 ng/mL (huIgG assay) or 100 ng/mL (mIgG assay) Poly-HRP40-Streptavidin (Fitzgerald; in PBS containing 1% BSA and 0.05% TWEEN™ (polysorbate)-20) was added and incubated for 30 min. After 4 washes, immune complexes were detected by addition of 30 µL/well of BM Chemiluminescence Substrate (Roche). The luminescence signal was measured using a luminescence plate reader and concentration calculated using the fitted standard curve. The sensitivity of the assay ranged from 10 µg/mL to 10 ng/mL.

Rabbit anti-transferrin antibody clone 2/99 showed properties comparable to that of the anti-transferrin receptor antibody 128.1. This can be seen from the following Table.

TABLE 40

Characterization of antibody 2/99 (SEQ ID NO. 178/179)

| origin | trans-cytosis loading [pg] | trans-cytosis % baso-lateral | total baso-lateral [pg] | total apical [pg] | sum transported [pg] | loading % of mAb 128.1 | total baso-lateral % of mAb 128.1 | total apical % of mAb 128.1 | sum transported % of mAb 128.1 | EC50 [ng/mL] FACS hTfR-CHO |
|---|---|---|---|---|---|---|---|---|---|---|
| mAb 128.1 | 2226 | 34 | 757 | 1229 | 1986 | 100 | 100 | 100 | 100 | 96 |
| clone-2/99 | 2773 | 36 | 998 | 1346 | 2344 | 125 | 132 | 110 | 118 | 275 |

| origin | max. geo. mean hTfR-CHO | EC50 [ng/mL] FACS cyTfR | max. geo. mean Cyno TfR-CHO | ratio EC50 Cyno/human | ratio max Cyno/human | BIACORE™ off-rate huTfR [1/s] | BIACORE™ t1/2 huTfR [min] | BIACORE™ off-rate cyTfR [1/s] | BIACORE™ t1/2 Cyno TfR [min] | ratio t1/2 human/Cyno |
|---|---|---|---|---|---|---|---|---|---|---|
| mAb128.1 | 78200 | 314 | 52100 | 3.3 | 0.6 | 6.06E−04 | 19 | 5.47E−02 | 0 | 90.2 |
| clone-2/99 | 55600 | 241 | 52000 | 0.9 | 1.0 | 6.16E−04 | 19 | 2.77E−04 | 42 | 0.4 |

The mouse anti-human transferrin-receptor antibody 128.1 (WO 93/10819) was taken as reference. The transferrin receptor binder 2/99 shows a transcytosis loading of 705 pg, whereof after 4 hours 170 pg (=24% of loading) can be found in the basolateral compartment and 294 pg (=42% of loading) can be found in the apical compartment.

The transferrin receptor binder 4/94 shows a transcytosis loading of 3510 pg, whereof after 4 hours 748 pg (=21% of loading) can be found in the basolateral compartment and 1503 pg (=43% of loading) can be found in the apical compartment.

Example 26: Epitope Mapping by Cell ELISA of CHO Cells Transfected with hTfR Mutants In order to be able determine the epitope regions on human transferrin receptor (hTfR), mutations were introduced into the hTfR sequence at positions, where a cluster of surface-exposed amino acids had different amino acids in the aligned mouse TfR sequence (see Table below), following the rationale that in spite of the significant homology between human and mouse TfR (77% identity), no antibodies directed to the extracellular part are known which show good cross-reactivity between both orthologous. Cloning of plasmids with the corresponding mutations is described above. To map binding of human TfR binders to those epitopes, CHO-Ki cells were transiently transfected with the described plasmids and antibody binding measured in a cell ELISA. Briefly, 104 cells were plated per well of a 96-well plate the day before experiment in normal growth medium (RPMI/10% FCS). The other day, medium was changed to OPTI-MEM® Serum-Reduced Medium (Gibco), and 10 μL of a mixture of 1200 μL OPTI-MEM®, 12 μg plasmid DNA and 12 μL XtremeGENE transfection reagent (Roche) were added to the wells after 30 minutes of pre-incubation. Cells were incubated for 2 days at 37° C./7.5% CO2, then medium was removed and TfR antibodies added at concentrations between 1 nM and 100 nM in growth medium, followed by 2 h incubation at 4° C. Afterwards, antibody solutions were replaced by 0.05% glutaraldehyde in PBS and cells fixed for 15 min. at RT, then washed twice with PBS and incubated with HRP-conjugated anti-human-Fc secondary antibody (BioRad; 1:2000 in ELISA Blocking Reagent (Roche)) for 1.5 hours at RT. Signal was generated after 3 washes with PBS using 50 μL of TMB per well and absorbance measured at 450 nm.

TABLE 41

| Plasmid # | mutations in hTfR |
|---|---|
| 10188 | — |
| 18909 | Thr518Asp/Gln520Lys/Phe521Ser/Gln524Arg |
| 18910 | Arg325 Gln |
| 18911 | Ser355Ala/Asp356Arg/Lys358Asn/Thr359Ile |
| 18912 | Asp204Gln/Lys205Ser/Arg208 Asn |
| 18913 | Lys574Gly/Glu575 Ala/Ile577Thr/Glu578Gln |
| 18914 | Ala196Ile/Gln197Gly/Asn198Gln/Ser199Asn/Val200Met/Ile201Val/Ile202Thr/Val203Ile/Asp204Val/Lys205Gln/Asn206Ser/Gly207Asn/Arg208Gly/Leu209Asn/Val210Leu/Tyr211Asp/Leu212Pro |
| 18974 | Asp245Glu/Tyr247Ser/Thr248Tyr/Pro249Ser |

Example 27: Surface Plasmon Resonance-Based Binding Assay for Human TfR-Antibody Interaction The binding experiment were carried out on a BIACORE™ B 4000 (GE Healthcare) equipped with C1 sensorchip (GE Healthcare, cat. no. BR1005-35) pre-treated with anti-human Fab antibody (GE Healthcare, cat. no 28-9583-25) using a standard amine coupling chemistry procedure accordingly to the vendor's manual.

For kinetic measurements the sample antibody was immobilized applying a contact time of 60 seconds and a flow rate of 10 μL/min in phosphate buffer saline pH 7.4, 0.05% TWEEN™ (polysorbate) 20 at 25° C. Recombinant His6-tagged human transferrin receptor (R&D systems, cat. no 2474-TR-050) was applied in increasing concentrations and the signal monitored over the time. An average time span of 150 seconds of association time and 600 seconds of dissociation time at 30 μL/min flow rate was recorded. Data were fit using a 1:1 binding model (Langmuir isotherm).

TABLE 42

Sequences of the epitopes of
human transferrin receptor (hTfR)

| SEQ ID NO | Sequence |
|---|---|
| 202 | IGQNMVTIVQSNGNL 20 |
| 203 | NMVTIVQSNGNLDPV |
| 204 | QSNGNLDPVESPEGY |

Example 28: Surface Plasmon Resonance-Based Binding Assay for Human TfR-Antibody Interaction The binding experiment were carried out on a BIACORE™ B 4000 (GE Healthcare) equipped with C1 sensor chip (GE Healthcare, cat. no. BR1005-35) pre-treated with anti-human Fab antibody (GE Healthcare, cat. no 28-9583-25) using a standard amine coupling chemistry procedure accordingly to the vendor's manual.

For kinetic measurements the sample antibody was immobilized applying a contact time of 60 seconds and a flow rate of 10 µL/min in phosphate buffer saline pH 7.4, 0.05% TWEEN™ (polysorbate) 20 at 25° C. Recombinant His6-tagged human transferrin receptor (R&D systems, cat. no 2474-TR-050) was applied in increasing concentrations and the signal monitored over the time. An average time span of 150 seconds of association time and 600 seconds of dissociation time at 30 µL/min flow rate was recorded. Data were fit using a 1:1 binding model (Langmuir isotherm).

Example 29: Humanization of the VH and VL Domains of Murine and Rabbit Anti-Transferrin Receptor Antibody The non-human anti-transferrin receptor antibodies were humanized as follows: Based on the characterization of encoding sequences and amino acid sequences that comprise the VH and VL domains of a the non-human anti-transferrin receptor antibodies of the IgG1 class with kappa light chain, a corresponding humanized anti-transferrin receptor antibody was generated by CDR grafting an backward/forward mutations based on the human germline framework VH4_3 and VK1_10 combination for clone 299.

The humanized antibodies of clone 2/99 as reported herein were not available by applying standard humanization techniques. It was required to introduce non-standard mutations in the amino acid sequence in order to obtain a humanized antibody with transferrin receptor binding off-rates within the intended range. This is especially important as the antibodies as reported herein are being developed for crossing the human blood-brain-barrier to shuttle the HER bispecific antibody as the therapeutic payload into the brain.

It has been found that in order to obtain a suitable and developable humanized antibody two cysteine amino acid residues in the light chain of the parental rabbit antibody had to be replaced by a proline and an asparagine amino acid residue, respectively. In addition to be within the given off-rate range a serine residue present in the middle of the rabbit CDRL3 had to be replaced by an alanine residue.

Is has further been found that it is advantageous to change three amino acid residues in the heavy chain at positions 65, 100 g and 105 (numbering according to Kabat). All numbering as used herein is based on the Kabat variable domain numbering scheme. Anti-transferrin receptor antibodies that specifically bind to human transferrin receptor (huTfR) and cynomolgus transferrin receptor (cyTfR) were obtained.

Example 30: Method to Determine Human/Cynomolgus TfR Receptor Affinity

In this example the method for the determination of the human transferrin receptor affinities for the comparison of the dissociation behavior is outlined.

For all analysis the Biotin CAPture Kit from GE Healthcare (Instruction 28-9242-34 AB) was used. First the chip was rehydrated by docking it in the BIACORE™ T200 instrument. After that, the chip was left on standby with running buffer overnight. For surface preparation the Biotin CAPture Reagent was diluted 1:100 in running buffer (1×PBS, supplemented with 0.25 M NaCl). This solution was injected on Flow Cells 1 to 4 for 360 sec with a flow rate of 2 µL/min. Next the sensor surface was conditioned with three one-minute injections of regeneration solution provided in the Biotin CAPture Kit. This has to be done for the docking procedure or for the first time or after storage. A 100 nM human or cynomolgus, respectively, mono-biotinylated transferrin receptor solution should be injected on Flow Cell 2 for 30 sec at a flow rate of 10 µL/min. For affinity determination injections with six concentrations (500, 250, 125, 62.5, 31.25, 15.625 and 0 nM) were applied. They were injected on the "hu-TfR-flow cell" (e.g. Flow Cell 2 as prepared as outlined above) with an injection time of 180 sec (association) and a flow rate of 10 µL/min. After dissociation phase of 600 sec the surface was regenerated according to the manufacturer's instructions with the regeneration solution provided in the Biotin CAPture Kit and the next cycle was carried out.

The kinetic data was evaluated using the BIACORE™ T200 evaluation software. Especially the dissociation rate constants of the different human transferrin receptor binders were taken into account after the application of the 1:1 Langmuir binding model.

Example 31: B4000 Relative Ranking of Human/Cynomolgus Transferrin Receptor Dissociation A CAP sensor chip (provided in the Biotin CAPture Kit, series S #28-9202-34 GE) was mounted into a BIACORE™ B4000 system, normalized and addressed in a hydrodynamic manner, according to the manufacturer's instructions. In the first cycle the CAP reagent (as provided in the Kit) was addressed to spot 1, 2, 4 and 5 with a flow rate of 10 µL/min for 300 sec. The human transferrin receptor capture took place in spot 1 (human transferrin receptor-biotinylated) and spot 5 (cynomolgus transferrin receptor-biotinylated) with a flow rate of 10 µL/min and a contact time of 30 sec. The receptors were diluted to a concentration of 50 nM with running buffer (1×PBS #28995084, GE Healthcare, supplemented with 0.25 M NaCl). The antibodies were injected into all flow cells in a concentration series of 100 nM, 50 nM, 25 nM and 0 nM for 180 sec at a flow speed of 30 µL/min. Dissociation time was set to 300 sec. Regeneration of the whole complex from the CAP chip has been performed utilizing the regeneration solution provided in the Biotin CAPture Kit (120 sec with a flow rate of 10 µL/min). To control the active protein concentration a second cycle was performed in spot 5 utilizing biotinylated protein A (#P2165-2MG, Sigma) with a flow rate of 10 µL/min and a contact time of 30 sec. Spot 1 was kept empty in this control cycle. The antibodies and the regeneration were handled like in cycle 1. Relevant kinetic data was calculated using the BIACORE™ B4000 evaluation software. The dissociation from the human transferrin receptor has been determined applying the 1:1 dissociation fit.

Results

The mouse anti-human transferrin-receptor antibody 128.1 (WO 93/10819) was taken as reference. The new humanized anti-transferrin receptor antibodies that specifically bind to human transferrin receptor (huTfR) and cynomolgus transferrin receptor (cyTfR) had an off-rate for the human transferrin receptor that was equal to or less than (i.e. at most) that of the anti-transferrin receptor antibody 128.1 for the cynomolgus transferrin receptor, whereby the off-rates are determined by surface plasmon resonance and bound with an off-rate for the human transferrin receptor that was between and including 0.1 l/s and 0.005 l/s. In the following Table the off-rates of humanization variants of the rabbit light chain variable domain of clone 2/99 in combination with humanization variants of the rabbit heavy chain variable domain of clone 2/99 are shown. Binding partner was human transferrin receptor (determined at 25° C.).

TABLE 43

| | VH | | | | | | | | | |
|---|---|---|---|---|---|---|---|---|---|---|
| VL | 0 (rb) | 1 | 2 | 5 | 6 | 7 | 8 | 9 | 11 | 12 |
| 0 (rb) | 4.34E−04 | 9.08E−04 | 8.06E−04 | 7.72E−04 | 6.63E−04 | 5.15E−04 | 4.06E−04 | 9.01E−04 | 9.05E−04 | 9.21E−04 |
| 1 | 5.69E−03 | 1.00E−03 | 1.00E−03 | 1.00E−03 | 1.00E−03 | 7.52E−03 | 3.19E−03 | 6.94E−03 | 1.00E−03 | 1.00E−03 |
| 2 | 1.25E−03 | 2.86E−03 | 2.75E−03 | 2.41E−03 | 1.87E−03 | 1.31E−03 | 1.01E−03 | 3.99E−03 | 3.85E−03 | 6.35E−03 |
| 3 | 1.32E−03 | 4.31E−03 | 3.84E−03 | 3.16E−03 | 2.82E−03 | 1.45E−03 | 1.00E−03 | 4.17E−03 | 5.65E−03 | 5.86E−03 |
| 4 | 1.36E−03 | 2.56E−03 | 2.63E−03 | 2.38E−03 | 1.87E−03 | 1.25E−03 | 7.88E−04 | 2.70E−03 | 3.88E−03 | 3.11E−03 |
| 5 | 1.94E−03 | 2.71E−03 | 2.62E−03 | 2.53E−03 | 1.66E−03 | 1.35E−03 | 1.07E−03 | 3.50E−03 | 4.56E−03 | 5.82E−03 |
| 6 | 1.90E−03 | 5.38E−03 | 5.55E−03 | 4.64E−03 | 3.06E−03 | 1.97E−03 | 1.40E−03 | 6.83E−03 | 6.71E−03 | 7.05E−03 |
| 7 | 4.63E−03 | 7.33E−03 | 7.50E−03 | 6.97E−03 | 5.63E−03 | 3.66E−03 | 2.31E−03 | 7.61E−03 | 7.81E−03 | 7.71E−03 |
| 8 | 1.39E−03 | 4.85E−03 | 3.94E−03 | 3.78E−03 | 3.01E−03 | 1.72E−03 | 1.16E−03 | 5.23E−03 | 5.52E−03 | 5.31E−03 |
| 9-NYA (SEQ ID NO 193) | 1.41E−03 | 2.46E−03 | 2.21E−03 | 2.03E−03 | 1.41E−03 | 1.21E−03 | 1.01E−03 | 2.52E−03 | 2.42E−03 | 2.19E−03 |
| 10 | 1.88E−03 | 6.77E−03 | 6.49E−03 | 6.53E−03 | 4.55E−03 | 2.64E−03 | 1.73E−03 | 7.19E−03 | 7.16E−03 | 7.79E−03 |
| 12 | 5.41E−03 | 7.05E−03 | 8.14E−03 | 1.00E−03 | 7.78E−03 | 7.75E−03 | 6.72E−03 | 1.00E−03 | 7.87E−03 | 1.00E−03 |
| 14 | 1.78E−03 | 2.99E−03 | 2.44E−03 | 2.33E−03 | 2.20E−03 | 1.53E−03 | 1.04E−03 | 3.32E−03 | 3.51E−03 | 5.46E−03 |
| 15 | 6.63E−03 | 6.69E−03 | 6.38E−03 | 6.37E−03 | 4.21E−03 | 2.73E−03 | 1.81E−03 | 7.39E−03 | 7.09E−03 | 7.76E−03 |
| 17 | 1.49E−03 | 7.56E−03 | 7.12E−03 | 7.45E−03 | 7.17E−03 | 1.87E−03 | 1.12E−03 | 4.25E−03 | 7.55E−03 | 7.27E−03 |

| | VH | | | | | | | | | |
|---|---|---|---|---|---|---|---|---|---|---|
| VL | 13 | 15 | 16 | 17 | 18 | 19 | 20 | 21 | 22 | 23-DANG |
| 0 (rb) | 4.82E−04 | 7.63E−04 | 6.53E−04 | 4.13E−04 | 1.09E−03 | 1.00E−03 | 1.11E−03 | 5.65E−04 | 5.06E−04 | 3.38E−04 |
| 1 | 1.00E−03 | 7.72E−03 | 7.71E−03 | 4.33E−03 | 1.00E−03 | 1.00E−03 | 1.00E−03 | 7.71E−03 | 5.78E−03 | 2.80E−03 |
| 2 | 2.46E−03 | 2.16E−03 | 1.97E−03 | 1.05E−03 | 4.89E−03 | 7.69E−03 | 5.25E−03 | 1.38E−03 | 1.26E−03 | 7.15E−04 |
| 3 | 2.77E−03 | 2.07E−03 | 1.73E−03 | 8.43E−04 | 6.65E−03 | 1.00E−03 | 7.15E−03 | 1.94E−03 | 1.43E−03 | 7.83E−04 |
| 4 | 1.30E−03 | 1.34E−03 | 1.27E−03 | 7.23E−04 | 3.35E−03 | 1.00E−03 | 4.36E−03 | 1.46E−03 | 1.18E−03 | 7.61E−04 |
| 5 | 2.18E−03 | 2.14E−03 | 2.23E−03 | 1.23E−03 | 3.49E−03 | 1.00E−03 | 3.52E−03 | 1.37E−03 | 1.41E−03 | 8.80E−04 |
| 6 | 3.65E−03 | 3.50E−03 | 3.39E−03 | 1.71E−03 | 6.74E−03 | 1.00E−03 | 6.06E−03 | 2.07E−03 | 2.14E−03 | 1.16E−03 |
| 7 | 6.68E−03 | 5.43E−03 | 5.25E−03 | 2.33E−03 | 7.66E−03 | 1.00E−03 | 7.14E−03 | 2.38E−03 | 3.37E−03 | 1.55E−03 |
| 8 | 2.47E−03 | 2.09E−03 | 1.97E−03 | 1.11E−03 | 6.77E−03 | 6.71E−03 | 6.58E−03 | 1.74E−03 | 1.65E−03 | 9.41E−04 |
| 9-NYA (SEQ ID NO 193) | 1.39E−03 | 1.42E−03 | 1.36E−03 | 9.34E−04 | 2.21E−03 | 6.17E−03 | 1.89E−03 | 1.13E−03 | 1.26E−03 | 7.69E−04 |
| 10 | 5.89E−03 | 3.99E−03 | 4.24E−03 | 1.88E−03 | 7.46E−03 | 1.00E−03 | 7.05E−03 | 2.11E−03 | 2.09E−03 | 1.20E−03 |
| 12 | 7.85E−03 | 7.64E−03 | 7.54E−03 | 2.84E−03 | 1.00E−03 | 1.00E−03 | 1.00E−03 | 7.54E−03 | 6.44E−03 | 1.87E−03 |
| 14 | 2.22E−03 | 1.94E−03 | 1.75E−03 | 1.05E−03 | 3.00E−03 | 7.96E−03 | 2.39E−03 | 1.03E−03 | 1.12E−03 | 7.33E−04 |
| 15 | 7.11E−03 | 6.03E−03 | 4.77E−03 | 1.56E−03 | 7.58E−03 | 1.00E−03 | 7.85E−03 | 1.92E−03 | 1.79E−03 | 9.86E−04 |
| 17 | 3.39E−03 | 1.69E−03 | 1.66E−03 | 9.88E−04 | 5.30E−03 | 1.00E−03 | 4.57E−03 | 9.97E−04 | 9.38E−04 | 6.94E−04 |

The combination of VH23-DANG with VL09-NYA (SEQ ID NO 193) was chosen as starting point for further engineering to develop a binding site that is reflecting the properties of the antibody 128.1 with respect to the binding to human transferrin receptor more closely.

In the following Table the off-rates of different exemplary variants of VH23-DANG and VL9-NYA (SEQ ID NO 193) as well as different other variable domain humanization variants for the human transferrin receptor are shown in comparison (determined according to Example 31 at 25° C.).

TABLE 44

|  | VK9-NYA (SEQ ID NO 193) | VK9-SYA | VK9-GYS | VK9-CYS | VH567-P...NYA | VK12-HYS | VK17-TYS | VK15-AYS | VK2-SYS | VK6-SYS |
|---|---|---|---|---|---|---|---|---|---|---|
| VH23-DANG | 8.83E−03 |  | 3.96E−03 |  | 4.62E−03 | 1.53E−02 | 2.29E−03 | 6.97E−03 | 5.22E−03 | 1.32E−02 |
| VH23-DASG (SEQ ID NO 192) | 3.95E−02 | 4.84E−04 | 3.73E−03 | 2.33E−03 |  |  |  |  |  |  |
| VH23-DAQG (SEQ ID NO 205) | 1.49E−02 | 7.55E−04 | 3.75E−03 | 1.51E−03 |  |  |  |  |  |  |
| VH9-DANG | 1.82E−03 |  |  | 6.52E−03 |  |  |  |  | 4.02E−02 |  |
| VH9-DAQG | 1.25E−03 |  |  |  |  |  |  |  |  |  |
| VH7-DANG |  |  |  |  |  |  |  |  |  | 3.08E−02 | reference: 128.1 = 7.78E−02 (determined for the cynomolgus transferrin receptor).

In the following Table the kinetic data of different exemplary variants of VH23 and VL9 are shown in comparison (determined according to Example 30).

TABLE 45

| BIACORE™ Assay @ 25° C. | TfR | kd [s$^{-1}$] | ka [s$^{-1}$M$^{-1}$] | kD [M] |
|---|---|---|---|---|
| mAb 128.1 | cynomolgus | 7.33E−02 | 5.41E+05 | 1.36E−07 |
| VH23-DASG/VL09-NYA (SEQ ID NO 192/193) | human | 3.95E−02 | 8.83E+04 | 4.47E−07 |
| VH23-DAQG/VL09-NYA (SEQ ID NO 205/193) | human | 1.37E−02 | 1.21E+05 | 1.13E−07 |
| VH23-DANG/VL09-NYA | human | 8.83E−03 | 1.55E+05 | 5.72E−08 |

In the following Table the off-rates of humanization variants of the murine light chain variable domain of clone 4/94 in combination with humanization variants of the murine heavy chain variable domain of clone 4/94 are shown. Binding partner was human transferrin receptor.

TABLE 46

| VL | 0 (mu) | VH 1 (SEQ ID NO 201) | VH 2 (SEQ ID NO 207) | VH 3 (SEQ ID NO 208) | VH 4 (SEQ ID NO 209) |
|---|---|---|---|---|---|
| 0 (mu) | 1.36E−04 | 1.37E−04 | 1.56E−04 | 1.48E−04 | 1.77E−04 |
| 1 (SEQ ID NO 194) | 3.70E−04 | 4.10E−04 | 4.54E−04 | 4.76E−04 | 4.48E−04 |
| 2 (SEQ ID NO 195) | 3.64E−04 | 3.99E−04 | 4.26E−04 | 4.15E−04 | 4.38E−04 |
| 3 (SEQ ID NO 196) | 3.39E−04 | 3.86E−04 | 4.30E−04 | 4.34E−04 | 4.52E−04 |
| 4 (SEQ ID NO 197) | 5.42E−04 | 6.57E−04 | 7.03E−04 | 6.83E−04 | 7.05E−04 |
| 5 (SEQ ID NO 198) | 5.44E−04 | 6.84E−04 | 7.17E−04 | 7.17E−04 | 7.28E−04 |
| 6 (SEQ ID NO 199) | 3.81E−04 | 4.86E−04 | 5.27E−04 | 5.50E−04 | 5.52E−04 |
| 7 (SEQ ID NO 200) | 2.32E−04 | 2.74E−04 | 2.99E−04 | 3.06E−04 | 3.26E−04 |

Example 32: In Vivo Characterization of Herceptarg-scFab(8D3)

A Her2-expressing intracranial tumor xenograft model was used to compare the brain tumor penetration of Herceptarg-brain shuttle to Herceptarg alone by 3D fluorescence ultramicroscopy.

Cell Lines

The human breast cancer cell line BT474 M1 was maintained in RPMI 1640 supplemented with 10% fetal calf serum and 2 mL L-glutamine. Propagation of cell lines followed standard cell culture protocols.

Intracranial Implantation of Tumor Cells in Mice

Female severe combined immunodeficient hairless outbred (SHO) mice (weight 20 to 27 g) were obtained from Charles River and were 7 to 9 weeks of age at initiation of experiments. Mice were anesthetized with i.p. injection of 100 mg/kg ketamine and 10 mg/kg xylazine. Scalp was disinfected and removed over the whole right hemisphere of the brain to expose the cranium. The periosteum was removed by a bone scraper. Next, a 0.7-mm burr hole in diameter was drilled 2 mm right of midline and 2 mm anterior to bregma with a dental drill. Mice were then placed in a small animal stereotactic frame and BT-474 M1 cell suspension ($5 \times 10^5$ cells in 3 μl) was injected using a Hamilton syringe with a 26s-gauge needle to a depth of 3 mm into the brain tissue. After injection, needle was slowly withdrawn and the hole was sealed with Cyano veneer tissue glue. All animal studies were approved by the local government (file number 55.2-1-54-2532.0-76-14, Government of Upper Bavaria, Germany).

Application of Substances 30 days after tumor cell implantation mice received an i.v. injection of Herceptarg(LALA)—scFab(8D3)—ALEXA™ Fluor 750 (5 mg/kg, n=7) or Herceptarg(LALA)—ALEXA™ Fluor 750 (3.75 mg/kg; n=5) 6 h before dissection. Five minutes before necropsy, mice were injected i.v. with 100 μg lectin-ALEXA™ Fluor 750 solution to allow visualization of blood vessels ex vivo. Substances were systemically given via the tail vein in a volume of 150 μl.

Necropsy, Fixation and Optical Clearance of Brains

Mice were sacrificed by cervical dislocation. Brains were explanted and transferred to 10% buffered formalin for about 12 hours at room temperature in the dark and thereafter were dehydrated in a graded tetrahydrofuran series (50%, 70%, 80%, 100% for 90 minutes each, 100% over night and 100% for 90 minutes). Afterwards brains were cleared in dibenzyl ether for 2 days until the specimen became optically transparent.

3D Imaging of Brains by Ultramicroscopy

The optical transparent samples were placed in a commercial ultramicroscope, equipped with an Imager 3QE camera (both LaVision Biotec), a 2 My PLAPO 2VC objective lens (Olympus) and a supercontinuum white light laser (SuperK EXTREME 80 mHz VIS; NKT Photonics). The samples were scanned with a standard magnification of 0.63 in 5.1 μm thick virtual sections with filter settings appropriate for ALEXA™ Fluor 647 (excitation range 655/15 nm, emission range 680/30 nm) and ALEXA™ Fluor 750 (excitation range 747/33 nm, emission range 786/22 nm) signal detection. Tiff raw data were converted to dicom files and visualized using the OsiriX software (Pixmeo). A 3D brain tumor region of interest (ROI) was defined according to the dimensions of chaotic vessel structures seen by lectin-ALEXA™ Fluor 750 staining. The determined 3D ROI was imported to 3D-reconstructed mab-ALEXA™ Fluor 750 data files to read out mean antibody fluorescent signals within the brain tumors.

The distinct fluorescent signal intensities of mab-ALEXA™ Fluor 750 at different distances from nearest lectin-ALEXA™ Fluor 647-stained blood vessels were quantified. This was done with a set of custom developed image analysis algorithms implemented as a "Definiens Cognition Network Technology" rule set (Definiens AG).

Figure 36:
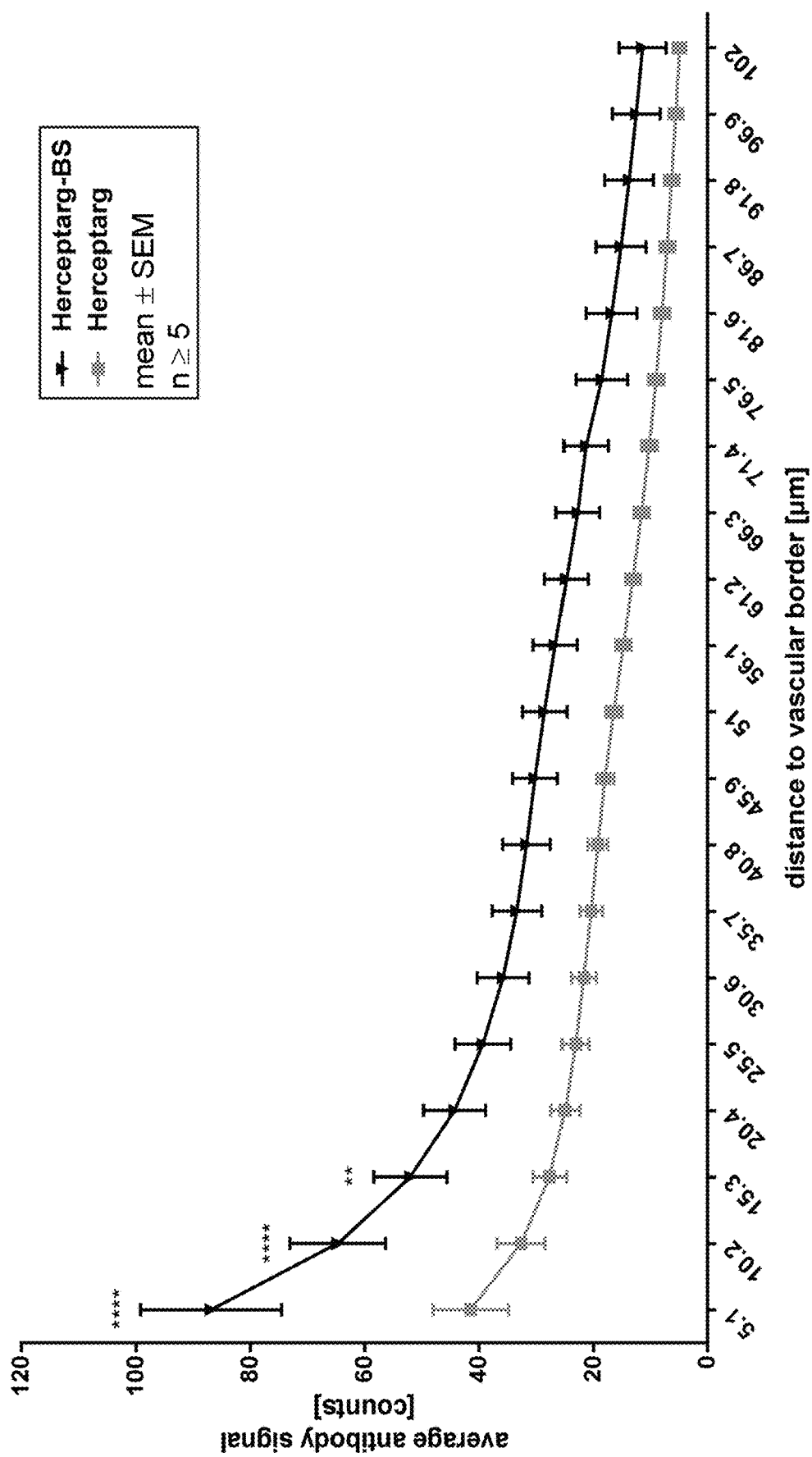
FIG. 36: Herceptarg(LALA)+/−scFab(8D3) penetration from vascular border into tumor tissue. Mean antibody signal in tumor tissue as a function of distance from the nearest tumor vessel shows that the brain shuttle (BS) increases penetration of Herceptarg into the brain tumor.

Statistical analysis was performed by GraphPad Prism software (GraphPad Software, Inc.) using 2-way ANOVA plus Sidak's multiple comparison test (FIG. 36). The significance levels are indicated by asterisks ($p < 0.01$ and **$P < 0.0001$). All data are presented as means f standard error of the mean.

The invention claimed is:

1. A trispecific antibody specifically binding to HER2 and a blood-brain barrier receptor (BBB-R), comprising a first monovalent antigen binding site specific for extracellular domain II of HER2 and a second monovalent antigen binding site specific for extracellular domain IV of HER2, and a third monovalent antigen binding site specific for a BBB-R, wherein the trispecific antibody comprises a first Fab molecule that specifically binds to extracellular domain II of HER2 and a second Fab molecule that specifically binds to extracellular domain IV of HER2; wherein the sequence of the variable light chain of the first Fab molecule is identical to the sequence of the variable light chain of the second Fab molecule; and wherein the trispecific antibody comprises:

(a) a first heavy chain comprising a heavy chain CDR1 comprising an amino acid sequence selected from the group consisting of SEQ ID NO: 55, SEQ ID NO: 58 and SEQ ID NO: 14; a heavy chain CDR 2 comprising an amino acid sequence selected from the group consisting of SEQ ID NO: 77; SEQ ID NO: 15 and SEQ ID NO: 60; and a heavy chain CDR 3 comprising an amino acid sequence selected from the group consisting of SEQ ID NO: 56 or SEQ ID NO: 59 and SEQ ID NO: 16; and (b) a second heavy chain comprising a heavy chain CDR1 comprising the amino acid sequence of SEQ ID NO: 20, a heavy chain CDR2 comprising the amino acid sequence of SEQ ID NO: 29 and a heavy chain CDR3 comprising an amino acid sequence selected from the group consisting of SEQ ID NO: 30 and SEQ ID NO: 79; and (c) a first and a second light chain, wherein the variable light chains of the first and second light chain comprise a light chain CDR1 comprising the amino acid sequence of SEQ ID NO: 89, a light chain CDR2 comprising the amino acid sequence of SEQ ID NO:90 and a light chain CDR3 comprising the amino acid sequence of SEQ ID NO: 19, and wherein the third antigen binding site specific for the BBB-R is a scFv or a scFab.

2. The trispecific antibody of claim 1, wherein the BBB-R of the third monovalent antigen binding site is selected from the group consisting of transferrin receptor (TfR), insulin receptor (InsR), insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

3. The trispecific antibody of claim 1, wherein the third monovalent antigen binding site specific for the BBB-R is a transferrin receptor.

4. The trispecific antibody of claim 3, wherein the third monovalent antigen binding site specifically binds to an epitope in the transferrin receptor comprised within the amino acid sequence of SEQ ID NO: 202, 203 and/or 204.

5. The trispecific antibody of claim 1, comprising two variable light chains comprising the amino acid sequence of SEQ ID NO: 54, a first heavy chain comprising a variable heavy chain comprising an amino acid sequence selected from the group consisting of SEQ ID NO: 64, SEQ ID NO: 70 and SEQ ID NO: 68, and a second heavy chain comprising a variable heavy chain comprising an amino acid sequence selected from the group consisting of SEQ ID NO: 92 and SEQ ID NO: 117.

6. The trispecific antibody of claim 1, wherein the scFv or scFab is connected to the N-terminus of an IgG molecule comprising the first monovalent antigen binding site and the second monovalent antigen binding site.

7. The trispecific antibody of claim 1, wherein the scFv or scFab is connected to the C-terminus of a C-terminal constant region of the first heavy chain or the second heavy chain.

8. The trispecific antibody of claim 1, wherein the third monovalent antigen binding site comprises a heavy chain CDR1 comprising the amino acid sequence of SEQ ID NO: 186, a heavy chain CDR2 comprising the amino acid sequence of SEQ ID NO: 187 and a heavy chain CDR3 comprising an amino acid sequence selected from the group consisting of SEQ ID NO: 188, SEQ ID NO: 206 and SEQ ID NO: 174; and a light chain CDR1 comprising the amino acid sequence of SEQ ID NO: 189, a light chain CDR2 comprising the amino acid sequence of SEQ ID NO: 190 and a light chain CDR3 comprising the amino acid sequence of SEQ ID NO: 191.

9. The trispecific antibody of claim 1, wherein the third monovalent antigen binding site comprises a heavy chain CDR1 comprising the amino acid sequence of SEQ ID NO: 172, a heavy chain CDR2 comprising the amino acid sequence of SEQ ID NO: 173 and a heavy chain CDR3 comprising the amino acid sequence of SEQ ID NO: 174;
and a light chain CDR1 comprising the amino acid sequence of SEQ ID NO: 175, a light chain CDR2 comprising the amino acid sequence of SEQ ID NO: 176 and a light chain CDR3 comprising the amino acid sequence of SEQ ID NO: 177.

10. The trispecific antibody of claim 1, wherein the third monovalent antigen binding site comprises a variable heavy chain comprising the amino acid sequence of SEQ ID NO: 178 and a variable light chain comprising the amino acid sequence of SEQ ID NO: 179 or a humanized version thereof.

11. The trispecific antibody of claim 1, wherein the third monovalent antigen binding site comprises a variable heavy chain comprising the amino acid sequence of SEQ ID NO: 192 or SEQ ID NO: 205 and a variable light chain comprising the amino acid sequence of SEQ ID NO: 193.

12. The trispecific antibody of claim 1, wherein the third monovalent antigen binding site comprises a heavy chain CDR1 comprising the amino acid sequence of SEQ ID NO: 180, a heavy chain CDR2 comprising the amino acid sequence of SEQ ID NO: 181 and a heavy chain CDR3 comprising the amino acid sequence of SEQ ID NO: 182;
and a light chain CDR1 comprising the amino acid sequence of SEQ ID NO: 183, a light chain CDR2 comprising the amino acid sequence of SEQ ID NO: 184 and a light chain CDR3 comprising the amino acid sequence of SEQ ID NO: 185.

13. The trispecific antibody of claim 1, wherein the third monovalent antigen binding site comprises a variable heavy chain comprising the amino acid sequence of SEQ ID NO: 166 and a variable light chain comprising the amino acid sequence of SEQ ID NO: 167 or a humanized version thereof.

14. The trispecific antibody of claim 1, wherein the third monovalent antigen binding site comprises a variable heavy chain comprising an amino acid sequence selected from the group consisting of SEQ ID NO: 92, SEQ ID NO: 195, SEQ ID NO: 196, SEQ ID NO: 197, SEQ ID NO: 198, SEQ ID NO: 199, and SEQ ID NO: 200, and a variable light chain comprising an amino acid sequence selected from the group consisting of SEQ ID NO: 201, SEQ ID NO: 207, SEQ ID NO: 208, and SEQ ID NO:209.

15. A pharmaceutical composition comprising the trispecific antibody of claim 1.

16. A nucleic acid sequence encoding the trispecific antibody of claim 1.

17. An expression vector comprising the nucleic acid sequence of claim 16.

18. A prokaryotic or eukaryotic host cell comprising the vector of claim 17.

19. A method of producing a trispecific antibody comprising culturing the host cell of claim 18 under conditions suitable for expression of the trispecific antibody, and recovering the trispecific antibody from the host cell.

* * * * *

SEQUENCE LISTING

```
<160> NUMBER OF SEQ ID NOS: 218

<210> SEQ ID NO 1
<211> LENGTH: 1995
<212> TYPE: DNA
<213> ORGANISM: Artificial sequence
<220> FEATURE:
<223> OTHER INFORMATION: Her2 ECD DNA

<400> SEQUENCE: 1
acccaagtgt gcaccggcac agacatgaag ctgcggctcc ctgccagtcc cgagacccac        60
ctggacatgc tccgccacct ctaccagggc tgccaggtgg tgcagggaaa cctggaactc       120
acctacctgc ccaccaatgc cagcctgtcc ttcctgcagg atatccagga ggtgcagggc       180
tacgtgctca tcgctcacaa ccaagtgagg caggtcccac tgcagaggct gcggattgtg       240
cgaggcaccc agctctttga ggacaactat gccctggccg tgctagacaa tggagacccg       300
ctgaacaata ccaccccctgt cacaggggcc tccccaggag gcctgcggga gctgcagctt       360
cgaagcctca cagagatctt gaaaggaggg gtcttgatcc agcggaaccc ccagctctgc       420
taccaggaca cgatttttgtg gaaggacatc ttccacaaga caaccagct ggctctcaca       480 ctgatagaca ccaaccgctc tcgggcctgc caccctgtt ctccgatgtg taagggctcc       540
cgctgctggg gagagagttc tgaggattgt cagagcctga cgcgcactgt ctgtgccggt       600
ggctgtgccc gctgcaaggg gccactgccc actgactgct gccatgagca gtgtgctgcc       660
```

```
ggctgcacgg gccccaagca ctctgactgc ctggcctgcc tccacttcaa ccacagtggc    720
atctgtgagc tgcactgccc agccctggtc acctacaaca cagacacgtt tgagtccatg    780
cccaatcccg agggccggta cattcggcc gccagctgtg tgactgcctg tccctacaac    840
tacctttcta cggacgtggg atcctgcacc ctcgtctgcc ccctgcacaa ccaagaggtg    900
acagcagagg atggaacaca gcggtgtgag aagtgcagca gccctgtgcc cgagtgtgc    960 tatggtctgg gcatggagca cttgcgagag gtgagggcag ttaccagtgc caatatccag   1020
gagtttgctg gctgcaagaa gatctttggg agcctggcat ttctgccgga gagctttgat   1080
ggggacccag cctccaacac tgccccgctc cagccagagc agctccaagt gtttgagact   1140
ctggaagaga tcacaggtta cctatacatc tcagcatggc cggacagcct gcctgacctc   1200
agcgtcttcc agaacctgca gtaatccgg ggacgaattc tgcacaatgg cgcctactcg   1260 ctgacccctgc aagggctggg catcagctgg ctggggctgc gctcactgag ggaactgggc   1320
agtggactgg ccctcatcca ccataacacc cacctctgct tcgtgcacac ggtgccctgg   1380
gaccagctct ttcggaaccc gcaccaagct ctgctccaca ctgccaaccg gccagaggac   1440
gagtgtgtgg gcgagggcct ggcctgccac cagctgtgcg cccgagggca ctgctggggt   1500
ccagggccca cccagtgtgt caactgcagc cagttccttc ggggccagga gtgcgtggag   1560
gaatgccgag tactgcaggg gctccccagg gagtatgtga atgccaggca ctgtttgccg   1620
tgccaccctg agtgtcagcc ccagaatggc tcagtgacct gttttggact ggaggctgac   1680
cagtgtgtgg cctgtgccca ctataaggac cctcccttct gcgtggcccg ctgccccagc   1740
ggtgtgaaac ctgacctctc ctacatgccc atctggaagt ttccagatga ggagggcgca   1800
tgccagcctt gccccatcaa ctgcacccac tcctgtgtgg acctggatga caagggctgc   1860
cccgccgagc agagagccag ccctctgacg gtcgacgaac agttatattt tcagggcggc   1920
tcaggcctga acgacatctt cgaggcccag aagatcgagt ggcacgaggc tcgagctcac   1980
caccatcacc atcac                                                    1995
```

<210> SEQ ID NO 2  
<211> LENGTH: 684  
<212> TYPE: PRT  
<213> ORGANISM: Artificial sequence  
<220> FEATURE:  
<223> OTHER INFORMATION: Her2 ECD

<400> SEQUENCE: 2

```
Met Gly Trp Ser Cys Ile Ile Leu Phe Leu Val Ala Thr Ala Thr Gly
1               5                   10                  15

Val His Ser Thr Gln Val Cys Thr Gly Thr Asp Met Lys Leu Arg Leu
                20                  25                  30

Pro Ala Ser Pro Glu Thr His Leu Asp Met Leu Arg His Leu Tyr Gln
            35                  40                  45

Gly Cys Gln Val Val Gln Gly Asn Leu Glu Leu Thr Tyr Leu Pro Thr
        50                  55                  60

Asn Ala Ser Leu Ser Phe Leu Gln Asp Ile Gln Glu Val Gln Gly Tyr
65                  70                  75                  80

Val Leu Ile Ala His Asn Gln Val Arg Gln Val Pro Leu Gln Arg Leu
                85                  90                  95

Arg Ile Val Arg Gly Thr Gln Leu Phe Glu Asp Asn Tyr Ala Leu Ala
            100                 105                 110

Val Leu Asp Asn Gly Asp Pro Leu Asn Asn Thr Thr Pro Val Thr Gly
            115                 120                 125
```

```
Ala Ser Pro Gly Gly Leu Arg Glu Leu Gln Leu Arg Ser Leu Thr Glu
    130                 135                 140

Ile Leu Lys Gly Gly Val Leu Ile Gln Arg Asn Pro Gln Leu Cys Tyr
145                 150                 155                 160

Gln Asp Thr Ile Leu Trp Lys Asp Ile Phe His Lys Asn Asn Gln Leu
                165                 170                 175

Ala Leu Thr Leu Ile Asp Thr Asn Arg Ser Arg Ala Cys His Pro Cys
            180                 185                 190

Ser Pro Met Cys Lys Gly Ser Arg Cys Trp Gly Glu Ser Ser Glu Asp
        195                 200                 205

Cys Gln Ser Leu Thr Arg Thr Val Cys Ala Gly Cys Ala Arg Cys
    210                 215                 220

Lys Gly Pro Leu Pro Thr Asp Cys Cys His Glu Gln Cys Ala Ala Gly
225                 230                 235                 240

Cys Thr Gly Pro Lys His Ser Asp Cys Leu Ala Cys Leu His Phe Asn
                245                 250                 255

His Ser Gly Ile Cys Glu Leu His Cys Pro Ala Leu Val Thr Tyr Asn
            260                 265                 270

Thr Asp Thr Phe Glu Ser Met Pro Asn Pro Gly Arg Tyr Thr Phe
        275                 280                 285

Gly Ala Ser Cys Val Thr Ala Cys Pro Tyr Asn Tyr Leu Ser Thr Asp
    290                 295                 300

Val Gly Ser Cys Thr Leu Val Cys Pro Leu His Asn Gln Glu Val Thr
305                 310                 315                 320

Ala Glu Asp Gly Thr Gln Arg Cys Glu Lys Cys Ser Lys Pro Cys Ala
                325                 330                 335

Arg Val Cys Tyr Gly Leu Gly Met Glu His Leu Arg Glu Val Arg Ala
            340                 345                 350

Val Thr Ser Ala Asn Ile Gln Glu Phe Ala Gly Cys Lys Lys Ile Phe
        355                 360                 365

Gly Ser Leu Ala Phe Leu Pro Glu Ser Phe Asp Gly Asp Pro Ala Ser
    370                 375                 380

Asn Thr Ala Pro Leu Gln Pro Glu Gln Leu Gln Val Phe Glu Thr Leu
385                 390                 395                 400

Glu Glu Ile Thr Gly Tyr Leu Tyr Ile Ser Ala Trp Pro Asp Ser Leu
                405                 410                 415

Pro Asp Leu Ser Val Phe Gln Asn Leu Gln Val Ile Arg Gly Arg Ile
            420                 425                 430

Leu His Asn Gly Ala Tyr Ser Leu Thr Leu Gln Gly Leu Gly Ile Ser
        435                 440                 445

Trp Leu Gly Leu Arg Ser Leu Arg Glu Leu Gly Ser Gly Leu Ala Leu
    450                 455                 460

Ile His His Asn Thr His Leu Cys Phe Val His Thr Val Pro Trp Asp
465                 470                 475                 480

Gln Leu Phe Arg Asn Pro His Gln Ala Leu Leu His Thr Ala Asn Arg
                485                 490                 495

Pro Glu Asp Glu Cys Val Gly Glu Gly Leu Ala Cys His Gln Leu Cys
            500                 505                 510

Ala Arg Gly His Cys Trp Gly Pro Gly Pro Thr Gln Cys Val Asn Cys
        515                 520                 525

Ser Gln Phe Leu Arg Gly Gln Glu Cys Val Glu Glu Cys Arg Val Leu
    530                 535                 540
```

Gln Gly Leu Pro Arg Glu Tyr Val Asn Ala Arg His Cys Leu Pro Cys
545                 550                 555                 560

His Pro Glu Cys Gln Pro Gln Asn Gly Ser Val Thr Cys Phe Gly Leu
            565                 570                 575

Glu Ala Asp Gln Cys Val Ala Cys Ala His Tyr Lys Asp Pro Pro Phe
        580                 585                 590

Cys Val Ala Arg Cys Pro Ser Gly Val Lys Pro Asp Leu Ser Tyr Met
        595                 600                 605

Pro Ile Trp Lys Phe Pro Asp Glu Gly Ala Cys Gln Pro Cys Pro
        610                 615                 620

Ile Asn Cys Thr His Ser Cys Val Asp Leu Asp Asp Lys Gly Cys Pro
625                 630                 635                 640

Ala Glu Gln Arg Ala Ser Pro Leu Thr Val Asp Glu Gln Leu Tyr Phe
                645                 650                 655

Gln Gly Gly Ser Gly Leu Asn Asp Ile Phe Glu Ala Gln Lys Ile Glu
                660                 665                 670

Trp His Glu Ala Arg Ala His His His His His
            675                 680

<210> SEQ ID NO 3
<211> LENGTH: 681
<212> TYPE: DNA
<213> ORGANISM: Artificial sequence
<220> FEATURE:
<223> OTHER INFORMATION: Fc (hole) DNA

<400> SEQUENCE: 3

```
gacaaaactc acacatgccc accgtgccca gcacctgaac tcctggggga ccgtcagtc      60
ttcctcttcc cccaaaacc caaggacacc ctcatgatct cccggacccc tgaggtcaca     120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtgcacc ctgcccccat cccgggatga gctgaccaag    420
aaccaggtca gcctctcgtg cgcagtcaaa ggcttctatc ccagcgacat cgccgtggag    480
tgggagagca atgggcagcc ggagaacaac tacaagacca cgcctcccgt gctggactcc    540
gacggctcct tcttcctcgt gagcaagctc accgtggaca agagcaggtg gcagcagggg    600
aacgtcttct catgctccgt gatgcatgag gctctgcaca accgcttcac gcagaagagc    660
ctctccctgt ctccgggtaa a                                              681
```

<210> SEQ ID NO 4
<211> LENGTH: 227
<212> TYPE: PRT
<213> ORGANISM: Artificial sequence
<220> FEATURE:
<223> OTHER INFORMATION: Fc (hole)

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

```
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Cys Thr Leu Pro Pro Ser Arg Asp Glu Leu Thr Lys Asn Gln Val Ser
130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn Arg Phe Thr Gln Lys Ser Leu Ser Leu Ser
210                 215                 220
Pro Gly Lys
225

<210> SEQ ID NO 5
<211> LENGTH: 2670
<212> TYPE: DNA
<213> ORGANISM: Artificial sequence
<220> FEATURE:
<223> OTHER INFORMATION: Her2 ECD-Fc(knob) DNA

<400> SEQUENCE: 5
acccaagtgt gcaccggcac agacatgaag ctgcggctcc ctgccagtcc cgagacccac      60
ctggacatgc tccgccacct ctaccagggc tgccaggtgg tgcagggaaa cctggaactc     120
acctacctgc ccaccaatgc cagcctgtcc ttcctgcagg atatccagga ggtgcagggc     180
tacgtgctca tcgctcacaa ccaagtgagg caggtcccac tgcagaggct gcggattgtg     240
cgaggcaccc agctctttga ggacaactat gccctggccg tgctagacaa tggagacccg     300
ctgaacaata ccaccccotgt cacaggggcc tccccaggag gcctgcggga gctgcagctt     360
cgaagcctca gagatcttg aaaggaggg gtcttgatcc agcggaaccc ccagctctgc     420
taccaggaca cgattttgtg gaaggacatc ttccacaaga caaccagct ggctctcaca     480
ctgatagaca ccaaccgctc tcgggcctgc caccctgtt ctccgatgtg taagggctcc     540
cgctgctggg gagagagttc tgaggattgt cagagcctga cgcgcactgt ctgtgccggt     600
ggctgtgccc gctgcaaggg gccactgccc actgactgct gccatgagca gtgtgctgcc     660
ggctgcacgg gccccaagca ctctgactgc ctggcctgcc tccacttcaa ccacagtggc     720
atctgtgagc tgcactgccc agcctggtc acctacaaca cagacacgtt tgagtccatg     780
cccaatcccg agggccggta cactttcggc gccagctgtg tgactgcctg tccctacaac     840
taccttcta cggacgtggg atcctgcacc ctcgtctgcc cctgcacaa ccaagaggtg     900
acagcagagg atgaacaca gcggtgtgag aagtgcagca gccctgtgc ccgagtgtgc     960
```

```
tatggtctgg gcatggagca cttgcgagag gtgagggcag ttaccagtgc caatatccag   1020
gagtttgctg gctgcaagaa gatctttggg agcctggcat ttctgccgga gagctttgat   1080
ggggacccag cctccaacac tgccccgctc cagccagagc agctccaagt gtttgagact   1140
ctggaagaga tcacaggtta cctatacatc tcagcatggc cggacagcct gcctgacctc   1200
agcgtcttcc agaacctgca gtaatccgg gacgaattc tgcacaatgg cgcctactcg    1260
ctgaccctgc aagggctggg catcagctgg ctggggctgc gctcactgag ggaactgggc   1320
agtggactgg ccctcatcca ccataacacc cacctctgct tcgtgcacac ggtgccctgg   1380
gaccagctct ttcggaaccc gcaccaagct ctgctccaca ctgccaaccg ccagaggac    1440 gagtgtgtgg gcgagggcct ggcctgccac cagctgtgcg cccgagggca ctgctggggt   1500
ccagggccca cccagtgtgt caactgcagc cagttccttc ggggccagga gtgcgtggag   1560
gaatgccgag tactgcaggg gctccccagg gagtatgtga atgccaggca ctgtttgccg   1620
tgccaccctg agtgtcagcc ccagaatggc tcagtgacct gttttggact ggaggctgac   1680
cagtgtgtgg cctgtgccca ctataaggac cctcccttct gcgtggcccg ctgccccagc   1740
ggtgtgaaac ctgacctctc ctacatgccc atctggaagt ttccagatga ggagggcgca   1800
tgccagcctt gccccatcaa ctgcacccac tcctgtgtgg acctggatga caagggctgc   1860
cccgccgagc agagagccag ccctctgacg gtcgacggtg gtagtccgac acctccgaca   1920
cccgggggtg gttctgcaga caaaactcac acatgcccac cgtgcccagc acctgaactc   1980
ctggggggac cgtcagtctt cctcttcccc ccaaaaccca aggacaccct catgatctcc   2040
cggacccctg aggtcacatg cgtggtggtg gacgtgagcc acgaagaccc tgaggtcaag   2100
ttcaactggt acgtggacgg cgtggaggtg cataatgcca agacaaagcc gcggaggag    2160 cagtacaaca gcacgtaccg tgtggtcagc gtcctcaccg tcctgcacca ggactggctg   2220
aatggcaagg agtacaagtg caaggtctcc aacaaagccc tcccagcccc catcgagaaa   2280
accatctcca aagccaaagg gcagcccga gaaccacagg tgtacaccct gcccccatgc    2340
cgggatgagc tgaccaagaa ccaggtcagc ctgtggtgcc tggtcaaagg cttctatccc   2400
agcgacatcg ccgtggagtg ggagagcaat gggcagccgg agaacaacta caagaccacg   2460
cctcccgtgc tggactccga cggctccttc ttcctctaca gcaagctcac cgtggacaag   2520
agcaggtggc agcaggggaa cgtcttctca tgctccgtga tgcatgaggc tctgcacaac   2580
cactacacgc agaagagcct ctccctgtct ccgggtaaat ccggaggcct gaacgacatc   2640
ttcgaggccc agaagattga atggcacgag                                   2670
```

<210> SEQ ID NO 6
<211> LENGTH: 890
<212> TYPE: PRT
<213> ORGANISM: Artificial sequence
<220> FEATURE:
<223> OTHER INFORMATION: Her2 ECD-Fc(knob)

<400> SEQUENCE: 6

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60
```

```
Ala His Asn Gln Val Arg Gln Val Pro Leu Gln Arg Leu Arg Ile Val
 65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
             100                 105                 110

Gly Gly Leu Arg Glu Leu Gln Leu Arg Ser Leu Thr Glu Ile Leu Lys
         115                 120                 125

Gly Gly Val Leu Ile Gln Arg Asn Pro Gln Leu Cys Tyr Gln Asp Thr
     130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480
```

```
Glu Cys Val Gly Glu Gly Leu Ala Cys His Gln Leu Cys Ala Arg Gly
            485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
            515                 520                 525

Pro Arg Glu Tyr Val Asn Ala Arg His Cys Leu Pro Cys His Pro Glu
            530                 535                 540

Cys Gln Pro Gln Asn Gly Ser Val Thr Cys Phe Gly Leu Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
            595                 600                 605

Thr His Ser Cys Val Asp Leu Asp Asp Lys Gly Cys Pro Ala Glu Gln
            610                 615                 620

Arg Ala Ser Pro Leu Thr Val Asp Gly Gly Ser Pro Thr Pro Pro Thr
625                 630                 635                 640

Pro Gly Gly Gly Ser Ala Asp Lys Thr His Thr Cys Pro Pro Cys Pro
            645                 650                 655

Ala Pro Glu Leu Leu Gly Gly Pro Ser Val Phe Leu Phe Pro Pro Lys
            660                 665                 670

Pro Lys Asp Thr Leu Met Ile Ser Arg Thr Pro Glu Val Thr Cys Val
            675                 680                 685

Val Val Asp Val Ser His Glu Asp Pro Glu Val Lys Phe Asn Trp Tyr
690                 695                 700

Val Asp Gly Val Glu Val His Asn Ala Lys Thr Lys Pro Arg Glu Glu
705                 710                 715                 720

Gln Tyr Asn Ser Thr Tyr Arg Val Val Ser Val Leu Thr Val Leu His
            725                 730                 735

Gln Asp Trp Leu Asn Gly Lys Glu Tyr Lys Cys Lys Val Ser Asn Lys
            740                 745                 750

Ala Leu Pro Ala Pro Ile Glu Lys Thr Ile Ser Lys Ala Lys Gly Gln
            755                 760                 765

Pro Arg Glu Pro Gln Val Tyr Thr Leu Pro Pro Cys Arg Asp Glu Leu
            770                 775                 780

Thr Lys Asn Gln Val Ser Leu Trp Cys Leu Val Lys Gly Phe Tyr Pro
785                 790                 795                 800

Ser Asp Ile Ala Val Glu Trp Glu Ser Asn Gly Gln Pro Glu Asn Asn
            805                 810                 815

Tyr Lys Thr Thr Pro Pro Val Leu Asp Ser Asp Gly Ser Phe Phe Leu
            820                 825                 830

Tyr Ser Lys Leu Thr Val Asp Lys Ser Arg Trp Gln Gln Gly Asn Val
            835                 840                 845

Phe Ser Cys Ser Val Met His Glu Ala Leu His Asn His Tyr Thr Gln
            850                 855                 860

Lys Ser Leu Ser Leu Ser Pro Gly Lys Gly Gly Leu Asn Asp Ile
865                 870                 875                 880

Phe Glu Ala Gln Lys Ile Glu Trp His Glu
            885                 890
```

<210> SEQ ID NO 7
<211> LENGTH: 2670
<212> TYPE: DNA
<213> ORGANISM: Artificial sequence
<220> FEATURE:
<223> OTHER INFORMATION: Her2 ECD(pertuzumab KO)-Fc(knob)DNA

<400> SEQUENCE: 7

```
acccaagtgt gcaccggcac agacatgaag ctgcggctcc ctgccagtcc cgagacccac        60
ctggacatgc tccgccacct ctaccagggc tgccaggtgg tgcagggaaa cctggaactc       120
acctacctgc ccaccaatgc cagcctgtcc ttcctgcagg atatccagga ggtgcagggc       180
tacgtgctca tcgctcacaa ccaagtgagg caggtccac tgcagaggct gcggattgtg        240
cgaggcaccc agctctttga ggacaactat gccctggccg tgctagacaa tggagacccg       300
ctgaacaata ccaccctgt cacagggcc tccccaggag gcctgcggga gctgcagctt         360
cgaagcctca cagagatctt gaaggagggg gtcttgatcc agcggaaccc ccagctctgc       420
taccaggaca cgattttgtg gaaggacatc ttccacaaga caaccagct ggctctcaca        480
ctgatagaca ccaaccgctc tcgggcctgc caccccctgtt ctccgatgtg taagggctcc      540
cgctgctggg gagagagttc tgaggattgt cagagcctga cgcgcactgt ctgtgccggt       600
ggctgtgccc gctgcaaggg gccactgccc actgactgct gccatgagca gtgtgctgcc      660
ggctgcacgg gccccaagca ctctgactgc ctggcctgcc tccacttcaa ccacagtggc      720
atctgtgagc tgcactgccc agccctggtc acctacaaca cagacacgcg ggagtccatg      780
cccaatcccg agggccggta tagattcggc gccagctgtg tgactgcctg tcctacaac       840
tacctttcta cggaccgggg atcctgcacc ctcgtctgcc cctggccaa ccaagaggtg        900
acagcagagg atggaacaca gcggtgtgag aagtgcagca gccctgtgc ccgagtgtgc       960
tatggtctgg gcatggagca cttgcgagag gtgagggcag ttaccagtgc caatatccag      1020
gagtttgctg gctgcaagaa gatctttggg agcctggcat ttctgccgga gagctttgat      1080
ggggacccag cctccaacac tgccccgctc cagccagagc agctccaagt gtttgagact      1140
ctggaagaga tcacaggtta cctatacatc tcagcatggc cggacagcct gcctgacctc      1200
agcgtcttcc agaacctgca agtaatccgg ggacgaattc tgcacaatgg cgcctactcg      1260
ctgaccctgc aagggctggg catcagctgg ctggggctgc gctcactgag ggaactgggc      1320
agtggactgg ccctcatcca ccataacacc cacctctgct tcgtgcacac ggtgccctgg      1380
gaccagctct ttcggaaccc gcaccaagct ctgctccaca ctgccaaccg gccagaggac      1440
gagtgtgtgg gcgagggcct ggcctgccac cagctgtgcg cccagggca ctgctgggt       1500
ccagggccca cccagtgtgt caactgcagc cagttccttc ggggccagga gtgcgtggag      1560
gaatgccgag tactgcaggg gctccccagg gagtatgtga atgccaggca ctgtttgccg      1620
tgccacccctg agtgtcagcc ccagaatggc tcagtgacct gttttggact ggaggctgac      1680
cagtgtgtgg cctgtgccca ctataaggac cctccctttc gcgtggcccg ctgccccagc      1740
ggtgtgaaac ctgacctctc ctacatgccc atctggaagt ttccagatga ggagggcgca      1800
tgccagcctt gccccatcaa ctgcacccac tcctgtgtgg acctggatga caagggctgc      1860
cccgccgagc agagagccag ccctctgacg gtcgacggtg gtagtccgac acctccgaca      1920
cccgggggtg gttctgcaga caaaactcac acatgcccac cgtgcccagc acctgaactc      1980
ctggggggac cgtcagtctt cctcttcccc ccaaaaccca aggacaccct catgatctcc      2040
cggacccctg aggtcacatg cgtggtggtg gacgtgagcc acgaagaccc tgaggtcaag      2100
```

```
ttcaactggt acgtggacgg cgtggaggtg cataatgcca agacaaagcc gcgggaggag    2160
cagtacaaca gcacgtaccg tgtggtcagc gtcctcaccg tcctgcacca ggactggctg    2220
aatggcaagg agtacaagtg caaggtctcc aacaaagccc tcccagcccc catcgagaaa    2280
accatctcca aagccaaagg gcagccccga gaaccacagg tgtacaccct gcccccatgc    2340
cgggatgagc tgaccaagaa ccaggtcagc ctgtggtgcc tggtcaaagg cttctatccc    2400
agcgacatcg ccgtggagtg ggagagcaat gggcagccgg agaacaacta caagaccacg    2460
cctcccgtgc tggactccga cggctccttc ttcctctaca gcaagctcac cgtggacaag    2520
agcaggtggc agcaggggaa cgtcttctca tgctccgtga tgcatgaggc tctgcacaac    2580
cactacacgc agaagagcct ctccctgtct ccgggtaaat ccggaggcct gaacgacatc    2640
ttcgaggccc agaagattga atggcacgag                                     2670
```

<210> SEQ ID NO 8
<211> LENGTH: 890
<212> TYPE: PRT
<213> ORGANISM: Artificial sequence
<220> FEATURE:
<223> OTHER INFORMATION: Her2 ECD(pertuzumab KO)-Fc(knob)

<400> SEQUENCE: 8

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Arg Glu Ser Met Pro Asn Pro Glu Gly Arg Tyr Arg Phe Gly Ala Ser
```

-continued

```
            260                 265                 270
Cys Val Thr Ala Cys Pro Tyr Asn Tyr Leu Ser Thr Asp Arg Gly Ser
        275                 280                 285
Cys Thr Leu Val Cys Pro Leu Ala Asn Gln Glu Val Thr Ala Glu Asp
        290                 295                 300
Gly Thr Gln Arg Cys Glu Lys Cys Ser Lys Pro Cys Ala Arg Val Cys
305                 310                 315                 320
Tyr Gly Leu Gly Met Glu His Leu Arg Glu Val Arg Ala Val Thr Ser
                325                 330                 335
Ala Asn Ile Gln Glu Phe Ala Gly Cys Lys Lys Ile Phe Gly Ser Leu
                340                 345                 350
Ala Phe Leu Pro Glu Ser Phe Asp Gly Asp Pro Ala Ser Asn Thr Ala
                355                 360                 365
Pro Leu Gln Pro Glu Gln Leu Gln Val Phe Glu Thr Leu Glu Glu Ile
            370                 375                 380
Thr Gly Tyr Leu Tyr Ile Ser Ala Trp Pro Asp Ser Leu Pro Asp Leu
385                 390                 395                 400
Ser Val Phe Gln Asn Leu Gln Val Ile Arg Gly Arg Ile Leu His Asn
                405                 410                 415
Gly Ala Tyr Ser Leu Thr Leu Gln Gly Leu Gly Ile Ser Trp Leu Gly
                420                 425                 430
Leu Arg Ser Leu Arg Glu Leu Gly Ser Gly Leu Ala Leu Ile His His
            435                 440                 445
Asn Thr His Leu Cys Phe Val His Thr Val Pro Trp Asp Gln Leu Phe
            450                 455                 460
Arg Asn Pro His Gln Ala Leu Leu His Thr Ala Asn Arg Pro Glu Asp
465                 470                 475                 480
Glu Cys Val Gly Glu Gly Leu Ala Cys His Gln Leu Cys Ala Arg Gly
                485                 490                 495
His Cys Trp Gly Pro Gly Pro Thr Gln Cys Val Asn Cys Ser Gln Phe
                500                 505                 510
Leu Arg Gly Gln Glu Cys Val Glu Glu Cys Arg Val Leu Gln Gly Leu
            515                 520                 525
Pro Arg Glu Tyr Val Asn Ala Arg His Cys Leu Pro Cys His Pro Glu
        530                 535                 540
Cys Gln Pro Gln Asn Gly Ser Val Thr Cys Phe Gly Leu Glu Ala Asp
545                 550                 555                 560
Gln Cys Val Ala Cys Ala His Tyr Lys Asp Pro Pro Phe Cys Val Ala
                565                 570                 575
Arg Cys Pro Ser Gly Val Lys Pro Asp Leu Ser Tyr Met Pro Ile Trp
            580                 585                 590
Lys Phe Pro Asp Glu Glu Gly Ala Cys Gln Pro Cys Pro Ile Asn Cys
            595                 600                 605
Thr His Ser Cys Val Asp Leu Asp Asp Lys Gly Cys Pro Ala Glu Gln
        610                 615                 620
Arg Ala Ser Pro Leu Thr Val Asp Gly Gly Ser Pro Thr Pro Thr
625                 630                 635                 640
Pro Gly Gly Gly Ser Ala Asp Lys Thr His Thr Cys Pro Pro Cys Pro
                645                 650                 655
Ala Pro Glu Leu Leu Gly Gly Pro Ser Val Phe Leu Phe Pro Pro Lys
            660                 665                 670
Pro Lys Asp Thr Leu Met Ile Ser Arg Thr Pro Glu Val Thr Cys Val
            675                 680                 685
```

```
Val Val Asp Val Ser His Glu Asp Pro Glu Val Lys Phe Asn Trp Tyr
    690             695                 700
Val Asp Gly Val Glu Val His Asn Ala Lys Thr Lys Pro Arg Glu Glu
705             710                 715                 720
Gln Tyr Asn Ser Thr Tyr Arg Val Val Ser Val Leu Thr Val Leu His
                725                 730                 735
Gln Asp Trp Leu Asn Gly Lys Glu Tyr Lys Cys Lys Val Ser Asn Lys
                740                 745                 750
Ala Leu Pro Ala Pro Ile Glu Lys Thr Ile Ser Lys Ala Lys Gly Gln
            755                 760                 765
Pro Arg Glu Pro Gln Val Tyr Thr Leu Pro Pro Cys Arg Asp Glu Leu
    770                 775                 780
Thr Lys Asn Gln Val Ser Leu Trp Cys Leu Val Lys Gly Phe Tyr Pro
785                 790                 795                 800
Ser Asp Ile Ala Val Glu Trp Glu Ser Asn Gly Gln Pro Glu Asn Asn
                805                 810                 815
Tyr Lys Thr Thr Pro Pro Val Leu Asp Ser Asp Gly Ser Phe Phe Leu
                820                 825                 830
Tyr Ser Lys Leu Thr Val Asp Lys Ser Arg Trp Gln Gln Gly Asn Val
            835                 840                 845
Phe Ser Cys Ser Val Met His Glu Ala Leu His Asn His Tyr Thr Gln
    850                 855                 860
Lys Ser Leu Ser Leu Ser Pro Gly Lys Ser Gly Gly Leu Asn Asp Ile
865                 870                 875                 880
Phe Glu Ala Gln Lys Ile Glu Trp His Glu
                885                 890

<210> SEQ ID NO 9
<211> LENGTH: 2667
<212> TYPE: DNA
<213> ORGANISM: Artificial sequence
<220> FEATURE:
<223> OTHER INFORMATION: Her2 ECD(trastuzumab KO)-Fc(knob)DNA

<400> SEQUENCE: 9
acccaagtgt gcaccggcac agacatgaag ctgcggctcc ctgccagtcc cgagacccac      60
ctggacatgc tccgccacct ctaccagggc tgccaggtgg tgcagggaaa cctggaactc     120
acctacctgc ccaccaatgc cagcctgtcc ttcctgcagg atatccagga ggtgcagggc     180
tacgtgctca tcgctcacaa ccaagtgagg caggtccact gcagaggct gcggattgtg     240 cgaggcaccc agctctttga ggacaactat gccctggccg tgctagacaa tggagacccg     300
ctgaacaata ccacccctgt cacaggggcc tccccaggag gctgcggga gctgcagctt     360 cgaagcctca cagagatctt gaaggagggg gtcttgatcc agcggaaccc ccagctctgc     420
taccaggaca cgattttgtg gaaggacatc ttccacaaga caaccagct ggctctcaca     480 ctgatagaca ccaaccgctc tcgggcctgc caccctgtt ctccgatgtg taagggctcc     540
cgctgctggg gagagagttc tgaggattgt cagagcctga cgcgcactgt ctgtgccggt     600
ggctgtgccc gctgcaaggg gccactgccc actgactgct ccatgagca gtgtgctgcc     660 ggctgcacgg gccccaagca ctctgactgc ctggcctgcc tccacttcaa ccacagtggc     720
atctgtgagc tgcactgccc agcctggtc acctacaaca gacacgtt gagtccatg     780 cccaatcccg agggccggta cattcggc gccagctgtg tgactgcctg tccctacaac     840
tacctttcta cggacgtggg atcctgcacc ctcgtctgcc ccctgcacaa ccaagaggtg     900
```

```
acagcagagg atggaacaca gcggtgtgag aagtgcagca agccctgtgc ccgagtgtgc    960
tatggtctgg gcatggagca cttgcgagag gtgagggcag ttaccagtgc caatatccag   1020
gagtttgctg gctgcaagaa gatctttggg agcctggcat ttctgccgga gagctttgat   1080
ggggacccag cctccaacac tgccccgctc cagccagagc agctccaagt gtttgagact   1140
ctggaagaga tcacaggtta cctatacatc tcagcatggc cggacagcct gcctgacctc   1200
agcgtcttcc agaacctgca agtaatccgg ggacgaattc tgcacaatgg cgcctactcg   1260
ctgaccctgc aagggctggg catcagctgg ctggggctgc gctcactgag ggaactgggc   1320
agtggactgg ccctcatcca ccataacacc cacctctgct tcgtgcacac ggtgccctgg   1380
gaccagctct ttcggaaccc gcaccaagct ctgctccaca ctgccaaccg ccagaggac   1440
gagtgtgtgg cgagggcct ggcctgccac cagctgtgcg cccgagggca ctgctggggt   1500
ccagggccca cccagtgtgt caactgcagc cagttccttc ggggccagga gtgcgtggag   1560
gaatgccgag tactgcaggg gctccccagg gagtatgtga atgccaggca ctgtttgccg   1620
tgccaccctg agtgtcagcc ccagaatggc tcagtgacct gttttggact ggaggctcgg   1680
cagtgtgtgg cctgtgccca ctataaggac agacggtgcg tggcccgctg ccccagcggt   1740
gtgaaacctg acctctccta catgcccatc tggaagtttc cagatgagga gggcgcatgc   1800
cagccttgcc ccatcaactg cacccactcc tgtgtggacc tggatgacaa gggctgcccc   1860
gccgagcaga gagccagccc tctgacggtc gacggtggta gtccgacacc tccgacaccc   1920
gggggtggtt ctgcagacaa aactcacaca tgcccaccgt gcccagcacc tgaactcctg   1980
ggggaccgt cagtcttcct cttccccca aaacccaagg acaccctcat gatctcccgg    2040
accctgagg tcacatgcgt ggtggtggac gtgagccacg aagaccctga ggtcaagttc   2100
aactggtacg tggacggcgt ggaggtgcat aatgccaaga caaagccgcg ggaggagcag   2160
tacaacagca cgtaccgtgt ggtcagcgtc ctcaccgtcc tgcaccagga ctggctgaat   2220
ggcaaggagt acaagtgcaa ggtctccaac aaagccctcc cagcccccat cgagaaaacc   2280
atctccaaag ccaaagggca gccccgagaa ccacaggtgt acaccctgcc cccatgccgg   2340
gatgagctga ccaagaacca ggtcagcctg tggtgcctgg tcaaaggctt ctatcccagc   2400
gacatcgccg tggagtggga gagcaatggg cagccggaga acaactacaa gaccacgcct   2460
cccgtgctg actccgacgg ctccttcttc ctctacagca agctcaccgt ggacaagagc   2520
aggtggcagc aggggaacgt cttctcatgc tccgtgatgc atgaggctct gcacaaccac   2580
tacacgcaga agagcctctc cctgtctccg ggtaaatccg gaggcctgaa cgacatcttc   2640
gaggcccaga agattgaatg gcacgag                                       2667
```

<210> SEQ ID NO 10
<211> LENGTH: 889
<212> TYPE: PRT
<213> ORGANISM: Artificial sequence
<220> FEATURE:
<223> OTHER INFORMATION: Her2 ECD(trastuzumab KO)-Fc(knob)

<400> SEQUENCE: 10

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45
```

```
Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460
```

-continued

```
Arg Asn Pro His Gln Ala Leu Leu His Thr Ala Asn Arg Pro Glu Asp
465                 470                 475                 480
Glu Cys Val Gly Glu Gly Leu Ala Cys His Gln Leu Cys Ala Arg Gly
                    485                 490                 495
His Cys Trp Gly Pro Gly Pro Thr Gln Cys Val Asn Cys Ser Gln Phe
                500                 505                 510
Leu Arg Gly Gln Glu Cys Val Glu Glu Cys Arg Val Leu Gln Gly Leu
            515                 520                 525
Pro Arg Glu Tyr Val Asn Ala Arg His Cys Leu Pro Cys His Pro Glu
        530                 535                 540
Cys Gln Pro Gln Asn Gly Ser Val Thr Cys Phe Gly Leu Glu Ala Arg
545                 550                 555                 560
Gln Cys Val Ala Cys Ala His Tyr Lys Asp Arg Arg Cys Val Ala Arg
                565                 570                 575
Cys Pro Ser Gly Val Lys Pro Asp Leu Ser Tyr Met Pro Ile Trp Lys
                580                 585                 590
Phe Pro Asp Glu Glu Gly Ala Cys Gln Pro Cys Pro Ile Asn Cys Thr
            595                 600                 605
His Ser Cys Val Asp Leu Asp Asp Lys Gly Cys Pro Ala Glu Gln Arg
        610                 615                 620
Ala Ser Pro Leu Thr Val Asp Gly Gly Ser Pro Thr Pro Thr Pro
625                 630                 635                 640
Gly Gly Gly Ser Ala Asp Lys Thr His Thr Cys Pro Pro Cys Pro Ala
                645                 650                 655
Pro Glu Leu Leu Gly Gly Pro Ser Val Phe Leu Phe Pro Pro Lys Pro
            660                 665                 670
Lys Asp Thr Leu Met Ile Ser Arg Thr Pro Glu Val Thr Cys Val Val
        675                 680                 685
Val Asp Val Ser His Glu Asp Pro Glu Val Lys Phe Asn Trp Tyr Val
690                 695                 700
Asp Gly Val Glu Val His Asn Ala Lys Thr Lys Pro Arg Glu Glu Gln
705                 710                 715                 720
Tyr Asn Ser Thr Tyr Arg Val Val Ser Val Leu Thr Val Leu His Gln
                725                 730                 735
Asp Trp Leu Asn Gly Lys Glu Tyr Lys Cys Lys Val Ser Asn Lys Ala
            740                 745                 750
Leu Pro Ala Pro Ile Glu Lys Thr Ile Ser Lys Ala Lys Gly Gln Pro
        755                 760                 765
Arg Glu Pro Gln Val Tyr Thr Leu Pro Pro Cys Arg Asp Glu Leu Thr
770                 775                 780
Lys Asn Gln Val Ser Leu Trp Cys Leu Val Lys Gly Phe Tyr Pro Ser
785                 790                 795                 800
Asp Ile Ala Val Glu Trp Glu Ser Asn Gly Gln Pro Glu Asn Asn Tyr
                805                 810                 815
Lys Thr Thr Pro Pro Val Leu Asp Ser Asp Gly Ser Phe Phe Leu Tyr
            820                 825                 830
Ser Lys Leu Thr Val Asp Lys Ser Arg Trp Gln Gln Gly Asn Val Phe
        835                 840                 845
Ser Cys Ser Val Met His Glu Ala Leu His Asn His Tyr Thr Gln Lys
850                 855                 860
Ser Leu Ser Leu Ser Pro Gly Lys Ser Gly Gly Leu Asn Asp Ile Phe
                865                 870                 875                 880
Glu Ala Gln Lys Ile Glu Trp His Glu
```

```
<210> SEQ ID NO 11
<211> LENGTH: 11
<212> TYPE: PRT
<213> ORGANISM: Artificial sequence
<220> FEATURE:
<223> OTHER INFORMATION: Pertuzumab wt VL CDR1

<400> SEQUENCE: 11

Lys Ala Ser Gln Asp Val Ser Ile Gly Val Ala
1               5                   10

<210> SEQ ID NO 12
<211> LENGTH: 7
<212> TYPE: PRT
<213> ORGANISM: Artificial sequence
<220> FEATURE:
<223> OTHER INFORMATION: Pertuzumab wt VL CDR2

<400> SEQUENCE: 12

Ser Ala Ser Tyr Arg Tyr Thr
1               5

<210> SEQ ID NO 13
<211> LENGTH: 9
<212> TYPE: PRT
<213> ORGANISM: Artificial sequence
<220> FEATURE:
<223> OTHER INFORMATION: Pertuzumab wt VL CDR3

<400> SEQUENCE: 13

Gln Gln Tyr Tyr Ile Tyr Pro Tyr Thr
1               5

<210> SEQ ID NO 14
<211> LENGTH: 10
<212> TYPE: PRT
<213> ORGANISM: Artificial sequence
<220> FEATURE:
<223> OTHER INFORMATION: Pertuzumab wt VH CDR1

<400> SEQUENCE: 14

Gly Phe Thr Phe Thr Asp Tyr Thr Met Asp
1               5                   10

<210> SEQ ID NO 15
<211> LENGTH: 17
<212> TYPE: PRT
<213> ORGANISM: Artificial sequence
<220> FEATURE:
<223> OTHER INFORMATION: Pertuzumab wt VH CDR2

<400> SEQUENCE: 15

Asp Val Asn Pro Asn Ser Gly Gly Ser Ile Tyr Asn Gln Arg Phe Lys
1               5                   10                  15

Gly

<210> SEQ ID NO 16
<211> LENGTH: 10
<212> TYPE: PRT
<213> ORGANISM: Artificial sequence
<220> FEATURE:
<223> OTHER INFORMATION: Pertuzumab wt VH CDR3

<400> SEQUENCE: 16
```

Asn Leu Gly Pro Ser Phe Tyr Phe Asp Tyr
1               5                   10

<210> SEQ ID NO 17
<211> LENGTH: 11
<212> TYPE: PRT
<213> ORGANISM: Artificial sequence
<220> FEATURE:
<223> OTHER INFORMATION: Trastuzumab wt VL CDR1

<400> SEQUENCE: 17

Arg Ala Ser Gln Asp Val Asn Thr Ala Val Ala
1               5                   10

<210> SEQ ID NO 18
<211> LENGTH: 7
<212> TYPE: PRT
<213> ORGANISM: Artificial sequence
<220> FEATURE:
<223> OTHER INFORMATION: Trastuzumab VL CDR2

<400> SEQUENCE: 18

Ser Ala Ser Phe Leu Tyr Ser
1               5

<210> SEQ ID NO 19
<211> LENGTH: 9
<212> TYPE: PRT
<213> ORGANISM: Artificial sequence
<220> FEATURE:
<223> OTHER INFORMATION: Trastuzumab VL CDR3

<400> SEQUENCE: 19

Gln Gln His Tyr Thr Thr Pro Pro Thr
1               5

<210> SEQ ID NO 20
<211> LENGTH: 10
<212> TYPE: PRT
<213> ORGANISM: Artificial sequence
<220> FEATURE:
<223> OTHER INFORMATION: Trastuzumab VH CDR1

<400> SEQUENCE: 20

Gly Phe Asn Ile Lys Asp Thr Tyr Ile His
1               5                   10

<210> SEQ ID NO 21
<211> LENGTH: 558
<212> TYPE: DNA
<213> ORGANISM: Artificial sequence
<220> FEATURE:
<223> OTHER INFORMATION: Pertuzumab wt VH (10289) DNA

<400> SEQUENCE: 21

```
gaggtgcagc tggtcgagtc tggcggcgga ctggtgcagc ctggcggcag cctgagactg      60
agctgcgccg ccagcggctt caccttcacc gactacacca tggactgggt gcggcaggcc     120
cctggcaagg gcctggaatg gtggccgac gtgaacccca acagcggcgg cagcatctac     180
aaccagcggt tcaagggccg gttcaccctg agcgtggaca gaagcaagaa cacccctgtac     240 ctccagatga acagcctgcg ggccgaggac accgccgtgt actactgcgc ccggaacctg     300
ggccccagct ctacttcga ctactggggc cagggcaccc tggtgaccgt gagcagcgct     360
agcaccaagg gcccatcggt cttccccctg gcaccctcct ccaagagcac ctctgggggc     420
```

```
acagcggccc tgggctgcct ggtcaaggac tacttcccgc aaccggtgac ggtgtcgtgg    480
aactcaggcg ccctgaccag cggcgtgcac accttcccgg ctgtcctaca gtcctcagga    540
ctctactccc tcagcagc                                                  558
```

```
<210> SEQ ID NO 22
<211> LENGTH: 119
<212> TYPE: PRT
<213> ORGANISM: Artificial sequence
<220> FEATURE:
<223> OTHER INFORMATION: Pertuzumab wt VH (10289)

<400> SEQUENCE: 22
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

```
<210> SEQ ID NO 23
<211> LENGTH: 321
<212> TYPE: DNA
<213> ORGANISM: Artificial sequence
<220> FEATURE:
<223> OTHER INFORMATION: Pertuzumab wt VL (10290) DNA

<400> SEQUENCE: 23
```

```
gacatccaga tgacccagag ccccagcagc ctgagcgcca gcgtgggcga cagagtgacc    60
atcacctgca aggccagcca ggacgtgtcc atcggcgtgg cctggtatca gcagaagccc    120
ggcaaggccc ccaagctgct gatctacagc gccagctacc ggtacacagg cgtgcccagc    180
cggttcagcg gcagcggctc cggcaccgac ttcaccctga ccatcagcag cctgcagccc    240
gaggacttcg ccacctacta ctgccagcag tactacatct accctacac cttcggccag    300 ggcaccaagg tggagatcaa g                                              321
```

```
<210> SEQ ID NO 24
<211> LENGTH: 107
<212> TYPE: PRT
<213> ORGANISM: Artificial sequence
<220> FEATURE:
<223> OTHER INFORMATION: Pertuzumab wt VL (10290)

<400> SEQUENCE: 24
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile 35                  40                  45
Tyr Ser Ala Ser Tyr Arg Tyr Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ile Tyr Pro Tyr
                 85                  90                  95

Thr Phe Gly Gln Gly Thr Lys Val Glu Ile Lys
            100                 105

<210> SEQ ID NO 25
<211> LENGTH: 321
<212> TYPE: DNA
<213> ORGANISM: Artificial sequence
<220> FEATURE:
<223> OTHER INFORMATION: Pertuzumab VL (Trast. L3) (10403) DNA

<400> SEQUENCE: 25
gacatccaga tgacccagag ccccagcagc ctgagcgcca gcgtgggcga cagagtgacc        60
atcacatgca aggccagcca ggacgtgtcc atcggcgtgg cctggtatca gcagaagccc       120
ggcaaggccc ccaagctgct gatctacagc gccagctacc ggtacaccgg cgtgcccagc       180
agattcagcg gcagcggctc cggcaccgac ttcaccctga ccatcagcag cctgcagccc       240
gaggacttcg ccacctacta ctgccagcag cactacacca cccccccccac cttcggccag      300 ggcaccaagg tggaaatcaa g                                                  321

<210> SEQ ID NO 26
<211> LENGTH: 107
<212> TYPE: PRT
<213> ORGANISM: Artificial sequence
<220> FEATURE:
<223> OTHER INFORMATION: Pertuzumab VL (Trast. L3) (10403)

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Ile Gly
             20                  25                  30

Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 27
<211> LENGTH: 321
<212> TYPE: DNA
<213> ORGANISM: Artificial sequence
<220> FEATURE:
<223> OTHER INFORMATION: Pertuzumab VL (Trast. H91) (10404) DNA

<400> SEQUENCE: 27
gacatccaga tgacccagag ccccagcagc ctgagcgcca gcgtgggcga cagagtgacc        60

-continued

```
atcacctgca aggccagcca ggacgtgtcc atcggcgtgg cctggtatca gcagaagccc    120
ggcaaggccc ccaagctgct gatctacagc gccagctacc ggtacacagg cgtgcccagc    180
cggttcagcg gcagcggctc cggcaccgac ttcaccctga ccatcagcag cctgcagccc    240
gaggacttcg ccacctacta ctgccagcag cactacatct accccctacac cttcggccag    300 ggcaccaagg tggagatcaa g                                              321
```

<210> SEQ ID NO 28
<211> LENGTH: 107
<212> TYPE: PRT
<213> ORGANISM: Artificial sequence
<220> FEATURE:
<223> OTHER INFORMATION: Pertuzumab VL (Trast. H91) (10404)

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ile Tyr Pro Tyr
                85                  90                  95

Thr Phe Gly Gln Gly Thr Lys Val Glu Ile Lys
            100                 105

<210> SEQ ID NO 29
<211> LENGTH: 17
<212> TYPE: PRT
<213> ORGANISM: Artificial sequence
<220> FEATURE:
<223> OTHER INFORMATION: Trastuzumab VH CDR2

<400> SEQUENCE: 29

Arg Ile Tyr Pro Thr Asn Gly Tyr Thr Arg Tyr Ala Asp Ser Val Lys
1               5                   10                  15

Gly

<210> SEQ ID NO 30
<211> LENGTH: 11
<212> TYPE: PRT
<213> ORGANISM: Artificial sequence
<220> FEATURE:
<223> OTHER INFORMATION: Trastuzumab wt VH CDR3

<400> SEQUENCE: 30

Trp Gly Gly Asp Gly Phe Tyr Ala Met Asp Tyr
1               5                   10

<210> SEQ ID NO 31
<211> LENGTH: 321
<212> TYPE: DNA
<213> ORGANISM: Artificial sequence
<220> FEATURE:
<223> OTHER INFORMATION: Pertuzumab VL (Tras.L3) K24R (10949) DNA

<400> SEQUENCE: 31

```
gacatccaga tgacccagag ccccagcagc ctgagcgcca gcgtgggcga cagagtgacc      60
atcacatgcc gggccagcca ggacgtgtcc atcggcgtgg cctggtatca gcagaagccc     120
ggcaaggccc ccaagctgct gatctacagc gccagctacc ggtacaccgg cgtgcccagc     180
agattcagcg gcagcggctc cggcaccgac ttcaccctga ccatcagcag cctgcagccc     240
gaggacttcg ccacctacta ctgccagcag cactacacca ccccccccac cttcggccag     300
ggcaccaagg tggaaatcaa g                                                321
```

<210> SEQ ID NO 32
<211> LENGTH: 107
<212> TYPE: PRT
<213> ORGANISM: Artificial sequence
<220> FEATURE:
<223> OTHER INFORMATION: Pertuzumab VL (Tras.L3) K24R (10949)

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 33
<211> LENGTH: 321
<212> TYPE: DNA
<213> ORGANISM: Artificial sequence
<220> FEATURE:
<223> OTHER INFORMATION: Pertuzumab VL(Tras.L3) S30N (10950) DNA

<400> SEQUENCE: 33

```
gacatccaga tgacccagag ccccagcagc ctgagcgcca gcgtgggcga cagagtgacc      60
atcacatgca aggccagcca ggacgtgaac atcggcgtgg cctggtatca gcagaagccc     120
ggcaaggccc ccaagctgct gatctacagc gccagctacc ggtacaccgg cgtgcccagc     180
agattcagcg gcagcggctc cggcaccgac ttcaccctga ccatcagcag cctgcagccc     240
gaggacttcg ccacctacta ctgccagcag cactacacca ccccccccac cttcggccag     300
ggcaccaagg tggaaatcaa g                                                321
```

<210> SEQ ID NO 34
<211> LENGTH: 107
<212> TYPE: PRT
<213> ORGANISM: Artificial sequence
<220> FEATURE:
<223> OTHER INFORMATION: Pertuzumab VL (Tras.L3) S30N (10950)

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Ile Gly

```
                20                  25                  30
Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 35
<211> LENGTH: 321
<212> TYPE: DNA
<213> ORGANISM: Artificial sequence
<220> FEATURE:
<223> OTHER INFORMATION: Pertuzumab VL (Tras.L3) I31T (10951) DNA

<400> SEQUENCE: 35
gacatccaga tgacccagag ccccagcagc ctgagcgcca gcgtgggcga cagagtgacc      60
atcacatgca aggccagcca ggacgtgtcc accggcgtgg cctggtatca gcagaagccc     120
ggcaaggccc ccaagctgct gatctacagc gccagctacc ggtacaccgg cgtgcccagc     180
agattcagcg gcagcggctc cggcaccgac ttcaccctga ccatcagcag cctgcagccc     240
gaggacttcg ccacctacta ctgccagcag cactacacca ccccccccac cttcggccag     300
ggcaccaagg tggaaatcaa g                                               321

<210> SEQ ID NO 36
<211> LENGTH: 107
<212> TYPE: PRT
<213> ORGANISM: Artificial sequence
<220> FEATURE:
<223> OTHER INFORMATION: Pertuzumab VL (Tras.L3) I31T (10951)

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 37
<211> LENGTH: 321
<212> TYPE: DNA
<213> ORGANISM: Artificial sequence
<220> FEATURE:
<223> OTHER INFORMATION: Pertuzumab VL (Tras.L3) I31V (10952) DNA

<400> SEQUENCE: 37
```

```
gacatccaga tgacccagag ccccagcagc ctgagcgcca gcgtgggcga cagagtgacc      60
atcacatgca aggccagcca ggacgtgtcc gtcggcgtgg cctggtatca gcagaagccc     120
ggcaaggccc ccaagctgct gatctacagc gccagctacc ggtacaccgg cgtgcccagc     180
agattcagcg gcagcggctc cggcaccgac ttcaccctga ccatcagcag cctgcagccc     240
gaggacttcg ccacctacta ctgccagcag cactacacca ccccccccac cttcggccag     300
ggcaccaagg tggaaatcaa g                                                321
```

<210> SEQ ID NO 38
<211> LENGTH: 107
<212> TYPE: PRT
<213> ORGANISM: Artificial sequence
<220> FEATURE:
<223> OTHER INFORMATION: Pertuzumab VL (Tras.L3) I31V (10952)

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Val Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 39
<211> LENGTH: 321
<212> TYPE: DNA
<213> ORGANISM: Artificial sequence
<220> FEATURE:
<223> OTHER INFORMATION: Pertuzumab VL (Tras.L3) G32A (10953) DNA

<400> SEQUENCE: 39

```
gacatccaga tgacccagag ccccagcagc ctgagcgcca gcgtgggcga cagagtgacc      60
atcacatgca aggccagcca ggacgtgtcc atcgccgtgg cctggtatca gcagaagccc     120
ggcaaggccc ccaagctgct gatctacagc gccagctacc ggtacaccgg cgtgcccagc     180
agattcagcg gcagcggctc cggcaccgac ttcaccctga ccatcagcag cctgcagccc     240
gaggacttcg ccacctacta ctgccagcag cactacacca ccccccccac cttcggccag     300
ggcaccaagg tggaaatcaa g                                                321
```

<210> SEQ ID NO 40
<211> LENGTH: 107
<212> TYPE: PRT
<213> ORGANISM: Artificial sequence
<220> FEATURE:
<223> OTHER INFORMATION: Pertuzumab VL (Tras.L3) G32A (10953)

<400> SEQUENCE: 40

```
Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 41
<211> LENGTH: 321
<212> TYPE: DNA
<213> ORGANISM: Artificial sequence
<220> FEATURE:
<223> OTHER INFORMATION: Pertuzumab VL (Tras.L3) Y53F (10954) DNA

<400> SEQUENCE: 41
gacatccaga tgacccagag ccccagcagc ctgagcgcca gcgtgggcga cagagtgacc      60
atcacatgca aggccagcca ggacgtgtcc atcggcgtgg cctggtatca gcagaagccc     120
ggcaaggccc ccaagctgct gatctacagc gccagcttcc ggtacaccgg cgtgcccagc     180
agattcagcg gcagcggctc cggcaccgac ttcaccctga ccatcagcag cctgcagccc     240
gaggacttcg ccacctacta ctgccagcag cactacacca ccccccccac cttcggccag     300
ggcaccaagg tggaaatcaa g                                               321

<210> SEQ ID NO 42
<211> LENGTH: 107
<212> TYPE: PRT
<213> ORGANISM: Artificial sequence
<220> FEATURE:
<223> OTHER INFORMATION: Pertuzumab VL (Tras.L3) Y53F (10954)

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 43
<211> LENGTH: 321
<212> TYPE: DNA
<213> ORGANISM: Artificial sequence
<220> FEATURE:
<223> OTHER INFORMATION: Pertuzumab (Tras.L3) R54L (10955) DNA
```

<400> SEQUENCE: 43

```
gacatccaga tgacccagag ccccagcagc ctgagcgcca gcgtgggcga cagagtgacc    60
atcacatgca aggccagcca ggacgtgtcc atcggcgtgg cctggtatca gcagaagccc   120
ggcaaggccc ccaagctgct gatctacagc gccagctacc tgtacaccgg cgtgcccagc   180
agattcagcg gcagcggctc cggcaccgac ttcaccctga ccatcagcag cctgcagccc   240
gaggacttcg ccacctacta ctgccagcag cactacacca ccccccccac cttcggccag   300
ggcaccaagg tggaaatcaa g                                             321
```

<210> SEQ ID NO 44
<211> LENGTH: 107
<212> TYPE: PRT
<213> ORGANISM: Artificial sequence
<220> FEATURE:
<223> OTHER INFORMATION: Pertuzumab VL (Tras.L3) R54L (10955)

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 45
<211> LENGTH: 321
<212> TYPE: DNA
<213> ORGANISM: Artificial sequence
<220> FEATURE:
<223> OTHER INFORMATION: Pertuzumab (Tras.L3) T56S (10956) DNA

<400> SEQUENCE: 45

```
gacatccaga tgacccagag ccccagcagc ctgagcgcca gcgtgggcga cagagtgacc    60
atcacatgca aggccagcca ggacgtgtcc atcggcgtgg cctggtatca gcagaagccc   120
ggcaaggccc ccaagctgct gatctacagc gccagctacc ggtacagcgg cgtgcccagc   180
agattcagcg gcagcggctc cggcaccgac ttcaccctga ccatcagcag cctgcagccc   240
gaggacttcg ccacctacta ctgccagcag cactacacca ccccccccac cttcggccag   300
ggcaccaagg tggaaatcaa g                                             321
```

<210> SEQ ID NO 46
<211> LENGTH: 107
<212> TYPE: PRT
<213> ORGANISM: Artificial sequence
<220> FEATURE:
<223> OTHER INFORMATION: Pertuzumab (Tras.L3) T56S (10956)

<400> SEQUENCE: 46

```
Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 47
<211> LENGTH: 321
<212> TYPE: DNA
<213> ORGANISM: Artificial sequence
<220> FEATURE:
<223> OTHER INFORMATION: Pertuzumab (Tras.L3) G66R (10957) DNA

<400> SEQUENCE: 47
gacatccaga tgacccagag ccccagcagc ctgagcgcca gcgtgggcga cagagtgacc    60
atcacatgca aggccagcca ggacgtgtcc atcggcgtgg cctggtatca gcagaagccc   120
ggcaaggccc ccaagctgct gatctacagc gccagctacc ggtacaccgg cgtgcccagc   180
agattcagcg gcagccgctc cggcaccgac ttcaccctga ccatcagcag cctgcagccc   240
gaggacttcg ccacctacta ctgccagcag cactacacca ccccccccac cttcggccag   300
ggcaccaagg tggaaatcaa g                                             321

<210> SEQ ID NO 48
<211> LENGTH: 107
<212> TYPE: PRT
<213> ORGANISM: Artificial sequence
<220> FEATURE:
<223> OTHER INFORMATION: Pertuzumab (Tras.L3) G66R (10957)

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 49
<211> LENGTH: 320
<212> TYPE: DNA
<213> ORGANISM: Artificial sequence
<220> FEATURE:
<223> OTHER INFORMATION: Pertuzumab (Tras.L3) T94Y (10958) DNA

<400> SEQUENCE: 49

```
acatccagat gacccagagc cccagcagcc tgagcgccag cgtgggcgac agagtgacca     60
tcacatgcaa ggccagccag gacgtgtcca tcggcgtggc ctggtatcag cagaagcccg    120
gcaaggcccc caagctgctg atctacagcg ccagctaccg gtacaccggc gtgcccagca    180
gattcagcgg cagcggctcc ggcaccgact caccctgac catcagcagc ctgcagcccg     240
aggacttcgc cacctactac tgccagcagc actacaccta cccccccacc ttcggccagg    300
gcaccaaggt ggaaatcaag                                                320
```

<210> SEQ ID NO 50
<211> LENGTH: 107
<212> TYPE: PRT
<213> ORGANISM: Artificial sequence
<220> FEATURE:
<223> OTHER INFORMATION: Pertuzumab (Tras.L3) T94Y (10958)

<400> SEQUENCE: 50

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Ile Gly
            20                  25                  30
Val Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Tyr Pro Pro
                85                  90                  95
Thr Phe Gly Gln Gly Thr Lys Val Glu Ile Lys
            100                 105
```

<210> SEQ ID NO 51
<211> LENGTH: 321
<212> TYPE: DNA
<213> ORGANISM: Artificial sequence
<220> FEATURE:
<223> OTHER INFORMATION: Pertuzumab (Tras.L3) P96Y (10959) DNA

<400> SEQUENCE: 51

```
gacatccaga tgacccagag ccccagcagc ctgagcgcca gcgtgggcga cagagtgacc     60
atcacatgca aggccagcca ggacgtgtcc atcggcgtgg cctggtatca gcagaagccc    120
ggcaaggccc ccaagctgct gatctacagc gccagctacc ggtacaccgg cgtgcccagc    180
agattcagcg gcagcggctc cggcaccgac ttcaccctga ccatcagcag cctgcagccc    240
gaggacttcg ccacctacta ctgccagcag cactacacca ccccctacac cttcggccag    300
ggcaccaagg tggaaatcaa g                                              321
```

<210> SEQ ID NO 52
<211> LENGTH: 107
<212> TYPE: PRT
<213> ORGANISM: Artificial sequence
<220> FEATURE:
<223> OTHER INFORMATION: Pertuzumab (Tras.L3) P96Y (10959)

<400> SEQUENCE: 52

```
Asp Ile Gln Met Thr Gln Ser Pro Ser Ser Leu Ser Ala Ser Val Gly
```

```
              1               5              10              15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gln Gly Thr Lys Val Glu Ile Lys
                100                 105

<210> SEQ ID NO 53
<211> LENGTH: 321
<212> TYPE: DNA
<213> ORGANISM: Artificial sequence
<220> FEATURE:
<223> OTHER INFORMATION: Pertuzumab (Tras.L3) (QM) (11055) DNA

<400> SEQUENCE: 53
gacatccaga tgacccagag ccccagcagc ctgtctgcca gcgtgggcga cagagtgacc      60
atcacatgca aggccagcca ggacgtgtcc acagccgtgg cctggtatca gcagaagcct    120
ggcaaggccc ccaagctgct gatctacagc gccagcttcc ggtacaccgg cgtgcccagc    180
agattcagcg gcagcagatc cggcaccgac ttcaccctga ccatcagctc cctgcagccc    240
gaggacttcg ccacctacta ctgccagcag cactacacca ccccccccac atttggccag    300
ggcaccaagg tggaaatcaa g                                              321

<210> SEQ ID NO 54
<211> LENGTH: 107
<212> TYPE: PRT
<213> ORGANISM: Artificial sequence
<220> FEATURE:
<223> OTHER INFORMATION: Pertuzumab (Tras.L3) (QM) (11055)

<400> SEQUENCE: 54

Asp Ile Gln Met Thr Gln Ser Pro Ser Ser Leu Ser Ala Ser Val Gly
1               5                  10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Arg Tyr Thr Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105

<210> SEQ ID NO 55
<211> LENGTH: 10
<212> TYPE: PRT
<213> ORGANISM: Artificial sequence
<220> FEATURE:
```

```
<223> OTHER INFORMATION: Pertuzumab aff.mat. clone D1- VH CDR1

<400> SEQUENCE: 55

Gly Phe Thr Phe Asn Asp Tyr Thr Met Asp
1               5                   10

<210> SEQ ID NO 56
<211> LENGTH: 10
<212> TYPE: PRT
<213> ORGANISM: Artificial sequence
<220> FEATURE:
<223> OTHER INFORMATION: Pertuzumab aff.mat. clone D1- VH CDR3

<400> SEQUENCE: 56

Asn Leu Gly Pro Phe Phe Tyr Phe Asp Tyr
1               5                   10

<210> SEQ ID NO 57
<211> LENGTH: 10
<212> TYPE: PRT
<213> ORGANISM: Artificial sequence
<220> FEATURE:
<223> OTHER INFORMATION: Pertuzumab aff.mat. clone B2- VH CDR3

<400> SEQUENCE: 57

Asn Leu Gly Pro Asn Phe Tyr Phe Asp Tyr
1               5                   10

<210> SEQ ID NO 58
<211> LENGTH: 10
<212> TYPE: PRT
<213> ORGANISM: Artificial sequence
<220> FEATURE:
<223> OTHER INFORMATION: Pertuzumab aff.mat. clone E1- VH CDR1

<400> SEQUENCE: 58

Gly Phe Thr Phe Ala Asp Tyr Thr Met Asp
1               5                   10

<210> SEQ ID NO 59
<211> LENGTH: 10
<212> TYPE: PRT
<213> ORGANISM: Artificial sequence
<220> FEATURE:
<223> OTHER INFORMATION: Pertuzumab aff.mat. clone E1- VH CDR3

<400> SEQUENCE: 59

Asn Leu Gly Pro Trp Phe Tyr Phe Asp Tyr
1               5                   10

<210> SEQ ID NO 60
<211> LENGTH: 17
<212> TYPE: PRT
<213> ORGANISM: Artificial sequence
<220> FEATURE:
<223> OTHER INFORMATION: Pertuzumab aff.mat. clone G2- VH CDR2

<400> SEQUENCE: 60

Asp Val Asn Pro Asn Ser Gly Gly Tyr Ile Val Asn Arg Arg Phe Lys
1               5                   10                  15

Gly

<210> SEQ ID NO 61
<211> LENGTH: 357
<212> TYPE: DNA
<213> ORGANISM: Artificial sequence
```

<220> FEATURE:
<223> OTHER INFORMATION: Pertuzumab aff.mat. clone D1 DNA

<400> SEQUENCE: 61

```
gaggtgcaat tggttgaaag cggtggtggt ctggttcagc ctggtggtag cctgcgtctg    60
agctgtgcag caagcggttt tacctttaac gattatacca tggattgggt tcgtcaggca   120
ccgggtaaag gtctggaatg ggttgcagat gttaatccga atagcggtgg tagcatttat   180
aaccagcgtt ttaaaggtcg ttttaccctg agcgttgatc gtagcaaaaa taccctgtat   240
ctgcaaatga atagtctgcg tgcagaggat accgcagtgt attattgtgc acgtaacctg   300
ggtccgttct tctactttga ttattggggt cagggcaccc tggttaccgt tagcagc     357
```

<210> SEQ ID NO 62
<211> LENGTH: 119
<212> TYPE: PRT
<213> ORGANISM: Artificial sequence
<220> FEATURE:
<223> OTHER INFORMATION: Pertuzumab aff.mat. clone D1

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser
        115
```

<210> SEQ ID NO 63
<211> LENGTH: 357
<212> TYPE: DNA
<213> ORGANISM: Artificial sequence
<220> FEATURE:
<223> OTHER INFORMATION: Pertuzumab aff.mat. clone D1-derived, DNA

<400> SEQUENCE: 63

```
gaggtgcaat tggttgaaag cggtggtggt ctggttcagc ctggtggtag cctgcgtctg    60
agctgtgcag caagcggttt tacctttaac gattatacca tggattgggt tcgtcaggca   120
ccgggtaaag gtctggaatg ggttgcagat gttaatccga atagcggtgg tagcattgtt   180
aaccgtcgtt ttaaaggtcg ttttaccctg agcgttgatc gtagcaaaaa taccctgtat   240
ctgcaaatga atagtctgcg tgcagaggat accgcagtgt attattgtgc acgtaacctg   300
ggtccgttct tctactttga ttattggggt cagggcaccc tggttaccgt tagcagc     357
```

<210> SEQ ID NO 64
<211> LENGTH: 119
<212> TYPE: PRT
<213> ORGANISM: Artificial sequence
<220> FEATURE:

<223> OTHER INFORMATION: Pertuzumab aff.mat. clone D1-derived

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser
        115

<210> SEQ ID NO 65
<211> LENGTH: 357
<212> TYPE: DNA
<213> ORGANISM: Artificial sequence
<220> FEATURE:
<223> OTHER INFORMATION: Pertuzumab aff.mat. clone B2, DNA

<400> SEQUENCE: 65
gaggtgcaat tggttgaaag cggtggtggt ctggttcagc ctggtggtag cctgcgtctg      60
agctgtgcag caagcggttt tacctttaac gattatacca tggattggtt tcgtcaggca     120
ccgggtaaag gtctggaatg ggttgcagat gttaatccga atagcggtgg tagcatttat     180
aaccagcgtt ttaaaggtcg ttttacccct gagcgttgatc gtagcaaaaa taccctgtat    240
ctgcaaatga atagtctgcg tgcagaggat accgcagtgt attattgtgc acgtaatctg    300
ggtccgaact tctactttga ttattggggt cagggcaccc tggttaccgt tagcagc       357

<210> SEQ ID NO 66
<211> LENGTH: 119
<212> TYPE: PRT
<213> ORGANISM: Artificial sequence
<220> FEATURE:
<223> OTHER INFORMATION: Pertuzumab aff.mat. clone B2

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Phe Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Asn Phe Tyr Phe Asp Tyr Trp Gly Gln Gly

Thr Leu Val Thr Val Ser Ser
        115

<210> SEQ ID NO 67
<211> LENGTH: 357
<212> TYPE: DNA
<213> ORGANISM: Artificial sequence
<220> FEATURE:
<223> OTHER INFORMATION: Pertuzumab aff.mat. clone E1, DNA

<400> SEQUENCE: 67
gaggtgcaat tggttgaaag cggtggtggt ctggttcagc ctggtggtag cctgcgtctg      60
agctgtgcag caagcggttt tacctttgca gattatacca tggattgggt tcgtcaggca     120
ccgggtaaag gtctggaatg ggttgcagat gttaatccga atagcggtgg tagcatttat     180
aaccagcgtt ttaaaggtcg ttttaccctg agcgttgatc gtagcaaaaa taccctgtat     240
ctgcaaatga atagtctgcg tgcagaggat accgcagtgt attattgtgc acgtaatctg     300
ggtccgtggt tctactttga ttattgggt cagggcaccc tggttaccgt tagcagc        357

<210> SEQ ID NO 68
<211> LENGTH: 119
<212> TYPE: PRT
<213> ORGANISM: Artificial sequence
<220> FEATURE:
<223> OTHER INFORMATION: Pertuzumab aff.mat. clone E1

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Trp Phe Tyr Phe Asp Tyr Trp Gly Gln Gly
            100                 105                 110

Thr Leu Val Thr Val Ser Ser
        115

<210> SEQ ID NO 69
<211> LENGTH: 357
<212> TYPE: DNA
<213> ORGANISM: Artificial sequence
<220> FEATURE:
<223> OTHER INFORMATION: Pertuzumab aff.mat. clone G2, DNA

<400> SEQUENCE: 69
gaggtgcaat tggttgaaag cggtggtggt ctggttcagc ctggtggtag cctgcgtctg      60
agctgtgcag caagcggttt tacctttacc gattacacaa tggattgggt tcgtcaggca     120
ccgggtaaag gtctggaatg ggttgcagat gttaatccga actctggtgg ttacattgtt     180
aaccgtcgtt ttaaaggtcg ttttaccctg agcgttgatc gtagcaaaaa taccctgtat     240

```
ctgcaaatga atagtctgcg tgcagaggat accgcagtgt attattgtgc acgtaatctg    300
ggtccgagct tctattttga ttattggggt cagggcaccc tggttaccgt tagcagc       357
```

<210> SEQ ID NO 70
<211> LENGTH: 119
<212> TYPE: PRT
<213> ORGANISM: Artificial sequence
<220> FEATURE:
<223> OTHER INFORMATION: Pertuzumab aff.mat. clone G2

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Tyr Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 71
<211> LENGTH: 357
<212> TYPE: DNA
<213> ORGANISM: Artificial sequence
<220> FEATURE:
<223> OTHER INFORMATION: Pertuzumab aff.mat. clone C8, DNA

<400> SEQUENCE: 71

```
gaggtgcaat tggttgaaag cggtggtggt ctggttcagc ctggtggtag cctgcgtctg    60
agctgtgcag caagcggttt tacctttacc gattacacaa tggattgggt tcgtcaggca    120
ccgggtaaag gtctggaatg ggttgcagat gttaatccga actctggtgg ttctattatg    180
aaccgtcgtt ttaaaggtcg ttttaccctg agcgttgatc gtagcaaaaa taccctgtat    240
ctgcaaatga atagtctgcg tgcagaggat accgcagtgt attattgtgc acgtaatctg    300
ggtccgagct tctattttga ttattggggt cagggcaccc tggttaccgt tagcagc       357
```

<210> SEQ ID NO 72
<211> LENGTH: 119
<212> TYPE: PRT
<213> ORGANISM: Artificial sequence
<220> FEATURE:
<223> OTHER INFORMATION: Pertuzumab aff.mat. clone C8

<400> SEQUENCE: 72

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45
```

Ala Asp Val Asn Pro Asn Ser Gly Gly Ser Ile Met Asn Arg Arg Phe
    50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Leu Val Thr Val Ser Ser
        115

<210> SEQ ID NO 73
<211> LENGTH: 357
<212> TYPE: DNA
<213> ORGANISM: Artificial sequence
<220> FEATURE:
<223> OTHER INFORMATION: Pertuzumab aff.mat. clone A1 DNA

<400> SEQUENCE: 73
gaggtgcaat tggttgaaag cggtggtggt ctggttcagc ctggtggtag cctgcgtctg      60
agctgtgcag caagcggttt tacctttacc gattacacaa tggattgggt tcgtcaggca     120
ccgggtaaag gtctggaatg ggttgcagat gttaatccga actctggtgg ttctattgtt     180
aaccagcgtt ttaaaggtcg ttttaccctg agcgttgatc gtagcaaaaa taccctgtat     240
ctgcaaatga atagtctgcg tgcagaggat accgcagtgt attattgtgc acgtaatctg     300
ggtccgtggt tctactttga ttattggggt cagggcaccc tggttaccgt tagcagc       357

<210> SEQ ID NO 74
<211> LENGTH: 119
<212> TYPE: PRT
<213> ORGANISM: Artificial sequence
<220> FEATURE:
<223> OTHER INFORMATION: Pertuzumab aff.mat. clone A1

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
                 20                  25                  30

Thr Met Asp Trp Val Arg Gln Ala Pro Gly Lys Gly Leu Glu Trp Val
             35                  40                  45

Ala Asp Val Asn Pro Asn Ser Gly Gly Ser Ile Val Asn Gln Arg Phe
    50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Trp Phe Tyr Phe Asp Tyr Trp Gly Gln Gly
                100                 105                 110

Thr Leu Val Thr Val Ser Ser
        115

<210> SEQ ID NO 75
<211> LENGTH: 17
<212> TYPE: PRT
<213> ORGANISM: Artificial sequence
<220> FEATURE:
<223> OTHER INFORMATION: Pertuzumab aff.mat. clone C8- VH CDR2

```
<400> SEQUENCE: 75

Asp Val Asn Pro Asn Ser Gly Gly Ser Ile Met Asn Arg Arg Phe Lys
1               5                   10                  15
Gly

<210> SEQ ID NO 76
<211> LENGTH: 17
<212> TYPE: PRT
<213> ORGANISM: Artificial sequence
<220> FEATURE:
<223> OTHER INFORMATION: Pertuzumab aff.mat. clone A1- VH CDR2

<400> SEQUENCE: 76

Asp Val Asn Pro Asn Ser Gly Gly Ser Ile Val Asn Gln Arg Phe Lys
1               5                   10                  15
Gly

<210> SEQ ID NO 77
<211> LENGTH: 17
<212> TYPE: PRT
<213> ORGANISM: Artificial sequence
<220> FEATURE:
<223> OTHER INFORMATION: Pertuzumab aff.mat. clone D1-derived VH CDR2

<400> SEQUENCE: 77

Asp Val Asn Pro Asn Ser Gly Gly Ser Ile Val Asn Arg Arg Phe Lys
1               5                   10                  15
Gly

<210> SEQ ID NO 78
<211> LENGTH: 11
<212> TYPE: PRT
<213> ORGANISM: Artificial sequence
<220> FEATURE:
<223> OTHER INFORMATION: Trastuzumab VH (D98N) (6636) CDR3

<400> SEQUENCE: 78

Trp Gly Gly Asn Gly Phe Tyr Ala Met Asp Tyr
1               5                   10

<210> SEQ ID NO 79
<211> LENGTH: 11
<212> TYPE: PRT
<213> ORGANISM: Artificial sequence
<220> FEATURE:
<223> OTHER INFORMATION: Trastuzumab VH CDR3

<400> SEQUENCE: 79

Trp Gly Gly Glu Gly Phe Tyr Ala Met Asp Tyr
1               5                   10

<210> SEQ ID NO 80
<211> LENGTH: 11
<212> TYPE: PRT
<213> ORGANISM: Artificial sequence
<220> FEATURE:
<223> OTHER INFORMATION: Trastuzumab VH (D98T) (6638) CDR3

<400> SEQUENCE: 80

Trp Gly Gly Thr Gly Phe Tyr Ala Met Asp Tyr
1               5                   10

<210> SEQ ID NO 81
<211> LENGTH: 321
```

<212> TYPE: DNA
<213> ORGANISM: Artificial sequence
<220> FEATURE:
<223> OTHER INFORMATION: Trastuzumab VL (4245) DNA

<400> SEQUENCE: 81

```
gacatccaga tgacccagag cccaagctct ctgtctgcct ctgtgggcga cagagtgacc      60
atcacctgca gagccagcca ggacgtgaac acagccgtgg cctggtatca gcagaagcca     120
ggcaaggccc caaagctgct gatctacagc gccagcttcc tgtacagcgg cgtgccaagc     180
agattcagcg gcagcagaag cggcacagac ttcaccctga ccatcagcag cctgcagcca     240
gaggacttcg ccacctacta ctgccagcag cactacacca cccaccaac cttcggacag      300
ggcaccaagg tggagatcaa g                                              321
```

<210> SEQ ID NO 82
<211> LENGTH: 107
<212> TYPE: PRT
<213> ORGANISM: Artificial sequence
<220> FEATURE:
<223> OTHER INFORMATION: Trastuzumab VL (4245)

<400> SEQUENCE: 82

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys
            100                 105
```

<210> SEQ ID NO 83
<211> LENGTH: 321
<212> TYPE: DNA
<213> ORGANISM: Artificial sequence
<220> FEATURE:
<223> OTHER INFORMATION: Trastuzumab VL T31A (6641) DNA

<400> SEQUENCE: 83

```
gatatccaga tgacccagtc tccatcctcc ctgtctgcat ctgtaggaga cagagtcacc      60
atcacttgcc gggcaagtca ggacgtgaac gccgctgtag cgtggtacca gcagaaacca     120
ggtaaggcac cgaagctatt aatttatagt gcgagcttcc tgtacagtgg ggtcccgtcg     180
cgttttagcg gctctcgatc cggcacggat tttaccctga ccattagcag cctgcagcct     240
gaagactttg cgacatatta ttgccaacag cactacacaa ctcctcccac ctttggccag     300
ggtacgaaag ttgaaattaa a                                              321
```

<210> SEQ ID NO 84
<211> LENGTH: 107
<212> TYPE: PRT
<213> ORGANISM: Artificial sequence
<220> FEATURE:
<223> OTHER INFORMATION: Trastuzumab VL T31A (6641)

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ala Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 85
<211> LENGTH: 322
<212> TYPE: DNA
<213> ORGANISM: Artificial sequence
<220> FEATURE:
<223> OTHER INFORMATION: Trastuzumab VL T31V (6642) DNA

<400> SEQUENCE: 85
gatatccaga tgacccagtc tccatcctcc ctgtctgcat ctgtaggaga cagagtcacc      60
atcacttgcc gggcaagtca ggacgtgaac gtggctgtag cgtggtacca gcagaaacca     120
ggtaaggcac cgaagctatt aatttatagt gcgagcttcc tgtacagtgg ggtcccgtcg     180
cgttttagcg gctctcgatc cggcacggat tttacccctga ccattagcag cctgcagcct    240
gaagactttg cgacatatta ttgccaacag cactacacaa ctcctcccac ctttggccag     300
ggtacgaaag ttgaaattaa ag                                              322

<210> SEQ ID NO 86
<211> LENGTH: 107
<212> TYPE: PRT
<213> ORGANISM: Artificial sequence
<220> FEATURE:
<223> OTHER INFORMATION: Trastuzumab VL T31V (6642)

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 87

```
<211> LENGTH: 11
<212> TYPE: PRT
<213> ORGANISM: Artificial sequence
<220> FEATURE:
<223> OTHER INFORMATION: Trastuzumab VH (G99A) (6639) CDR3

<400> SEQUENCE: 87

Trp Gly Gly Asp Ala Phe Tyr Ala Met Asp Tyr
1               5                   10

<210> SEQ ID NO 88
<211> LENGTH: 11
<212> TYPE: PRT
<213> ORGANISM: Artificial sequence
<220> FEATURE:
<223> OTHER INFORMATION: Trastuzumab VH (G99S) (6640) CDR3

<400> SEQUENCE: 88

Trp Gly Gly Asp Ser Phe Tyr Ala Met Asp Tyr
1               5                   10

<210> SEQ ID NO 89
<211> LENGTH: 11
<212> TYPE: PRT
<213> ORGANISM: Artificial sequence
<220> FEATURE:
<223> OTHER INFORMATION: Pertuzumab (Tras.L3) (QM)-CDR1

<400> SEQUENCE: 89

Lys Ala Ser Gln Asp Val Ser Thr Ala Val Ala
1               5                   10

<210> SEQ ID NO 90
<211> LENGTH: 7
<212> TYPE: PRT
<213> ORGANISM: Artificial sequence
<220> FEATURE:
<223> OTHER INFORMATION: Pertuzumab (Tras.L3) (QM)-CDR2

<400> SEQUENCE: 90

Ser Ala Ser Phe Arg Tyr Thr
1               5

<210> SEQ ID NO 91
<211> LENGTH: 360
<212> TYPE: DNA
<213> ORGANISM: Artificial sequence
<220> FEATURE:
<223> OTHER INFORMATION: Trastuzumab VH (11345) DNA

<400> SEQUENCE: 91
gaagtgcaat tggtggaaag cggcggcggc ctggtgcaac cgggcggcag cctgcgtctg      60
agctgcgcgg cctccggatt aacataaag gacacataca tccactgggt gcgccaagca     120
cctgggaagg gtctcgagtg gtggctcgga atttacccaa caaatggcta caccaggtat     180
gcggatagcg tgaaaggccg ttttaccatt tcagctgata cttcgaagaa caccgcctat     240
ctgcaaatga acagcctgcg tgcggaagat acggccgtgt attattgctc gcgttgggga     300
ggagacgggt tctatgctat ggattactgg ggccaaggca ccctggtgac ggttagctca     360

<210> SEQ ID NO 92
<211> LENGTH: 120
<212> TYPE: PRT
<213> ORGANISM: Artificial sequence
<220> FEATURE:
<223> OTHER INFORMATION: Trastuzumab VH (11345)
```

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 93
<211> LENGTH: 360
<212> TYPE: DNA
<213> ORGANISM: Artificial sequence
<220> FEATURE:
<223> OTHER INFORMATION: Trastuzumab VH (D98N) (6636) DNA

<400> SEQUENCE: 93
gaagtgcaat tggtggaaag cggcggcggc ctggtgcaac cgggcggcag cctgcgtctg    60
agctgcgcgg cctccggatt aacataaag gacacataca tccactgggt gcgccaagca   120
cctgggaagg gtctcgagtg gtggctcgg atttacccaa caaatggcta caccaggtat   180
gcggatagcg tgaaaggccg ttttaccatt tcagctgata cttcgaagaa caccgcctat   240
ctgcaaatga acagcctgcg tgcggaagat acggccgtgt attattgctc gcgttgggga   300
ggaaacgggt tctatgctat ggattactgg ggccaaggca ccctggtgac ggttagctca   360

<210> SEQ ID NO 94
<211> LENGTH: 120
<212> TYPE: PRT
<213> ORGANISM: Artificial sequence
<220> FEATURE:
<223> OTHER INFORMATION: Trastuzumab VH (D98N) (6636)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asn Gly Phe Tyr Ala Met Asp Tyr Trp Gly Gln
            100                 105                 110

```
Gly Thr Leu Val Thr Val Ser Ser
        115                 120

<210> SEQ ID NO 95
<211> LENGTH: 360
<212> TYPE: DNA
<213> ORGANISM: Artificial sequence
<220> FEATURE:
<223> OTHER INFORMATION: Trastuzumab VH (D98E) (6637) DNA

<400> SEQUENCE: 95
gaagtgcaat tggtggaaag cggcggcggc ctggtgcaac cgggcggcag cctgcgtctg    60
agctgcgcgg cctccggatt aacataaag gacacataca tccactgggt gcgccaagca   120
cctgggaagg gtctcgagtg ggtggctcgg atttacccaa caaatggcta caccaggtat   180
gcggatagcg tgaaaggccg ttttaccatt tcagctgata cttcgaagaa caccgcctat   240
ctgcaaatga acagcctgcg tgcggaagat acggccgtgt attattgctc gcgttgggga   300
ggagaggggt tctatgctat ggattactgg ggccaaggca ccctggtgac ggttagctca   360

<210> SEQ ID NO 96
<211> LENGTH: 120
<212> TYPE: PRT
<213> ORGANISM: Artificial sequence
<220> FEATURE:
<223> OTHER INFORMATION: Trastuzumab VH (D98E) (6637)

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser
        115                 120

<210> SEQ ID NO 97
<211> LENGTH: 360
<212> TYPE: DNA
<213> ORGANISM: Artificial sequence
<220> FEATURE:
<223> OTHER INFORMATION: Trastuzumab VH (D98T) (6638) DNA

<400> SEQUENCE: 97
gaagtgcaat tggtggaaag cggcggcggc ctggtgcaac cgggcggcag cctgcgtctg    60
agctgcgcgg cctccggatt aacataaag gacacataca tccactgggt gcgccaagca   120
cctgggaagg gtctcgagtg ggtggctcgg atttacccaa caaatggcta caccaggtat   180
gcggatagcg tgaaaggccg ttttaccatt tcagctgata cttcgaagaa caccgcctat   240
ctgcaaatga acagcctgcg tgcggaagat acggccgtgt attattgctc gcgttgggga   300
```

-continued

```
ggaaccgggt tctatgctat ggattactgg ggccaaggca ccctggtgac ggttagctca    360
```

<210> SEQ ID NO 98
<211> LENGTH: 120
<212> TYPE: PRT
<213> ORGANISM: Artificial sequence
<220> FEATURE:
<223> OTHER INFORMATION: Trastuzumab VH (D98T) (6638)

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser
        115                 120

<210> SEQ ID NO 99
<211> LENGTH: 360
<212> TYPE: DNA
<213> ORGANISM: Artificial sequence
<220> FEATURE:
<223> OTHER INFORMATION: Trastuzumab VH (G99A) (6639) DNA

<400> SEQUENCE: 99

```
gaagtgcaat tggtggaaag cggcggcggc ctggtgcaac cgggcggcag cctgcgtctg    60
agctgcgcgg cctccggatt aacataaag gacacataca tccactgggt gcgccaagca   120
cctgggaagg gtctcgagtg ggtggctcgg atttacccaa caaatggcta caccaggtat   180
gcggatagcg tgaaaggccg ttttaccatt tcagctgata cttcgaagaa caccgcctat   240
ctgcaaatga acagcctgcg tgcggaagat acggccgtgt attattgctc gcgttgggga   300
ggagacgcct tctatgctat ggattactgg ggccaaggca ccctggtgac ggttagctca   360
```

<210> SEQ ID NO 100
<211> LENGTH: 120
<212> TYPE: PRT
<213> ORGANISM: Artificial sequence
<220> FEATURE:
<223> OTHER INFORMATION: Trastuzumab VH (G99A) (6639)

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val

```
                    50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                     85                  90                  95

Ser Arg Trp Gly Gly Asp Ala Phe Tyr Ala Met Asp Tyr Trp Gly Gln
                100                 105                 110

Gly Thr Leu Val Thr Val Ser Ser
            115                 120

<210> SEQ ID NO 101
<211> LENGTH: 360
<212> TYPE: DNA
<213> ORGANISM: Artificial sequence
<220> FEATURE:
<223> OTHER INFORMATION: Trastuzumab VH (G99S) (6640) DNA

<400> SEQUENCE: 101
gaagtgcaat tggtggaaag cggcggcggc ctggtgcaac cgggcggcag cctgcgtctg      60
agctgcgcgg cctccggatt taacataaag gacacataca tccactgggt gcgccaagca     120
cctgggaagg gtctcgagtg ggtggctcgg atttacccaa caaatggcta caccaggtat     180
gcggatagcg tgaaaggccg ttttaccatt tcagctgata cttcgaagaa caccgcctat     240
ctgcaaatga acagcctgcg tgcggaagat acggccgtgt attattgctc gcgttgggga     300
ggagacagct tctatgctat ggattactgg ggccaaggca ccctggtgac ggttagctca     360

<210> SEQ ID NO 102
<211> LENGTH: 120
<212> TYPE: PRT
<213> ORGANISM: Artificial sequence
<220> FEATURE:
<223> OTHER INFORMATION: Trastuzumab VH (G99S) (6640)

<400> SEQUENCE: 102

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Ser Phe Tyr Ala Met Asp Tyr Trp Gly Gln
                100                 105                 110

Gly Thr Leu Val Thr Val Ser Ser
            115                 120

<210> SEQ ID NO 103
<211> LENGTH: 11
<212> TYPE: PRT
<213> ORGANISM: Artificial sequence
<220> FEATURE:
<223> OTHER INFORMATION: Trastuzumab VL T31A (6641) CDR1

<400> SEQUENCE: 103
```

Arg Ala Ser Gln Asp Val Asn Ala Ala Val Ala
1               5                   10

<210> SEQ ID NO 104
<211> LENGTH: 11
<212> TYPE: PRT
<213> ORGANISM: Artificial sequence
<220> FEATURE:
<223> OTHER INFORMATION: Trastuzumab VL CDR1

<400> SEQUENCE: 104

Arg Ala Ser Gln Asp Val Asn Val Ala Val Ala
1               5                   10

<210> SEQ ID NO 105
<211> LENGTH: 120
<212> TYPE: PRT
<213> ORGANISM: Artificial sequence
<220> FEATURE:
<223> OTHER INFORMATION: Trastuzumab CDRG VH (D98E, CDRG)

<400> SEQUENCE: 105

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile His Trp Val Arg Gln Ala Pro Gly Gln Gly Leu Glu Trp Met
            35                  40                  45

Gly Arg Ile Tyr Pro Thr Asn Gly Tyr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Met Val Thr Val Ser Ser
        115                 120

<210> SEQ ID NO 106
<211> LENGTH: 107
<212> TYPE: PRT
<213> ORGANISM: Artificial sequence
<220> FEATURE:
<223> OTHER INFORMATION: Trastuzumab CDRG VL (N30T, CDRG)

<400> SEQUENCE: 106

Asp Ile Gln Leu Thr Gln Pro Pro Ser Val Ser Val Ala Pro Gly Gln
1               5                   10                  15

Thr Ala Arg Ile Thr Cys Gly Ala Ser Gln Asp Val Ser Thr Ala Val
                20                  25                  30

Ala Trp Tyr Gln Gln Lys Pro Gly Gln Ala Pro Val Leu Val Val Tyr
            35                  40                  45

Ser Ala Ser Phe Leu Tyr Ser Gly Ile Pro Ser Arg Phe Ser Gly Ser
    50                  55                  60

Arg Ser Gly Thr Asp Phe Thr Leu Thr Ile Ser Arg Val Glu Ala Gly
65                  70                  75                  80

Asp Glu Ala Asp Tyr Tyr Cys Gln Gln His Tyr Thr Thr Pro Pro Thr
                85                  90                  95

Phe Gly Thr Gly Thr Lys Val Thr Val Leu Arg
            100                 105

<210> SEQ ID NO 107
<211> LENGTH: 11
<212> TYPE: PRT
<213> ORGANISM: Artificial sequence
<220> FEATURE:
<223> OTHER INFORMATION: Trastuzumab CDRG VL CDR1

<400> SEQUENCE: 107

Gly Ala Ser Gln Asp Val Ser Thr Ala Val Ala
1               5                   10

<210> SEQ ID NO 108
<211> LENGTH: 17
<212> TYPE: PRT
<213> ORGANISM: Artificial sequence
<220> FEATURE:
<223> OTHER INFORMATION: Trastuzumab CDRG VH CDR2

<400> SEQUENCE: 108

Arg Ile Tyr Pro Thr Asn Gly Tyr Thr Arg Tyr Ala Gln Lys Phe Gln
1               5                   10                  15

Gly

<210> SEQ ID NO 109
<211> LENGTH: 453
<212> TYPE: PRT
<213> ORGANISM: Artificial sequence
<220> FEATURE:
<223> OTHER INFORMATION: XPertuzumab heavy chain

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

```
Thr His Gln Gly Leu Ser Ser Pro Val Thr Lys Ser Phe Asn Arg Gly
    210                 215                 220

Glu Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 110
<211> LENGTH: 212
<212> TYPE: PRT
<213> ORGANISM: Artificial sequence
<220> FEATURE:
<223> OTHER INFORMATION: XPertuzumab light chain

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Ser Ser Ala Ser Thr
            100                 105                 110
```

```
Lys Gly Pro Ser Val Phe Pro Leu Ala Pro Ser Ser Lys Thr Ser
            115                 120                 125

Gly Gly Thr Ala Ala Leu Gly Cys Leu Val Lys Asp Tyr Phe Pro Glu
        130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
        210

<210> SEQ ID NO 111
<211> LENGTH: 450
<212> TYPE: PRT
<213> ORGANISM: Artificial sequence
<220> FEATURE:
<223> OTHER INFORMATION: Trastuzumab CDRG heavy chain (VHCH1)

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Arg Ile Tyr Pro Thr Asn Gly Tyr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
        340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 112
<211> LENGTH: 213
<212> TYPE: PRT
<213> ORGANISM: Artificial sequence
<220> FEATURE:
<223> OTHER INFORMATION: Trastuzumab CDRG light chain (VLCL)

<400> SEQUENCE: 112

Asp Ile Gln Leu Thr Gln Pro Pro Ser Val Ser Val Ala Pro Gly Gln
1               5                   10                  15

Thr Ala Arg Ile Thr Cys Gly Ala Ser Gln Asp Val Ser Thr Ala Val
            20                  25                  30

Ala Trp Tyr Gln Gln Lys Pro Gly Gln Ala Pro Val Leu Val Val Tyr
        35                  40                  45

Ser Ala Ser Phe Leu Tyr Ser Gly Ile Pro Ser Arg Phe Ser Gly Ser
    50                  55                  60

Arg Ser Gly Thr Asp Phe Thr Leu Thr Ile Ser Arg Val Glu Ala Gly
65                  70                  75                  80

Asp Glu Ala Asp Tyr Tyr Cys Gln Gln His Tyr Thr Thr Pro Pro Thr
                85                  90                  95

Phe Gly Thr Gly Thr Lys Val Thr Val Leu Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 113
<211> LENGTH: 107
<212> TYPE: PRT
<213> ORGANISM: Artificial sequence
<220> FEATURE:
<223> OTHER INFORMATION: Pertuzumab wt CL

<400> SEQUENCE: 113

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 114
<211> LENGTH: 98
<212> TYPE: PRT
<213> ORGANISM: Artificial sequence
<220> FEATURE:
<223> OTHER INFORMATION: Pertuzumab wt CH1

<400> SEQUENCE: 114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 115
<211> LENGTH: 107
<212> TYPE: PRT
<213> ORGANISM: Artificial sequence

```
<220> FEATURE:
<223> OTHER INFORMATION: Trastuzumab CH1

<400> SEQUENCE: 115

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 116
<211> LENGTH: 106
<212> TYPE: PRT
<213> ORGANISM: Artificial sequence
<220> FEATURE:
<223> OTHER INFORMATION: Trastuzumab CL

<400> SEQUENCE: 116

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 117
<211> LENGTH: 120
<212> TYPE: PRT
<213> ORGANISM: Artificial sequence
<220> FEATURE:
<223> OTHER INFORMATION: Trastuzumab VH (D98E)

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

-continued

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser
            115                 120

<210> SEQ ID NO 118
<211> LENGTH: 108
<212> TYPE: PRT
<213> ORGANISM: Artificial sequence
<220> FEATURE:
<223> OTHER INFORMATION: Trastuzumab VL (T31V)

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 119
<211> LENGTH: 453
<212> TYPE: PRT
<213> ORGANISM: Artificial sequence
<220> FEATURE:
<223> OTHER INFORMATION: Pertuzumab heavy chain

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
130                 135                 140

```
Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 120
<211> LENGTH: 214
<212> TYPE: PRT
<213> ORGANISM: Artificial sequence
<220> FEATURE:
<223> OTHER INFORMATION: Pertuzumab light chain

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45
```

```
Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 121
<211> LENGTH: 450
<212> TYPE: PRT
<213> ORGANISM: Artificial sequence
<220> FEATURE:
<223> OTHER INFORMATION: XTrastuzumab heavy chain

<400> SEQUENCE: 121

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Glu Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 122
<211> LENGTH: 212
<212> TYPE: PRT
<213> ORGANISM: Artificial sequence
<220> FEATURE:
<223> OTHER INFORMATION: XTrastuzumab light chain

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys Ser Ser Ala Ser Thr
            100                 105                 110
Lys Gly Pro Ser Val Phe Pro Leu Ala Pro Ser Ser Lys Ser Thr Ser
            115                 120                 125
Gly Gly Thr Ala Ala Leu Gly Cys Leu Val Lys Asp Tyr Phe Pro Glu
            130                 135                 140
Pro Val Thr Val Ser Trp Asn Ser Gly Ala Leu Thr Ser Gly Val His
145                 150                 155                 160
Thr Phe Pro Ala Val Leu Gln Ser Ser Gly Leu Tyr Ser Leu Ser Ser
                165                 170                 175
Val Val Thr Val Pro Ser Ser Leu Gly Thr Gln Thr Tyr Ile Cys
            180                 185                 190
Asn Val Asn His Lys Pro Ser Asn Thr Lys Val Asp Lys Lys Val Glu
                195                 200                 205
Pro Lys Ser Cys
    210
```

<210> SEQ ID NO 123
<211> LENGTH: 214
<212> TYPE: PRT
<213> ORGANISM: Artificial sequence
<220> FEATURE:
<223> OTHER INFORMATION: Light chain (kappa) [Trastuzumab, 1016]

<400> SEQUENCE: 123

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210
```

<210> SEQ ID NO 124

<211> LENGTH: 711
<212> TYPE: PRT
<213> ORGANISM: Artificial sequence
<220> FEATURE:
<223> OTHER INFORMATION: Heavy chain [Trastuzumab + scFv Omnitarg, RB40]

<400> SEQUENCE: 124

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys Gly Gly Gly Gly Ser Gly Gly Gly Gly Ser Gly Gly Gly Gly
    450                 455                 460

Ser Glu Val Gln Leu Val Glu Ser Gly Gly Gly Leu Val Gln Pro Gly
465                 470                 475                 480

Gly Ser Leu Arg Leu Ser Cys Ala Ala Ser Gly Phe Thr Phe Thr Asp
                485                 490                 495

Tyr Thr Met Asp Trp Val Arg Gln Ala Pro Gly Lys Cys Leu Glu Trp
            500                 505                 510

Val Ala Asp Val Asn Pro Asn Ser Gly Gly Ser Ile Tyr Asn Gln Arg
            515                 520                 525

Phe Lys Gly Arg Phe Thr Leu Ser Val Asp Arg Ser Lys Asn Thr Leu
        530                 535                 540

Tyr Leu Gln Met Asn Ser Leu Arg Ala Glu Asp Thr Ala Val Tyr Tyr
545                 550                 555                 560

Cys Ala Arg Asn Leu Gly Pro Ser Phe Tyr Phe Asp Tyr Trp Gly Gln
                565                 570                 575

Gly Thr Leu Val Thr Val Ser Ser Gly Gly Gly Gly Ser Gly Gly Gly
            580                 585                 590

Gly Ser Gly Gly Gly Gly Ser Gly Gly Gly Gly Ser Asp Ile Gln Met
        595                 600                 605

Thr Gln Ser Pro Ser Ser Leu Ser Ala Ser Val Gly Asp Arg Val Thr
    610                 615                 620

Ile Thr Cys Lys Ala Ser Gln Asp Val Ser Ile Gly Val Ala Trp Tyr
625                 630                 635                 640

Gln Gln Lys Pro Gly Lys Ala Pro Lys Leu Leu Ile Tyr Ser Ala Ser
                645                 650                 655

Tyr Arg Tyr Thr Gly Val Pro Ser Arg Phe Ser Gly Ser Gly Ser Gly
            660                 665                 670

Thr Asp Phe Thr Leu Thr Ile Ser Ser Leu Gln Pro Glu Asp Phe Ala
        675                 680                 685

Thr Tyr Tyr Cys Gln Gln Tyr Ile Tyr Pro Tyr Thr Phe Gly Cys
    690                 695                 700

Gly Thr Lys Val Glu Ile Lys
705                 710

<210> SEQ ID NO 125
<211> LENGTH: 471
<212> TYPE: PRT
<213> ORGANISM: Artificial sequence
<220> FEATURE:
<223> OTHER INFORMATION: Light chain [scFv Trastuzumab + Omnitarg, RB34]

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

-continued

```
Val Ala Trp Tyr Gln Gln Lys Pro Gly Lys Ala Pro Lys Leu Leu Ile
    35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Gly Gly Gly Gly Ser
                100                 105                 110
Gly Gly Gly Gly Ser Gly Gly Gly Gly Ser Glu Val Gln Leu Val Glu
            115                 120                 125
Ser Gly Gly Gly Leu Val Gln Pro Gly Gly Ser Leu Arg Leu Ser Cys
130                 135                 140
Ala Ala Ser Gly Phe Asn Ile Lys Asp Thr Tyr Ile His Trp Val Arg
145                 150                 155                 160
Gln Ala Pro Gly Lys Gly Leu Glu Trp Val Ala Arg Ile Tyr Pro Thr
                165                 170                 175
Asn Gly Tyr Thr Arg Tyr Ala Asp Ser Val Lys Gly Arg Phe Thr Ile
                180                 185                 190
Ser Ala Asp Thr Ser Lys Asn Thr Ala Tyr Leu Gln Met Asn Ser Leu
            195                 200                 205
Arg Ala Glu Asp Thr Ala Val Tyr Tyr Cys Ser Arg Trp Gly Gly Asp
    210                 215                 220
Gly Phe Tyr Ala Met Asp Tyr Trp Gly Gln Gly Thr Leu Val Thr Val
225                 230                 235                 240
Ser Ser Gly Gly Gly Gly Ser Gly Gly Gly Gly Ser Gly Gly Gly Gly
                245                 250                 255
Ser Asp Ile Gln Met Thr Gln Ser Pro Ser Ser Leu Ser Ala Ser Val
            260                 265                 270
Gly Asp Arg Val Thr Ile Thr Cys Lys Ala Ser Gln Asp Val Ser Ile
        275                 280                 285
Gly Val Ala Trp Tyr Gln Gln Lys Pro Gly Lys Ala Pro Lys Leu Leu
    290                 295                 300
Ile Tyr Ser Ala Ser Tyr Arg Tyr Thr Gly Val Pro Ser Arg Phe Ser
305                 310                 315                 320
Gly Ser Gly Ser Gly Thr Asp Phe Thr Leu Thr Ile Ser Ser Leu Gln
                325                 330                 335
Pro Glu Asp Phe Ala Thr Tyr Tyr Cys Gln Gln Tyr Tyr Ile Tyr Pro
                340                 345                 350
Tyr Thr Phe Gly Gln Gly Thr Lys Val Glu Ile Lys Arg Thr Val Ala
            355                 360                 365
Ala Pro Ser Val Phe Ile Phe Pro Pro Ser Asp Glu Gln Leu Lys Ser
370                 375                 380
Gly Thr Ala Ser Val Val Cys Leu Leu Asn Asn Phe Tyr Pro Arg Glu
385                 390                 395                 400
Ala Lys Val Gln Trp Lys Val Asp Asn Ala Leu Gln Ser Gly Asn Ser
                405                 410                 415
Gln Glu Ser Val Thr Glu Gln Asp Ser Lys Asp Ser Thr Tyr Ser Leu
            420                 425                 430
Ser Ser Thr Leu Thr Leu Ser Lys Ala Asp Tyr Glu Lys His Lys Val
        435                 440                 445
```

Tyr Ala Cys Glu Val Thr His Gln Gly Leu Ser Ser Pro Val Thr Lys
450                 455                 460

Ser Phe Asn Arg Gly Glu Cys
465                 470

<210> SEQ ID NO 126
<211> LENGTH: 449
<212> TYPE: PRT
<213> ORGANISM: Artificial sequence
<220> FEATURE:
<223> OTHER INFORMATION: Heavy chain (Omnitarg, RB33)

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 127
<211> LENGTH: 470
<212> TYPE: PRT
<213> ORGANISM: Artificial sequence
<220> FEATURE:
<223> OTHER INFORMATION: Light chain [Trastuzumab + scFvOmnitarg, RB35]

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Asp Ile Gln Met Thr Gln Ser Pro Ser Ser Leu
225                 230                 235                 240

Ser Ala Ser Val Gly Asp Arg Val Thr Ile Thr Cys Lys Ala Ser Gln
```

245                 250                 255
Asp Val Ser Ile Gly Val Ala Trp Tyr Gln Gln Lys Pro Gly Lys Ala
            260                 265                 270

Pro Lys Leu Leu Ile Tyr Ser Ala Ser Tyr Arg Tyr Thr Gly Val Pro
            275                 280                 285

Ser Arg Phe Ser Gly Ser Gly Ser Gly Thr Asp Phe Thr Leu Thr Ile
            290                 295                 300

Ser Ser Leu Gln Pro Glu Asp Phe Ala Thr Tyr Tyr Cys Gln Gln Tyr
305                 310                 315                 320

Tyr Ile Tyr Pro Tyr Thr Phe Gly Gln Gly Thr Lys Val Glu Ile Lys
                325                 330                 335

Gly Gly Gly Gly Ser Gly Gly Gly Ser Gly Gly Gly Ser Glu
            340                 345                 350

Val Gln Leu Val Glu Ser Gly Gly Leu Val Gln Pro Gly Gly Ser
            355                 360                 365

Leu Arg Leu Ser Cys Ala Ala Ser Gly Phe Thr Phe Thr Asp Tyr Thr
            370                 375                 380

Met Asp Trp Val Arg Gln Ala Pro Gly Lys Gly Leu Glu Trp Val Ala
385                 390                 395                 400

Asp Val Asn Pro Asn Ser Gly Gly Ser Ile Tyr Asn Gln Arg Phe Lys
                405                 410                 415

Gly Arg Phe Thr Leu Ser Val Asp Arg Ser Lys Asn Thr Leu Tyr Leu
            420                 425                 430

Gln Met Asn Ser Leu Arg Ala Glu Asp Thr Ala Val Tyr Tyr Cys Ala
            435                 440                 445

Arg Asn Leu Gly Pro Ser Phe Tyr Phe Asp Tyr Trp Gly Gln Gly Thr
            450                 455                 460

Leu Val Thr Val Ser Ser
465                 470

<210> SEQ ID NO 128
<211> LENGTH: 450
<212> TYPE: PRT
<213> ORGANISM: Artificial sequence
<220> FEATURE:
<223> OTHER INFORMATION: Heavy chain [Trastuzumab, 1036]

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala

```
                130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 129
<211> LENGTH: 214
<212> TYPE: PRT
<213> ORGANISM: Artificial sequence
<220> FEATURE:
<223> OTHER INFORMATION: Light chain (kappa) [Trastuzumab, 1016]

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
```

-continued

```
            35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 130
<211> LENGTH: 711
<212> TYPE: PRT
<213> ORGANISM: Artificial sequence
<220> FEATURE:
<223> OTHER INFORMATION: Heavy chain [Trastuzumab + scFvOmnitarg, RB43]

<400> SEQUENCE: 130

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
```

```
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys Gly Gly Gly Gly Ser Gly Gly Gly Ser Gly Gly Gly Gly
        450                 455                 460
Ser Asp Ile Gln Met Thr Gln Ser Pro Ser Ser Leu Ser Ala Ser Val
465                 470                 475                 480
Gly Asp Arg Val Thr Ile Thr Cys Lys Ala Ser Gln Asp Val Ser Ile
                485                 490                 495
Gly Val Ala Trp Tyr Gln Gln Lys Pro Gly Lys Ala Pro Lys Leu Leu
            500                 505                 510
Ile Tyr Ser Ala Ser Tyr Arg Tyr Thr Gly Val Pro Ser Arg Phe Ser
        515                 520                 525
Gly Ser Gly Ser Gly Thr Asp Phe Thr Leu Thr Ile Ser Ser Leu Gln
        530                 535                 540
Pro Glu Asp Phe Ala Thr Tyr Tyr Cys Gln Gln Tyr Ile Tyr Pro
545                 550                 555                 560
Tyr Thr Phe Gly Cys Gly Thr Lys Val Glu Ile Lys Gly Gly Gly Gly
                565                 570                 575
Ser Gly Gly Gly Gly Ser Gly Gly Gly Gly Ser Gly Gly Gly Gly Ser
            580                 585                 590
Glu Val Gln Leu Val Glu Ser Gly Gly Gly Leu Val Gln Pro Gly Gly
        595                 600                 605
```

```
Ser Leu Arg Leu Ser Cys Ala Ala Ser Gly Phe Thr Phe Thr Asp Tyr
    610                 615                 620

Thr Met Asp Trp Val Arg Gln Ala Pro Gly Lys Cys Leu Glu Trp Val
625                 630                 635                 640

Ala Asp Val Asn Pro Asn Ser Gly Gly Ser Ile Tyr Asn Gln Arg Phe
                645                 650                 655

Lys Gly Arg Phe Thr Leu Ser Val Asp Arg Ser Lys Asn Thr Leu Tyr
                660                 665                 670

Leu Gln Met Asn Ser Leu Arg Ala Glu Asp Thr Ala Val Tyr Tyr Cys
            675                 680                 685

Ala Arg Asn Leu Gly Pro Ser Phe Tyr Phe Asp Tyr Trp Gly Gln Gly
        690                 695                 700

Thr Leu Val Thr Val Ser Ser
705                 710

<210> SEQ ID NO 131
<211> LENGTH: 480
<212> TYPE: PRT
<213> ORGANISM: Artificial sequence
<220> FEATURE:
<223> OTHER INFORMATION: Light chain [Trastuzumab + scFv Omnitarg, RB61]

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gly Gly Gly Ser Asp Ile Gln Met Thr Gln
225                 230                 235                 240

Ser Pro Ser Ser Leu Ser Ala Ser Val Gly Asp Arg Val Thr Ile Thr
                245                 250                 255
```

```
Cys Lys Ala Ser Gln Asp Val Ser Ile Gly Val Ala Trp Tyr Gln Gln
                260                 265                 270

Lys Pro Gly Lys Ala Pro Lys Leu Leu Ile Tyr Ser Ala Ser Tyr Arg
            275                 280                 285

Tyr Thr Gly Val Pro Ser Arg Phe Ser Gly Ser Gly Ser Gly Thr Asp
        290                 295                 300

Phe Thr Leu Thr Ile Ser Ser Leu Gln Pro Glu Asp Phe Ala Thr Tyr
305                 310                 315                 320

Tyr Cys Gln Gln Tyr Tyr Ile Tyr Pro Tyr Thr Phe Gly Cys Gly Thr
                325                 330                 335

Lys Val Glu Ile Lys Gly Gly Gly Ser Gly Gly Gly Gly Ser Gly
                340                 345                 350

Gly Gly Gly Ser Gly Gly Gly Gly Ser Glu Val Gln Leu Val Glu Ser
            355                 360                 365

Gly Gly Gly Leu Val Gln Pro Gly Gly Ser Leu Arg Leu Ser Cys Ala
370                 375                 380

Ala Ser Gly Phe Thr Phe Thr Asp Tyr Thr Met Asp Trp Val Arg Gln
385                 390                 395                 400

Ala Pro Gly Lys Cys Leu Glu Trp Val Ala Asp Val Asn Pro Asn Ser
                405                 410                 415

Gly Gly Ser Ile Tyr Asn Gln Arg Phe Lys Gly Arg Phe Thr Leu Ser
                420                 425                 430

Val Asp Arg Ser Lys Asn Thr Leu Tyr Leu Gln Met Asn Ser Leu Arg
            435                 440                 445

Ala Glu Asp Thr Ala Val Tyr Tyr Cys Ala Arg Asn Leu Gly Pro Ser
        450                 455                 460

Phe Tyr Phe Asp Tyr Trp Gly Gln Gly Thr Leu Val Thr Val Ser Ser
465                 470                 475                 480

<210> SEQ ID NO 132
<211> LENGTH: 450
<212> TYPE: PRT
<213> ORGANISM: Artificial sequence
<220> FEATURE:
<223> OTHER INFORMATION: Heavy chain [Trastuzumab, 1036]

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 133
<211> LENGTH: 696
<212> TYPE: PRT
<213> ORGANISM: Artificial sequence
<220> FEATURE:
<223> OTHER INFORMATION: scFab Trastuzumab heavy chain 1

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys Gly Gly Gly Ser Gly Gly Gly Gly Ser
     210                 215                 220

Gly Gly Gly Gly Ser Gly Gly Gly Ser Gly Gly Gly Gly Ser Gly
225                 230                 235                 240

Gly Gly Gly Ser Gly Gly Glu Val Gln Leu Val Glu Ser Gly Gly
             245                 250                 255

Leu Val Gln Pro Gly Gly Ser Leu Arg Leu Ser Cys Ala Ala Ser Gly
         260                 265                 270

Phe Asn Ile Lys Asp Thr Tyr Ile His Trp Val Arg Gln Ala Pro Gly
     275                 280                 285

Lys Gly Leu Glu Trp Val Ala Arg Ile Tyr Pro Thr Asn Gly Tyr Thr
290                 295                 300

Arg Tyr Ala Asp Ser Val Lys Gly Arg Phe Thr Ile Ser Ala Asp Thr
305                 310                 315                 320

Ser Lys Asn Thr Ala Tyr Leu Gln Met Asn Ser Leu Arg Ala Glu Asp
             325                 330                 335

Thr Ala Val Tyr Tyr Cys Ser Arg Trp Gly Gly Glu Gly Phe Tyr Ala
         340                 345                 350

Met Asp Tyr Trp Gly Gln Gly Thr Leu Val Thr Val Ser Ser Ala Ser
     355                 360                 365

Thr Lys Gly Pro Ser Val Phe Pro Leu Ala Pro Ser Ser Lys Ser Thr
     370                 375                 380

Ser Gly Gly Thr Ala Ala Leu Gly Cys Leu Val Lys Asp Tyr Phe Pro
385                 390                 395                 400

Glu Pro Val Thr Val Ser Trp Asn Ser Gly Ala Leu Thr Ser Gly Val
             405                 410                 415

His Thr Phe Pro Ala Val Leu Gln Ser Ser Gly Leu Tyr Ser Leu Ser
         420                 425                 430

Ser Val Val Thr Val Pro Ser Ser Ser Leu Gly Thr Gln Thr Tyr Ile
         435                 440                 445

Cys Asn Val Asn His Lys Pro Ser Asn Thr Lys Val Asp Lys Lys Val
450                 455                 460
```

Glu Pro Lys Ser Cys Asp Lys Thr His Thr Cys Pro Pro Cys Pro Ala
465                 470                 475                 480

Pro Glu Leu Leu Gly Gly Pro Ser Val Phe Leu Phe Pro Pro Lys Pro
            485                 490                 495

Lys Asp Thr Leu Met Ile Ser Arg Thr Pro Glu Val Thr Cys Val Val
            500                 505                 510

Val Asp Val Ser His Glu Asp Pro Glu Val Lys Phe Asn Trp Tyr Val
            515                 520                 525

Asp Gly Val Glu Val His Asn Ala Lys Thr Lys Pro Arg Glu Glu Gln
            530                 535                 540

Tyr Asn Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Ala
            565                 570                 575

Leu Pro Ala Pro Ile Glu Lys Thr Ile Ser Lys Ala Lys Gly Gln Pro
            580                 585                 590

Arg Glu Pro Gln Val Tyr Thr Leu Pro Pro Cys Arg Asp Glu Leu Thr
            595                 600                 605

Lys Asn Gln Val Ser Leu Trp Cys Leu Val Lys Gly Phe Tyr Pro Ser
610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
            645                 650                 655

Ser Lys Leu Thr Val Asp Lys Ser Arg Trp Gln Gln Gly Asn Val Phe
            660                 665                 670

Ser Cys Ser Val Met His Glu Ala Leu His Asn His Tyr Thr Gln Lys
            675                 680                 685

Ser Leu Ser Leu Ser Pro Gly Lys
            690                 695

<210> SEQ ID NO 134
<211> LENGTH: 449
<212> TYPE: PRT
<213> ORGANISM: Artificial sequence
<220> FEATURE:
<223> OTHER INFORMATION: Pertuzumab heavy chain 2

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 135
<211> LENGTH: 214
<212> TYPE: PRT
<213> ORGANISM: Artificial sequence
<220> FEATURE:
<223> OTHER INFORMATION: Pertuzumab light chain 1

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile

-continued

```
                35                  40                  45
Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 136
<211> LENGTH: 449
<212> TYPE: PRT
<213> ORGANISM: Artificial sequence
<220> FEATURE:
<223> OTHER INFORMATION: Pertuzumab heavy chain 1

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180              185              190
    Ser Ser Leu Gly Thr Gln Thr Tyr Ile Cys Asn Val Asn His Lys Pro
            195              200              205
    Ser Asn Thr Lys Val Asp Lys Lys Val Glu Pro Lys Ser Cys Asp Lys
            210              215              220
    Thr His Thr Cys Pro Pro Cys Pro Ala Pro Glu Leu Leu Gly Gly Pro
    225              230              235              240
    Ser Val Phe Leu Phe Pro Pro Lys Pro Lys Asp Thr Leu Met Ile Ser
            245              250              255
    Arg Thr Pro Glu Val Thr Cys Val Val Val Asp Val Ser His Glu Asp
            260              265              270
    Pro Glu Val Lys Phe Asn Trp Tyr Val Asp Gly Val Glu Val His Asn
            275              280              285
    Ala Lys Thr Lys Pro Arg Glu Glu Gln Tyr Asn Ser Thr Tyr Arg Val
            290              295              300
    Val Ser Val Leu Thr Val Leu His Gln Asp Trp Leu Asn Gly Lys Glu
    305              310              315              320
    Tyr Lys Cys Lys Val Ser Asn Lys Ala Leu Pro Ala Pro Ile Glu Lys
            325              330              335
    Thr Ile Ser Lys Ala Lys Gly Gln Pro Arg Glu Pro Gln Val Cys Thr
            340              345              350
    Leu Pro Pro Ser Arg Asp Glu Leu Thr Lys Asn Gln Val Ser Leu Ser
            355              360              365
    Cys Ala Val Lys Gly Phe Tyr Pro Ser Asp Ile Ala Val Glu Trp Glu
    370              375              380
    Ser Asn Gly Gln Pro Glu Asn Asn Tyr Lys Thr Thr Pro Pro Val Leu
    385              390              395              400
    Asp Ser Asp Gly Ser Phe Phe Leu Val Ser Lys Leu Thr Val Asp Lys
                    405              410              415
    Ser Arg Trp Gln Gln Gly Asn Val Phe Ser Cys Ser Val Met His Glu
                    420              425              430
    Ala Leu His Asn His Tyr Thr Gln Lys Ser Leu Ser Leu Ser Pro Gly
            435              440              445
    Lys

<210> SEQ ID NO 137
<211> LENGTH: 214
<212> TYPE: PRT
<213> ORGANISM: Artificial sequence
<220> FEATURE:
<223> OTHER INFORMATION: Pertuzumab light chain 1

<400> SEQUENCE: 137

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Ile Gly
            20                  25                  30
Val Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Tyr
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 138
<211> LENGTH: 696
<212> TYPE: PRT
<213> ORGANISM: Artificial sequence
<220> FEATURE:
<223> OTHER INFORMATION: scFab Trastuzumab heavy chain 2

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys Gly Gly Gly Ser Gly Gly Gly Ser Gly Gly Gly Gly
450                 455                 460

Ser Gly Gly Gly Ser Gly Gly Gly Ser Gly Gly Gly Gly Ser
465                 470                 475                 480

Gly Gly Asp Ile Gln Met Thr Gln Ser Pro Ser Ser Leu Ser Ala Ser
            485                 490                 495

Val Gly Asp Arg Val Thr Ile Thr Cys Arg Ala Ser Gln Asp Val Asn
                500                 505                 510

Val Ala Val Ala Trp Tyr Gln Gln Lys Pro Gly Lys Ala Pro Lys Leu
            515                 520                 525

Leu Ile Tyr Ser Ala Ser Phe Leu Tyr Ser Gly Val Pro Ser Arg Phe
        530                 535                 540

Ser Gly Ser Arg Ser Gly Thr Asp Phe Thr Leu Thr Ile Ser Ser Leu
545                 550                 555                 560

Gln Pro Glu Asp Phe Ala Thr Tyr Tyr Cys Gln Gln His Tyr Thr Thr
                565                 570                 575

Pro Pro Thr Phe Gly Gln Gly Thr Lys Val Glu Ile Lys Arg Thr Val
            580                 585                 590

Ala Ala Pro Ser Val Phe Ile Phe Pro Pro Ser Asp Glu Gln Leu Lys
            595                 600                 605

Ser Gly Thr Ala Ser Val Val Cys Leu Leu Asn Asn Phe Tyr Pro Arg
        610                 615                 620

Glu Ala Lys Val Gln Trp Lys Val Asp Asn Ala Leu Gln Ser Gly Asn
625                 630                 635                 640

Ser Gln Glu Ser Val Thr Glu Gln Asp Ser Lys Asp Ser Thr Tyr Ser
                645                 650                 655
```

-continued

Leu Ser Ser Thr Leu Thr Leu Ser Lys Ala Asp Tyr Glu Lys His Lys
                660                 665                 670

Val Tyr Ala Cys Glu Val Thr His Gln Gly Leu Ser Ser Pro Val Thr
            675                 680                 685

Lys Ser Phe Asn Arg Gly Glu Cys
        690                 695

<210> SEQ ID NO 139
<211> LENGTH: 695
<212> TYPE: PRT
<213> ORGANISM: Artificial sequence
<220> FEATURE:
<223> OTHER INFORMATION: scFab Pertuzumab heavy chain 1

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

-continued

```
Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Cys Thr
        340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Ser Gly Gly Gly Gly Ser
450                 455                 460

Gly Gly Gly Gly Ser Gly Gly Gly Ser Gly Gly Gly Gly Ser Gly
465                 470                 475                 480

Gly Asp Ile Gln Met Thr Gln Ser Pro Ser Ser Leu Ser Ala Ser Val
                485                 490                 495

Gly Asp Arg Val Thr Ile Thr Cys Lys Ala Ser Gln Asp Val Ser Ile
            500                 505                 510

Gly Val Ala Trp Tyr Gln Gln Lys Pro Gly Lys Ala Pro Lys Leu Leu
        515                 520                 525

Ile Tyr Ser Ala Ser Tyr Arg Tyr Thr Gly Val Pro Ser Arg Phe Ser
    530                 535                 540

Gly Ser Gly Ser Gly Thr Asp Phe Thr Leu Thr Ile Ser Ser Leu Gln
545                 550                 555                 560

Pro Glu Asp Phe Ala Thr Tyr Tyr Cys Gln Gln Tyr Tyr Ile Tyr Pro
                565                 570                 575

Tyr Thr Phe Gly Gln Gly Thr Lys Val Glu Ile Lys Arg Thr Val Ala
            580                 585                 590

Ala Pro Ser Val Phe Ile Phe Pro Pro Ser Asp Glu Gln Leu Lys Ser
        595                 600                 605

Gly Thr Ala Ser Val Val Cys Leu Leu Asn Asn Phe Tyr Pro Arg Glu
    610                 615                 620

Ala Lys Val Gln Trp Lys Val Asp Asn Ala Leu Gln Ser Gly Asn Ser
625                 630                 635                 640

Gln Glu Ser Val Thr Glu Gln Asp Ser Lys Asp Ser Thr Tyr Ser Leu
                645                 650                 655

Ser Ser Thr Leu Thr Leu Ser Lys Ala Asp Tyr Glu Lys His Lys Val
            660                 665                 670

Tyr Ala Cys Glu Val Thr His Gln Gly Leu Ser Ser Pro Val Thr Lys
        675                 680                 685

Ser Phe Asn Arg Gly Glu Cys
    690                 695

<210> SEQ ID NO 140
<211> LENGTH: 450
<212> TYPE: PRT
<213> ORGANISM: Artificial sequence
<220> FEATURE:
<223> OTHER INFORMATION: Trastuzumab heavy chain 2
```

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp 405                 410                 415
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 141
<211> LENGTH: 213
<212> TYPE: PRT
<213> ORGANISM: Artificial sequence
<220> FEATURE:
<223> OTHER INFORMATION: Trastuzumab light chain 2

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 142
<211> LENGTH: 450
<212> TYPE: PRT
<213> ORGANISM: Artificial sequence
<220> FEATURE:
<223> OTHER INFORMATION: Trastuzumab heavy chain 1

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

```
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Glu Gly Phe Tyr Ala Met Asp Tyr Trp Gly Gln
             100                 105                 110
Gly Thr Leu Val Thr Val Ser Ser Ala Ser Thr Lys Gly Pro Ser Val
             115                 120                 125
Phe Pro Leu Ala Pro Ser Ser Lys Ser Thr Ser Gly Gly Thr Ala Ala
         130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
             195                 200                 205
Pro Ser Asn Thr Lys Val Asp Lys Lys Val Glu Pro Lys Ser Cys Asp
         210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
             275                 280                 285
Asn Ala Lys Thr Lys Pro Arg Glu Glu Gln Tyr Asn Ser Thr Tyr Arg
         290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Cys Arg Asp Glu Leu Thr Lys Asn Gln Val Ser Leu
             355                 360                 365
Trp Cys Leu Val Lys Gly Phe Tyr Pro Ser Asp Ile Ala Val Glu Trp
         370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
         435                 440                 445
Gly Lys
```

<210> SEQ ID NO 143
<211> LENGTH: 214
<212> TYPE: PRT
<213> ORGANISM: Artificial sequence
<220> FEATURE:
<223> OTHER INFORMATION: Trastuzumab light chain 1

<400> SEQUENCE: 143

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Val Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 144
<211> LENGTH: 695
<212> TYPE: PRT
<213> ORGANISM: Artificial sequence
<220> FEATURE:
<223> OTHER INFORMATION: scFab Pertuzumab heavy chain 2

<400> SEQUENCE: 144

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gly Gly Gly Gly Ser
450                 455                 460

Gly Gly Gly Gly Ser Gly Gly Gly Ser Gly Gly Gly Gly Ser Gly
465                 470                 475                 480

Gly Asp Ile Gln Met Thr Gln Ser Pro Ser Ser Leu Ser Ala Ser Val
                485                 490                 495

Gly Asp Arg Val Thr Ile Thr Cys Lys Ala Ser Gln Asp Val Ser Ile
```

```
                500             505             510
Gly Val Ala Trp Tyr Gln Gln Lys Pro Gly Lys Ala Pro Lys Leu Leu
                515             520             525
Ile Tyr Ser Ala Ser Tyr Arg Tyr Thr Gly Val Pro Ser Arg Phe Ser
        530             535             540
Gly Ser Gly Ser Gly Thr Asp Phe Thr Leu Thr Ile Ser Ser Leu Gln
545             550             555             560
Pro Glu Asp Phe Ala Thr Tyr Tyr Cys Gln Gln Tyr Tyr Ile Tyr Pro
                565             570             575
Tyr Thr Phe Gly Gln Gly Thr Lys Val Glu Ile Lys Arg Thr Val Ala
        580             585             590
Ala Pro Ser Val Phe Ile Phe Pro Pro Ser Asp Glu Gln Leu Lys Ser
        595             600             605
Gly Thr Ala Ser Val Val Cys Leu Leu Asn Asn Phe Tyr Pro Arg Glu
        610             615             620
Ala Lys Val Gln Trp Lys Val Asp Asn Ala Leu Gln Ser Gly Asn Ser
625             630             635             640
Gln Glu Ser Val Thr Glu Gln Asp Ser Lys Asp Ser Thr Tyr Ser Leu
                645             650             655
Ser Ser Thr Leu Thr Leu Ser Lys Ala Asp Tyr Glu Lys His Lys Val
                660             665             670
Tyr Ala Cys Glu Val Thr His Gln Gly Leu Ser Ser Pro Val Thr Lys
        675             680             685
Ser Phe Asn Arg Gly Glu Cys
    690             695

<210> SEQ ID NO 145
<211> LENGTH: 701
<212> TYPE: PRT
<213> ORGANISM: Artificial sequence
<220> FEATURE:
<223> OTHER INFORMATION: Heavy chain with scFv Trastuzumab stabilized
      with disulphide bonding

<400> SEQUENCE: 145

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Thr Met Asp Trp Val Arg Gln Ala Pro Gly Lys Gly Leu Glu Trp Val
        35                  40                  45
Ala Asp Val Asn Pro Asn Ser Gly Gly Ser Ile Tyr Asn Gln Arg Phe
    50                  55                  60
Lys Gly Arg Phe Thr Leu Ser Val Asp Arg Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asn Leu Gly Pro Ser Phe Tyr Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys Gly Gly Gly Gly Ser Gly Gly Gly Ser Glu Val Gln Leu Val
            450                 455                 460
Glu Ser Gly Gly Gly Leu Val Gln Pro Gly Gly Ser Leu Arg Leu Ser
465                 470                 475                 480
Cys Ala Ala Ser Gly Phe Asn Ile Lys Asp Thr Tyr Ile His Trp Val
            485                 490                 495
Arg Gln Ala Pro Gly Lys Gly Leu Glu Trp Val Ala Arg Ile Tyr Pro
            500                 505                 510
Thr Asn Gly Tyr Thr Arg Tyr Ala Asp Ser Val Lys Gly Arg Phe Thr
            515                 520                 525
Ile Ser Ala Asp Thr Ser Lys Asn Thr Ala Tyr Leu Gln Met Asn Ser
            530                 535                 540
Leu Arg Ala Glu Asp Thr Ala Val Tyr Tyr Cys Ser Arg Trp Gly Gly
545                 550                 555                 560
Glu Gly Phe Tyr Ala Met Asp Tyr Trp Gly Cys Gly Thr Leu Val Thr
            565                 570                 575
Val Ser Ser Gly Gly Gly Gly Ser Gly Gly Gly Gly Ser Gly Gly Gly
```

```
                 580              585               590
Gly Ser Asp Ile Gln Met Thr Gln Ser Pro Ser Ser Leu Ser Ala Ser
            595                 600             605

Val Gly Asp Arg Val Thr Ile Thr Cys Arg Ala Ser Gln Asp Val Asn
        610                 615             620

Val Ala Val Ala Trp Tyr Gln Gln Lys Pro Gly Lys Cys Pro Lys Leu
625                 630             635                 640

Leu Ile Tyr Ser Ala Ser Phe Leu Tyr Ser Gly Val Pro Ser Arg Phe
            645             650                 655

Ser Gly Ser Arg Ser Gly Thr Asp Phe Thr Leu Thr Ile Ser Ser Leu
                660             665             670

Gln Pro Glu Asp Phe Ala Thr Tyr Tyr Cys Gln Gln His Tyr Thr Thr
            675             680             685

Pro Pro Thr Phe Gly Gln Gly Thr Lys Val Glu Ile Lys
            690             695             700

<210> SEQ ID NO 146
<211> LENGTH: 214
<212> TYPE: PRT
<213> ORGANISM: Artificial sequence
<220> FEATURE:
<223> OTHER INFORMATION: Pertuzumab light chain

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 147
<211> LENGTH: 26
<212> TYPE: DNA
```

<213> ORGANISM: Artificial sequence
<220> FEATURE:
<223> OTHER INFORMATION: LMB3

<400> SEQUENCE: 147
caggaaacag ctatgaccat gattac                                    26

<210> SEQ ID NO 148
<211> LENGTH: 57
<212> TYPE: DNA
<213> ORGANISM: Artificial sequence
<220> FEATURE:
<223> OTHER INFORMATION: AM_omni_H1_TN-ba
<220> FEATURE:
<221> NAME/KEY: misc_feature
<222> LOCATION: (26)..(26)
<223> OTHER INFORMATION: T=60%, S/G/R/N/D=20% (4% each), rest=20% (1.7%
      each)
<220> FEATURE:
<221> NAME/KEY: misc_feature
<222> LOCATION: (27)..(27)
<223> OTHER INFORMATION: D=60%, S/N/T/A/R/E/Q/G=30% (3.8% each),
      rest=10% (1.1% each)
<220> FEATURE:
<221> NAME/KEY: misc_feature
<222> LOCATION: (28)..(28)
<223> OTHER INFORMATION: Y=60%, F/S/H/N/D/T=30% (5.0% each), rest=10%
      (0.9%)
<220> FEATURE:
<221> NAME/KEY: misc_feature
<222> LOCATION: (29)..(29)
<223> OTHER INFORMATION: T=60%, A/G/V/S/P/D/N=30% (4.3% each), rest=10%
      (1.0%)

<400> SEQUENCE: 148
ccggtgcctg acgaacccaa tccatnnnna aaggtaaaac cgcttgctgc acagctc    57

<210> SEQ ID NO 149
<211> LENGTH: 32
<212> TYPE: DNA
<213> ORGANISM: Artificial sequence
<220> FEATURE:
<223> OTHER INFORMATION: RJH108 (omni_3'H1_fo)

<400> SEQUENCE: 149
atggattggg ttcgtcaggc accgggtaaa gg                              32

<210> SEQ ID NO 150
<211> LENGTH: 33
<212> TYPE: DNA
<213> ORGANISM: Artificial sequence
<220> FEATURE:
<223> OTHER INFORMATION: RJH109 (omni_5'H3_re)

<400> SEQUENCE: 150
attacgtgca cataatacag ctgcggtatc ctc                             33

<210> SEQ ID NO 151
<211> LENGTH: 66
<212> TYPE: DNA
<213> ORGANISM: Artificial sequence
<220> FEATURE:
<223> OTHER INFORMATION: AM_omni_H3_TN_fo
<220> FEATURE:
<221> NAME/KEY: misc_feature
<222> LOCATION: (26)..(26)
<223> OTHER INFORMATION: N=60%, G/D/E/Q/V/S/A/P/R/L/T/Y=40% (3.3% each)
<220> FEATURE:
<221> NAME/KEY: misc_feature
<222> LOCATION: (27)..(27)
<223> OTHER INFORMATION: L=60%, G/Y/S/A/D/T/R/P/V/N/W/F/I/E=40% (2.9%

```
      each)
<220> FEATURE:
<221> NAME/KEY: misc_feature
<222> LOCATION: (28)..(28)
<223> OTHER INFORMATION: G=60%, Y/S/A/D/T/R/P/L/V/N/W/F/I/E=40% (2.9%
      each)
<220> FEATURE:
<221> NAME/KEY: misc_feature
<222> LOCATION: (29)..(29)
<223> OTHER INFORMATION: P=60%, G/Y/S/A/D/T/R/L/V/N/W/F/I/E=40% (2.9%
      each)
<220> FEATURE:
<221> NAME/KEY: misc_feature
<222> LOCATION: (30)..(30)
<223> OTHER INFORMATION: S=60%, G/Y/P/A/D/T/R/L/V/N/W/F/I/E=40% (2.9%
      each)
<220> FEATURE:
<221> NAME/KEY: misc_feature
<222> LOCATION: (34)..(34)
<223> OTHER INFORMATION: Y=60%, G/A/P/W/S/D/T/F/R/K/H=40% (3.6% each)

<400> SEQUENCE: 151
taccgcagtg tattattgtg cacgtnnnnn ttcntttgat tattggggtc agggcaccct    60
ggttac                                                              66

<210> SEQ ID NO 152
<211> LENGTH: 28
<212> TYPE: DNA
<213> ORGANISM: Artificial sequence
<220> FEATURE:
<223> OTHER INFORMATION: RJH99

<400> SEQUENCE: 152
ggctgagact cctcaagaga aggattag                                      28

<210> SEQ ID NO 153
<211> LENGTH: 32
<212> TYPE: DNA
<213> ORGANISM: Artificial sequence
<220> FEATURE:
<223> OTHER INFORMATION: RJH110(omni_5'H2_ba)

<400> SEQUENCE: 153
attaacatct gcaacccatt ccagaccttt ac                                 32

<210> SEQ ID NO 154
<211> LENGTH: 69
<212> TYPE: DNA
<213> ORGANISM: Artificial sequence
<220> FEATURE:
<223> OTHER INFORMATION: AM_omni_h2_TN_fo
<220> FEATURE:
<221> NAME/KEY: misc_feature
<222> LOCATION: (28)..(28)
<223> OTHER INFORMATION: P=60%, G/A/S/T/D/N/F/Y=30% (3.8% each),
      rest=10% (1.0% each)
<220> FEATURE:
<221> NAME/KEY: misc_feature
<222> LOCATION: (29)..(29)
<223> OTHER INFORMATION: N=60%, S/D/G/T/R/A=30% (5.0% each), rest=10%
      (0.8%)
<220> FEATURE:
<221> NAME/KEY: misc_feature
<222> LOCATION: (30)..(30)
<223> OTHER INFORMATION: S=60%, G=10%, rest=30% (1.8% each)
<220> FEATURE:
<221> NAME/KEY: misc_feature
<222> LOCATION: (31)..(31)
<220> FEATURE:
<221> NAME/KEY: misc_feature
<222> LOCATION: (31)..(31)
<223> OTHER INFORMATION: n is a, c, g, or t
```

```
<220> FEATURE:
<221> NAME/KEY: misc_feature
<222> LOCATION: (35)..(35)
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (39)..(39)
<220> FEATURE:
<221> NAME/KEY: misc_feature
<222> LOCATION: (39)..(39)
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 154
ggtctggaat gggttgcaga tgttaatnnn nggtnattna acncgtttta aaggtcgttt    60
taccctgag                                                            69

<210> SEQ ID NO 155
<211> LENGTH: 19
<212> TYPE: PRT
<213> ORGANISM: Artificial sequence
<220> FEATURE:
<223> OTHER INFORMATION: Leader Peptide 1

<400> SEQUENCE: 155

Met Asp Trp Thr Trp Arg Ile Leu Phe Leu Val Ala Ala Thr Gly
 1               5                  10                  15

Ala His Ser

<210> SEQ ID NO 156
<211> LENGTH: 22
<212> TYPE: PRT
<213> ORGANISM: Artificial sequence
<220> FEATURE:
<223> OTHER INFORMATION: Leader Peptide 2

<400> SEQUENCE: 156

Met Asp Met Arg Val Pro Ala Gln Leu Leu Gly Leu Leu Leu Leu Trp
 1               5                  10                  15

Phe Pro Gly Ala Arg Cys
                20

<210> SEQ ID NO 157
<211> LENGTH: 19
<212> TYPE: PRT
<213> ORGANISM: Artificial sequence
<220> FEATURE:
<223> OTHER INFORMATION: Leader Peptide 3

<400> SEQUENCE: 157

Met Gly Trp Ser Cys Ile Ile Leu Phe Leu Val Ala Thr Ala Thr Gly
 1               5                  10                  15

Val His Ser

<210> SEQ ID NO 158
<211> LENGTH: 11
<212> TYPE: PRT
<213> ORGANISM: Artificial sequence
```

<220> FEATURE:
<223> OTHER INFORMATION: Trastuzumab VL N30S CDR1

<400> SEQUENCE: 158

Arg Ala Ser Gln Asp Val Ser Thr Ala Val Ala
1               5                   10

<210> SEQ ID NO 159
<211> LENGTH: 450
<212> TYPE: PRT
<213> ORGANISM: Artificial sequence
<220> FEATURE:
<223> OTHER INFORMATION: Trastuzumab VHCH1- Fc KNOB

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu

```
              325                 330                 335
Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 160
<211> LENGTH: 1350
<212> TYPE: PRT
<213> ORGANISM: Artificial sequence
<220> FEATURE:
<223> OTHER INFORMATION: Trastuzumab VHCH1- Fc KNOB DNA

<400> SEQUENCE: 160

Gly Ala Ala Gly Thr Gly Cys Ala Ala Thr Gly Gly Thr Gly Gly
1               5                   10                  15

Ala Ala Ala Gly Cys Gly Gly Cys Gly Gly Cys Gly Gly Cys Cys Thr
            20                  25                  30

Gly Gly Thr Gly Cys Ala Ala Cys Cys Gly Gly Cys Gly Gly Cys
        35                  40                  45

Ala Gly Cys Cys Thr Gly Cys Gly Thr Cys Thr Gly Ala Gly Cys Thr
50                  55                  60

Gly Cys Gly Cys Gly Gly Cys Cys Thr Cys Cys Gly Gly Ala Thr Thr
65                  70                  75                  80

Thr Ala Ala Cys Ala Thr Ala Ala Gly Gly Ala Cys Ala Cys Ala
            85                  90                  95

Thr Ala Cys Ala Thr Cys Cys Ala Cys Thr Gly Gly Thr Gly Cys
            100                 105                 110

Gly Cys Cys Ala Ala Gly Cys Ala Cys Cys Thr Gly Gly Gly Ala Ala
        115                 120                 125

Gly Gly Gly Thr Cys Thr Cys Gly Ala Gly Thr Gly Gly Gly Thr Gly
        130                 135                 140

Gly Cys Thr Cys Gly Gly Ala Thr Thr Ala Cys Cys Cys Ala Ala
145                 150                 155                 160

Cys Ala Ala Ala Thr Gly Gly Cys Thr Ala Cys Ala Cys Cys Ala Gly
            165                 170                 175

Gly Thr Ala Thr Gly Cys Gly Gly Ala Thr Ala Gly Cys Gly Thr Gly
            180                 185                 190

Ala Ala Ala Gly Gly Cys Cys Gly Thr Thr Thr Ala Cys Cys Ala
        195                 200                 205

Thr Thr Thr Cys Ala Gly Cys Thr Gly Ala Thr Ala Cys Thr Cys
        210                 215                 220

Gly Ala Ala Gly Ala Ala Cys Ala Cys Cys Gly Cys Cys Thr Ala Thr
```

-continued

```
225                 230                 235                 240

Cys Thr Gly Cys Ala Ala Ala Thr Gly Ala Ala Cys Ala Gly Cys Cys
                245                 250                 255

Thr Gly Cys Gly Thr Gly Cys Gly Gly Ala Ala Gly Ala Thr Ala Cys
            260                 265                 270

Gly Gly Cys Cys Gly Thr Gly Thr Ala Thr Thr Ala Thr Thr Gly Cys
        275                 280                 285

Thr Cys Gly Cys Gly Thr Thr Gly Gly Gly Gly Ala Gly Gly Ala Gly
    290                 295                 300

Ala Cys Gly Gly Gly Thr Thr Cys Thr Ala Thr Gly Cys Thr Ala Thr
305                 310                 315                 320

Gly Gly Ala Thr Thr Ala Cys Thr Gly Gly Gly Gly Cys Cys Ala Ala
                325                 330                 335

Gly Gly Cys Ala Cys Cys Cys Thr Gly Gly Thr Gly Ala Cys Gly Gly
            340                 345                 350

Thr Thr Ala Gly Cys Thr Cys Ala Gly Cys Thr Ala Gly Cys Ala Cys
        355                 360                 365

Cys Ala Ala Gly Gly Gly Cys Cys Cys Ala Thr Cys Gly Gly Thr Cys
    370                 375                 380

Thr Thr Cys Cys Cys Cys Cys Thr Gly Gly Cys Ala Cys Cys Cys Thr
385                 390                 395                 400

Cys Cys Thr Cys Cys Ala Ala Gly Ala Gly Cys Ala Cys Cys Thr Cys
                405                 410                 415

Thr Gly Gly Gly Gly Gly Cys Ala Cys Ala Gly Cys Gly Gly Cys Cys
            420                 425                 430

Cys Thr Gly Gly Gly Cys Thr Gly Cys Cys Thr Gly Gly Thr Cys Ala
        435                 440                 445

Ala Gly Gly Ala Cys Thr Ala Cys Thr Thr Cys Cys Cys Cys Gly Ala
    450                 455                 460

Ala Cys Cys Gly Gly Thr Gly Ala Cys Gly Gly Thr Gly Thr Cys Gly
465                 470                 475                 480

Thr Gly Gly Ala Ala Cys Thr Cys Ala Gly Gly Cys Gly Cys Cys Cys
                485                 490                 495

Thr Gly Ala Cys Cys Ala Gly Cys Gly Gly Cys Gly Thr Gly Cys Ala
            500                 505                 510

Cys Ala Cys Cys Thr Thr Cys Cys Cys Gly Gly Cys Thr Gly Thr Cys
        515                 520                 525

Cys Thr Ala Cys Ala Gly Thr Cys Cys Thr Cys Ala Gly Gly Ala Cys
    530                 535                 540

Thr Cys Thr Ala Cys Thr Cys Cys Cys Thr Cys Ala Gly Cys Ala Gly
545                 550                 555                 560

Cys Gly Thr Gly Gly Thr Gly Ala Cys Cys Gly Thr Gly Cys Cys Cys
                565                 570                 575

Thr Cys Cys Ala Gly Cys Ala Gly Cys Thr Thr Gly Gly Gly Cys Ala
            580                 585                 590

Cys Cys Cys Ala Gly Ala Cys Cys Thr Ala Cys Ala Thr Cys Thr Gly
        595                 600                 605

Cys Ala Ala Cys Gly Thr Gly Ala Ala Thr Cys Ala Cys Ala Ala Gly
    610                 615                 620

Cys Cys Cys Ala Gly Cys Ala Ala Cys Ala Cys Cys Ala Ala Gly Gly
625                 630                 635                 640

Thr Gly Gly Ala Cys Ala Ala Gly Ala Ala Ala Gly Thr Thr Gly Ala
                645                 650                 655
```

-continued

Gly Cys Cys Cys Ala Ala Ala Thr Cys Thr Thr Gly Thr Gly Ala Cys
                660              665            670

Ala Ala Ala Ala Cys Thr Cys Ala Cys Ala Cys Ala Thr Gly Cys Cys
            675            680              685

Cys Ala Cys Cys Gly Thr Gly Cys Cys Ala Gly Cys Ala Cys Cys
        690              695            700

Thr Gly Ala Ala Cys Thr Cys Cys Thr Gly Gly Gly Gly Ala
705              710              715              720

Cys Cys Gly Thr Cys Ala Gly Thr Cys Thr Thr Cys Cys Cys Thr
                725            730              735

Thr Cys Cys Cys Cys Cys Cys Ala Ala Ala Cys Cys Ala Ala
            740              745            750

Gly Gly Ala Cys Ala Cys Cys Thr Cys Ala Thr Gly Ala Thr Cys
            755              760              765

Thr Cys Cys Cys Gly Gly Ala Cys Cys Cys Thr Gly Ala Gly Gly
            770              775            780

Thr Cys Ala Cys Ala Thr Gly Cys Gly Thr Gly Gly Thr Gly Gly Thr
785              790              795              800

Gly Gly Ala Cys Gly Thr Gly Ala Gly Cys Cys Ala Cys Gly Ala Ala
                805              810              815

Gly Ala Cys Cys Cys Thr Gly Ala Gly Gly Thr Cys Ala Ala Gly Thr
                820              825              830

Thr Cys Ala Ala Cys Thr Gly Gly Thr Ala Cys Gly Thr Gly Gly Ala
                835              840              845

Cys Gly Gly Cys Gly Thr Gly Gly Ala Gly Gly Thr Gly Cys Ala Thr
                850              855              860

Ala Ala Thr Gly Cys Cys Ala Ala Gly Ala Cys Ala Ala Ala Gly Cys
865              870              875              880

Cys Gly Cys Gly Gly Gly Ala Gly Gly Ala Gly Cys Ala Gly Thr Ala
                885              890              895

Cys Ala Ala Cys Ala Gly Cys Ala Cys Gly Thr Ala Cys Cys Gly Thr
                900              905              910

Gly Thr Gly Gly Thr Cys Ala Gly Cys Gly Thr Cys Cys Thr Cys Ala
                915              920              925

Cys Cys Gly Thr Cys Cys Thr Gly Cys Ala Cys Cys Ala Gly Gly Ala
                930              935              940

Cys Thr Gly Gly Cys Thr Gly Ala Ala Thr Gly Gly Cys Ala Ala Gly
945              950              955              960

Gly Ala Gly Thr Ala Cys Ala Ala Gly Thr Gly Cys Ala Ala Gly Gly
                965              970              975

Thr Cys Thr Cys Cys Ala Ala Cys Ala Ala Ala Gly Cys Cys Cys Thr
                980              985              990

Cys Cys Cys Ala Gly Cys Cys Cys Cys Ala Thr Cys Gly Ala Gly
            995              1000            1005

Ala Ala Ala Ala Cys Cys Ala Thr Cys Thr Cys Cys Ala Ala Ala
    1010            1015              1020

Gly Cys Cys Ala Ala Ala Gly Gly Gly Cys Ala Gly Cys Cys Cys
    1025            1030              1035

Cys Gly Ala Gly Ala Ala Cys Cys Ala Cys Ala Gly Gly Thr Gly
    1040            1045              1050

Thr Ala Cys Ala Cys Cys Cys Thr Gly Cys Cys Cys Cys Cys Ala
    1055            1060              1065

Thr Gly Cys Cys Gly Gly Ala Thr Gly Ala Gly Cys Thr Gly
1070                1075                1080

Ala Cys Cys Ala Ala Gly Ala Ala Cys Cys Ala Gly Gly Thr Cys
    1085                1090                1095

Ala Gly Cys Cys Thr Gly Thr Gly Gly Thr Gly Cys Cys Thr Gly
1100                1105                1110

Gly Thr Cys Ala Ala Ala Gly Gly Cys Thr Thr Cys Thr Ala Thr
    1115                1120                1125

Cys Cys Cys Ala Gly Cys Gly Ala Cys Ala Thr Cys Gly Cys Cys
1130                1135                1140

Gly Thr Gly Gly Ala Gly Thr Gly Gly Gly Ala Gly Ala Gly Cys
    1145                1150                1155

Ala Ala Thr Gly Gly Cys Ala Gly Cys Cys Gly Gly Ala Gly
1160                1165                1170

Ala Ala Cys Ala Ala Cys Thr Ala Cys Ala Ala Gly Ala Cys Cys
    1175                1180                1185

Ala Cys Gly Cys Cys Thr Cys Cys Cys Gly Thr Gly Cys Thr Gly
1190                1195                1200

Gly Ala Cys Thr Cys Cys Gly Ala Cys Gly Gly Cys Thr Cys Cys
    1205                1210                1215

Thr Thr Cys Thr Thr Cys Cys Thr Cys Thr Ala Cys Ala Gly Cys
1220                1225                1230

Ala Ala Gly Cys Thr Cys Ala Cys Cys Gly Thr Gly Gly Ala Cys
    1235                1240                1245

Ala Ala Gly Ala Gly Cys Ala Gly Gly Thr Gly Gly Cys Ala Gly
1250                1255                1260

Cys Ala Gly Gly Gly Ala Ala Cys Gly Thr Cys Thr Thr Cys
    1265                1270                1275

Thr Cys Ala Thr Gly Cys Thr Cys Cys Gly Thr Gly Ala Thr Gly
1280                1285                1290

Cys Ala Thr Gly Ala Gly Gly Cys Thr Cys Thr Gly Cys Ala Cys
    1295                1300                1305

Ala Ala Cys Cys Ala Cys Thr Ala Cys Ala Cys Gly Cys Ala Gly
1310                1315                1320

Ala Ala Gly Ala Gly Cys Cys Thr Cys Thr Cys Cys Cys Thr Gly
    1325                1330                1335

Thr Cys Thr Cys Cys Gly Gly Gly Thr Ala Ala Ala
1340                1345                1350

<210> SEQ ID NO 161
<211> LENGTH: 214
<212> TYPE: PRT
<213> ORGANISM: Artificial sequence
<220> FEATURE:
<223> OTHER INFORMATION: Common light chain VLCL

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 162
<211> LENGTH: 642
<212> TYPE: PRT
<213> ORGANISM: Artificial sequence
<220> FEATURE:
<223> OTHER INFORMATION: Common light chain VLCL - DNA

<400> SEQUENCE: 162

Gly Ala Cys Ala Thr Cys Cys Ala Gly Ala Thr Gly Ala Cys Cys Cys
1               5                   10                  15

Ala Gly Ala Gly Cys Cys Cys Ala Gly Cys Ala Gly Cys Cys Thr
            20                  25                  30

Gly Thr Cys Thr Gly Cys Cys Ala Gly Cys Gly Thr Gly Gly Gly Cys
        35                  40                  45

Gly Ala Cys Ala Gly Ala Gly Thr Gly Ala Cys Cys Ala Thr Cys Ala
    50                  55                  60

Cys Ala Thr Gly Cys Ala Ala Gly Gly Cys Ala Gly Cys Cys Ala
65                  70                  75                  80

Gly Gly Ala Cys Gly Thr Gly Thr Cys Cys Ala Cys Ala Gly Cys Cys
                85                  90                  95

Gly Thr Gly Gly Cys Cys Thr Gly Gly Thr Ala Thr Cys Ala Gly Cys
            100                 105                 110

Ala Gly Ala Ala Gly Cys Cys Thr Gly Gly Cys Ala Ala Gly Gly Cys
        115                 120                 125

Cys Cys Cys Cys Ala Ala Gly Cys Thr Gly Cys Thr Gly Ala Thr Cys
    130                 135                 140

Thr Ala Cys Ala Gly Cys Gly Cys Cys Ala Gly Cys Thr Thr Cys Cys
145                 150                 155                 160

Gly Gly Thr Ala Cys Ala Cys Cys Gly Gly Cys Gly Thr Gly Cys Cys
                165                 170                 175

Cys Ala Gly Cys Ala Gly Ala Thr Thr Cys Ala Gly Cys Gly Gly Cys
            180                 185                 190

Ala Gly Cys Ala Gly Ala Thr Cys Cys Gly Gly Cys Ala Cys Cys Gly
        195                 200                 205

-continued

Ala Cys Thr Thr Cys Ala Cys Cys Cys Thr Gly Ala Cys Cys Ala Thr
    210                 215                 220

Cys Ala Gly Cys Thr Cys Cys Cys Thr Gly Cys Ala Gly Cys Cys Cys
225                 230                 235                 240

Gly Ala Gly Gly Ala Cys Thr Thr Cys Gly Cys Cys Ala Cys Cys Thr
                245                 250                 255

Ala Cys Thr Ala Cys Thr Gly Cys Cys Ala Gly Cys Ala Gly Cys Ala
            260                 265                 270

Cys Thr Ala Cys Ala Cys Cys Ala Cys Cys Cys Cys Cys Cys Cys Cys
        275                 280                 285

Ala Cys Ala Thr Thr Thr Gly Gly Cys Cys Ala Gly Gly Gly Cys Ala
    290                 295                 300

Cys Cys Ala Ala Gly Gly Thr Gly Gly Ala Ala Ala Thr Cys Ala Ala
305                 310                 315                 320

Gly Cys Gly Thr Ala Cys Gly Gly Thr Gly Gly Cys Thr Gly Cys Ala
                325                 330                 335

Cys Cys Ala Thr Cys Thr Gly Thr Cys Thr Thr Cys Ala Thr Cys Thr
            340                 345                 350

Thr Cys Cys Cys Gly Cys Cys Ala Thr Cys Thr Gly Ala Thr Gly Ala
        355                 360                 365

Gly Cys Ala Gly Thr Thr Gly Ala Ala Ala Thr Cys Thr Gly Gly Ala
    370                 375                 380

Ala Cys Thr Gly Cys Cys Thr Cys Thr Gly Thr Thr Gly Thr Gly Thr
385                 390                 395                 400

Gly Cys Cys Thr Gly Cys Thr Gly Ala Ala Thr Ala Ala Cys Thr Thr
                405                 410                 415

Cys Thr Ala Thr Cys Cys Cys Ala Gly Ala Gly Ala Gly Gly Cys Cys
            420                 425                 430

Ala Ala Ala Gly Thr Ala Cys Ala Gly Thr Gly Gly Ala Ala Gly Gly
        435                 440                 445

Thr Gly Gly Ala Thr Ala Ala Cys Gly Cys Cys Cys Thr Cys Cys Ala
    450                 455                 460

Ala Thr Cys Gly Gly Gly Thr Ala Ala Cys Thr Cys Cys Cys Ala Gly
465                 470                 475                 480

Gly Ala Gly Ala Gly Thr Gly Thr Cys Ala Cys Ala Gly Ala Gly Cys
                485                 490                 495

Ala Gly Gly Ala Cys Ala Gly Cys Ala Ala Gly Gly Ala Cys Ala Gly
            500                 505                 510

Cys Ala Cys Cys Thr Ala Cys Ala Gly Cys Cys Thr Cys Ala Gly Cys
        515                 520                 525

Ala Gly Cys Ala Cys Cys Cys Thr Gly Ala Cys Gly Cys Thr Gly Ala
    530                 535                 540

Gly Cys Ala Ala Ala Gly Cys Ala Gly Ala Cys Thr Ala Cys Gly Ala
545                 550                 555                 560

Gly Ala Ala Ala Cys Ala Cys Ala Ala Ala Gly Thr Cys Thr Ala Cys
                565                 570                 575

Gly Cys Cys Thr Gly Cys Gly Ala Ala Gly Thr Cys Ala Cys Cys Cys
            580                 585                 590

Ala Thr Cys Ala Gly Gly Gly Cys Cys Thr Gly Ala Gly Cys Thr Cys
        595                 600                 605

Gly Cys Cys Cys Gly Thr Cys Ala Cys Ala Ala Ala Gly Ala Gly Cys
    610                 615                 620

Thr Thr Cys Ala Ala Cys Ala Gly Gly Gly Gly Ala Gly Ala Gly Thr

Gly Thr

<210> SEQ ID NO 163
<211> LENGTH: 449
<212> TYPE: PRT
<213> ORGANISM: Artificial sequence
<220> FEATURE:
<223> OTHER INFORMATION: Pertuzumab VHCH1 Fc hole

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

```
Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 164
<211> LENGTH: 1347
<212> TYPE: DNA
<213> ORGANISM: Artificial sequence
<220> FEATURE:
<223> OTHER INFORMATION: Pertuzumab VHCH1 Fc hole DNA

<400> SEQUENCE: 164

```
gaagttcagc tggttgaaag cggtggtggt ctggttcagc ctggtggtag cctgcgtctg     60
agctgtgcag caagcggttt tacctttaac gattatacca tggattgggt tcgtcaggca    120
ccgggtaaag gtctggaatg ggttgcagat gttaatccga atagcggtgg tagcattgtt    180
aaccgtcgtt ttaaaggtcg ttttaccctg agcgttgatc gtagcaaaaa taccctgtat    240
ctgcaaatga atagtctgcg tgcagaggat accgcagtgt attattgtgc acgtaacctg    300
ggtccgttct tctactttga ttattggggt cagggcaccc tggttaccgt tagcagcgct    360
agcaccaagg gcccaagcgt gttccctctg gcccccagca gcaagagcac aagcggcgga    420
acagccgccc tgggctgcct ggtcaaggac tacttccccg agcccgtgac agtgtcctgg    480
aacagcggag ccctgaccag cggcgtgcac acctttccag ccgtgctgca gagcagcggc    540
ctgtacagcc tgagcagcgt ggtcacagtg cctagcagca gcctgggcac ccagacctac    600
atctgcaacg tgaaccacaa gcccagcaac accaaggtgg acaagaaggt ggagcccaag    660
agctgcgaca agacccacac ctgtccccct tgtcctgccc ctgagctgct gggcggaccc    720
agcgtgttcc tgttcccccc aaagcccaag gacaccctga tgatcagccg gacccccgaa    780
gtgacctgcg tggtggtgga cgtgtcccac gaggaccctg aagtgaagtt caattggtac    840
gtggacggcg tggaggtgca caatgccaag accaagcccc gggaggaaca gtacaacagc    900
acctaccggg tggtgtccgt gctgaccgtg ctgcaccagg actggctgaa cggcaaagag    960
tacaagtgca aggtctccaa caaggccctg cctgccccca tcgagaaaac catcagcaag   1020
gccaagggcc agcccagaga accccaggtg tgcaccctgc cccccagcag agatgagctg   1080
accaagaacc aggtgtccct gagctgtgcc gtcaagggct tctaccccag cgatatcgcc   1140
gtggagtggg agagcaacgg ccagcctgag aacaactaca agaccacccc ccctgtgctg   1200
gacagcgacg gcagcttctt cctggtgtcc aaactgaccg tggacaagag ccggtggcag   1260
cagggcaacg tgttcagctg cagcgtgatg cacgaggccc tgcacaacca ctacacccag   1320
aagtccctga gcctgagccc cggcaag                                       1347
```

<210> SEQ ID NO 165

<211> LENGTH: 934
<212> TYPE: PRT
<213> ORGANISM: Artificial sequence
<220> FEATURE:
<223> OTHER INFORMATION: Her-knob-scFab(8D3) Heavy chain (21832)

<400> SEQUENCE: 165

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380
```

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Gly Gly Ser Gly Gly Gly Ser Gly Gly Gly Ser Gly Gly
    450                 455                 460

Gly Gly Ser Asp Ile Gln Met Thr Gln Ser Pro Ala Ser Leu Ser Ala
465                 470                 475                 480

Ser Leu Glu Glu Ile Val Thr Ile Thr Cys Gln Ala Ser Gln Asp Ile
            485                 490                 495

Gly Asn Trp Leu Ala Trp Tyr Gln Gln Lys Pro Gly Lys Ser Pro Gln
            500                 505                 510

Leu Leu Ile Tyr Gly Ala Thr Ser Leu Ala Asp Gly Val Pro Ser Arg
        515                 520                 525

Phe Ser Gly Ser Arg Ser Gly Thr Gln Phe Ser Leu Lys Ile Ser Arg
        530                 535                 540

Val Gln Val Glu Asp Ile Gly Ile Tyr Tyr Cys Leu Gln Ala Tyr Asn
545                 550                 555                 560

Thr Pro Trp Thr Phe Gly Gly Gly Thr Lys Val Glu Ile Lys Arg Thr
            565                 570                 575

Val Ala Ala Pro Ser Val Phe Ile Phe Pro Pro Ser Asp Glu Gln Leu
        580                 585                 590

Lys Ser Gly Thr Ala Ser Val Val Cys Leu Leu Asn Asn Phe Tyr Pro
        595                 600                 605

Arg Glu Ala Lys Val Gln Trp Lys Val Asp Asn Ala Leu Gln Ser Gly
        610                 615                 620

Asn Ser Gln Glu Ser Val Thr Glu Gln Asp Ser Lys Asp Ser Thr Tyr
625                 630                 635                 640

Ser Leu Ser Ser Thr Leu Thr Leu Ser Lys Ala Asp Tyr Glu Lys His
            645                 650                 655

Lys Val Tyr Ala Cys Glu Val Thr His Gln Gly Leu Ser Ser Pro Val
            660                 665                 670

Thr Lys Ser Phe Asn Arg Gly Glu Cys Gly Gly Gly Ser Gly Gly
        675                 680                 685

Gly Gly Ser Gly Gly Gly Ser Gly Gly Gly Ser Gly Gly
    690                 695                 700

Gly Ser Gly Gly Gly Ser Gly Gly Glu Val Gln Leu Val Glu Ser
705                 710                 715                 720

Gly Gly Gly Leu Val Gln Pro Gly Asn Ser Leu Thr Leu Ser Cys Val
        725                 730                 735

Ala Ser Gly Phe Thr Phe Ser Asn Tyr Gly Met His Trp Ile Arg Gln
            740                 745                 750

Ala Pro Lys Lys Gly Leu Glu Trp Ile Ala Met Ile Tyr Tyr Asp Ser
        755                 760                 765

Ser Lys Met Asn Tyr Ala Asp Thr Val Lys Gly Arg Phe Thr Ile Ser
        770                 775                 780

Arg Asp Asn Ser Lys Asn Thr Leu Tyr Leu Glu Met Asn Ser Leu Arg
785                 790                 795                 800
```

```
Ser Glu Asp Thr Ala Met Tyr Tyr Cys Ala Val Pro Thr Ser His Tyr
            805                 810                 815

Val Val Asp Val Trp Gly Gln Gly Val Ser Val Thr Val Ser Ser Ala
            820                 825                 830

Ser Thr Lys Gly Pro Ser Val Phe Pro Leu Ala Pro Ser Ser Lys Ser
            835                 840                 845

Thr Ser Gly Gly Thr Ala Ala Leu Gly Cys Leu Val Lys Asp Tyr Phe
            850                 855                 860

Pro Glu Pro Val Thr Val Ser Trp Asn Ser Gly Ala Leu Thr Ser Gly
865                 870                 875                 880

Val His Thr Phe Pro Ala Val Leu Gln Ser Ser Gly Leu Tyr Ser Leu
            885                 890                 895

Ser Ser Val Val Thr Val Pro Ser Ser Ser Leu Gly Thr Gln Thr Tyr
            900                 905                 910

Ile Cys Asn Val Asn His Lys Pro Ser Asn Thr Lys Val Asp Lys Lys
            915                 920                 925

Val Glu Pro Lys Ser Cys
    930

<210> SEQ ID NO 166
<211> LENGTH: 119
<212> TYPE: PRT
<213> ORGANISM: Artificial sequence
<220> FEATURE:
<223> OTHER INFORMATION: 4/94  VH

<400> SEQUENCE: 166

Glu Val Gln Leu Gln Gln Ser Gly Ala Val Leu Val Lys Pro Gly Ala
1               5                   10                  15

Ser Val Lys Leu Ser Cys Pro Ala Ser Gly Phe Asn Ile Lys Asp Thr
            20                  25                  30

Tyr Ile His Trp Val Ile Gln Arg Pro Glu Gln Gly Leu Glu Trp Ile
        35                  40                  45

Gly Arg Ile Asp Pro Ala Asn Gly Asp Thr Lys Cys Asp Pro Lys Phe
    50                  55                  60

Gln Val Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Val Arg Asp Tyr Leu Tyr Pro Tyr Tyr Phe Asp Phe Trp Gly Gln Gly
            100                 105                 110

Thr Thr Leu Thr Val Ser Ser
        115

<210> SEQ ID NO 167
<211> LENGTH: 108
<212> TYPE: PRT
<213> ORGANISM: Artificial sequence
<220> FEATURE:
<223> OTHER INFORMATION: 4/94  VL

<400> SEQUENCE: 167

Lys Ile Val Met Thr Gln Ser Pro Lys Ser Met Ser Met Ser Val Gly
1               5                   10                  15

Glu Arg Val Thr Leu Asn Cys Arg Ala Ser Glu Ser Val Asp Thr Tyr
            20                  25                  30

Val Ser Trp Tyr Gln Gln Lys Pro Glu Gln Ser Pro Glu Leu Leu Ile
        35                  40                  45
```

```
Tyr Gly Ala Ser Asn Arg Tyr Thr Gly Val Pro Asp Arg Phe Thr Gly
            50                  55                  60

Ser Gly Ser Ala Thr Asp Phe Thr Leu Thr Ile Ser Ser Val Gln Ala
 65                  70                  75                  80

Glu Asp Leu Ala Asp Tyr Tyr Cys Gly Gln Thr Tyr Asn Tyr Pro Leu
                 85                  90                  95

Thr Phe Gly Ala Gly Thr Lys Leu Glu Leu Lys Arg
                100                 105

<210> SEQ ID NO 168
<211> LENGTH: 934
<212> TYPE: PRT
<213> ORGANISM: Artificial sequence
<220> FEATURE:
<223> OTHER INFORMATION: Her-knob-LALA-PG-scFab(8D3) Heavy chain (21834)

<400> SEQUENCE: 168

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Cys Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Gly Gly Ser Gly Gly Gly Ser Gly Gly Gly Ser Gly Gly
450                 455                 460

Gly Gly Ser Asp Ile Gln Met Thr Gln Ser Pro Ala Ser Leu Ser Ala
465                 470                 475                 480

Ser Leu Glu Glu Ile Val Thr Ile Thr Cys Gln Ala Ser Gln Asp Ile
                485                 490                 495

Gly Asn Trp Leu Ala Trp Tyr Gln Gln Lys Pro Gly Lys Ser Pro Gln
                500                 505                 510

Leu Leu Ile Tyr Gly Ala Thr Ser Leu Ala Asp Gly Val Pro Ser Arg
            515                 520                 525

Phe Ser Gly Ser Arg Ser Gly Thr Gln Phe Ser Leu Lys Ile Ser Arg
            530                 535                 540

Val Gln Val Glu Asp Ile Gly Ile Tyr Tyr Cys Leu Gln Ala Tyr Asn
545                 550                 555                 560

Thr Pro Trp Thr Phe Gly Gly Gly Thr Lys Val Glu Ile Lys Arg Thr
                565                 570                 575

Val Ala Ala Pro Ser Val Phe Ile Phe Pro Pro Ser Asp Glu Gln Leu
            580                 585                 590

Lys Ser Gly Thr Ala Ser Val Val Cys Leu Leu Asn Asn Phe Tyr Pro
            595                 600                 605

Arg Glu Ala Lys Val Gln Trp Lys Val Asp Asn Ala Leu Gln Ser Gly
    610                 615                 620

Asn Ser Gln Glu Ser Val Thr Glu Gln Asp Ser Lys Asp Ser Thr Tyr
625                 630                 635                 640

Ser Leu Ser Ser Thr Leu Thr Leu Ser Lys Ala Asp Tyr Glu Lys His
                645                 650                 655

Lys Val Tyr Ala Cys Glu Val Thr His Gln Gly Leu Ser Ser Pro Val
                660                 665                 670

Thr Lys Ser Phe Asn Arg Gly Glu Cys Gly Gly Gly Ser Gly Gly
            675                 680                 685

Gly Gly Ser Gly Gly Gly Ser Gly Gly Gly Ser Gly Gly
            690                 695                 700

Gly Ser Gly Gly Gly Gly Ser Gly Gly Glu Val Gln Leu Val Glu Ser
705                 710                 715                 720
```

Gly Gly Gly Leu Val Gln Pro Gly Asn Ser Leu Thr Leu Ser Cys Val
            725                 730                 735

Ala Ser Gly Phe Thr Phe Ser Asn Tyr Gly Met His Trp Ile Arg Gln
        740                 745                 750

Ala Pro Lys Lys Gly Leu Glu Trp Ile Ala Met Ile Tyr Tyr Asp Ser
        755                 760                 765

Ser Lys Met Asn Tyr Ala Asp Thr Val Lys Gly Arg Phe Thr Ile Ser
        770                 775                 780

Arg Asp Asn Ser Lys Asn Thr Leu Tyr Leu Glu Met Asn Ser Leu Arg
785                 790                 795                 800

Ser Glu Asp Thr Ala Met Tyr Tyr Cys Ala Val Pro Thr Ser His Tyr
                805                 810                 815

Val Val Asp Val Trp Gly Gln Gly Val Ser Val Thr Val Ser Ser Ala
                820                 825                 830

Ser Thr Lys Gly Pro Ser Val Phe Pro Leu Ala Pro Ser Ser Lys Ser
                835                 840                 845

Thr Ser Gly Gly Thr Ala Ala Leu Gly Cys Leu Val Lys Asp Tyr Phe
        850                 855                 860

Pro Glu Pro Val Thr Val Ser Trp Asn Ser Gly Ala Leu Thr Ser Gly
865                 870                 875                 880

Val His Thr Phe Pro Ala Val Leu Gln Ser Ser Gly Leu Tyr Ser Leu
                885                 890                 895

Ser Ser Val Val Thr Val Pro Ser Ser Leu Gly Thr Gln Thr Tyr
                900                 905                 910

Ile Cys Asn Val Asn His Lys Pro Ser Asn Thr Lys Val Asp Lys Lys
        915                 920                 925

Val Glu Pro Lys Ser Cys
    930

<210> SEQ ID NO 169
<211> LENGTH: 449
<212> TYPE: PRT
<213> ORGANISM: Artificial sequence
<220> FEATURE:
<223> OTHER INFORMATION: Per-hole LALA-PG Heavy chain (21836)

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
            325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
            435                 440                 445

Lys

<210> SEQ ID NO 170
<211> LENGTH: 450
<212> TYPE: PRT
<213> ORGANISM: Artificial sequence
<220> FEATURE:
<223> OTHER INFORMATION: Her-knob-LALA-PG Heavy Chain (21835)

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Glu Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Asp Glu Leu Thr Lys Asn Gln Val Ser Leu
                355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 171

<211> LENGTH: 450
<212> TYPE: PRT
<213> ORGANISM: Artificial sequence
<220> FEATURE:
<223> OTHER INFORMATION: pETR13573Her-knob heavy chain

<400> SEQUENCE: 171

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Asn | Ile | Lys | Asp | Thr |
| | | | 20 | | | | | 25 | | | | | 30 | | |
| Tyr | Ile | His | Trp | Val | Arg | Gln | Ala | Pro | Gly | Lys | Gly | Leu | Glu | Trp | Val |
| | | 35 | | | | | 40 | | | | | 45 | | | |
| Ala | Arg | Ile | Tyr | Pro | Thr | Asn | Gly | Tyr | Thr | Arg | Tyr | Ala | Asp | Ser | Val |
| | 50 | | | | | 55 | | | | | 60 | | | | |
| Lys | Gly | Arg | Phe | Thr | Ile | Ser | Ala | Asp | Thr | Ser | Lys | Asn | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ser | Arg | Trp | Gly | Gly | Glu | Gly | Phe | Tyr | Ala | Met | Asp | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Cys | Arg | Asp | Glu | Leu | Thr | Lys | Asn | Gln | Val | Ser | Leu |
| | | 355 | | | | | 360 | | | | | 365 | | | |
| Trp | Cys | Leu | Val | Lys | Gly | Phe | Tyr | Pro | Ser | Asp | Ile | Ala | Val | Glu | Trp |
| | 370 | | | | | 375 | | | | | 380 | | | | |

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 172
<211> LENGTH: 6
<212> TYPE: PRT
<213> ORGANISM: Artificial sequence
<220> FEATURE:
<223> OTHER INFORMATION: 2/99 CDR-H1

<400> SEQUENCE: 172

Phe Ser Leu Ser Ser Tyr
1               5

<210> SEQ ID NO 173
<211> LENGTH: 14
<212> TYPE: PRT
<213> ORGANISM: Artificial sequence
<220> FEATURE:
<223> OTHER INFORMATION: 2/99  CDR-H2

<400> SEQUENCE: 173

Tyr Ile Trp Ser Gly Gly Ser Thr Asp Tyr Ala Ser Trp Ala
1               5                   10

<210> SEQ ID NO 174
<211> LENGTH: 17
<212> TYPE: PRT
<213> ORGANISM: Artificial sequence
<220> FEATURE:
<223> OTHER INFORMATION: 2/99  CDR-H3

<400> SEQUENCE: 174

Arg Tyr Gly Thr Ser Tyr Pro Asp Tyr Gly Asp Ala Asn Gly Phe Asp
1               5                   10                  15

Pro

<210> SEQ ID NO 175
<211> LENGTH: 11
<212> TYPE: PRT
<213> ORGANISM: Artificial sequence
<220> FEATURE:
<223> OTHER INFORMATION: 2/99  CDR-L1

<400> SEQUENCE: 175

Gln Ala Ser Gln Ser Ile Ser Ser Tyr Leu Ser
1               5                   10

<210> SEQ ID NO 176
<211> LENGTH: 3
<212> TYPE: PRT
<213> ORGANISM: Artificial sequence
<220> FEATURE:
<223> OTHER INFORMATION: 2/99  CDR-L2

<400> SEQUENCE: 176
```

Arg Ala Ser
1

<210> SEQ ID NO 177
<211> LENGTH: 9
<212> TYPE: PRT
<213> ORGANISM: Artificial sequence
<220> FEATURE:
<223> OTHER INFORMATION: 2/99 CDR-L3

<400> SEQUENCE: 177

Cys Tyr Ser Ser Ser Asn Val Asp Asn
1               5

<210> SEQ ID NO 178
<211> LENGTH: 122
<212> TYPE: PRT
<213> ORGANISM: Artificial sequence
<220> FEATURE:
<223> OTHER INFORMATION: 2/99 VH

<400> SEQUENCE: 178

Gln Ser Met Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Tyr Ile Trp Ser Gly Gly Ser Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Arg Tyr
                85                  90                  95

Gly Thr Ser Tyr Pro Asp Tyr Gly Asp Ala Asn Gly Phe Asp Pro Trp
            100                 105                 110

Gly Pro Gly Thr Leu Val Thr Val Ser Ser
        115                 120

<210> SEQ ID NO 179
<211> LENGTH: 111
<212> TYPE: PRT
<213> ORGANISM: Artificial sequence
<220> FEATURE:
<223> OTHER INFORMATION: 2/99 VL

<400> SEQUENCE: 179

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Cys Tyr Ser Ser Ser Asn
                85                  90                  95

Val Asp Asn Thr Phe Gly Gly Gly Thr Glu Val Val Lys Arg
            100                 105                 110

<210> SEQ ID NO 180
<211> LENGTH: 7
<212> TYPE: PRT
<213> ORGANISM: Artificial sequence
<220> FEATURE:
<223> OTHER INFORMATION: 4/94 CDR-H1

<400> SEQUENCE: 180

Gly Phe Asn Ile Lys Asp Thr
1               5

<210> SEQ ID NO 181
<211> LENGTH: 16
<212> TYPE: PRT
<213> ORGANISM: Artificial sequence
<220> FEATURE:
<223> OTHER INFORMATION: 4/94 CDR-H2

<400> SEQUENCE: 181

Arg Ile Asp Pro Ala Asn Gly Asp Thr Lys Cys Asp Pro Lys Phe Gln
1               5                   10                  15

<210> SEQ ID NO 182
<211> LENGTH: 8
<212> TYPE: PRT
<213> ORGANISM: Artificial sequence
<220> FEATURE:
<223> OTHER INFORMATION: 4/94 CDR-H3

<400> SEQUENCE: 182

Tyr Leu Tyr Pro Tyr Tyr Phe Asp
1               5

<210> SEQ ID NO 183
<211> LENGTH: 7
<212> TYPE: PRT
<213> ORGANISM: Artificial sequence
<220> FEATURE:
<223> OTHER INFORMATION: 4/94 CDR-L1

<400> SEQUENCE: 183

Ser Glu Ser Val Asp Thr Tyr
1               5

<210> SEQ ID NO 184
<211> LENGTH: 3
<212> TYPE: PRT
<213> ORGANISM: Artificial sequence
<220> FEATURE:
<223> OTHER INFORMATION: 4/94 CDR-L2

<400> SEQUENCE: 184

Gly Ala Ser
1

<210> SEQ ID NO 185
<211> LENGTH: 6
<212> TYPE: PRT
<213> ORGANISM: Artificial sequence
<220> FEATURE:
<223> OTHER INFORMATION: 4/94 CDR-L3

<400> SEQUENCE: 185

Thr Tyr Asn Tyr Pro Leu

<210> SEQ ID NO 186
<211> LENGTH: 5
<212> TYPE: PRT
<213> ORGANISM: Artificial sequence
<220> FEATURE:
<223> OTHER INFORMATION: Humanized 2/99 CDR-H1

<400> SEQUENCE: 186

Ser Tyr Ala Met Ser
1               5

<210> SEQ ID NO 187
<211> LENGTH: 16
<212> TYPE: PRT
<213> ORGANISM: Artificial sequence
<220> FEATURE:
<223> OTHER INFORMATION: Humanized 2/99 CDR-H2

<400> SEQUENCE: 187

Tyr Ile Trp Ser Gly Gly Ser Thr Asp Tyr Ala Ser Trp Ala Lys Ser
1               5                   10                  15

<210> SEQ ID NO 188
<211> LENGTH: 17
<212> TYPE: PRT
<213> ORGANISM: Artificial sequence
<220> FEATURE:
<223> OTHER INFORMATION: Humanized 2/99 CDR-H3

<400> SEQUENCE: 188

Arg Tyr Gly Thr Ser Tyr Pro Asp Tyr Gly Asp Ala Ser Gly Phe Asp
1               5                   10                  15

Pro

<210> SEQ ID NO 189
<211> LENGTH: 11
<212> TYPE: PRT
<213> ORGANISM: Artificial sequence
<220> FEATURE:
<223> OTHER INFORMATION: Humanized 2/99 CDR-L1

<400> SEQUENCE: 189

Arg Ala Ser Gln Ser Ile Ser Ser Tyr Leu Ala
1               5                   10

<210> SEQ ID NO 190
<211> LENGTH: 7
<212> TYPE: PRT
<213> ORGANISM: Artificial sequence
<220> FEATURE:
<223> OTHER INFORMATION: Humanized 2/99 CDR-L2

<400> SEQUENCE: 190

Arg Ala Ser Thr Leu Ala Ser
1               5

<210> SEQ ID NO 191
<211> LENGTH: 12
<212> TYPE: PRT
<213> ORGANISM: Artificial sequence
<220> FEATURE:
<223> OTHER INFORMATION: Humanized 2/99 CDR-L3

<400> SEQUENCE: 191

```
Gln Gln Asn Tyr Ala Ser Ser Asn Val Asp Asn Thr
1               5                   10
```

<210> SEQ ID NO 192
<211> LENGTH: 122
<212> TYPE: PRT
<213> ORGANISM: Artificial sequence
<220> FEATURE:
<223> OTHER INFORMATION: Humanized 2/99 VH

<400> SEQUENCE: 192

```
Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Tyr Ala
                20                  25                  30

Met Ser Trp Ile Arg Gln His Pro Gly Lys Gly Leu Glu Trp Ile Gly
            35                  40                  45

Tyr Ile Trp Ser Gly Gly Ser Thr Asp Tyr Ala Ser Trp Ala Lys Ser
        50                  55                  60

Arg Val Thr Ile Ser Lys Thr Ser Thr Val Ser Leu Lys Leu Ser
65                  70                  75                  80

Ser Val Thr Ala Ala Asp Thr Ala Val Tyr Tyr Cys Ala Arg Arg Tyr
                85                  90                  95

Gly Thr Ser Tyr Pro Asp Tyr Gly Asp Ala Ser Gly Phe Asp Pro Trp
            100                 105                 110

Gly Gln Gly Thr Leu Val Thr Val Ser Ser
        115                 120
```

<210> SEQ ID NO 193
<211> LENGTH: 109
<212> TYPE: PRT
<213> ORGANISM: Artificial sequence
<220> FEATURE:
<223> OTHER INFORMATION: Humanized 2/99 VL

<400> SEQUENCE: 193

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile
            100                 105
```

<210> SEQ ID NO 194
<211> LENGTH: 119
<212> TYPE: PRT
<213> ORGANISM: Artificial sequence
<220> FEATURE:
<223> OTHER INFORMATION: Humanized 2/99 VH variant 1

<400> SEQUENCE: 194

```
Gln Val Gln Leu Val Gln Ser Gly Ala Glu Val Lys Lys Pro Gly Ala
```

-continued

```
              1               5                  10                 15
            Ser Val Lys Val Ser Cys Lys Ala Ser Gly Phe Asn Ile Lys Asp Thr
                            20                 25                 30

Tyr Ile His Trp Val Ile Gln Ala Pro Gly Gln Gly Leu Glu Trp Met
                        35                 40                 45

Gly Arg Ile Asp Pro Ala Asn Gly Asp Thr Lys Ser Asp Pro Lys Phe
                    50                 55                 60

Gln Val Arg Val Thr Ile Thr Ala Asp Thr Ser Thr Ser Thr Val Tyr
            65                 70                 75                 80

Met Glu Leu Ser Ser Leu Arg Ser Glu Asp Thr Ala Val Tyr Tyr Cys
                            85                 90                 95

Val Arg Asp Tyr Leu Tyr Pro Tyr Tyr Phe Asp Phe Trp Gly Gln Gly
                            100                105                110

Thr Thr Val Thr Val Ser Ser
                        115

<210> SEQ ID NO 195
<211> LENGTH: 119
<212> TYPE: PRT
<213> ORGANISM: Artificial sequence
<220> FEATURE:
<223> OTHER INFORMATION: Humanized 2/99 VH variant 2

<400> SEQUENCE: 195

Gln Val Gln Leu Val Gln Ser Gly Ala Glu Val Lys Lys Pro Gly Ala
1               5                  10                 15

Ser Val Lys Val Ser Cys Lys Ala Ser Gly Phe Asn Ile Lys Asp Thr
                20                 25                 30

Tyr Ile His Trp Val Ile Gln Ala Pro Gly Gln Gly Leu Glu Trp Met
            35                 40                 45

Gly Arg Ile Asp Pro Ala Asn Gly Asp Thr Lys Ser Ala Pro Lys Phe
        50                 55                 60

Gln Val Arg Val Thr Ile Thr Ala Asp Thr Ser Thr Ser Thr Val Tyr
65                 70                 75                 80

Met Glu Leu Ser Ser Leu Arg Ser Glu Asp Thr Ala Val Tyr Tyr Cys
                85                 90                 95

Val Arg Asp Tyr Leu Tyr Pro Tyr Tyr Phe Asp Phe Trp Gly Gln Gly
                100                105                110

Thr Thr Val Thr Val Ser Ser
            115

<210> SEQ ID NO 196
<211> LENGTH: 119
<212> TYPE: PRT
<213> ORGANISM: Artificial sequence
<220> FEATURE:
<223> OTHER INFORMATION: Humanized 2/99 VH variant 3

<400> SEQUENCE: 196

Gln Val Gln Leu Val Gln Ser Gly Ala Glu Val Lys Lys Pro Gly Ala
1               5                  10                 15

Ser Val Lys Val Ser Cys Lys Ala Ser Gly Phe Asn Ile Lys Asp Thr
                20                 25                 30

Tyr Ile His Trp Val Ile Gln Ala Pro Gly Gln Gly Leu Glu Trp Met
            35                 40                 45

Gly Arg Ile Asp Pro Ala Asn Gly Asp Thr Lys Ser Asp Pro Lys Phe
        50                 55                 60
```

```
Gln Gly Arg Val Thr Ile Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Val Arg Asp Tyr Leu Tyr Pro Tyr Tyr Phe Asp Phe Trp Gly Gln Gly
            100                 105                 110

Thr Thr Val Thr Val Ser Ser
            115

<210> SEQ ID NO 197
<211> LENGTH: 119
<212> TYPE: PRT
<213> ORGANISM: Artificial sequence
<220> FEATURE:
<223> OTHER INFORMATION: Humanized 2/99 VH variant 4

<400> SEQUENCE: 197

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Ile His Trp Val Ile Gln Ala Pro Gly Gln Gly Leu Glu Trp Met
        35                  40                  45

Gly Arg Ile Asp Pro Ala Asn Gly Asp Thr Lys Ser Asp Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Asp Tyr Leu Tyr Pro Tyr Tyr Phe Asp Phe Trp Gly Gln Gly
            100                 105                 110

Thr Thr Val Thr Val Ser Ser
            115

<210> SEQ ID NO 198
<211> LENGTH: 119
<212> TYPE: PRT
<213> ORGANISM: Artificial sequence
<220> FEATURE:
<223> OTHER INFORMATION: Humanized 2/99 VH variant 5

<400> SEQUENCE: 198

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Ile His Trp Val Ile Gln Arg Pro Gly Gln Gly Leu Glu Trp Met
        35                  40                  45

Gly Arg Ile Asp Pro Ala Asn Gly Asp Thr Lys Ser Asp Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Asp Tyr Leu Tyr Pro Tyr Tyr Phe Asp Phe Trp Gly Gln Gly
            100                 105                 110

Thr Thr Val Thr Val Ser Ser
            115
```

```
<210> SEQ ID NO 199
<211> LENGTH: 119
<212> TYPE: PRT
<213> ORGANISM: Artificial sequence
<220> FEATURE:
<223> OTHER INFORMATION: Humanized 2/99  VH variant 6

<400> SEQUENCE: 199

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asn Ile Lys Asp Thr
            20                  25                  30

Tyr Ile His Trp Val Ile Gln Arg Pro Gly Lys Gly Leu Glu Trp Ile
        35                  40                  45

Gly Arg Ile Asp Pro Ala Asn Gly Asp Thr Lys Ser Asp Pro Ser Leu
    50                  55                  60

Gln Ser Arg Val Thr Ile Ser Ala Asp Thr Ser Lys Asn Gln Ala Ser
65                  70                  75                  80

Leu Lys Leu Ser Ser Val Thr Ala Ala Asp Thr Ala Val Tyr Tyr Cys
                85                  90                  95

Val Arg Asp Tyr Leu Tyr Pro Tyr Tyr Phe Asp Phe Trp Gly Gln Gly
            100                 105                 110

Thr Thr Val Thr Val Ser Ser
        115

<210> SEQ ID NO 200
<211> LENGTH: 119
<212> TYPE: PRT
<213> ORGANISM: Artificial sequence
<220> FEATURE:
<223> OTHER INFORMATION: Humanized 2/99  VH variant 7

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Ile Gln Ala Pro Gly Lys Gly Leu Glu Trp Val
        35                  40                  45

Gly Arg Ile Asp Pro Ala Asn Gly Asp Thr Lys Ser Asp Pro Ser Val
    50                  55                  60

Gln Val Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Tyr Leu Tyr Pro Tyr Tyr Phe Asp Phe Trp Gly Gln Gly
            100                 105                 110

Thr Thr Val Thr Val Ser Ser
        115

<210> SEQ ID NO 201
<211> LENGTH: 106
<212> TYPE: PRT
<213> ORGANISM: Artificial sequence
<220> FEATURE:
<223> OTHER INFORMATION: Humanized 2/99  VL variant 1

<400> SEQUENCE: 201
```

```
Lys Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Thr Tyr
            20                  25                  30

Val Ser Trp Tyr Gln Gln Lys Pro Gly Lys Ala Pro Lys Leu Leu Ile
            35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gly Gln Thr Tyr Asn Tyr Pro Leu
            85                  90                  95

Thr Phe Gly Gln Gly Thr Lys Leu Glu Ile
            100                 105
```

<210> SEQ ID NO 202
<211> LENGTH: 15
<212> TYPE: PRT
<213> ORGANISM: Artificial sequence
<220> FEATURE:
<223> OTHER INFORMATION: Human transferring receptor (hTFR) epitope 1

<400> SEQUENCE: 202

```
Ile Gly Gln Asn Met Val Thr Ile Val Gln Ser Asn Gly Asn Leu
1               5                   10                  15
```

<210> SEQ ID NO 203
<211> LENGTH: 15
<212> TYPE: PRT
<213> ORGANISM: Artificial sequence
<220> FEATURE:
<223> OTHER INFORMATION: Human transferring receptor (hTFR) epitope 2

<400> SEQUENCE: 203

```
Asn Met Val Thr Ile Val Gln Ser Asn Gly Asn Leu Asp Pro Val
1               5                   10                  15
```

<210> SEQ ID NO 204
<211> LENGTH: 15
<212> TYPE: PRT
<213> ORGANISM: Artificial sequence
<220> FEATURE:
<223> OTHER INFORMATION: Human transferring receptor (hTFR) epitope 3

<400> SEQUENCE: 204

```
Gln Ser Asn Gly Asn Leu Asp Pro Val Glu Ser Pro Glu Gly Tyr
1               5                   10                  15
```

<210> SEQ ID NO 205
<211> LENGTH: 122
<212> TYPE: PRT
<213> ORGANISM: Artificial sequence
<220> FEATURE:
<223> OTHER INFORMATION: Humanized 2/99 VH variant

<400> SEQUENCE: 205

```
Gln Ser Met Gln Glu Ser Gly Pro Gly Leu Val Lys Pro Ser Gln Thr
1               5                   10                  15

Leu Ser Leu Thr Cys Thr Val Ser Gly Phe Ser Leu Ser Ser Tyr Ala
            20                  25                  30

Met Ser Trp Ile Arg Gln His Pro Gly Lys Gly Leu Glu Trp Ile Gly
            35                  40                  45
```

```
Tyr Ile Trp Ser Gly Gly Ser Thr Asp Tyr Ala Ser Trp Ala Lys Ser
     50                  55                  60
Arg Val Thr Ile Ser Lys Thr Ser Thr Val Ser Leu Lys Leu Ser
 65                  70                  75                  80
Ser Val Thr Ala Ala Asp Thr Ala Val Tyr Tyr Cys Ala Arg Arg Tyr
                 85                  90                  95
Gly Thr Ser Tyr Pro Asp Tyr Gly Asp Ala Gln Gly Phe Asp Pro Trp
            100                 105                 110
Gly Gln Gly Thr Leu Val Thr Val Ser Ser
        115                 120

<210> SEQ ID NO 206
<211> LENGTH: 17
<212> TYPE: PRT
<213> ORGANISM: Artificial sequence
<220> FEATURE:
<223> OTHER INFORMATION: Humanized 2/99 CDR-H3 variant

<400> SEQUENCE: 206

Arg Tyr Gly Thr Ser Tyr Pro Asp Tyr Gly Asp Ala Gln Gly Phe Asp
 1               5                  10                  15
Pro

<210> SEQ ID NO 207
<211> LENGTH: 106
<212> TYPE: PRT
<213> ORGANISM: Artificial sequence
<220> FEATURE:
<223> OTHER INFORMATION: Humanized 2/99  VL variant 2

<400> SEQUENCE: 207

Lys Ile Val Leu Thr Gln Ser Pro Gly Thr Leu Ser Leu Ser Pro Gly
 1               5                  10                  15
Glu Arg Ala Thr Leu Ser Cys Arg Ala Ser Glu Ser Val Asp Thr Tyr
                 20                  25                  30
Val Ser Trp Tyr Gln Gln Lys Pro Gly Gln Ala Pro Arg Leu Leu Ile
             35                  40                  45
Tyr Gly Ala Ser Asn Arg Tyr Thr Gly Val Pro Asp Arg Phe Ser Gly
         50                  55                  60
Ser Gly Ser Gly Thr Asp Phe Thr Leu Thr Ile Ser Arg Leu Glu Pro
 65                  70                  75                  80
Glu Asp Phe Ala Asp Tyr Tyr Cys Gln Thr Tyr Asn Tyr Pro Leu
                 85                  90                  95
Thr Phe Gly Gln Gly Thr Lys Leu Glu Ile
            100                 105

<210> SEQ ID NO 208
<211> LENGTH: 106
<212> TYPE: PRT
<213> ORGANISM: Artificial sequence
<220> FEATURE:
<223> OTHER INFORMATION: Humanized 2/99  VL variant 3

<400> SEQUENCE: 208

Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Glu Ser Val Asp Thr Tyr
                 20                  25                  30
Val Ser Trp Tyr Gln Gln Lys Pro Gly Gln Ala Pro Arg Leu Leu Ile
             35                  40                  45
```

Tyr Gly Ala Ser Asn Arg Tyr Thr Gly Val Pro Asp Arg Phe Ser Gly
            50                  55                  60

Ser Gly Ser Gly Thr Asp Phe Thr Leu Thr Ile Ser Arg Leu Glu Pro
 65                  70                  75                  80

Glu Asp Phe Ala Asp Tyr Tyr Cys Gly Gln Thr Tyr Asn Tyr Pro Leu
                 85                  90                  95

Thr Phe Gly Gln Gly Thr Lys Leu Glu Ile
                100                 105

<210> SEQ ID NO 209
<211> LENGTH: 106
<212> TYPE: PRT
<213> ORGANISM: Artificial sequence
<220> FEATURE:
<223> OTHER INFORMATION: Humanized 2/99 VL variant 4

<400> SEQUENCE: 209

Lys Ile Val Leu Thr Gln Ser Pro Gly Thr Leu Ser Leu Ser Pro Gly
 1               5                  10                  15

Glu Arg Ala Thr Leu Ser Cys Arg Ala Ser Glu Ser Val Asp Thr Tyr
                 20                  25                  30

Val Ser Trp Tyr Gln Gln Lys Pro Gly Gln Ala Pro Arg Leu Leu Ile
             35                  40                  45

Tyr Gly Ala Ser Asn Arg Tyr Thr Gly Ile Pro Asp Arg Phe Ser Gly
         50                  55                  60

Ser Gly Ser Gly Thr Asp Phe Thr Leu Thr Ile Ser Arg Leu Glu Pro
 65                  70                  75                  80

Glu Asp Phe Ala Asp Tyr Tyr Cys Gly Gln Thr Tyr Asn Tyr Pro Leu
                 85                  90                  95

Thr Phe Gly Gln Gly Thr Lys Leu Glu Ile
                100                 105

<210> SEQ ID NO 210
<211> LENGTH: 219
<212> TYPE: PRT
<213> ORGANISM: Artificial sequence
<220> FEATURE:
<223> OTHER INFORMATION: 8936_pTau_RbMab86_VL_huIgkappa

<400> SEQUENCE: 210

Ala Gln Val Leu Thr Gln Thr Thr Ser Pro Val Ser Ala Ala Val Gly
 1               5                  10                  15

Ser Thr Val Thr Ile Ser Cys Gln Ser Ser Gln Ser Val Arg Thr Asn
                 20                  25                  30

Lys Leu Ala Trp Phe Gln Gln Lys Pro Gly Gln Pro Pro Lys Arg Leu
             35                  40                  45

Ile Tyr Ser Ala Ser Thr Leu Asp Phe Gly Val Pro Ser Arg Phe Ser
         50                  55                  60

Ala Ser Gly Ser Gly Thr Gln Phe Thr Leu Thr Ile Ser Asp Val Gln
 65                  70                  75                  80

Cys Asp Asp Ala Ala Thr Tyr Tyr Cys Leu Gly Tyr Phe Asp Cys Ser
                 85                  90                  95

Ile Ala Asp Cys Val Ala Phe Gly Gly Gly Thr Glu Val Val Val Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe

```
                    130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 211
<211> LENGTH: 438
<212> TYPE: PRT
<213> ORGANISM: Artificial sequence
<220> FEATURE:
<223> OTHER INFORMATION: 8975-pTau-Rb86-hugamma1-SS-hole

<400> SEQUENCE: 211

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
                20                  25                  30

Ile Asn Trp Val Arg Gln Ala Pro Gly Lys Gly Leu Glu Trp Ile Gly
            35                  40                  45

Tyr Ile Ala Val Ser Gly Asn Thr Tyr Tyr Ala Ser Trp Ala Lys Gly
50                  55                  60

Arg Phe Thr Ile Ser Lys Ala Ser Thr Thr Val Asp Leu Lys Met Thr
65                  70                  75                  80

Ser Pro Thr Ala Glu Asp Thr Gly Thr Tyr Phe Cys Gly Lys Ser Asn
                85                  90                  95

Ile Trp Gly Pro Gly Thr Leu Val Thr Val Ser Leu Ala Ser Thr Lys
            100                 105                 110

Gly Pro Ser Val Phe Pro Leu Ala Pro Ser Ser Lys Ser Thr Ser Gly
        115                 120                 125

Gly Thr Ala Ala Leu Gly Cys Leu Val Lys Asp Tyr Phe Pro Glu Pro
    130                 135                 140

Val Thr Val Ser Trp Asn Ser Gly Ala Leu Thr Ser Gly Val His Thr
145                 150                 155                 160

Phe Pro Ala Val Leu Gln Ser Ser Gly Leu Tyr Ser Leu Ser Ser Val
                165                 170                 175

Val Thr Val Pro Ser Ser Ser Leu Gly Thr Gln Thr Tyr Ile Cys Asn
            180                 185                 190

Val Asn His Lys Pro Ser Asn Thr Lys Val Asp Lys Lys Val Glu Pro
        195                 200                 205

Lys Ser Cys Asp Lys Thr His Thr Cys Pro Pro Cys Pro Ala Pro Glu
    210                 215                 220

Leu Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
```

275                 280                 285
Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Cys Thr Leu Pro Pro Ser Arg Asp Glu Leu Thr Lys Asn
            340                 345                 350

Gln Val Ser Leu Ser Cys Ala Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Val Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
        435

<210> SEQ ID NO 212
<211> LENGTH: 922
<212> TYPE: PRT
<213> ORGANISM: Artificial sequence
<220> FEATURE:
<223> OTHER INFORMATION: 8976-pTau-Rb86-hugamma1-SS-knob-mTfR-8D3-scFab

<400> SEQUENCE: 212

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Ile Asn Trp Val Arg Gln Ala Pro Gly Lys Gly Leu Glu Trp Ile Gly
        35                  40                  45

Tyr Ile Ala Val Ser Gly Asn Thr Tyr Tyr Ala Ser Trp Ala Lys Gly
    50                  55                  60

Arg Phe Thr Ile Ser Lys Ala Ser Thr Thr Val Asp Leu Lys Met Thr
65                  70                  75                  80

Ser Pro Thr Ala Glu Asp Thr Gly Thr Tyr Phe Cys Gly Lys Ser Asn
                85                  90                  95

Ile Trp Gly Pro Gly Thr Leu Val Thr Val Ser Leu Ala Ser Thr Lys
                100                 105                 110

Gly Pro Ser Val Phe Pro Leu Ala Pro Ser Ser Lys Ser Thr Ser Gly
            115                 120                 125

Gly Thr Ala Ala Leu Gly Cys Leu Val Lys Asp Tyr Phe Pro Glu Pro
        130                 135                 140

Val Thr Val Ser Trp Asn Ser Gly Ala Leu Thr Ser Gly Val His Thr
145                 150                 155                 160

Phe Pro Ala Val Leu Gln Ser Ser Gly Leu Tyr Ser Leu Ser Ser Val
                165                 170                 175

Val Thr Val Pro Ser Ser Ser Leu Gly Thr Gln Thr Tyr Ile Cys Asn
            180                 185                 190

Val Asn His Lys Pro Ser Asn Thr Lys Val Asp Lys Lys Val Glu Pro

-continued

```
            195                 200                 205
Lys Ser Cys Asp Lys Thr His Thr Cys Pro Pro Cys Pro Ala Pro Glu
    210                 215                 220

Leu Leu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Ala Pro Ile Glu Lys Thr Ile Ser Lys Ala Lys Gly Gln Pro Arg Glu
                325                 330                 335

Pro Gln Val Tyr Thr Leu Pro Pro Cys Arg Asp Glu Leu Thr Lys Asn
            340                 345                 350

Gln Val Ser Leu Trp Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Gly Gly Ser Gly Gly Gly Ser Gly Gly Gly
        435                 440                 445

Gly Ser Gly Gly Gly Ser Asp Ile Gln Met Thr Gln Ser Pro Ala
    450                 455                 460

Ser Leu Ser Ala Ser Leu Glu Glu Ile Val Thr Ile Thr Cys Gln Ala
465                 470                 475                 480

Ser Gln Asp Ile Gly Asn Trp Leu Ala Trp Tyr Gln Gln Lys Pro Gly
                485                 490                 495

Lys Ser Pro Gln Leu Leu Ile Tyr Gly Ala Thr Ser Leu Ala Asp Gly
            500                 505                 510

Val Pro Ser Arg Phe Ser Gly Ser Arg Ser Gly Thr Gln Phe Ser Leu
        515                 520                 525

Lys Ile Ser Arg Val Gln Val Glu Asp Ile Gly Ile Tyr Tyr Cys Leu
    530                 535                 540

Gln Ala Tyr Asn Thr Pro Trp Thr Phe Gly Gly Gly Thr Lys Val Glu
545                 550                 555                 560

Ile Lys Arg Thr Val Ala Ala Pro Ser Val Phe Ile Phe Pro Pro Ser
                565                 570                 575

Asp Glu Gln Leu Lys Ser Gly Thr Ala Ser Val Val Cys Leu Leu Asn
            580                 585                 590

Asn Phe Tyr Pro Arg Glu Ala Lys Val Gln Trp Lys Val Asp Asn Ala
        595                 600                 605

Leu Gln Ser Gly Asn Ser Gln Glu Ser Val Thr Glu Gln Asp Ser Lys
    610                 615                 620
```

-continued

```
Asp Ser Thr Tyr Ser Leu Ser Thr Leu Thr Leu Ser Lys Ala Asp
625                 630                 635                 640

Tyr Glu Lys His Lys Val Tyr Ala Cys Glu Val Thr His Gln Gly Leu
            645                 650                 655

Ser Ser Pro Val Thr Lys Ser Phe Asn Arg Gly Glu Cys Gly Gly Gly
        660                 665                 670

Gly Ser Gly Gly Gly Ser Gly Gly Gly Ser Gly Gly Gly
    675                 680                 685

Ser Gly Gly Gly Ser Gly Gly Gly Ser Gly Gly Glu Val Gln
690                 695                 700

Leu Val Glu Ser Gly Gly Gly Leu Val Gln Pro Gly Asn Ser Leu Thr
705                 710                 715                 720

Leu Ser Cys Val Ala Ser Gly Phe Thr Phe Ser Asn Tyr Gly Met His
            725                 730                 735

Trp Ile Arg Gln Ala Pro Lys Lys Gly Leu Glu Trp Ile Ala Met Ile
        740                 745                 750

Tyr Tyr Asp Ser Ser Lys Met Asn Tyr Ala Asp Thr Val Lys Gly Arg
            755                 760                 765

Phe Thr Ile Ser Arg Asp Asn Ser Lys Asn Thr Leu Tyr Leu Glu Met
770                 775                 780

Asn Ser Leu Arg Ser Glu Asp Thr Ala Met Tyr Tyr Cys Ala Val Pro
785                 790                 795                 800

Thr Ser His Tyr Val Val Asp Val Trp Gly Gln Gly Val Ser Val Thr
            805                 810                 815

Val Ser Ser Ala Ser Thr Lys Gly Pro Ser Val Phe Pro Leu Ala Pro
        820                 825                 830

Ser Ser Lys Ser Thr Ser Gly Gly Thr Ala Ala Leu Gly Cys Leu Val
            835                 840                 845

Lys Asp Tyr Phe Pro Glu Pro Val Thr Val Ser Trp Asn Ser Gly Ala
850                 855                 860

Leu Thr Ser Gly Val His Thr Phe Pro Ala Val Leu Gln Ser Ser Gly
865                 870                 875                 880

Leu Tyr Ser Leu Ser Ser Val Val Thr Val Pro Ser Ser Leu Gly
            885                 890                 895

Thr Gln Thr Tyr Ile Cys Asn Val Asn His Lys Pro Ser Asn Thr Lys
        900                 905                 910

Val Asp Lys Lys Val Glu Pro Lys Ser Cys
915                 920
```

<210> SEQ ID NO 213
<211> LENGTH: 37
<212> TYPE: DNA
<213> ORGANISM: Artificial sequence
<220> FEATURE:
<223> OTHER INFORMATION: rbHC.up

<400> SEQUENCE: 213
aagcttgcca ccatggagac tgggctgcgc tggcttc        37

<210> SEQ ID NO 214
<211> LENGTH: 21
<212> TYPE: DNA
<213> ORGANISM: Artificial sequence
<220> FEATURE:
<223> OTHER INFORMATION: rbHCf.do

<400> SEQUENCE: 214

```
ccattggtga gggtgcccga g                                                     21

<210> SEQ ID NO 215
<211> LENGTH: 34
<212> TYPE: DNA
<213> ORGANISM: Artificial sequence
<220> FEATURE:
<223> OTHER INFORMATION: rbLC.up

<400> SEQUENCE: 215
aagcttgcca ccatggacay gagggccccc actc                                       34

<210> SEQ ID NO 216
<211> LENGTH: 26
<212> TYPE: DNA
<213> ORGANISM: Artificial sequence
<220> FEATURE:
<223> OTHER INFORMATION: rbLC.do

<400> SEQUENCE: 216
cagagtrctg ctgaggttgt aggtac                                                26

<210> SEQ ID NO 217
<211> LENGTH: 20
<212> TYPE: DNA
<213> ORGANISM: Artificial sequence
<220> FEATURE:
<223> OTHER INFORMATION: BcPCR_FHLC_leader.fw

<400> SEQUENCE: 217
atggacatga gggtccccgc                                                       20

<210> SEQ ID NO 218
<211> LENGTH: 24
<212> TYPE: DNA
<213> ORGANISM: Artificial sequence
<220> FEATURE:
<223> OTHER INFORMATION: BcPCR_huCkappa.rev

<400> SEQUENCE: 218
gatttcaact gctcatcaga tggc                                                  24
```